US007714013B2

(12) United States Patent
Mjalli et al.

(10) Patent No.: US 7,714,013 B2
(45) Date of Patent: May 11, 2010

(54) AZOLE DERIVATIVES AND FUSED BICYCLIC AZOLE DERIVATIVES AS THERAPEUTIC AGENTS

(75) Inventors: Adnan M. M. Mjalli, Oak Ridge, NC (US); Robert C. Andrews, Jamestown, NC (US); Ramesh Gopalaswamy, Jamestown, NC (US); Anitha Hari, High Point, NC (US); Kwasi A. Avor, High Point, NC (US); Ghassan Qabaja, Jamestown, NC (US); Xiao-Chuan Guo, High Point, NC (US); Suparna Gupta, Greensboro, NC (US); David R. Jones, Asheboro, NC (US); Xin Chen, High Point, NC (US)

(73) Assignee: Transtech Pharma, Inc., High Point, NC (US)

( * ) Notice: Subject to any disclaimer, the term of this patent is extended or adjusted under 35 U.S.C. 154(b) by 0 days.

(21) Appl. No.: 11/511,163

(22) Filed: Aug. 28, 2006

(65) Prior Publication Data

US 2007/0021386 A1    Jan. 25, 2007

Related U.S. Application Data

(62) Division of application No. 10/382,203, filed on Mar. 5, 2003, now Pat. No. 7,361,678.

(60) Provisional application No. 60/361,983, filed on Mar. 5, 2002.

(51) Int. Cl.
*A61K 31/4164* (2006.01)
*A61K 31/4178* (2006.01)
*C07D 233/64* (2006.01)
*C07D 403/02* (2006.01)

(52) U.S. Cl. ............... 514/397; 514/399; 548/110; 548/314.7; 548/336.1

(58) Field of Classification Search ............ 514/397, 514/399; 548/110, 314.7, 336.1
See application file for complete search history.

(56) References Cited

U.S. PATENT DOCUMENTS

| | | | |
|---|---|---|---|
| 3,708,598 | A | 1/1973 | Griot |
| 4,024,271 | A | 5/1977 | Durant et al. |
| 4,032,522 | A | 6/1977 | Baldwin et al. |
| 4,265,874 | A | 5/1981 | Bonsen et al. |
| 4,356,108 | A | 10/1982 | Schwab et al. |
| 4,873,313 | A | 10/1989 | Crawford et al. |
| 4,933,422 | A | 6/1990 | Hammer et al. |
| 4,963,539 | A | 10/1990 | Delaney et al. |
| 5,011,849 | A | 4/1991 | Gassner et al. |
| 5,153,226 | A | 10/1992 | Chucholowski et al. |
| 5,166,214 | A | 11/1992 | Billheimer et al. |
| 5,179,210 | A | 1/1993 | Ebel et al. |
| 5,192,785 | A | 3/1993 | Lo et al. |
| 5,202,424 | A | 4/1993 | Vlassara et al. |
| 5,318,984 | A | 6/1994 | Billheimer et al. |
| 5,358,960 | A | 10/1994 | Ulrich et al. |
| 5,500,436 | A | 3/1996 | Schonafinger et al. |
| 5,523,317 | A | 6/1996 | Masaki et al. |
| 5,585,344 | A | 12/1996 | Vlassara et al. |
| 5,589,496 | A | 12/1996 | Hamanaka et al. |
| 5,663,186 | A | 9/1997 | Nelson et al. |
| 5,688,653 | A | 11/1997 | Ulrich et al. |
| 5,817,823 | A | 10/1998 | Hong et al. |
| 5,864,018 | A | 1/1999 | Morser et al. |
| 5,939,526 | A | 8/1999 | Gaugler et al. |
| 5,962,500 | A | 10/1999 | Eide et al. |
| 5,962,535 | A | 10/1999 | Miyamoto et al. |
| 6,034,250 | A | 3/2000 | Goldstein et al. |
| 6,100,098 | A | 8/2000 | Newkirk et al. |
| 6,197,791 | B1 | 3/2001 | Venkatesan et al. |
| 6,201,002 | B1 | 3/2001 | Beere et al. |
| 6,265,351 | B1 | 7/2001 | La Porta et al. |
| 6,277,853 | B1 | 8/2001 | Perez et al. |
| 6,300,356 | B1 | 10/2001 | Segal et al. |

(Continued)

FOREIGN PATENT DOCUMENTS

EP    0 584 588    3/1994

(Continued)

OTHER PUBLICATIONS

Bierhaus et al., Circulation, 1997, vol. 96, 2262-2271, especially pp. 2263.*

(Continued)

*Primary Examiner*—Golam M. M. Shameem
*Assistant Examiner*—Susannah Chung
(74) *Attorney, Agent, or Firm*—Kilpatrick Stockton LLP

(57) ABSTRACT

This invention provides certain compounds, methods of their preparation, pharmaceutical compositions comprising the compounds, and their use in treating human or animal disorders. The compounds of the invention are useful as modulators of the interaction between the receptor for advanced glycated end products (RAGE) and its ligands, such as advanced glycated end products (AGEs), S100/calgranulin/EN-RAGE, β-amyloid and amphoterin, and for the management, treatment, control, or as an adjunct treatment for diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

14 Claims, No Drawings

U.S. PATENT DOCUMENTS

| | | | |
|---|---|---|---|
| 6,353,009 | B1 | 3/2002 | Fujiwara et al. |
| 6,416,733 | B1 | 7/2002 | Barrett et al. |
| 6,441,023 | B1 | 8/2002 | Venkatesan et al. |
| 6,441,064 | B1 | 8/2002 | Shah et al. |
| 6,538,013 | B2 | 3/2003 | Goebel et al. |
| 6,541,639 | B2 | 4/2003 | Zhou et al. |
| 6,613,801 | B2 | 9/2003 | Mjalli et al. |
| 6,673,810 | B2 | 1/2004 | Lam et al. |
| 6,673,927 | B2 | 1/2004 | Gordon et al. |
| 6,677,299 | B2 | 1/2004 | Stern et al. |
| 6,730,796 | B2 | 5/2004 | Cheng et al. |
| 6,825,164 | B1 | 11/2004 | Stern et al. |
| 6,919,338 | B2 | 7/2005 | Mortlock et al. |
| 7,361,678 | B2* | 4/2008 | Mjalli et al. ............... 514/397 |
| 7,421,177 | B2* | 9/2008 | Schmid et al. ............. 385/129 |
| 2001/0039256 | A1 | 11/2001 | Stern et al. |
| 2002/0116725 | A1 | 8/2002 | Stern et al. |
| 2002/0122799 | A1 | 9/2002 | Stern et al. |
| 2003/0207896 | A1 | 11/2003 | Konno et al. |
| 2003/0236282 | A1 | 12/2003 | Hemaus et al. |
| 2004/0127692 | A1 | 7/2004 | David et al. |
| 2005/0026811 | A1 | 2/2005 | Mjalli et al. |

FOREIGN PATENT DOCUMENTS

| | | |
|---|---|---|
| EP | 0 586 806 | 3/1994 |
| EP | 0 633 026 | 1/1995 |
| EP | 0 707 000 | 4/1996 |
| EP | 1 139 990 | 5/2004 |
| FR | 2 773 800 | 7/1999 |
| GB | 2 005 674 | 4/2005 |
| JP | 06-80656 | 3/1994 |
| JP | 09-40651 | 2/1997 |
| JP | 2003-12690 | 1/2003 |
| JP | 2003-40888 | 2/2003 |
| JP | 2003-313170 | 11/2003 |
| JP | 2003-313172 | 11/2003 |
| JP | 2004-221557 | 8/2004 |
| WO | WO 93-09100 | 5/1993 |
| WO | WO 95-01340 | 1/1995 |
| WO | WO 95-02591 | 1/1995 |
| WO | WO 95-09838 | 4/1995 |
| WO | WO 95-30647 | 11/1995 |
| WO | WO 95-35279 | 12/1995 |
| WO | WO 96-32385 | 10/1996 |
| WO | WO 97-22618 | 6/1997 |
| WO | WO 97-26913 | 7/1997 |
| WO | WO 97-39121 | 10/1997 |
| WO | WO 97-39125 | 10/1997 |
| WO | WO 98-22138 | 5/1998 |
| WO | WO 98-33492 | 8/1998 |
| WO | WO 98-35945 | 8/1998 |
| WO | WO 98-37877 | 9/1998 |
| WO | WO 99-07402 | 2/1999 |
| WO | WO 99-16755 | 4/1999 |
| WO | WO 99-18987 | 4/1999 |
| WO | WO 99-25690 | 5/1999 |
| WO | WO 99-50230 | 10/1999 |
| WO | WO 99-54485 | 10/1999 |
| WO | WO 00-19994 | 4/2000 |
| WO | WO 00-20458 | 4/2000 |
| WO | WO 00-20621 | 4/2000 |
| WO | WO 00-38635 | 7/2000 |
| WO | WO 00-66102 | 11/2000 |
| WO | WO 01-32604 | 5/2001 |
| WO | WO 02-069965 | 9/2002 |
| WO | WO 03-024937 | 3/2003 |
| WO | WO 03-053922 | 7/2003 |
| WO | WO 03-086390 | 10/2003 |
| WO | WO 2004-035061 | 4/2004 |
| WO | WO 2004-046141 | 6/2004 |
| WO | WO 2004-087653 | 10/2004 |
| WO | WO 2005-019185 | 3/2005 |

OTHER PUBLICATIONS

Morcos, Diabetes, vol. 51, Dec. 2002, 3532-3544, especially p. 3532.*

Parent U.S. Appl. No. 10/382,203.*

Yan et al., Nature, vol. 382, 1996, p. 691, col. 2, last paragraph.*

Albercio, et al, "Coupling Reagents and Activation Methods in Enzymology", vol. 289, pp. 104-126, Academic Press, San Diego (1997).

Barton et al., "In Protection of N—H Bonds and $NR_3$", Protective Groups in Organic Chemistry, J.F.W. McOmie, Ed., Plenum Press, New York, NY, (1973).

Berge et al., "Pharmaceutical Salts" Journal of Pharmaceutical Sciences, vol. 66, pp. 1-19 (1977).

Bierhaus el al., "Advanced Glycation End Product (AGE)-Mediated Induction of Tissue Factor in Cultured Endothelial Cells is Dependent on RAGE" Circulation, vol. 96, pp. 2262-2271 (1997).

Bonnardel-Phu et al., "Acute Modulation of Albumin Microvascular Leakage by Advanced Glycation End Products in Microcirculation of Diabetic Rats in Vivo" Diabetes, vol. 48, pp. 2052-2058 (1999).

Chitaley et al., "Antagonism of Rho-Kinase Stimulates Rate Penile Erection via a Nitric Oxide-Independent Pathway" Nature Medicine, vol. 7, pp. 119-122 (2001).

Coskun et al., "The First Region-and Diastereoselective Synthesis of Homochiral Perhydrolmidazoisoxazoles Via the 1,3-Dipolar Cycloaddition of Imidazoline 2 -oxides with (1S)-(−)-β-piene," Tetrahedron: Asymmetry, vol. 12, pp. 1463-1487 (2001).

Degenhardt et al., "Chemical Modification of Proteins by Methylglyoxal" Cellular and Molecular Biology, vol. 44, pp. 1139-1145 (1998).

Denny W A, "Structure-Activity Relationships for 2-Phenylbenzimidazole—4—Carboxamides, A New Class of Minimal DNA—Intercalating Agents Which May Not Act Via Topoisomerase II" Journal of Medicinal Chemistry, vol. 33, pp. 814-819 (1990).

Dyer et al., "Accumulation of Mailard Reaction Products in Skin Collagen in Diabetes and Aging" Journal of Clinical Investigation, vol. 91, pp. 2463-2469 (1993).

Dyer et al., "Formation of Pentosidine During Non-enzymatic Browning of Proteins by Glucose" Journal or Biological Chemistry, vol. 266, pp. 11654-11660 (1991).

Eriks J C et al., "Histamine H2—Receptor Agonists. Synthesis, In Vitro Pharmacology, and Qualitative Substituted 4- and 5-(2-aminoethyl) Thiazoles" Journal of Medicinal Chemistry, vol. 35, pp. 3239-3246 (1992).

Evans D et al., "Synthesis of a Group of 1H-benzimidazoles and Their Screening for Anti-Inflammatory Activity" European Journal of Medicinal Chemistry, vol. 31, pp. 635-642 (1996).

Fink et al., "Novel Structural Templates for Estrogen-Receptor Ligands and Prospects for Combinatorial Synthesis of Estrogens" Chemistry and Biology, vol. 6, pp. 205-219 (1999).

Goova et al., "Blockade of Receptor for Advanced Glycation End Products Restores Effective Wound Healing in Diabetic Mice" American Journal of Pathology, vol. 159, pp. 513-525 (2001).

Greene et al., "Protection for the Amino Group" Protective Groups in Organic Synthesis, John Wiley and Sons, New York, NY, Chapter 7 (1981).

Hammes et al., "Diabetic Retinopathy Risk Correlates with Intracellular Concentrations of the Glycoxidation Product N—(Carboxymethyl) Lysine Independently of Glycohaemoglobin Concentrations" Diabetologia, vol. 42, pp. 603-607 (1999).

Hoffman et al., "RAGE Mediates a Novel Proinflammatory Axis: A Central Cell Surface Receptor for S100/Calgranulin Polypeptides" Cell, vol. 97, pp. 889-901 (1999).

Hori et al., "The Receptor for Advanced Glycation End Products (RAGE) Is a Cellular Binding Site for Amphoterin" Journal of Biological Chemistry, vol. 270, pp. 25752-25761 (1995).

Huttunen et al., "Receptor for Advanced Glycation End Products (RAGE)-Mediated Neurite Outgrowth and Activation of NF-Kappa B Require the Cytoplasmic Domain of the Receptor but Different Downstream Signaling Pathways" Journal of Biological Chemistry, vol. 274, pp. 19919-19924 (1999).

International Search Report for related PCT application, PCT/US03/06749, mailed Sep. 29, 2003.

International Search Report for related PCT application, PCT/US03/06749 mailed Jul. 14, 2003.

Katzenellenbogen et al., STN International HCAPLUS Database, Columbus, Oh Accession No. 2000:240935, Reg. No. 234093-17-5 (2000).

Kislinger et al., "Receptor for Advanced Glycation End Products Mediates Inflammation and Enhanced Expression of Tissue Factor in Vasculature of Diabetic Apollpoprotein E-Null Mice" Arteriosclerosis, Thrombosis, and Vascular Biology, vol. 21, pp. 906-910 (2001).

Kumar et al., "RAGE at the Blood-Brain Barrier Mediates Neurovascular Dysfunction Caused by Amyloid Beta Peptide" Neuroscience Program, 141-#255.19 (2000).

Lampe et al., "Cardiotonic Agents. 6. Histamine Analogues As Potential Cardiovascular Selective H2 Agonists" Journal of Medicinal Chemistry, vol. 33, pp. 1688-1697 (1990).

Lander et al., "Activation of the Receptor for Advanced Glycation End Products Triggers a p21$^{ras}$-Dependent Mitogen-Activated Protein Kinase Pathway Regulated by Oxidant Stress" The Journal of Biological Chemistry, vol. 272, pp. 17810-17814 (1997).

Leder et al., "v-HA-ras Transgene Abrogates the Initiation Step in Mouse Skin Tumor Genesis: Effects of Phorbol Esters and Retinoic Acid" Proceedings of the National Academy of Sciences of the USA, vol. 87, pp. 9178-9181 (1990).

Li et al., "Characterization and Functional Analysis of the Promoter of RAGE, the Receptor for Advanced Glycation End Products" Journal of Biological Chemistry, vol. 272, pp. 16498-16506 (1997).

Li et al., "Sp 1-Binding elements in the Promoter of RAGE are Essential for Amphoterin-Mediated Gene Expression in Cultured Neuroblastoma Cells" Journal of Biological Chemistry, vol. 273, pp. 30870-30878 (1998).

Lugering et al., "The Myeloic Related Protein MRP8/14 (27E10 Antigen)—Usefulness as a Potential Marker for Disease Activity in Ulcerative Colitis and Putative Biological Function" European Journal of Chemistry, vol. 25, pp. 659-664 (1995).

Mackic et al., "Human Blood-Brain Barrier Receptors for Alzheimer's Amyloid-β1-40. Asymmetrical Binding, Endocytosis, and Transcytosis at the Apical Side of Brain Microvascular Endothelial Cell Monolayer" Journal of Clinical Investigation, vol. 102, pp. 734-743 (1998).

Miyata et al., "Beta2—Micro Globulin Modified with Advanced Glycation End Products Is a Major Component of Hemodialysis-Associated Amyloidosis" Journal of Clinical Investigation, vol. 92, pp. 1243-1252 (1993).

Miyata et al., "The Receptor for Advanced Glycation End Products (RAGE) is a Central Mediator of the Interaction of AGE-Beta2 Micro Globulin with Human Mononuclear Phagocytes Via an Oxidant-Sensitive Pathway" Journal of Clinical Investigation, vol. 98, pp. 1088-1094 (1996).

Morcos et al., "Activation of Tubular Epithelial Cells in Diabetic Nephropathy" Diabetes, vol. 51, pp. 3532-3544 (2002).

Morgan T.K. et al., "Synthesis and Pharmacological Studies of N-[4-[2-hydroxy-3-[[2-4-(1H-imidazol-1-71)phenoxyl)ethyl]amino]propoxy]phenyl)methane Sulfonamide, a Novel Antiarrhythmic Agent with Class II and Class III Activities" Journal of Medicinal Chemistry, vol. 33, pp. 1087-1090 (1990).

Neeper et al., "Cloning and Expression of a Cell Surface Receptor for Advanced Glycosylation End Products of Proteins" Journal of Biological Chemistry, vol. 267, pp. 14998-15004 (1992).

Oldfield et al., "Advanced Glycation End Products Cause Epithelialmyofibroblast Transdifferentiation Via the Receptor for Advanced Glycation End Products (RAGE)" The Journal of Clinical Investigation, vol. 108, pp. 1853-1863 (2001).

Parkkinen et al., "Amphoterin, the 30 -kDa Protein in a Family of HMG1-Type Polypeptides" Journal of Biological Chemistry, vol. 268, pp. 19726-19738 (1993).

Penning et al., "Structure-Activity Relationship Studies on 1-'2-(4-Phenylphenoxy) ethyll Pyrrolidine (SC-22716), a Potent Inhibitor of Leukotriene A4 (LTA4) Hydrolase" Journal of Medicinal Chemistry, vol. 43, pp. 721-735 (2000).

Porretta G.C. et al., "Chemotherapeutic Agents with an Imidazole Moiety III, Synthesis and Microbiological Activity of New 1,4-diarylimidazole and 1,4-pyrrolimidazolphenylene Derivatives" Farmaco, Societa Chimica Italiana, Pavia, It, vol. 46, pp. 913-924 (1991).

Rammes et al., "Myeloid-Related Protein (MRP) 8 and MRP 14, Calcium-Binding Proteins of the S100 Family, are Secreted by Activated Monocytes Via a Novel. Tubulin-Dependent Pathway" Journal of Biological Chemistry, vol. 272, pp. 9496-9502 (1997).

Rauvala et al., "Isolation and Some Characteristics of an Adhesive Factor of Brain That Enhances Neurite Outgrowth in Central Neurons" Journal of Biological Chemistry, vol. 262, pp. 16625-16635 (1987).

Reddy et al., "N—(Carboxymethyl) Lysine is a Dominant Advanced Glycation End Product (AGE) Antigen in Tissue Proteins" Biochemistry, vol. 34, pp. 10872-10878 (1995).

Sanfilippo P J: "Synthesis of Aryloxyalkylamines. 1. Novel Antisecretory Agents with H+K+-ATPase Inhibitory Activity" Journal of Medicinal Chemistry, vol. 31, pp. 1778-1785 (1988).

Sanfilippo Pauline J, "Synthesis of (aryloxy) Alkylamines. 2. Novel Imidazo-Fused Heterocycles with Calcium Channel Blocking and Local Anesthetic Activity" Journal of Medicinal Chemistry, vol. 31, pp. 2221-2227 (1988).

Schafer et al., "The S100 Family of EF-Hand Calcium-Binding Proteins: Functions an Pathology" TIBS, vol. 21, pp. 134-140 (1996).

Schleicher et al., "Increased Accumulation of the Glycoxidation Product N-(Carboxymethyl) Lysine in Human Tissues in Diabetes and Aging" Journal of Clinical Investigation, vol. 99, pp. 457-468 (1997).

Schmidt et al., "Advanced Glycation End Products Interacting with Their Endothelial Receptor Induce Expression of Vascular Cell Adhesion Molecule-1 (VCAM-1) in Cultured Human Endothelial Cells and in Mice" Journal of Clinical Investigation, vol. 96, pp. 1395-1403 (1995).

Schmidt et al., "Receptor for Advanced Glycation End Products (AGEs) Has a Central Role in Vessel Wall Interactions and Gene Activation in Response to Circulating AGE Proteins" Proceedings of the National Academy of Sciences of the USA, vol. 91, pp. 8807-8811 (1994).

Schmidt et al., "The Dark side of Glucose" Nature Medicine, vol. 1, pp. 1002-1004 (1995).

Schmidt et al., "The V-Domain of Receptor for Advanced Glycation Endproducts (RAGE) Mediates Binding of AGEs: A Novel Target for Therapy of Diabetic Complications" Supplement to Circulation vol. 96, pp. 1-37 (1987).

Scozzafava A. et al., "Carbonic Anhydrase Activators-Part 21" European Journal of Medicinal Chemistry, vol. 35, pp. 31-39 (2000).

Taguchi et al., "Blockade of RAGE-Amphoterin Signaling Suppresses Tumor Growth and Metastases" Nature, vol. 405, pp. 354-360 (2000).

Tanaka et al., "The Receptor for Advanced Glycation End Protocols is Induced by the Glycation Products Themselves and Tumor Necrosis Factor-a through Nuclear Fact- kB, and 17 β-Estradoil Through Sp-1 in Human Vascular Endothelial Cells" Journal of Biological Chemistry, vol. 275, pp. 25781-25790 (2000).

Teillet et al., "Food Restriction Prevents Advanced Glycation End Product Accumulation and Retards Kidney Aging in Lean Rats" Journal of the American Society of Nephrology, vol. 11, pp. 1488-1497 (2000).

Vlassara et al., "Advanced Glycation End-Products and Atherosclerosis" Annals of Medicine, vol. 28, pp. 418-426 (1996).

Wautier et al., "Advanced Glycation End Products (AGEs) on the Surface of Diabetic Erythrocytes Bind to the Vessel Wall Via a Specific Receptor Inducing Oxidant Stress in the Vasculature: A link Between Surface Associated AGEs and Diabetic Complications" Proceedings of the National Academy of Sciences of the USA, vol. 91, pp. 7742-7746 (1994).

Wautier et al., "Receptor-Mediated Endothelial Cell Dysfunction in Diabetic Vasculopathy: Soluble Receptor for Advanced Glycation End Products Blocks Hyper Permeability in Diabetic Rats" Journal of Clinical Investigation, vol. 97, pp. 238-243 (1996).

Yan et al., "An Intracellular Protein that Binds Amyloid-β Peptide and Mediates Neurotoxicity in Alzheimer's Disease" Nature, vol. 389, 689-695 (1997).

Yan et al., "Amyloid-β Peptide—Receptor for Advanced Glycation Endproducts Interaction Elicitis Neuronal Expression of Macrophage—Colony Stimulating Factor: A Proinflammatory Pathway in Alzheimer Disease" Proceedings of the National Academy of Sciences of the USA, vol. 94, pp. 5298-5301 (1997).

Yan at al., "Enhanced Cellular Oxidant Stress by the Interaction of Advanced Glycation Endproducts with Their Receptors Binding Proteins" Journal of Biological Chemistry, vol. 269, pp. 9889-9897 (1994).

Yan at al., "RAGE and Amyloid-β Peptide Neurotoxicity in Alzheimer's Disease" Nature, vol. 382, pp. 685-691 (1996).

Yan et al., "Receptor-Dependent Cell Stress and Amyloid Accumulation in Systemic Amyloidosis" Nature Medicine, vol. 6, pp. 643-651 (2000).

Yeh et al., "Requirement for p38 and p44/p42 Mitogen-Activated Protein Kinases in RAGE-Mediated Nuclear Factor-κB Transcriptional Activation and Cytokine Secretion" Diabetes, vol. 50, pp. 1495-1504 (2001).

Zimmer et al., "The S100 Protein Family: History, Function, and Expression" Brain Research Bulletin, vol. 37, pp. 417-429 (1995).

Ohkubo et al., "Studies on Cerebral Protective Agents. VII. Synthesis of Novel 4-Arylazole Derivatives with Anti-anoxic Activity" Chemical Pharmaceutical Bulletin, vol. 43, pp. 947-954, (1995).

Office Action mailed Jan. 16, 2009 for U.S. Appl. No. 12/019,045.

Interview Summary mailed May 1, 2009 for U.S. Appl. No. 12/019,045.

Blacker, D. et al., "Reliability and Validity of NINCDS-ADRDA Criteria for Alzheimer's Disease," Arch. Neurol., 1994, 51:1198-1204.

Deane, R. et al., "RAGE Mediates Amyloid-Beta Peptide Transport Across the Blood-Brain Barrier and Accumulation in Brain," Nature Medicine, 2003, 9:907-913.

Girouard, H. et al., "Neurovascular Coupling in the Normal Brain and in Hypertension, Stroke, and Alzheimer Disease," J. Appl. Physiol., 2006, 100:328-335.

McKhann, G. et al., "Clinical Diagnosis of Alzheimer's Disease: Report of the NINCDS-ADRDA Work Group Under the Auspices of Department of Health and Human Services Task Force on Alzheimer's Disease," Neurology, 1984, 34:939-944.

Ranginwala, N. et al., "Clinical Criteria for the Diagnosis of Alzheimer Disease: Still Good After All These Years," Am. J. Geriatr. Psychiatry, 2008, 16:384-388.

Snowdon, D., "Healthy Aging and Dementia: Findings from the Nun Study," Ann Intern Med., 2003, 139:450-454.

Non-Final Office Action for U.S. Appl. No. 12/019,045 mailed Aug. 19, 2008.

Final Office Action for U.S. Appl. No. 11/362,993 mailed Apr. 4, 2008.

Non-Final Office Action for U.S. Appl. No. 11/362,993 mailed Nov. 14, 2008.

Examiner's Report mailed Jul. 15, 2008 corresponding to Australian Patent Application Serial No. 2007202350.

Notice of Acceptance mailed Jul. 20, 2009 corresponding to Australian Patent Application Serial No. 2007202350.

Office Action mailed Sep. 5, 2008 corresponding to Canadian Patent Application Serial No. 2,476,594.

Office Action mailed Jul. 16, 2009 corresponding to Canadian Patent Application Serial No. 2,476,594.

Office Action mailed Sep. 26, 2008 corresponding to European Patent Application Serial No. 03 713 918.5.

Office Action mailed Feb. 26, 2009 corresponding to European Patent Application Serial No. 03 713 918.5.

Office Action mailed Jul. 22, 2008 corresponding to Japanese Patent Application Serial No. 2003-574195.

Office Action mailed Jan. 6, 2009 corresponding to Japanese Patent Application Serial No. 2003-574195.

Office Action mailed Nov. 17, 2008 corresponding to Japanese Patent Application Serial No. 2003-574195.

Examiner's Report mailed Feb. 20, 2006 corresponding to Australian Patent Application Serial No. 2003217943.

Notice of Acceptance mailed Apr. 20, 2007 corresponding to Australian Patent Application Serial No. 2003217943.

Office Action mailed Nov. 11, 2005 corresponding to Chinese Patent Application Serial No. 03 8 05204.0.

Office Action mailed Dec. 28, 2007 corresponding to Chinese Patent Application Serial No. 03 8 05204.0.

Office Action mailed Sep. 29, 2008 corresponding to Chinese Patent Application Serial No. 03 8 05204.0.

Notice of Grant mailed Apr. 10, 2009 corresponding to Chinese Patent Application Serial No. 03 8 05204.0.

Office Action mailed Jun. 22, 2009 corresponding to U.S. Appl. No. 12/019,045.

Notice of Allowance mailed Aug. 12, 2009 corresponding to U.S. Appl. No. 11/800,085.

Office Action mailed Nov. 13, 2008 corresponding to U.S. Appl. No. 11/800,085.

Office Action mailed Aug. 19, 2009 corresponding to U.S. Appl. No. 11/946,641.

Buttke, K. et al., "Synthese, Struktur und photophysikalische Eigenschaften von polyarylierten Imidazolen und Oxazolen," J. prakt. Chem., 1997, 339:721-728.

Heinze, J. et al., "Über eine neue Synthese von Tetraaryl-imidazolen und Pentaaryl-imidazolium-Salzen," Chem. Ber., 1968, 101:3504-3516.

Chemische Berichte, 1968, 101(10), 3504-3016, STN online, CA70:3953.

* cited by examiner

AZOLE DERIVATIVES AND FUSED BICYCLIC AZOLE DERIVATIVES AS THERAPEUTIC AGENTS

STATEMENT OF RELATED APPLICATION

The present application is a divisional application of U.S. application Ser. No. 10/382,203, filed Mar. 5, 2003 now U.S. Pat. No. 7,361,678, entitled "Azole Derivatives and Fused Bicyclic Azole Derivatives as Therapeutic Agents," which claims priority under 35 USC 119(e) from U.S. Provisional Application No. 60/361,983, filed Mar. 5, 2002, entitled "Azole Derivatives as Therapeutic Agents," the entirety of which is herein incorporated by reference.

FIELD OF THE INVENTION

This invention relates to compounds which are modulators of the receptor for advanced glycated end products (RAGE) and interaction with its ligands such as advanced glycated end products (AGEs), S100/calgranulin/EN-RAGE, β-amyloid and amphoterin, for the management, treatment, control, or as an adjunct treatment of diseases caused by RAGE.

BACKGROUND OF THE INVENTION

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycosylation End Products (AGEs). Factors which promote formation of AGEs included delayed protein turnover (e.g. as in amyloidoses), accumulation of macromolecules having high lysine content, and high blood glucose levels (e.g. as in diabetes) (Hori et al., *J. Biol. Chem.* 270: 25752-761, (1995)). AGEs have implicated in a variety of disorders including complications associated with diabetes and normal aging.

AGEs display specific and saturable binding to cell surface receptors on endothelial cells of the microvasculature, monocytes and macrophages, smooth muscle cells, mesengial cells, and neurons. The Receptor for Advanced Glycated End-products (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., *J. Biol. Chem.* 267:14998-15004 (1992)). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al., *J. Biol. Chem.* 270:25752-761 (1995)). Increased levels of RAGE are also found in aging tissues (Schleicher et al., *J. Clin. Invest.* 99 (3): 457-468 (1997)), and the diabetic retina, vasculature and kidney (Schmidt et al., *Nature Med.* 1:1002-1004 (1995)). Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.* 97:238-243 (1995)), nephropathy (Teillet et al., *J. Am. Soc. Nephrol.* 11:1488-1497 (2000)), atherosclerosis (Vlassara et. al., *The Finnish Medical Society DUODECIM, Ann. Med.* 28:419-426 (1996)), and retinopathy (Hammes et al., *Diabetologia* 42:603-607 (1999)). RAGE has also been implicated in Alzheimer's disease (Yan et al., *Nature* 382: 685-691, (1996)), erectile dysfunction, and in tumor invasion and metastasis (Taguchi et al., *Nature* 405: 354-357, (2000)).

In addition to AGEs, other compounds can bind to, and modulate RAGE. In normal development, RAGE interacts with amphoterin, a polypeptide which mediates neurite outgrowth in cultured embryonic neurons (Hori et al., 1995). RAGE has also been shown to interact with EN-RAGE, a protein having substantial-similarity to calgranulin (Hofmann et al., *Cell* 97:889-901 (1999)). RAGE has also been shown to interact with β-amyloid (Yan et al., *Nature* 389:589-595, (1997); Yan et al., *Nature* 382:685-691 (1996); Yan et al., *Proc. Natl. Acad. Sci.,* 94:5296-5301 (1997)).

Binding of ligands such as AGEs, S100/calgranulin/EN-RAGE, β-amyloid, CML ($N^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21 ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target for down-regulation of the pathophysiological changes brought about by excessive concentrations of AGEs and other ligands for RAGE.

Thus, there is a need for the development of compounds that antagonize binding of physiological ligands to the RAGE receptor.

SUMMARY OF THE INVENTION

This invention provides substituted benzimidazole compounds. Embodiments of the present invention provide compounds of Formula (I) as depicted below, methods of their preparation, pharmaceutical compositions comprising the compounds, and methods for their use in treating human or animal disorders. Compounds of the invention are useful as modulators of the interaction of the receptor for advanced glycated end products (RAGE) with its ligands such as advanced glycated end products (AGEs), S100/calgranulin/EN-RAGE, β-amyloid and amphoterin. The compounds are useful in a variety of applications including the management, treatment, control, and/or as an adjunct of diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

DETAILED DESCRIPTION OF THE INVENTION

In a first aspect, the present invention provides certain substituted azole compounds. Such compounds are useful in the modulation, preferably in the inhibition, of the interaction of RAGE with its physiological ligands, as will be discussed in more detail below.

In a second aspect, the present invention provides compounds of Formula (I):

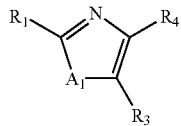

wherein
R₁ comprises -hydrogen, -aryl, -heteroaryl, -cycloalkyl, -heterocyclyl, -alkyl, -alkenyl, -alkynyl, -alkylene-aryl, -alkylene-heteroaryl, -alkylene-heterocyclyl, -alkylene-cycloalkyl, -fused cycloalkylaryl, -fused cycloalkylheteroaryl, -fused heterocyclylaryl, -fused heterocyclylheteroaryl, -alkylene-fused cycloalkylaryl, -alkylene-fused cycloalkylheteroaryl, -alkylene-fused heterocyclylaryl, -alkylene-fused heterocyclylheteroaryl, or -G₁-G₂-G₃-R₅
wherein
G₁ and G₃ independently comprise alkylene, alkenylene, alkynylene, cycloalkylene, heterocyclylene, arylene, heteroarylene, (aryl)alkylene, (heteroaryl)alkylene, (aryl)alkenylene, (heteroaryl)alkenylene, or a direct bond;
G₂ comprises —O—, —S—, —S(O)—, —N(R₆)—, —S(O)₂—, —C(O)—, —O—C(O)—, —C(O)—O—, —C(O)N(R₆)—, —N(R₆)C(O)—, —S(O₂)N(R₆)—, N(R₆)S(O₂)—, —O-alkylene-C(O)—, —(O)C-alkylene-O—, —O-alkylene-, -alkylene-O—, alkylene, alkenylene, alkynylene, cycloalkylene, heterocyclylene, arylene, heteroarylene, fused cycloalkylarylene, fused cycloalkylheteroarylene, fused heterocyclylarylene, fused heterocyclylheteroarylene, or a direct bond, wherein R₆ comprises hydrogen, aryl, alkyl, -alkylene-aryl, alkoxy, or -alkylene-O-aryl; and
R₅ comprises hydrogen, aryl, heteroaryl, cycloalkyl, heterocyclyl, alkyl, alkenyl, alkynyl, -alkylene-aryl, -alkylene-heteroaryl, -alkylene-heterocyclyl, -alkylene-cycloalkyl, fused cycloalkylaryl, fused cycloalkylheteroaryl, fused heterocyclylaryl, fused heterocyclylheteroaryl, -alkylene-fused cycloalkylaryl, -alkylene-fused cycloalkylheteroaryl, -alkylene-fused heterocyclylaryl, or -alkylene-fused heterocyclylheteroaryl;
A₁ comprises O, S, or —N(R₂)—;
wherein
R₂ comprises
  a) —H;
  b) -aryl;
  c) -heteroaryl;
  d) -cycloalkyl
  e) heterocyclyl;
  f) -alkyl;
  g) -alkenyl;
  h) -alkynyl;
  i) -alkylene-aryl,
  j) -alkylene-heteroaryl,
  k) -alkylene-heterocyclyl,
  l) -alkylene-cycloalkyl;
  m) -fused cycloalkylaryl,
  n) -fused cycloalkylheteroaryl,
  o) -fused heterocyclylaryl,
  p) -fused heterocyclylheteroaryl;
  q) -alkylene-fused cycloalkylaryl,
  r) -alkylene-fused cycloalkylheteroaryl,
  s) -alkylene-fused heterocyclylaryl,
  t) -alkylene-fused heterocyclylheteroaryl; or
  u) a group of the formula

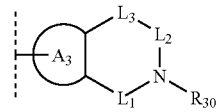

wherein
A₃ comprises an aryl or heteroaryl group;
L₁ and L₂ independently comprise alkylene or alkenylene; and
L₃ comprises a direct bond, alkylene, —O—, —S—, —S(O₂)—, —C(O)—, —CON(H)—, —NHC(O)—, —NHCON(H)—, —NHSO₂—, —SO₂N(H)—, —C(O)—O—, —O—C(O)—, —NHSO₂NH—,

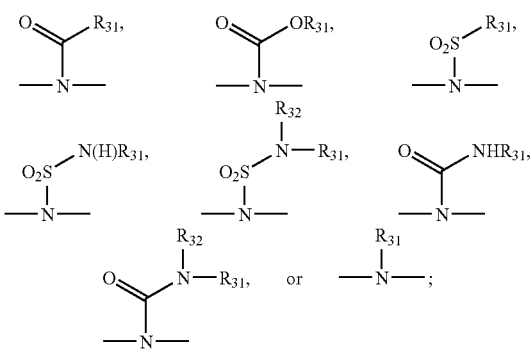

wherein R₃₀, R₃₁, and R₃₂ independently comprise hydrogen, aryl, heteroaryl, alkyl, alkylene-aryl, or -alkylene-heteroaryl;
R₃ and R₄ independently comprise
  a) -hydrogen,
  b) -halogen,
  c) -hydroxyl,
  d) -cyano,
  e) -carbamoyl,
  f) -carboxyl,
  g) -aryl,
  h) -heteroaryl,
  i) -cycloalkyl,
  j) -heterocyclyl,
  k) -alkyl,
  l) -alkenyl,
  m) -alkynyl,
  n) -alkylene-aryl,
  o) -alkylene-heteroaryl,
  p) -alkylene-heterocyclyl,
  q) -alkylene-cycloalkyl,
  r) -fused cycloalkylaryl,
  s) -fused cycloalkylheteroaryl,
  t) -fused heterocyclylaryl,
  u) -fused heterocyclylheteroaryl,
  v) -alkylene-fused cycloalkylaryl,
  w) -alkylene-fused cycloalkylheteroaryl,
  x) -alkylene-fused heterocyclylaryl,
  y) -alkylene-fused heterocyclylheteroaryl;

z) —C(O)—O-alkyl;
aa) —C(O)—O-alkylene-aryl;
bb) —C(O)—NH-alkyl;
cc) —C(O)—NH-alkylene-aryl;
dd) —SO$_2$-alkyl;
ee) —SO$_2$-alkylene-aryl;
ff) —SO$_2$-aryl;
gg) —SO$_2$—NH-alkyl;
hh) —SO$_2$—NH— alkylene-aryl;
ii) —C(O)-alkyl;
jj) —C(O)-alkylene-aryl;
kk) -G$_4$-G$_5$-G$_6$-R$_7$;
ll) —Y$_1$-alkyl;
mm) —Y$_1$-aryl;
nn) —Y$_1$-heteroaryl;
oo) —Y$_1$-alkylene-aryl;
pp) —Y$_1$-alkylene-heteroaryl;
qq) —Y$_1$-alkylene-NR$_9$R$_{10}$; or
rr) —Y$_1$-alkylene-W$_1$—R$_{11}$;
  wherein
  G$_4$ and G$_6$ independently comprise alkylene, alkenylene, alkynylene, cycloalkylene, heterocyclylene, arylene, heteroarylene, (aryl)alkylene, (heteroaryl)alkylene, (aryl)alkenylene, (heteroaryl)alkenylene, or a direct bond;
  G$_5$ comprises —O—, —S—, —N(R$_8$)—, —S(O)—, —S(O)$_2$—, —C(O)—, —O—C(O)—, —C(O)—O—, —C(O)N(R$_8$)—, N(R$_8$)C(O)—, —S(O$_2$)N(R$_8$)—, N(R$_8$)S(O$_2$)—, —O-alkylene-C(O)—, —(O)C-alkylene-O—, —O-alkylene-, -alkylene-O—, alkylene, alkenylene, alkynylene, cycloalkylene, heterocyclylene, arylene, heteroarylene, fused cycloalkylarylene, fused cycloalkylheteroarylene, fused heterocyclylarylene, fused heterocyclylheteroarylene, or a direct bond, wherein R$_8$ comprises -hydrogen, -aryl, -alkyl, -alkylene-aryl, or -alkylene-O-aryl;
  R$_7$ comprises hydrogen, aryl, heteroaryl, cycloalkyl, heterocyclyl, alkyl, alkenyl, alkynyl, alkylene-aryl, -alkylene-heteroaryl, -alkylene-heterocyclyl, -alkylene-cycloalkyl, fused cycloalkylaryl, fused cycloalkylheteroaryl, fused heterocyclylaryl, fused heterocyclylheteroaryl, alkylene-fused cycloalkylaryl, -alkylene-fused cycloalkylheteroaryl, -alkylene-fused heterocyclylaryl, or -alkylene-fused heterocyclylheteroaryl;
  Y$_1$ and W$_1$ independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

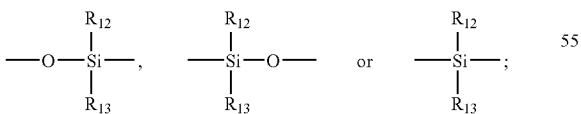

wherein R$_{12}$ and R$_{13}$ independently comprise aryl, alkyl, -alkylene-aryl, alkoxy, or -alkylene-O-aryl; and
  R$_9$, R$_{10}$, and R$_{11}$ independently comprise aryl, heteroaryl, alkyl, -alkylene-heteroaryl, or -alkylene-aryl; and R$_9$ and R$_{10}$ may be taken together to form a ring having the formula —(CH$_2$)$_o$—X$_1$—(CH$_2$)$_p$— bonded to the nitrogen atom to which R$_9$ and R$_{10}$ are attached, wherein
o and p are, independently, 1, 2, 3, or 4; and
X$_1$ comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

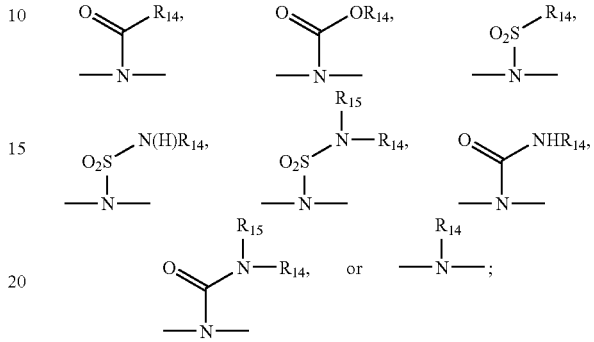

wherein R$_{14}$ and R$_{15}$ independently hydrogen, aryl, heteroaryl, alkyl, -alkylene-aryl, or -alkylene-heteroaryl;
wherein
  the aryl and/or alkyl group(s) in R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, and R$_{15}$ may be optionally substituted 1-4 times with a substituent group, wherein said substituent group(s) or the term substituted refers to a group comprising:
  a) —H,
  b) -halogen,
  c) -hydroxyl,
  d) -cyano,
  e) -carbamoyl,
  f) -carboxyl,
  g) —Y$_2$-alkyl;
  h) —Y$_2$-aryl;
  i) —Y$_2$-heteroaryl;
  j) —Y$_2$-alkylene-heteroarylaryl;
  k) —Y$_2$-alkylene-aryl;
  l) —Y$_2$-alkylene-W$_2$—R$_{18}$;
  m) —Y$_3$—Y$_4$—NR$_{23}$R$_{24}$,
  n) —Y$_3$—Y$_4$—NH—C(=NR$_{25}$)NR$_{23}$R$_{24}$,
  o) —Y$_3$—Y$_4$—C(=NR$_{25}$)NR$_{23}$R$_{24}$, or
  p) —Y$_3$—Y$_4$—Y$_5$-A$_2$,
  wherein
  Y$_2$ and W$_2$ independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—S(O)$_2$—, —O—CO—,

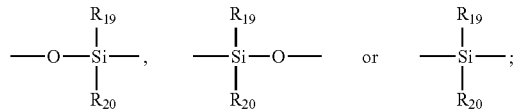

wherein;
  R$_{19}$ and R$_{20}$ independently comprise hydrogen, aryl, alkyl, -alkylene-aryl, alkoxy, or -alkylene-O-aryl; and $R_{18}$ comprises aryl, alkyl, -alkylene-aryl, -alkylene-heteroaryl, and -alkylene-O-aryl;

$Y_3$ and $Y_5$ independently comprise a direct bond, —$CH_2$—, —O—, —N(H)—, —S—, $SO_2$—, —C(O)—, —CON(H)—, —NHC(O)—, —NH-CON(H)—, —$NHSO_2$—, —$SO_2N(H)$—, —C(O)—O—, —$NHSO_2NH$—, —O—CO—,

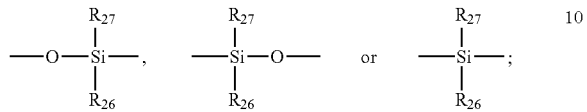

wherein $R_{27}$ and $R_{26}$ independently comprise aryl, alkyl, -alkylene-aryl, alkoxy, or -alkyl-O-aryl;

$Y_4$ comprises
 a) -alkylene;
 b) -alkenylene;
 c) -alkynylene;
 d) -arylene;
 e) -heteroarylene;
 f) -cycloalkylene;
 g) -heterocyclylene;
 h) -alkylene-arylene;
 i) -alkylene-heteroarylene;
 j) -alkylene-cycloalkylene;
 k) -alkylene-heterocyclylene;
 l) -arylene-alkylene;
 m) -heteroarylene-alkylene;
 n) -cycloalkylene-alkylene;
 o) -heterocyclylene-alkylene;
 p) —O—;
 q) —S—;
 r) —$S(O_2)$—; or
 s) —S(O)—;
 wherein said alkylene groups may optionally contain one or more O, S, S(O), or $SO_2$ atoms;

$A_2$ comprises
 a) heterocyclyl, fused arylheterocyclyl, or fused heteroarylheterocyclyl, containing at least one basic nitrogen atom,
 b) -imidazolyl, or
 c) -pyridyl; and $R_{23}$, $R_{24}$, and $R_{25}$ independently comprise hydrogen, aryl, heteroaryl, -alkylene-heteroaryl, alkyl, -alkylene-aryl, -alkylene-O-aryl, or -alkylene-O-heteroaryl; and $R_{23}$ and $R_{24}$ may be taken together to form a ring having the formula —$(CH_2)_s$—$X_3$—$(CH_2)_t$— bonded to the nitrogen atom to which $R_{23}$ and $R_{24}$ are attached wherein
s and t are, independently, 1, 2, 3, or 4;

$X_3$ comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

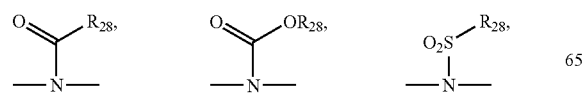

-continued

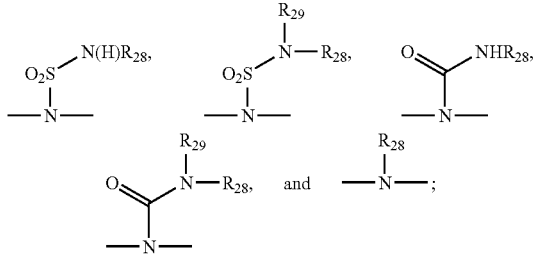

wherein $R_{28}$ and $R_{29}$ independently comprise hydrogen, aryl, heteroaryl, alkyl, -alkylene-aryl, or -alkylene-heteroaryl;

wherein
 either
  at least one of the groups $R_1$, $R_2$, $R_3$ and $R_4$ are substituted with at least one group of the formula —$Y_3$—$Y_4$—$NR_{23}R_{24}$, —$Y_3$—$Y_4$—NH—C(=$NR_{25}$)$NR_{23}R_{24}$, —$Y_3$—$Y_4$—C(=$NR_{25}$)$NR_{23}R_{24}$, or —$Y_3$—$Y_4$—$Y_5$-$A_2$, with the proviso that no more than one of $R_{23}$, $R_{24}$, and $R_{25}$ may comprise aryl or heteroaryl;
 or
  $R_2$ is a group of the formula

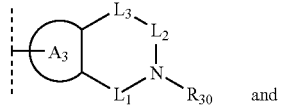

and wherein
 one of $R_3$ and $R_4$, $R_3$ and $R_2$, or $R_1$ and $R_2$ may be taken together to constitute, together with the atoms to which they are bonded, an aryl, heteroaryl, fused arylcycloalkyl, fused arylheterocyclyl, fused heteroarylcycloalkyl, or fused heteroarylheterocyclyl ring system,
wherein
said ring system or $R_1$, $R_2$, $R_3$, or $R_4$ is substituted with at least one group of the formula
 a) —$Y_5$—$Y_6$—$NR_{33}R_{34}$;
 b) —$Y_5$—$Y_6$—NH—C(=$NR_{35}$)$NR_{33}R_{34}$;
 c) —$Y_5$—$Y_6$—C(=$NR_{35}$)$NR_{33}R_{34}$; or
 d) —$Y_5$—$Y_6$—$Y_7$-$A_4$;
wherein
 $Y_5$ and $Y_7$ independently comprise a direct bond, —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

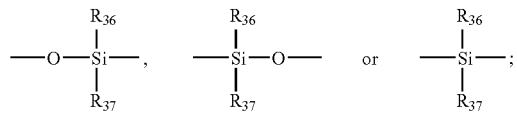

wherein $R_{36}$ and $R_{37}$ independently comprise aryl, alkyl, -alkylene-aryl, alkoxy, or -alkyl-O-aryl;

$Y_6$ comprises
 a) alkylene;
 b) alkenylene;

c) alkynylene;
d) arylene;
e) heteroarylene;
f) cycloalkylene;
g) heterocyclylene;
h) alkylene-arylene;
i) alkylene-heteroarylene;
j) alkylene-cycloalkylene;
k) alkylene-heterocyclylene;
l) arylene-alkylene;
m) heteroarylene-alkylene;
n) cycloalkylene-alkylene;
o) heterocyclylene-alkylene;
p) —O—;
q) —S—;
r) —S(O$_2$)—; or
s) —S(O)—;
wherein said alkylene groups may optionally contain one or more O, S, S(O), or SO$_2$ atoms;

A$_4$ comprises
a) heterocyclyl, fused arylheterocyclyl, or fused heteroarylheterocyclyl, containing at least one basic nitrogen atom,
b) -imidazolyl, or
c) -pyridyl; and R$_{33}$, R$_{34}$ and R$_{35}$ independently comprise hydrogen, aryl, heteroaryl, alkyl, -alkylene-aryl, or -alkylene-O-aryl; with the proviso that no two of R$_{33}$, R$_{34}$ and R$_{35}$ are aryl and/or heteroaryl; and R$_{33}$ and R$_{34}$ may be taken together to form a ring having the formula —(CH$_2$)$_u$—X$_4$—(CH$_2$)$_v$— bonded to the nitrogen atom to which R$_{33}$ and R$_{34}$ are attached,
wherein
u and v are, independently, 1, 2, 3, or 4;
X$_4$ comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

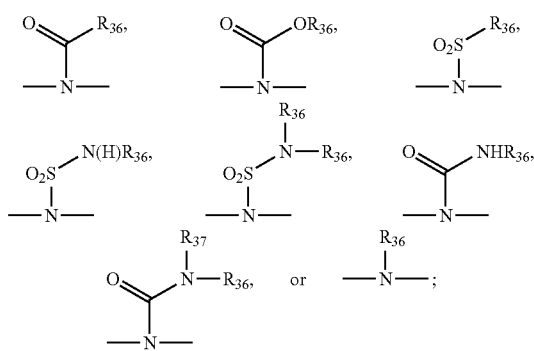

wherein R$_{36}$ and R$_{37}$ independently comprise hydrogen, aryl, heteroaryl, alkyl, -alkylene-aryl, or -alkylene-heteroaryl; and wherein said ring system is optionally substituted with substituents comprising
a) —H;
b) -halogen;
c) -hydroxyl;
d) -cyano;
e) -carbamoyl;
f) -carboxyl;
g) —Y$_8$-alkyl;
h) —Y$_8$-aryl;
i) —Y$_8$-heteroaryl;
j) —Y$_8$-alkylene-aryl;
k) —Y$_8$-alkylene-heteroaryl;
l) —Y$_8$-alkylene-NR$_{38}$R$_{39}$; or
m) —Y$_8$-alkylene-W$_3$—R$_{40}$;
wherein
Y$_8$ and W$_3$ independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

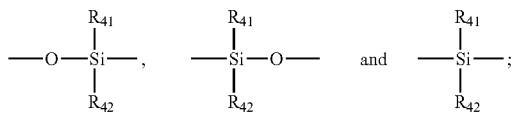

wherein R$_{41}$ and R$_{42}$ independently comprise aryl, alkyl, -alkylene-aryl, alkoxy, or -alkyl-O-aryl; and R$_{38}$, R$_{39}$, and R$_{40}$ independently comprise hydrogen, aryl, alkyl, -alkylene-aryl, -alkylene-heteroaryl, and -alkyene-O-aryl; and R$_{38}$ and R$_{39}$ may be taken together to form a ring having the formula —(CH$_2$)$_w$—X$_7$—(CH$_2$)$_x$— bonded to the nitrogen atom to which R$_{38}$ and R$_{39}$ are attached wherein w and x are, independently, 1, 2, 3, or 4;
X$_7$ comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

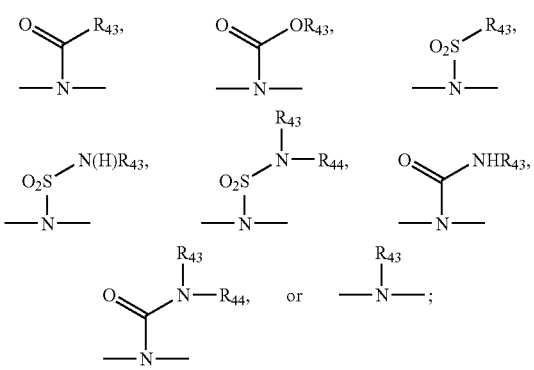

wherein R$_{43}$ and R$_{44}$ independently comprise hydrogen, aryl, heteroaryl, alkyl, -alkylene-aryl, or -alkylene-heteroaryl;

or a pharmaceutically acceptable salt thereof.

In a preferred embodiment, the compound of Formula (I) comprises a compound of the Formula (Ia)

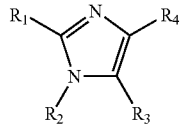

(Ia)

wherein
R₁ comprises -hydrogen, -aryl, -heteroaryl, -cycloalkyl, -heterocyclyl, -alkyl, -alkylene-aryl, -alkylene-heteroaryl, -alkylene-heterocyclyl, -alkylene-cycloalkyl, or -G₁-G₂-G₃-R₅
wherein
G₁ and G₃ independently comprise alkylene or a direct bond;
G₂ comprises —O—, —CO₂—, or a direct bond; and
R₅ comprises hydrogen, aryl, heteroaryl, cycloalkyl, heterocyclyl, alkyl, alkenyl, alkynyl, -alkylene-aryl, -alkylene-heteroaryl, -alkylene-heterocyclyl, or -alkylene-cycloalkyl.
R₂ comprises
  a) -hydrogen,
  b) -aryl,
  c) -heteroaryl,
  d) -heterocyclyl,
  e) -alkyl,
  f) -alkylene-aryl,
  g) -alkylene-heteroaryl,
  h) -alkylene-heterocyclyl,
  i) -fused cycloalkylaryl,
  j) -fused cycloalkylheteroaryl,
  k) -fused heterocyclylaryl,
  l) -fused heterocyclylheteroaryl;
  m) -alkylene-fused cycloalkylaryl,
  n) -alkylene-fused cycloalkylheteroaryl,
  o) -alkylene-fused heterocyclylaryl,
  p) -alkylene-fused heterocyclylheteroaryl; or
  q) a group of the formula

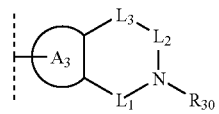

wherein
  A₃ comprises an aryl or heteroaryl group;
  L₁ and L₂ independently comprise alkylene or alkenylene;
  L₃ comprises a direct bond, alkylene, —O—, —S—, —S(O₂)—, —C(O)—, —CON(H)—, —NHC(O)—, —NHCON(H)—, —NHSO₂—, —SO₂N(H)—, —C(O)—O—, —O—C(O)—, —NHSO₂NH—,

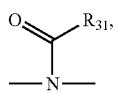 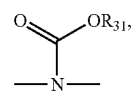 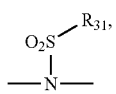

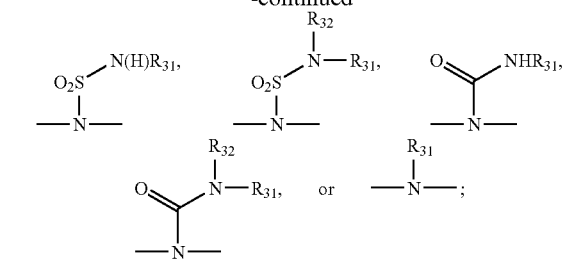

wherein R₃₀, R₃₁, and R₃₂ independently comprise hydrogen, aryl, heteroaryl, alkyl, alkylene-aryl, or -alkylene-heteroaryl;
R₃ and R₄ independently comprise
  a) -hydrogen;
  b) -halogen,
  c) -hydroxyl,
  d) -cyano,
  e) -carbamoyl,
  f) -carboxyl;
  g) -aryl,
  h) -heteroaryl,
  i) -cycloalkyl,
  j) -heterocyclyl,
  k) -alkyl,
  l) -alkenyl,
  m) -alkynyl,
  n) -alkylene-aryl,
  o) -alkylene-heteroaryl,
  p) -alkylene-heterocyclyl,
  q) -alkylene-cycloalkyl,
  r) -fused cycloalkylaryl,
  s) -fused cycloalkylheteroaryl,
  t) -fused heterocyclylaryl,
  u) -fused heterocyclylheteroaryl,
  v) -alkylene-fused cycloalkylaryl,
  w) -alkylene-fused cycloalkylheteroaryl,
  x) -alkylene-fused heterocyclylaryl,
  y) -alkylene-fused heterocyclylheteroaryl;
  z) —C(O)—O-alkyl;
  aa) —C(O)—O-alkylene-aryl;
  bb) —C(O)—NH-alkyl;
  cc) —C(O)—NH-alkylene-aryl;
  dd) —SO₂-alkyl;
  ee) —SO₂-alkylene-aryl;
  ff) —SO₂-aryl;
  gg) —SO₂—NH-alkyl;
  hh) —SO₂—NH— alkylene-aryl
  ii) —C(O)-alkyl;
  jj) —C(O)-alkylene-aryl;
  kk) -G₄-G₅-G₆-R₇
  ll) —Y₁-alkyl;
  mm) —Y₁-aryl;
  nn) —Y₁-heteroaryl;
  oo) —Y₁-alkylene-aryl;
  pp) —Y₁-alkylene-heteroaryl;
  qq) —Y₁-alkylene-NR₉R₁₀; and
  rr) —Y₁-alkylene-W₁—R₁₁;
  wherein
    G₄ and G₆ independently comprise alkylene, alkenylene, alkynylene, cycloalkylene, heterocyclylene, arylene, heteroarylene, (arylalkylene, (heteroary)alkylene, (aryl)alkenylene, (heteroaryl)alkenylene, or a direct bond;

$G_5$ comprises —O—, —S—, —N($R_8$)—, —S(O)—, —S(O)$_2$—, —C(O)—, —C(O)N($R_8$)—, N($R_8$)C(O)—, —S(O$_2$)N($R_8$)—, N($R_8$)S(O$_2$)—, —O-alkylene-C(O)—, —(O)C-alkylene-O—, —O-alkylene-, -alkylene-O—, alkylene, alkenylene, alkynylene, cycloalkylene, heterocyclylene, arylene, heteroarylene, fused cycloalkylaryl, fused cycloalkylheteroaryl, fused heterocyclylaryl, fused heterocyclylheteroaryl, or a direct bond, wherein $R_8$ comprises -hydrogen, -aryl, -alkyl, -alkylene-aryl, or -alkylene-O-aryl;

$R_7$ comprises hydrogen; aryl, heteroaryl, cycloalkyl, heterocyclyl, alkyl, alkenyl, alkynyl, alkylene-aryl, -alkylene-heteroaryl, -alkylene-heterocyclyl, -alkylene-cycloalkyl, fused cycloalkylaryl, fused cycloalkylheteroaryl, fused heterocyclylaryl, fused heterocyclylheteroaryl, alkylene-fused cycloalkylaryl, -alkylene-fused cycloalkylheteroaryl, -alkylene-fused heterocyclylaryl, or -alkylene-fused heterocyclylheteroaryl;

$Y_1$ and $W_1$ independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

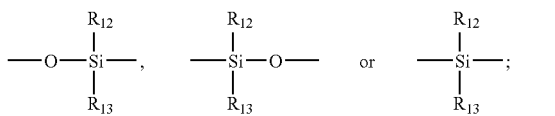

wherein $R_{12}$ and $R_{13}$ independently comprise aryl, alkyl, -alkylene-aryl, alkoxy, or -alkylene-O-aryl;

$R_9$, $R_{10}$, and $R_{11}$ independently comprise aryl, heteroaryl, alkyl, -alkylene-heteroaryl, or -alkylene-aryl; and $R_9$ and $R_{10}$ may be taken together to form a ring having the formula —(CH$_2$)$_o$—X$_1$—(CH$_2$)$_p$— bonded to the nitrogen atom to which $R_9$ and $R_{10}$ are attached, wherein o and p are, independently, 1, 2, 3, or 4;

$X_1$ comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

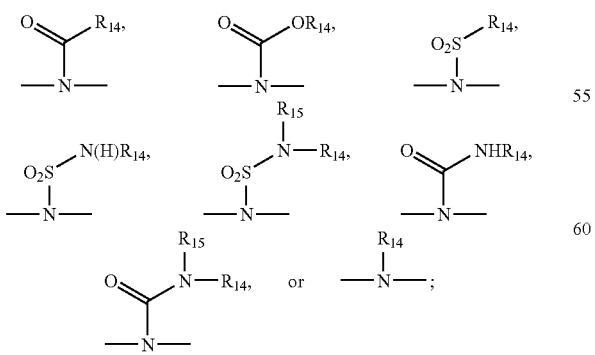

with the proviso that $R_3$ and $R_4$ can not both be hydrogen.

In one group of preferred embodiments of Formula (Ia), $R_1$ comprises a hydrogen, methyl, ethyl, propyl, butyl, iso-butyl, cyclopropyl, cyclobutyl, cyclopentyl, cyclohexyl, 3-butenyl, tert-butyl, 3-cyclohexyl-propyl, 3-phenoxy-propyl, methoxymethyl, 4-fluoro-phenyl, 3-(4-chlorophenoxy)-propyl, 2,4,4-trimethyl-pentyl, 1-ethyl-propyl, 1-propyl-butyl, benzyloxymethyl, 2-cyclopropy-ethyl, 2-phenyl-ethyl, 4-tert-butylphenoxymethyl, 4-tert-butylcyclohexyl, 4-butylcyclohexyl, 4-ethylcyclohexyl, 3-methoxycarbonyl-1-propyl, or 2-(pyridin-3-yl)-ethyl group.

In another group of preferred embodiments of Formula (Ia), $R_2$ comprises a phenyl or 1,2,3,4-tetrahydroisoquinoline group, wherein the phenyl group is substituted with at least one substitutent comprising a) —$Y_2$-alkyl;
b) —$Y_2$-aryl;
c) —$Y_2$-heteroaryl;
d) —$Y_2$-alkylene-heteroarylaryl;
e) —$Y_2$-alkylene-aryl;
f) —$Y_2$-alkylene-$W_2$—$R_{18}$;
g) —$Y_3$—$Y_4$—NR$_{23}$R$_{24}$;
h) —$Y_3$—$Y_4$—NH—C(=NR$_{25}$)NR$_{23}$R$_{24}$;
i) —$Y_3$—$Y_4$—C(=NR$_{25}$)NR$_{23}$R$_{24}$; or
j) —$Y_3$—$Y_4$—$Y_5$-$A_2$;

wherein $Y_2$ and $W_2$ independently comprise —CH$_2$— or —O—, and $R_{18}$ comprises aryl, alkyl, -alkylene-aryl, -alkylene-heteroaryl, or -alkylene-O-aryl;

$Y_3$ and $Y_5$ independently comprise a direct bond, —CH$_2$—, —O—, —N(H), —S—, SO$_2$—, —C(O)—, —CON(H)—, —NHC(O)—, —NHCON(H)—, —NHSO$_2$—, —SO$_2$N(H)—, —C(O)—O—, —NHSO$_2$NH—, —O—CO—,

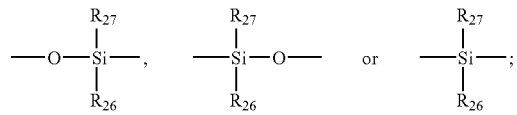

wherein $R_{27}$ and $R_{26}$ independently comprise aryl, alkyl, -alkylene-aryl, alkoxy, or -alkyl-O-aryl;

$Y_4$ comprises a) -alkylene;
b) -alkenylene;
c) -alkynylene;
d) -arylene;
e) -heteroarylene;
f) -cycloalkylene;
g) -heterocyclylene;
h) -alkylene-arylene;
i) -alkylene-heteroarylene;
j) -alkylene-cycloalkylene;
k) -alkylene-heterocyclylene;
l) -arylene-alkylene;
m) -heteroarylene-alkylene;
n) -cycloalkylene-alkylene;
t) -heterocyclylene-alkylene;
u) —O—;
v) —S—;
w) —S(O$_2$)—; or
x) —S(O)—;
  wherein said alkylene groups may optionally contain one or more O, S, S(O), or SO$_2$ atoms;

$A_2$ comprises a) heterocyclyl, fused arylheterocyclyl, or fused heteroarylheterocyclyl, containing at least one basic nitrogen atom, b) -imidazolyl, or c) -pyridyl; and $R_{23}$, $R_{24}$, and $R_{25}$ independently comprise hydrogen, aryl, heteroaryl, -alkylene-heteroaryl, alkyl, -alkylene-aryl, -alkylene-O-aryl, or -alkylene-O-heteroaryl; and $R_{23}$ and $R_{24}$ may be taken together to form a ring having the formula —($CH_2$)$_s$—$X_3$—($CH_2$)$_t$— bonded to the nitrogen atom to which $R_{23}$ and $R_{24}$ are attached wherein s and t are, independently, 1, 2, 3, or 4;

$X_3$ comprises direct bond, —$CH_2$—, —O—, —S—, —S($O_2$)—, —C(O)—, —CON(H)—, —NHC(O)—, —NHCON(H)—, —$NHSO_2$—, —$SO_2$N(H)—, —C(O)—O—, —O—C(O)—, —$NHSO_2$NH—,

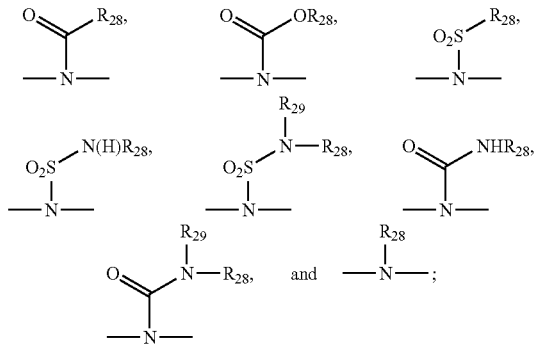

wherein $R_{28}$ and $R_{29}$ independently comprise hydrogen, aryl, heteroaryl, alkyl, -alkylene-aryl, or -alkylene-heteroaryl.

In another group of preferred embodiments of compounds of Formula (Ia), $R_2$ comprises 4-[3-(N,N'-diethylamino)-propoxy]-phenyl, 4-[3-(N,N'-dimethylamino)-propoxy]-phenyl, 3-[3-(N,N'-diethylamino)-propoxy]-phenyl, 4-(3-fluoro-4-trifluoromethyl-phenoxy)-phenyl, 4-(4-fluoro-3-trifluoromethyl-phenoxy)-phenyl, 4-(4-trifluoromethoxy-phenoxy)-phenyl, 4-(3,4-dichloro-phenoxy)-phenyl, 4-(3,5-bis-trifluoromethyl-phenoxy)-phenyl, 4-benzyloxy-phenyl, 4-(4-methyloxy-phenoxy)-phenyl, 4-(2-hexyl-4-chloro-phenoxy)-phenyl, 4-(4-phenyl-phenoxy)-phenyl, 4-(4-acetamido-phenoxy)-phenyl, 4-(4-methyl-phenoxy)-phenyl, 4-(4-fluoro-phenoxy)-phenyl, 4-(4-bromo-phenoxy)-phenyl, 4-(4-chloro-phenoxy)-phenyl, 4-(4-amino-phenoxy)-phenyl, 4-(3-ethyl-4-chloro-phenoxy)-phenyl, 4-[2-(N-ethylamino)-ethoxy]-phenyl, 4-[2,2'-dimethyl-3-(N,N'-dimethylamino)-propoxy]-phenyl, 1,2,3,4-tetrahydroisoquinolin-7-yl, 4-(4-benzamido-phenoxy)-phenyl, 4-(4-isonicotinamido-phenoxy)-phenyl, 4-[2-(N-methyl-N'-pyrid-4-yl)-ethoxy]-phenyl, 4-[3-(diethylmethyl ammonium)-propoxy)]-phenyl, 4-(2,5-di-fluoro-benzyloxy)-phenyl, 4-(2,4-dichloro-phenoxy)-phenyl, 4-(naphthalen-2-yloxy)-phenyl, 4-(6-methoxy-naphthalen-2-yloxy)-phenyl, 4-(4-methoxy-naphthalen-2-yloxy)-phenyl, 4-(6-hydroxy-naphthalen-2-yloxy)-phenyl, 4-(dibenzofuran-2-yloxy)-phenyl, 4-[2-(1-methyl-pyrrolidin-2-yl)-ethoxy]-phenyl, 4-[2-(piperazin-1-yl)-ethoxy]-phenyl, or 4-(4-tert-butyl-phenoxy)-phenyl.

In another group of preferred embodiments of Formula (Ia), $R_3$ comprises hydrogen; and $R_4$ comprises a phenyl group, wherein the phenyl group is substituted with at least one substituent comprising a) —$Y_2$-alkyl;

b) —$Y_2$-aryl;

c) —$Y_2$-heteroaryl;

d) —$Y_2$-alkylene-heteroarylaryl;

e) —$Y_2$-alkylene-aryl;

f) —$Y_2$-alkylene-$W_2$—$R_{18}$;

g) —$Y_3$—$Y_4$—$NR_{23}R_{24}$;

h) —$Y_3$—$Y_4$—NH—C(=$NR_{25}$)$NR_{23}R_{24}$;

i) —$Y_3$—$Y_4$—C(=$NR_{25}$)$NR_{23}R_{24}$; or j) —$Y_3$—$Y_4$—$Y_5$-$A_2$;

wherein $Y_2$ and $W_2$ independently comprise —$CH_2$— or —O—;

$R_{18}$ comprises aryl, alkyl, -alkylene-aryl, -alkylene-heteroaryl, or -alkylene-O-aryl;

$Y_3$ and $Y_5$ independently comprise a direct bond, —$CH_2$—, —O—, —N(H), —S—, $SO_2$—, —C(O)—, —CON(H)—, —NHC(O)—, —NHCON(H)—, —$NHSO_2$—, —$SO_2$N(H)—, —C(O)—O—, —$NHSO_2$NH—, —O—CO—,

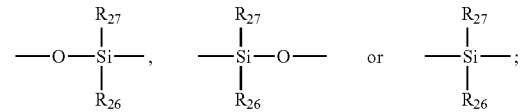

wherein $R_{27}$ and $R_{26}$ independently comprise aryl, alkyl, -alkylene-aryl, alkoxy, or -alkyl-O-aryl;

$Y_4$ comprises a) -alkylene;

b) -alkenylene;

c) -alkynylene;

d) -arylene;

e) -heteroarylene;

f) -cycloalkylene;

g) -heterocyclylene;

h) -alkylene-arylene;

i) -alkylene-heteroarylene;

j) -alkylene-cycloalkylene;

k) -alkylene-heterocyclylene;

l) -arylene-alkylene;

m) -heteroarylene-alkylene;

n) -cycloalkylene-alkylene;

o) -heterocyclylene-alkylene;

p) —O—;

q) —S—;

r) —S($O_2$)—; or s) —S(O)—;

wherein said alkylene groups may optionally contain one or more O, S, S(O), or $SO_2$ atoms;

$A_2$ comprises a) heterocyclyl, fused arylheterocyclyl, or fused heteroarylheterocyclyl, containing at least one basic nitrogen atom, b) -imidazolyl, or c) -pyridyl;

$R_{23}$, $R_{24}$, and $R_{25}$ independently comprise hydrogen, aryl, heteroaryl, -alkylene-heteroaryl, alkyl, -alkylene-aryl, -alkylene-O-aryl, or -alkylene-O-heteroaryl; and $R_{23}$ and $R_{24}$ may be taken together to form a ring having the formula —(CH$_2$)$_s$—X$_3$—(CH$_2$)$_t$— bonded to the nitrogen atom to which R$_{23}$ and R$_{24}$ are attached
wherein
s and t are, independently, 1, 2, 3, or 4;
X$_3$ comprises direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

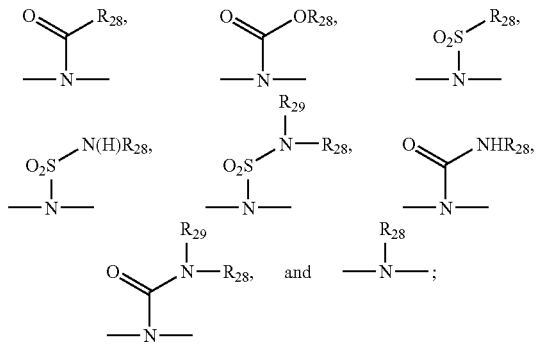

wherein R$_{28}$ and R$_{29}$ independently comprise hydrogen, aryl, heteroaryl, alkyl, -alkylene-aryl, or -alkylene-heteroaryl.

In a more preferred group of compounds of Formula (Ia), R$_3$ comprises hydrogen and R$_4$ comprises 4-{2-[(4-chlorophenyl)-ethoxy]}-phenyl, 4-[3-(N,N'-diethylamino)-propoxy]-phenyl, 4-(2-amino-ethoxy)-phenyl, 4-[2-(N-methyl-N'-pyridin-4-yl-amino)-ethoxy]-phenyl, 4-[2-(N-ethyl-N'-pyridin-4-yl-amino)-ethoxy]-phenyl, 4-[2-(N-pyridin-4-yl-amino)-ethoxy]-phenyl, 4-(4-amino-pyridin-3-yl-oxy)-phenyl, 4-[(pyridin-4-yl)-amino]-phenyl, 4-[2-(N,N'-bis-pyridin-2-ylmethyl-amino)-ethoxy]-phenyl, 4-[2-(guanidinyl)-ethoxy]-phenyl, 4-(2-[4-(pyridin-4-yl)-piperazin-1-yl]-2-oxo-ethoxy)-phenyl, 4-[2-(N-methyl-N'-3-methylpyridin-4-yl-amino)-ethoxy]-phenyl, 4-(4-hydroxy-pyrrolidin-2-ylmethyloxy)-phenyl, 4-(4-amino-3,5-dimethyl-pyrrolidin-2-ylmethyloxy)-phenyl, dibenzofuran-2-yl, 4-[3-(piperazin-1-yl)-propoxy]-phenyl, 4-(piperazin-4-yloxy)-phenyl, 4-[5-(piperazin-1-yl)-pentoxy]-phenyl, 4-[3-(N,N'-dimethylamino)-propoxy]-phenyl, 4-(3-fluoro-4-trifluoromethyl-phenoxy)-phenyl, 4-(4-fluoro-3-trifluoromethyl-phenoxy)-phenyl, 4-(4-phenyl-phenoxy)-phenyl, 4-(3-trifluoromethoxy-phenoxy)-phenyl, 4-(4-trifluoromethyl-benzyloxy)-phenyl, 4-(3,4-dichloro-phenoxy)-phenyl, 4-(2,4-dichloro-phenoxy)-phenyl, 4-(1-ethyl-piperidin-3-yloxy)-phenyl, 4-benzyloxy-phenyl, 4-[(1-ethyl-piperidin-3-yl)-methoxy]-phenyl, 4-(4-phenoxy-benzyloxy)-phenyl, 4-(4-benzyloxy-benzyloxy)-phenyl, 4-(2-benzenesulfonylmethyl-benzyloxy)-phenyl, 4-(3,4,5-trimethoxybenzyloxy)-phenyl, 4-[2-(pyrrolidin-1-yl)-ethoxy]-phenyl, 4-[2-(piperidin-1-yl)-ethoxy]-phenyl, 4-[2,2'-dimethyl-3-(N,N'-dimethylamino)-propoxy]-phenyl, 4-[2-(N,N'-diisopropylamino)-ethoxy]-phenyl, 4-(adamantan-1-ylmethoxy)-phenyl, 3-[(2,6-dichlorophenyl)-4-methyl-isoxazol-5-ylmethyloxy]-phenyl, 4-(4-bromo-benzyloxy)-phenyl, 4-(4-chlorophenoxy)-phenyl, 4-[4-{(1-ethyl-piperidin-4-yl)-methylamino}-phenoxy]-phenyl, 4-(3,3-diphenylpropoxy)-phenyl, 4-[3,3-Bis-(4-fluorophenyl)-propoxy]-phenyl, 4-[3,3-Bis-(4-chlorophenyl)-allyoxy]-phenyl, 4-(4-chlorophenoxy)-naphthalenyl, 4-[2-(biphenyl-4-yl)-acetamido]-phenyl, 4-[2-(9H-carbazole)-ethoxy]-phenyl, 4-[4-methoxyphenyoxy]-phenyl, 4-(4-tert-butyl-phenoxy)-phenyl, or 4-(naphthylen-2-ylmethoxy)-phenyl.

In another preferred embodiment, the compound Formula (I) comprises the compound of Formula (Ib),

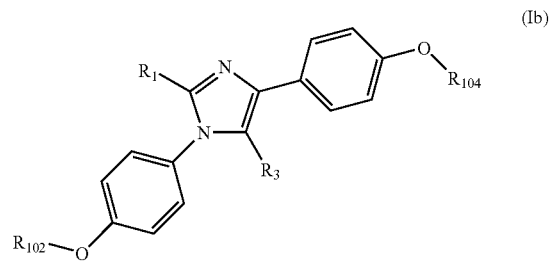

wherein
R$_1$ comprises-hydrogen, -aryl, -heteroaryl, -cycloalkyl, -heterocyclyl, -alkyl, -alkenyl, -alkylene-aryl, -alkylene-heteroaryl, -alkylene-heterocyclyl, -alkylene-cycloalkyl, -fused cycloalkylaryl, -fused cycloalkylheteroaryl, -fused heterocyclylaryl, -fused heterocyclylheteroaryl, -alkylene-fused cycloalkylaryl, -alkylene-fused cycloalkylheteroaryl, -alkylene-fused heterocyclylaryl, -alkylene-fused heterocyclylheteroaryl, or -G$_1$-G$_2$-G$_3$-R$_5$
wherein
G$_1$ and G$_3$ independently comprise alkylene, alkenylene, alkynylene, cycloalkylene, heterocyclylene, arylene, heteroarylene, (aryl)alkylene, (heteroaryl)alkylene, (aryl)alkenylene, (heteroaryl)alkenylene, or a direct bond;
G$_2$ comprises —O—, —S—, —S(O)—, —N(R$_6$)—, —S(O)$_2$—, —C(O)—, —CO$_2$—, —C(O)N(R$_6$)—, N(R$_6$)C(O)—, —S(O$_2$)N(R$_6$)—, N(R$_6$)S(O$_2$)—, —O-alkylene-C(O)—, —(O)C-alkylene-O—, —O-alkylene-, -alkylene-O—, alkylene, alkenylene, alkynylene, cycloalkylene, heterocyclylene, arylene, heteroarylene, fused cycloalkylaryl, fused cycloalkylheteroaryl, fused heterocyclylaryl, fused heterocyclylheteroaryl, or a direct bond, wherein R$_6$ comprises hydrogen, aryl, alkyl, -alkylene-aryl, alkoxy, or -alkylene-O-aryl; and
R$_5$ comprises hydrogen, aryl, heteroaryl, cycloalkyl, heterocyclyl, alkyl, alkenyl, alkynyl, -alkylene-aryl, -alkylene-heteroaryl, -alkylene-heterocyclyl, -alkylene-cycloalkyl, fused cycloalkylaryl, fused cycloalkylheteroaryl, fused heterocyclylaryl, fused heterocyclylheteroaryl; -alkylene-fused cycloalkylaryl, -alkylene-fused cycloalkylheteroaryl, -alkylene-fused heterocyclylaryl, or -alkylene-fused heterocyclylheteroaryl;
R$_3$ comprises hydrogen or an alkyl group; and
R$_{102}$ and R$_{104}$ independently comprise
a) —H;
b) -alkyl;
c) -aryl;
d) -heteroaryl;
e) -alkylene-heteroarylaryl;
f) -alkylene-aryl;
g) -alkylene-W$_2$—R$_{18}$;
h) —Y$_4$—NR$_{23}$R$_{24}$;
i) —Y$_4$—NH—C(=NR$_{25}$)NR$_{23}$R$_{24}$;

j) —Y$_4$—C(=NR$_{25}$)NR$_{23}$R$_{24}$; or
k) —Y$_4$—Y$_5$-A$_2$;
    wherein
    W$_2$ comprises —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—S(O)$_2$—, —O—CO—,

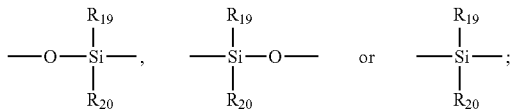

wherein R$_{19}$ and R$_{20}$ independently comprise hydrogen, aryl, alkyl, -alkylene-aryl, alkoxy, or -alkylene-O-aryl; and
R$_{18}$ comprises aryl, alkyl, -alkylene-aryl, -alkylene-heteroaryl, and -alkylene-O-aryl;
Y$_5$ comprises a direct bond, —CH$_2$—, —O—, —N(H), —S—, SO$_2$—, —C(O)—, —CON(H)—, —NHC(O)—, —NHCON(H)—, —NHSO$_2$—, —SO$_2$N(H)—, —C(O)—O—, —NHSO$_2$NH—, —O—CO—,

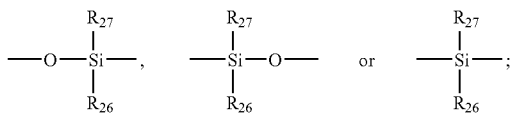

wherein R$_{27}$ and R$_{26}$ independently comprise aryl, alkyl, -alkylene-aryl, alkoxy, or -alkyl-O-aryl;
Y$_4$ comprises
    a) -alkylene;
    b) -alkenylene;
    c) -alkynylene;
    d) -arylene;
    e) -heteroarylene;
    f) -cycloalkylene;
    g) -heterocyclylene;
    h) -alkylene-arylene;
    i) -alkylene-heteroarylene;
    j) -alkylene-cycloalkylene;
    k) -alkylene-heterocyclylene;
    l) -arylene-alkylene;
    m) -heteroarylene-alkylene;
    n) -cycloalkylene-alkylene;
    o) -heterocyclylene-alkylene;
    p) —O—;
    q) —S—;
    r) —S(O$_2$)—; or
    s) —S(O)—;
        wherein said alkylene groups may optionally contain one or more O, S, S(O), or SO$_2$ atoms;
A$_2$ comprises
    a) heterocyclyl, fused arylheterocyclyl, or fused heteroarylheterocyclyl, containing at least one basic nitrogen atom,
    b) -imidazolyl, or
    c) -pyridyl;
R$_{23}$, R$_{24}$, and R$_{25}$ independently comprise hydrogen, aryl, heteroaryl, -alkylene-heteroaryl, alkyl, -alkylene-aryl, -alkylene-O-aryl, or -alkylene-O-heteroaryl; and R$_{23}$ and R$_{24}$ may be taken together to form a ring having the formula —(CH$_2$)$_s$—X$_3$—(CH$_2$)$_t$— bonded to the nitrogen atom to which R$_{23}$ and R$_{24}$ are attached
    wherein
    s and t are, independently, 1, 2, 3, or 4;
    X$_3$ comprises direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

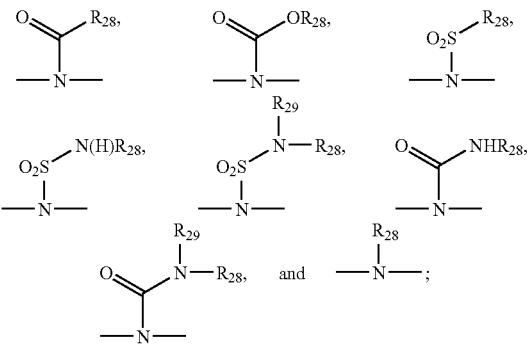

wherein R$_{28}$ and R$_{29}$ independently comprise hydrogen, aryl, heteroaryl, alkyl, -alkylene-aryl, or -alkylene-heteroaryl;
wherein
    the alkyl and/or aryl groups of R$_{102}$ and R$_{104}$ may be optionally substituted 1-4 times with a substituent group, wherein said substituent group(s) or the term substituted refers to a group comprising:
        a) halogen;
        b) perhaloalkyl;
        c) alkyl;
        d) cyano;
        e) alkyloxy;
        f) aryl; or
        g) aryloxy.
In a group of preferred embodiments of the compound of Formula (Ib), R$_1$ comprises a hydrogen, methyl, ethyl, propyl, butyl, iso-butyl, cyclopropyl, cyclobutyl, cyclopentyl, cyclohexyl, 3-butenyl, tert-butyl, 3-cyclohexyl-propyl, 3-phenoxy-propyl, methoxymethyl, 4-fluoro-phenyl, 3-(4-chlorophenoxy)-propyl, 2,4,4-trimethyl-pentyl, 1-ethyl-propyl, 1-propyl-butyl, benzyloxymethyl, 2-cyclopropy-ethyl, 2-phenyl-ethyl, 4-tert-butylphenoxymethyl, 4-tert-butylcyclohexyl, 4-ethylcyclohexyl, 4-butylcyclohexyl, 3-methoxycarbonyl-1-propyl, or 2-(pyridin-3-yl)-ethyl group, and R$_3$ comprises hydrogen.
In another group of preferred embodiments of the compound of Formula (Ib), R$_{102}$ and R$_{104}$ independently comprise 2-(4-chlorophenyl)-ethyl, 3-(N,N'-diethylamino)-propyl, 2-amino-ethyl, 2-(N-methyl-N'-pyridin-4-yl-amino)-ethyl, 2-(N-ethyl-N'-pyridin-4-yl-amino)-ethyl, 2-(N-pyridin-4-yl-amino)-ethoxy, 4-(4-amino-pyridin-3-yl-oxy), 4-(pyridin-4-yl)-amino, 2-(N,N'-bis-pyridin-2-ylmethyl-amino)-ethyl, 2-(guanidinyl)-ethyl, 2-[4-(pyridin-4-yl)-piperazin-1-yl]-2-oxo-ethyl, 2-(N-methyl-N'-3-methylpyridin-4-yl-amino)-ethyl, 4-hydroxy-pyrrolidin-2-ylmethyl, 4-amino-3,5-dimethyl-pyrrolidin-2-ylmethyl, dibenzofuran-2-yl, 3-(piperazin-1-yl)-propyl, piperazin-4-yl, 5-(piperazin-1-yl)-pentyl, 3-(N,N'-dimethylamino)-propyl, 3-fluoro-4-trifluoromethyl-phenyl, 4-fluoro-3-trifluoromethyl-phenyl, 4-phenyl-phenyl, 3-trifluoromethoxy-phenyl, 4-trifluoromethyl-benzyl, 3,4-dichloro-phenyl, 2,4-dichloro-phenyl, 1-ethyl-piperidin-3-yl, benzyl, (1-ethyl-piperidin-3-yl)-methyl, 4-phenoxy-benzyl, 4-benzyloxy-benzyl, 2-benzenesulfonylmethyl-benzyl, 3,4,5-trimethoxybenzyl, 2-(pyrrolidin-1-yl)-ethyl, 2-(piperidin-1-yl)-ethyl, 2,2'-dimethyl-3-(N, N'-dimethylamino)-propyl, 2-(N,N'-diisopropylamino)-ethyl, 3-(2,6-dichlorophenyl)-4-methyl-isoxazol-5-ylmethyl, 4-bromo-benzyl, 4-chlorophenyl, 4-{(1-ethyl-piperidin-4-yl)-methylamino}-phenyl, 3,3-diphenylpropyl, 3,3-Bis-(4-fluorophenyl)-propyl, 3,3-Bis-(4-chlorophenyl)-allyl, 4-(4-chlorophenoxy)-naphthalenyl, 4-[2-(biphenyl-4-yl)-acetamido]-phenyl, 2-(9H-carbazole)-ethyl, 4-methoxyphenyl, 4-tert-butyl-phenyl, or naphthylen-2-ylmethyl.

In another group of preferred embodiments of the compound of Formula (Ib), $R_1$ comprises -alkyl, -alkylene-cycloalkylene-alkyl, -cycloalkyl, -heterocyclyl, -alkylene-cycloalkyl, -alkylene-heteroaryl, -alkylene-heterocyclyl, or -alkylene-heterocyclylene-alkyl; $R_3$ comprises hydrogen; $R_{102}$ comprises -aryl or -alkylene-aryl substituted with at least one of a halogen, a perhaloalkyl, or an alkoxy group; and $R_{104}$ comprises $—Y_4—NR_{23}R_{24}$ or $—Y_4—Y_5-A_2$.

In another group of preferred embodiments of the compound of Formula (Ib), $R_1$ comprises -heterocyclyl, heterocyclylene-heteroaryl, -alkylene-cycloalkyl, -alkylene-heteroaryl, -alkylene-heterocyclyl, or -alkylene-heterocyclylene-alkyl; $R_3$ comprises hydrogen; and $R_{102}$ and $R_{104}$ independently comprise -aryl or -alkylene-aryl, wherein the alkyl or ary groups are optionally substituted with at least one of a halogen, a perhaloalkyl, or an alkoxy group, and wherein at least one of $R_{102}$ and $R_{104}$ comprise $—Y_4—_{NR23}R_{24}$ or $—Y_4—Y_5-A_2$, wherein $Y_4$ comprises alkylene.

In a preferred embodiment, the compound of Formula (I) comprises a compound of the Formula (Ic)

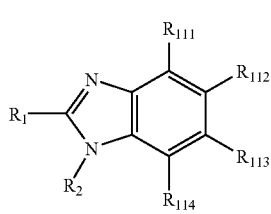

(Ic)

wherein
  $R_1$ comprises-hydrogen, -aryl, -heteroaryl, -cycloalkyl, -heterocyclyl, -alkyl, -alkenyl, -alkynyl, -alkylene-aryl, -alkylene-heteroaryl, -alkylene-heterocyclyl, -alkylene-cycloalkyl, -fused cycloalkylaryl, -fused cycloalkylheteroaryl, -fused heterocyclylaryl, -fused heterocyclylheteroaryl, -alkylene-fused cycloalkylaryl, -alkylene-fused cycloalkylheteroaryl, -alkylene-fused heterocyclylaryl, -alkylene-fused heterocyclylheteroaryl, or -$G_1$-$G_2$-$G_3$-$R_5$
  wherein
    $G_1$ and $G_3$ independently comprise alkylene, alkenylene, alkynylene, cycloalkylene, heterocyclylene, arylene, heteroarylene, (aryl)alkylene, (heteroaryl)alkylene, (aryl)alkenylene, (heteroaryl)alkenylene, or a direct bond;
    $G_2$ comprises —O—, —S—, —S(O)—, —N($R_6$)—, —S(O)$_2$—, —C(O)—, —CO$_2$—, —C(O)N($R_6$)—, N($R_6$)C(O)—, —S(O$_2$)N($R_6$)—, N($R_6$)S(O$_2$)—, —O-alkylene-C(O)—, —(O)C-alkylene-O—, —O-alkylene-, -alkylene-O—, alkylene, alkenylene, alkynylene, cycloalkylene, heterocyclylene, arylene, heteroarylene, fused cycloalkylaryl, fused cycloalkylheteroaryl, fused heterocyclylaryl, fused heterocyclylheteroaryl, or a direct bond, wherein $R_6$ comprises hydrogen, aryl, alkyl, -alkylene-aryl, alkoxy, or -alkylene-O-aryl; and
    $R_5$ comprises hydrogen, aryl, heteroaryl, cycloalkyl, heterocyclyl, alkyl, alkenyl, alkynyl, -alkylene-aryl, -alkylene-heteroaryl, -alkylene-heterocyclyl, -alkylene-cycloalkyl, fused cycloalkylaryl, fused cycloalkylheteroaryl, fused heterocyclylaryl, fused heterocyclylheteroaryl; -alkylene-fused cycloalkylaryl, -alkylene-fused cycloalkylheteroaryl, -alkylene-fused heterocyclylaryl, or -alkylene-fused heterocyclylheteroaryl;
  $R_2$ comprises
    a) -hydrogen,
    b) -aryl,
    c) -heteroaryl,
    d) -cycloalkyl,
    e) -heterocyclyl;
    f) -alkyl,
    g) -alkenyl,
    h) -alkynyl,
    i) -alkylene-aryl,
    j) -alkylene-heteroaryl,
    k) -alkylene-heterocyclyl,
    l) -alkylene-cycloalkyl;
    m) fused cycloalkylaryl,
    n) fused cycloalkylheteroaryl,
    o) fused heterocyclylaryl,
    p) fused heterocyclylheteroaryl;
    q) -alkylene-fused cycloalkylaryl,
    r) -alkylene-fused cycloalkylheteroaryl,
    s) -alkylene-fused heterocyclylaryl, or
    t) -alkylene-fused heterocyclylheteroaryl,
  $R_{111}$, $R_{112}$, $R_{113}$ and $R_{114}$ independently comprise
    a) -hydrogen,
    b) -halogen,
    c) -hydroxyl,
    d) -cyano,
    e) -carbamoyl,
    f) -carboxyl,
    g) —$Y_8$-alkyl,
    h) —$Y_8$-aryl,
    i) —$Y_8$-heteroaryl,
    j) —$Y_8$-alkylene-aryl,
    k) —$Y_8$-alkylene-heteroaryl,
    l) —$Y_8$-alkylene-$W_3$—$R_{40}$,
    m) —$Y_5$—$Y_6$—$NR_{33}R_{34}$,
    n) —$Y_5$—$Y_6$—NH—C(=$NR_{35}$)$NR_{33}R_{34}$,
    o) —$Y_5$—$Y_6$—(=$NR_{35}$)$NR_{33}R_{34}$, or
    p) —$Y_5$—$Y_6$—$Y_7$-$A_4$;
    wherein
      $Y_5$ and $Y_7$ independently comprise a direct bond, —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

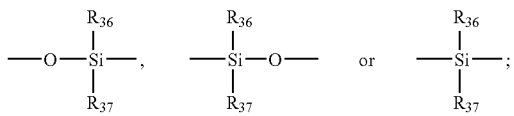

wherein $R_{36}$ and $R_{37}$ independently comprise aryl, alkyl, -alkylene-aryl, alkoxy, or -alkyl-O-aryl;

$Y_6$ comprises
a) alkylene;
b) alkenylene;
c) alkynylene;
d) arylene;
e) heteroarylene;
f) cycloalkylene;
g) heterocyclylene;
h) alkylene-arylene;
i) alkylene-heteroarylene;
j) alkylene-cycloalkylene;
k) alkylene-heterocyclylene;
l) arylene-alkylene;
m) heteroarylene-alkylene;
n) cycloalkylene-alkylene;
o) heterocyclylene-alkylene;
p) —O—;
q) —S—;
r) —S(O$_2$)—; or
s) —S(O)—;
wherein said alkylene groups may optionally contain one or more O, S, S(O), or SO$_2$ atoms;

$A_4$ comprises
a) heterocyclyl, fused arylheterocyclyl, or fused heteroarylheterocyclyl, containing at least one basic nitrogen atom,
b) -imidazolyl, or
c) -pyridyl;

$R_{33}$, $R_{34}$ and $R_{35}$ independently comprise hydrogen, aryl, heteroaryl, alkyl, -alkylene-aryl, or -alkylene-O-aryl; and $R_{33}$ and $R_{34}$ may be taken together to form a ring having the formula —(CH$_2$)$_u$—X$_4$—(CH$_2$)$_v$— bonded to the nitrogen atom to which $R_{33}$ and $R_{34}$ are attached, wherein u and v are, independently, 1, 2, 3, or 4;

$X_4$ comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

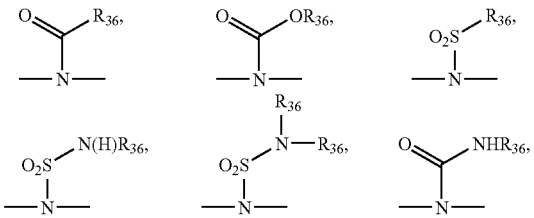

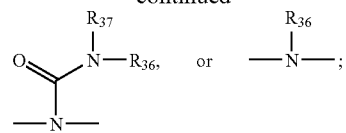

wherein $R_{36}$ and $R_{37}$ independently comprise hydrogen, aryl, heteroaryl, alkyl, -alkylene-aryl, or -alkylene-heteroaryl;

$Y_8$ and $W_3$ independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

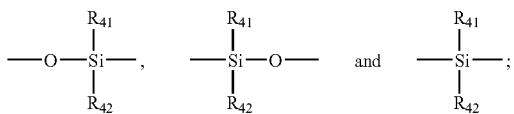

wherein $R_{41}$ and $R_{42}$ independently comprise aryl, alkyl, -alkylene-aryl, alkoxy, or -alkyl-O-aryl; and $R_{40}$ comprises hydrogen, aryl, alkyl, -alkylene-aryl, -alkylene-heteroaryl, and -alkyene-O-aryl;

wherein at least one of $R_{111}$, $R_{112}$, $R_{113}$, and $R_{114}$ comprise a group of the formula —Y$_5$—Y$_6$—NR$_{33}$R$_{34}$, —Y$_5$—Y$_6$—NH—C(=NR$_{35}$)NR$_{33}$R$_{34}$, —Y$_5$—Y$_6$—C(=NR$_{35}$)NR$_{33}$R$_{34}$, or —Y$_5$—Y$_6$—Y$_7$-A$_4$.

In one group of preferred embodiments of the compound of Formula (Ic), $R_2$ comprises hydrogen or alkyl.

In another group of preferred embodiments of the compound of Formula (Ic), $R_1$ comprises a phenyl group substituted by one or more substituents comprising
a) —Y$_2$-alkyl;
b) —Y$_2$-aryl;
c) —Y$_2$-heteroaryl;
d) —Y$_2$-alkylene-heteroarylaryl;
e) —Y$_2$-alkylene-aryl;
f) —Y$_2$-alkylene-W$_2$—R$_{18}$;
g) —Y$_3$—Y$_4$—NR$_{23}$R$_{24}$
h) —Y$_3$—Y$_4$—NH—C(=NR$_{25}$)NR$_{23}$R$_{24}$
i) —Y$_3$—Y$_4$—C(=NR$_{25}$)NR$_{23}$R$_{24}$
j) —Y$_3$—Y$_4$—Y$_5$-A$_2$;
wherein $Y_2$ and $W_2$ independently comprise —CH$_2$—, —O—, and $R_{18}$ comprises aryl, alkyl, -alkylene-aryl, -alkylene-heteroaryl, or -alkylene-O-aryl;

$Y_3$ and $Y_5$ independently comprise a direct bond, —CH$_2$—, —O—, —N(H), —S—, SO$_2$—, —C(O)—, —CON(H)—, —NHC(O)—, —NHCON(H)—, —NHSO$_2$—, —SO$_2$N(H)—, —C(O)—O—, —NHSO$_2$NH—, —C—CO—,

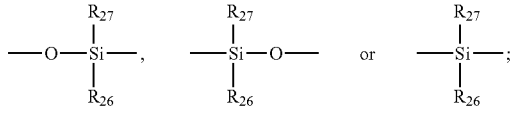

wherein $R_{27}$ and $R_{26}$ independently comprise aryl, alkyl, -alkylene-aryl, alkoxy, or -alkyl-O-aryl;

$Y_4$ comprises
a) -alkylene;
b) -alkenylene;
c) -alkynylene;
d) -arylene;
e) -heteroarylene;
f) -cycloalkylene;
g) -heterocyclylene;
h) -alkylene-arylene;
i) -alkylene-heteroarylene;
j) -alkylene-cycloalkylene;
k) -alkylene-heterocyclylene;
l) -arylene-alkylene;
m) -heteroarylene-alkylene;
n) -cycloalkylene-alkylene;
o) -heterocyclylene-alkylene;
p) —O—;
q) —S—;
r) —S(O$_2$)—; or
s) —S(O)—;
wherein said alkylene groups may optionally contain one or more O, S, S(O), or SO$_2$ atoms;

$A_2$ comprises
a) heterocyclyl, fused arylheterocyclyl, or fused heteroarylheterocyclyl, containing at least one basic nitrogen atom,
b) -imidazolyl, or
c) -pyridyl;

$R_{23}$, $R_{24}$, and $R_{25}$ independently comprise hydrogen, aryl, heteroaryl, -alkylene-heteroaryl, alkyl, -alkylene-aryl, -alkylene-O-aryl, or -alkylene-O-heteroaryl; and $R_{23}$ and $R_{24}$ may be taken together to form a ring having the formula —(CH$_2$)$_s$—X$_3$—(CH$_2$)$_t$— bonded to the nitrogen atom to which $R_{23}$ and $R_{24}$ are attached wherein
s and t are, independently, 1, 2, 3, or 4;
$X_3$ comprises direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

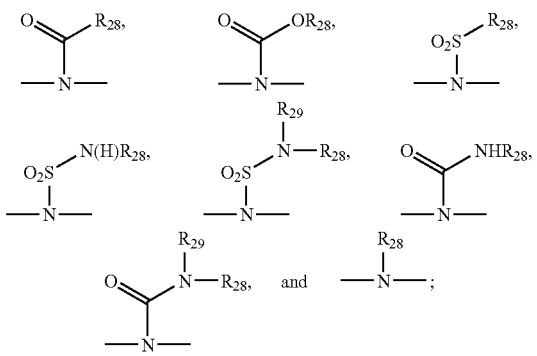

wherein $R_{28}$ and $R_{29}$ independently comprise hydrogen, aryl, heteroaryl, alkyl, -alkylene-aryl, or -alkylene-heteroaryl.

In another group of preferred embodiments of the compound of Formula (Ic), $R_1$ comprises 2-methoxy-3,5-dimethyoxy-phenyl, 3-(4-tert-butyl-phenoxy)-phenyl, 4-[3-(N,N'-diethylamino)-propoxy]-phenyl, 4-[3-(N,N'-dimethylamino)-propoxy]-phenyl, 4-[(pyrrolidin-1-yl)-ethoxy]-phenyl, 3-[(pyrrolidin-1-yl)-ethoxy]-phenyl, 2-[(pyrrolidin-1-yl)-ethoxy]-phenyl, 3-(naphthalen-2-yloxy)-phenyl, 4-biphenyl, 3-(3,3-dimethylbutoxy)-phenyl, 3-(phenoxy)-phenyl, 3-(3,4-dichloro-phenoxy)-phenyl, 3-(3,5-dichloro-phenoxy)-phenyl, 4-tert-butyl-phenyl, 4-(dibutylamino)-phenyl, 4-[2-(4-methoxy-phenyl)-ethoxy]-phenyl, 2-naphthyl, 2-benzofuranyl, 3-(3-trifluoromethyl-phenoxy)-phenyl, 4-chloro-phenyl, 2-benzhydryl, 4-isopropoxy-phenyl, 3-(4-tertbutyl-phenoxy)-phenyl, 4-[2-(4-chloro-phenyl)-ethoxy]-phenyl, 3-[2-(4-chloro-phenyl)-ethoxy]-phenyl, 2-3-[2-(4-chloro-phenyl)-ethoxy]-phenyl]-ethyl, 2-{4-[2-(4-methoxy-phenyl)-ethoxy]-phenyl}-ethyl, or 2-[3-(N,N-diethylamino)-propoxy)]-4-[2-(4-chloro-phenyl)-ethoxy]-phenyl.

In another group of preferred embodiments of the compound of Formula (Ic), $R_1$ comprises 4-[2-(4-chloro-phenyl)-ethoxy]-phenyl, 3-[2-(4-chloro-phenyl)-ethoxy]-phenyl, 2-{3-[2-(4-chloro-phenyl)-ethoxy]-phenyl]-ethyl, 2-{4-[2-(4-methoxy-phenyl)-ethoxy]-phenyl}-ethyl, or 2-[3-(N,N-diethylamino)-propoxy)]-4-[2-(4-chloro-phenyl)-ethoxy]-phenyl.

In another group of preferred embodiments of the compound of Formula (Ic), $R_{111}$, $R_{112}$ and $R_{114}$ comprise hygrogen; and $R_{113}$ comprises —Y$_3$—Y$_4$—NR$_{23}$R$_{24}$, or —Y$_3$—Y$_4$—Y$_5$-A$_2$.

In another group of preferred embodiments of the compound of Formula (Ic), $R_1$ comprises 4-[2-(4-chloro-phenyl)-ethoxy]-phenyl, 3-[2-(4-chloro-phenyl)-ethoxy]-phenyl, 2-{3-[2-(4-chloro-phenyl)-ethoxy]-phenyl]-ethyl, 2-(4-[2-(4-methoxy-phenyl)-ethoxy]-phenyl}-ethyl, or 2-[3-(N,N-diethylamino)-propoxy)]-4-[2-(4-chloro-phenyl)-ethoxy]-phenyl; $R_2$ comprises alkyl; $R_{112}$ and $R_{114}$ comprise hygrogen; and $R_{111}$ and $R_{113}$ comprise —Y$_3$—Y$_4$—NR$_{23}$R$_{24}$, or —Y$_3$—Y$_4$—Y$_5$-A$_2$.

In the compounds of Formula (I), the various functional groups represented should be understood to have a point of attachment at the functional group having the hyphen. In other words, in the case of —C$_{1-6}$ alkylaryl, it should be understood that the point of attachment is the alkyl group; an example would be benzyl. In the case of a group such as —C(O)—NH—C$_{1-6}$ alkylaryl, the point of attachment is the carbonyl carbon.

Also included within the scope of the invention are the individual enantiomers of the compounds represented by Formula (I) above as well as any wholly or partially racemic mixtures thereof. The present invention also covers the individual enantiomers of the compounds represented by the Formula above as mixtures with diastereoisomers thereof in which one or more stereocenters are inverted.

Compounds of the present invention preferred for their high biological activity are listed by name below in Table 1.

TABLE 1

| Ex. | Structure | Name |
|---|---|---|
| 1 | 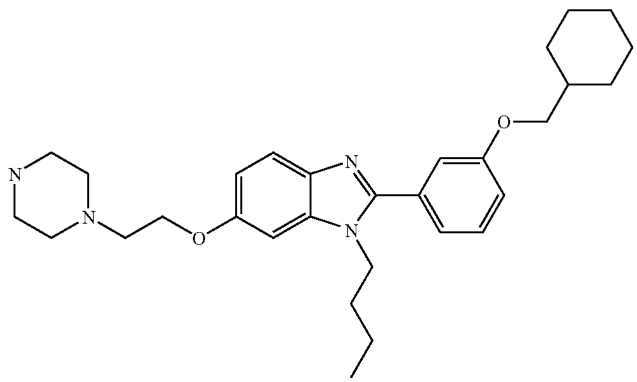 | 1-butyl-2-(3-cyclohexylmethoxy-phenyl)-6-(2-piperazin-1-yl-ethoxy)-1H-benzoimidazole |
| 2 | 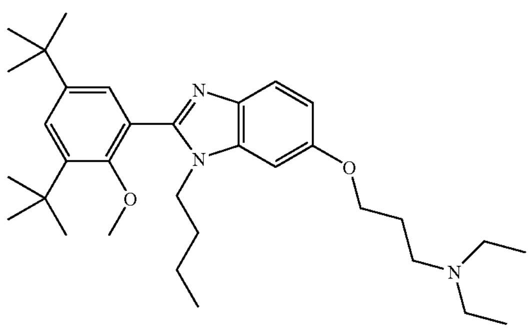 | {3-[3-butyl-2-(3,5-di-tert-butyl-2-methoxy-phenyl)-3H-benzimidazol-5-yloxy]-propyl}-diethyl-amine |
| 3 | 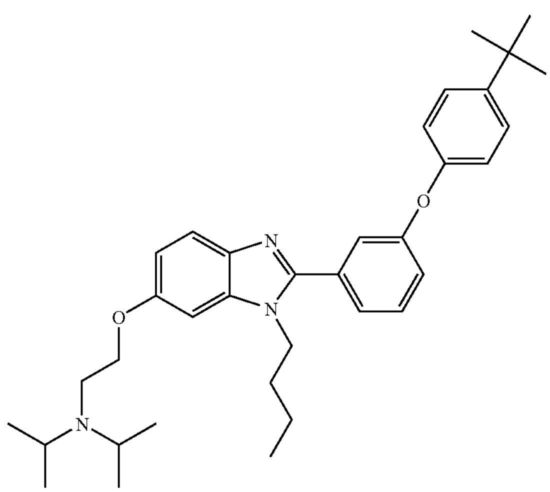 | (2-{3-butyl-2-[3-(4-tert-butyl-phenoxy)-phenyl]-3H-benzoimidazol-5-yloxy}-ethyl)-diisopropyl-amine |
| 4 | 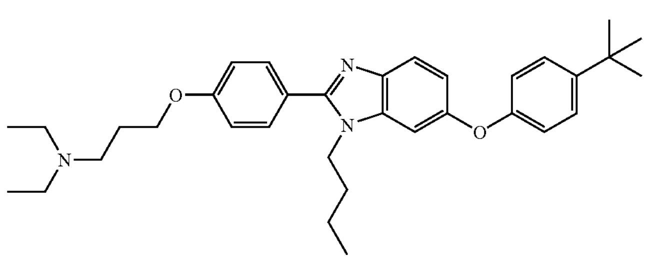 | (3-{4-[1-butyl-6-(4-tert-butyl-phenoxy)-1H-benzimidazol-2-yl]-phenoxy}-propyl)-diethyl-amine |

TABLE 1-continued

| Ex. | Structure | Name |
|---|---|---|
| 5 | 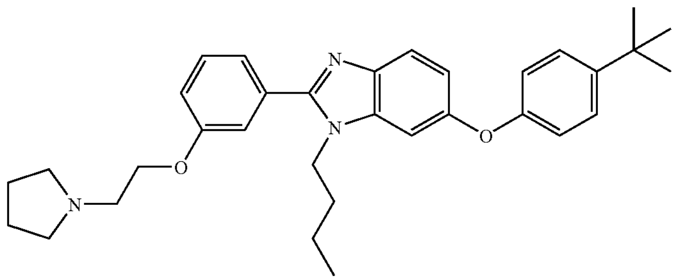 | 1-butyl-6-(4-tert-butyl-phenoxy)-2-[3-(2-pyrrolidin-1-yl-ethoxy)-phenyl]-1H-benzimidazole |
| 6 | 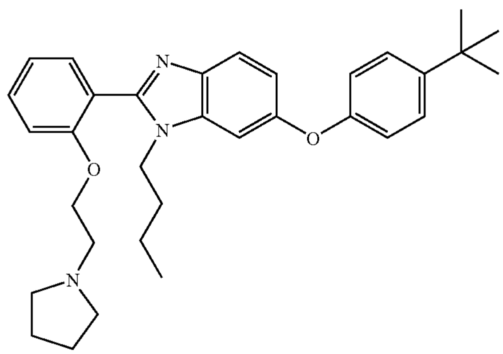 | 1-butyl-6-(4-tert-butyl-phenoxy)-2-[2-(2-pyrrolidin-1-yl-ethoxy)-phenyl]-1H-benzimidazole |
| 7 | 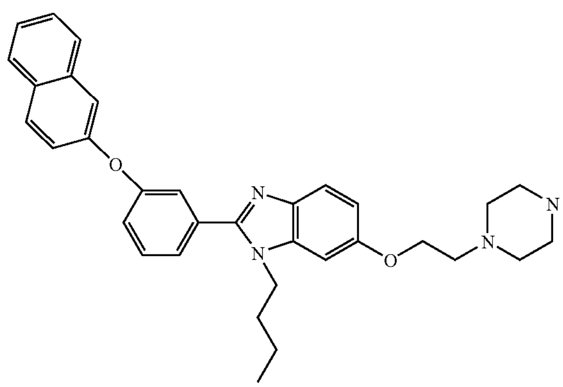 | 1-butyl-2-[3-(naphthalen-2-yloxy)-phenyl]-6-(2-piperazin-1-yl-ethoxy)-1H-benzoimidazole |
| 8 | 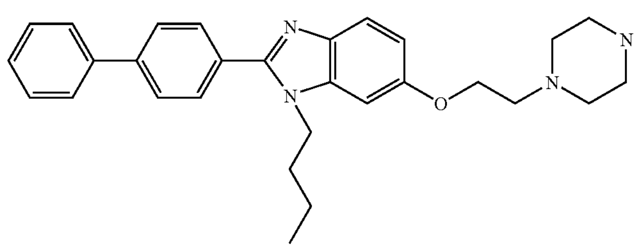 | 2-biphenyl-4-yl-1-butyl-6-(2-piperazin-1-yl-ethoxy)-1H-benzimidazole |
| 9 | 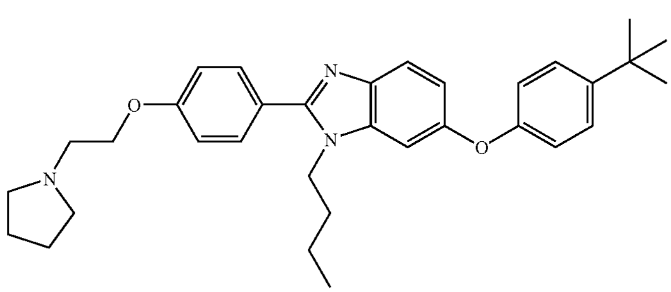 | 1-butyl-6-(4-tert-butyl-phenoxy)-2-[4-(2-pyrrolidin-1-yl-ethoxy)-phenyl]-1H-benzimidazole |

TABLE 1-continued
| Ex. | Structure | Name |
|---|---|---|
| 10 | 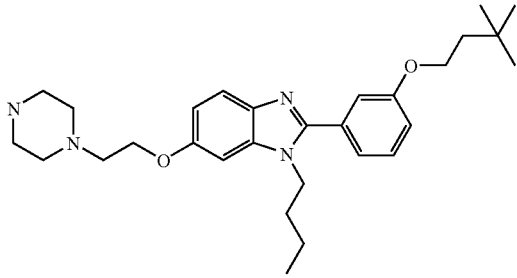 | 1-butyl-2-[3-(3,3-dimethyl-butoxy)-phenyl]-6-(2-piperazin-1-yl-ethoxy)-1H-benzoimidazole |
| 11 | 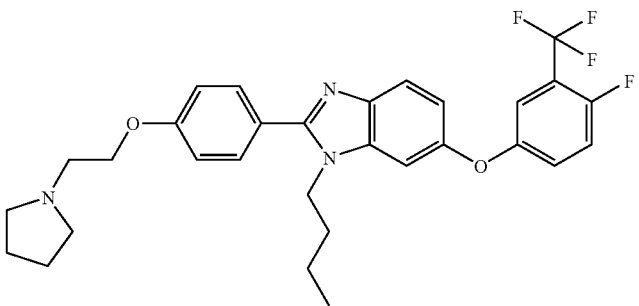 | 1-butyl-6-(4-fluoro-3-trifluoromethyl-phenoxy)-2-[4-(2-pyrrolidin-1-yl-ethoxy)-phenyl]-1H-benzimidazole |
| 12 | 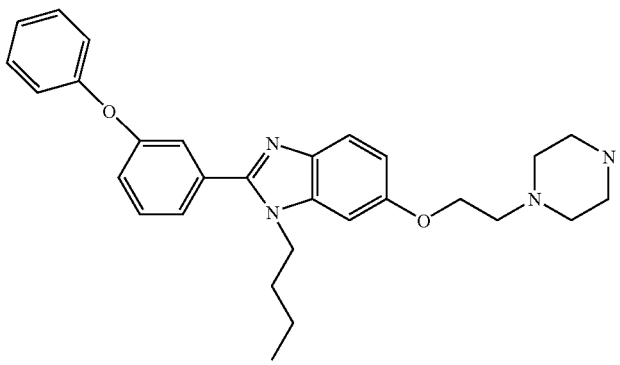 | 1-butyl-2-(3-phenoxy-phenyl)-6-(2-piperazin-1-yl-ethoxy)-1H-benzoimidazole |
| 13 | 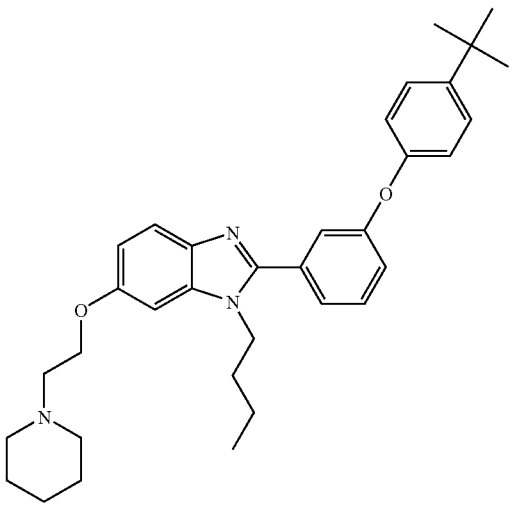 | 1-butyl-2-[3-(4-tert-butyl-phenoxy)-phenyl]-6-(2-piperidin-1-yl-ethoxy)-1H-benzimidazole |

TABLE 1-continued

| Ex. | Structure | Name |
|---|---|---|
| 14 | 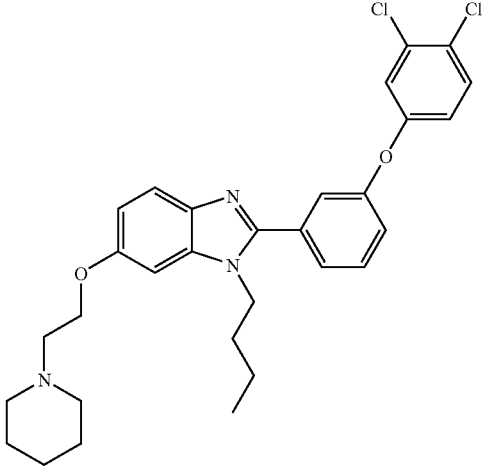 | 1-butyl-2-[3-(3,4-dichloro-phenoxy)-phenyl]-6-(2-piperidin-1-yl-ethoxy)-1H-benzimidazole |
| 15 | 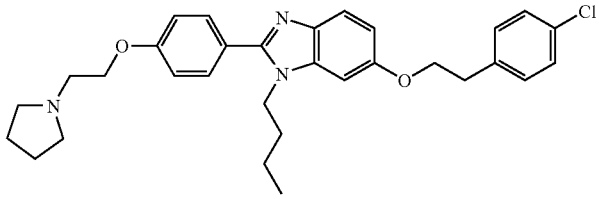 | 1-butyl-6-[2-(4-chloro-phenyl)-ethoxy]-2-[4-(2-pyrrolidin-1-yl-ethoxy)-phenyl]-1H-benzimidazole |
| 16 | 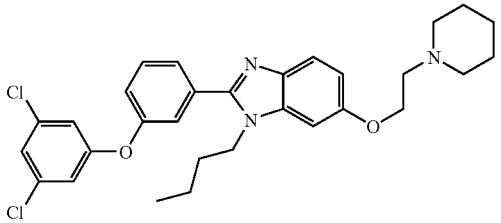 | 1-butyl-2-[3-(3,5-dichloro-phenoxy)-phenyl]-6-(2-piperidin-1-yl-ethoxy)-1H-benzimidazole |
| 17 | 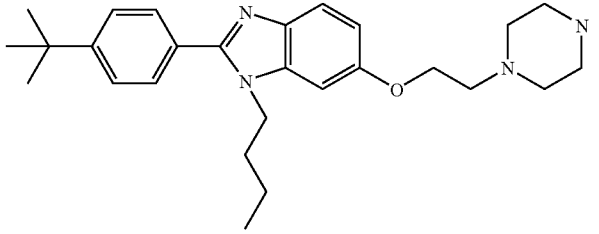 | 1-butyl-2-(4-tert-butyl-phenyl)-6-(2-piperazin-1-yl-ethoxy)-1H-benzoimidazole |
| 18 | 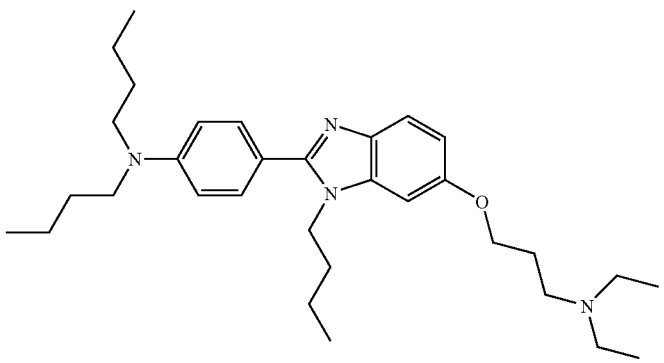 | dibutyl-{4-[1-butyl-6-(3-diethylamino-propoxy)-1H-benzimidazol-2-yl]-phenyl}-amine |

TABLE 1-continued

| Ex. | Structure | Name |
|---|---|---|
| 19 | 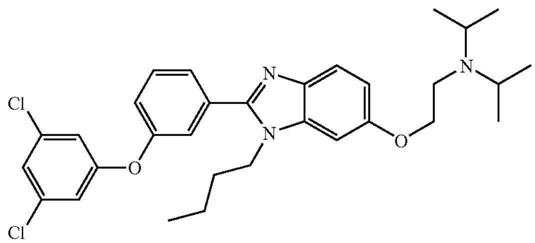 | (2-{3-butyl-2-[3-(3,5-dichloro-phenoxy)-phenyl]-3H-benzoimidazol-5-yloxy}-ethyl)-diisopropyl-amine |
| 20 | 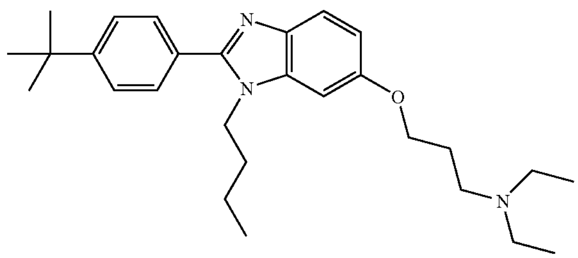 | {3-[3-butyl-2-(4-tert-butyl-phenyl)-3H-benzimidazol-5-yloxy]-propyl}-diethyl-amine |
| 21 | 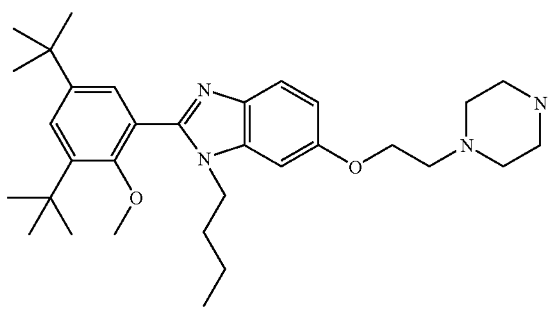 | 1-butyl-2-(3,5-di-tert-butyl-2-methoxy-phenyl)-6-(2-piperazin-1-ylethoxy)-1H-benzoimidazole |
| 22 | 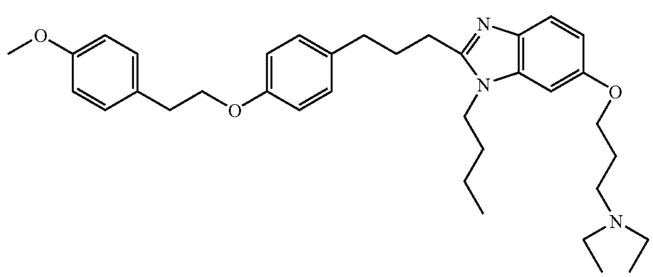 | {3-[3-butyl-2-(3-(4-[2-(4-methoxy-phenyl)-ethoxy]-phenyl}-propyl)-3H-benzimidazol-5-yloxy]-propyl}-diethyl-amine |
| 23 | 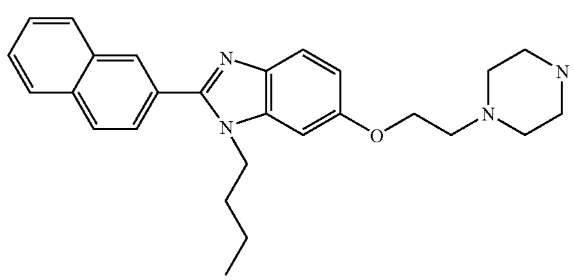 | 1-butyl-2-naphthalen-2-yl-6-(2-piperazin-1-yl-ethoxy)-1H-benzimidazole |

TABLE 1-continued

| Ex. | Structure | Name |
|---|---|---|
| 24 | 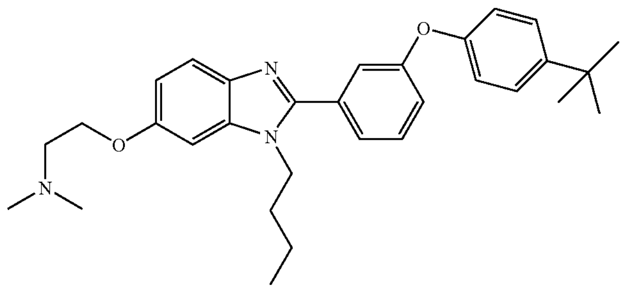 | (2-{3-butyl-2-[3-(4-tert-butyl-phenoxy)-phenyl]-3H-benzoimidazol-5-yloxy}-ethyl)-dimethyl-amine |
| 25 | 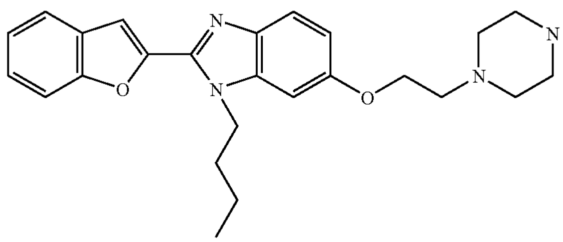 | 2-benzofuran-2-yl-1-butyl-6-(2-piperazin-1-yl-ethoxy)-1H-benzimidazole |
| 26 | 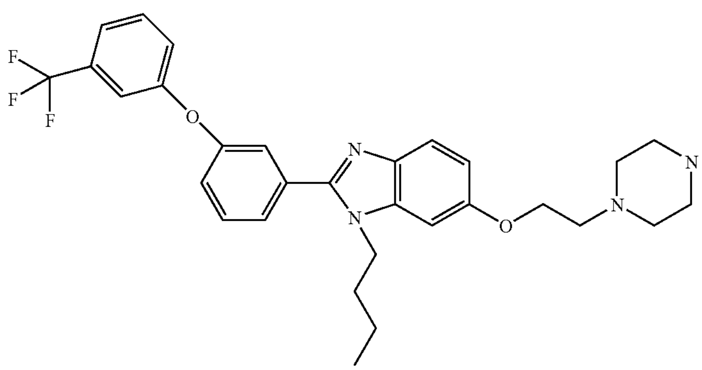 | 1-butyl-6-(2-piperazin-1-yl-ethoxy)-2-[3-(3-trifluoromethyl-phenoxy)-phenyl]-1H-benzimidazole |
| 27 | 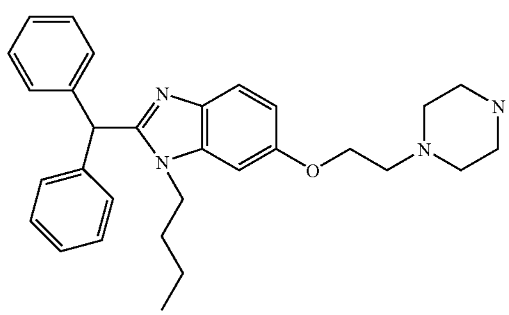 | 2-benzhydryl-1-butyl-6-(2-piperazin-1-yl-ethoxy)-1H-benzimidazole |
| 28 | 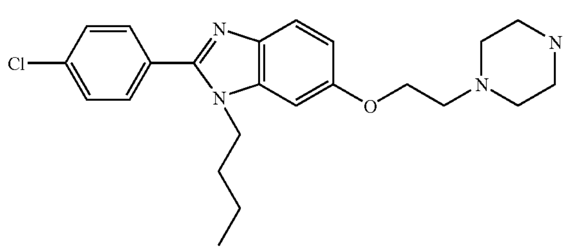 | 1-Butyl-2-(4-chloro-phenyl)-6-(2-piperazin-1-yl-ethoxy)-1H-benzoimidazole |

TABLE 1-continued

| Ex. | Structure | Name |
|---|---|---|
| 29 | 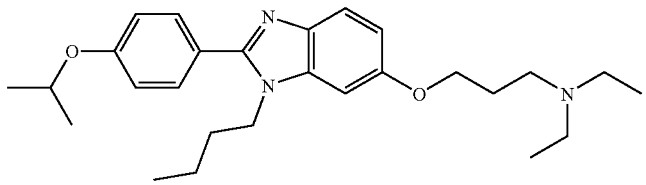 | {3-[3-Butyl-2-(4-isopropoxy-phenyl)-3H-benzoimidazol-5-yloxy]-propyl}-diethyl-amine |
| 30 | 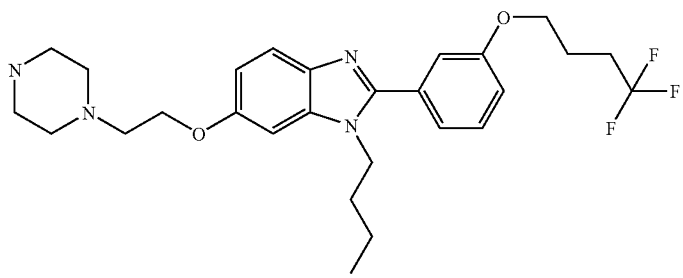 | 1-Butyl-6-(2-piperazin-1-yl-ethoxy)-2-[3-(4,4,4-trifluoro-butoxy)-phenyl]-1H-benzoimidazole |
| 31 | 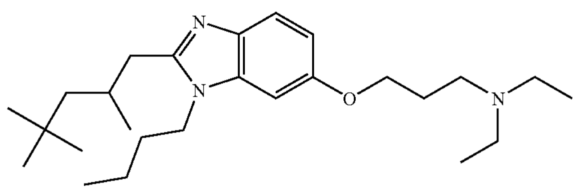 | {3-[3-Butyl-2-(2,4,4-trimethyl-pentyl)-3H-benzoimidazol-5-yloxy]-propyl}-diethyl-amine |
| 32 | 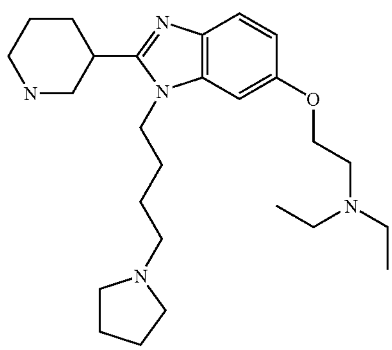 | Diethyl-{2-[2-piperidin-3-yl-3-(4-pyrrolidin-1-yl-butyl)-3H-benzoimidazol-5-yloxy]-ethyl}-amine |
| 33 | 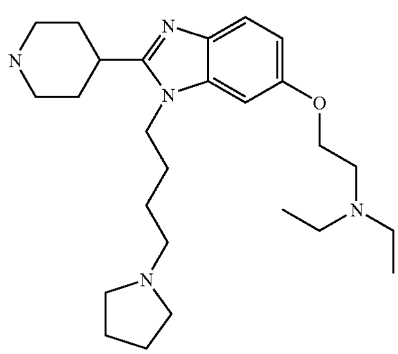 | Diethyl-{2-[2-piperidin-4-yl-3-(4-pyrrolidin-1-yl-butyl)-3H-benzoimldazol-5-yloxy]-ethyl}-amine |

TABLE 1-continued

| Ex. | Structure | Name |
|---|---|---|
| 34 | 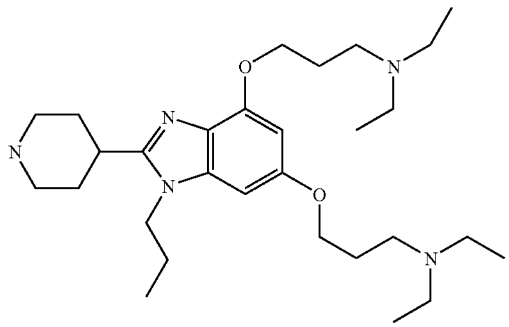 | {3-[1-Butyl-6-(3-diethylamino-propoxy)-2-piperidin-4-yl-1H-benzoimidazol-4-yloxy]-propyl}-diethyl-amine |
| 35 | 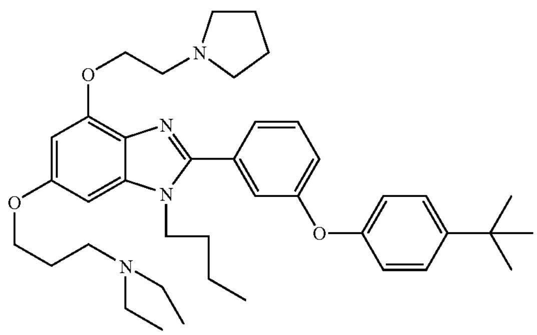 | {3-[3-butyl-2-[3-(4-tert-butyl-phenoxy)-phenyl]-7-(2-pyrrolidin-1-yl-ethoxy)-3H-benzimidazol-5-yloxy]-propyl}-diethyl-amine |
| 36 | 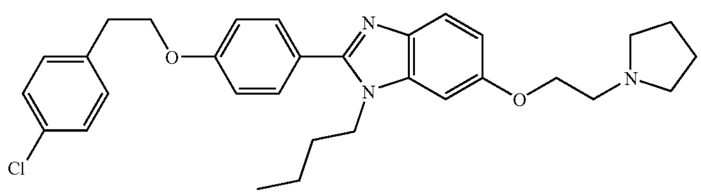 | 1-Butyl-2-(4-[2-(4-chloro-phenyl)-ethoxy]-phenyl}-6-(2-pyrrolidin-1-yl-ethoxy)-1H-benzoimidazole |
| 37 | 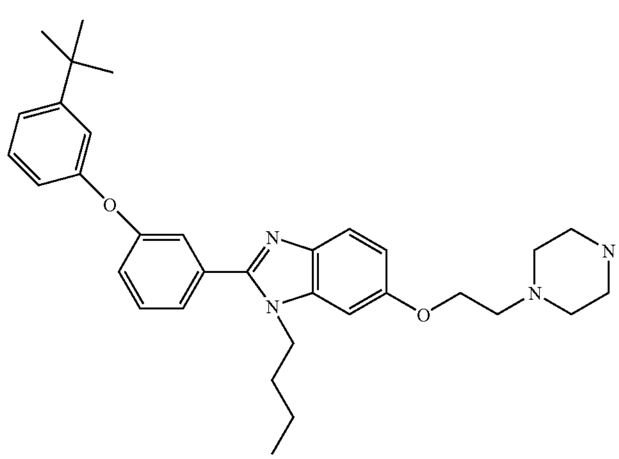 | 1-butyl-2-[3-(3-tert-butyl-phenoxy)-phenyl]-6-(2-piperazin-1-yl-ethoxy)-1H-benzoimidazole |

TABLE 1-continued

| Ex. | Structure | Name |
|---|---|---|
| 38 | 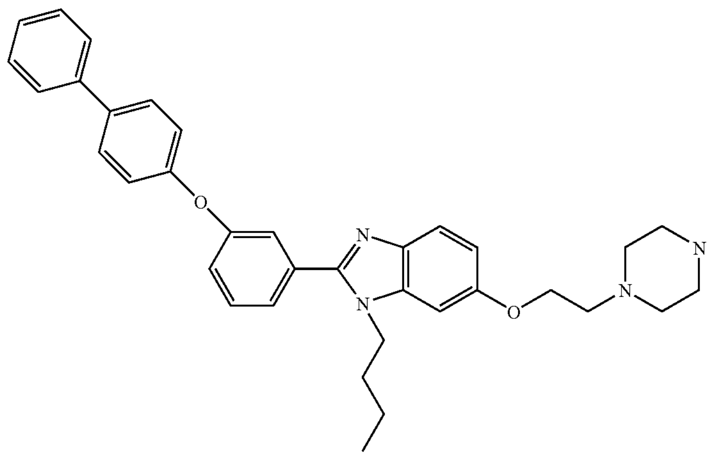 | 2-[3-(biphenyl-4-yloxy)-phenyl]-1-butyl-6-(2-piperazin-1-yl-ethoxy)-1H-benzoimidazole |
| 39 | 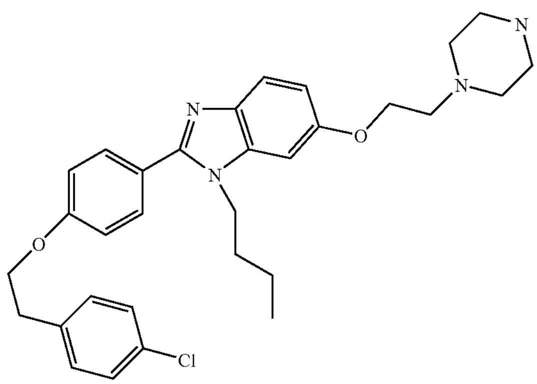 | 1-butyl-2-{4-[2-(4-chloro-phenyl)-ethoxy]-phenyl}-6-(2-piperazin-1-yl-ethoxy)-1H-benzimidazole |
| 40 | 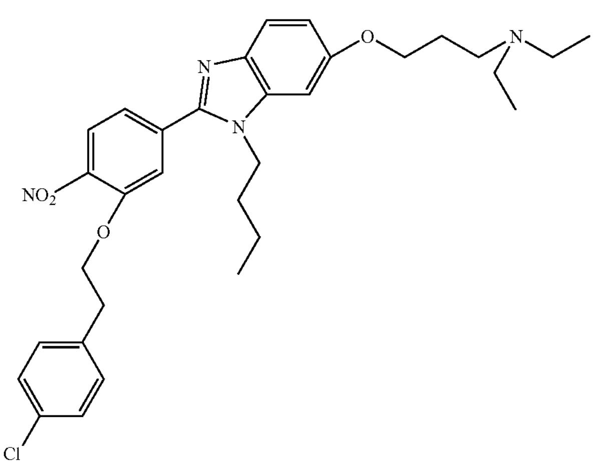 | [3-(3-butyl-2-{3-[2-(4-chloro-phenyl)-ethoxy]-4-nitro-phenyl}-3H-benzimidazol-5-yloxy)-propyl]-diethyl-amine |

TABLE 1-continued

| Ex. | Structure | Name |
|---|---|---|
| 41 | 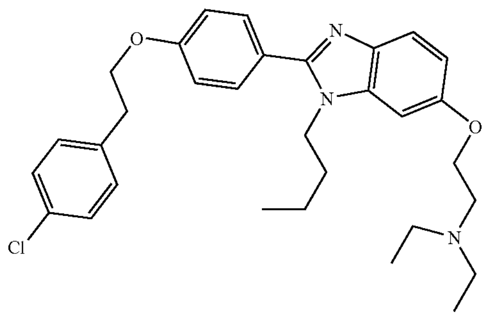 | [2-(3-butyl-2-{4-[2-(4-chloro-phenyl)-ethoxy]-phenyl}-3H-benzimidazol-5-yloxy)-ethyl]-diethyl-amine |
| 42 | 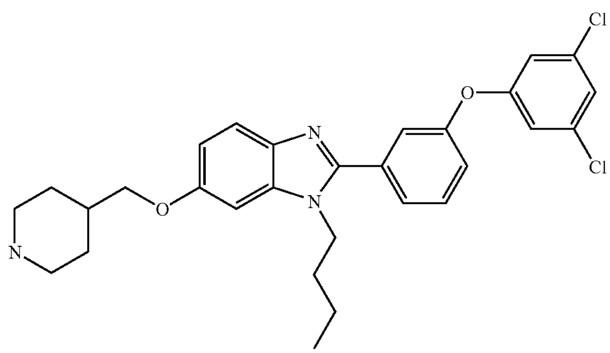 | 1-butyl-2-[3-(3,5-dichloro-phenoxy)-phenyl]-6-(piperidin-4-ylmethoxy)-1H-benzoimidazole |
| 43 | 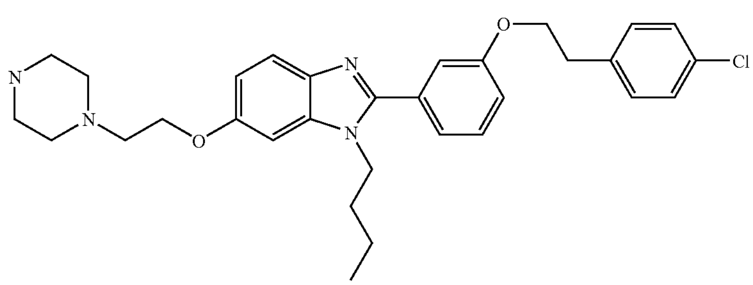 | 1-butyl-2-{3-[2-(4-chloro-phenyl)-ethoxy]-phenyl}-6-(2-piperazin-1-yl-ethoxy)-1H-benzoimidazole |
| 44 | 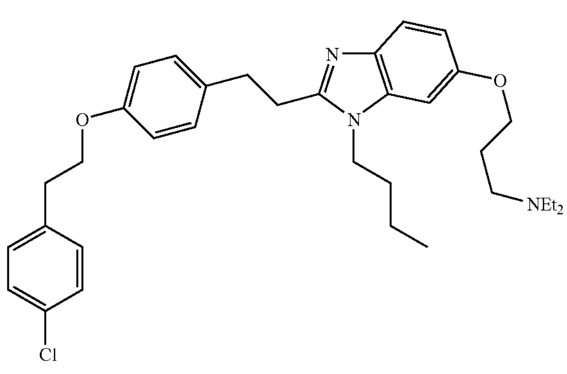 | {3-[3-butyl-2-(2-{4-[2-(4-chlorophenyl)-ethoxyl-phenyl}-ethyl)-3H-benzimidazol-5-yloxy]-propyl}-diethyl-amine |

TABLE 1-continued

| Ex. | Structure | Name |
| --- | --- | --- |
| 45 | 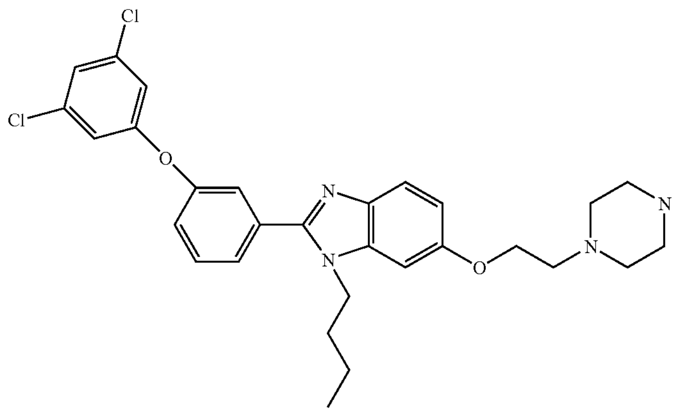 | 1-butyl-2-[3-(3,5-dichloro-phenoxy)-phenyl]-6-(2-piperazin-1-yl-ethoxy)-1H-benzimidazole |
| 46 | 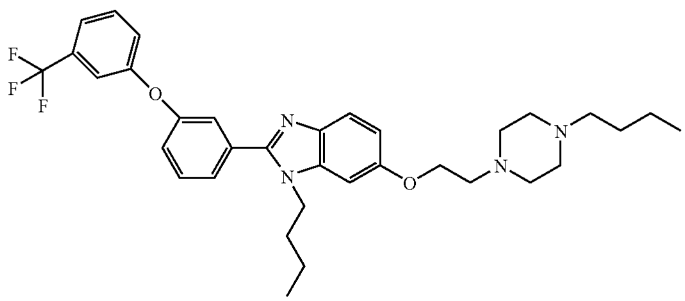 | 1-butyl-6-[2-(4-butyl-piperazin-1-yl)-ethoxy]-2-[3-(3-trifluoromethyl-phenoxy)-phenyl]-1H-benzimidazole |
| 47 | 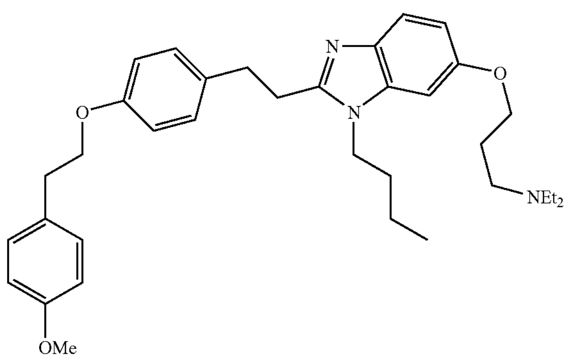 | {3-[3-butyl-2-(2-{4-[2-(4-chlorophenyl)-ethoxy]-phenyl}-ethyl)-3H-benzimidazol-5-yloxy]-propyl}-diethyl-amine |
| 48 | 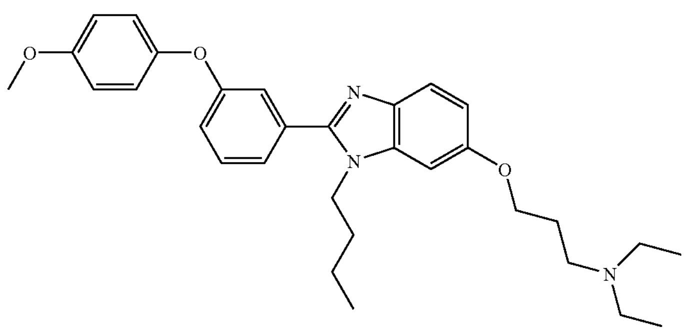 | (3-{3-butyl-2-[3-(4-methoxy-phenoxy)-phenyl]-3H-benzimidazol-5-yloxy}-propyl)-diethyl-amine |

TABLE 1-continued

| Ex. | Structure | Name |
|---|---|---|
| 49 | 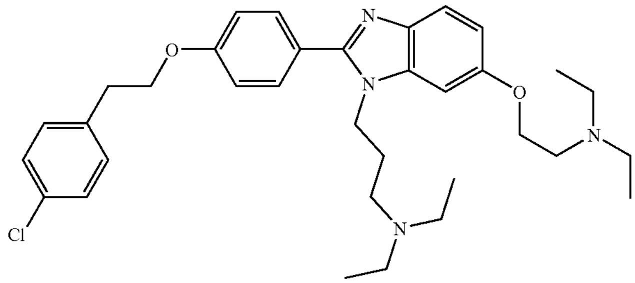 | {3-[2-{4-[2-(4-chloro-phenyl)-ethoxy]-phenyl}-6-(2-diethylamino-ethoxy)-benzimidazol-1-yl]-propyl}-diethyl-amine |
| 50 | 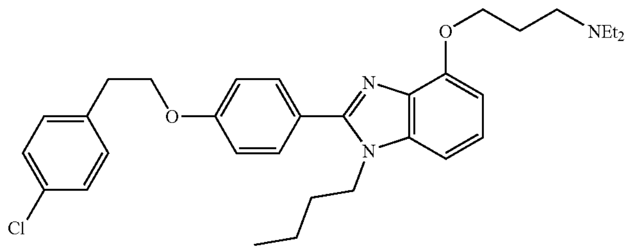 | [3-(1-butyl-2-{4-[2-(4-chloro-phenyl)-ethoxy]-phenyl}-1H-benzimidazol-4-yloxy)-propyl]-diethyl-amine |
| 51 | 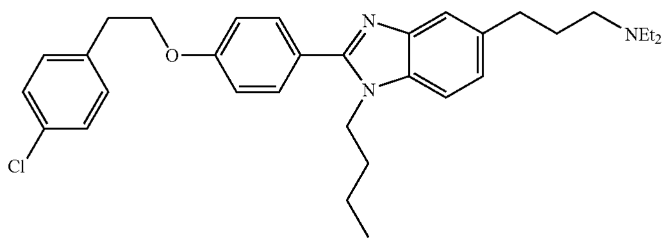 | [3-(1-butyl-2-{4-[2-(4-chloro-phenyl)-ethoxy]-phenyl}-1H-benzimidazol-5-yl)-propyl]-diethyl-amine |
| 52 | 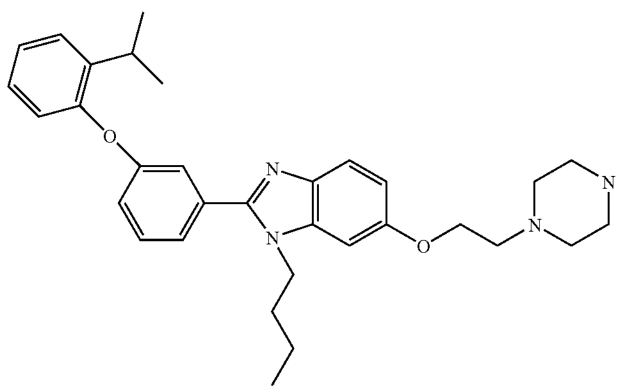 | 1-butyl-2-[3-(2-isopropyl-phenoxy)-phenyl]-6-(2-piperazin-1-yl-ethoxy)-1H-benzoimidazole |
| 53 | 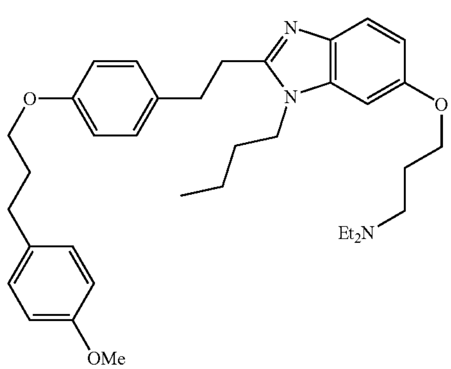 | {3-[3-butyl-2-(2-(4-[3-(4-methoxy-phenyl)-propoxy]-phenyl}-ethyl)-3H-benzimidazol-5-yloxy]-propyl}-diethyl-amine |

TABLE 1-continued

| Ex. | Structure | Name |
|---|---|---|
| 54 | 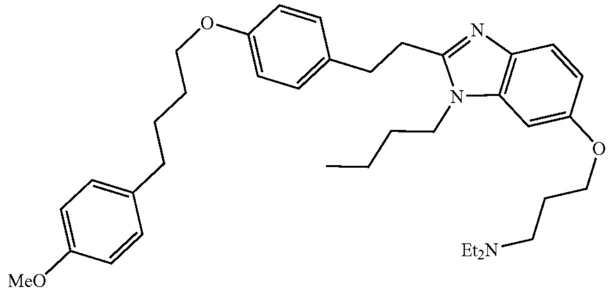 | {3-[3-butyl-2-(2-{4-[4-(4-methoxy-phenyl)-butoxy]-phenyl}-ethyl)-3H-benzimidazol-5-yloxy]-propyl}-diethyl-amine |
| 55 | 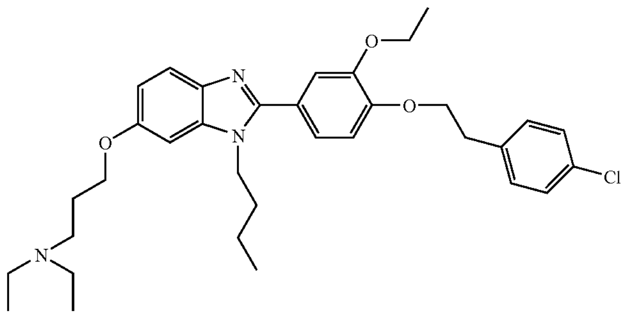 | [3-(3-butyl-2-{4-[2-(4-chloro-phenyl)-ethoxy]-3-ethoxy-phenyl}-3H-benzimidazol-5-yloxy)-propyl]-diethyl-amine |
| 56 | 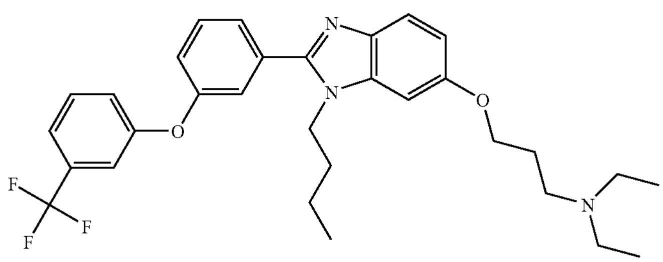 | (3-{3-butyl-2-[3-(3-trifluoromethyl-phenoxy)-phenyl]-3H-benzimidazol-5-yloxy}-propyl)-diethyl-amine |
| 57 | 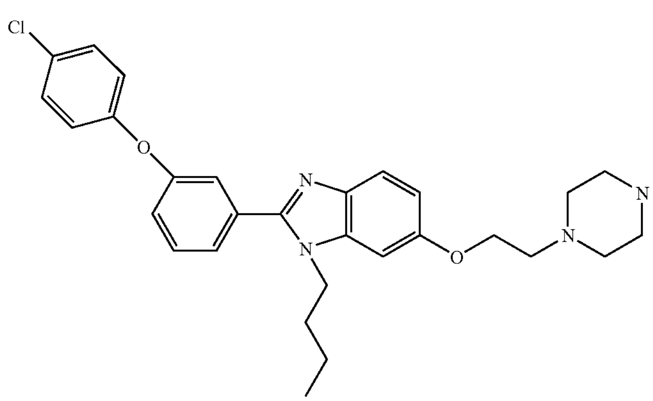 | 1-butyl-2-[3-(4-chloro-phenoxy)-phenyl]-6-(2-piperazin-1-yl-ethoxy)-1H-benzoimidazole |

TABLE 1-continued

| Ex. | Structure | Name |
|---|---|---|
| 58 | 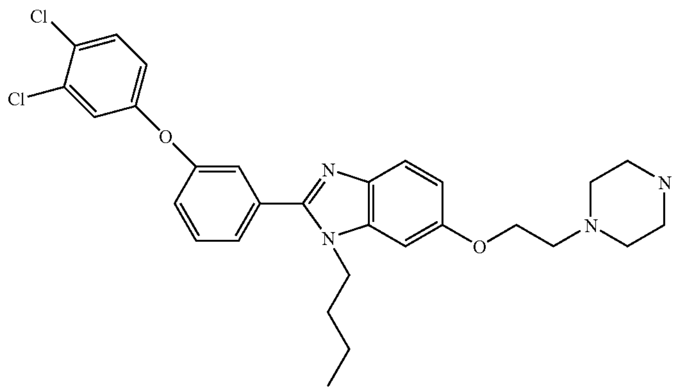 | 1-butyl-2-[3-(3,4-dichloro-phenoxy)-phenyl]-6-(2-piperazin-1-yl-ethoxy)-1H-benzoimidazole |
| 59 | 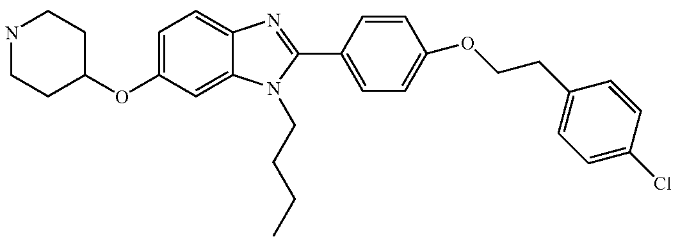 | 1-butyl-2-{4-[2-(4-chloro-phenyl)-ethoxy]-phenyl}-6-(piperidin-4-yloxy)-1H-benzoimidazole |
| 60 | 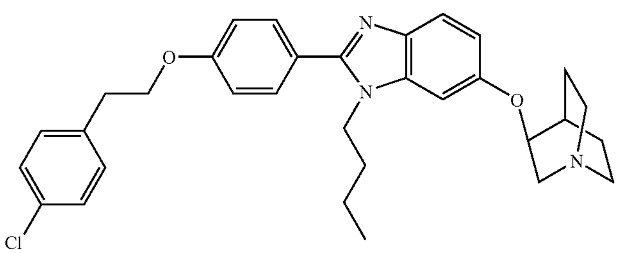 | 3-(3-butyl-2-{4-[2-(4-chloro-phenyl)-ethoxy]-phenyl}-3H-benzoimidazol-5-yloxy)-1-aza-bicyclo[2.2.2]octane |
| 61 | 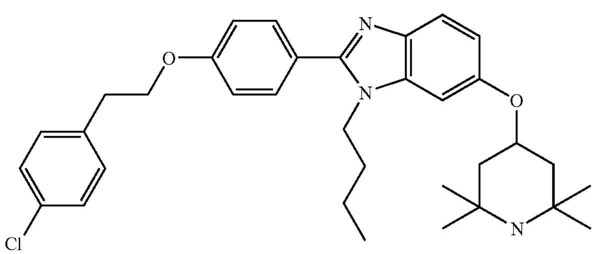 | 1-butyl-2-{4-[2-(4-chloro-phenyl)-ethoxy]-phenyl}-6-(2,2,6,6,-tetramethyl-piperidin-4-yloxy)-1H-benzoimidazole |
| 62 | 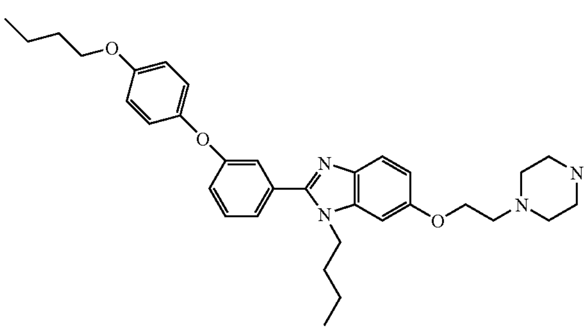 | 2-[3-(4-butoxy-phenoxy)-phenyl]-1-butyl-6-(2-piperazin-1-yl-ethoxy)-1H-benzoimidazole |

TABLE 1-continued

| Ex. | Structure | Name |
|---|---|---|
| 63 | 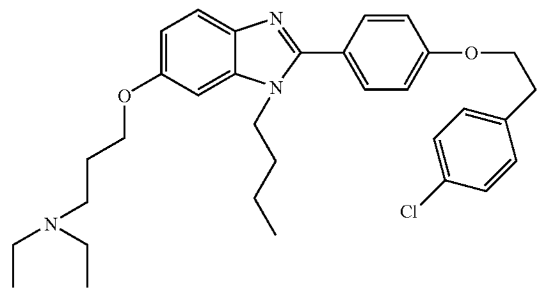 | [3-(3-butyl-2-{4-[2-(4-chloro-phenyl)-ethoxy]-phenyl}-3H-benzimidazol-5-yloxy)-propyl]-diethyl-amine |
| 64 | 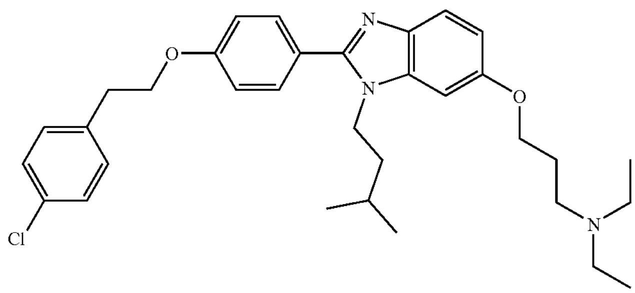 | {3-[2-{4-[2-(4-chloro-phenyl)-ethoxy]-phenyl}-3-(3-methyl-butyl)-3H-benzimidazol-5-yloxy]-propyl}-diethyl-amine |
| 65 | 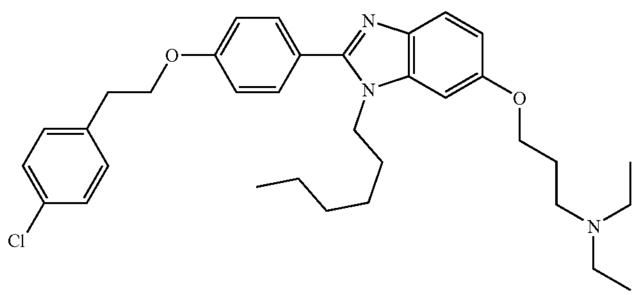 | [3-(2-{4-[2-(4-chloro-phenyl)-ethoxy]-phenyl}-3-hexyl-3H-benzimidazol-5-yloxy)-propyl]-diethyl-amine |
| 66 | 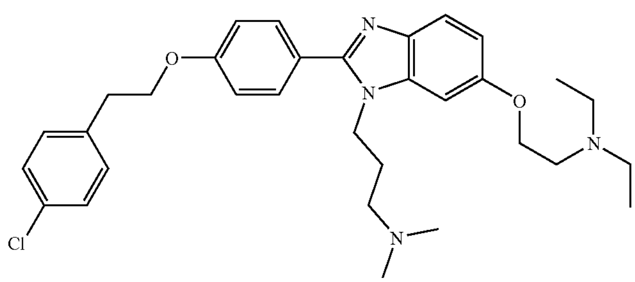 | {3-[2-{4-[2-(4-chloro-phenyl)-ethoxy]-phenyl}-6-(2-diethylamino-ethoxy)-benzimidazol-1-yl]-propyl}-dimethyl-amine |
| 67 | 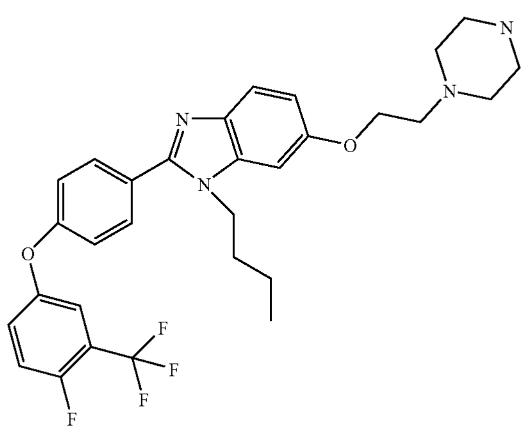 | 1-butyl-2-[4-(4-fluoro-3-trifluoromethyl-phenoxy)-phenyl]-6-(2-piperazin-1-ylethoxy)-1H-benzoimidazole |

TABLE 1-continued

| Ex. | Structure | Name |
|---|---|---|
| 68 | 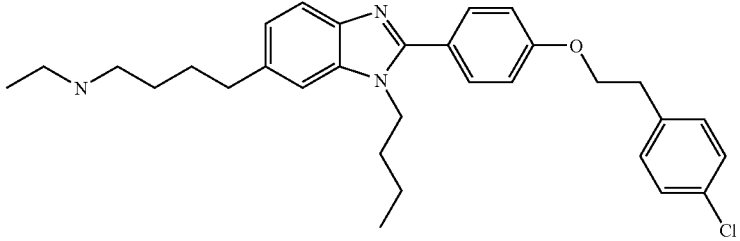 | [3-(3-butyl-2-(4-[2-(4-chloro-phenyl)-ethoxy]-phenyl}-3H-benzimidazol-5-yloxy)-propyl]-diethyl-amine |
| 69 | 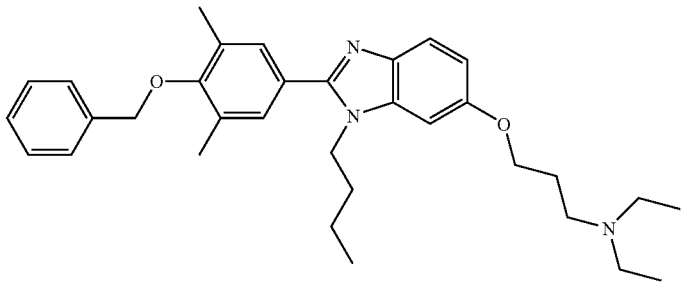 | {3-[2-(4-benzyloxy-3,5-dimethyl-phenyl)-3-butyl-3H-benzimidazol-5-yloxy]-propyl}-diethyl-amine |
| 70 | 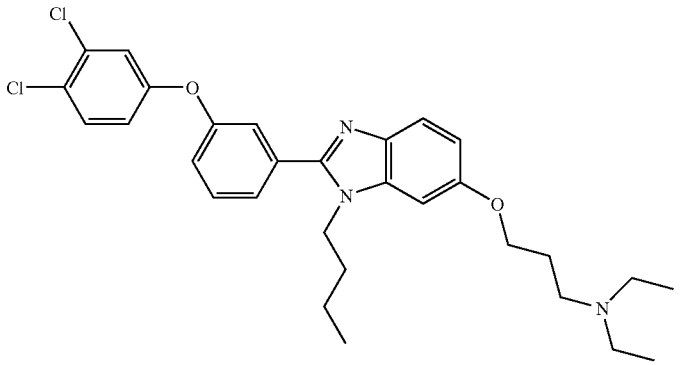 | {3-[3-butyl-2-(3-(3,4-dichloro-phenoxy)-phenyl]-3H-benzimidazol-5-yloxy]-propyl}-diethyl-amine |
| 71 | 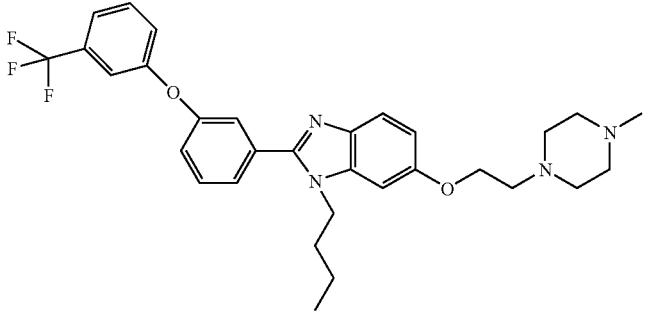 | 1-butyl-6-[2-(4-methyl-piperazin-1-yl)-ethoxy]-2-[3-(3-trifluoromethyl-phenoxy)-phenyl]-1H-benzimidazole |
| 72 | 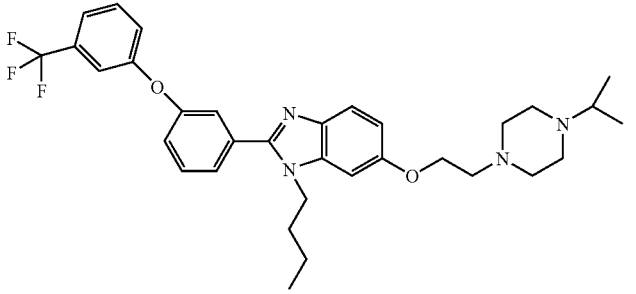 | 1-butyl-6-[2-(4-isopropyl-piperazin-1-yl)-ethoxy]-2-[3-(3-trifluoromethyl-phenoxy)-phenyl]-1H-benzoimidazole |

TABLE 1-continued

| Ex. | Structure | Name |
|---|---|---|
| 73 | 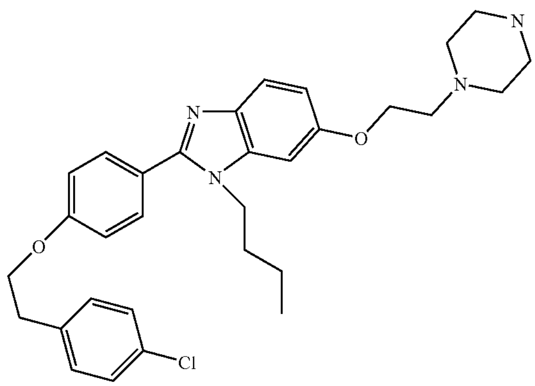 | 1-butyl-2-{4-[2-(4-chloro-phenyl)-ethoxy]-phenyl)-6-(3-piperazin-1-yl-propoxy)-1H-benzoimidazole |
| 74 | 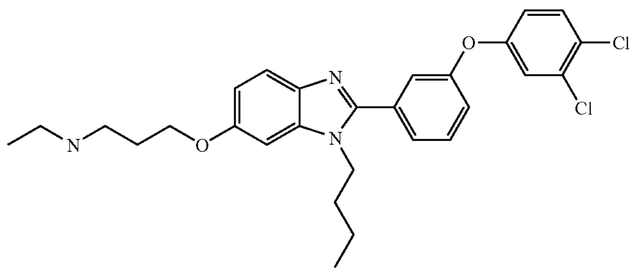 | (3-{3-butyl-2-[3-(3,4-dichloro-phenoxy)-phenyl]-3H-benzimidazol-5-yloxy}-propyl)-diethyl-amine |
| 75 | 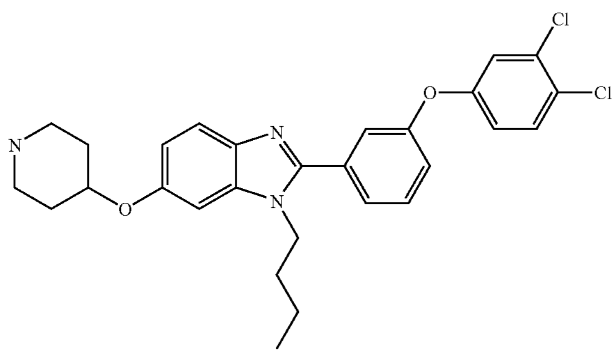 | 1-butyl-2-[3-(3,4-dimethoxy-phenoxy)-phenyl]-6-(2-piperidin-4-yloxy)-1H-benzoimidazole |
| 76 | 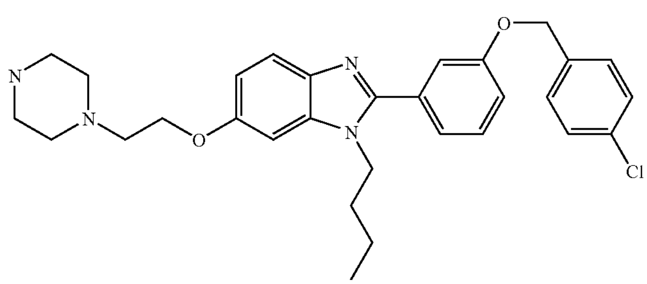 | 1-butyl-2-[3-(4-chloro-benzyloxy)-phenyl]-6-(2-piperazin-1-yl-ethoxy)-1H-benzoimidazole |
| 77 | 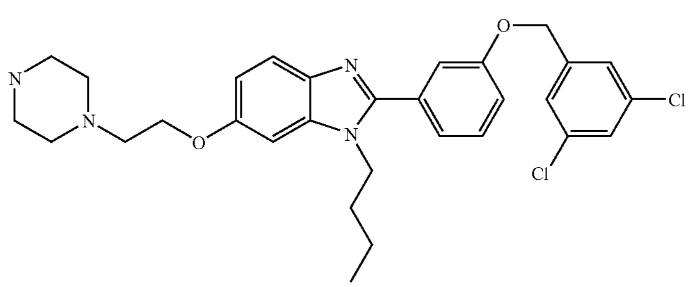 | 1-butyl-2-[3-(3,5-dichloro-phenoxy)-phenyl]-6-(2-piperazin-1-yl-ethoxy)-1H-benzoimidazole |

TABLE 1-continued

| Ex. | Structure | Name |
|---|---|---|
| 78 | 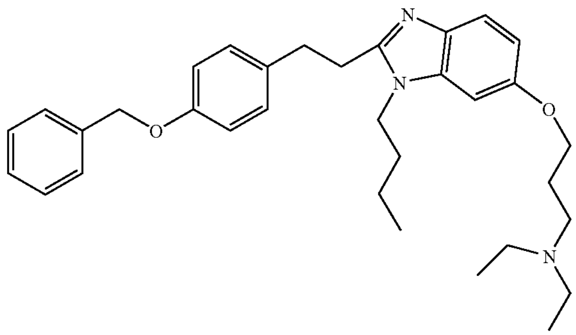 | (3-{2-[2-(4-benzyloxy-phenyl)-ethyl]-3-butyl-3H-benzimidazol-5-yloxy}-propyl)-diethyl-amine |
| 79 | 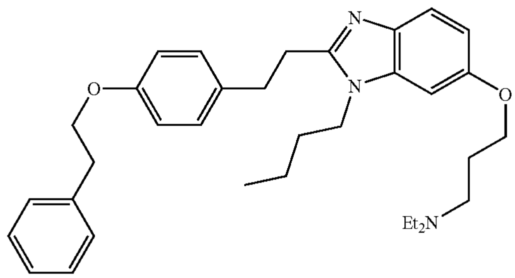 | (3-{3-butyl-2-[2-(4-phenethyloxy-phenyl)-ethyl]-3H-benzimidazol-5-yloxy}-propyl)-diethyl-amine |
| 80 | 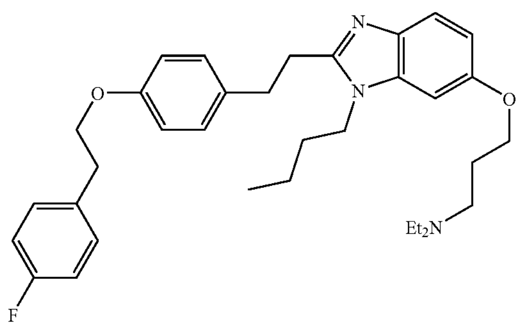 | {3-[3-butyl-2-(2-{4-[2-(4-fluoro-phenyl)-ethoxy]-phenyl}-ethyl)-3H-benzimidazol-5-yloxy]-propyl}-diethyl-amine |
| 81 | 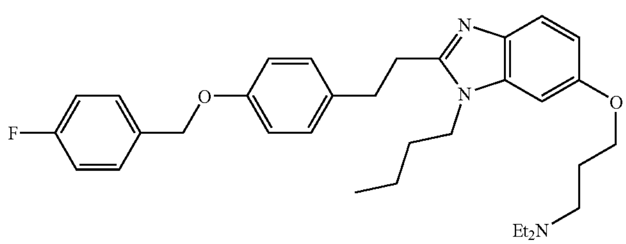 | [3-(3-butyl-2-{2-[4-(4-chloro-benzyloxy)-phenyl]-ethyl}-3H-benzimidazol-5-yloxy)-propyl]-diethyl-amine |
| 82 | 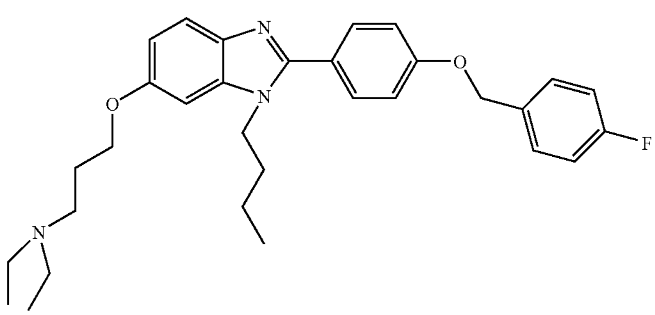 | (3-{3-butyl-2-[4-(4-fluoro-benzyloxy)-phenyl]-3H-benzimidazol-5-yloxy}-propyl)-diethyl-amine |

TABLE 1-continued

| Ex. | Structure | Name |
|---|---|---|
| 83 | 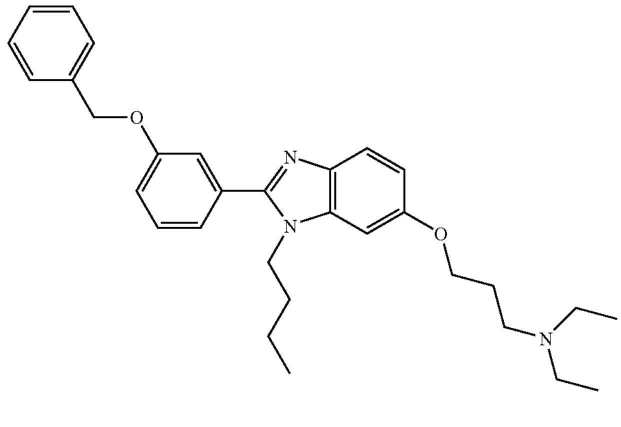 | (3-[2-(3-benzyloxy-phenyl)-3-butyl-3H-benzimidazol-5-yloxy]-propyl}-diethyl-amine |
| 84 | 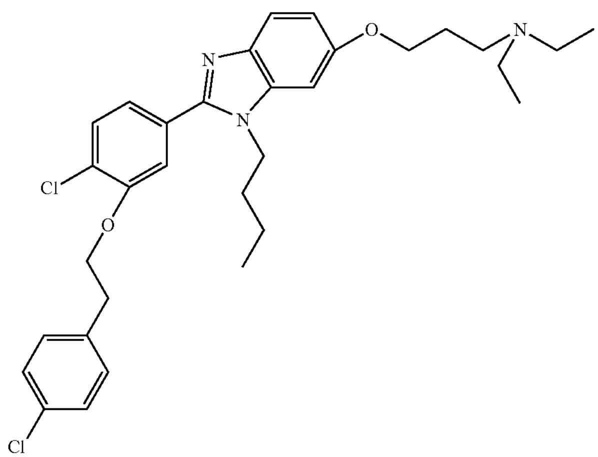 | [3-(3-butyl-2-{4-chloro-3-[2-(4-chloro-phenyl)-ethoxy]-phenyl}-3H-benzimidazol-5-yloxy)-propyl]-diethyl-amine |
| 85 | 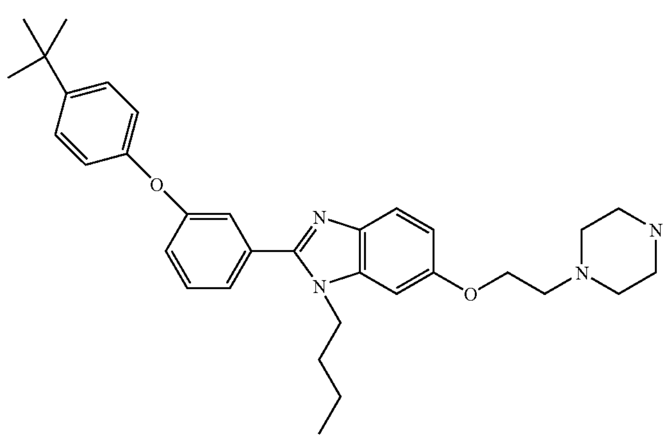 | 1-butyl-2-[3-(4-tert-butyl-phenoxy)-phenyl]-6-(2-piperazin-1-yl-ethoxy)-1H-benzimidazole |

TABLE 1-continued

| Ex. | Structure | Name |
|---|---|---|
| 86 | 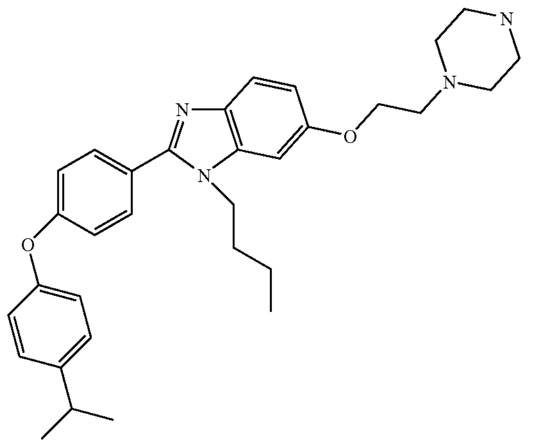 | 1-butyl-2-[4-(4-isopropyl-phenoxy)-phenyl]-6-(2-piperazin-1-yl-ethoxy)-1H-benzoimidazole |
| 87 | 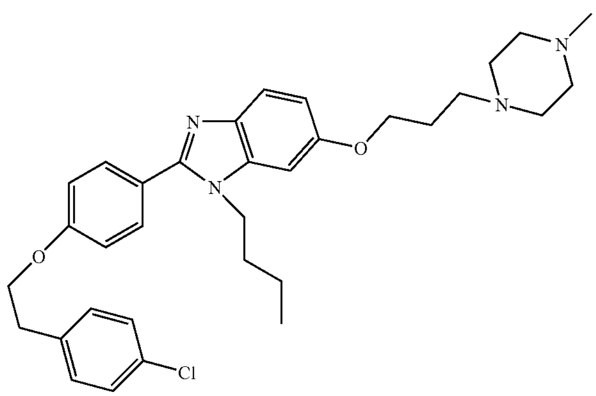 | 1-butyl-2-(4-[2-(4-chloro-phenyl)-ethoxy]-phenyl}-6-[3-(4-methyl-piperazin-1-yl)-propoxy]-1H-benzoimidazole |
| 88 | 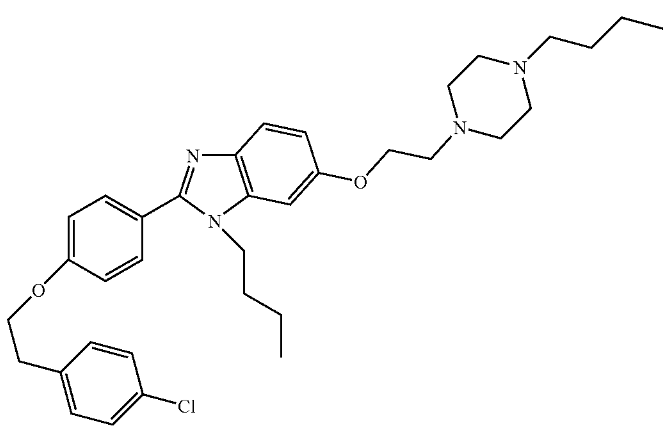 | 1-butyl-6-[2-(4-butyl-piperazin-1-yl)-ethoxy]-2-{4-[2-(4-chloro-phenyl)-ethoxy]-phenyl}-1H-benzoimidazole |

TABLE 1-continued

| Ex. | Structure | Name |
|---|---|---|
| 89 | 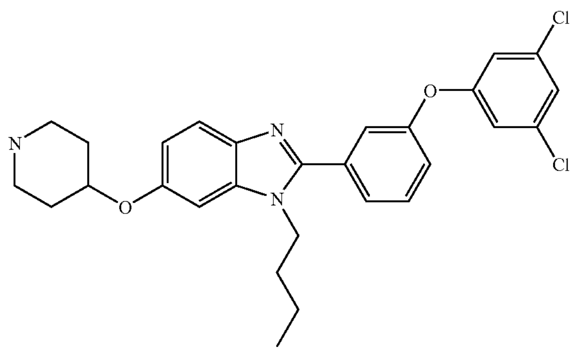 | 1-butyl-2-[3-(3,4-dimethoxy-phenoxy)-phenyl]-6-(2-piperazin-1-yl-ethoxy)-1H-benzoimidazole |
| 90 | 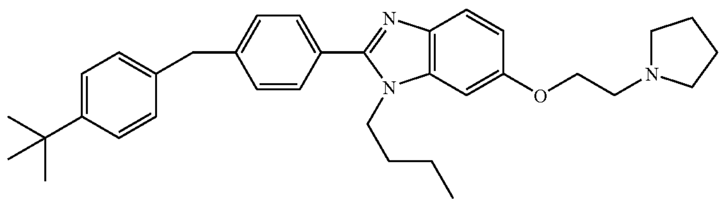 | 1-butyl-2-[4-(4-tert-butyl-benzyl)-phenyl]-6-(2-piperazin-1-yl-ethoxy)-1H-benzoimidazole |
| 91 | 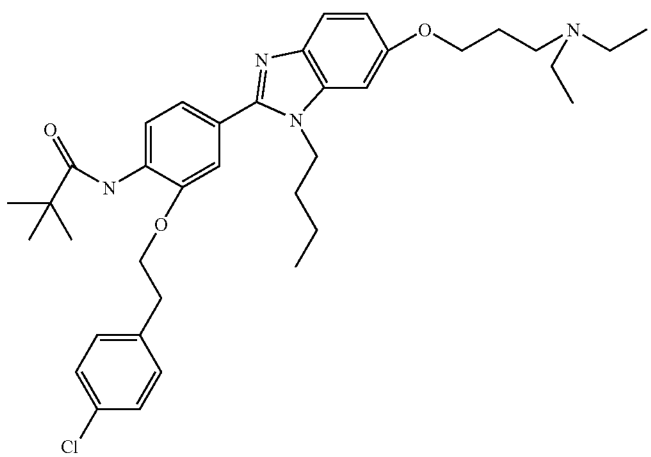 | N-{4-[1-butyl-6-(3-diethylamino-propoxy)-1H-benzimidazol-2-yl]-2-[2-(4-chloro-phenyl)-ethoxy]-phenyl}-2,2-dimethyl-propioinamide |
| 92 | 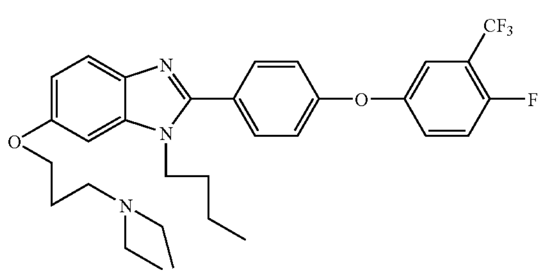 | (3-{3-butyl-2-[4-(4-fluoro-3-trifluoromethyl-phenoxy)-phenyl]-3H-benzimidazol-5-yloxy}-propyl)-diethyl-amine |

TABLE 1-continued

| Ex. | Structure | Name |
|---|---|---|
| 93 | 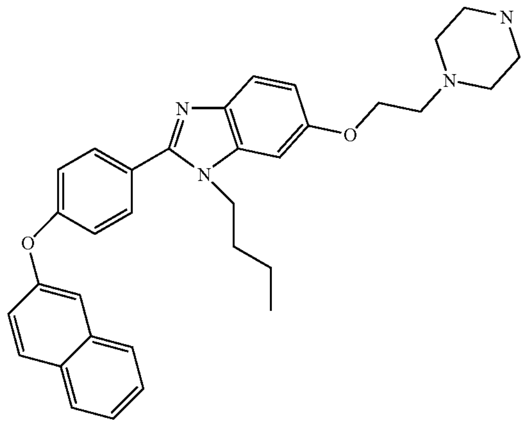 | 1-butyl-2-[4-(naphthalen-2-yloxy)-phenyl]-6-(2-piperazin-1-yl-ethoxy)-1H-benzoimidazole |
| 94 | 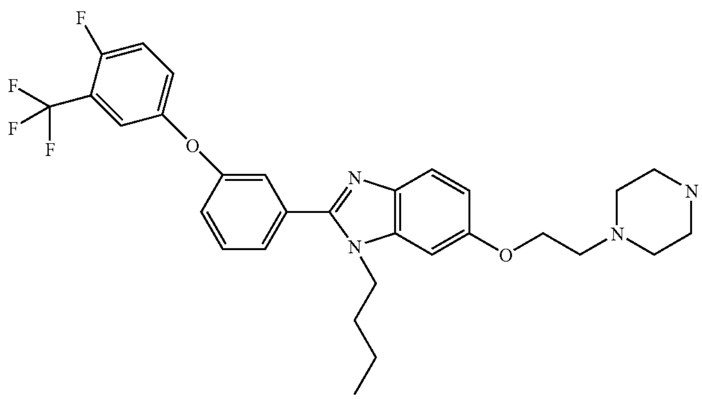 | 1-butyl-2-[3-(4-fluoro-3-trifluoromethyl-phenoxy)-phenyl]-6-(2-piperazin-1-yl-ethoxy)-1H-benzoimidazole |
| 95 | 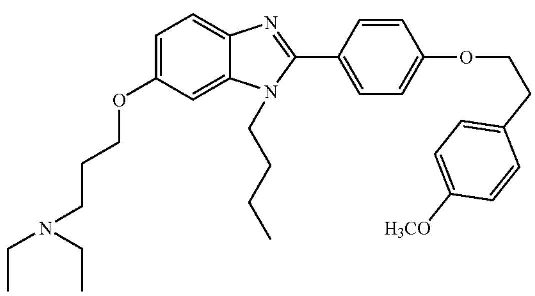 | [3-(3-butyl-2-{4-[2-(4-methoxy-phenyl)-ethoxy]-phenyl}-3H-benzimidazol-5-yloxy)-propyl]-diethyl-amine |
| 96 | 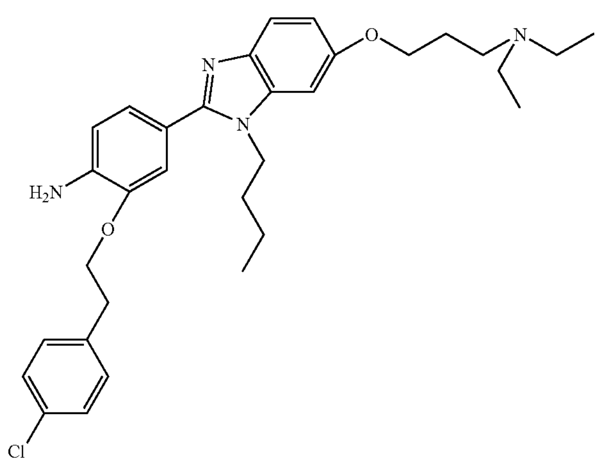 | 4-[1-butyl-6-(3-diethylamino-propoxy)-1H-benzimidazol-2-yl]-2-[2-(4-chloro-phenyl)-ethoxy]-phenylamine |

TABLE 1-continued

| Ex. | Structure | Name |
|---|---|---|
| 97 | 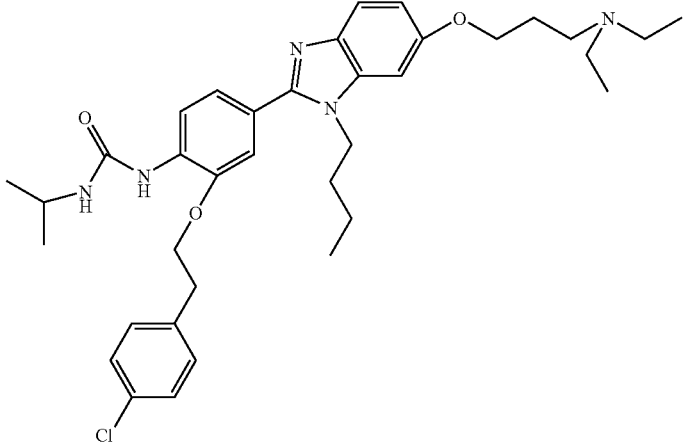 | 1-{4-[1-butyl-6-(3-diethylamino-propoxy)-1H-benzimidazol-2-yl]-2-[2-(4-chloro-phenyl)-ethoxy]-phenyl}-3-isopropyl-urea |
| 98 | 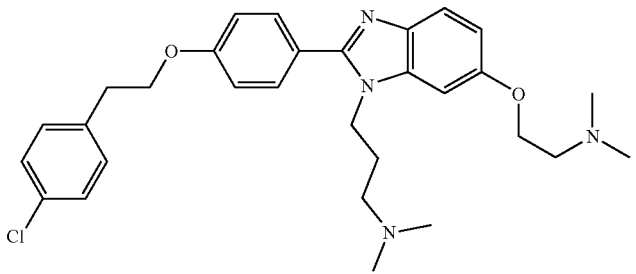 | {3-[2-{4-[2-(4-chloro-phenyl)-ethoxy]-phenyl}-6-(2-dimethylamino-ethoxy)-benzimidazol-1-yl]-propyl}-dimethyl-amine |
| 99 | 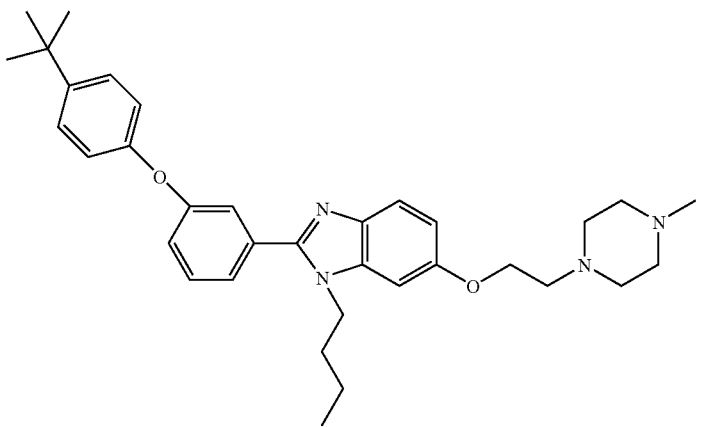 | 1-butyl-2-[3-(4-tert-butyl-phenoxy)-phenyl]-6-[2-(4-methyl-piperazin-1-yl)-ethoxy]-1H-benzimidazole |
| 100 | 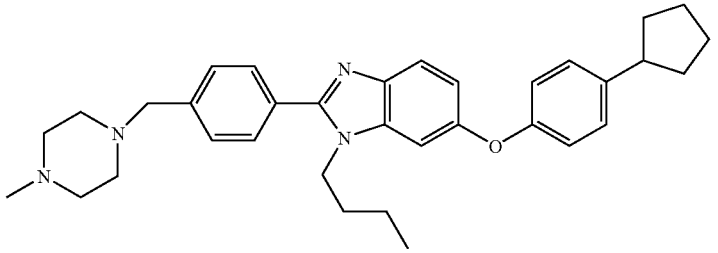 | 1-butyl-6-(4-cyclopentyl-phenoxy)-2-[4-(4-methyl-piperazin-1-ylmethyl)-phenyl]-1H-benzoimidazole |

TABLE 1-continued

| Ex. | Structure | Name |
|---|---|---|
| 101 | 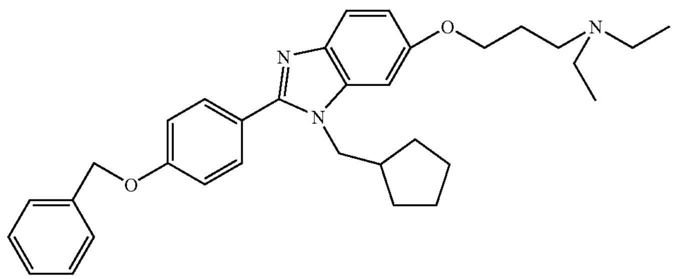 | {3-[2-(4-benzyloxy-phenyl)-3-cyclopentylmethyl-3H-benzimidazol-5-yloxy]-propyl}-diethyl-amine |
| 102 | 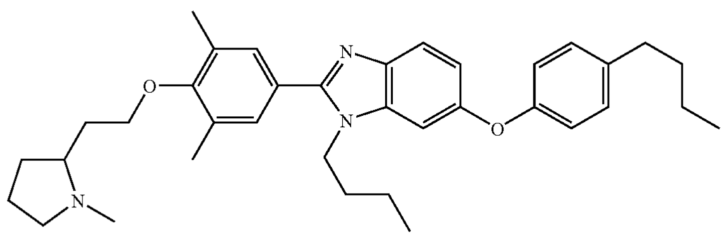 | 1-butyl-6-(4-butyl-phenoxy)-2-{3,5-dimethyl-4-[2-(1-methyl-pyrrolidin-2-yl)-ethoxy]-phenyl}-1H-benzoimidazole |
| 103 | 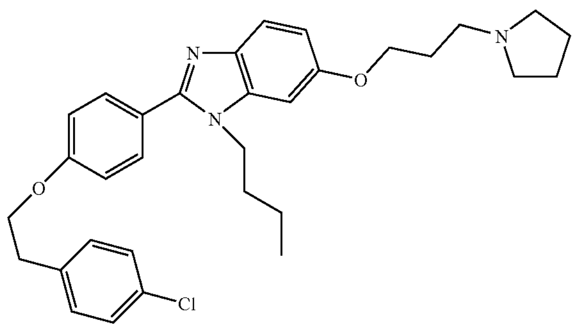 | 1-butyl-2-(4-[2-(4-chloro-phenyl)-ethoxy]-phenyl}-6-(3-pyrrolidin-1-yl-propoxy)-1H-benzoimidazole |
| 104 | 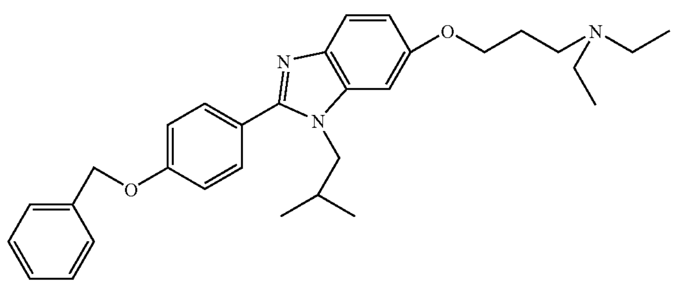 | {3-[2-(4-benzyloxy-phenyl)-3-isobutyl-3H-benzimidazol-5-yloxy]-propyl}-diethyl-amine |
| 105 | 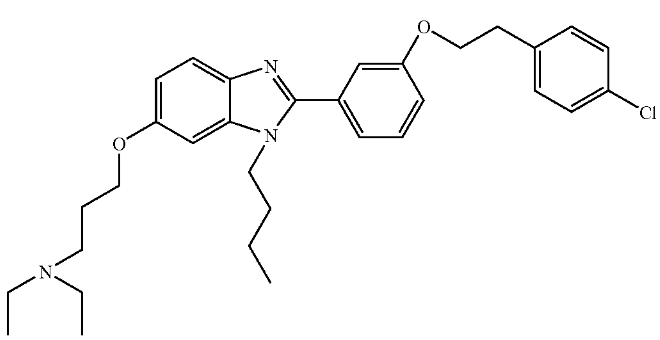 | [3-(3-butyl-2-{3-[2-(4-chloro-phenyl)-ethoxy]-phenyl}-3H-benzimidazol-5-yloxy)-propyl]-diethyl-amine |

TABLE 1-continued

| Ex. | Structure | Name |
|---|---|---|
| 106 | 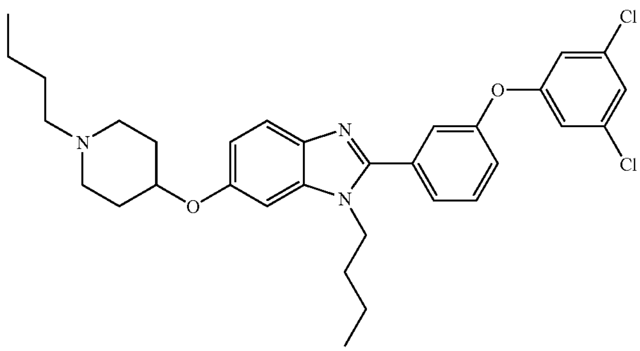 | 1-butyl-6-(1-butyl-piperidin-4-yloxy)-2-[3-(3,5-dichloro-phenoxy)-phenyl]-1H-benzoimidazole |
| 107 | 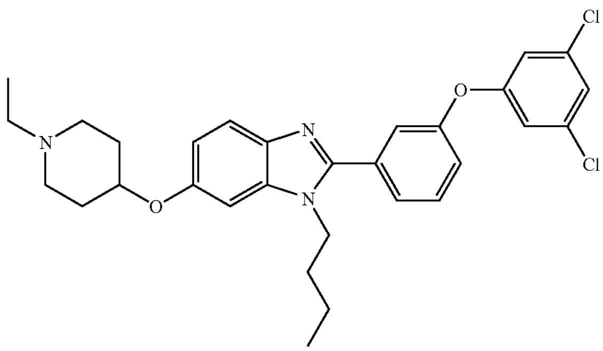 | 1-butyl-2-[3-(3,5-dichloro-phenoxy)-phenyl]-6-(1-ethyl-piperidin-4-yloxy)-1H-benzoimidazole |
| 108 | 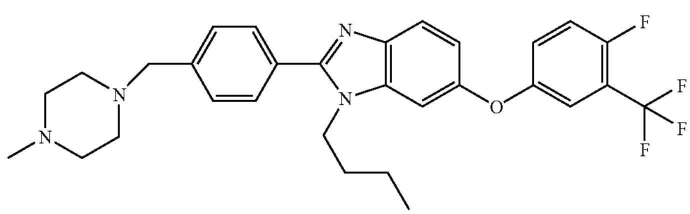 | 1-butyl-6-(4-fluoro-3-trifluoromethyl-phenoxy)-2-[4-(4-methyl-piperazin-1-ylmethyl)-phenyl]-1H-benzoimidazole |
| 109 | 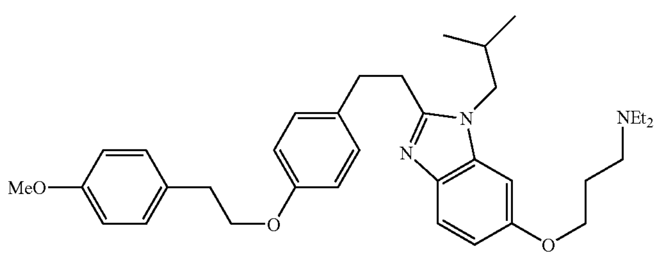 | diethyl-{3-[3-isobutyl-2-(2-{4-[2-(4-methoxy-phenyl)-ethoxy]-phenyl}-ethyl)-3H-benzimidazol-5-yloxy]-propyl}-amine |
| 110 | 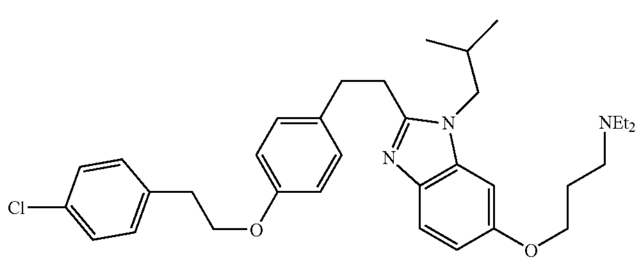 | {3-[2-(2-{4-[2-(4-chlorophenyl)-ethoxy]-phenyl}-ethyl)-3-isobutyl-3H-benzimidazol-5-yloxy]-propyl}-diethyl-amine |

TABLE 1-continued

| Ex. | Structure | Name |
|---|---|---|
| 111 | 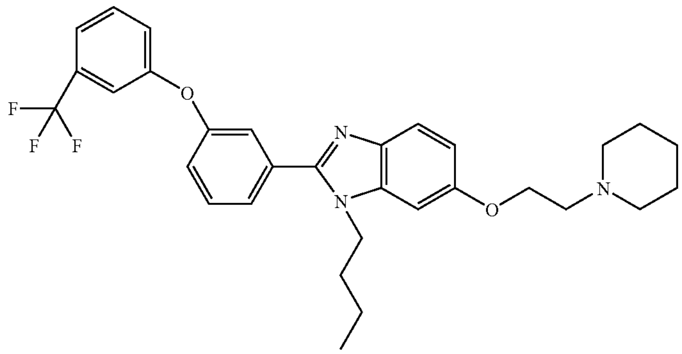 | 1-butyl-6-(2-piperazin-1-yl-ethoxy)-2-[3-(3-trifluoromethyl-phenoxy)-phenyl]-1H-benzimidazole |
| 112 | 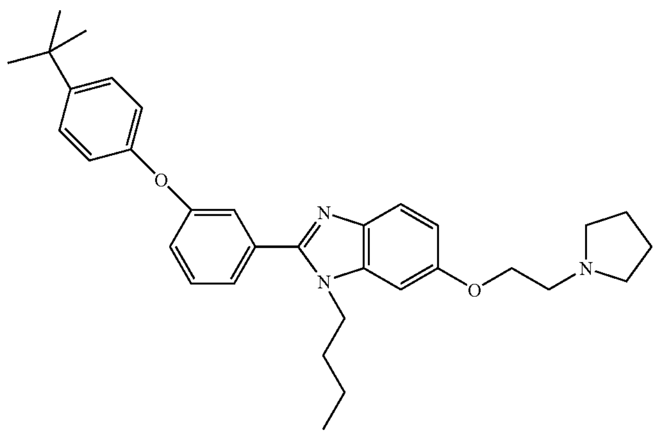 | 1-butyl-2-[3-(4-tert-butyl-phenoxy)-phenyl]-6-(2-pyrrolidin-1-yl-ethoxy)-1H-benzimidazole |
| 113 | 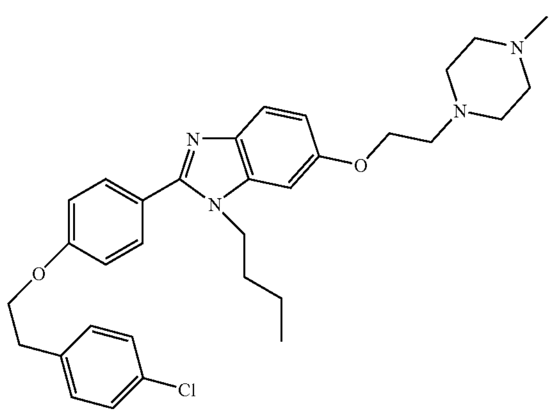 | 1-butyl-2-{4-[2-(4-chloro-phenyl)-ethoxy]-phenyl}-6-[2-(4-methyl-piperazin-1-yl)-ethoxy]-1H-benzimidazole |
| 114 | 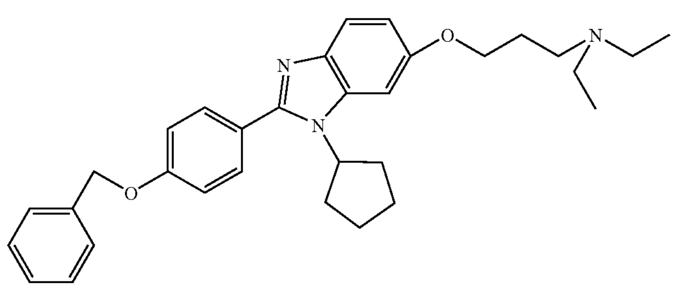 | {3-[2-(4-benzyloxy-phenyl)-3-cyclopentyl-3H-benzimidazol-5-yloxy)-propyl]-diethyl-amine |

TABLE 1-continued

| Ex. | Structure | Name |
|---|---|---|
| 115 | 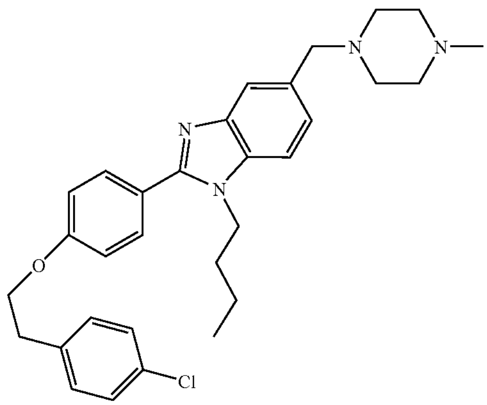 | 1-Butyl-2-{4-[2-(4-chloro-phenyl)-ethoxy]-phenyl}-5-(4-methyl-piperazin-1-ylmethyl)-1H-benzoimidazole |
| 116 | 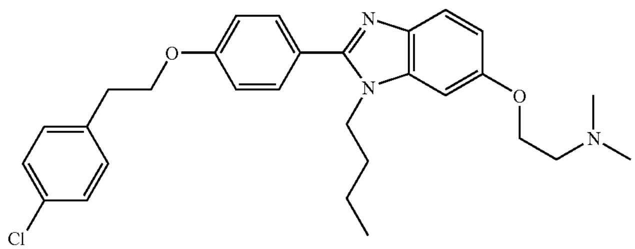 | [2-(3-butyl-2-{4-[2-(4-chloro-phenyl)-ethoxy]-phenyl}-3H-benzimidazol-5-yloxy)-ethyl]-dimethyl-amine |
| 117 | 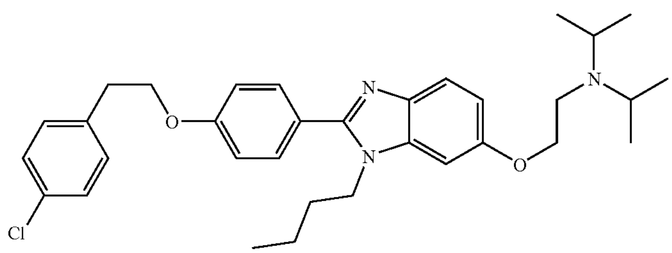 | [2-(3-butyl-2-{4-[2-(4-chloro-phenyl)-ethoxy]-phenyl)-3H-benzimidazol-5-yloxy)-ethyl]-diisopropyl-amine |
| 118 | 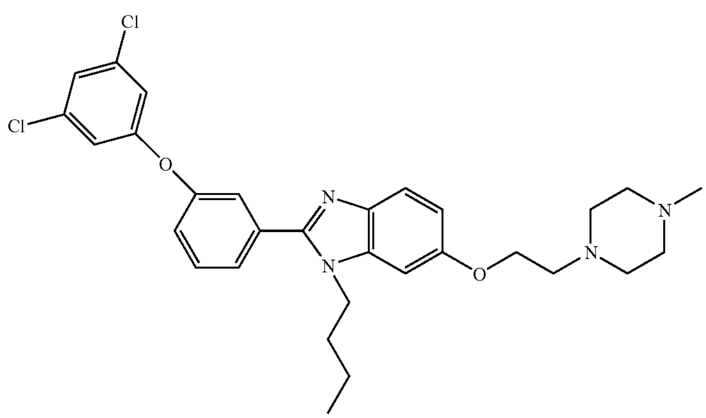 | 1-butyl-2-[3-(3,5-dichloro-phenoxy)-phenyl]-6-[2-(4-methyl-piperazin-1-yl)-ethoxy]-1H-benzimidazole |
| 119 | 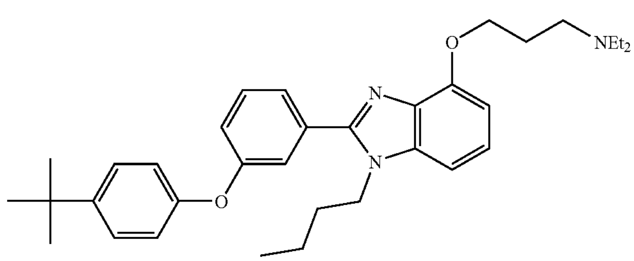 | (3-{1-butyl-2-(3-(4-tert-butyl-phenoxy)-phenyl]-1H-benzimidazol-4-yloxy}-propyl)-diethyl-amine |

TABLE 1-continued

| Ex. | Structure | Name |
|---|---|---|
| 120 | 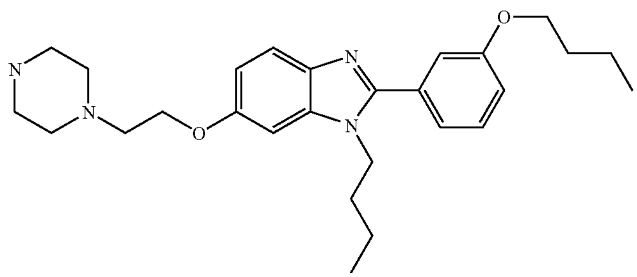 | 2-(3-butoxy-phenyl)-1-butyl-6-(2-piperazin-1-yl-ethoxy)-1H-benzimidazole |
| 121 | 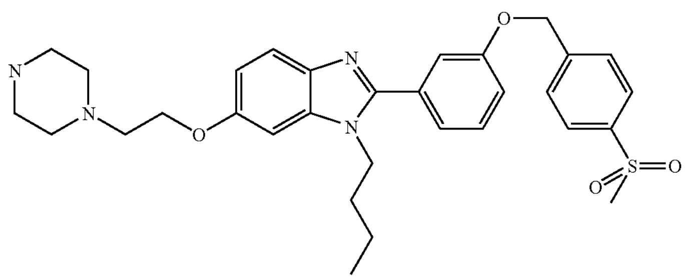 | 1-butyl-2-[3-(4-methanesulfonyl-benzyloxy)-phenyl]-6-(2-piperazin-1-yl-ethoxy)-1H-benzoimidazole |
| 122 | 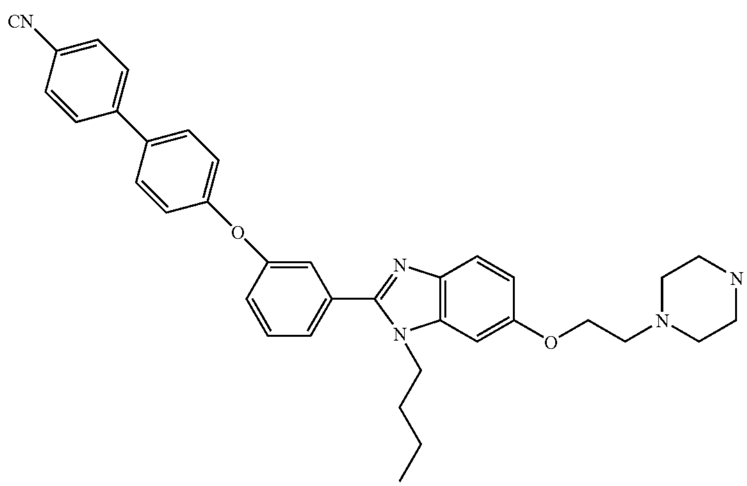 | 4'{3-[1-butyl-6-(2-piperazin-1-yl-ethoxy)-1H-benzoimidazol-2-yl]-phenoxy}-biphenyl-4-carbonitrile |
| 123 | 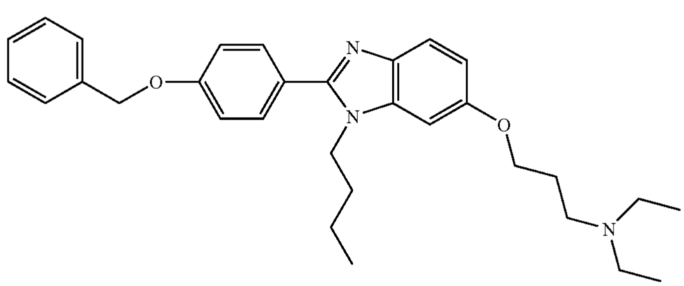 | {3-[2-(4-benzyloxy-phenyl)-3-butyl-3H-benzimidazol-5-yloxy]-propyl}-diethyl-amine |
| 124 | 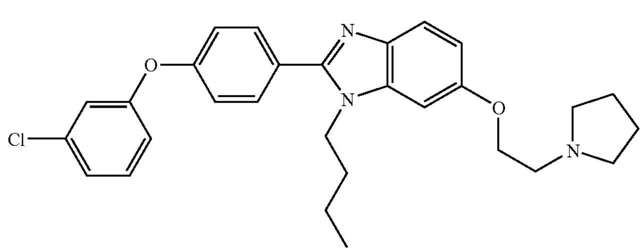 | 1-Butyl-2-[4-(3-chloro-phenoxy)-phenyl]-6-(2-pyrrolidin-1-yl-ethoxy)-1H-benzoimidazole |

TABLE 1-continued

| Ex. | Structure | Name |
|---|---|---|
| 125 | 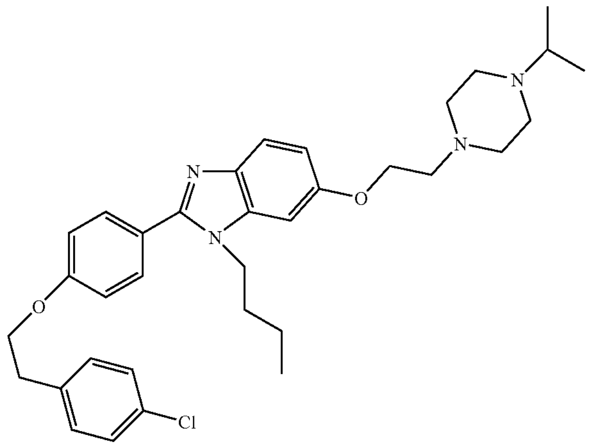 | 1-butyl-2-{4-[2-(4-chloro-phenyl)-ethoxy]-phenyl)-6-[2-(4-isopropyl-piperazin-1-yl)-ethoxy]-1H-benzoimidazole |
| 126 | 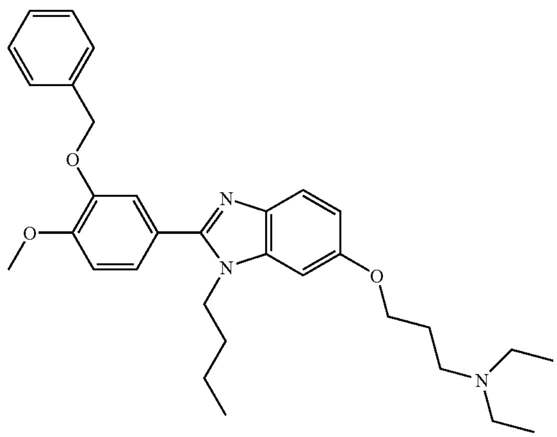 | (3-[2-(3-benzyloxy-4-methoxy-phenyl)-3-butyl-3H-benzimidazol-5-yloxy)-propyl]-diethyl-amine |
| 127 | 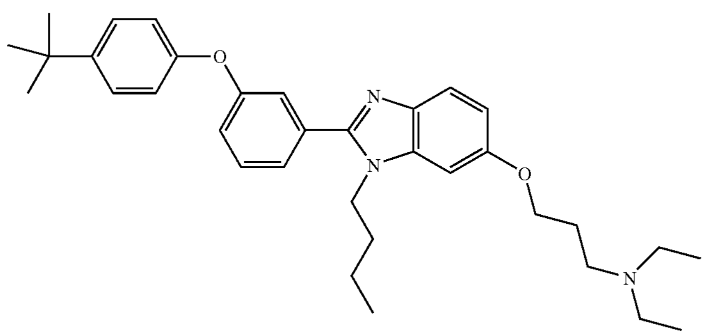 | (3-{3-butyl-2-[3-(4-tert-butyl-phenoxy)-phenyl]-3H-benzimidazol-5-yloxy}-propyl)-diethyl-amine |
| 128 | 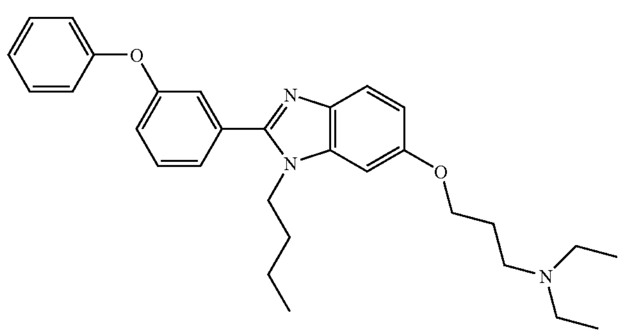 | {3-[3-butyl-2-(3-phenoxy-phenyl)-3H-benzimidazol-5-yloxy]-propyl}-diethyl-amine |

TABLE 1-continued

| Ex. | Structure | Name |
|---|---|---|
| 129 | 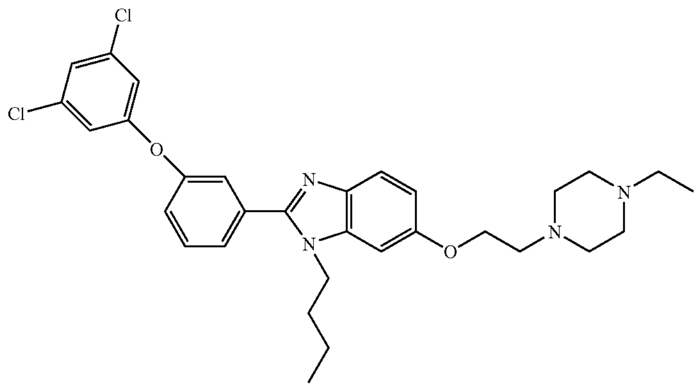 | 1-butyl-2-[3-(3,5-dichloro-phenoxy)-phenyl]-6-[2-(4-ethyl-piperazin-1-yl)-ethoxy]-1H-benzimidazole |
| 130 | 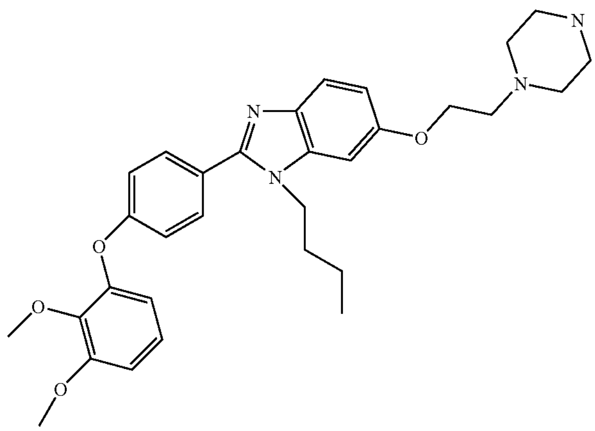 | 1-butyl-2-[4-(2,3-di-methoxy-phenoxy)-phenyl]-6-(2-piperazin-1-ylethoxy)-1H-benzoimidazole |
| 131 | 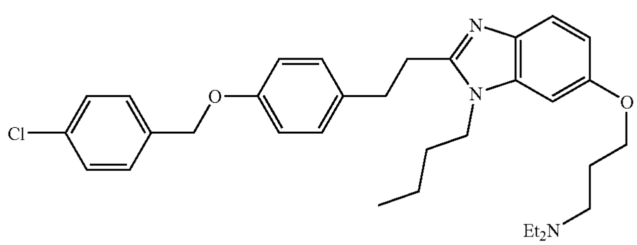 | [3-(3-butyl-2-{2-[4-(4-chloro-benzyloxy)-phenyl]-ethyl}-3H-benzimidazol-5-yloxy)-propyl]-diethyl-amine |
| 132 | 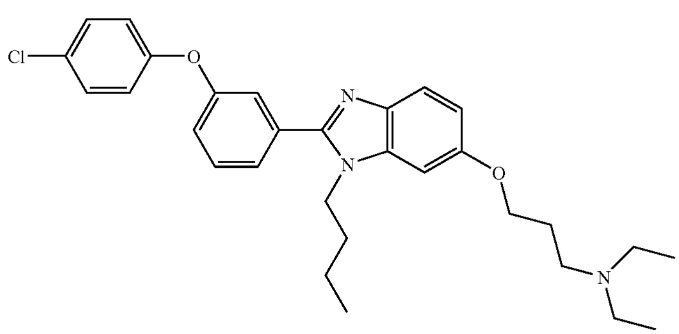 | (3-{3-butyl-2-[3-(4-chloro-phenoxy)-phenyl]-3H-benzimidazol-5-yloxy}-propyl)-diethyl-amine |

TABLE 1-continued

| Ex. | Structure | Name |
|---|---|---|
| 133 | 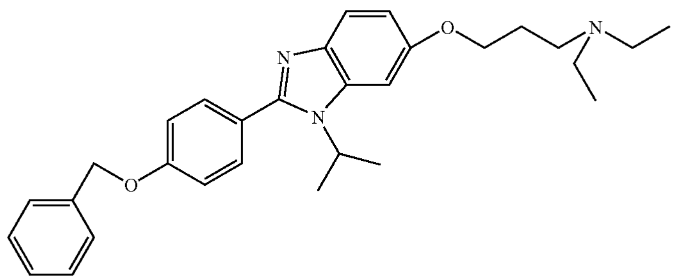 | {3-[2-(4-benzyloxy-phenyl)-3-isopropyl-3H-benzimidazol-5-yloxy]-propyl}-diethyl-amine |
| 134 | 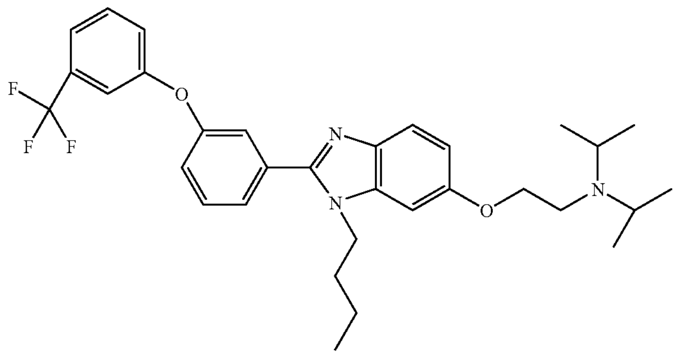 | (2-{3-butyl-2-[3-(3-trifluoromethyl-phenoxy)-phenyl]-3H-benzoimidazol-5-yloxy}-ethyl)-diisopropyl-amine |
| 135 | 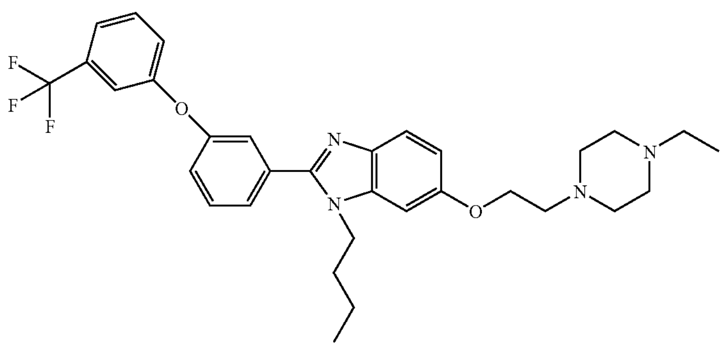 | 1-butyl-6-[2-(4-ethyl-piperazin-1-yl)-ethoxy]-2-[3-(3-trifluoromethyl-phenoxy)-phenyl]-1H-benzimidazole |
| 136 | 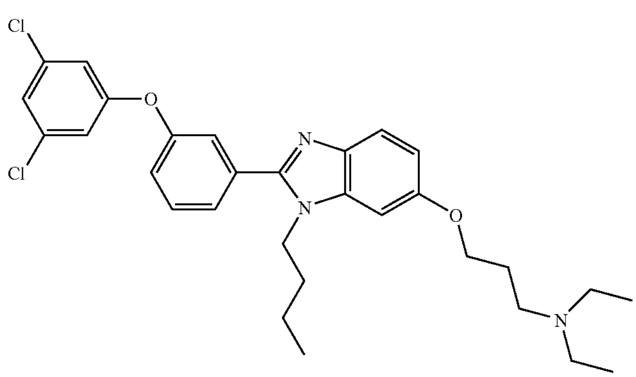 | {3-[3-butyl-2-[3-(3,5-dichloro-phenoxy)-phenyl]-3H-benzimidazol-5-yloxy]-propyl}-diethyl-amine |

TABLE 1-continued

| Ex. | Structure | Name |
|---|---|---|
| 137 | 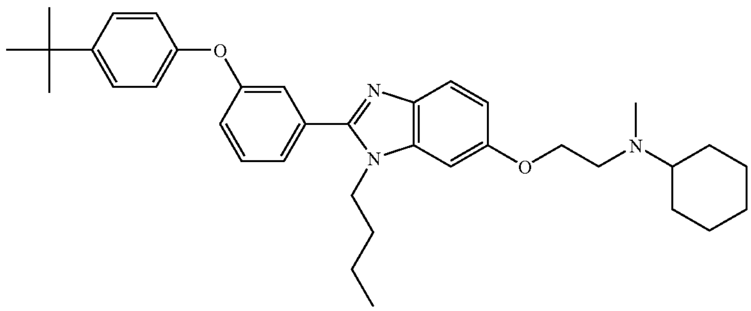 | (3-{2-butyl-2-[3-(4-tert-butyl-phenoxy)-phenyl]-3H-benzimidazol-5-yloxy}-ethyl)-cyclohexyl-methyl-amine |
| 138 | 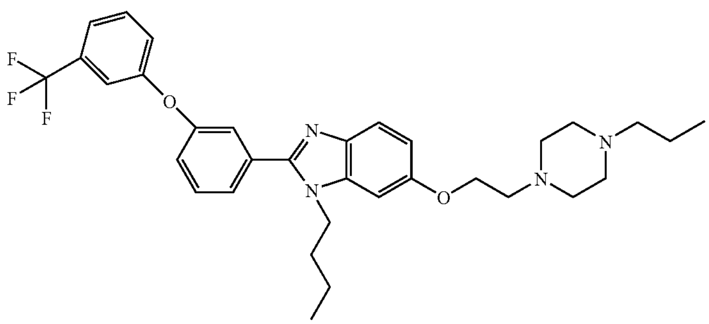 | 1-butyl-6-[2-(4-propyl-piperazin-1-yl)-ethoxy]-2-[3-(3-trifluoromethyl-phenoxy)-phenyl]-1H-benzimidazole |
| 139 | 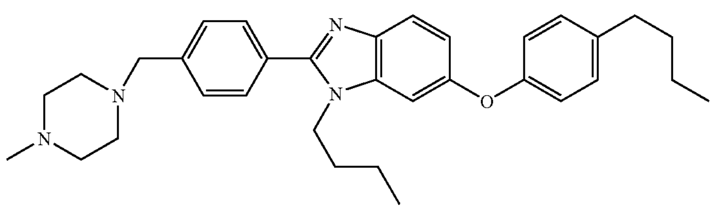 | 1-butyl-6-(4-butyl-phenoxy)-2-[4-(4-methyl-piperazin-1-ylmethyl)-phenyl]-1H-benzoimidazole |
| 140 | 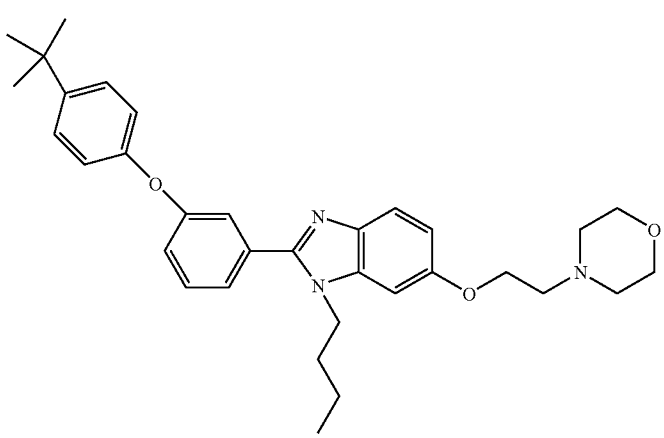 | 1-butyl-2-[3-(4-tert-butyl-phenoxy)-phenyl]-6-(2-morpholin-4-yl-ethoxy)-1H-benzimidazole |

TABLE 1-continued

| Ex. | Structure | Name |
|---|---|---|
| 141 | 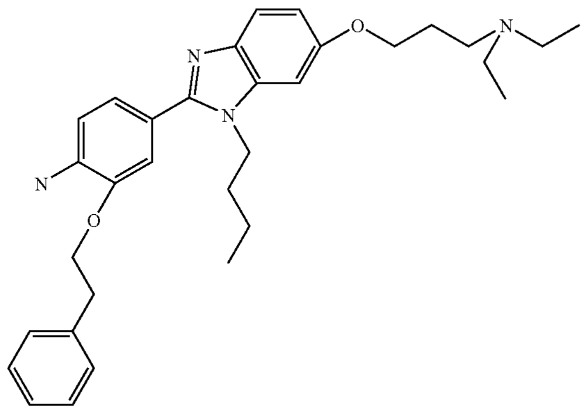 | 4-[1-butyl-6-(3-diethylamino-propoxy)-1H-benzimidazol-2-yl]-2-phenethyloxy-phenylamine |
| 142 | 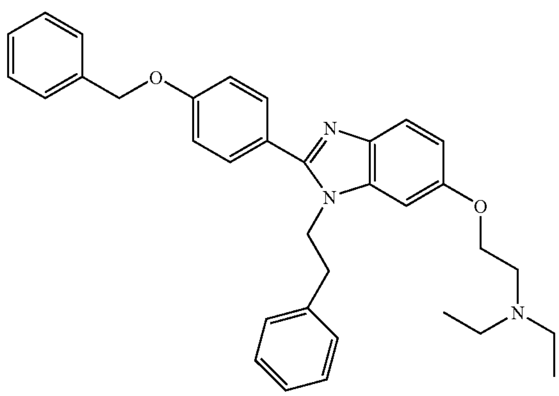 | {2-[2-(4-benzyloxy-phenyl)-3-phenethyl-3H-benzimidazol-5-yloxy]-ethyl}-diethyl-amine |
| 143 | 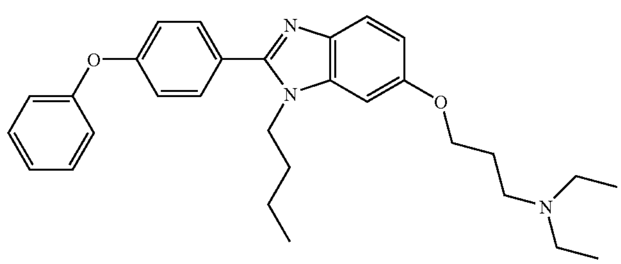 | {3-[3-butyl-2-(4-phenoxy-phenyl)-3H-benzimidazol-5-yloxy]-propyl}-diethyl-amine |
| 144 | 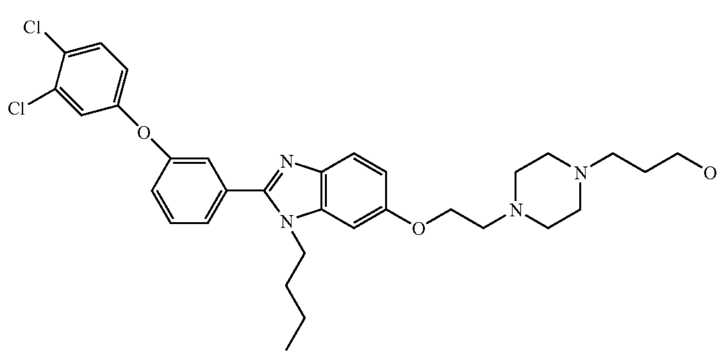 | 3-[4-(2-{3-butyl-2-[3-(3,4-dichloro-phenoxy)-phenyl]-3H-benzimidazol-5-yloxy}-ethyl)-piperazin-1-yl]-propan-1-ol |

TABLE 1-continued

| Ex. | Structure | Name |
|---|---|---|
| 145 | 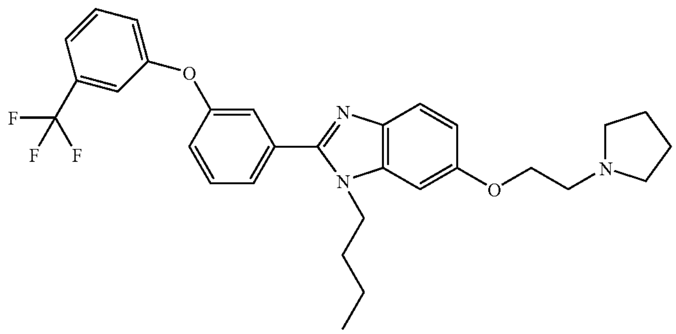 | 1-butyl-6-(2-pyrrolidin-1-yl-ethoxy)-2-[3-(3-trifluoromethyl-phenoxy)-phenyl]-1H-benzimidazole |
| 146 | 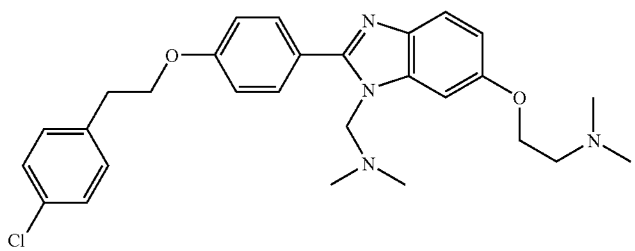 | {2-[2-[4-[2-(4-chloro-phenyl)-ethoxy]-phenyl}-6-(2-diethylamino-ethoxy)-benzimidazol-1-yl]-ethyl}-dimethyl-amine |
| 147 | 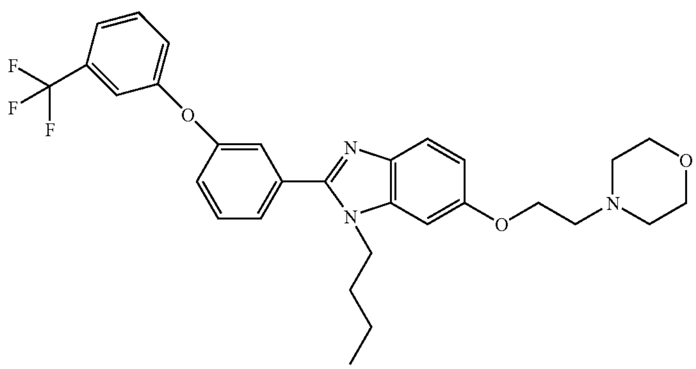 | 1-butyl-6-(2-morpholin-4-yl-ethoxy)-2-[3-(3-trifluoromethyl-phenoxy)-phenyl]-1H-benzimidazole |
| 148 | 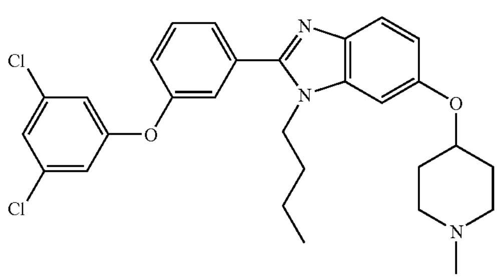 | 1-butyl-2-[3-(3,5-dichloro-phenoxy)-phenyl]-6-(1-methyl-piperidin-4-yloxy)-1H-benzoimidazole |
| 149 | 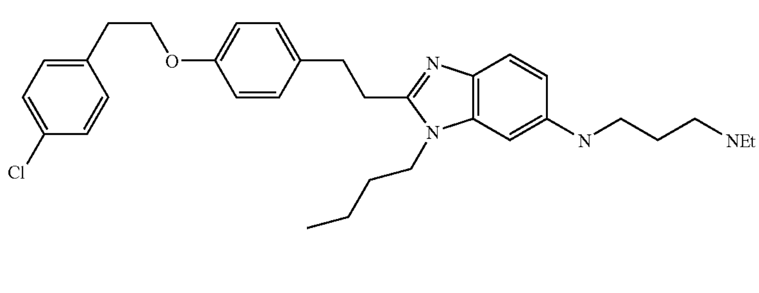 | N'-[3-butyl-2-(2-{4-[2-(4-chloro-phenyl)-ethoxy]-phenyl}-ethyl)-3H-benzimidazol-5-yl]-N,N-diethyl-propane-1,3-diamine |

TABLE 1-continued
| Ex. | Structure | Name |
|---|---|---|
| 150 | 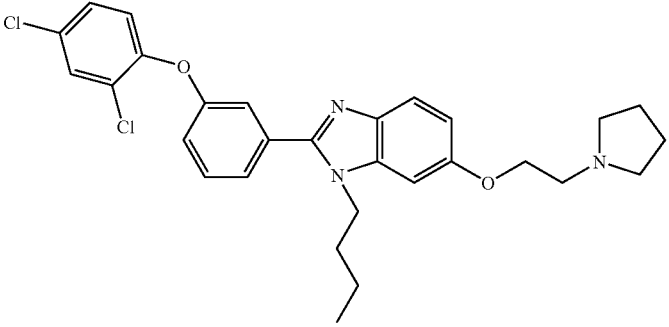 | 1-butyl-2-[3-(2,4-dichloro-phenoxy)-phenyl]-6-(2-pyrrolidin-1-yl-ethoxy)-1H-benzimidazole |
| 151 | 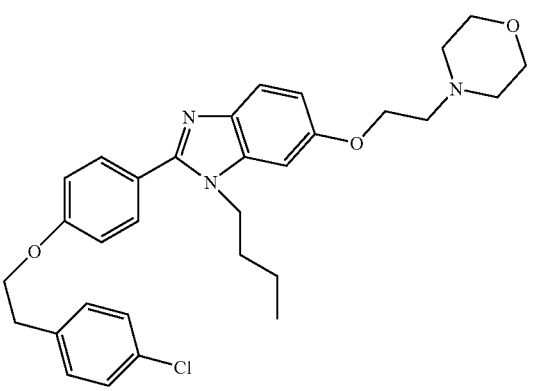 | 1-butyl-2-{4-[2-(4-chloro-phenyl)-ethoxy]-phenyl}-6-(2-morpholin-4-yl-ethoxy)-1H-benzimidazole |
| 152 | 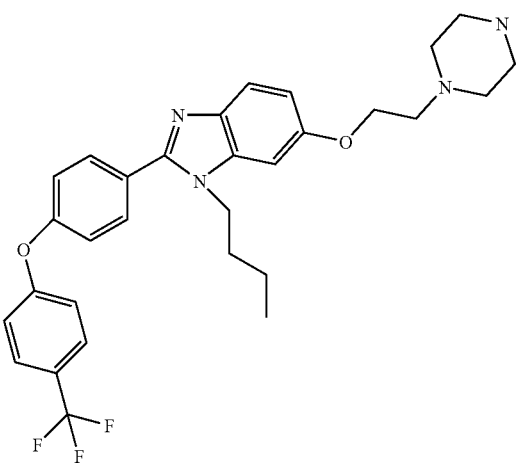 | 1-butyl-6-(2-piperazin-1-yl-ethoxy)-2-[4-(4-trifluoromethyl-phenoxy)-phenyl]-1H-benzoimidazole |

TABLE 1-continued

| Ex. | Structure | Name |
|---|---|---|
| 153 | 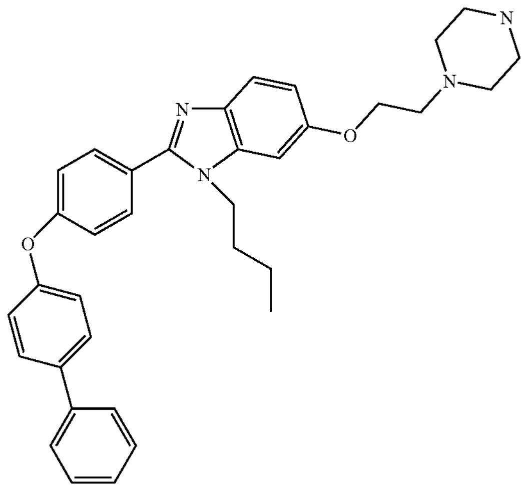 | 2-[4-(biphenyl-4-yloxy)-phenyl]-1-butyl-6-(2-piperazin-1-yl-ethoxy)-1H-benzoimidazole |
| 154 | 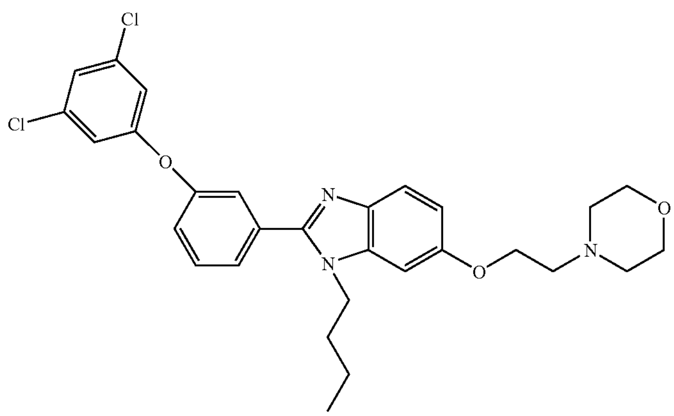 | 1-butyl-2-[3-(3,5-dichloro-phenoxy)-phenyl]-6-(2-morpholin-4-yl-ethoxy)-1H-benzimidazole |
| 155 | 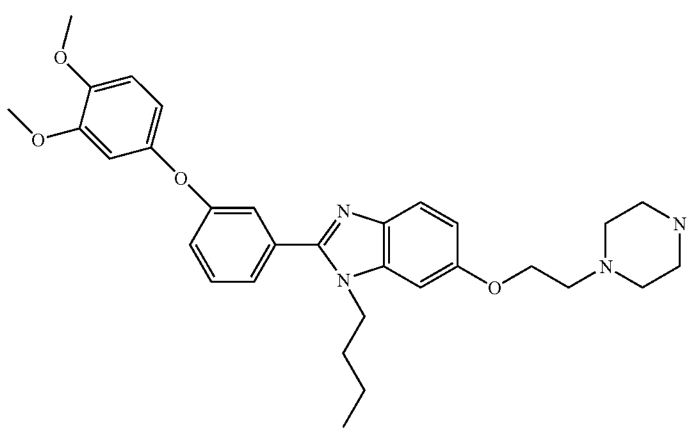 | 1-butyl-2-[3-(3,4-dimethoxy-phenoxy)-phenyl]-6-(2-piperazin-1-yl-ethoxy)-1H-benzoimidazole |

TABLE 1-continued

| Ex. | Structure | Name |
|---|---|---|
| 156 | 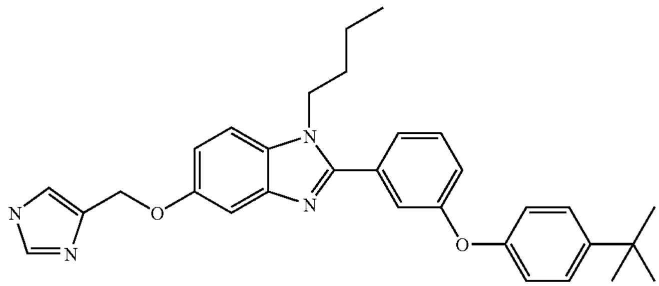 | 1-butyl-2-[3-(4-tert-butyl-phenoxy)-phenyl]-5-(1H-imidazol-4-ylmethoxy)-1H-benzoimidazole |
| 157 | 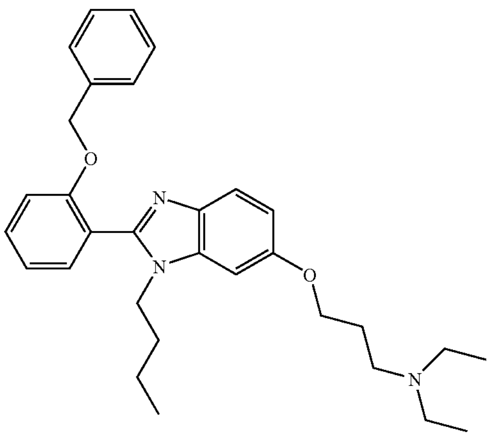 | {3-[2-(2-benzyloxy-phenyl)-3-butyl-3H-benzimidazol-5-yloxy]-propyl}-diethyl-amine |
| 158 | 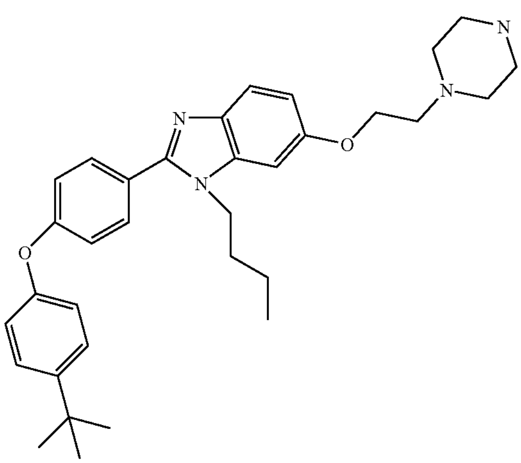 | {3-[1-Butyl-6-(3-diethylamino-propoxy)-2-piperidin-4-yl-1H-benzoimidazol-4-yloxy]-propyl}-diethyl-amine |
| 159 | 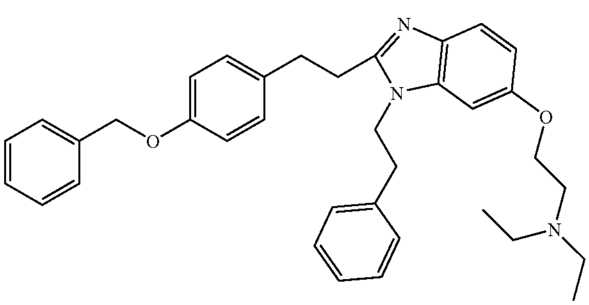 | (2-{2-[2-(4-Benzyloxy-phenyl)-ethyl]-3-phenethyl-3H-benzoimidazol-5-yloxy}-ethyl)-diethyl-amine |

TABLE 1-continued

| Ex. | Structure | Name |
|---|---|---|
| 160 | 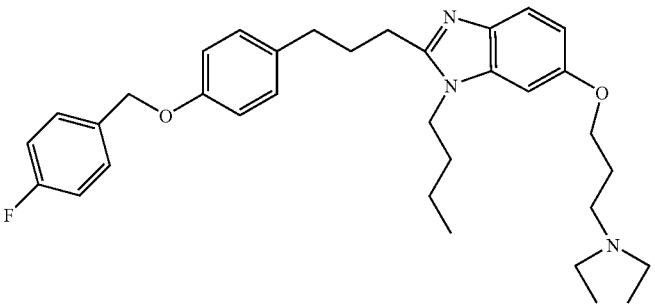 | [3-(3-Butyl-2-{3-[4-(4-fluoro-benzyloxy)-phenyl]-propyl}-3H-benzoimidazol-5-yloxy)-propyl]-diethyl-amine |
| 161 | 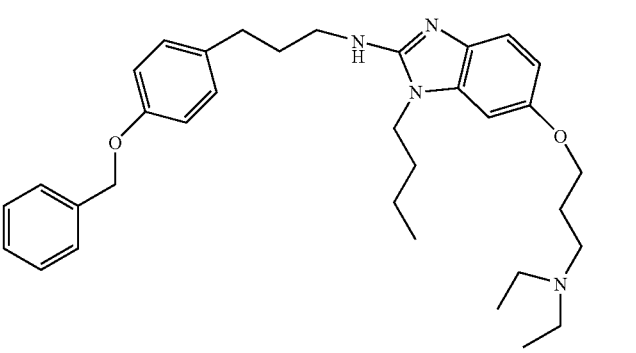 | [3-(4-Benzyloxy-phenyl)-propyl]-[1-butyl-6-(3-diethylamino-propoxy)-1H-benzoimidazol-2-yl]-amine |
| 162 | 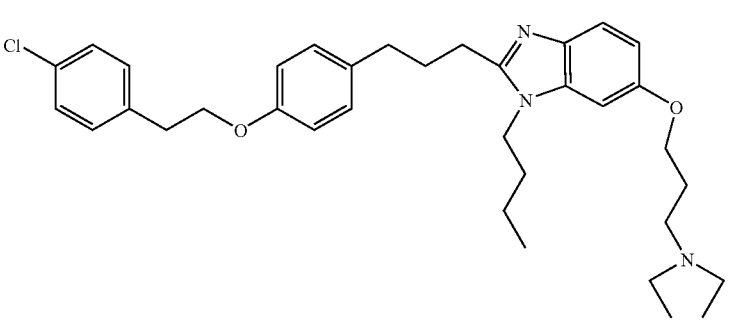 | {3-[3-Butyl-2-(3-(4-[2-(4-chloro-phenyl)-ethoxy]-phenyl]-propyl)-3H-benzoimidazol-5-yloxy]-propyl}-diethyl-amine |
| 163 | 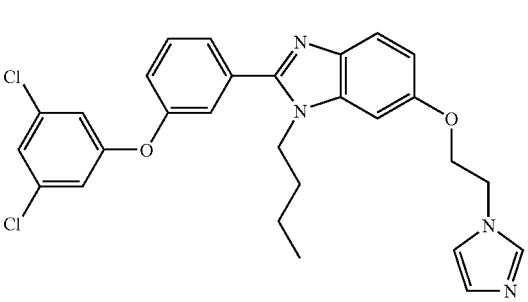 | 1-Butyl-2-[3-(3,5-dichloro-phenoxy)-phenyl]-6-(2-imidazol-1-yl-ethoxy)-1H-benzoimidazole |
| 164 | 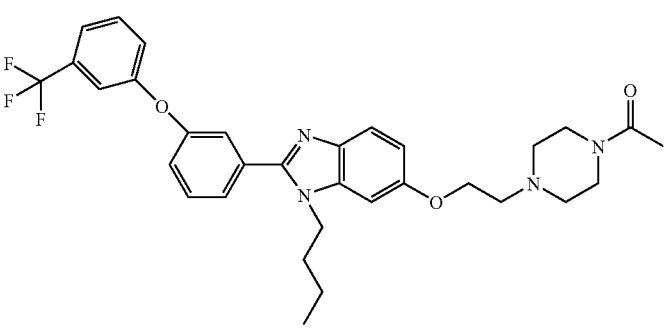 | 1-[4-(2-{3-Butyl-2-[3-(3-trifluoromethyl-phenoxy)-phenyl]-3H-benzoimidazol-5-yloxy}-ethyl)-piperazin-1-yl]-ethanone |

TABLE 1-continued

| Ex. | Structure | Name |
|---|---|---|
| 165 | 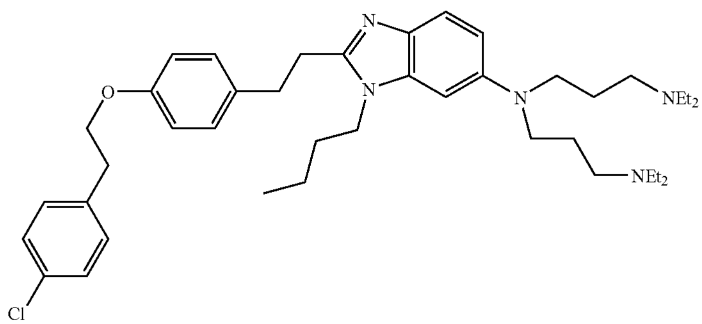 | N-[3-Butyl-2-(2-{4-[2-(4-chloro-phenyl)-ethoxy]-phenyl}-ethyl)-3H-benzoimidazol-5-yl]-N-(3-diethylamino-propyl)-N',N'-diethyl-propane-1,3-diamine |
| 166 | 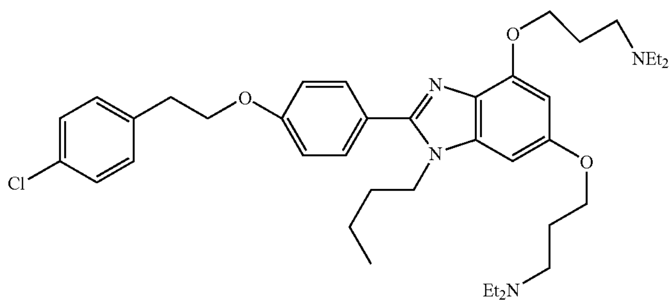 | {3-[1-butyl-2-{4-[2-(4-chloro-phenyl)-ethoxy]-phenyl}-6-(3-diethylamino-propoxy)-1H-benzimidazol-4-yl]-propyl}-diethyl-amine |
| 167 | 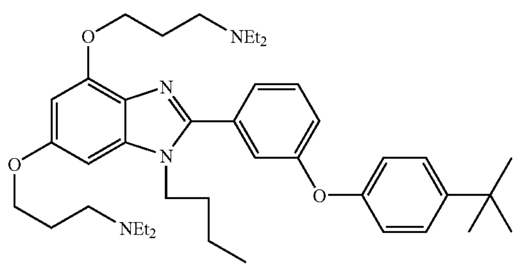 | {3-[1-Butyl-2-[3-(4-tert-butyl-phenoxy)-phenyl]-6-(3-diethylamino-propoxy)-1H-benzoimidazol-4-yloxy]-propyl}-diethyl-amine |
| 168 | 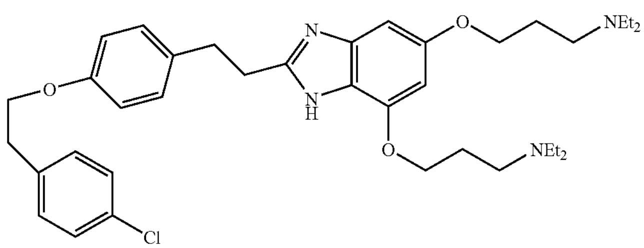 | {3-[2-(2-{4-[2-(4-chloro-phenyl)-ethoxy]-phenyl}-ethyl)-6-(3-diethylamino-propoxy)-3H-benzimidazol-4-yloxy]-propyl}-diethyl-amine |
| 169 | 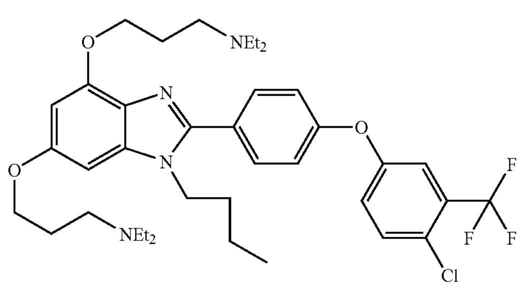 | {1-[1-Butyl-2-[4-(4-chloro-3-trifluoromethyl-phenoxy)-phenyl]-6-(3-diethylamino-propoxy)-1H-benzoimidazol-4-yloxy]-propyl}-diethyl-amine |

TABLE 1-continued

| Ex. | Structure | Name |
|---|---|---|
| 170 | 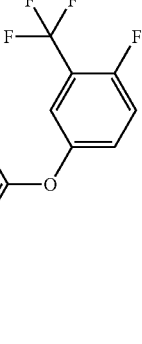 | (3-{1-Butyl-6-(3-diethylamino-propoxy)-2-[4-(4-fluoro-3-trifluoromethyl-phenoxy)-phenyl]-1H-benzoimidazol-4-yloxy}-propyl)-diethyl-amine |
| 171 | 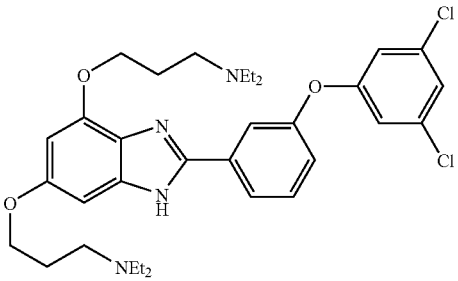 | {3-[2-[3-(3,5-Dichloro-phenoxy)-phenyl]-6-(3-diethylamino-propoxy)-1H-benzoimidazol-4-yloxy]-propyl}-diethyl-amine |
| 172 | 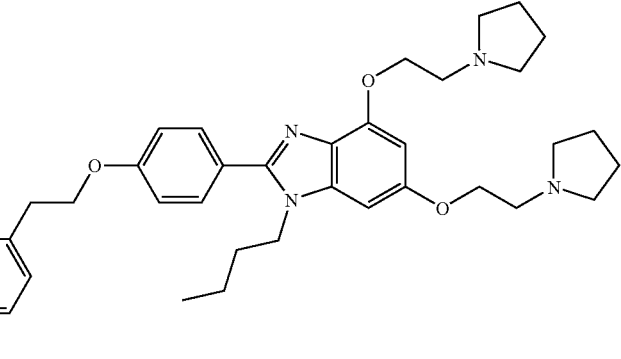 | 1-Butyl-2-{4-[2-(4-chloro-phenyl)-ethoxy]-phenyl}-4,6-bis-(2-pyrrolidin-1-yl-ethoxy)-1H-benzoimidazole |
| 173 | 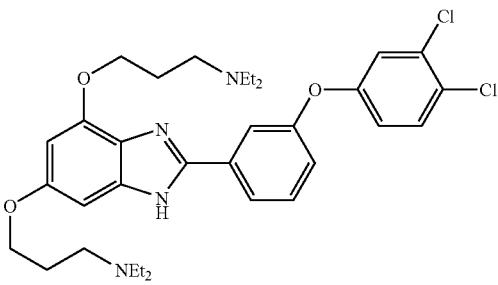 | {3-(2-[3-(3,4-Dichloro-phenoxy)-phenyl]-6-(3-diethylamino-propoxy)-1H-benzoimidazol-4-yloxy]-propyl}-diethyl-amine |
| 174 | 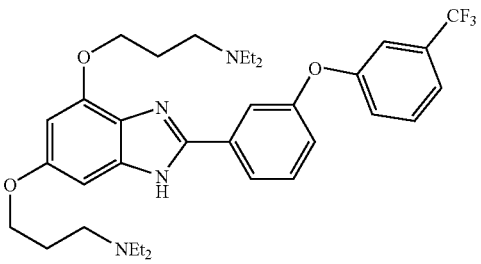 | (3-{6-(3-diethylamino-propoxy)-2-(3-(3-trifluoromethyl-phenoxy)-phenyl]-1H-benzimidazol-4-yloxy}-propyl)-diethyl-amine |

TABLE 1-continued

| Ex. | Structure | Name |
| --- | --- | --- |
| 175 | 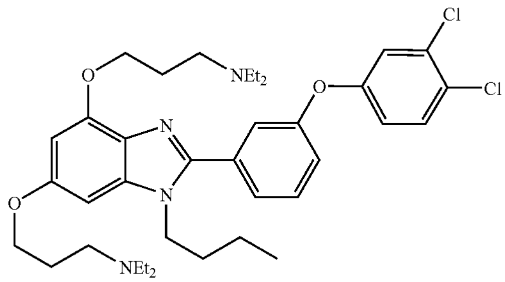 | {3-[1-Butyl-2-[3-(3,4-dichloro-phenoxy)-phenyl]-6-(3-diethylamino-propoxy)-1H-benzoimidazol-4-yloxy]-propyl}-diethyl-amine |
| 176 | 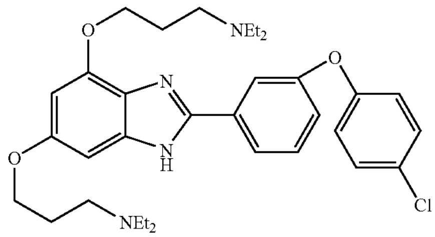 | {3-[2-[3-(4-Chloro-phenoxy)-phenyl]-6-(3-diethylamino-propoxy)-1H-benzoimidazol-4-yloxy]-propyl}-diethyl-amine |
| 177 | 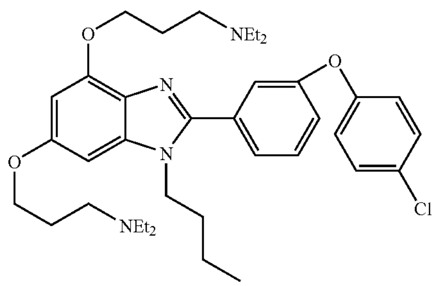 | {3-[1-Butyl-2-[3-(4-chloro-phenoxy)-phenyl]-6-(3-diethylamino-propoxy)-1H-benzoimidazol-4-yloxy]-propyl}-diethyl-amine |
| 178 | 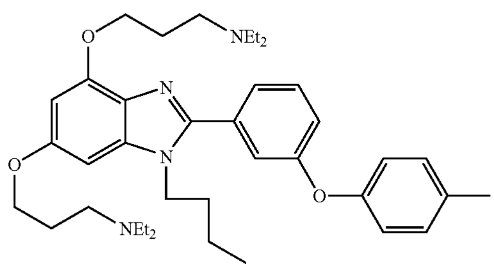 | {3-[1-Butyl-6-(3-diethylamino-propoxy)-2-(3-p-tolyloxy-phenyl)-1H-benzoimidazol-4-yloxy]-propyl}-diethyl-amine |
| 179 | 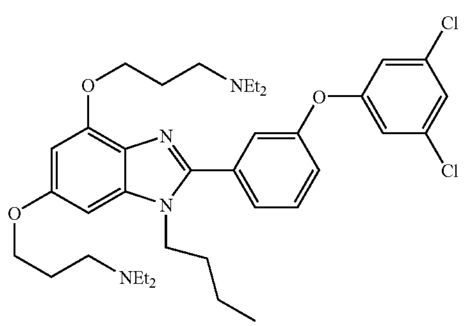 | {3-[1-Butyl-2-[3-(3,5-dichloro-phenoxy)-phenyl]-6-(3-diethylamino-propoxy)-1H-benzoimidazol-4-yloxy]-propyl}-diethyl-amine |

TABLE 1-continued

| Ex. | Structure | Name |
|---|---|---|
| 180 | 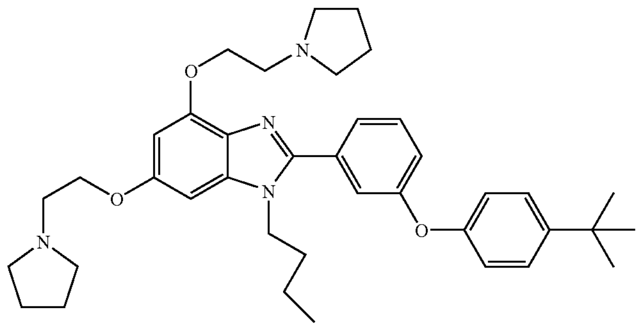 | 1-Butyl-2-[3-(4-tert-butyl-phenoxy)-phenyl]-4,6-bis-(2-pyrrolidin-1-yl-ethoxy)-1H-benzoimidazole |
| 181 | 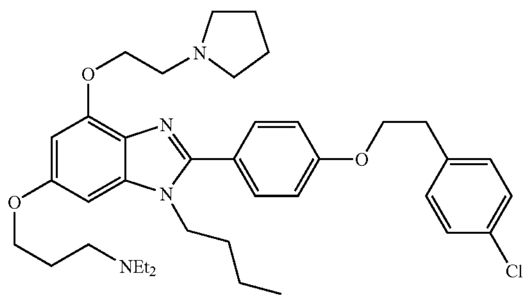 | {3-[3-Butyl-2-(4-[2-(4-chloro-phenyl)-ethoxy]-phenyl}-7-(2-pyrrolidin-1-yl-ethoxy)-3H-benzoimidazol-5-yloxy]-propyl}-diethyl-amine |
| 182 | 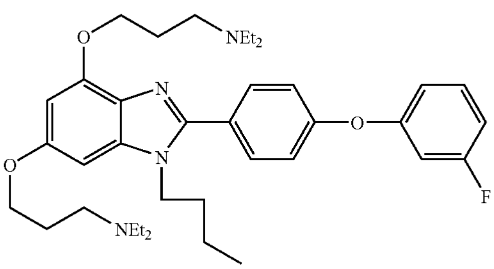 | (3-{1-butyl-6-(3-diethylamino-propoxy)-2-[4-(3-fluoro-phenoxy)-phenyl]-1H-benzimidazol-4-yloxy}-propyl)-diethyl-amine |
| 183 | 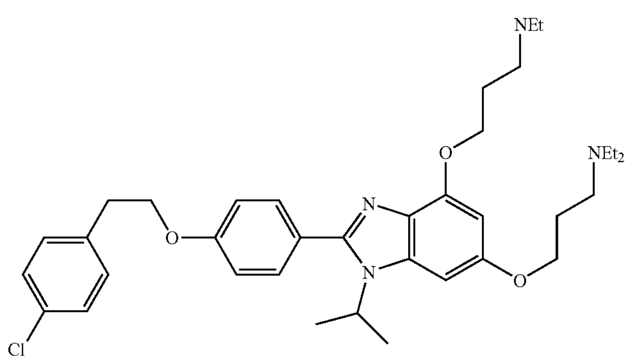 | {3-[2-{4-[2-(4-chloro-phenyl)-ethoxy]-phenyl}-6-(3-diethylamino-propoxy)-1-isopropyl-1H-benzimidazol-4-yloxyl-propyl]-diethyl-amine |

TABLE 1-continued

| Ex. | Structure | Name |
|---|---|---|
| 184 | 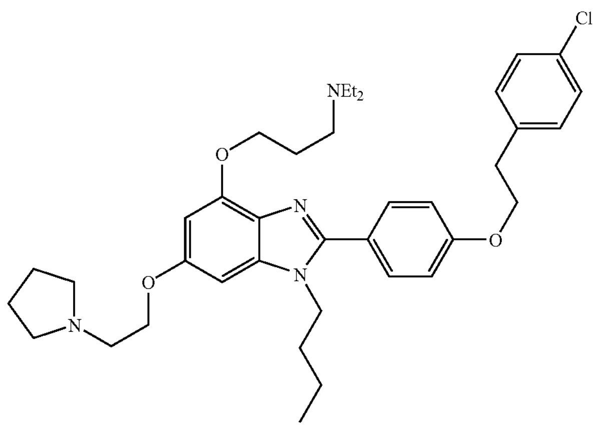 | {3-[1-Butyl-2-{4-[2-(4-chloro-phenyl)-ethoxy]-phenyl}-6-(2-pyrrolidin-1-yl-ethoxy)-1H-benzoimidazol-4-yloxy]-propyl}-diethyl-amine |
| 185 | 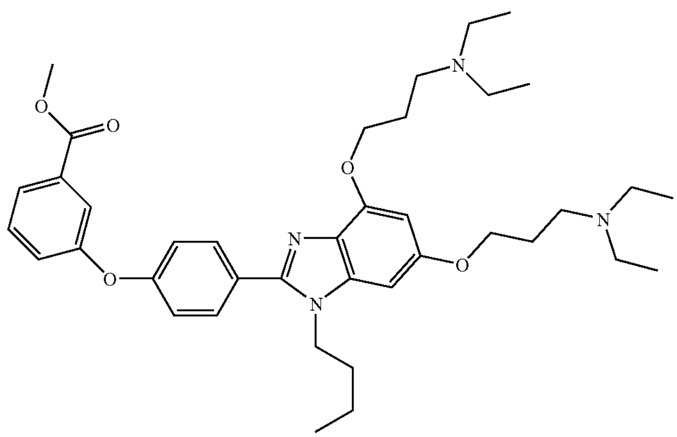 | 2-{4-[1-butyl-4,6-bis-(3-diethylamino-propoxy)-1H-benzimidazol-2-yl-phenoxy}-benzoic acid methyl ester |
| 186 | 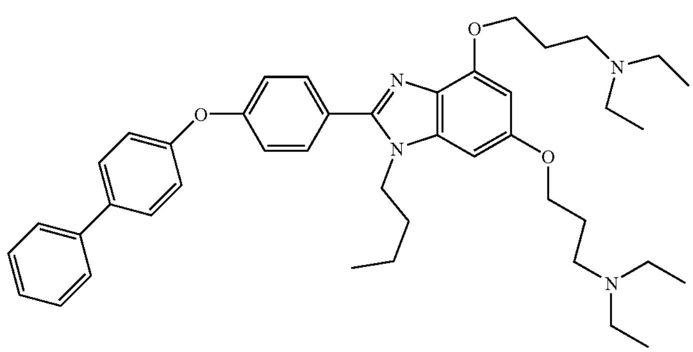 | (3-[2-[4-(biphenyl-4-yloxy)-phenyl]-1-butyl-6-(3-diethylamino-propoxy)-1H-benzoimidazol-4-yloxy]-propyl}-diethyl-amine |
| 187 | 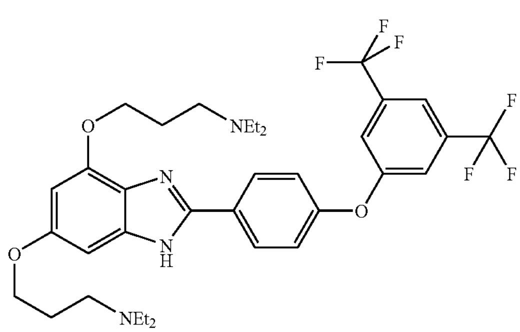 | {3-[2-[4-(3,5-Bis-trifluoromethyl-phenoxy)-phenyl]-6-(3-diethylamino-propoxy)-1H-benzoimidazol-4-yloxy]-propyl}-diethyl-amine |

TABLE 1-continued

| Ex. | Structure | Name |
| --- | --- | --- |
| 188 | 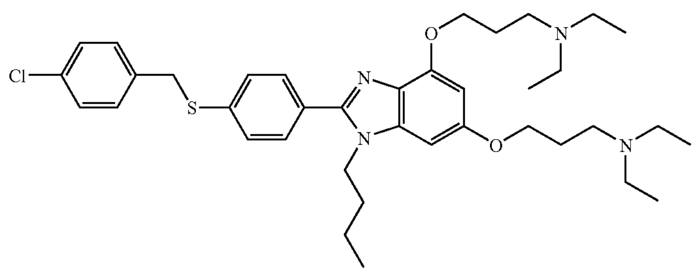 | (3-[1-butyl-2-[4-(4-chloro-benzylsulfanyl)-phenyl]-6-(3-diethylamino-propoxy)-1H-benzimidazol-4-yloxy]-propyl}-diethyl-amine |
| 189 | 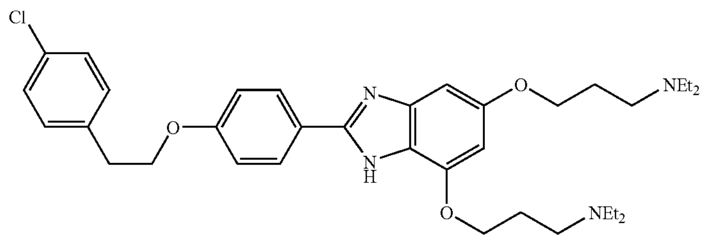 | {3-[2-{4-[2-(4-chloro-phenyl)-ethoxy]-phenyl}-6-(3-diethylamino-propoxy)-3H-benzimidazol-4-yloxy]-propyl}-diethyl-amine |
| 190 | 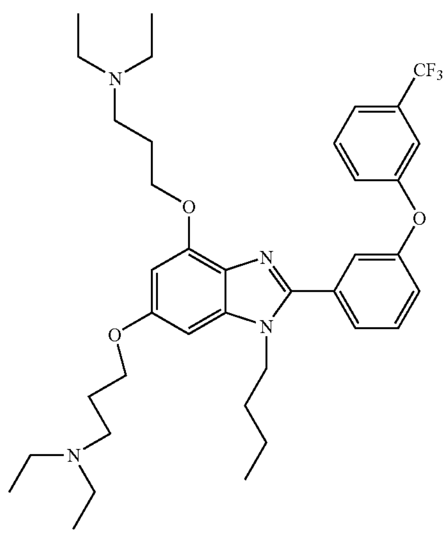 | (3-{1-butyl-6-(3-diethylamino-propoxy)-2-[3-(3-trifluoromethyl-phenoxy)-phenyl]-1H-benzimidazol-4-yloxy}-propyl)-diethyl-amine |
| 191 | 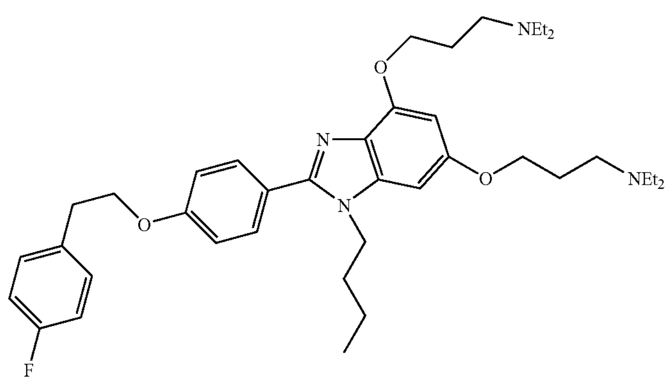 | [3-(1-butyl-6-(3-diethylamino-propoxy)-2-{4-[2-(4-fluoro-phenyl)-ethoxy]-phenyl}-1H-benzimidazol-4-yloxy}-propyl)-diethyl-amine |

TABLE 1-continued

| Ex. | Structure | Name |
|---|---|---|
| 192 | 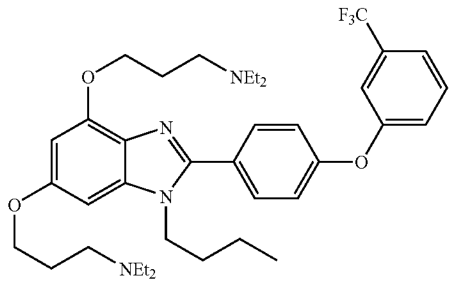 | (3-{1-butyl-6-(3-diethylamino-propoxy)-2-[4-(3-trifluoromethyl-phenoxy)-phenyl]-1H-benzimidazol-4-yloxy}-propyl)-diethyl-amine |
| 193 | 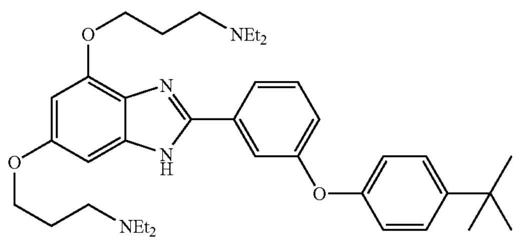 | {3-[2-[3-(4-tert-Butyl-phenoxy)-phenyl]-6-(3-diethylamino-propoxy)-1H-benzoimidazol-4-yloxy]-propyl}-diethyl-amine |
| 194 | 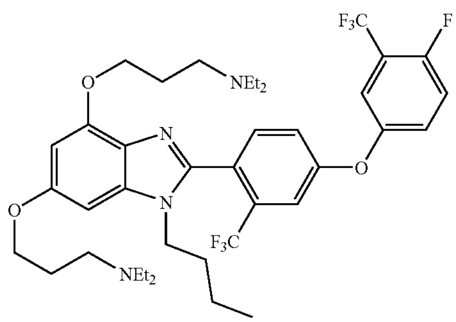 | (3-{1-Butyl-6-(3-diethylamino-propoxy)-2-[4-(4-fluoro-3-trifluoromethyl-phenoxy)-2-trifluoromethyl-phenyl]-1H-benzoimidazol-4-yloxy}-propyl)-diethyl-amine |
| 195 | 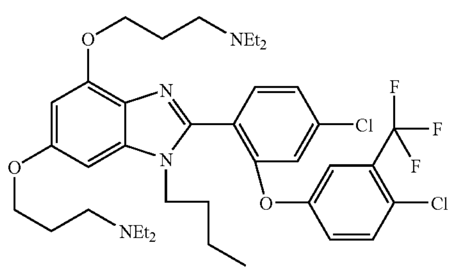 | {3-[1-Butyl-2-[4-chloro-2-(4-chloro-3-trifluoromethyl-phenoxy)-phenyl]-6-(3-diethylamino-propoxy)-1H-benzoimidazol-4-yloxyl-propyl}-diethyl-amine |
| 196 | 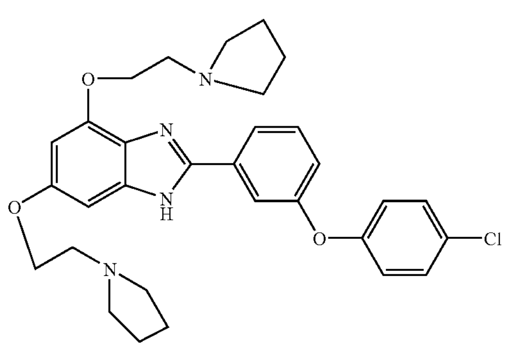 | 2-[3-(4-Chloro-phenoxy)-phenyl]-4,6-bis-(2-pyrrolidin-1-yl-ethoxy)-1H-benzoimidazole |

TABLE 1-continued

| Ex. | Structure | Name |
|---|---|---|
| 197 | 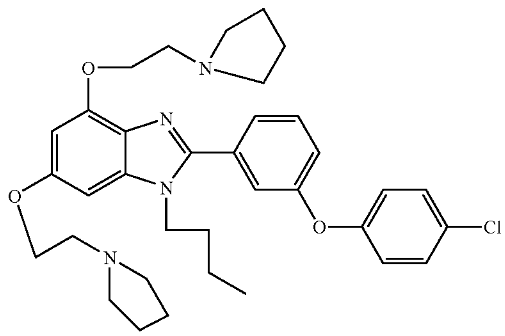 | 1-Butyl-2-[3-(4-chloro-phenoxy)-phenyl]-4,6-bis-(2-pyrrolidin-1-yl-ethoxy)-1H-benzoimidazole |
| 198 | 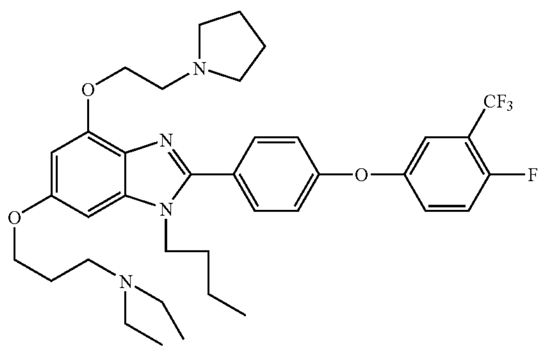 | {3-[3-butyl-2-[4-(4-fluoro-3-trifluoromethyl-phenoxy)-phenyl]-7-(2-pyrrolidin-1-yl-ethoxy)-3H-benzimidazol-5-yloxy]-propyl}-diethyl-amine |
| 199 | 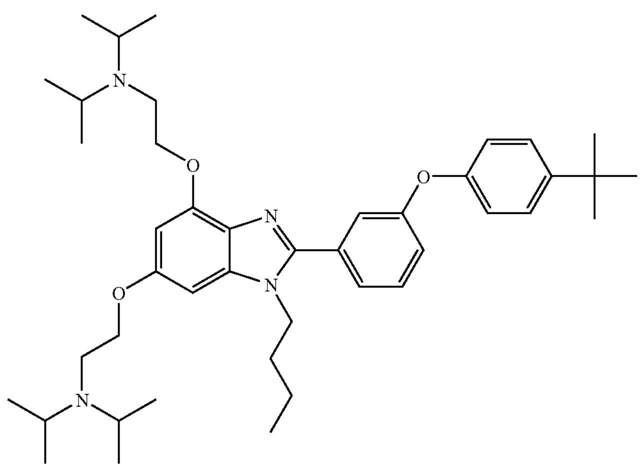 | {2-[1-butyl-2-[3-(4-tert-butyl-phenoxy)-phenyl]-6-(2-diisopropylamino-ethoxy)-1H-benzimidazol-4-yloxy]-ethyl}-diethyl-amine |
| 200 | 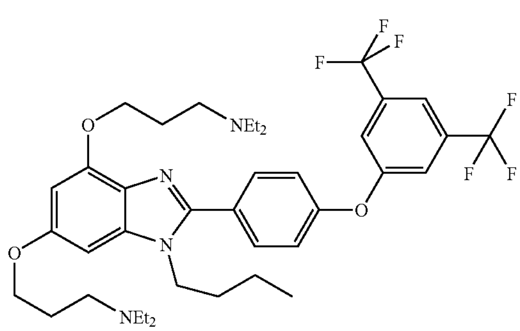 | {3-[2-[4-(3,5-Bis-trifluoromethyl-phenoxy)-phenyl]-1-butyl-6-(3-diethylamino-propoxy)-1H-benzoimidazol-4-yloxy]-propyl}-diethyl-amine |

TABLE 1-continued

| Ex. | Structure | Name |
|---|---|---|
| 201 | 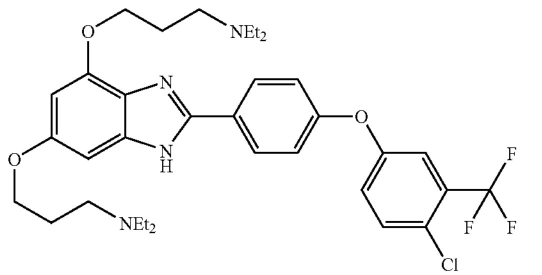 | {3-[2-[4-(3,5-Bis-trifluoromethyl-phenoxy)-phenyl]-1-butyl-6-(3-diethylamino-propoxy)-1H-benzoimidazol-4-yloxy]-propyl}-diethyl-amine |
| 202 | 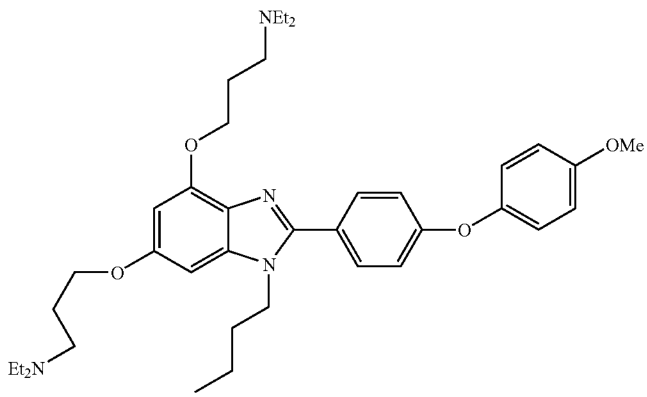 | (3-{1-butyl-6-(3-diethylamino-propoxy)-2-[4-(4-methoxy-phenoxy)-phenyl]-1H-benzimidazol-4-yloxy}-propyl)-diethyl-amine |
| 203 | 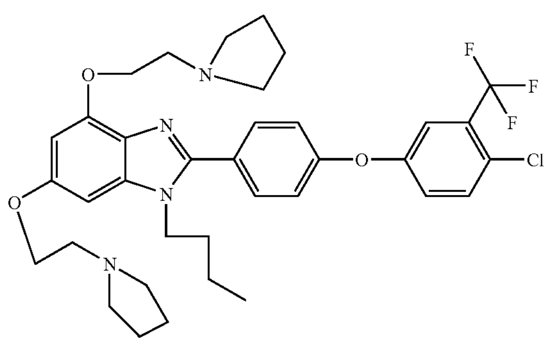 | 1-Butyl-2-[4-(4-chloro-3-trifluoromethyl-phenoxy)-phenyl]-4,6-bis-(2-pyrrolidin-1-yl-ethoxy)-1H-benzoimidazole |
| 204 | 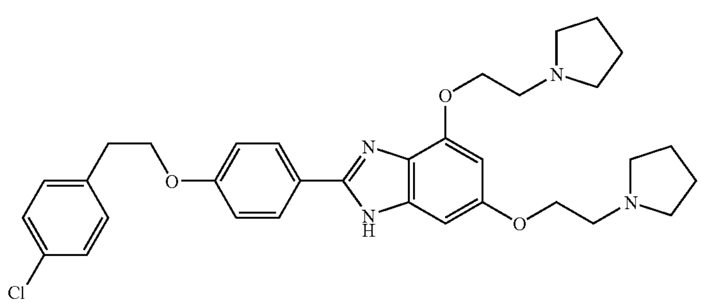 | 2-{4-[2-(4-Chloro-phenyl)-ethoxy]-phenyl}-4,6-bis-(2-pyrrolidin-1-yl-ethoxy)-1H-benzoimidazole |

TABLE 1-continued

| Ex. | Structure | Name |
|---|---|---|
| 205 | 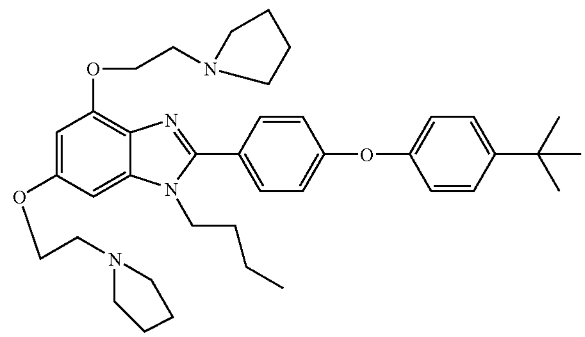 | 1-Butyl-2-[4-(4-tert-butyl-phenoxy)-phenyl]-4,6-bis-(2-pyrrolidin-1-yl-ethoxy)-1H-benzoimidazole |
| 206 | 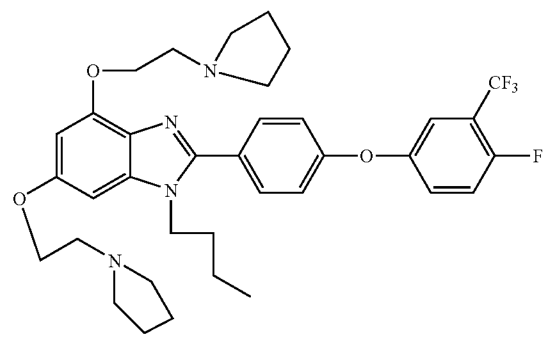 | 1-Butyl-2-[4-(4-fluoro-3-trifluoromethyl-phenoxy)-phenyl]-4,6-bis-(2-pyrrolidin-1-yl-ethoxy)-1H-benzoimidazole |
| 207 | 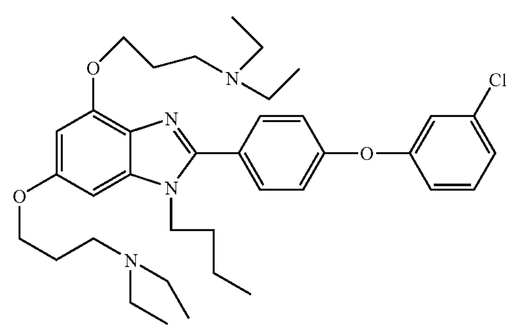 | {3-[1-Butyl-2-[4-(3-chloro-phenoxy)-phenyl]-6-(3-diethylamino-propoxy)-1H-benzoimidazol-4-yloxyl-propyl}-diethyl-amine |
| 208 | 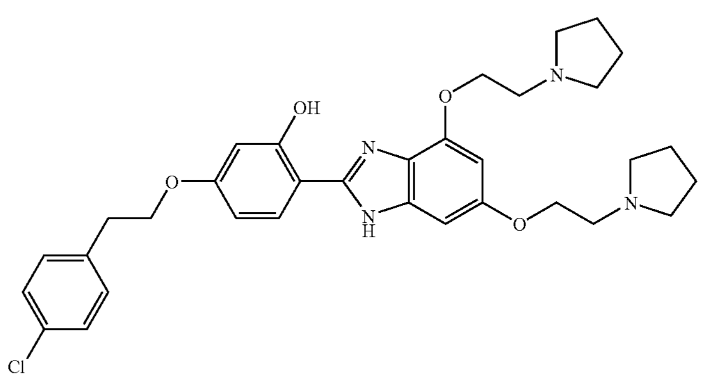 | 2-[5,7-bis-(2-pyrrolidin-1-yl-ethoxy)-1H-benzimidazol-2-yl]-5-[2-(4-chloro-phenyl)-ethoxy]-phenol |

TABLE 1-continued

| Ex. | Structure | Name |
|---|---|---|
| 209 | 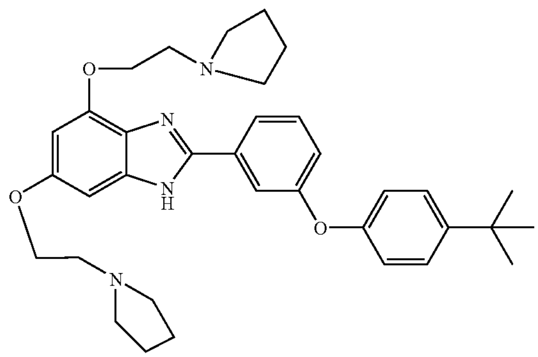 | 2-[3-(4-tert-butyl-phenoxy)-phenyl]-4,6-bis-(2-pyrrolodin-1-yl-ethoxy)-1H-benzimidazole |
| 210 | 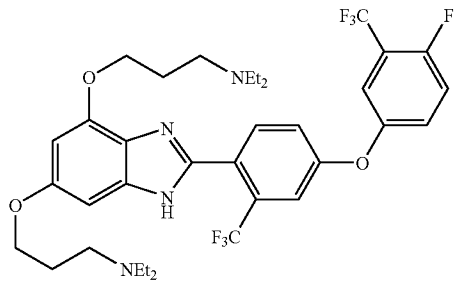 | (3-{6-(3-Diethylamino-propoxy)-2-[2-(1,1-difluoro-ethyl)-4-(4-fluoro-3-trifluoromethyl-phenoxy)-phenyl]-1H-benzoimidazol-4-yloxy}-propyl)-diethyl-amine |
| 211 | 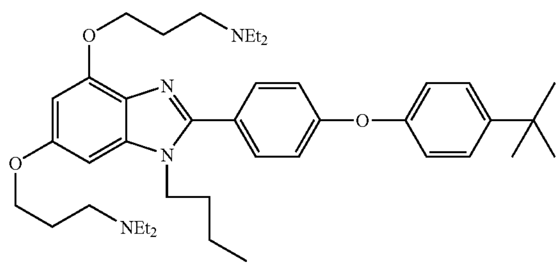 | {3-[1-Butyl-2-[4-(4-tert-butyl-phenoxy)-phenyl]-6-(3-diethylamino-propoxy)-1H-benzoimidazol-4-yloxy]-propyl}-diethyl-amine |
| 212 | 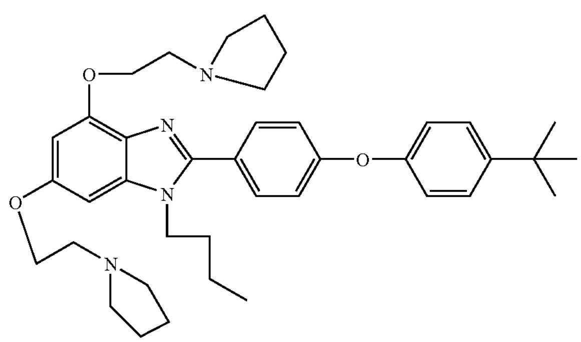 | 2-[4-(4-tert-Butyl-phenoxy)-phenyl]-4,6-bis-(2-pyrrolidin-1-yl-ethoxy)-1H-benzoimidazole |
| 213 | 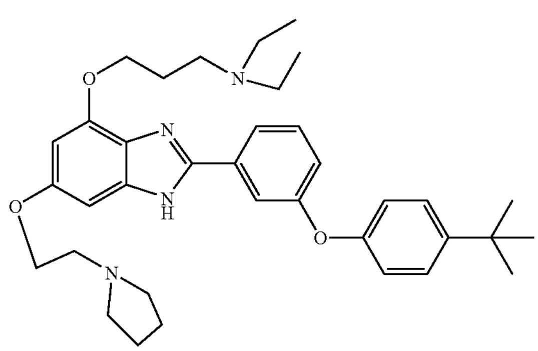 | {3-[1-Butyl-2-[3-(4-tert-butyl-phenoxy)-phenyl]-6-(2-pyrrolidin-1-yl-ethoxy)-1H-benzoimidazol-4-yloxy]-propyl}-diethyl-amine |

TABLE 1-continued

| Ex. | Structure | Name |
|---|---|---|
| 214 | 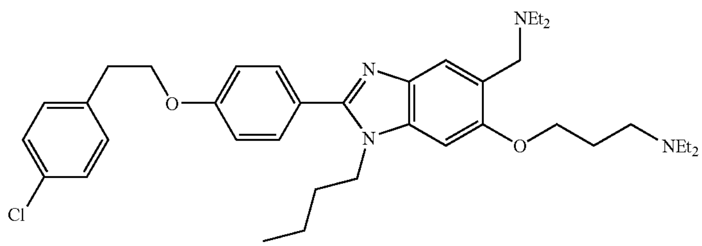 | [3-(3-butyl-2-(4-[2-(4-chloro-phenyl)-ethoxy]-phenyl}-6-diethylaminomethyl-3H-benzimidazol-5-yloxy)-propyl]-diethyl-amine |
| 215 | 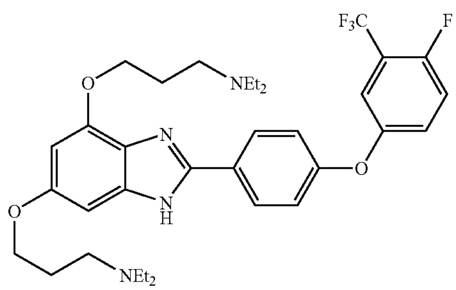 | (3-{6-(3-Diethylamino-propoxy)-2-[4-(4-fluoro-3-trifluoromethyl-phenoxy)-phenyl]-1H-benzoimidazol-4-yloxy}-propyl)-diethyl-amine |
| 216 | 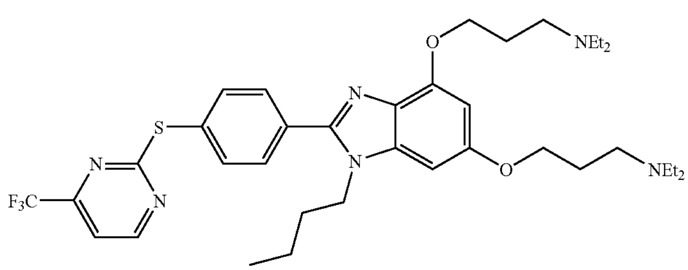 | (3-{1-butyl-6-(3-diethylamino-propoxy)-2-[4-(4-trifluoromethyl-pyrimidin-2-ylsulfanyl)-phenyl]-1H-benzoimidazol-4-yloxy}-propyl)-diethyl-amine |
| 217 | 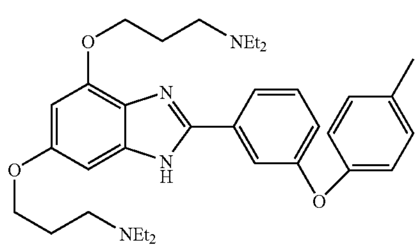 | {3-[6-(3-Diethylamino-propoxy)-2-(3-p-tolyloxy-phenyl)-1H-benzoimidazol-4-yloxy]-propyl}-diethyl-amine |
| 218 | 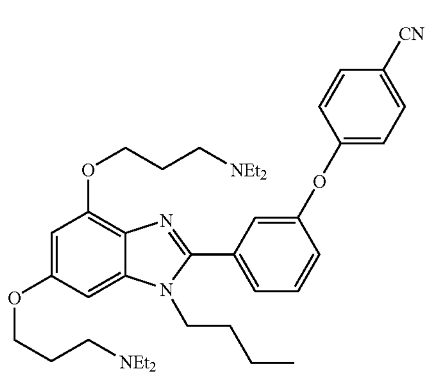 | 4-{3-[1-Butyl-4,6-bis-(3-diethylamino-propoxy)-1H-benzoimidazol-2-yl]-phenoxy}-benzonitrile |

TABLE 1-continued

| Ex. | Structure | Name |
|-----|-----------|------|
| 219 | 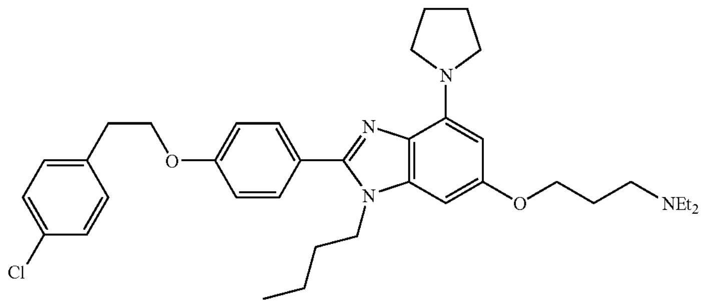 | [3-(3-Butyl-2-{4-[2-(4-chloro-phenyl)-ethoxy]-phenyl]-7-pyrrolidin-1-yl-3H-benzoimidazol-5-yloxy)-propyl]-diethyl-amine |
| 220 | 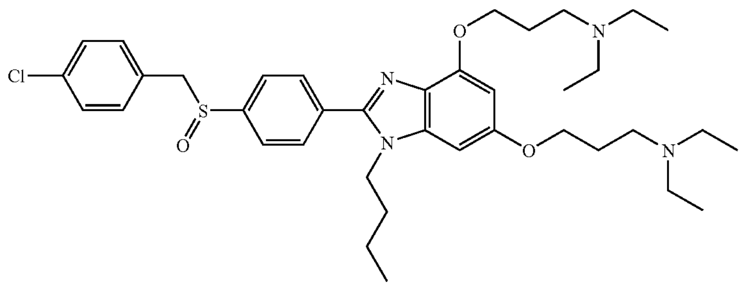 | {3-[1-butyl-2-[4-(4-chloro-phenylmethanesulfinyl)-phenyl]-6-(3-diethylamino-propoxy)-1H-benzimidazol-4-yloxy]-propyl}-diethyl-amine |
| 221 | 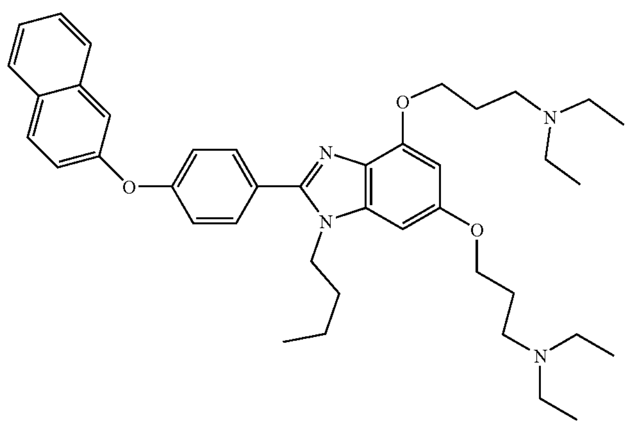 | (3-{1-butyl-6-(3-diethylamino-propoxy)-2-[4-(naphthalen-2-yloxy)-phenyl]-1H-benzoimidazole-4-yloxy}-propyl)-diethyl-amine |
| 222 | 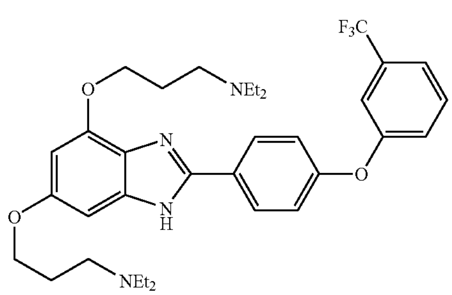 | (3-{6-(3-diethylamino-propoxy)-2-[4-(3-trifluoromethyl-phenoxy)-phenyl]-1H-benzimidazol-4-yloxy}-propyl)-diethyl-amine |

TABLE 1-continued

| Ex. | Structure | Name |
|---|---|---|
| 223 | 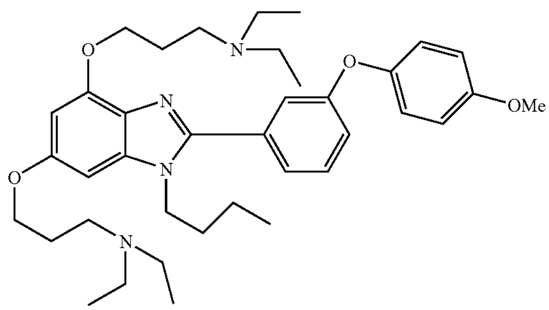 | (3-{1-butyl-6-(3-diethylamino-propoxy)-2-[3-(4-methoxy-phenoxy)-phenyl]-1H-benzimidazol-4-yloxyl-propyl)-diethyl-amine |
| 224 | 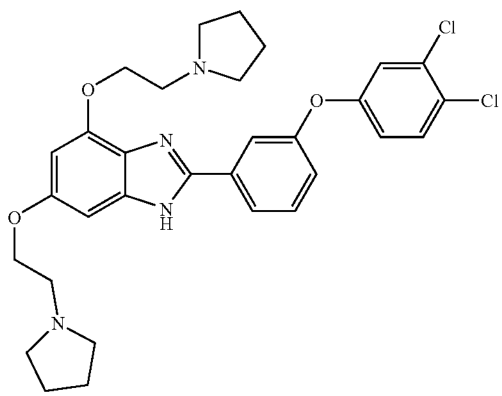 | 2-[3-(3,4-Dichloro-phenoxy)-phenyl]-4,6-bis-(2-pyrrolidin-1-yl-ethoxy)-1H-benzoimidazole |
| 225 | 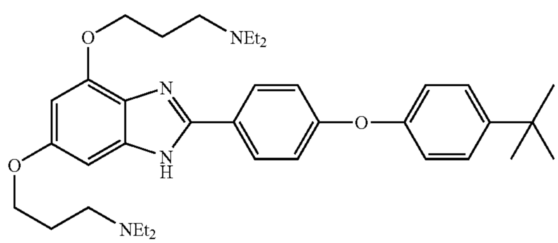 | {3-[2-[4-(4-tert-Butyl-phenoxy)-phenyl)-6-(3-diethylamino-propoxy)-1H-benzoimidazol-4-yloxy]-propyl}-diethyl-amine |
| 226 | 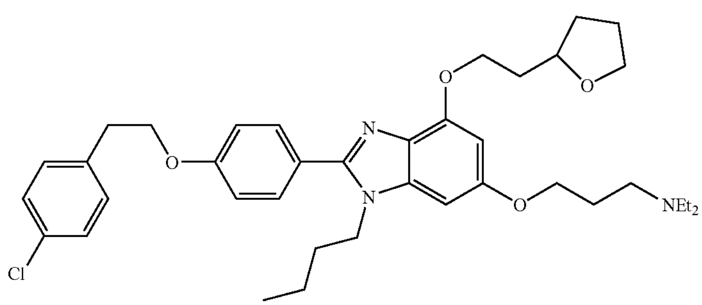 | {3-[3-butyl-2-{4-[2-(4-chloro-phenyl)-ethoxy]-phenyl}-7-[2-(tetrahydro-furan-2-yl)-ethoxy]-3H-benzimidazol-5-yloxy}-propyl)-diethyl-amine |
| 227 | 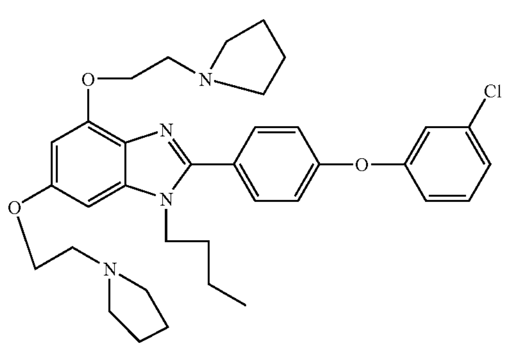 | 1-Butyl-2-[4-(3-chloro-phenoxy)-phenyl]-4,6-bis-(2-pyrrolidin-1-yl-ethoxy)-1H-benzoimidazole |

TABLE 1-continued

| Ex. | Structure | Name |
|---|---|---|
| 228 | 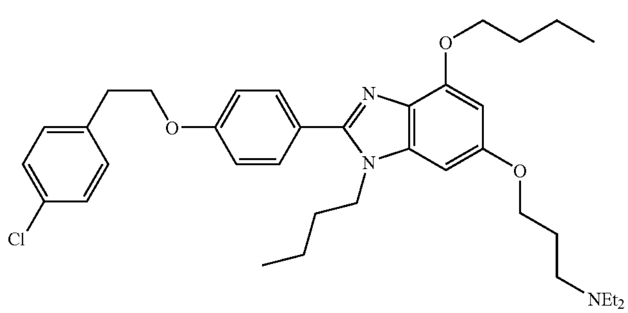 | [3-(7-Butoxy-3-butyl-2-{4-[2-(4-chloro-phenyl)-ethoxy]-phenyl}-3H-benzoimidazol-5-yloxy)-propyl]-diethyl-amine |
| 229 | 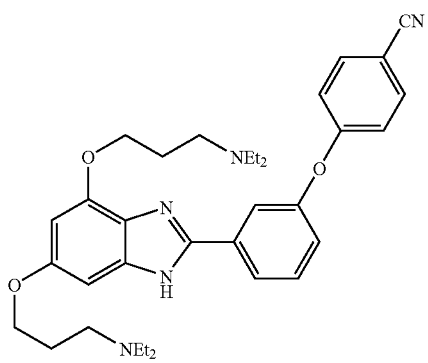 | 4-{3-[4,6-Bis-(3-diethylamino-propoxy)-1H-benzoimidazol-2-yl]-phenoxy}-benzonitrile |
| 230 | 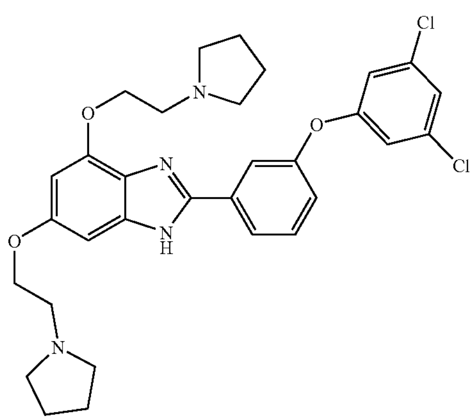 | 2-[3-(3,5-Dichloro-phenoxy)-phenyl]-4,6-bis-(2-pyrrolidin-1-yl-ethoxy)-1H-benzoimidazole |
| 231 | 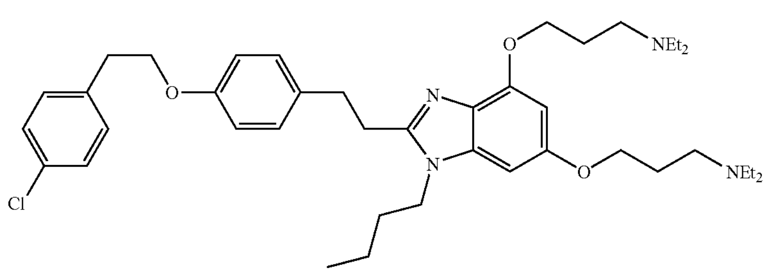 | {3-[1-butyl-2-(2-{4-[2-(4-chloro-phenyl)-ethoxy]-phenyl}-ethyl)-6-(3-diethylamino-propoxy)-1H-benzimidazol-4-yloxy]-propyl}-diethyl-amine |

TABLE 1-continued

| Ex. | Structure | Name |
|---|---|---|
| 232 | 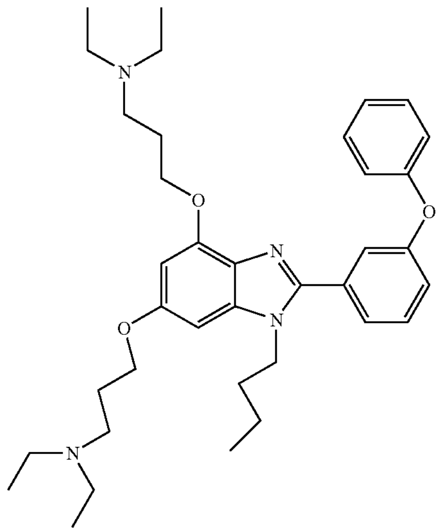 | {3-[1-butyl-6-(3-diethylamino-propoxy)-2-(3-phenoxy-phenyl)-1H-benzimidazol-4-yloxy]-propyl]-diethyl-amine |
| 233 | 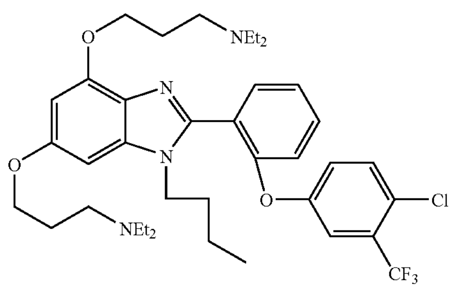 | {3-[1-Butyl-2-[2-(4-chloro-3-trifluoromethyl-phenoxy)-phenyl]-6-(3-diethylamino-propoxy)-1H-benzoimidazol-4-yloxy]-propyl}-diethyl-amine |
| 234 | 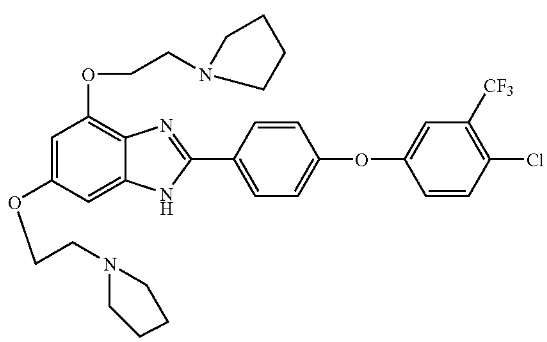 | 2-[4-(4-Chloro-3-trifluoromethyl-phenoxy)-phenyl]-4,6-bis-(2-pyrrolidin-1-yl-ethoxy)-1H-benzoimidazole |
| 235 | 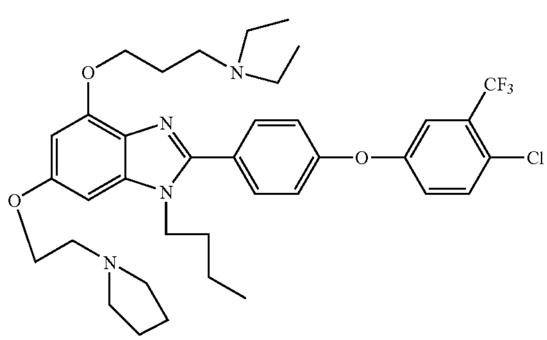 | {3-(1-Butyl-2-[4-(4-fluoro-3-trifluoromethyl-phenoxy)-phenyl]-6-(2-pyrrolidin-1-yl-ethoxy)-1H-benzoimidazol-4-yloxy]-propyl)-diethyl-amine |

TABLE 1-continued

| Ex. | Structure | Name |
|---|---|---|
| 236 | 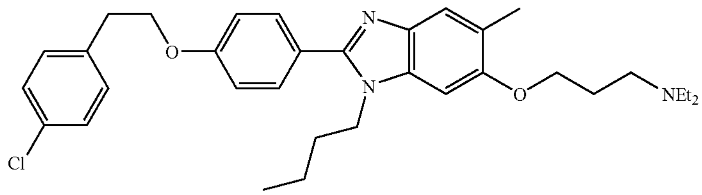 | [3-(3-butyl-2-{4-[2-(4-chloro-phenyl)-ethoxy]-phenyl}-6-methyl-3H-benzimidazol-5-yloxy)-propyl]-diethyl-amine |
| 237 | 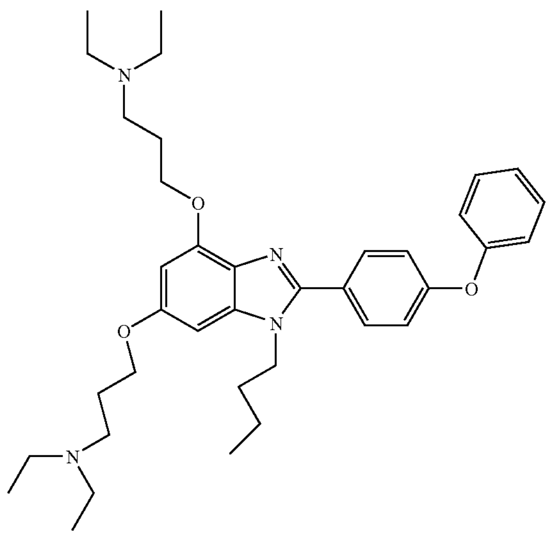 | {3-[1-butyl-6-(3-diethylamino-propoxy)-2-(4-phenoxy-phenyl)-1H-benzimidazol-4-yloxy]-propyl}-diethyl-amine |
| 238 | 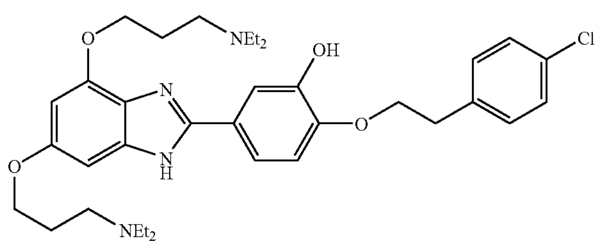 | 5-[4,6-bis-(3-diethylamino-propoxy)-1H-benzoimidazlo-2-yl]-2-[2-(4-chloro-phenyl)-ethoxy]-phenol |
| 239 | 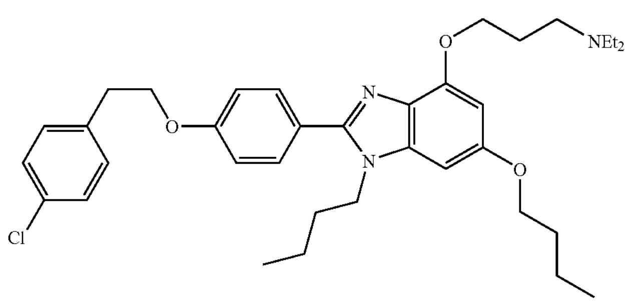 | [3-(6-Butoxy-1-butyl-2-(4-[2-(4-chloro-phenyl)-ethoxy]-phenyl}-1H-benzoimidazol-4-yloxy)-propyl]-diethyl-amine |
| 240 | 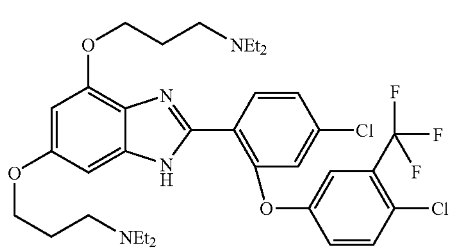 | {3-[2-[4-Chloro-2-(4-chloro-3-trifluoromethyl-phenoxy)-phenyl]-6-(3-diethylamino-propoxy)-1H-benzoimidazol-4-yloxy]-propyl}-diethyl-amine |

TABLE 1-continued

| Ex. | Structure | Name |
|---|---|---|
| 241 | 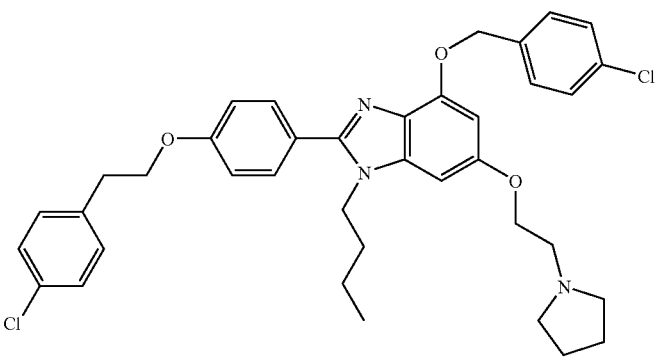 | 1-butyl-4-(4-chloro-benzyloxy)-2-{4-[2-(4-chloro-phenyl)-ethoxy]-phenyl}-6-(2-pyrrolidin-1-yl-ethoxy)-1H-benzimidazole |
| 242 | 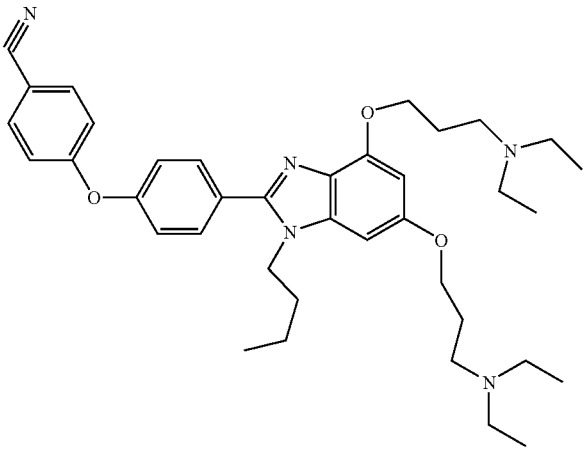 | 4-{4-[1-butyl-4,6-bis-(3-diethylamino-propoxy)-1H-benzimidazol-2-yl]-phenoxy}-benzonitrile |
| 243 | 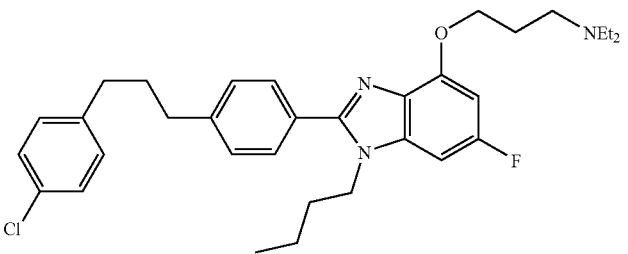 | [3-(1-Butyl-2-{4-[2-(4-chloro-phenyl)-ethoxy]-phenyl}-6-fluoro-1H-benzoimidazol-4-yloxy)-propyl]-diethyl-amine |
| 244 | 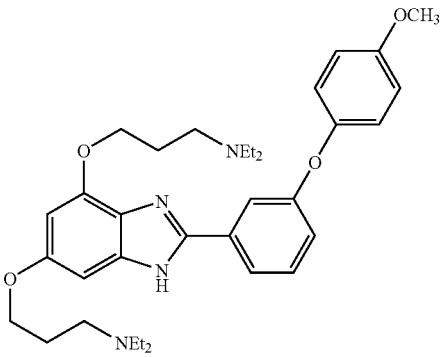 | (3-{6-(3-diethylamino-propoxy)-2-[3-(4-methoxy-phenoxy)-phenyl]-1H-benzimidazol-4-yloxy}-propyl)-diethyl-amine |

TABLE 1-continued

| Ex. | Structure | Name |
|---|---|---|
| 245 | 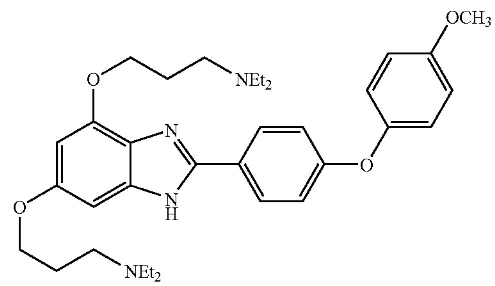 | (3-{6-(3-diethylamino-propoxy)-2-[4-(4-methoxy-phenoxy)-phenyl]-1H-benzimidazol-4-yloxy}-propyl)-diethyl-amine |
| 246 | 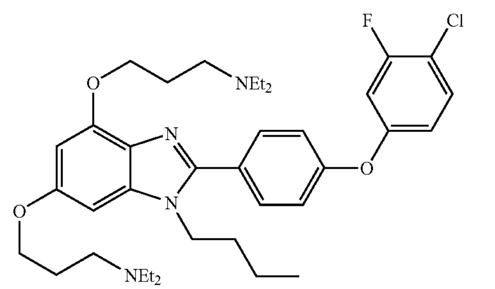 | {3-[1-butyl-2-[4-(4-chloro-3-fluoro-phenoxy)-phenyl]-6-(3-diethylamino-propoxy)-1H-benzimidazol-4-yl]-propyl}-diethyl-amine |
| 247 | 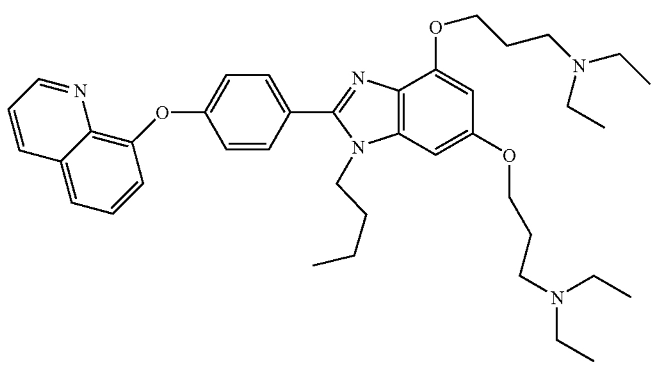 | (3-{1-butyl-6-(3-diethylamino-propoxy)-2-[4-(quinolin-8-yloxy)-phenyl]-1H-benzimidazol-4-yloxy]-propyl}-diethyl-amine |
| 248 | 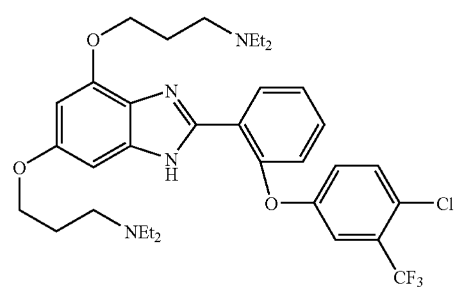 | {3-(2-[2-(4-chloro-3-trifluoromethyl-phenoxy)-phenyl]-6-(3-diethylamino-propoxy)-1H-benzoimidazol-4-yloxy]-propyl}-diethyl-amine |
| 249 | 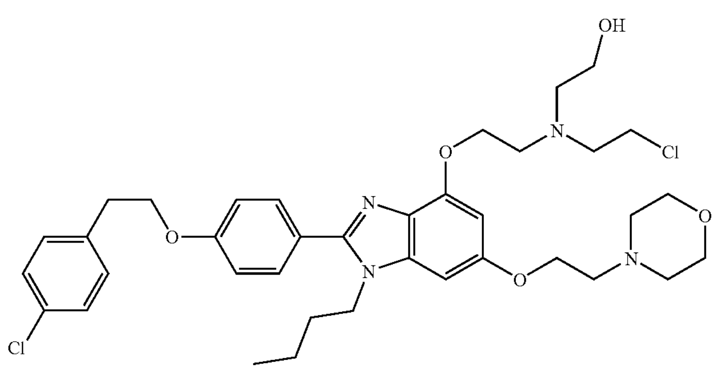 | 2-[{2-[1-Butyl-2-{4-[2-(4-chloro-phenyl)-ethoxy]-phenyl}-6-(2-morpholin-4-yl-ethoxy)-1H-benzoimidazol-4-yloxy]-ethyl}-(2-chloro-ethyl)-aminol-ethanol |

TABLE 1-continued

| Ex. | Structure | Name |
|---|---|---|
| 250 | 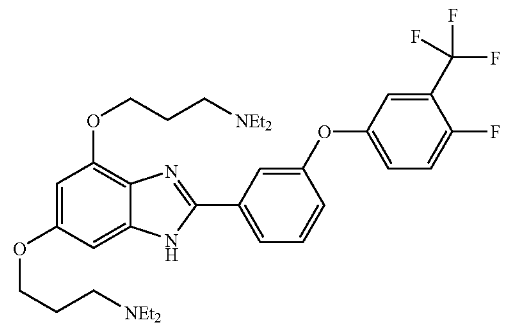 | (3-{6-(3-Diethylamino-propoxy)-2-[3-(4-fluoro-3-trifluoromethyl-phenoxy)-phenyl]-1H-benzoimidazol-4-yloxy)-propyl)-diethyl-amine |
| 251 | 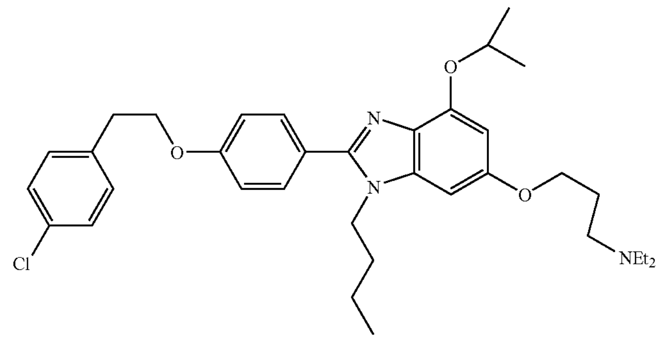 | [3-(3-butyl-2-{4-[2-(4-chloro-phenyl)-ethoxy]-phenyl}-7-isopropoxy-3H-benzimidazol-5-yloxy)-propyl]-diethyl-amine |
| 252 | 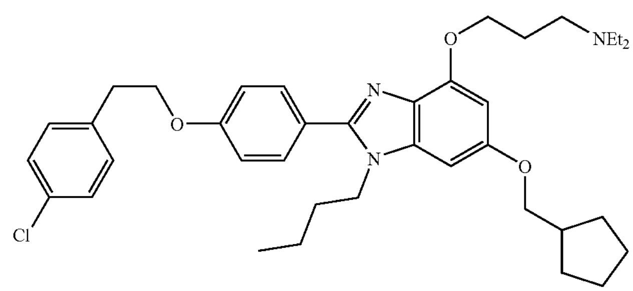 | [3-(1-Butyl-2-{4-[2-(4-chloro-phenyl)-ethoxy]-phenyl}-6-cyclopentylmethoxy-1H-benzoimidazol-4-yloxy)-propyl]-diethyl-amine |
| 253 | 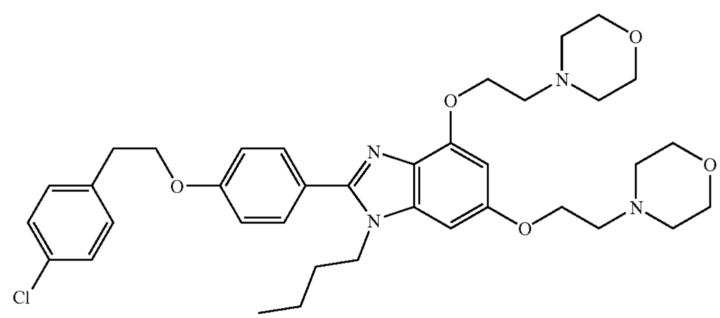 | 1-Butyl-2-{4-[2-(4-chloro-phenyl)-ethoxy]-phenyl}-4,6-bis-(2-morpholin-4-yl-ethoxy)-1H-benzoimidazole |
| 254 | 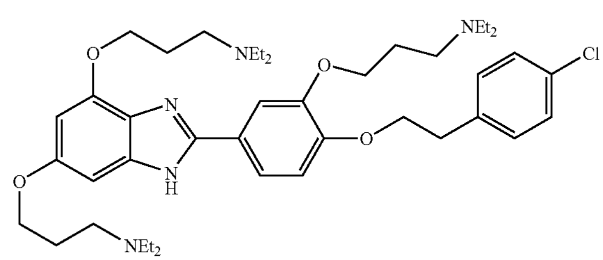 | {3-[2-[4-[2-(4-Chloro-phenyl)-ethoxy]-3-(3-diethylamino-propoxy)-phenyl]-6-(3-diethylamino-propoxy)-1H-benzoimidazol-4-yloxy]-propyl}-diethyl-amine |

TABLE 1-continued

| Ex. | Structure | Name |
|---|---|---|
| 255 | 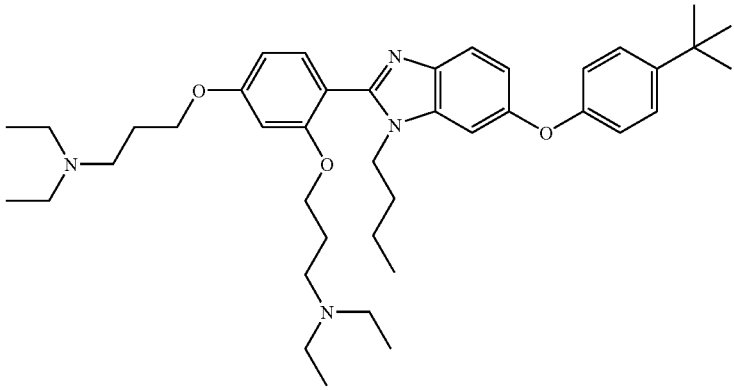 | {3-[2-[1-butyl-6-(4-tert-butyl-phenoxy)-1H-benzimidazol-2-yl]-5-(3-diethylamino-propoxy)-phenoxy]-propyl}-diethyl-amine |
| 256 | 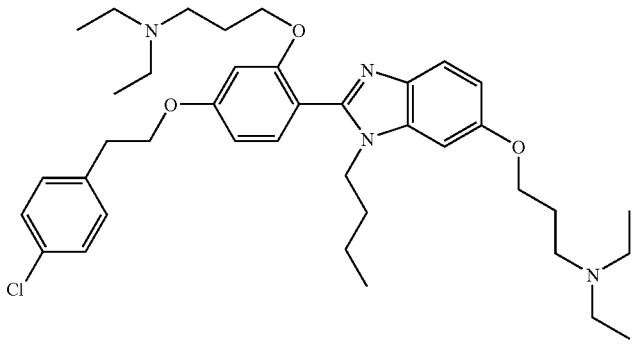 | (3-{2-[1-butyl-6-(3-diethylamino-propoxy)-1H-benzimidazol-2-yl]-5-[2-(4-chloro-phenyl)-ethoxy]-phenoxy}-propyl)-diethyl-amine |
| 257 | 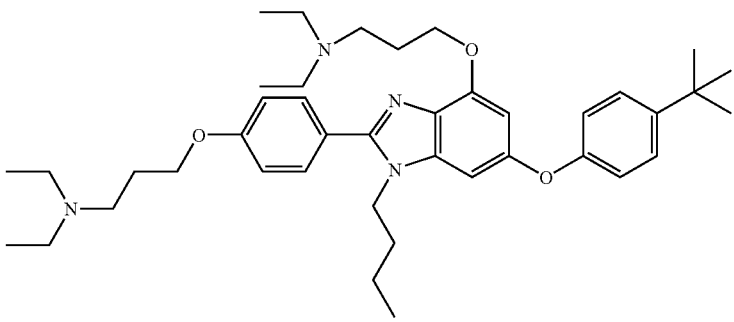 | (3-{1-butyl-6-(4-tert-butyl-phenoxy)-2-[4-(3-diethylamino-propoxy)-phenyl]-1H-benzoimidazol-4-yloxy}-propyl)-diethyl-amine |
| 258 | 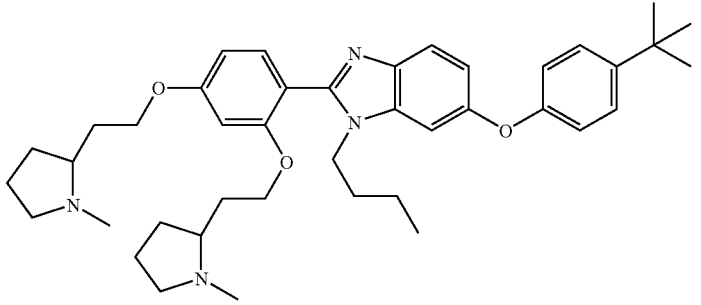 | 2-{2,4-bis-(2-(1-methyl-pyrrolidin-2-yl)-ethoxy]-phenyl}-1-butyl-6-(4-tert-butyl-phenoxy)-1H-benzoimidazole |

TABLE 1-continued

| Ex. | Structure | Name |
|---|---|---|
| 259 | 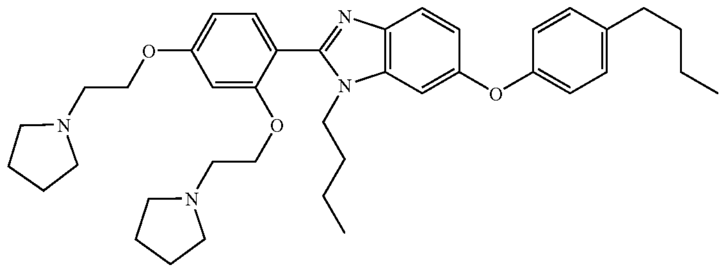 | 2-[2,4-bis-(2-pyrrolidin-1-yl-ethoxy)-phenyl]-1-butyl-6-(4-butyl-phenoxy)-1H-benzoimidazole |
| 260 | 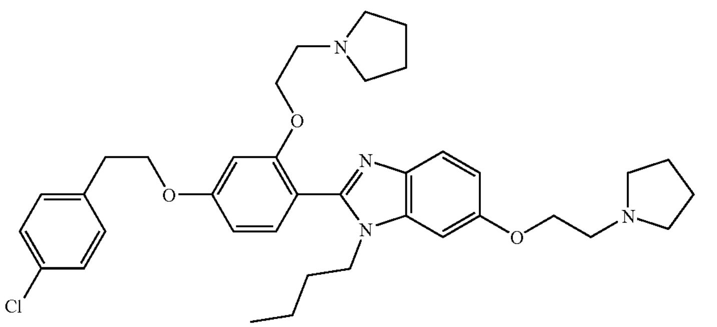 | 1-butyl-2-[4-[2-(4-chloro-phenyl)-ethoxy]-2-(2-pyrrolodin-1-yl-ethoxy)-phenyl]-6-(2-pyrrolodin-1-yl-ethoxy)-1H-benzoimidazole |
| 261 | 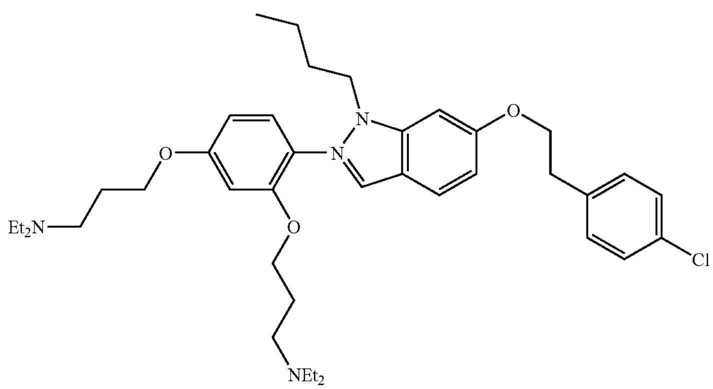 | {3-[2-{1-butyl-6-[2-(4-chloro-phenyl)-ethoxy]-1H-benzimidazol-2-yl]-5-(3-diethylamino-propoxy)-phenoxy]-propyl}-diethyl-amine |
| 262 | 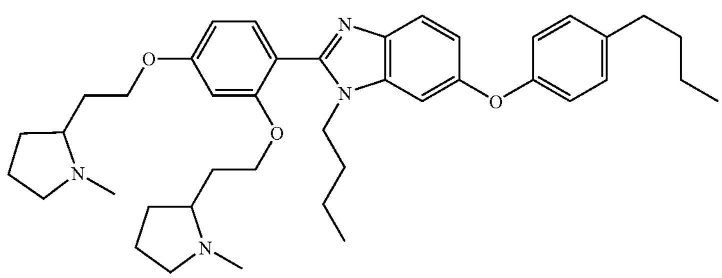 | 2-{2,4-bis-[2-(1-methyl-pyrrolidin-2-yl)-ethoxy]-phenyl}-1-butyl-6-(4-butyl-phenoxy)-1H-benzoimidazole |
| 263 | 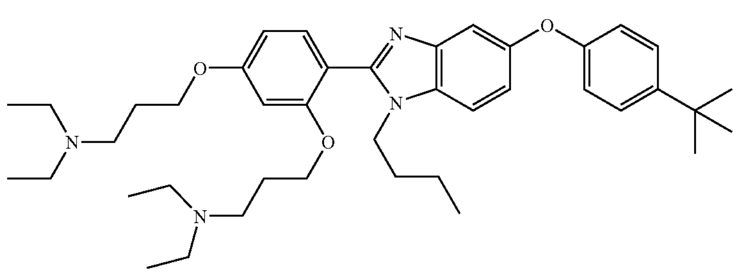 | {3-[2-[1-butyl-5-(4-tert-butyl-phenoxy)-1H-benzimidazol-1-yl]-5-(3-diethylamino-propoxy)-phenoxy]-propyl}-diethyl-amine |

TABLE 1-continued

| Ex. | Structure | Name |
|---|---|---|
| 264 | 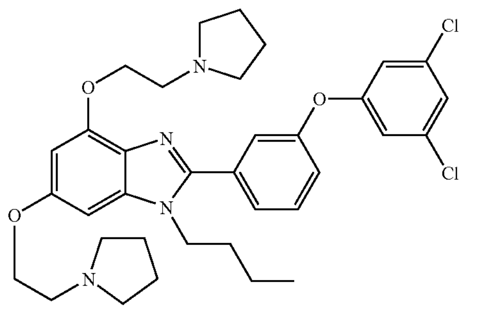 | 1-Butyl-2-[3-(3,5-dichloro-phenoxy)-phenyl]-4,6-bis-(2-pyrrolidin-1-yl-ethoxy)-1H-benzoimidazole |
| 265 | 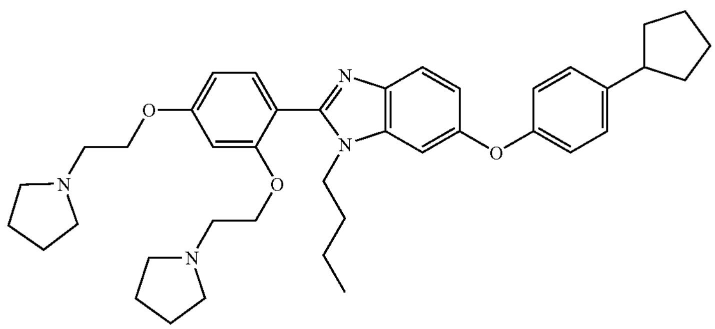 | 2-[2,4-bis-(2-pyrrolidin-1-yl-ethoxy)-phenyl]-1-butyl-6-(4-cyclopentyl-phenoxy)-1H-benzoimidazole |
| 266 | 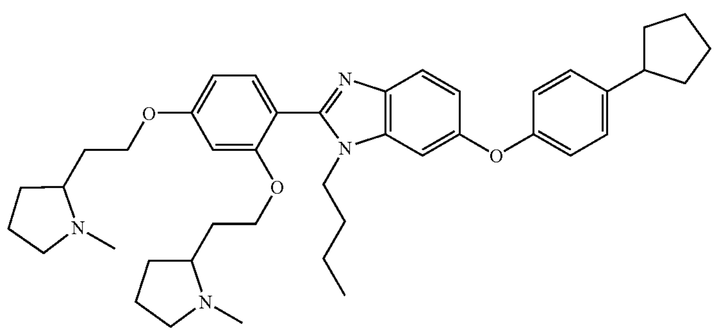 | 2-{2,4-bis-[2-(1-methyl-pyrrolidin-2-yl)-ethoxy]-phenyl}-1-butyl-6-(4-cyclopentyl-phenoxy)-1H-benzoimidazole |
| 267 | 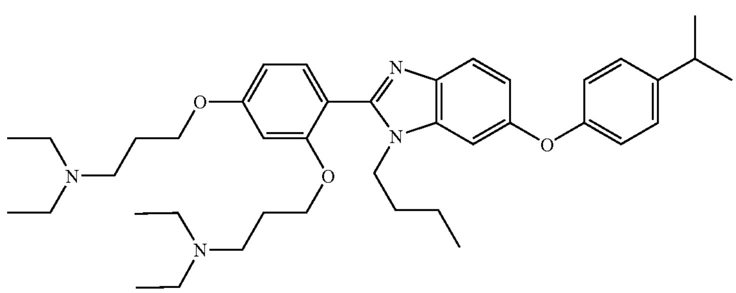 | {3-[2-[1-butyl-6-(4-iospropyl-p4henoxy)-1H-benzimidazol-2-yl]-5-(3-diethylamino-propoxy)-phenoxy]-propyl}-diethyl-amine |
| 268 | 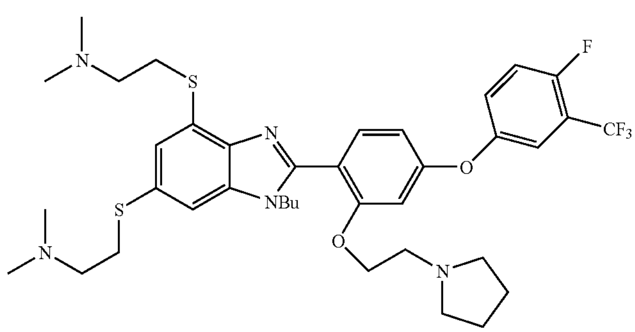 | (2-{1-butyl-6-(2-dimethylamino-ethylsulfanyl)-2-[4-(4-fluoro-3-trifluoromethyl-phenoxy)-2-(2-pyrrolidin-1-yl-ethoxy)-phenyl]-1H-benzoimidazol-4-ylsulfanyl}-ethyl)-dimethyl-amine |

TABLE 1-continued

| Ex. | Structure | Name |
|---|---|---|
| 269 | 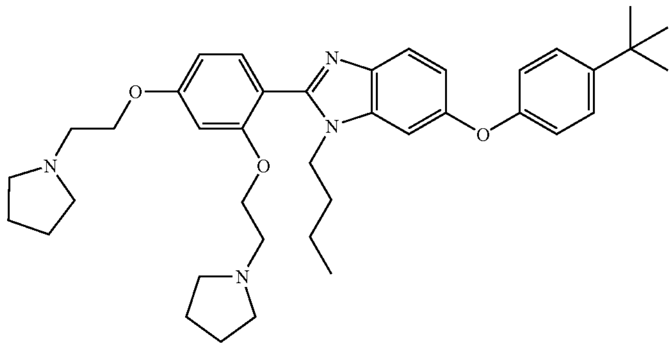 | 2-[2,4-bis-(2-pyrrolidin-1-yl-ethoxy)-phenyl]-1-butyl-6-(4-tert-butyl-phenoxy)-1H-benzimidazole |
| 270 | 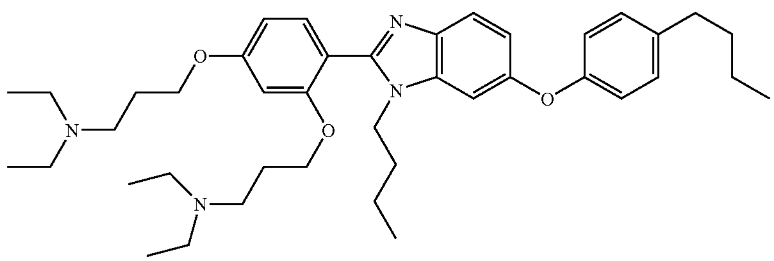 | {3-[2-[1-butyl-6-(4-butyl-phenoxy)-1H-benzimidazol-2-yl]-5-(3-diethylamino-propoxy)-phenoxy]-propyl]-diethyl-amine |
| 271 | 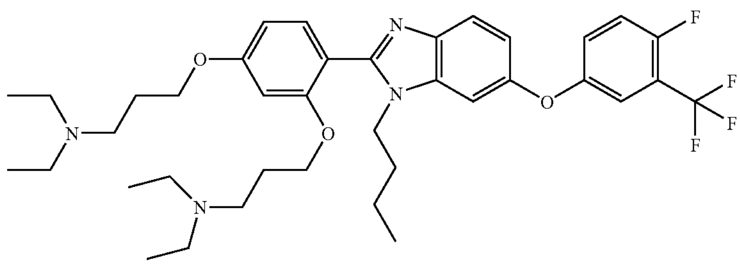 | {3-[2-[1-butyl-6-(4-fluoro-3-trifluoromethyl-phenoxy)-1H-benzimidazol-2-yl]-5-(3-diethylamino-propoxy)-phenoxy]-propyl}-diethyl-amine |
| 272 | 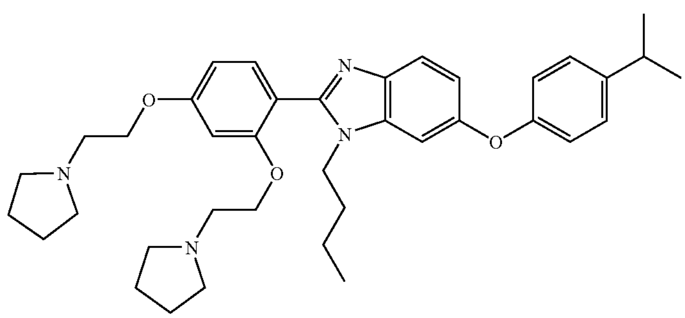 | 2-[2,4-bis-(2-pyrrolidin-1-yl-ethoxy)-phenyl]-1-butyl-6-(4-isopropyl-phenoxy)-1H-benzoimidazole |
| 273 | 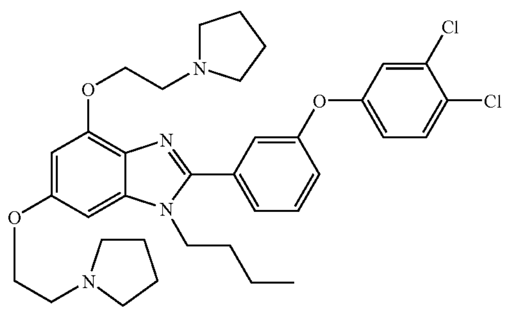 | 1-Butyl-2-[3-(3,4-dichloro-phenoxy)-phenyl]-4,6-bis-(2-pyrrolidin-1-yl-ethoxy)-1H-benzoimidazole |

TABLE 1-continued

| Ex. | Structure | Name |
|---|---|---|
| 274 | 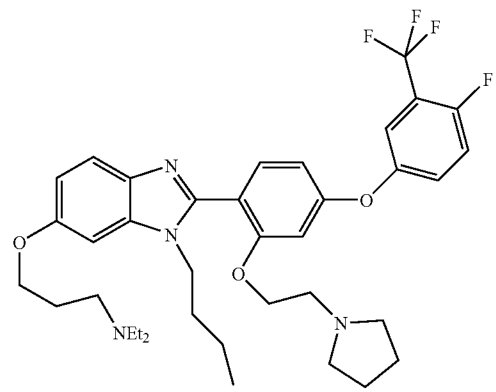 | (3-{3-Butyl-2-[4-(4-fluoro-3-trifluoromethyl-phenoxy)-2-(2-pyrrolidin-1-yl-ethoxy)-phenyl]-3H-benzoimidazol-5-yloxy}-propyl)-diethyl-amine |
| 275 | 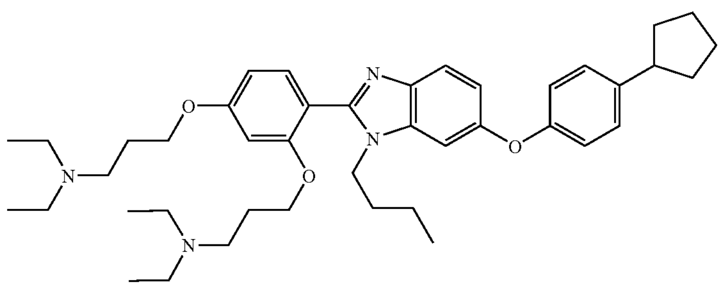 | {3-[2-[1-butyl-6-(4-cyclopentyl-phenoxy)-1H-benzimidazol-2-yl]-5-(3-diethylamino-propoxy)-phenoxy]-propyl}-diethyl-amine |
| 276 | 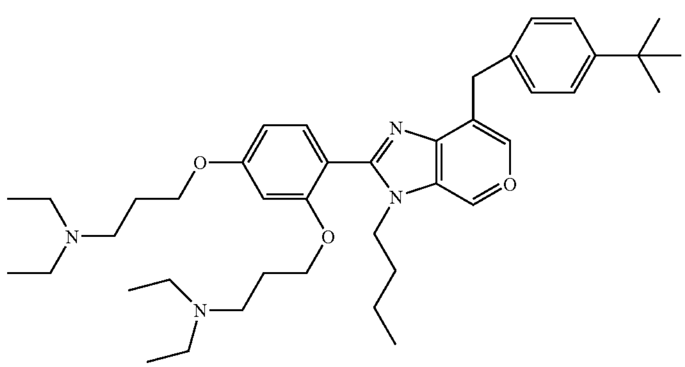 | {3-[2-[1-butyl-4-(4-tert-butyl-phenoxy)-1H-benzimidazol-2-yl]-5-(3-diethylamino-propoxy)-phenoxy]-propyl}-diethyl-amine |
| 277 | 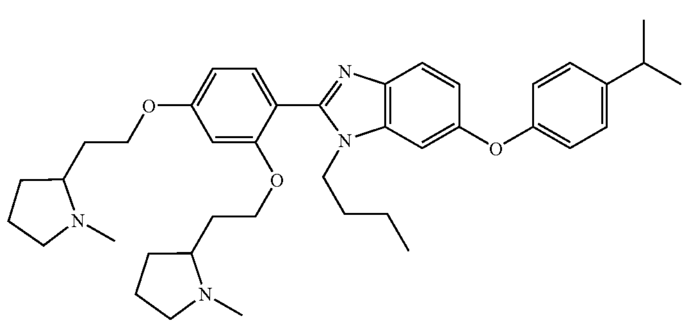 | 2-{2,4-bis-[2-(1-methyl-pyrrolidin-2-yl)-ethoxy]-phenyl}-1-butyl-6-(4-isopropyl-phenoxy)-1H-benzoimidazole |

TABLE 1-continued

| Ex. | Structure | Name |
|---|---|---|
| 278 | 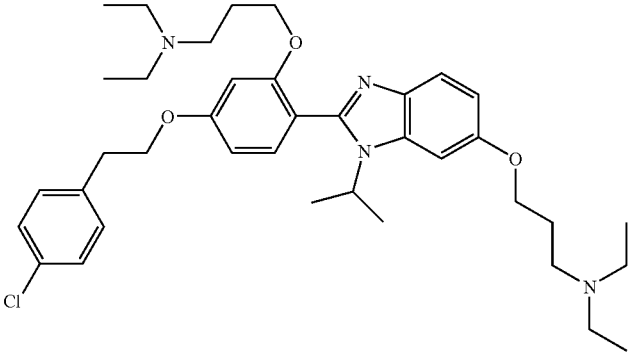 | (3-{5-[2-(4-chloro-phenyl)-ethoxy]-2-[6-(3-diethylamino-propoxy)-1-isopropyl-1H-benzimidazol-2-yl]-phenoxy}-propyl)-diethyl-amine |
| 279 | 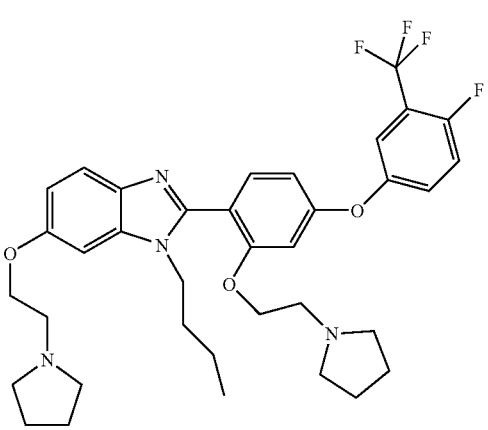 | 1-Butyl-2-[4-(4-fluoro-3-trifluoromethyl-phenoxy)-2-(2-pyrrolidin-1-yl-ethoxy)-phenyl]-6-(2-pyrrolidin-1-yl-ethoxy)-1H-benzoimidazole |
| 280 | 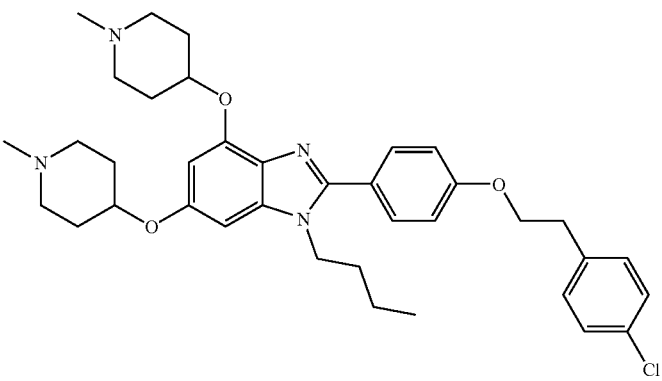 | 1-butyl-2-{4-[2-(4-chloro-phenyl)-ethoxy]-phenyl}-4,6-bis-(1-methyl-piperidin-4-yloxy)-1H-benzimidazole |
| 281 | 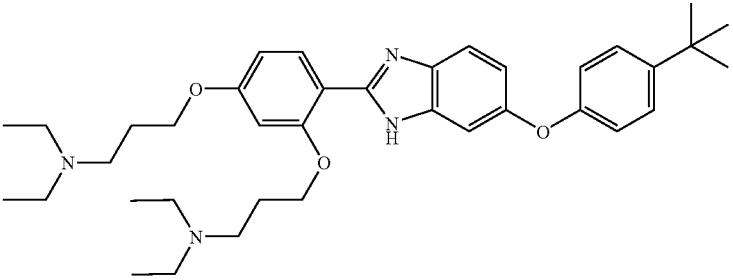 | {3-[2-[6-(4-tert-butyl-phenoxy)-1H-benzimidazol-2-yl]-5-(3-diethylamino-propoxy)-phenoxy]-propyl}-diethyl-amine |

TABLE 1-continued

| Ex. | Structure | Name |
| --- | --- | --- |
| 282 | 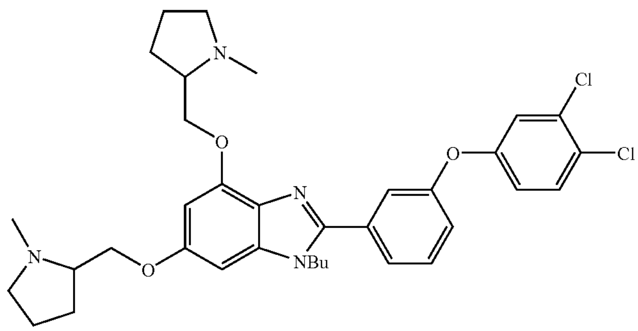 | 1-butyl-2-[3-(3,4-dichloro-phenoxy)-phenyl]-4,6-bis-(1-methyl-pyrrolidin-2-ylmethoxy)-1H-benzoimidazole |
| 283 | 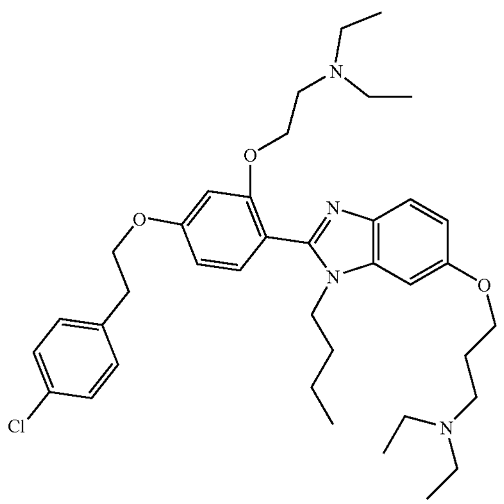 | (3-(3-butyl-2-[4-[2-(4-chloro-phenyl)-ethoxy]-2-(2-diethylamino-ethoxy)-phenyl]-3H-benzimidazol-5-yloxy}-propyl)-diethyl-amine |
| 284 | 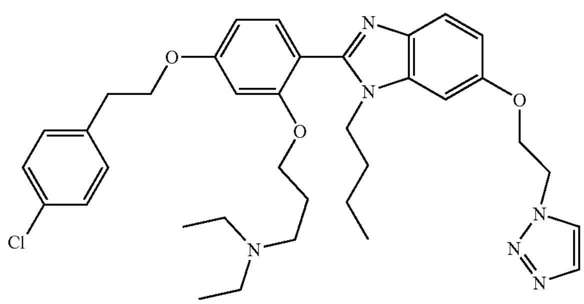 | (3-{2-[1-Butyl-6-(2-imidazol-1-yl-ethoxy)-1H-benzoimidazol-2-yl]-5-[2-(4-chloro-phenyl)-ethoxy]-phenoxy}-propyl)-diethyl-amine |
| 285 | 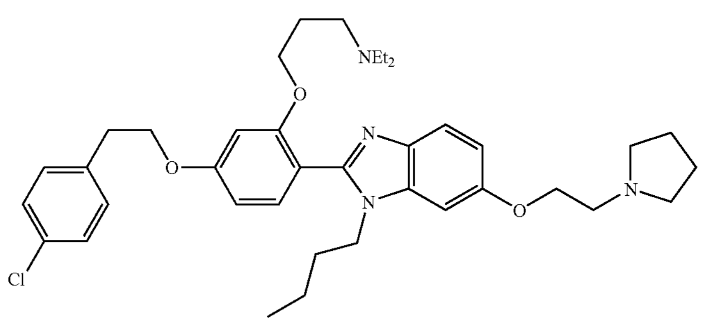 | (3-{2-[1-Butyl-6-(2-pyrrolidin-1-yl-ethoxy)-1H-benzoimidazol-2-yl]-5-[2-(4-chloro-phenyl)-ethoxy]-phenoxy}-propyl)-diethyl-amine |

TABLE 1-continued

| Ex. | Structure | Name |
|---|---|---|
| 286 | 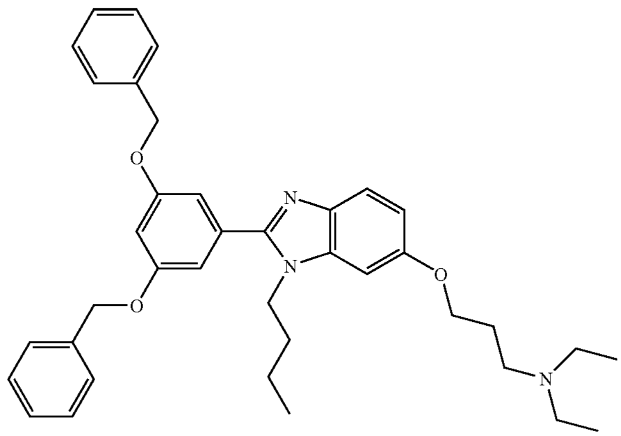 | {3-[2-(3,5-bis-benzyloxy-phenyl)-3-butyl-3H-benzimidazol-5-yloxy]-propyl}-diethyl-amine |
| 287 | 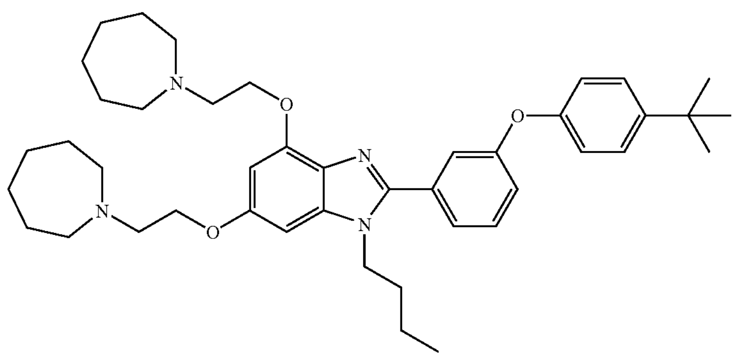 | 4,6-bis-(2-azepan-1-yl-ethoxy)-1-butyl-2-[3-(4-tert-butyl-phenoxy)-phenyl]-1H-benzoimidazole |
| 288 | 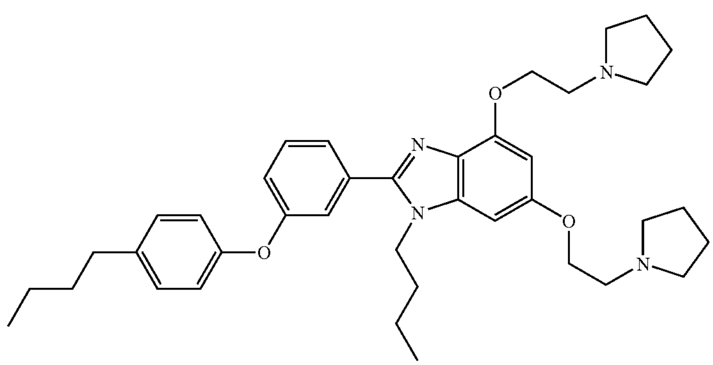 | 1-butyl-2-[3-(4-butyl-phenoxy)-phenyl]-4,6-bis-(2-pyrrolidin-1-yl-ethoxy)-1H-benzoimidazole |
| 289 | 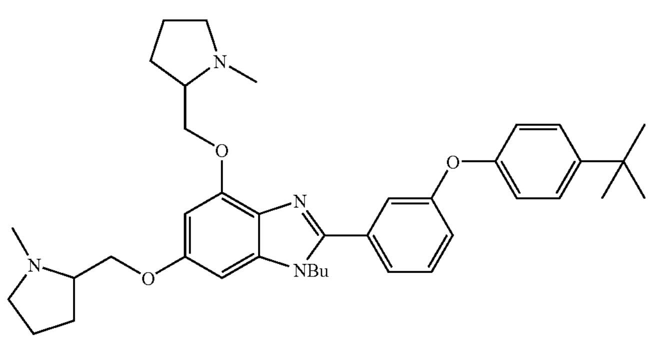 | 1-butyl-2-[3-(4-tert-butyl-phenoxy)-phenyl]-4,6-bis-(1-methyl-pyrrolidin-2-ylmethoxy)-1H-benzoimidazole |

TABLE 1-continued

| Ex. | Structure | Name |
|---|---|---|
| 290 | 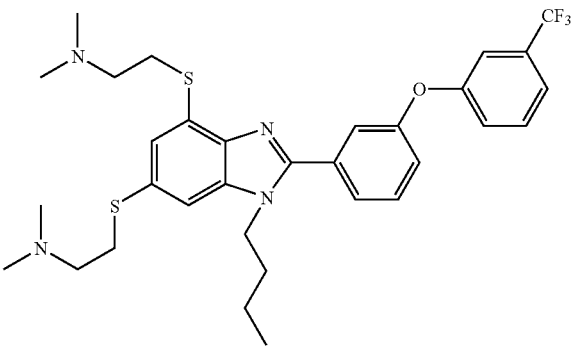 | (2-{1-butyl-6-(2-dimethylamino-ethylsulfanyl)-2-[3-(3-trifluoromethyl-phenoxy)-phenyl]-1H-benzoimidazole-4-ylsufanyl}-ethyl)-dimethyl-amine |
| 291 | 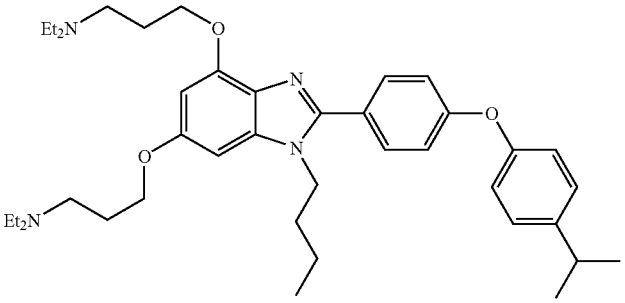 | (3-{1-butyl-6-(3-diethylamino-propoxy)-2-[4-(4-isopropyl-phenoxy)-phenyl]-1H-benzimidazol-4-yloxy}-propyl)-diethyl-amine |
| 292 | 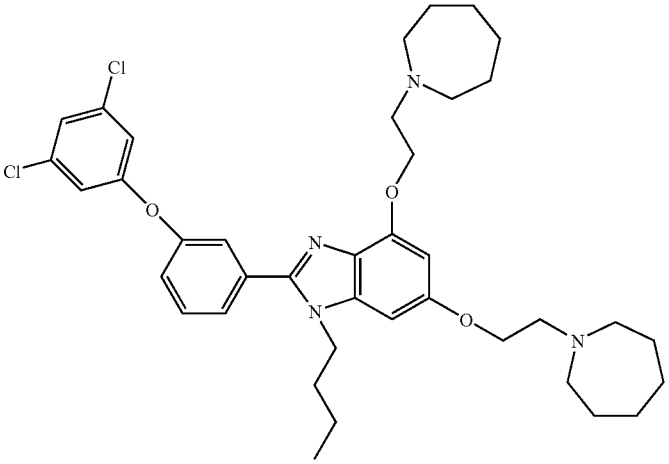 | 4,6-bis-(2-azepan-1-yl-ethoxy)-1-butyl-2-[3-(3,5-dichlorophenoxy)-phenyl]-1H-benzoimidazole |
| 293 | 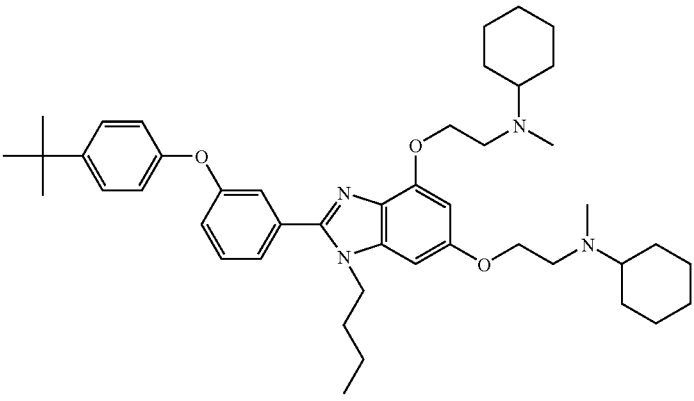 | 1-butyl-2-[3-(4-tert-butyl-phenoxy)-phenyl]-4,6-bis-[2-(cyclohexyl-methyl-amino)-ethoxy]-1H-benzoimidazole |

TABLE 1-continued

| Ex. | Structure | Name |
|---|---|---|
| 294 | 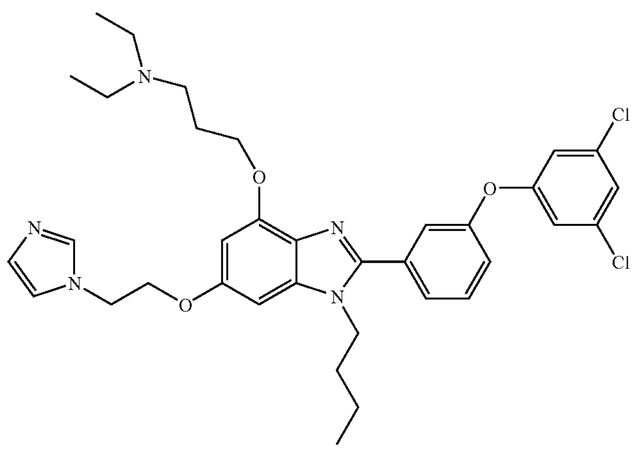 | {3-[1-butyl-2-[3-(3,5-dichloro-phenoxy)-phenyl]-6-(2-imidazol-1-yl-ethoxy)-1H-benzimidazol-4-yloxy]-propyl}-diethyl-amine |
| 295 | 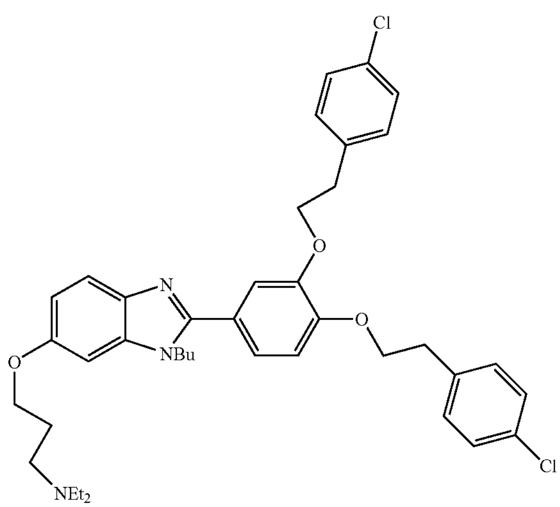 | [3-(2-{3,4-bis-[2-(4-chloro-phenyl)-ethoxy]-phenyl}-3-butyl-3H-benzimidazol-5-yloxy)-propyl]-diethyl-amine |
| 296 | 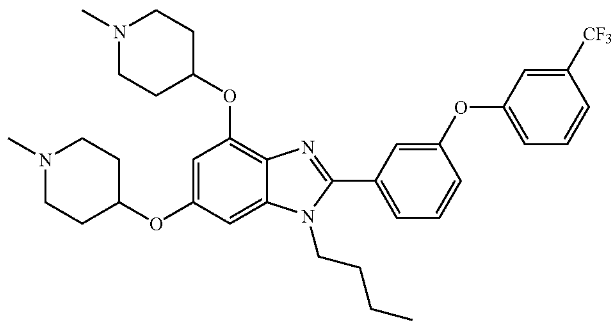 | 1-butyl-4,6-bis-(1-methyl-piperidin-4-yloxy)-2-[3-(3-trifluoromethyl-phenoxy)-phenyl]-1H-benzoimidazole |

TABLE 1-continued

| Ex. | Structure | Name |
|---|---|---|
| 297 | 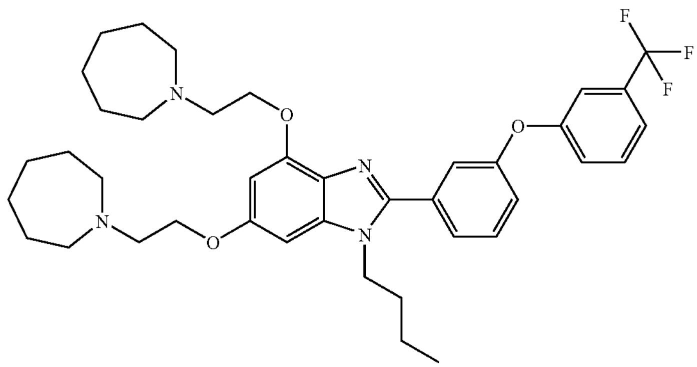 | 4,6-bis-(2-azepan-1-yl-ethoxy)-1-butyl-2-[3-(3-trifluoromethyl-phenoxy)-phenyl]-1H-benzoimidazole |
| 298 | 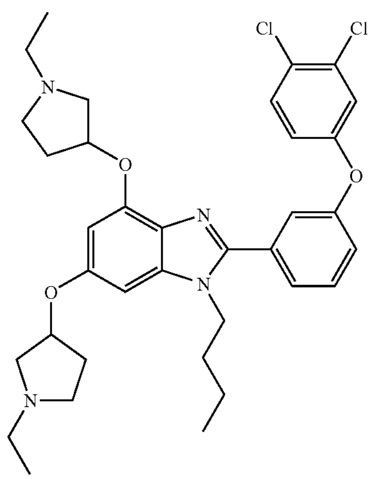 | 1-butyl-2-[3-(3,4-dichloro-phenoxy)-phenyl]-4,6-bis-(1-ethyl-pyrrolidin-2-ylmethoxy)-1H-benzoimidazole |
| 299 | 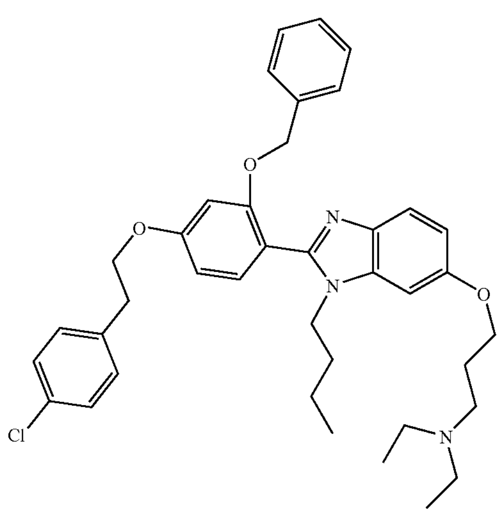 | [3-(2-{2-benzyloxy-4-[2-(4-chloro-phenyl)-ethoxy]-phenyl}-3-butyl-3H-benzimidazol-5-yloxy]-propyl}-diethyl-amine |

TABLE 1-continued

| Ex. | Structure | Name |
|---|---|---|
| 300 | 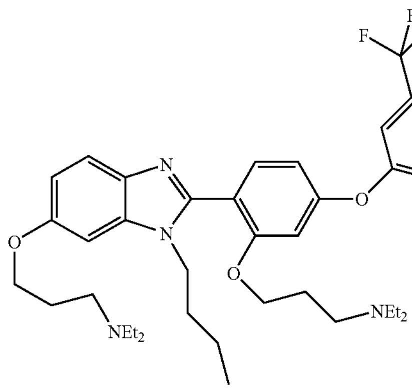 | {3-[2-[1-Butyl-6-(3-diethylamino-propoxy)-1H-benzoimidazol-2-yl]-5-(4-fluoro-3-trifluoromethyl-phenoxy)-phenoxy]-propyl}-diethyl-amine |
| 301 | 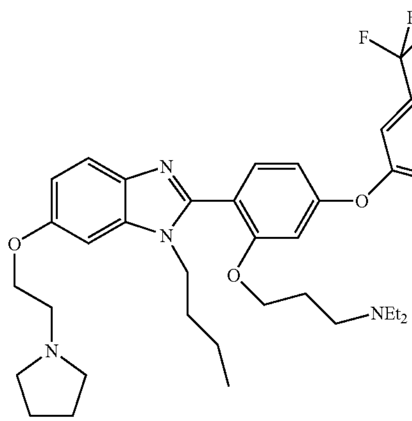 | {3-[2-[1-Butyl-6-(2-pyrrolidin-1-yl-ethoxy)-1H-benzoimidazol-2-yl]-5-(4-fluoro-3-trifluoromethyl-phenoxy)-phenoxy]-propyl}-diethyl-amine |
| 302 | 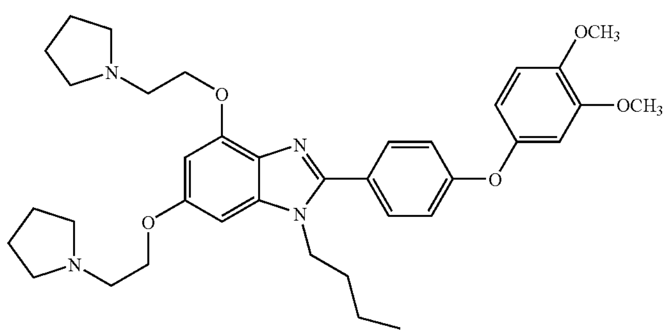 | 1-butyl-2-[3-(3,4-dimethoxy-phenoxy)-phenyl]-4,6-bis-(2-pyrrolidin-1-yl-ethoxy)-1H-benzimidazole |
| 303 | 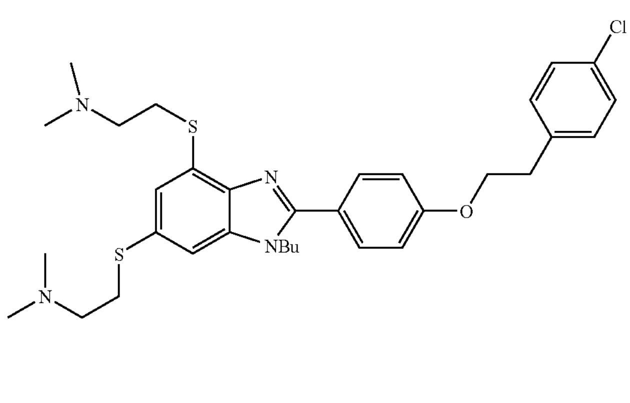 | (2-{1-butyl-2-(4-[2-(4-chloro-phenyl)-ethoxy]-phenyl}-6-(2-dimethylamino-ethylsulfanyl)-1H-benzoimidazol-4-ylsulfanyl}-ethyl)-dimethyl-amine |

TABLE 1-continued

| Ex. | Structure | Name |
|---|---|---|
| 304 | 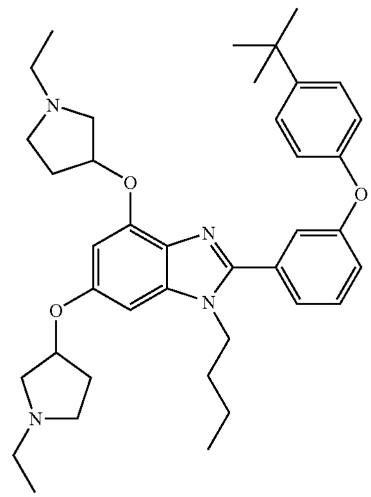 | 1-butyl-2-[3-(4-tert-butyl-phenoxy)-phenyl]-4,6-bis-(1-ethyl-pyrrolidin-3-yloxy)-1H-benzoimidazole |
| 305 | 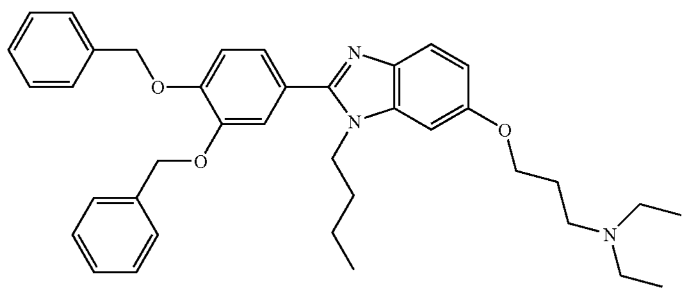 | {3-[2-[3-(3,4-bis-benzyloxy-phenyl)-3-butyl-3H-benzimidazol-5-yloxy]-propyl}-diethyl-amine |
| 306 | 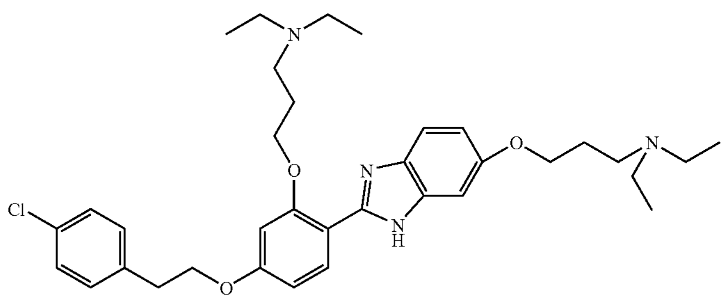 | (3-{5-[2-(4-chloro-phenyl)-ethoxy]-2-[6-(3-diethylamino-propoxy)-1H-benzimidazol-2-yl]-phenoxy}-propyl)-diethyl-amine |
| 307 | 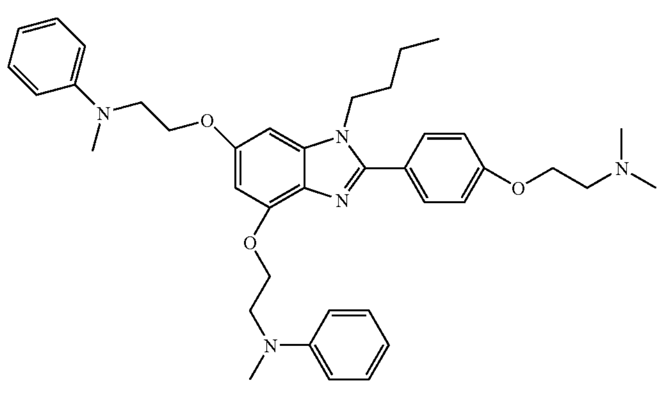 | 1-butyl-2-[4-(2-diethylamino-ethoxy)-phenyl]-4,6-bis-[2-(methyl-phenyl-amino)-ethoxy]-1H-benzimidazole |

TABLE 1-continued

| Ex. | Structure | Name |
|---|---|---|
| 308 | 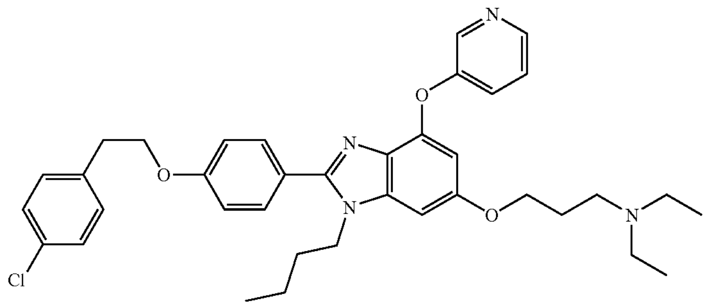 | {3-[3-butyl-2-{4-[2-(4-chlorophenyl)-ethoxy]-phenyl}-7-(pyridin-3-yloxy)-3H-benzimidazol-5-yloxy]-propyl}-diethyl-amine |
| 309 | 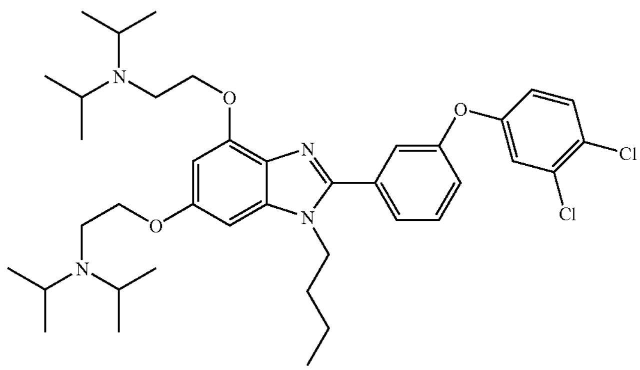 | {2-[1-butyl-2-[3-(3,4-dichloro-phenoxy)-phenyl]-6-(2-diisopropylamino-ethoxy)-1H-benzimidazol-4-yloxy]-ethyl}-diethyl-amine |
| 310 | 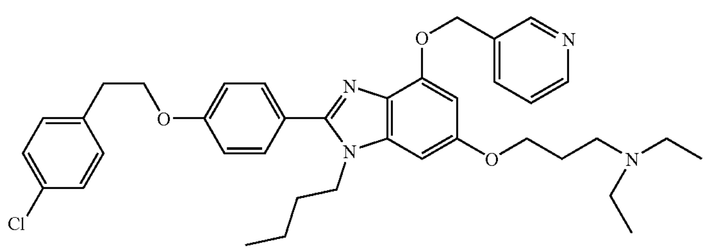 | {3-[3-butyl-2-{4-[2-(4-chloro-phenyl)-ethoxy]-phenyl}-7-(pyridin-3-ylmethoxy)-3H-benzimidazol-5-yloxy]-propyl}-diethyl-amine |
| 311 | 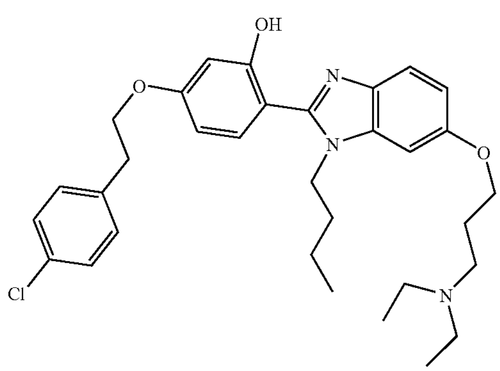 | 2-[1-butyl-6-(3-diethylamino-propoxy)-1H-benzoimidazlo-2-yl]-5-[2-(4-chloro-phenyl)-ethoxy]-phenol |

TABLE 1-continued

| Ex. | Structure | Name |
|---|---|---|
| 312 | 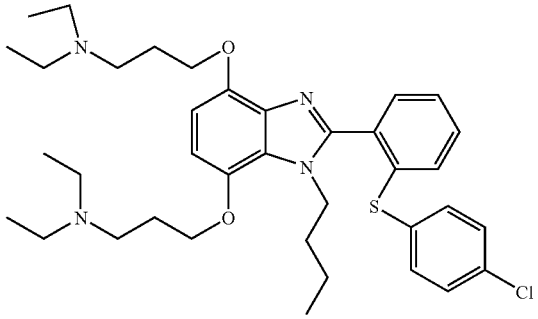 | {3-[3-butyl-2-[2-(4-chloro-phenylsulfanyl)-phenyl]-7-(3-diethylamino-propoxy)-3H-benzimidazol-4-yloxy}-propyl)-diethyl-amine |
| 313 | 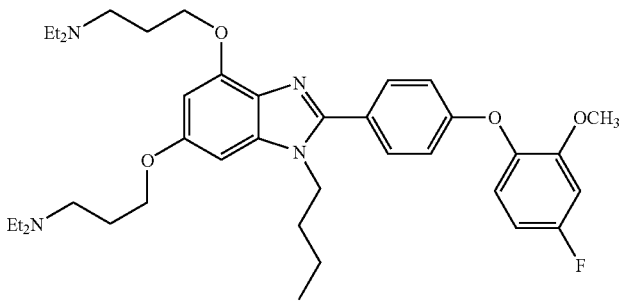 | (3-{1-butyl-6-(3-diethylamino-propoxy)-2-[4-(4-fluoro-2-methoxy-phenoxy)-phenyl]-1H-benzimidazol-4-yloxy}-propyl)-diethyl-amine |
| 314 | 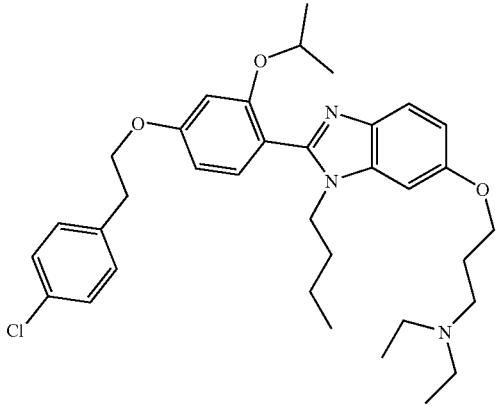 | [3-(3-butyl-2-{4-[2-(4-chloro-phenyl)-ethoxy]-2-isopropoxy-phenyl}-3H-benzimidazol-5-yloxy)-propyl]-diethyl-amine |
| 315 | 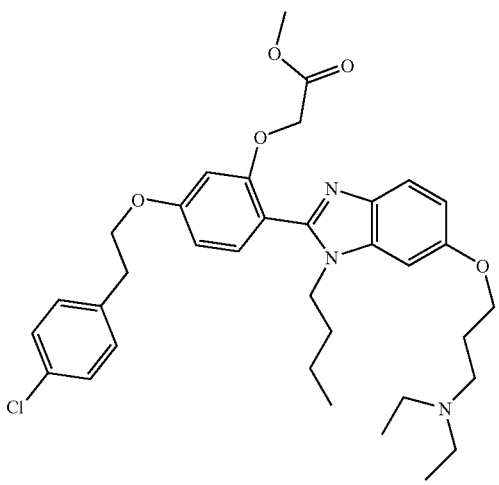 | {2-[1-butyl-6-(3-diethylamino-propoxy)-1H-benzoimidazlo-2-yl]-5-[2-(4-chloro-phenyl)-ethoxy]-phenoxy}-acetic acid methyl ester |

TABLE 1-continued

| Ex. | Structure | Name |
|---|---|---|
| 316 | 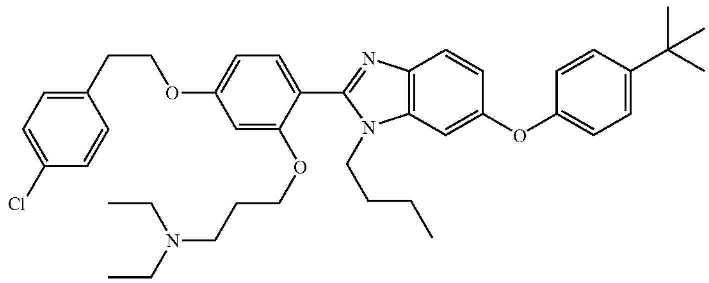 | (3-{2-[1-butyl-6-(4-tert-butyl-phenoxy)-1H-benzimidazol-2-yl]-5-[2-(4-chloro-phenyl)-ethoxy]-phenoxy}-propyl)-diethyl-amine |
| 317 | 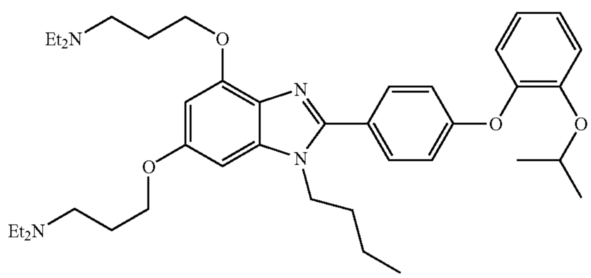 | (3-{1-butyl-6-(3-diethylamino-propoxy)-2-[4-(2-isopropoxy-phenoxy)-phenyl]-1H-benzoimidazol-4-yloxy}-propyl)-diethyl-amine |
| 318 | 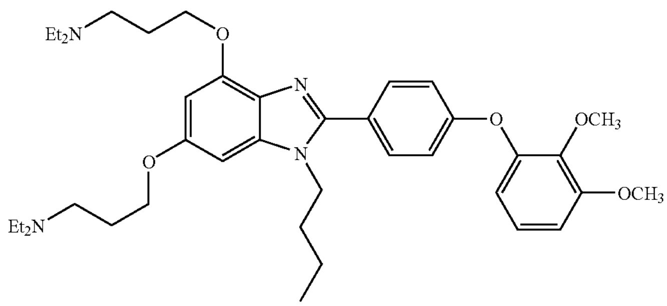 | (3-{1-butyl-6-(3-diethylamino-propoxy)-2-[4-(2,3-dimethoxy-phenoxy)-phenyl]-1H-benzoimidazol-4-yloxy}-propyl)-diethyl-amine |
| 319 | 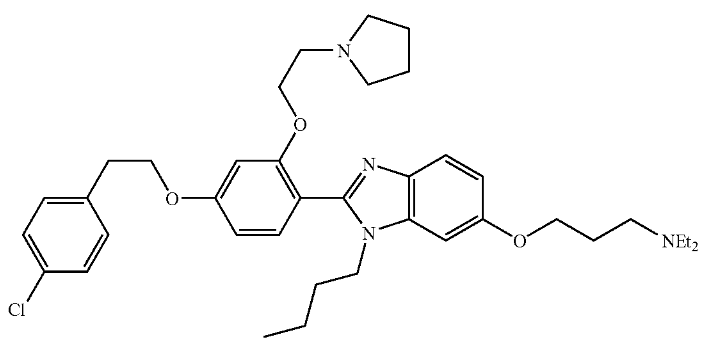 | (3-{3-Butyl-2-[4-[2-(4-chloro-phenyl)-ethoxy]-2-(2-pyrrolidin-1-yl-ethoxy)-phenyl]-3H-benzoimidazol-5-yloxy}-propyl)-diethyl-amine |
| 320 | 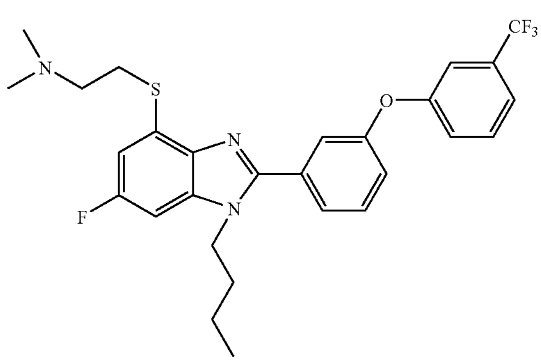 | (2-{1-butyl-6-fluoro-2-[3-(3-trifluoromethyl-phenoxy)-phenyl]-1H-benzoimidazole-4-ylsufanyl}-ethyl)-dimethyl-amine |

TABLE 1-continued

| Ex. | Structure | Name |
|---|---|---|
| 321 | 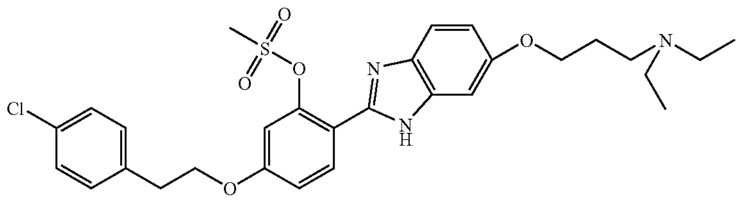 | Methanesulfonic acid 5-[2-(4-chloro-phenyl)-ethoxy]-2-[6-(3-diethylamino-propoxy)-1H-benzoimidazol-2-yl]-phenyl ester |
| 322 | 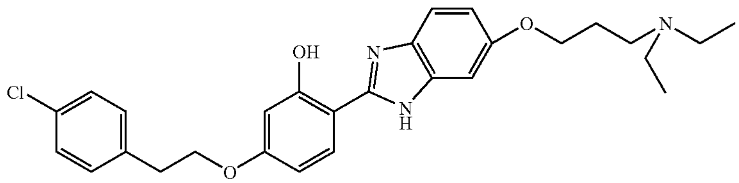 | 5-[2-(4-Chloro-phenyl)-ethoxy]-2-[6-(3-diethylamino-propoxy)-1H-benzoimidazol-2-yl]-phenol |
| 323 | 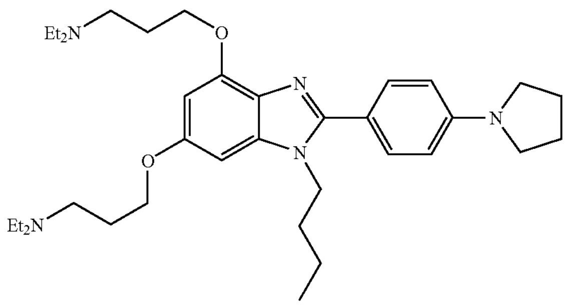 | {3-[1-butyl-6-(3-diethylamino-propoxy)-2-(4-pyrrolidin-1-yl-phenyl)-1H-benzoimidazol-4-yloxy]-propyl}-diethyl-amine |
| 324 | 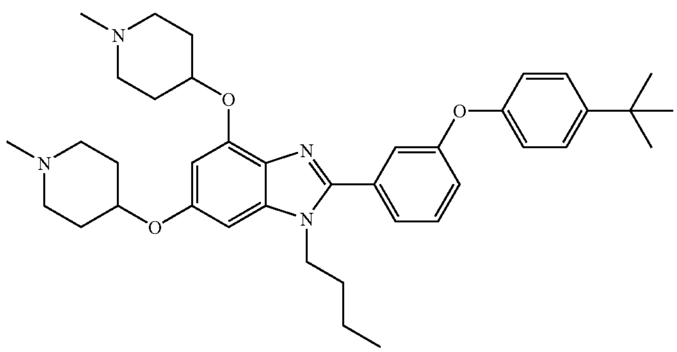 | 1-butyl-2-[3-(4-tert-butyl-phenoxy)-phenyl]-4,6-bis-(1-methyl-piperidin-4-yloxy)-1H-benzimidazole |
| 325 | 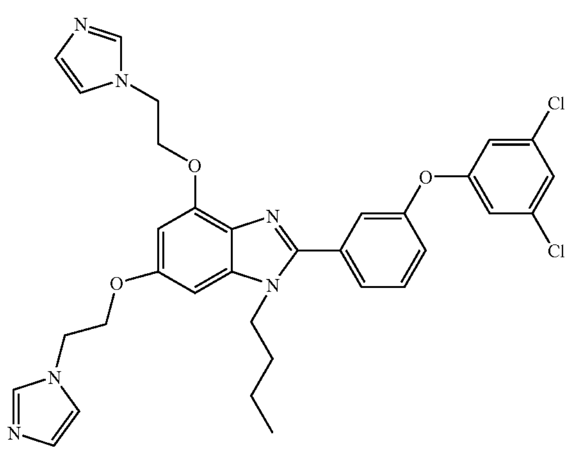 | 1-butyl-2-[3-(3,5-dichloro-phenoxy)-phenyl]-4,6-bis-(2-imidazol-1-yl-ethoxy)-1H-benzoimidazole |

TABLE 1-continued

| Ex. | Structure | Name |
|---|---|---|
| 326 | 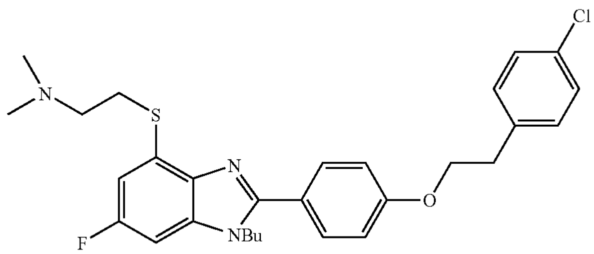 | [2-(1-butyl-2-{4-[2-(4-chloro-phenyl)-ethoxy]-phenyl}-6-fluoro-1H-benzoimidazol-4-ylsulfanyl)-ethyl]-dimethyl-amine |
| 327 | 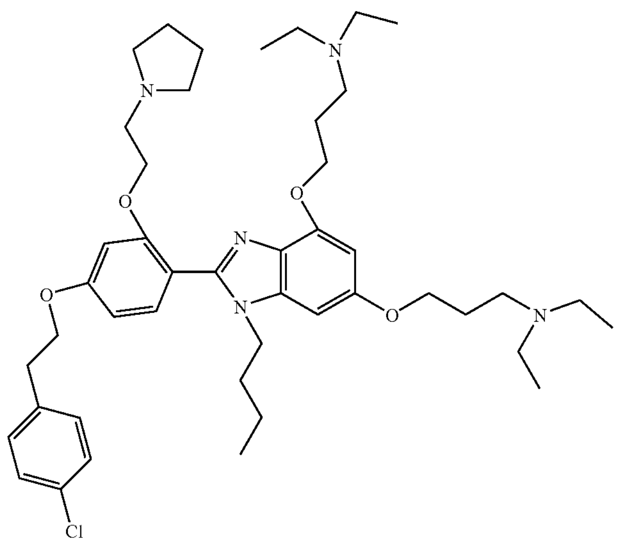 | {3-[1-Butyl-2-[4-[2-(4-chloro-phenyl)-ethoxy]-2-(2-(pyrrolidin-1-yl-ethoxy)-phenyl]-6-(3-diethylamino-propoxy)-1H-benzimidazol-4-yloxy]-propyl}-diethyl-amine |
| 328 | 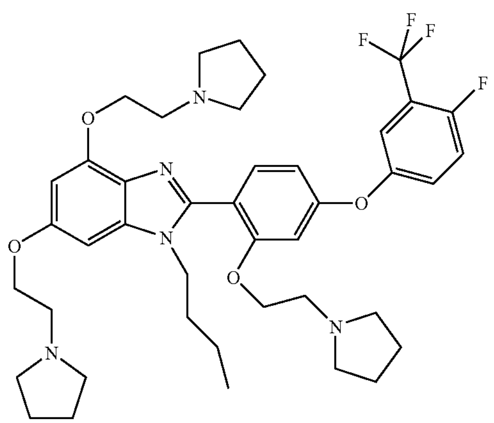 | 1-Butyl-2-[4-(4-fluoro-3-trifluoromethyl-phenoxy)-2-(2-pyrrolidin-1-yl-ethoxy)-phenyl]-4,6-bis-(2-pyrrolidin-1-yl-ethoxy)-1H-benzoimidazole |

TABLE 1-continued

| Ex. | Structure | Name |
|---|---|---|
| 329 | 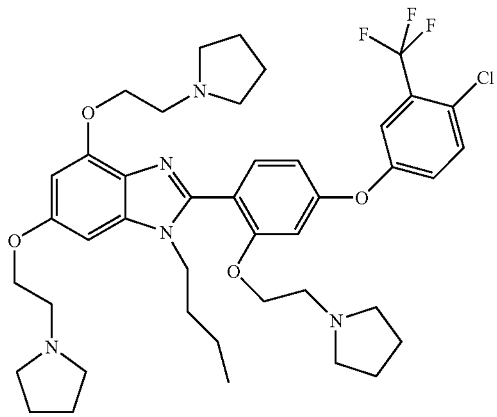 | 1-Butyl-2-[4-(4-chloro-3-trifluoromethyl-phenoxy)-2-(2-pyrrolidin-1-yl-ethoxy)-phenyl]-4,6-bis-(2-pyrrolidin-1-yl-ethoxy)-1H-benzoimidazole |
| 330 | 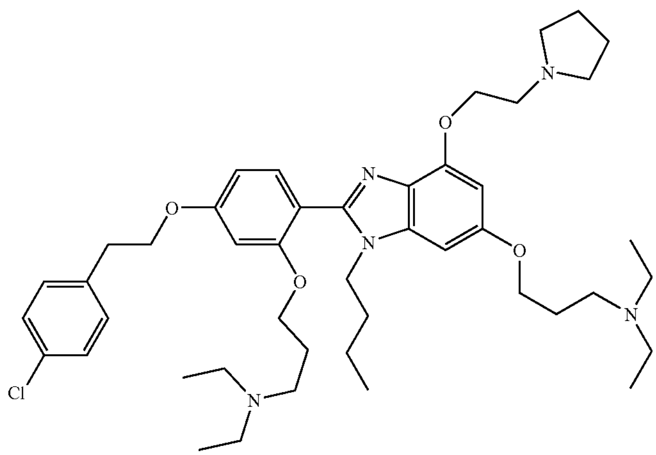 | (3-{2-[1-butyl-6-(3-diethylamino-propoxy)-4-(2-pyrrolidin-1-yl-ethoxy)-1H-benzimidazol-2-yl]-5-[2-(4-chloro-phenyl)-ethoxy]-phenoxy}-propyl)-diethyl-amine |
| 331 | 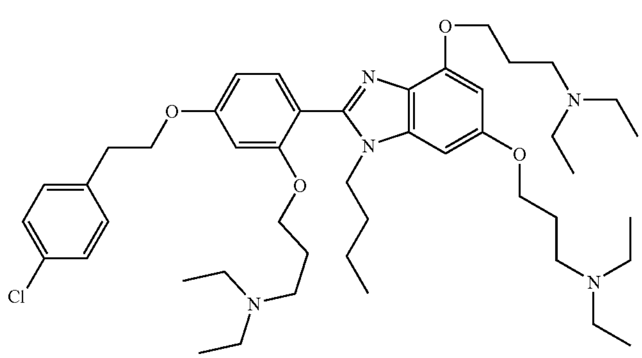 | (3-{2-[1-butyl-4,6-bis-(3-diethylamino-propoxy)-1H-benzimidazol-2-yl]-5-[2-(4-chloro-phenyl)-ethoxy]-phenoxy}-propyl)-diethyl-amine |

TABLE 1-continued

| Ex. | Structure | Name |
|---|---|---|
| 332 | 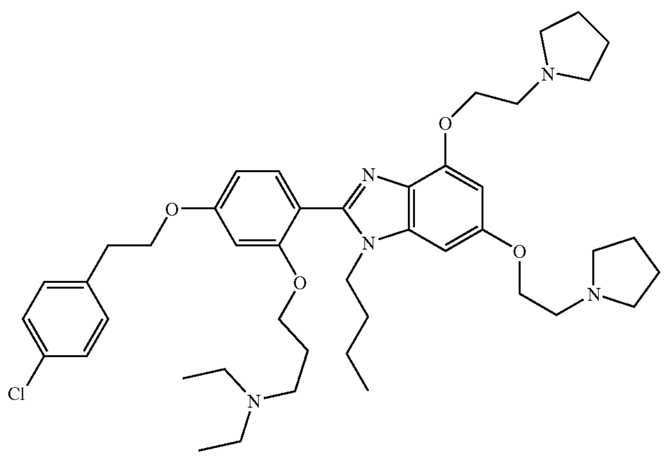 | (3-{2-[1-Butyl-4,6-bis-(2-pyrrolidin-1-yl-ethoxy)-1H-benzoimidazol-2-yl]-5-[2-(4-chloro-phenyl)-ethoxy]-phenoxy}-propyl)-diethyl-amine |
| 333 | 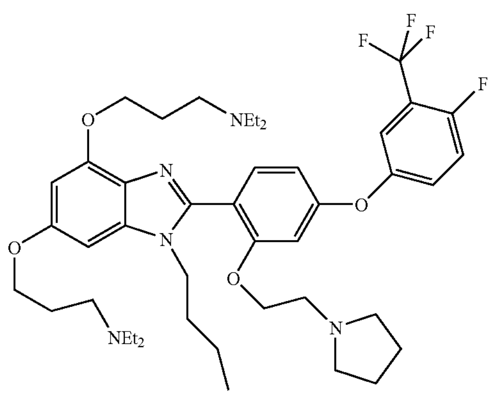 | (3-{1-Butyl-6-(3-diethylamino-propoxy)-2-[4-(4-fluoro-3-trifluoromethyl-phenoxy)-2-(2-pyrrolidin-1-yl-ethoxy)-phenyl]-1H-benzoimidazol-4-yloxy}-propyl)-diethyl-amine |
| 334 | 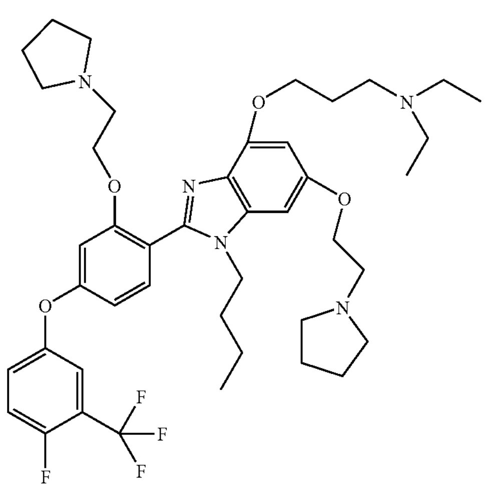 | {3-[1-Butyl-2-[4-(4-fluoro-3-trifluoromethyl-phenoxy)-2-(2-pyrrolidin-1-yl-ethoxy)-phenyl]-6-(2-pyrrolidin-1-yl-ethoxy)-1H-benzoimidazol-4-yloxy]-propyl}-diethyl-amine |

TABLE 1-continued

| Ex. | Structure | Name |
|---|---|---|
| 335 | 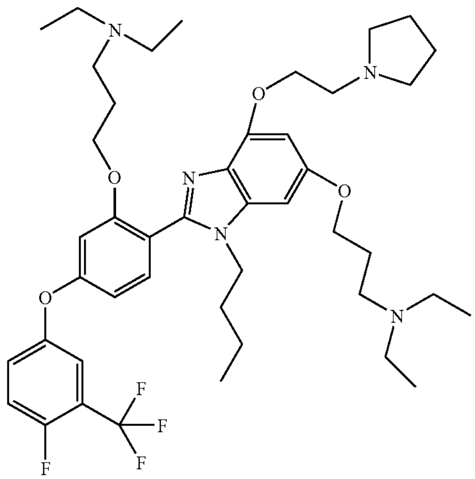 | {3-[2-[1-Butyl-6-(3-diethylamino-propoxy)-4-(2-pyrrolidin-1-yl-ethoxy)-1H-benzoimidazol-2-yl]-5-(4-fluoro-3-trifluoromethyl-phenoxy)-phenoxy]-propyl}-diethyl-amine |
| 336 | 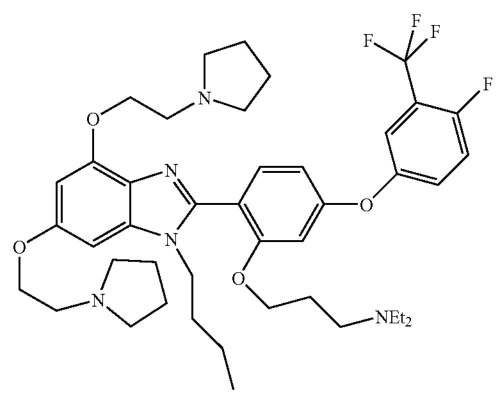 | {3-[2-[1-Butyl-4,6-bis-(2-pyrrolidin-1-yl-ethoxy).-1H-benzoimidazol-2-yl]-5-(4-fluoro-3-trifluoromethyl-phenoxy)-phenoxy]-propyl}-diethyl-amine |
| 337 | 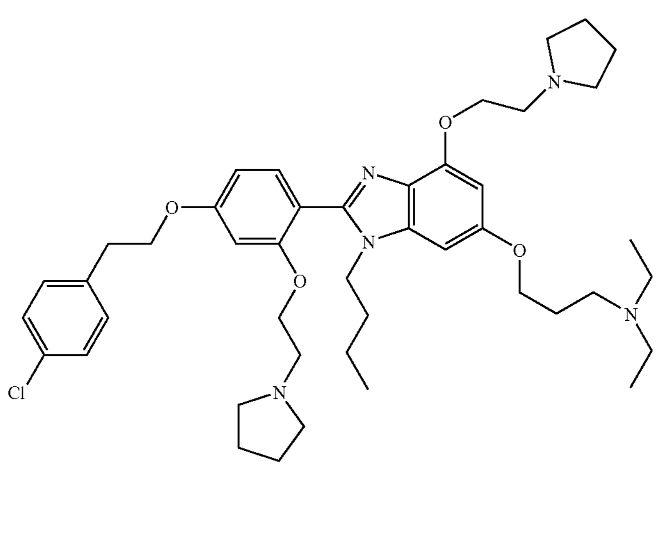 | {3-[3-butyl-2-[4-[2-(4-chloro-phenyl)-ethoxy]-2-(2-pyrrolidin-1-yl-ethoxy)-phenyl]-7-(2-pyrrolidin-1-yl-ethoxy)-3H-benzimidazol-5-yloxy]-propyl}-diethyl-amine |

TABLE 1-continued

| Ex. | Structure | Name |
|---|---|---|
| 338 | 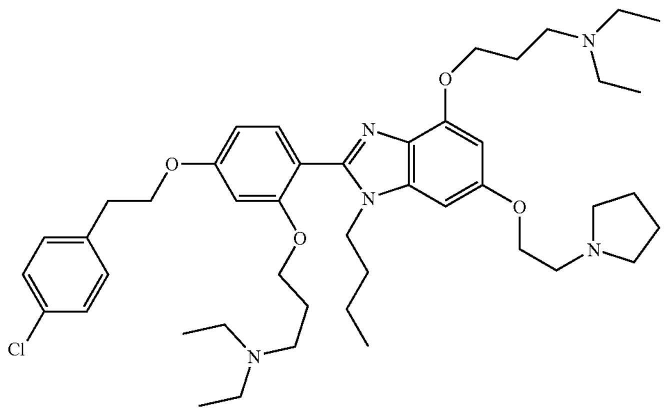 | (3-{2-[1-Butyl-4-(3-diethylamino-propoxy)-6-(2-pyrrolidin-1-yl-ethoxy)-1H-benzoimidazol-2-yl]-5-[2-(4-chloro-phenyl)-ethoxy]-phenoxy}-propyl)-diethyl-amine |
| 339 | 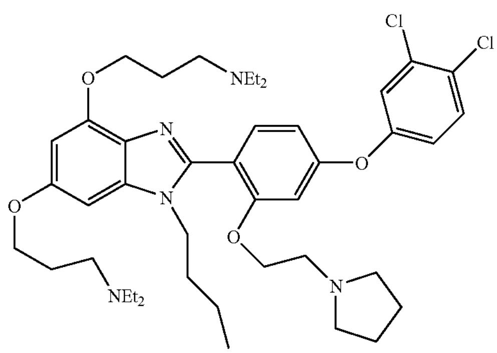 | {3-[1-butyl-2-[4-(3,4-dichloro-phenoxy)-2-(2-pyrrolidin-1-yl-ethoxy)-phenyl]-6-(3-diethylamino-propoxy)-1H-benzimidazol-4-yloxy]-propyl]-diethyl-amine |
| 340 | 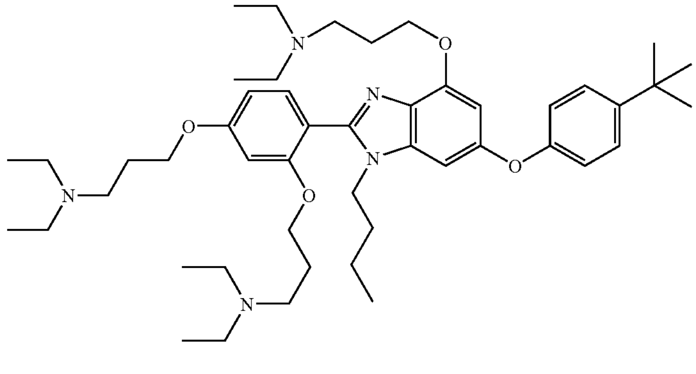 | {3-[2-[2,4-bis-(3-diethylamino-propoxy)-phenyl]-1-butyl-6-(4-tert-butyl-phenoxy)-1H-benzoimidazol-4-yloxy]-propyl}-diethyl-amine |

TABLE 1-continued

| Ex. | Structure | Name |
|---|---|---|
| 341 | 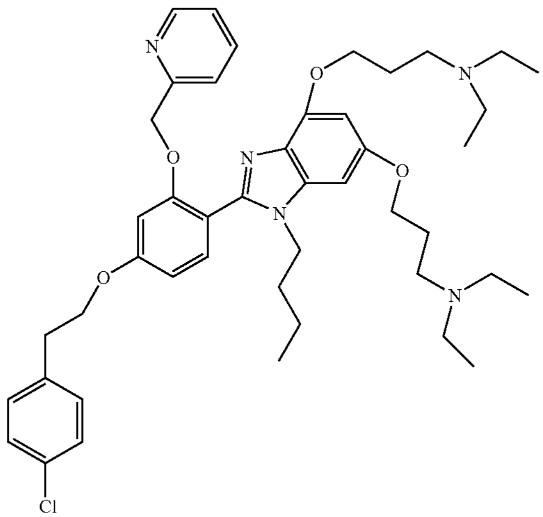 | {3-[1-butyl-2-[4-[2-(4-chloro-phenyl)-ethoxy]-2-(pyridin-2-ylmethoxy)-phenyl]-6-(3-diethylamino-propoxy)-1H-benzimidazol-4-yl]-phenyl}-diethyl-amine |
| 342 | 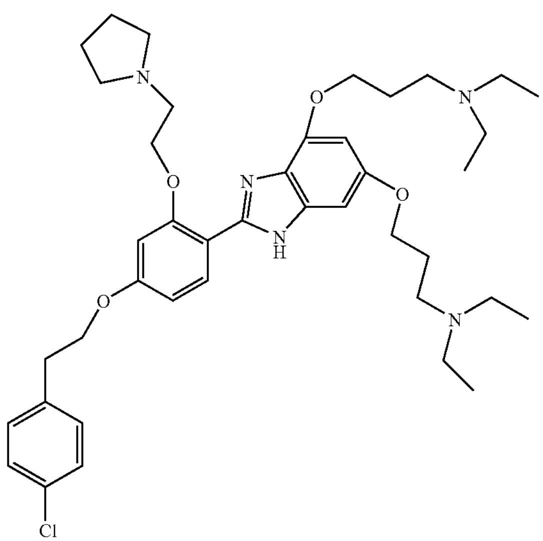 | {3-[2-[4-[2-(4-Chloro-phenyl)-ethoxy]-2-(2-pyrrolidin-1-yl-ethoxy)-phenyl]-6-(3-diethylamino-propoxy)-1H-benzoimidazol-4-yloxy]-propyl}-diethyl-amine |
| 343 | 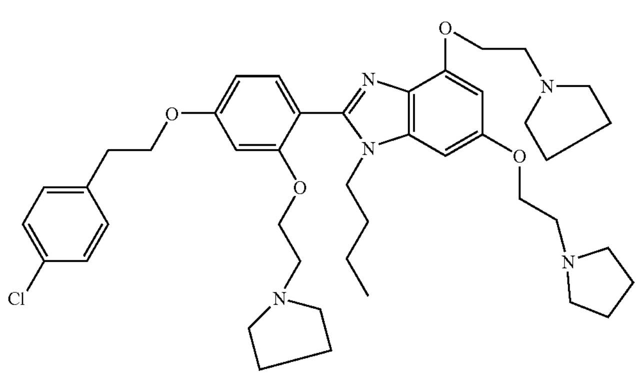 | 1-Butyl-2-[4-[2-(4-chloro-phenyl)-ethoxy]-2-(2-pyrrolidin-1-yl-ethoxy)-phenyl]-4,6-bis-(2-pyrrolidin-1-yl-ethoxy)-1H-benzoimidazole |

TABLE 1-continued

| Ex. | Structure | Name |
|---|---|---|
| 344 | 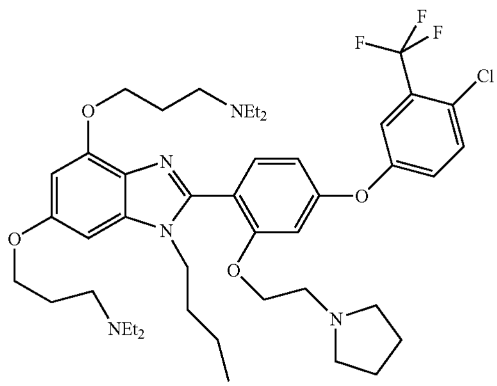 | {3-[1-Butyl-2-[4-(4-chloro-3-trifluoromethyl-phenoxy)-2-(2-pyrrolidin-1-yl-ethoxy)-phenyl]-6-(3-diethylamino-propoxy)-1H-benzoimidazol-4-yloxy]-propyl}-diethyl-amine |
| 345 | 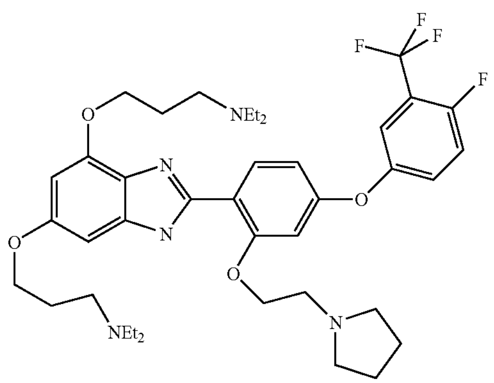 | (3-{6-(3-Diethylamino-propoxy)-2-[4-(4-fluoro-3-trifluoromethyl-phenoxy)-2-(2-pyrrolidin-1-yl-ethoxy)-phenyl]-1H-benzoimidazol-4-yloxy}-propyl)-diethyl-amine |
| 346 | 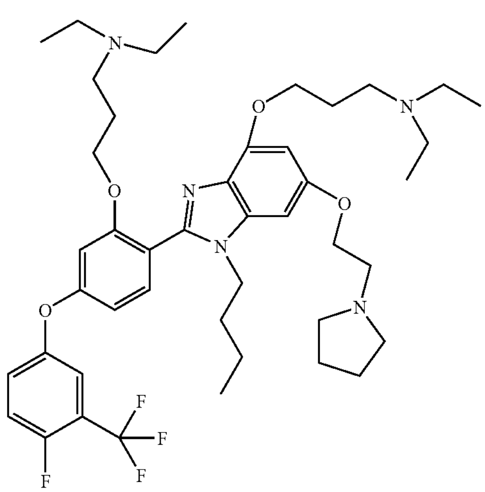 | {3-[2-[1-Butyl-4-(3-diethylamino-propoxy)-6-(2-pyrrolidin-1-yl-ethoxy)-1H-benzoimidazol-2-yl]-5-(4-fluoro-3-trifluoromethyl-phenoxy)-phenoxy]-propyl}-diethyl-amine |

TABLE 1-continued

| Ex. | Structure | Name |
|---|---|---|
| 347 | 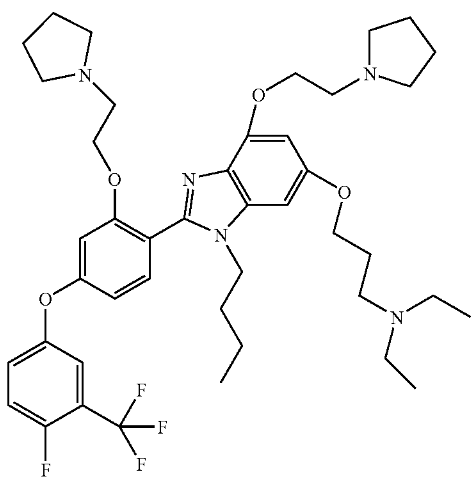 | {3-[3-Butyl-2-[4-(4-fluoro-3-trifluoromethyl-phenoxy)-2-(2-pyrrolidin-1-yl-ethoxy)-phenyl]-7-(2-pyrrolidin-1-yl-ethoxy)-3H-benzoimidazol-5-yloxy]-propyl}-diethyl-amine |
| 348 | 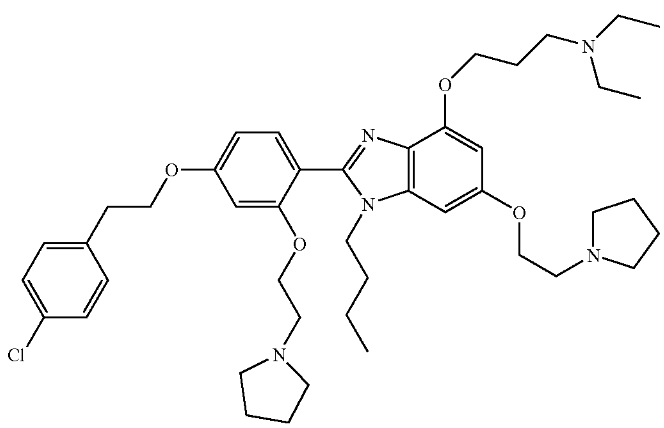 | {3-[1-butyl-2-[4-[2-(4-chloro-phenyl)-ethoxy]-2-(2-pyrrolidin-1-yl-ethoxy)-phenyl]-6-(2-pyrrolidin-1-yl-ethoxy)-1H-benzimidazol-4-yloxy]-propyl}-diethyl-amine |
| 349 | 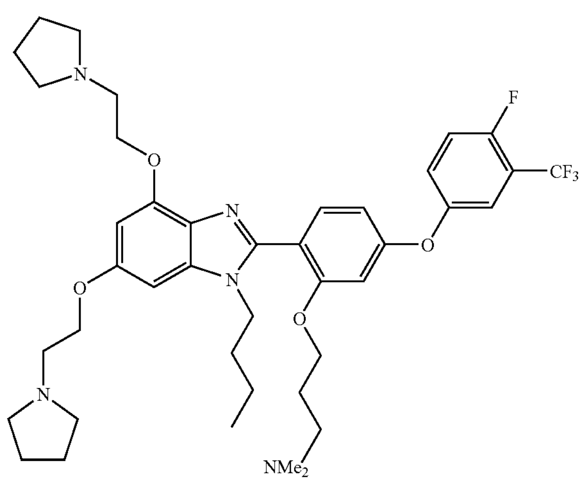 | {3-[2-[1-butyl-4,6-bis-(2-pyrrolodin-1-yl-ethoxy)-1H-benzimidazol-2-yl]-5-(4-fluoro-3-trifluoromethyl-phenoxy)-phenyl]-propyl}-diethyl-amine |

TABLE 1-continued

| Ex. | Structure | Name |
|---|---|---|
| 350 | 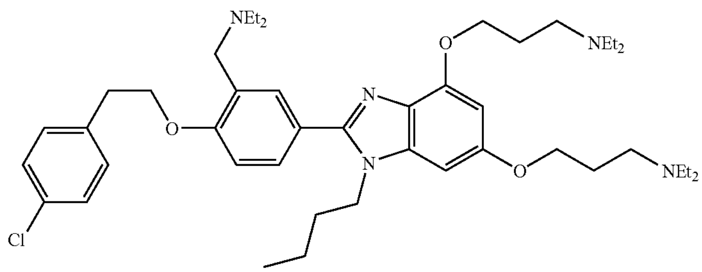 | {3-[1-butyl-2-{4-[2-(4-chloro-phenyl)-ethoxy]-3-diethylaminomethyl-phenyl}-6-(3-diethylamino-propoxy)-1H-benzimidazoI-4-yloxy]-propyl}-diethyl-amine |
| 351 | 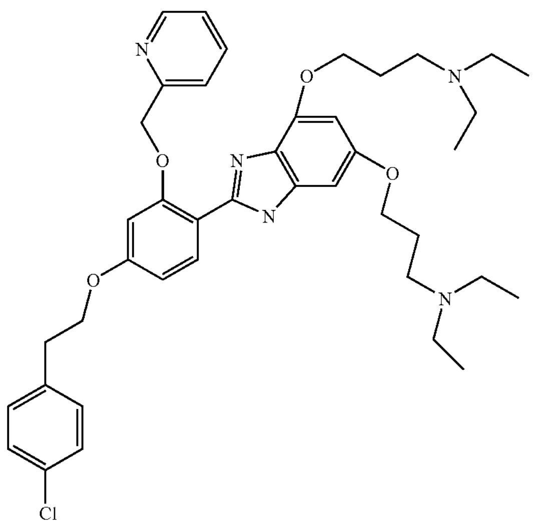 | {3-[2-[4-[2-(4-chloro-phenyl)-ethoxy]-2-(pyridin-2-ylmethoxy)-phenyl]-6-(3-diethylamino-propoxy)-1H-benzimidazoI-4-yl]-propyl}-diethyl-amine |
| 352 | 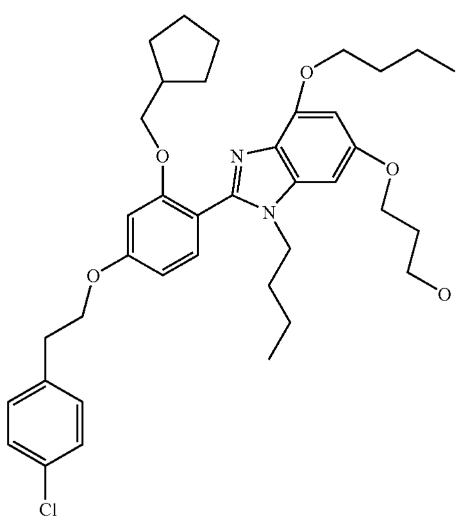 | 3-(7-Butoxy-3-butyl-2-(4-[2-(4-chloro-phenyl)-ethoxy]-2-cyclopentylmethoxy-phenyl}-3H-benzoimidazol-5-yloxy)-propan-1-ol |

TABLE 1-continued

| Ex. | Structure | Name |
|---|---|---|
| 353 | 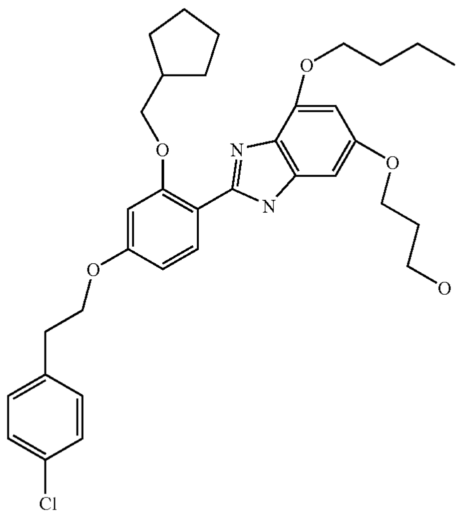 | 3-(7-Butoxy-2-{4-[2-(4-chloro-phenyl)-ethoxy]-2-cyclopentylmethoxy-phenyl}-3H-benzoimidazol-5-yloxy)-propan-1-ol |
| 354 | 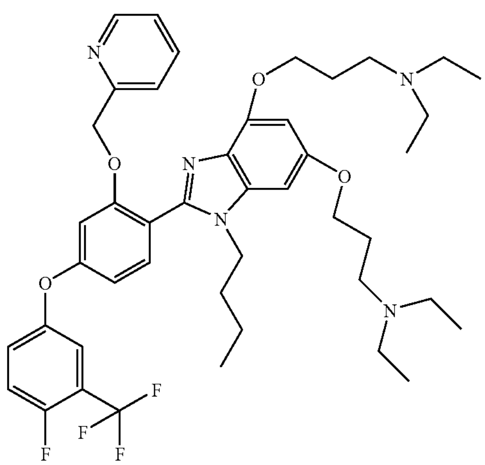 | (3-{1-Butyl-6-(3-diethylamino-propoxy)-2-[4-(4-fluoro-3-trifluoromethyl-phenoxy)-2-(pyridin-2-ylmethoxy)-phenyl]-1H-benzoimidazol-4-yloxy}-propyl)-diethyl-amine |
| 355 | 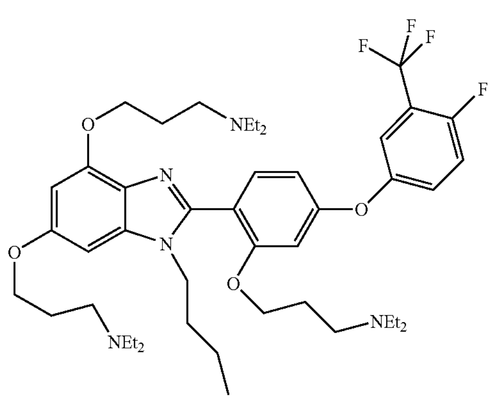 | {3-[2-[1-Butyl-4,6-bis-(3-diethylamino-propoxy)-1H-benzoimidazol-2-yl]-5-(4-fluoro-3-trifluoromethyl-phenoxy)-phenoxy]-propyl}-diethyl-amine |

TABLE 1-continued

| Ex. | Structure | Name |
|---|---|---|
| 356 | 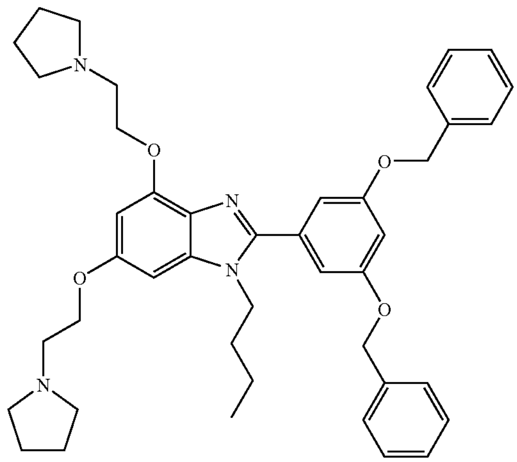 | 2-(3,5-bis-benzyloxy-phenyl)-1-butyl-4,6-bis-(2-pyrrolodin-1-yl-ethoxy)-1H-benzimidazole |
| 357 | 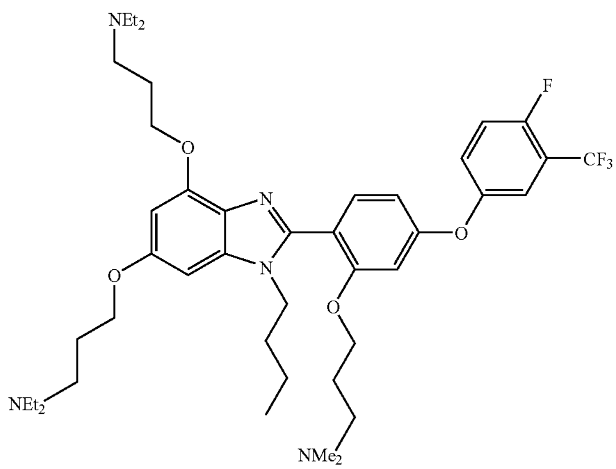 | {3-[2-[1-butyl-4,6-bis-(3-diethylamino-propoxy)-1H-benzimidazol-2-yl]-5-(4-fluoro-3-trifluoromethyl-phenoxy)-phenyl]-propyl}-diethyl-amine |
| 358 | 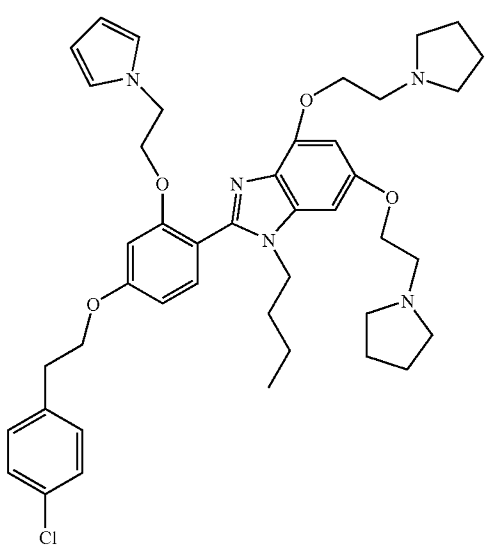 | 1-butyl-2-[4-[2-(4-chloro-phenyl)-ethoxy]-2-(2-pyrrol-1-yl-ethoxy)-phenyl]-4,6-bis-(2-pyrrolodin-1-yl-ethoxy)-1H-benzoimidazole |

TABLE 1-continued

| Ex. | Structure | Name |
|---|---|---|
| 359 | 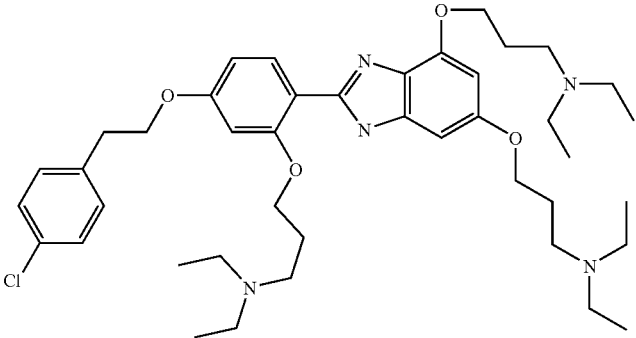 | {3-[2-(4-[2-(4-chloro-phenyl)-ethoxy]-2-(3-diethylamino-propoxy)-phenyl}-6-(3-diethylamino-propoxy)-1H-benzimidazol-4-yloxy]-propyl}-diethyl-amine |
| 360 | 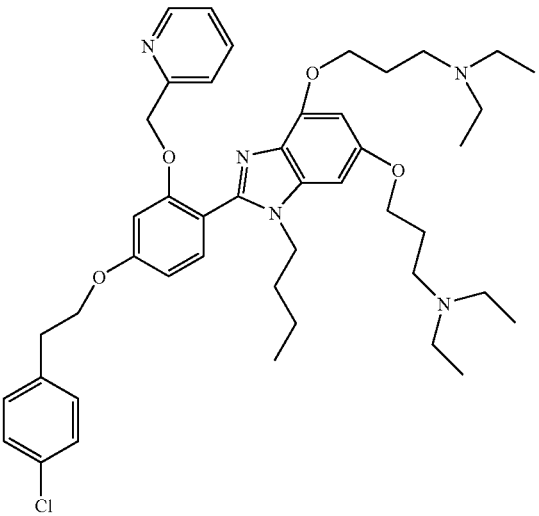 | {3-[1-Butyl-2-[4-[2-(4-chloro-phenyl)-ethoxy]-2-(pyridin-3-ylmethoxy)-phenyl]-6-(3-diethylamino-propoxy)-1H-benzoimidazol-4-yloxy]-propyl}-diethyl-amine |
| 361 | 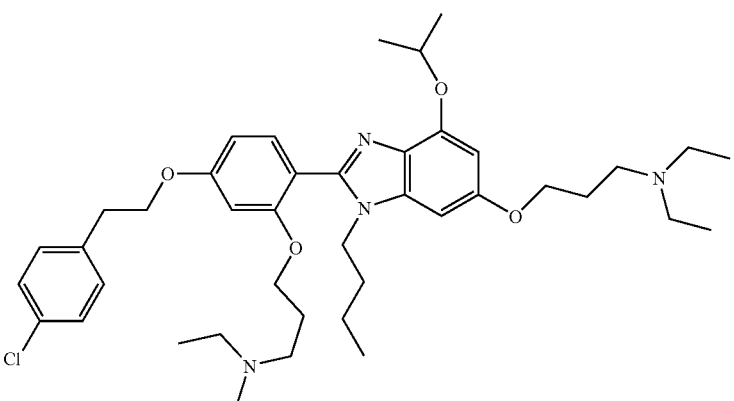 | (3-{3-Butyl-2-[4-[2-(4-chloro-phenyl)-ethoxy]-2-(3-diethylamino-propoxy)-phenyl]-7-isopropoxy-3H-benzoimidazol-5-yloxyl-propyl)-diethyl-amine |

TABLE 1-continued

| Ex. | Structure | Name |
| --- | --- | --- |
| 362 | 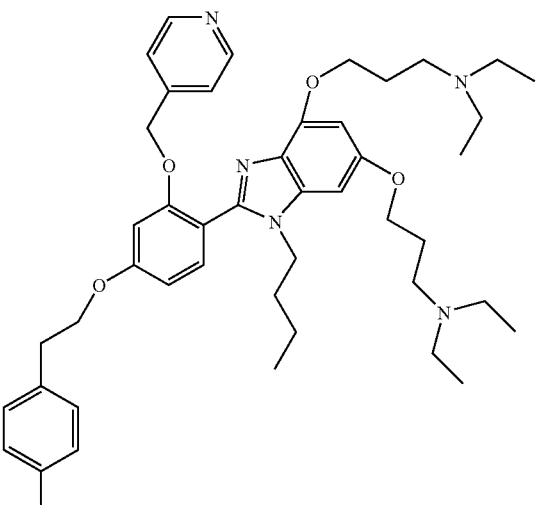 | {3-[1-Butyl-2-[4-[2-(4-chloro-phenyl)-ethoxy]-2-(pyridin-4-ylmethoxy)-phenyl]-6-(3-diethylamino-propoxy)-1H-benzoimidazol-4-yloxy]-propyl]-diethyl-amine |
| 363 | 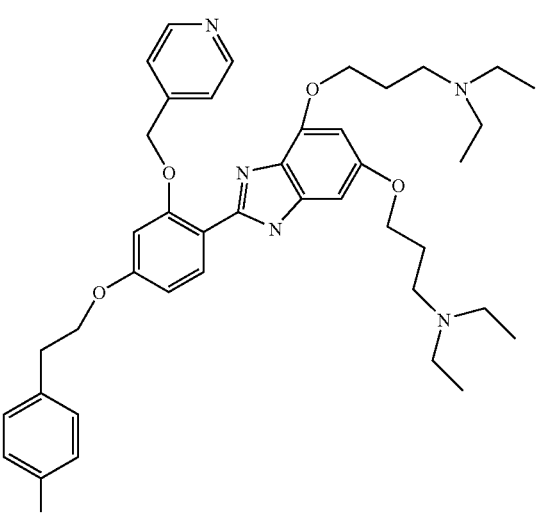 | {3-[2-[4-[2-(4-Chloro-phenyl)-ethoxy]-2-(pyridin-4-ylmethoxy)-phenyl]-6-(3-diethylamino-propoxy)-1H-benzoimidazol-4-yloxy]-propyl}-diethyl-amine |
| 364 | 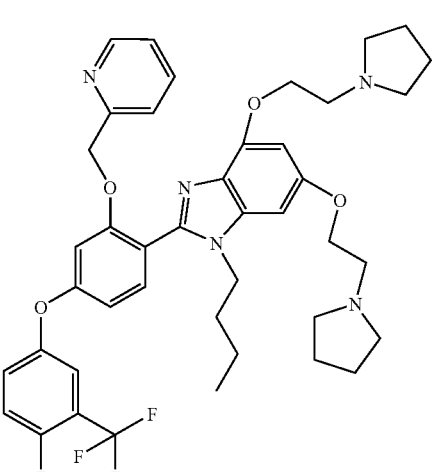 | 1-Butyl-Butyl-2-[4-(4-fluoro-3-trifluoromethyl-phenoxy)-2-(pyridin-2-ylmethoxy)-phenyl]-4,6-bis-(2-pyrrolidin-1-yl-ethoxy)-1H-benzoimidazole |

TABLE 1-continued

| Ex. | Structure | Name |
|---|---|---|
| 365 correct | 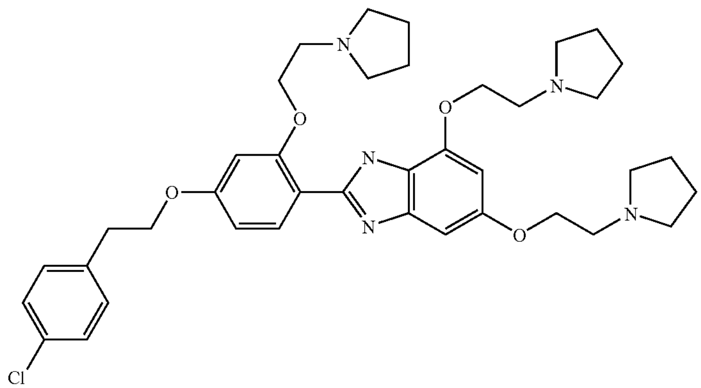 | 2-[4-[2-(4-chloro-phenyl)-ethoxy]-2-(2-pyrrolidin-1-yl-ethoxy)-phenyl]-5,7-bis-(2-pyrrolidin-1-yl-ethoxy)-1H-benzimidazole |
| 366 | 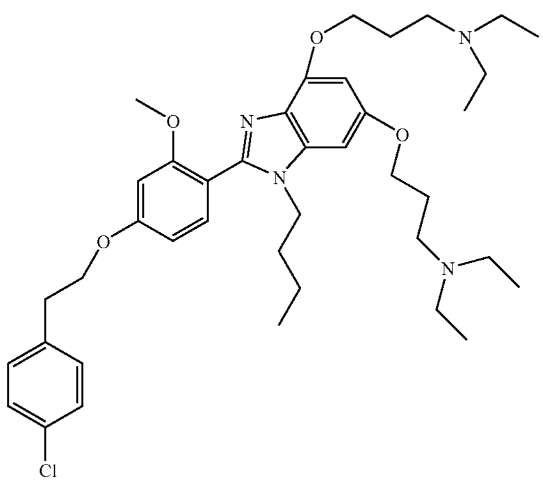 | {3-[1-Butyl-2-{4-[2-(4-chloro-phenyl)-ethoxy]-2-methoxy-phenyl}-6-(3-diethylamino-propoxy)-1H-benzoimidazol-4-yloxy]-propyl]-diethyl-amine |
| 367 | 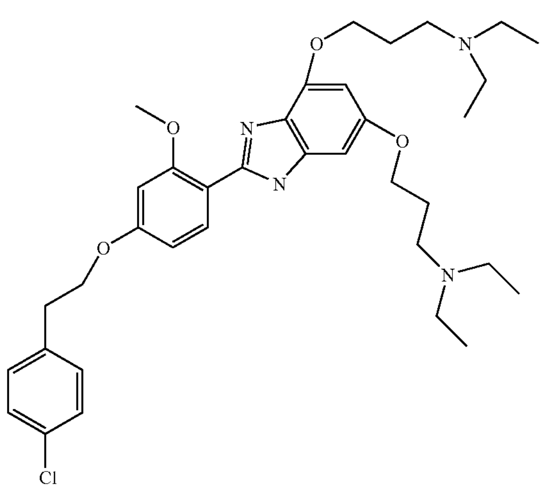 | {3-[2-{4-[2-(4-Chloro-phenyl)-ethoxy]-2-methoxy-phenyl}-6-(3-diethylamino-propoxy)-1H-benzoimidazol-4-yloxy]-propyl}-diethyl-amine |

TABLE 1-continued

| Ex. | Structure | Name |
|---|---|---|
| 368 | 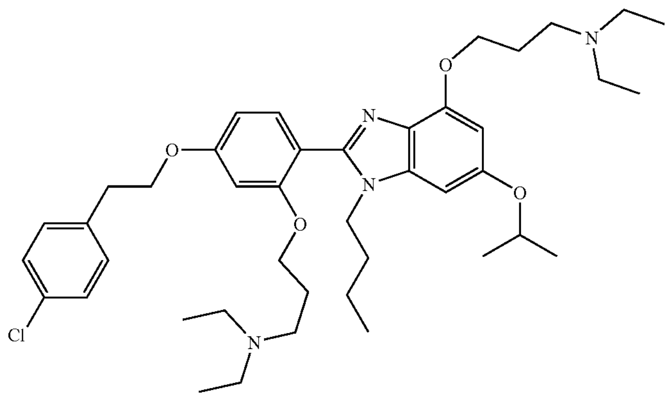 | (3-{1-Butyl-2-[4-[2-(4-chloro-phenyl)-ethoxy]-2-(3-diethylamino-propoxy)-phenyl]-6-isopropoxy-1H-benzoimidazol-4-yloxy}-propyl)-diethyl amine |
| 369 | 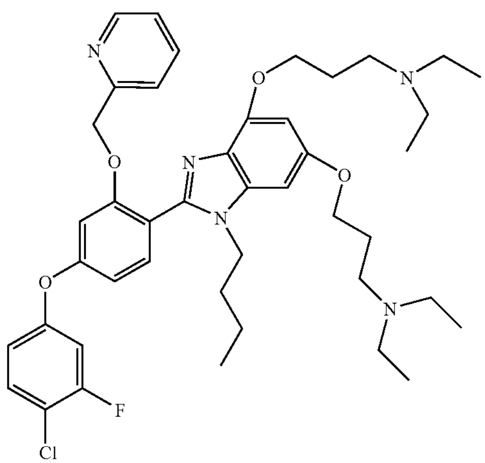 | {3-[1-Butyl-2-[4-(4-chloro-3-methyl-phenoxy)-2-(pyridin-2-ylmethoxy)-phenyl]-6-(3-diethylamino-propoxy)-1H-benzoimidazol-4-yloxy]-propyl}-diethyl-amine |
| 370 | 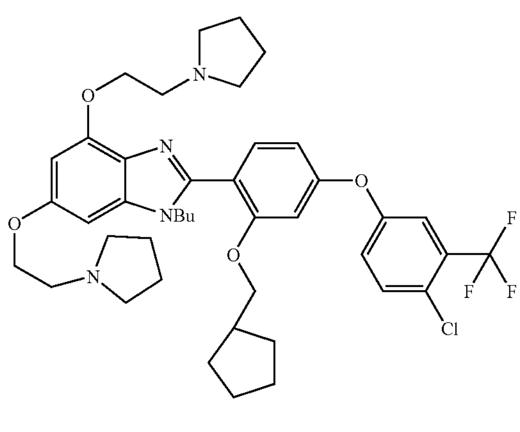 | 1-Butyl-2-[4-(4-chloro-3-trifluoromethyl-phenoxy)-2-cyclopentylmethoxy-phenyl]-4,6-bis-(2-pyrrolidin-1-yl-ethoxy)-1H-benzoimidazole |

TABLE 1-continued

| Ex. | Structure | Name |
|---|---|---|
| 371 | 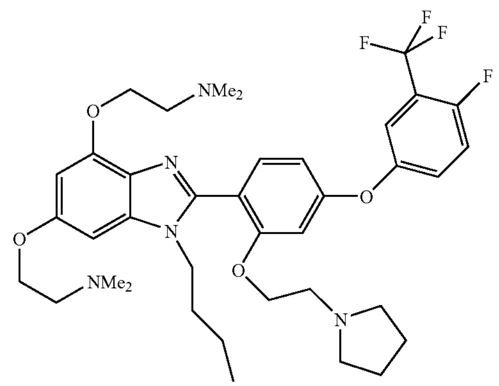 | (2-{1-butyl-6-(2-dimethylamino-ethoxy)-2-[4-(4-fluoro-3-trifluoromethyl-phenoxy)-2-(2-pyrrolidin-1-yl-ethoxy)-phenyl]-1H-benzoimidazole-4-yloxy}-ethyl)-dimethyl-amine |
| 372 | 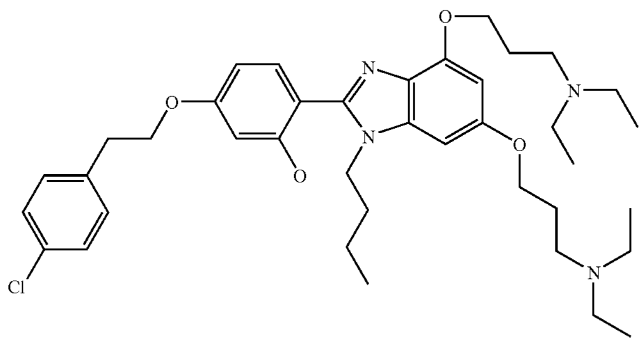 | 2-[1-butyl-4,6-bis-(3-diethylamino-propoxy)-1H-benzimidazol-2-yl]-5-[2-(4-chloro-phenyl)-ethoxy]-phenol |
| 373 | 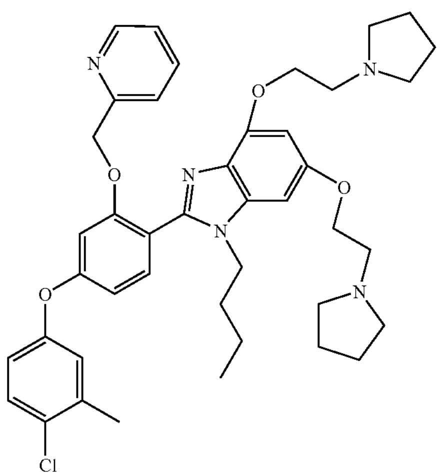 | 1-Butyl-2-[4-(4-chloro-3-methyl-phenoxy)-2-(pyridin-2-ylmethoxy)-phenyl]-4,6-bis-(2-pyrrolidin-1-yl-ethoxy)-1H-benzoimidazole |
| 374 | 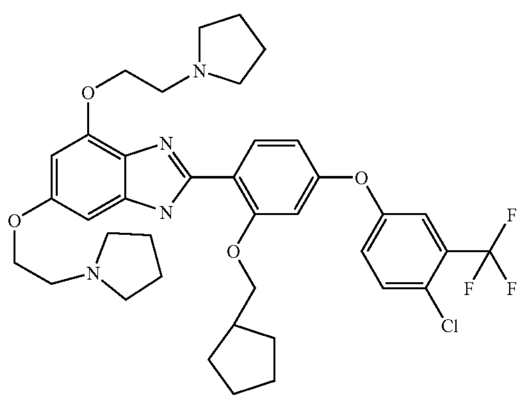 | 2-[4-(4-Chloro-3-trifluoromethyl-phenoxy)-2-cyclopentylmethoxy-phenyl]-4,6-bis-(2-pyrrolidin-1-yl-ethoxy)-1H-benzoimidazole |

TABLE 1-continued

| Ex. | Structure | Name |
|---|---|---|
| 375 | 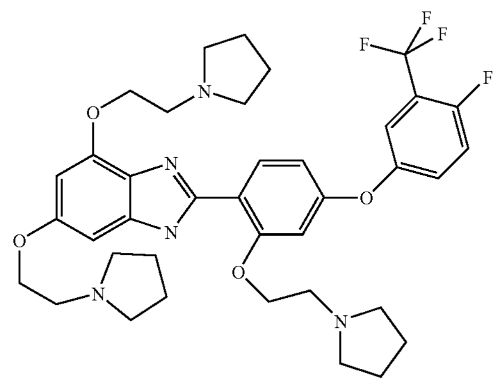 | 2-[4-(4-Fluoro-3-trifluoromethyl-phenoxy)-2-(2-pyrrolidin-1-yl-ethoxy)-phenyl]-4,6-bis-(2-pyrrolidin-1-yl-ethoxy)-1H-benzoimidazole |
| 376 | 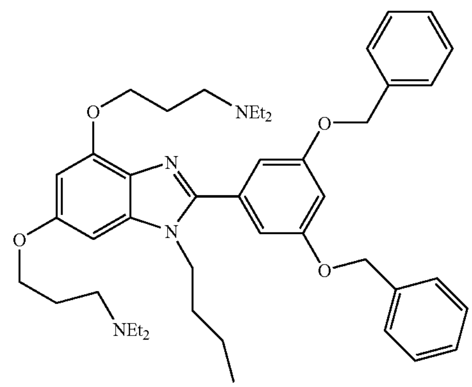 | {3-[2-(3,5-bis-benzyloxy-phenyl)-1-butyl-6-(3-diethylamino-propoxy)-1H-benzimidazol-4-yloxy]-propyl}-diethyl-amine |
| 377 | 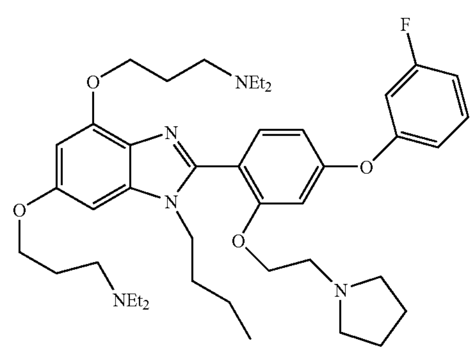 | (3-{1-butyl-6-(3-dimethylamino-propoxy)-2-[4-(3-fluoro-phenoxy)-2-(2-pyrrolidin-1-yl-ethoxy)-phenyl]-1H-benzoimidazole-4-yloxy}-propyl)-diethyl-amine |
| 378 | 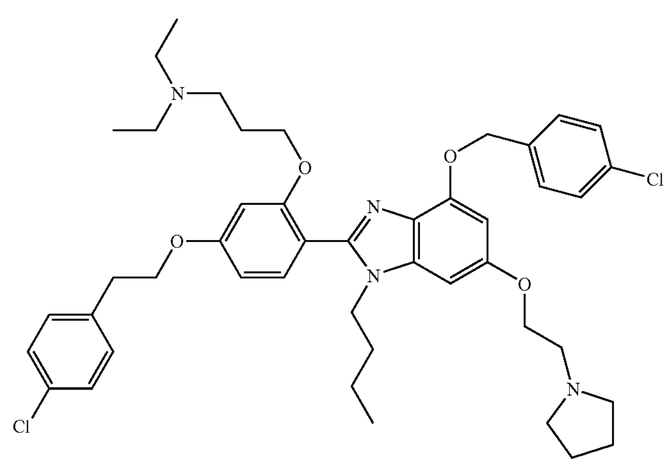 | {3-[2-{1-butyl-4-(4-chloro-benzyloxy)-6-(2-pyrrolidin-1-yl-ethoxy)-1H-benzimidazol-2-yl]-5-[2-(4-chloro-phenyl)-ethoxy]-phenoxy}-propyl)-diethyl-amine |

TABLE 1-continued

| Ex. | Structure | Name |
|---|---|---|
| 379 | 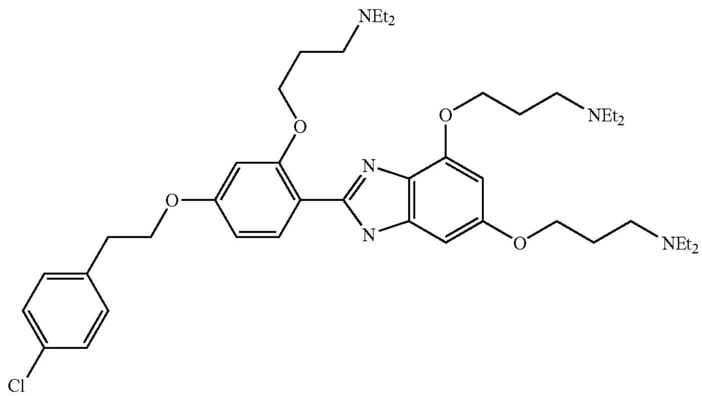 | {3-[2-{4-[2-(4-chloro-phenyl)-ethoxy]-2-(3-diethylamino-propoxy)-phenyl]-6-(3-diethylamino-propoxy)-3H-benzimidazol-4-yloxy]-propyl}-diethyl-amine |
| 380 | 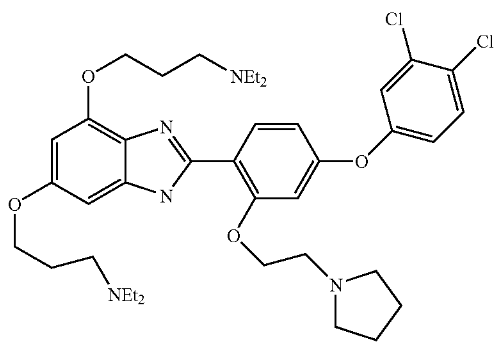 | {3-[2-[4-(3,4-dichloro-phenoxy)-2-(2-pyrrolidin-1-yl-ethoxy)-phenyl]-6-(3-diethylamino-propoxy)-1H-benzimidazol-4-yloxy]-propyl}-diethyl-amine |
| 381 | 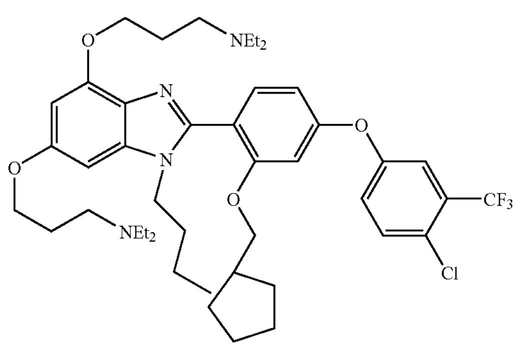 | {3-[1-Butyl-2-[4-(4-chloro-3-trifluoromethyl-phenoxy)-2-cyclopentylmethoxy-phenyl]-6-(3-diethylamino-propoxy)-1H-benzoimidazol-4-yloxy]-propyl}-diethyl-amine |
| 382 | 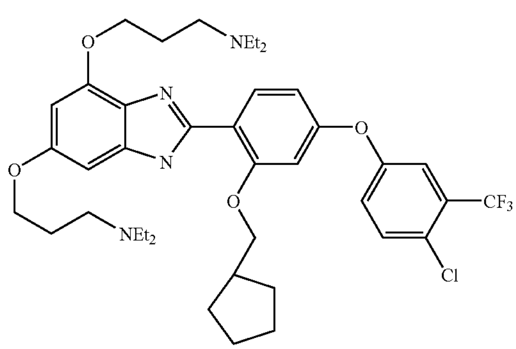 | {3-[2-[4-(4-chloro-3-trifluoromethyl-phenoxy)-2-cyclopentylmethoxy-phenyl]-6-(3-diethylamino-propoxy)-1H-benzoimidazol-4-yloxy]-propyl}-diethyl-amine |

TABLE 1-continued

| Ex. | Structure | Name |
|---|---|---|
| 383 | 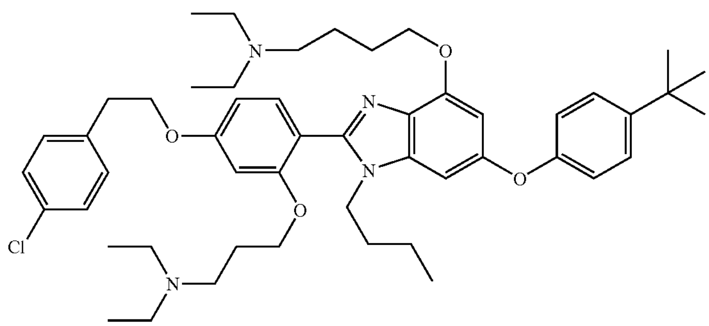 | (3-{1-butyl-6-(4-tert-butyl-phenoxy)-2-[4-[2-(4-chloro-phenyl)-ethoxy]-2-(3-diethylamino-propoxy)-phenyl]-1H-benzimidazol-4-yloxyl-propyl)-diethyl-amine |
| 384 | 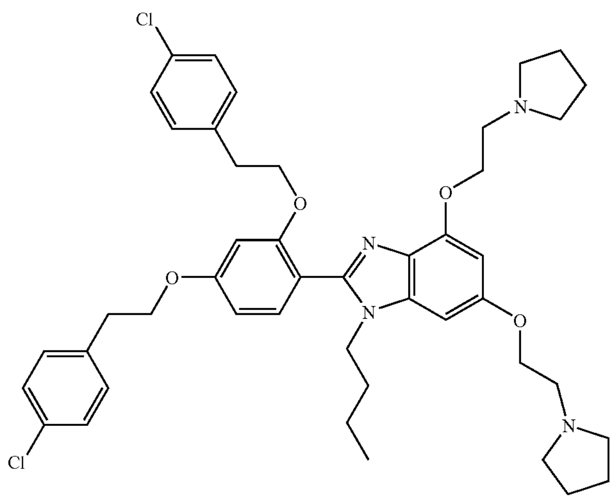 | 2-{2,4-bis-[2-(4-chloro-phenyl)-ethoxy]-phenyl}-1-butyl-4,6-bis-(2-pyrrolidin-1-yl-ethoxy)-1H-benzimidzole |
| 385 | 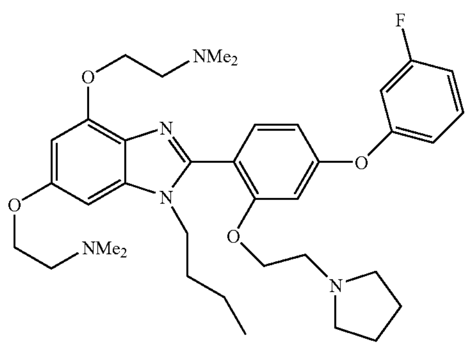 | (2-{1-butyl-6-(2-dimethylamino-ethoxy)-2-[4-(3-fluoro-phenoxy)-2-(2-pyrrolidin-1-yl-ethoxy)-phenyl]-1H-benzoimidazole-4-yloxy}-ethyl)-dimethyl-amine |
| 386 | 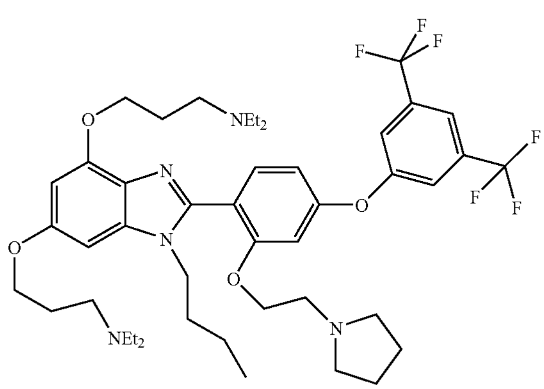 | {3-[2-[4-(3,5-bis-trifluoromethyl-phenoxy)-2-(2-pyrrolidin-1-yl-ethoxy)-phenyl]-1-butyl-6-(3-diethylamino-propoxy)-1H-benzimidazol-4-yloxy]-propyl}-diethyl-amine |

TABLE 1-continued

| Ex. | Structure | Name |
| --- | --- | --- |
| 387 | 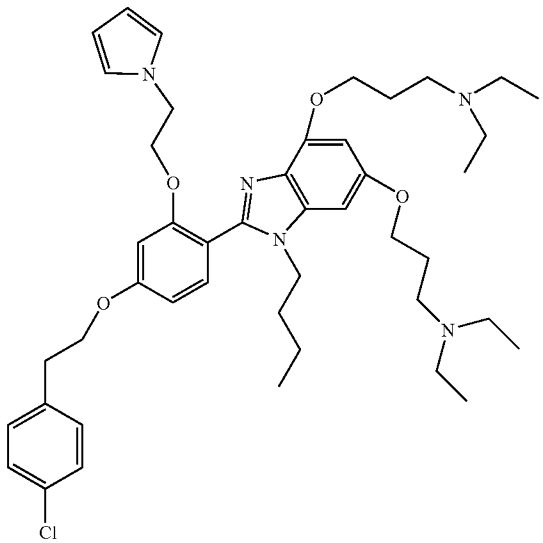 | {3-[1-butyl-2-[4-[2-(4-chloro-phenyl)-ethoxy]-2-(2-pyrrolidin-1-yl-ethoxy)-phenyl]-6-(3-diethylamino-propoxy)-1H-benzimidazol-4-yloxyl-propyl}-diethyl-amine |
| 388 | 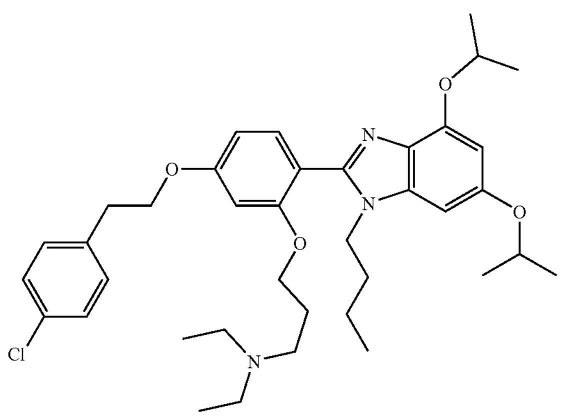 | (3-{2-(1-Butyl-4,6-diisopropoxy-1H-benzoimidazol-2-yl)-5-[2-(4-chloro-phenyl)-ethoxy]-phenoxy}-propyl)-diethyl-amine |
| 389 | 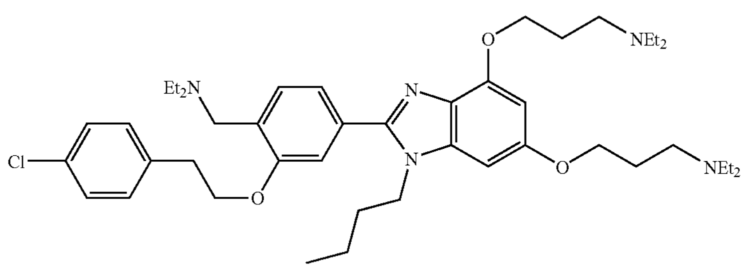 | {3-[1-butyl-2-{3-[2-(4-chloro-phenyl)-ethoxy]-4-diethylaminomethyl-phenyl]-6-(3-diethylamino-propoxy)-1H-benzimidazol-4-yloxy]-propyl}-diethyl-amine |
| 390 | 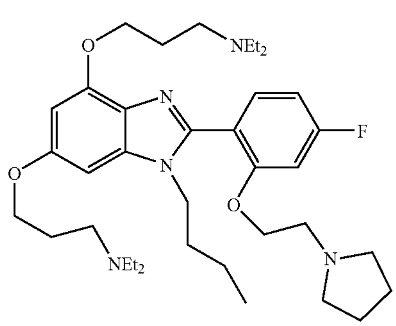 | (3-{1-Butyl-6-(3-diethylamino-propoxy)-2-[4-fluoro-2-(2-pyrrolidin-1-yl-ethoxy)-phenyl]-1H-benzoimidazol-4-yloxy}-propyl)-diethyl-amine |

TABLE 1-continued

| Ex. | Structure | Name |
|---|---|---|
| 391 | 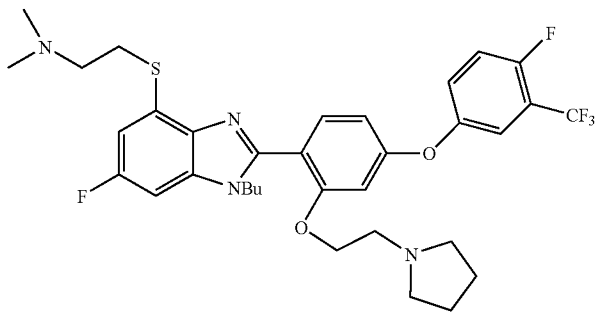 | (2-{1-butyl-6-fluoro-2-[4-(4-fluoro-3-trifluoromethyl-phenoxy)-2-(2-pyrrolidin-1-yl-ethoxy)-phenyl]-1H-benzoimidazol-4-ylsulfanyl}-ethyl)-dimethyl-amine |
| 392 | 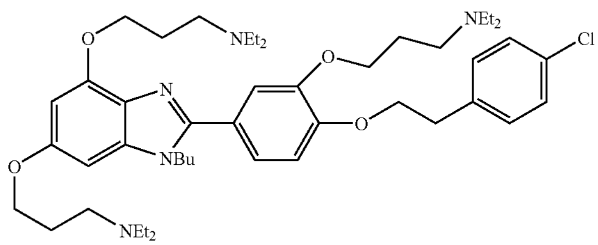 | {3-[1-Butyl-2-[4-[2-(4-chloro-phenyl)-ethoxy]-3-(3-diethylamino-propoxy)-phenyl]-6-(3-diethylamino-propoxy)-1H-benzoimidazol-4-yloxy]-propyl}-diethyl-amine |
| 393 | 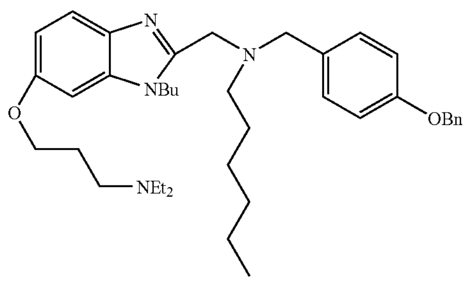 | (4-benzyloxy-benzyl)-[1-butyl-6-(3-diethylamino-propoxy)-1H-benzimidazol-2-ylmethyl]-hexyl-amine |
| 394 | 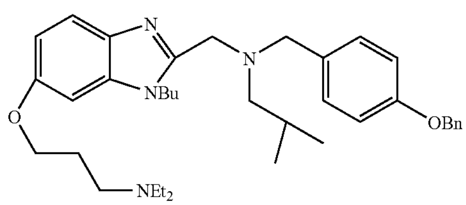 | (4-benzyloxy-benzyl)-[1-butyl-6-(3-diethylamino-propoxy)-1H-benzimidazol-2-ylmethyl]-isobutyl-amine |
| 395 | 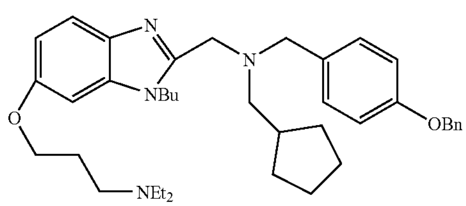 | [3-(2-{[(4-benzyloxy-benzyl)-cyclopentylmethyl-amino]-methyl}-3-butyl-3H-benzimidazol-5-yloxy)-propyl]-diethyl-amine |
| 396 | 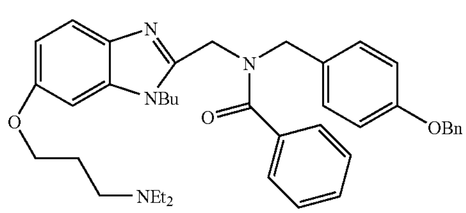 | N-(4-benzyloxy-benzyl)-N-[1-butyl-6-(3-diethylamino-propoxy)-1H-benzimidazol-2-ylmethyl]-benzamide |

TABLE 1-continued

| Ex. | Structure | Name |
|---|---|---|
| 397 | 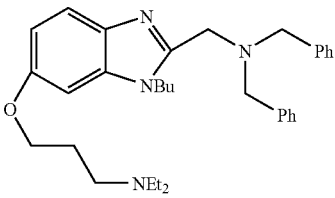 | (3-{3-butyl-2-[(dibenzylamino)-methyl]-3H-benzimidazol-5-yloxy)-propyl]-diethyl-amine |
| 398 | 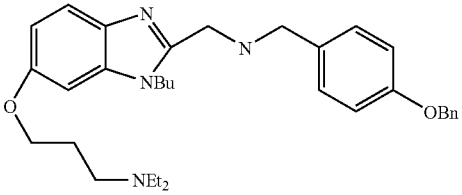 | (3-{2-[(4-benzyloxy-benzylamino)-methyl]-3-butyl-3H-benzimidazol-5-yloxy}-propyl)-diethyl-amine |
| 399 | 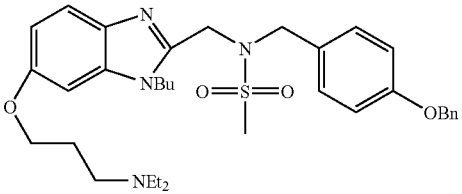 | N-(4-benzyloxy-benzyl)-N-[1-butyl-6-(3-diethylamino-propoxy)-1H-benzimidazol-2-ylmethyl]-methanesulfonamide |
| 400 | 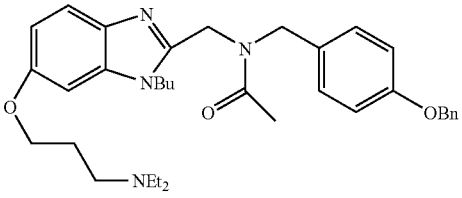 | N-(4-benzyloxy-benzyl)-N-[1-butyl-6-(3-diethylamino-propoxy)-1H-benzimidazol-2-ylmethyl]-acetamide |
| 401 | 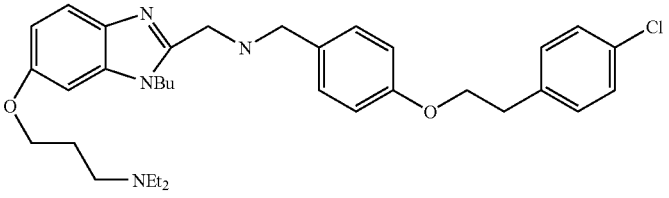 | {3-[3-butyl-2-({4-[2-(4-chloro-phenyl)-ethoxy]-benzylamino}-methyl)-3H-benzimidazol-5-yloxy)-propyl]-diethyl-amine |
| 402 | 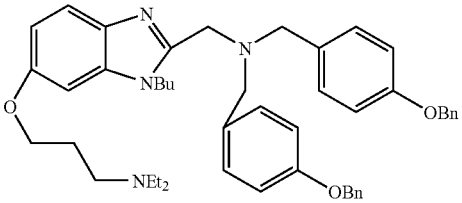 | [3-(2-{[Bis-(4-benzyloxy-benzyl)-amino]-methyl}-3-butyl-3H-benzoimidazol-5-yloxy)-propyl]-diethyl-amine |
| 403 | 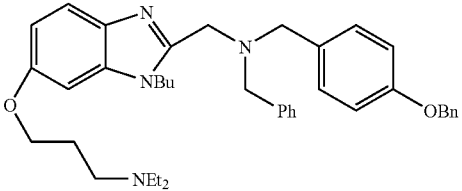 | [3-(2-{[Benzyl-(4-benzyloxy-benzyl)-amino]-methyl}-3-butyl-3H-benzoimidazol-5-yloxy)-propyl]-diethyl-amine |

TABLE 1-continued

| Ex. | Structure | Name |
|---|---|---|
| 404 | 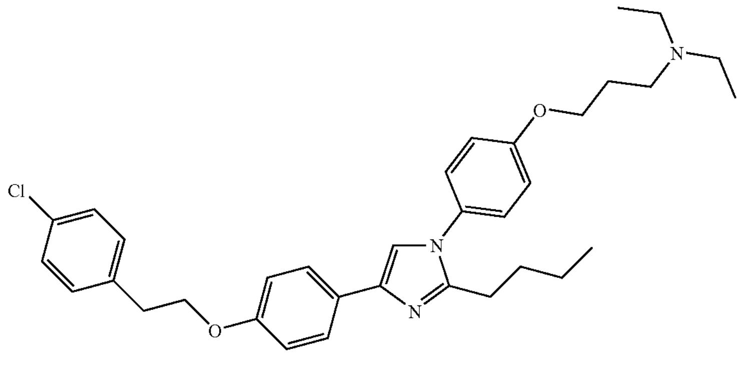 | {3-[4-(2-butyl-4-{4-[2-(4-chloro-phenyl)-ethoxy]-phenyl}-imidazol-1-yl)-phenoxy]-propyl]-diethyl-amine |
| 405 | 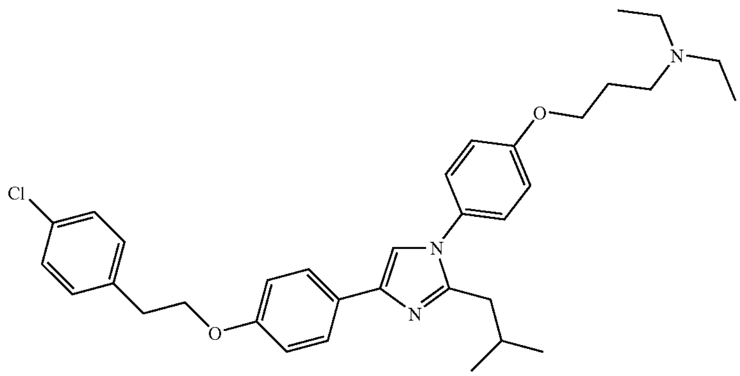 | {3-[4-(4-{4-[2-(4-chloro-phenyl)-ethoxy]-phenyl}-2-isobutyl-imidazol-1-yl)-phenoxy]-propyl)-diethyl-amine |
| 406 | 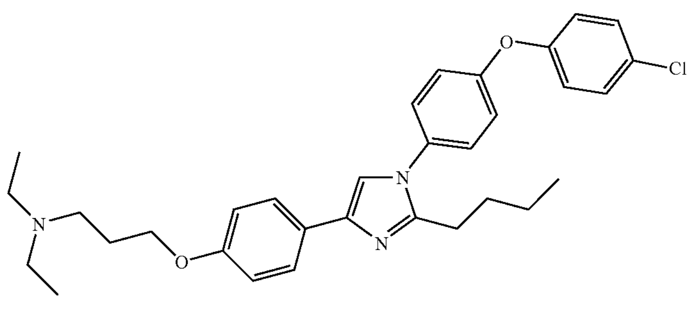 | [3-(4-{2-butyl-1-[4-(4-chloro-phenoxy)-phenyl]-1H-imidazol-4-yl}-phenoxy)-propyl]-diethyl-amine |
| 407 | 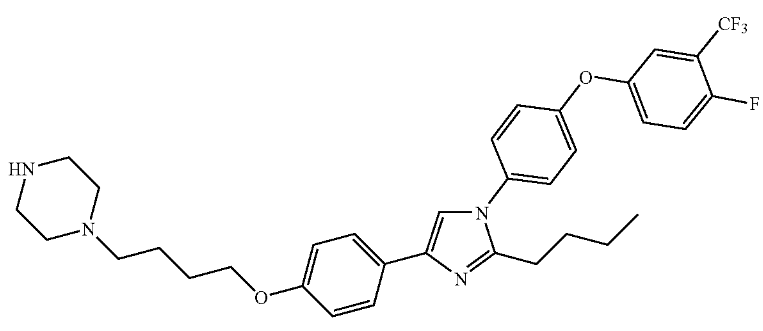 | 1-[4-(4-{2-butyl-1-[4-(4-fluoro-3-trifluoromethyl-phenoxy)-phenyl]-1H-imidazol-4-yl}-phenoxy)-butyl]-piperazine |

TABLE 1-continued

| Ex. | Structure | Name |
| --- | --- | --- |
| 408 | 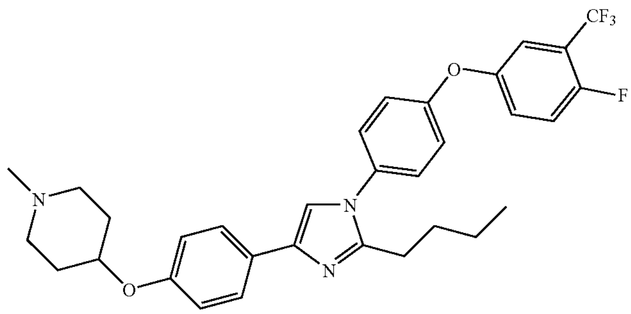 | 4-(4-{2-butyl-1-[4-(4-fluoro-3-trifluoromethyl-phenoxy)-phenyl]-1H-imidazol-4-yl]-phenoxy)-1-methyl-piperidine |
| 409 | 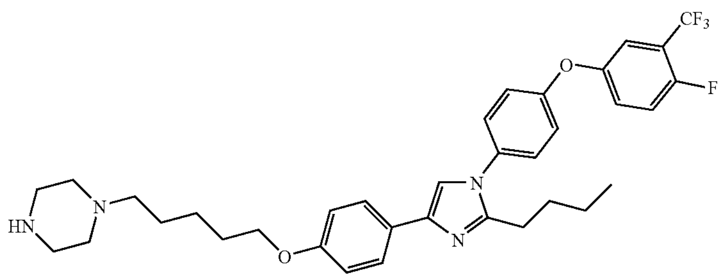 | 1-[5-(4-{2-butyl-1-[4-(4-fluoro-3-trifluoromethyl-phenoxy)-phenyl]-1H-imidazol-4-yl}-phenoxy)-pentyl]-piperazine |
| 410 | 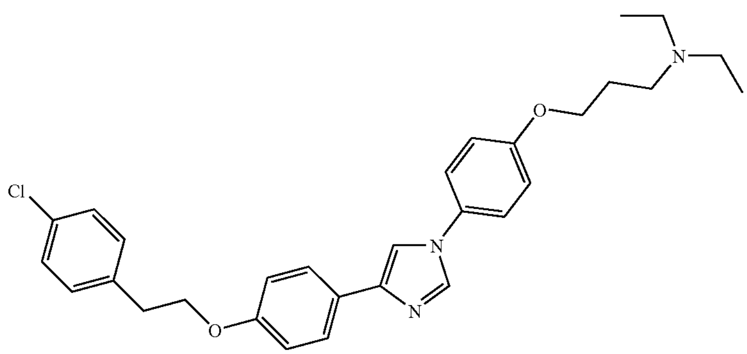 | {3-[4-(4-{4-[2-(4-chloro-phenyl)-ethoxy]-phenyl}-imidazol-1-yl)-phenoxy]-propyl}-diethyl-amine |
| 411 | 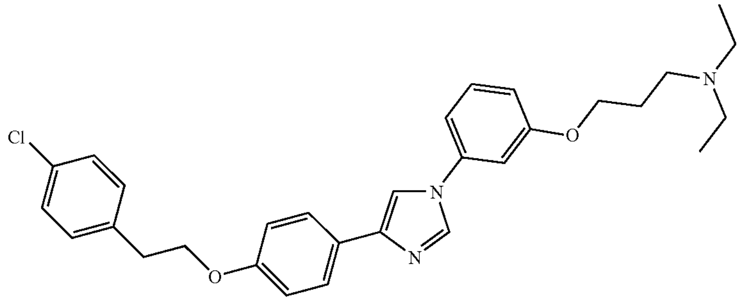 | {3-[3-(4-{4-[2-(4-chloro-phenyl)-ethoxy]-phenyl}-imidazol-1-yl)-phenoxy]-propyl}-diethyl-amine |

TABLE 1-continued

| Ex. | Structure | Name |
| --- | --- | --- |
| 412 | 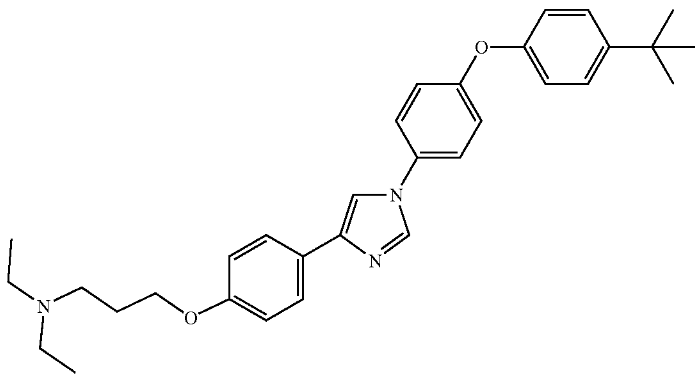 | [3-(4-{1-[4-(4-tert-butyl-phenoxy)-phenyl]-1H-imidazol-4-yl)-phenoxy)-propyl]-diethyl-amine |
| 413 | 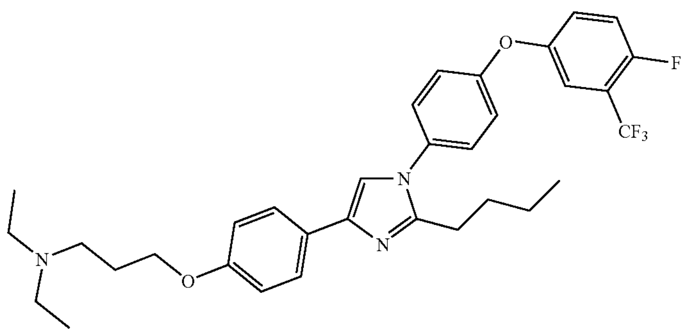 | [3-(4-{2-butyl-1-[4-(4-fluoro-3-trifluoromethyl-phenoxy)-phenyl]-1H-imidazol-4-yl}-phenoxy)-propyl]-diethyl-amine |
| 414 | 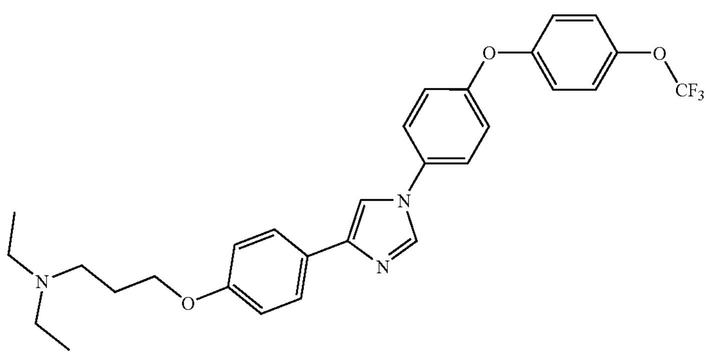 | diethyl-[3-(4-{1-[4-(4-trifluoromethoxy-phenoxy)-phenyl]-1H-imidazol-4-yl}-phenoxy)-propyl]-amine |
| 415 | 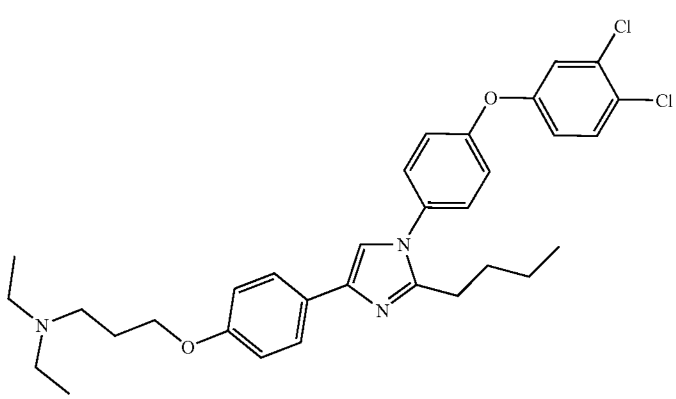 | [3-(4-{2-butyl-1-[4-(3,4-dichloro-phenoxy)-phenyl]-1H-imidazol-4-yl}-phenoxy)-propyl]-diethyl-amine |

TABLE 1-continued

| Ex. | Structure | Name |
|---|---|---|
| 416 | 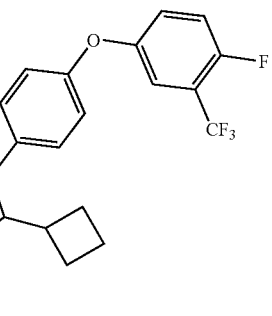 | [3-(4-{2-cyclobutyl-1-[4-(4-fluoro-3-trifluoromethyl-phenoxy)-phenyl]-1H-imidazol-4-yl}-phenoxy)-propyl]-diethyl-amine |
| 417 | 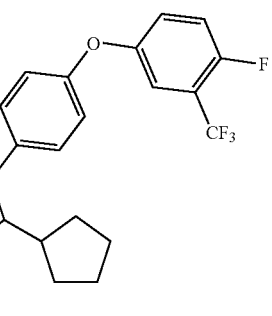 | [3-(4-{2-cyclopentyl-1-[4-(4-fluoro-3-trifluoromethyl-phenoxy)-phenyl]-1H-imidazol-4-yl}-phenoxy)-propyl]-diethyl-amine |
| 418 | 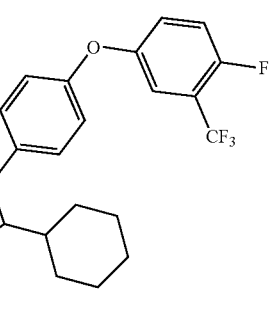 | [3-(4-{2-cyclohexyl-1-[4-(4-fluoro-3-trifluoromethyl-phenoxy)-phenyl]-1H-imidazol-4-yl)-phenoxy)-propyl]-diethyl-amine |
| 419 | 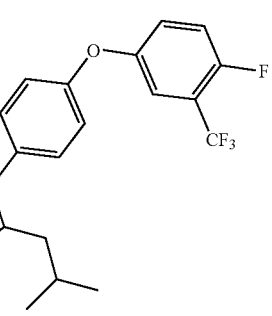 | diethyl-[3-(4-{1-[4-(4-fluoro-3-trifluoromethyl-phenoxy)-phenyl]-2-isobutyl-1H-imidazol-4-yl}-phenoxy)-propyl]-amine |

TABLE 1-continued

| Ex. | Structure | Name |
|---|---|---|
| 420 | 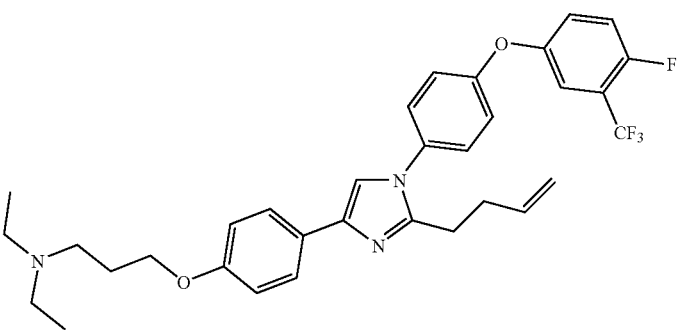 | [3-(4-{2-but-3-enyl-1-[4-(4-fluoro-3-trifluoromethyl-phenoxy)-phenyl]-1H-imidazol-4-yl}-phenoxy)-propyl]-diethyl-amine |
| 421 | 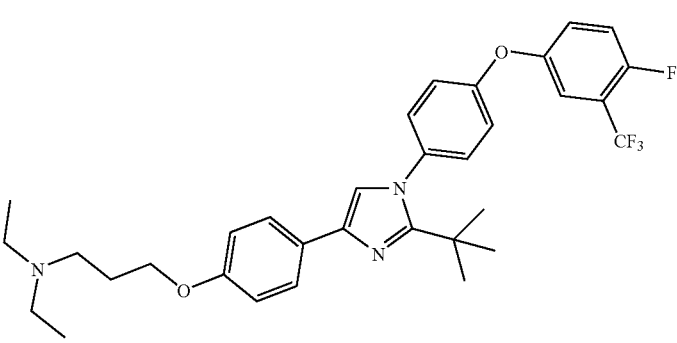 | [3-(4-{2-tert-butyl-1-[4-(4-fluoro-3-trifluoromethyl-phenoxy)-phenyl]-1H-imidazol-4-yl}-phenoxy)-propyl]-diethyl-amine |
| 422 | 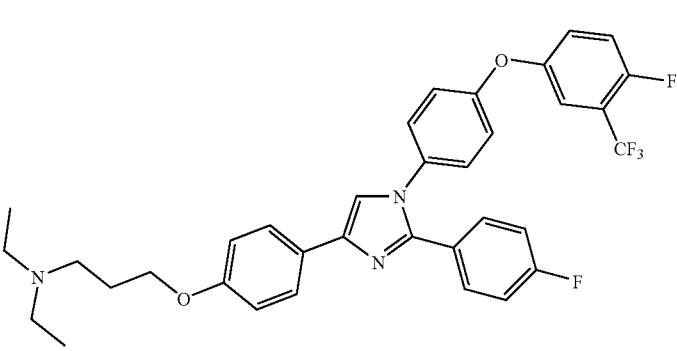 | diethyl-[3-(4-{2-(4-fluoro-phenyl)-1-[4-(4-fluoro-3-trifluoromethyl-phenoxy)-phenyl]-1H-imidazol-4-yl}-phenoxy)-propyl]-amine |
| 423 | 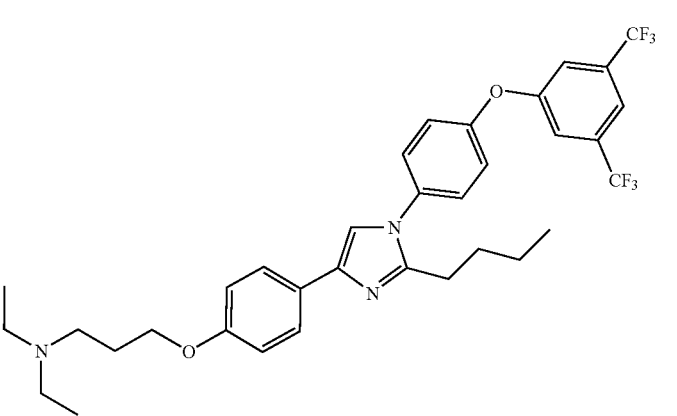 | [3-(4-{1-[4-(3,5-bis-trifluoromethyl-phenoxy)-phenyl]-2-butyl-1H-imidazol-4-yl}-phenoxy)-propyl]-diethyl-amine |

TABLE 1-continued

| Ex. | Structure | Name |
|---|---|---|
| 424 | 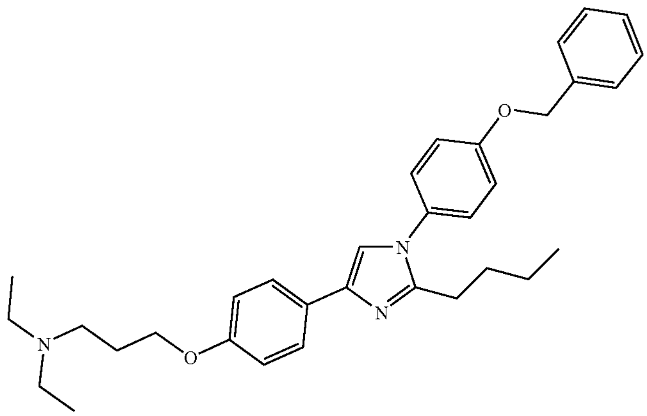 | (3-{4-[1-(4-benzyloxy-phenyl)-2-butyl-1H-imidazol-4-yl]-phenoxy}-propyl)-diethyl-amine |
| 425 | 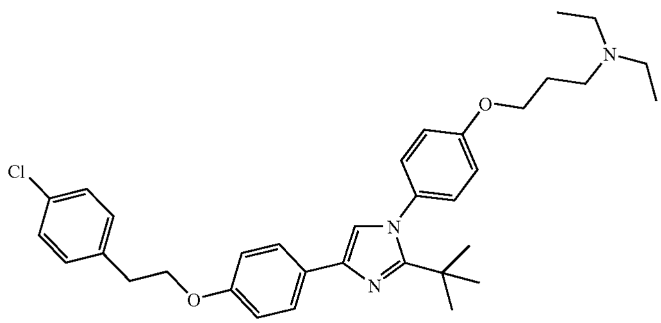 | {3-[4-(2-tert-butyl-4-{4-[2-(4-chloro-phenyl)-ethoxy]-phenyl}-imidazol-1-yl)-phenoxyl-propyl}-diethyl-amine |
| 426 | 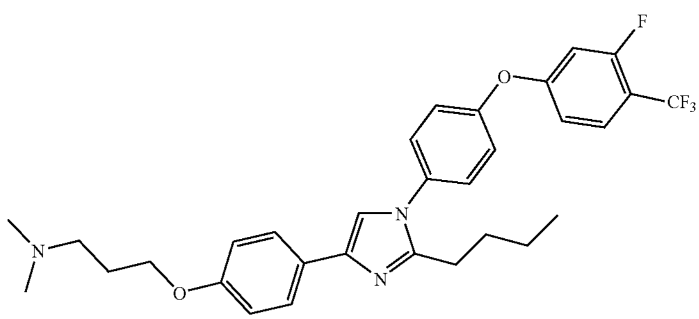 | [3-(4-{2-butyl-1-[4-(3-fluoro-4-trifluoromethyl-phenoxy)-phenyl]-1H-imidazol-4-yl}-phenoxy)-propyl]-diethyl-amine |
| 427 | 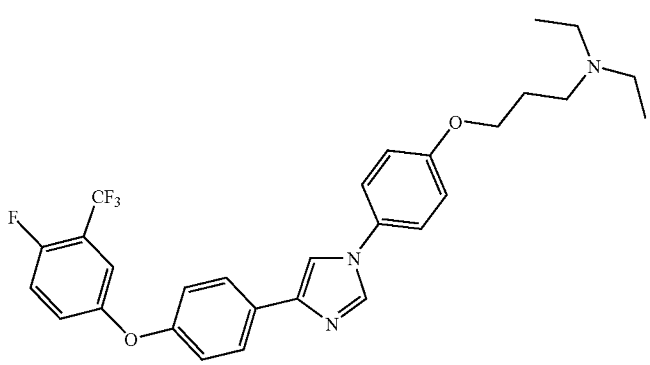 | diethyl-[3-(4-{4-[4-(4-fluoro-3-trifluoromethyl-phenoxy)-phenyl]-imidazol-1-yl}-phenoxy)-propyl]-amine |

TABLE 1-continued

| Ex. | Structure | Name |
| --- | --- | --- |
| 428 | 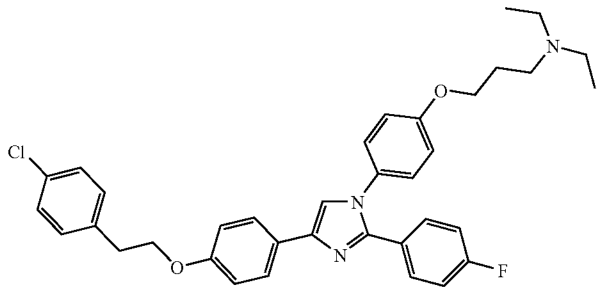 | (3-{4-[4-{4-[2-(4-chloro-phenyl)-ethoxy]-phenyl}-2-(4-fluoro-phenyl)-imidazol-1-yl]-phenoxy}-propyl)-diethyl-amine |
| 429 | 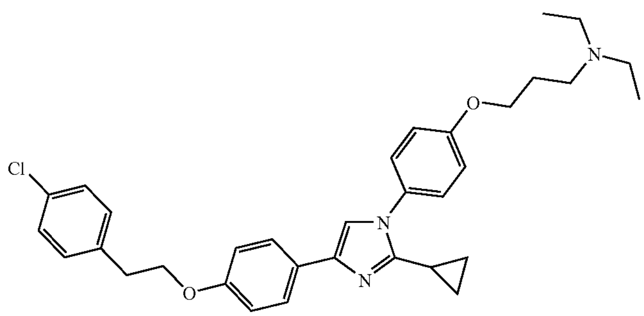 | (3-[4-(4-{4-[2-(4-chloro-phenyl)-ethoxy]-phenyl}-2-cyclopropyl-imidazol-1-yl)-phenoxy]-propyl}-diethyl-amine |
| 430 | 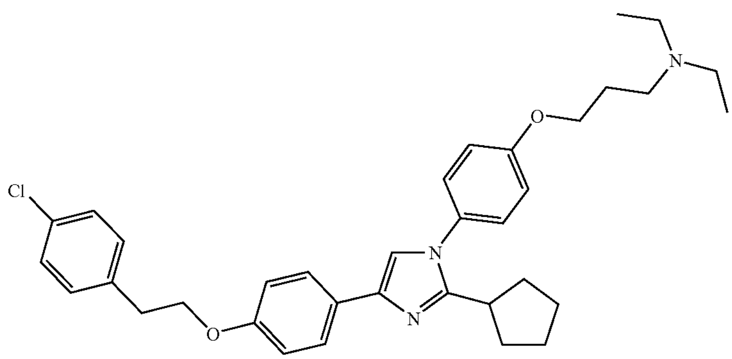 | {3-[4-(4-{4-[2-(4-chloro-phenyl)-ethoxy]-phenyl}-2-cyclopentyl-imidazol-1-yl)-phenoxy]-propyl}-diethyl-amine |
| 431 | 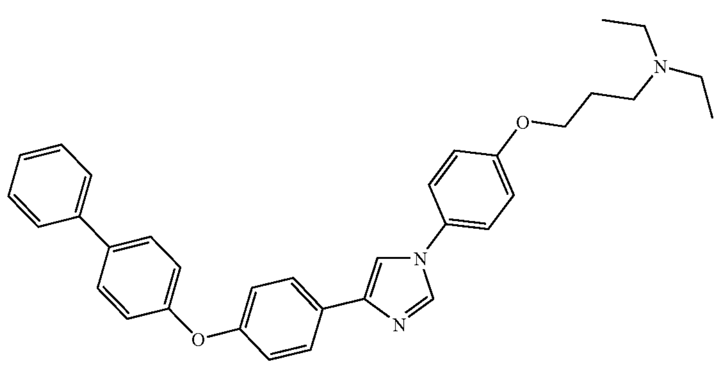 | [3-(4-{4-[4-(biphenyl-4-yloxy)-phenyl]-imidazol-1-yl]-phenoxy)-propyl]-diethyl-amine |

TABLE 1-continued

| Ex. | Structure | Name |
|---|---|---|
| 432 | 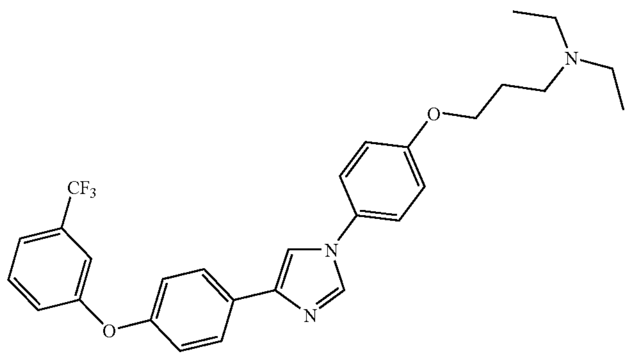 | diethyl-[3-(4-{4-[4-(3-trifluoromethyl-phenoxy)-phenyl]-imidazol-1-yl}-phenoxy)-propyl]-amine |
| 433 | 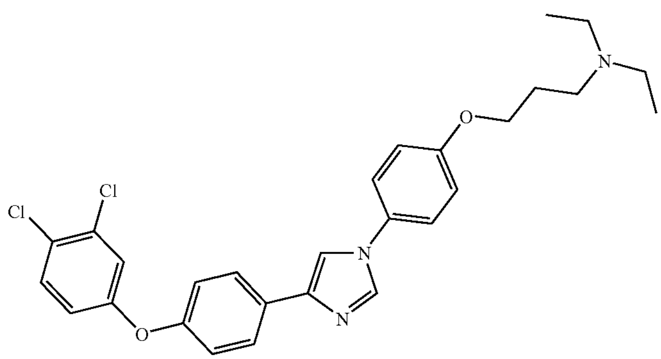 | [3-(4-{4-[4-(3,4-dichloro-phenoxy)-phenyl]-imidazol-1-yl}-phenoxy)-propyl]-diethyl-amine |
| 434 | 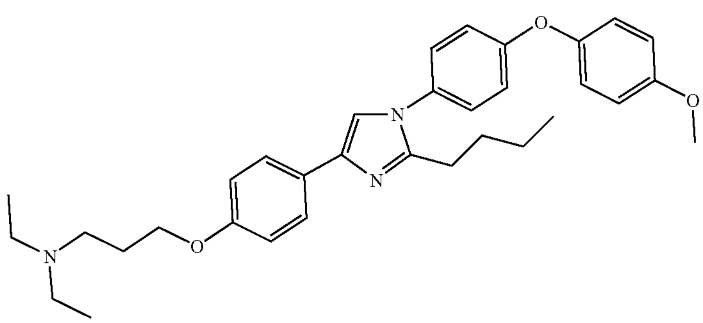 | [3-(4-{2-butyl-1-[4-(4-methoxy-phenoxy)-phenyl]-1H-imidazol-4-yl}-phenoxy)-propyl]-diethyl-amine |
| 435 | 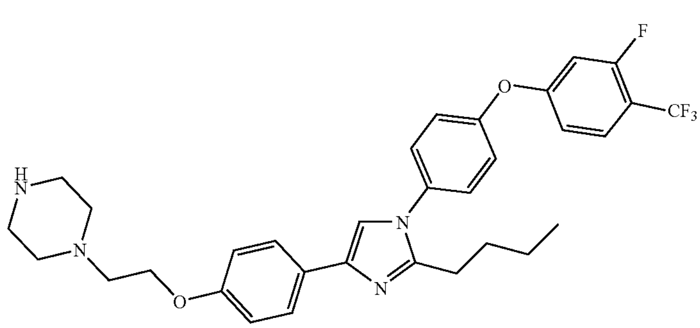 | 1-[2-(4-{2-butyl-1-[4-(3-fluoro-4-trifluoromethyl-phenoxy)-phenyl]-1H-imidazol-4-yl}-phenoxy)-ethyl]-piperazine |

TABLE 1-continued

| Ex. | Structure | Name |
| --- | --- | --- |
| 436 | 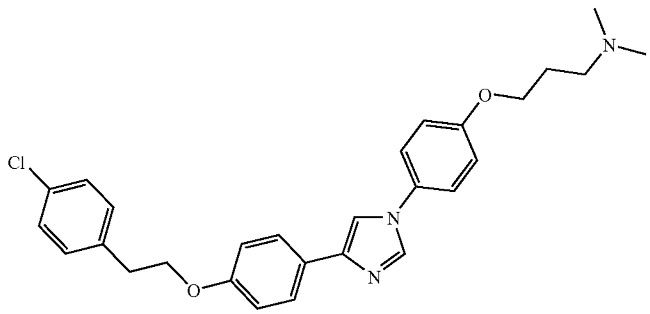 | {3-[4-(4-{4-[2-(4-chloro-phenyl)-ethoxy]-phenyl}-imidazol-1-yl)-phenoxy]-propyl}-dimethyl-amine |
| 437 | 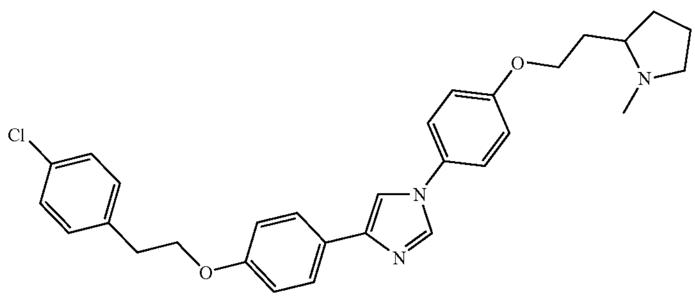 | 4-{4-[2-(4-chloro-phenyl)-ethoxy]-phenyl}-1-{4-[2-(1-methyl-pyrrolidin-2-yl)-ethoxy]-phenyl]-1H-imidazole |
| 438 | 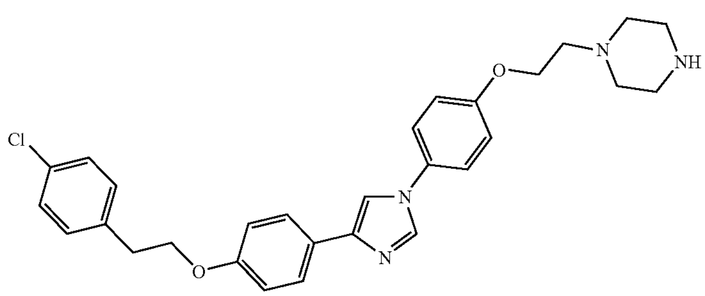 | 1-{2-[4-(4-{4-[2-(4-chloro-phenyl)-ethoxy]-phenyl}-imidazol-1-yl)-phenoxy]-ethyl}-piperazine |
| 439 | 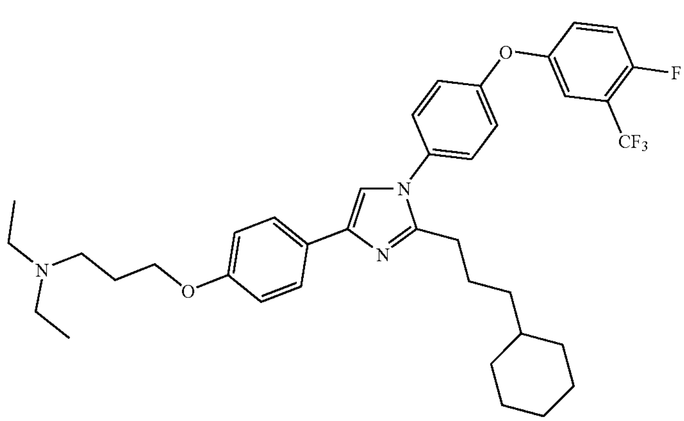 | [3-(4-{2-(3-cyclohexyl-propyl)-1-[4-(4-fluoro-3-trifluoromethyl-phenoxy)-phenyl]-1H-imidazol-4-yl}-phenoxy)-propyl]-diethyl-amine |

TABLE 1-continued

| Ex. | Structure | Name |
|---|---|---|
| 440 | 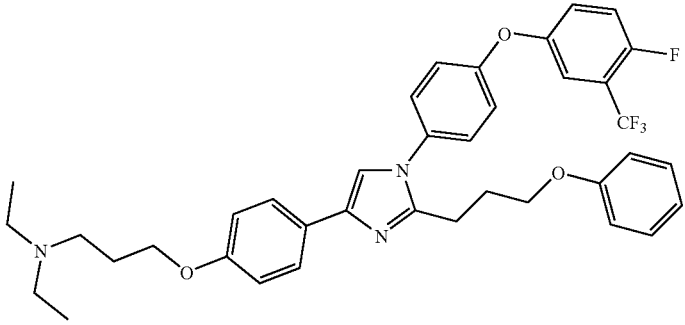 | diethyl-(3-{4-[1-[4-(4-fluoro-3-trifluoromethyl-phenoxy)-phenyl]-2-(3-phenoxy-propyl)-1H-imidazol-4-yl]-phenoxy}-propyl)-amine |
| 441 | 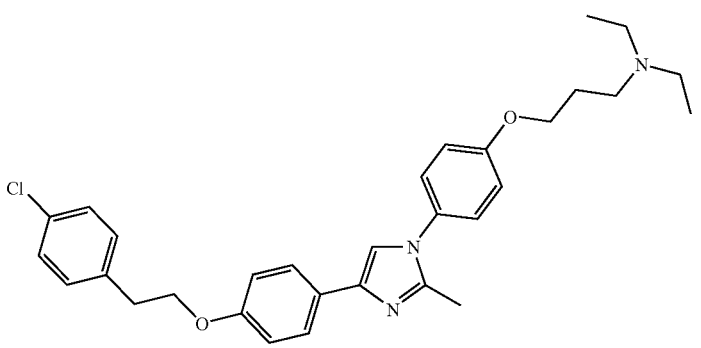 | {3-[4-(4-{4-[2-(4-chloro-phenyl)-ethoxy]-phenyl}-2-methyl-imidazol-1-yl)-phenoxy]-propyl}-diethyl-amine |
| 442 | 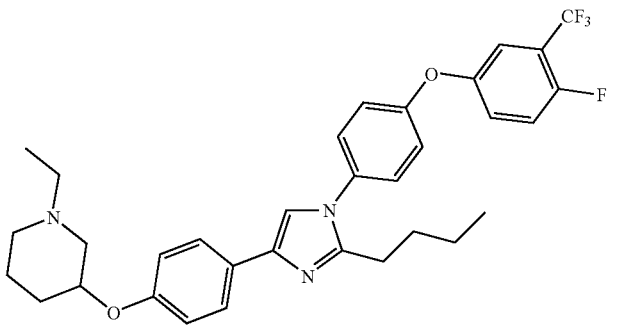 | 3-(4-{2-butyl-1-[4-(4-fluoro-3-trifluoromethyl-phenoxy)-phenyl]-1H-imidazol-4-yl}-phenoxy)-1-ethyl-piperidine |
| 443 | 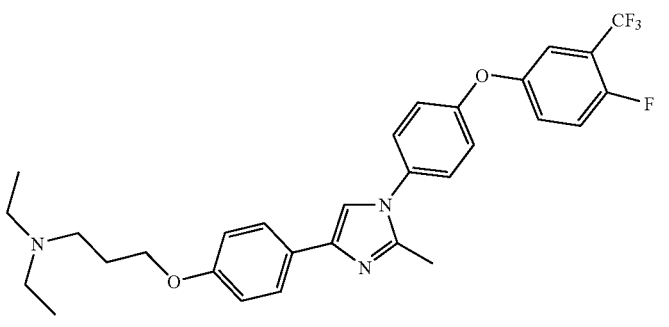 | diethyl-[3-(4-{1-[4-(4-fluoro-3-trifluoromethyl-phenoxy)-phenyl]-2-methyl-1H-imidazol-4-yl}-phenoxy)-propyl]-amine |

TABLE 1-continued

| Ex. | Structure | Name |
|---|---|---|
| 444 | 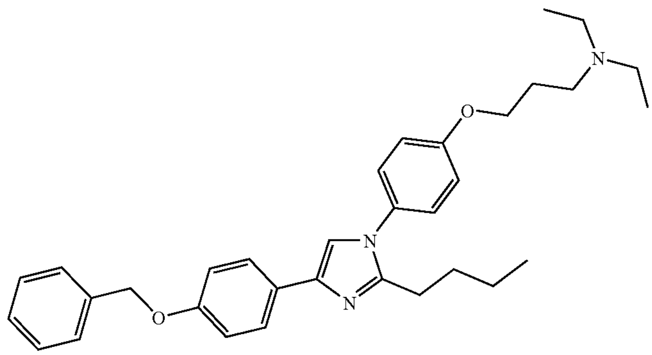 | (3-{4-[4-(4-benzyloxy-phenyl)-2-butyl-imidazol-1-yl]-phenoxy}-propyl)-diethyl-amine |
| 445 | 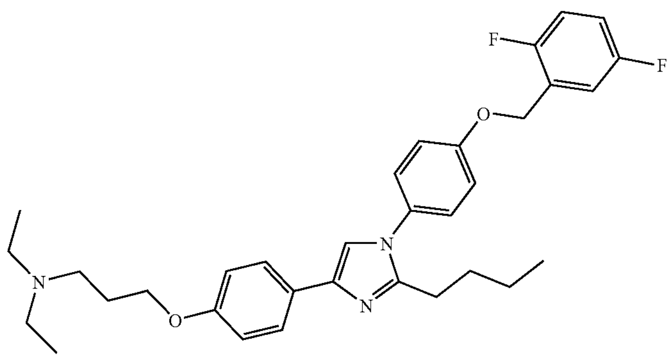 | [3-(4-{2-butyl-1-[4-(2,5-difluoro-benzyloxy)-phenyl]-1H-imidazol-4-yl}-phenoxy)-propyl]-diethyl-amine |
| 446 | 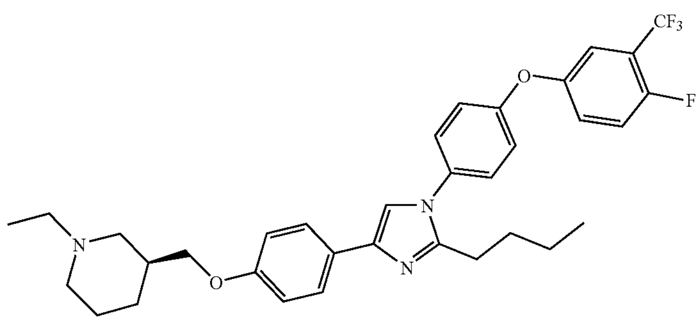 | 3-(S)-(4-{2-butyl-1-[4-(4-fluoro-3-trifluoromethyl-phenoxy)-phenyl]-1H-imidazol-4-yl}-phenoxymethyl)-1-ethyl-piperidine |
| 447 | 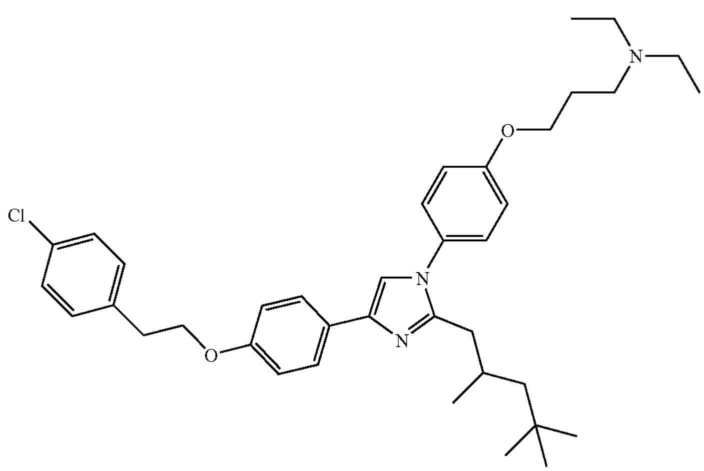 | (3-{4-[4-{4-[2-(4-chloro-phenyl)-ethoxy]-phenyl}-2-(2,4,4-trimethyl-pentyl)-imidazol-1-yl]-phenoxy}-propyl)-diethyl-amine |

TABLE 1-continued

| Ex. | Structure | Name |
|---|---|---|
| 448 | 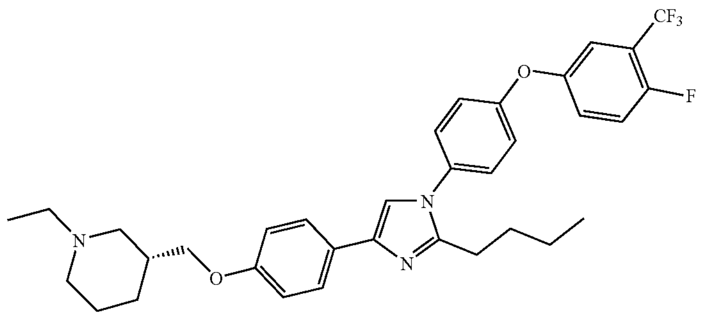 | 3-(R)-(4-{2-butyl-1-[4-(4-fluoro-3-trifluoromethyl-phenoxy)-phenyl]-1H-imidazol-4-yl}-phenoxymethyl)-1-ethyl-piperidine |
| 449 | 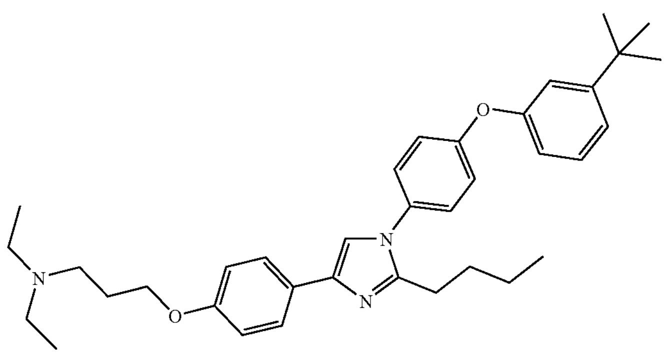 | [3-(4-{2-butyl-1-[4-(3-tert-butyl-phenoxy)-phenyl]-1H-imidazol-4-yl}-phenoxy)-propyl]-diethyl-amine |
| 450 | 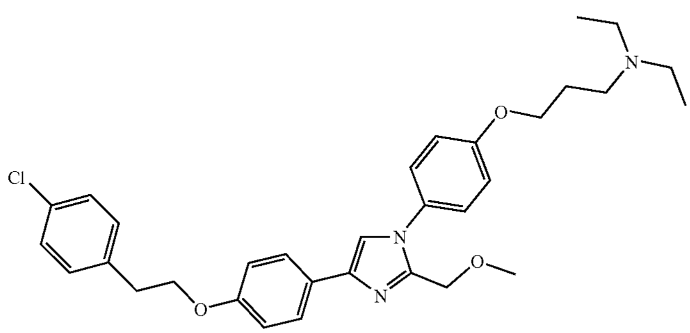 | {3-[4-(4-{4-[2-(4-chloro-phenyl)-ethoxy]-phenyl}-2-methoxymethyl-imidazol-1-yl)-phenoxyl-propyl]-diethyl-amine |
| 451 | 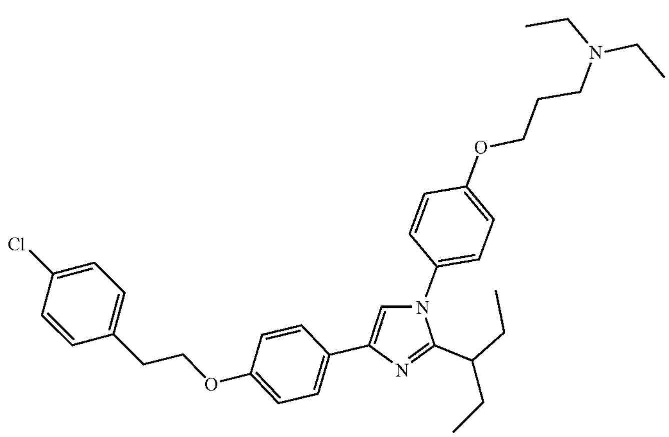 | (3-{4-[4-{4-[2-(4-chloro-phenyl)-ethoxy]-phenyl}-2-(1-ethyl-propyl)-imidazol-1-yl]-phenoxy}-propyl)-diethyl-amine |

TABLE 1-continued

| Ex. | Structure | Name |
| --- | --- | --- |
| 452 | 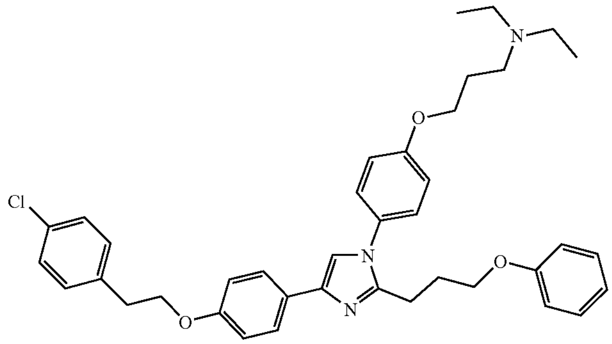 | (3-{4-[4-{4-t2-(4-chloro-phenyl)-ethoxy]-phenyl}-2-(3-phenoxy-propyl)-imidazol-1-yl]-phenoxy}-propyl)-diethyl-amine |
| 453 | 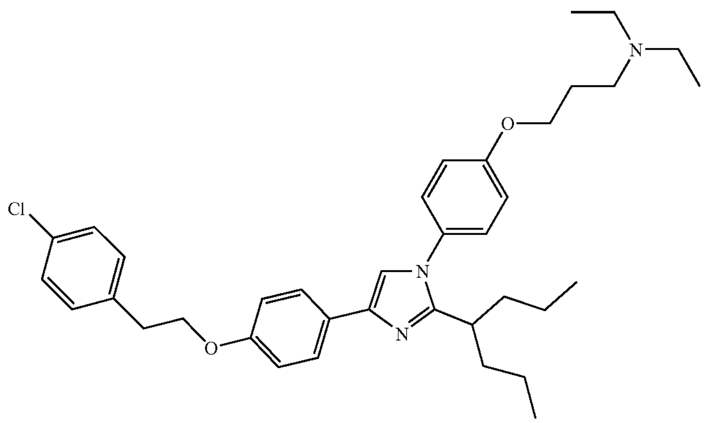 | (3-{4-[4-{4-[2-(4-chloro-phenyl)-ethoxy]-phenyl}-2-(1-propyl-butyl)-imidazol-1-yl]-phenoxy}-propyl)-diethyl-amine |
| 454 | 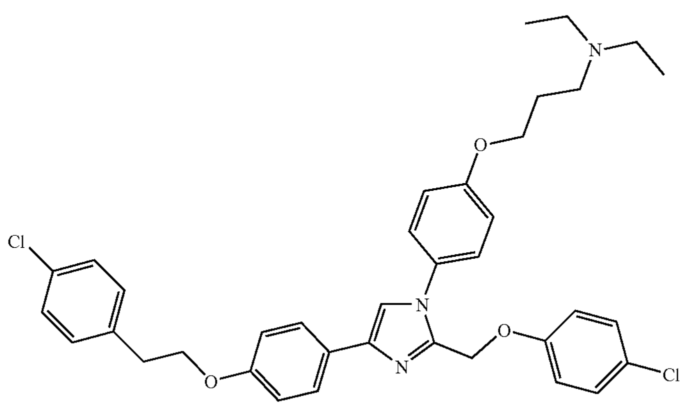 | {3-[4-(2-(4-chloro-phenoxymethyl)-4-{4-[2-(4-chloro-phenyl)-ethoxy]-phenyl}-imidazol-1-yl)-phenoxy]-propyl]-diethyl-amine |
| 455 | 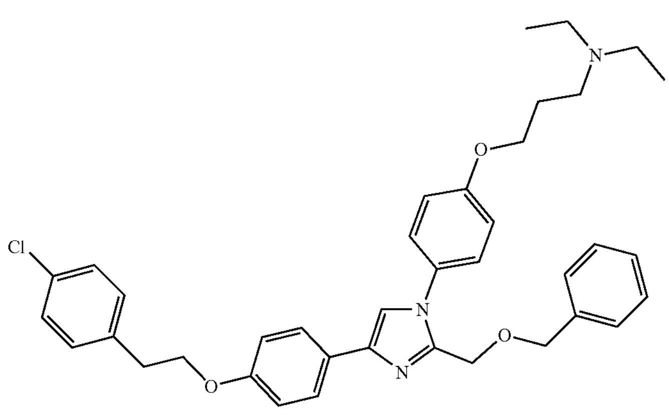 | {3-[4-(2-benzyloxymethyl-4-{4-[2-(4-chloro-phenyl)-ethoxy]-phenyl}-imidazol-1-yl)-phenoxy]-propyl}-diethyl-amine |

TABLE 1-continued

| Ex. | Structure | Name |
|---|---|---|
| 456 | 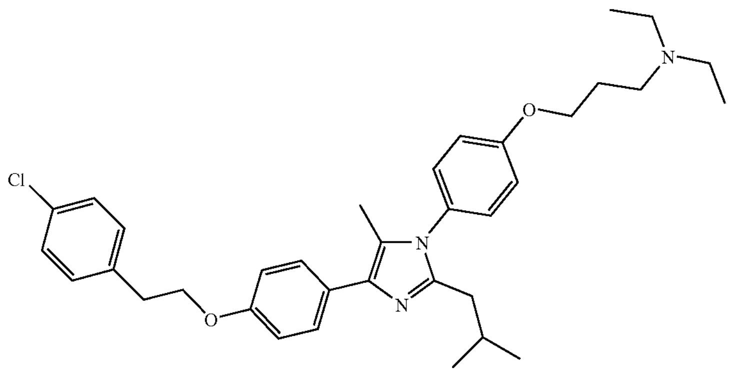 | {3-[4-(4-{4-[2-(4-chloro-phenyl)-ethoxy]-phenyl)-2-isobutyl-5-methyl-imidazol-1-yl)-phenoxy]-propyl]-diethyl-amine |
| 457 | 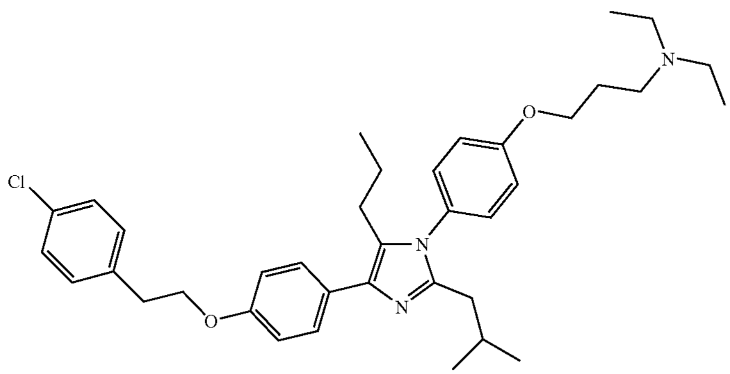 | {3-[4-(4-{4-[2-(4-chloro-phenyl)-ethoxy]-phenyl)-2-isobutyl-5-propyl-imidazol-1-yl)-phenoxy]-propyl}-diethyl-amine |
| 458 | 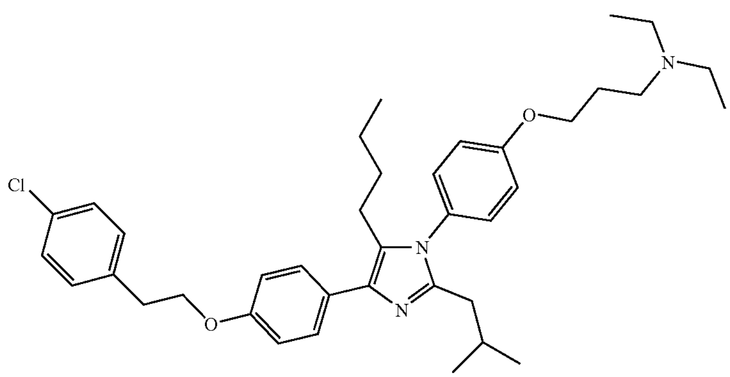 | {3-[4-(5-butyl-4-(4-[2-(4-chloro-phenyl)-ethoxy]-phenyl}-2-isobutyl-imidazol-1-yl)-phenoxy]-propyl}-diethyl-amine |
| 459 | 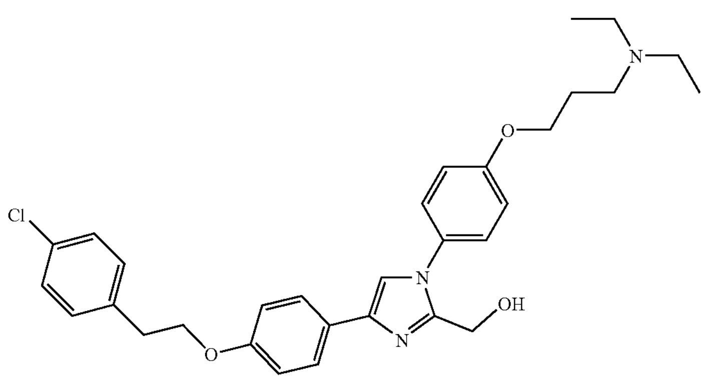 | {4-{4-{2-(4-chloro-phenyl)-ethoxy]-phenyl}-1-[4-(3-diethylamino-propoxy)-phenyl]-1H-imidazol-2-yl}-MeOH |

TABLE 1-continued

| Ex. | Structure | Name |
|---|---|---|
| 460 | 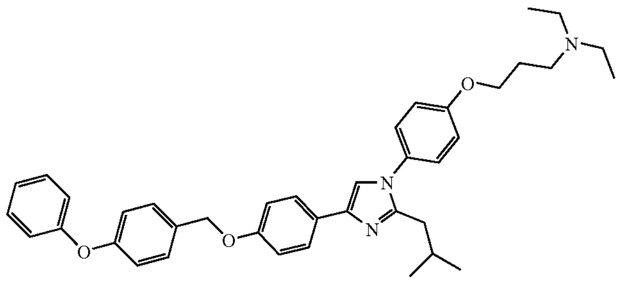 | diethyl-[3-(4-{2-isobutyl-4-[4-(4-phenoxy-benzyloxy)-phenyl]-imidazol-1-yl}-phenoxy)-propyl]-amine |
| 461 | 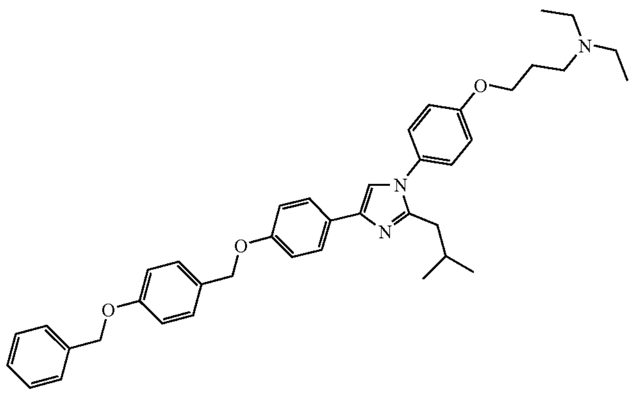 | [3-(4-{4-[4-(4-benzyloxy-benzyloxy)-phenyl]-2-isobutyl-imidazol-1-yl}-phenoxy)-propyl]-diethyl-amine |
| 462 | 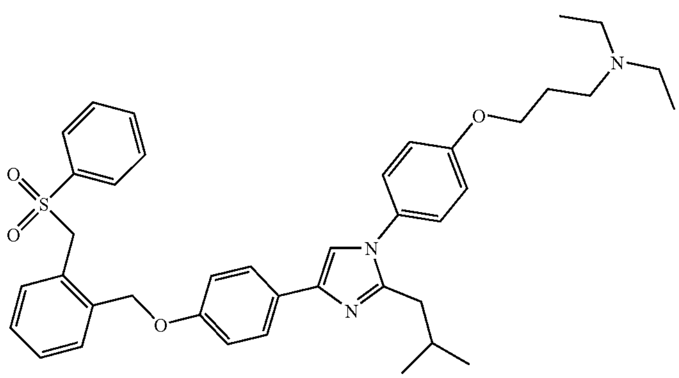 | [3-(4-{4-[4-(2-benzenesulfonylmethylbenzyloxy)-phenyl]-2-isobutyl-imidazol-1-yl}-phenoxy)-propyl]-diethyl-amine |
| 463 | 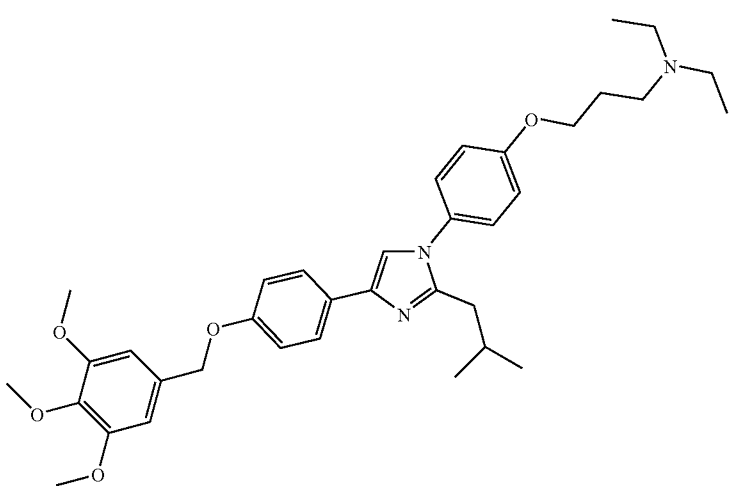 | diethyl-[3-(4-{2-isobutyl-4-[4-(3,4,5-trimethoxy-benzyloxy)-phenyl]-imidazol-1-yl}-phenoxy)-propyl]-amine |

TABLE 1-continued

| Ex. | Structure | Name |
|---|---|---|
| 464 | 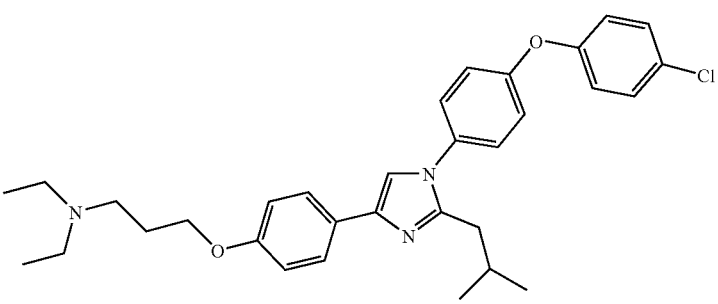 | [3-(4-{1-[4-(4-chloro-phenoxy)-phenyl]-2-isobutyl-1H-imidazol-4-yl}-phenoxy)-propyl]-diethyl-amine |
| 465 | 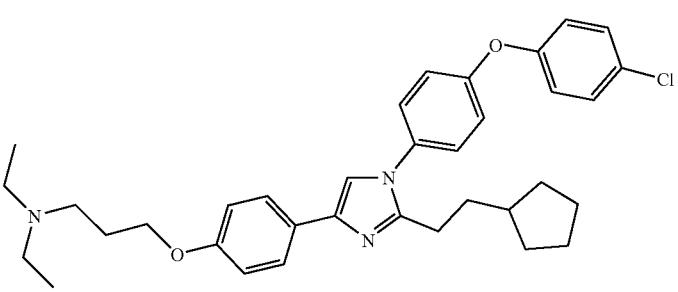 | [3-(4-{1-[4-(4-chloro-phenoxy)-phenyl]-2-(2-cyclopentyl-ethyl)-1H-imidazol-4-yl}-phenoxy)-propyl]-diethyl-amine |
| 466 | 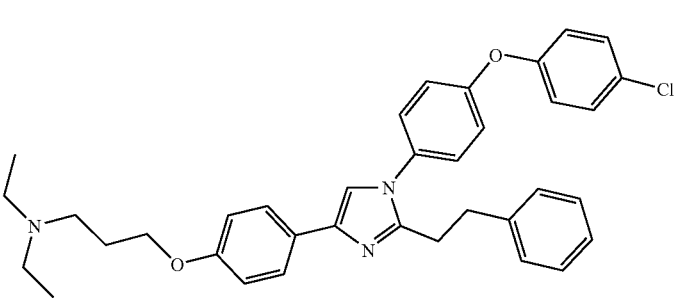 | [3-(4-{1-[4-(4-chloro-phenoxy)-phenyl]-2-phenethyl-1H-imidazol-4-yl}-phenoxy)-propyl]-diethyl-amine |
| 467 | 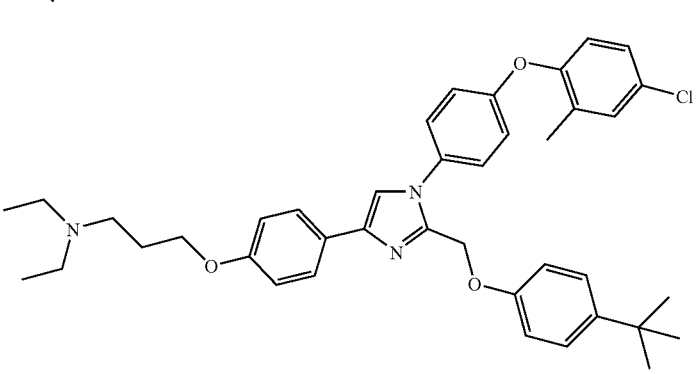 | [3-(4-{2-(4-tert-butyl-phenoxymethyl)-1-[4-(4-chloro-phenoxy)-phenyl]-1H-imidazol-4-yl}-phenoxy)-propyl]-diethyl-amine |
| 468 | 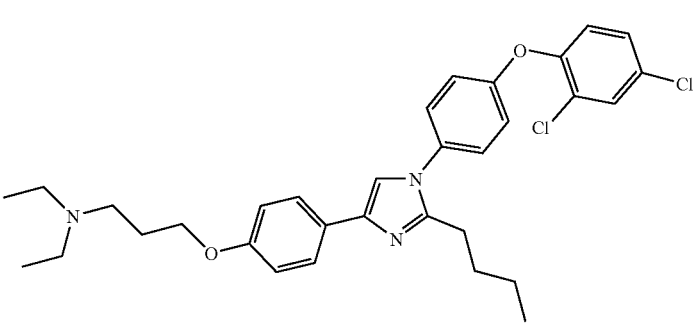 | [3-(4-(2-butyl-1-[4-(2,4-dichloro-phenoxy)-phenyl]-1H-imidazol-4-yl}-phenoxy)-propyl]-diethyl-amine |

TABLE 1-continued

| Ex. | Structure | Name |
| --- | --- | --- |
| 469 | 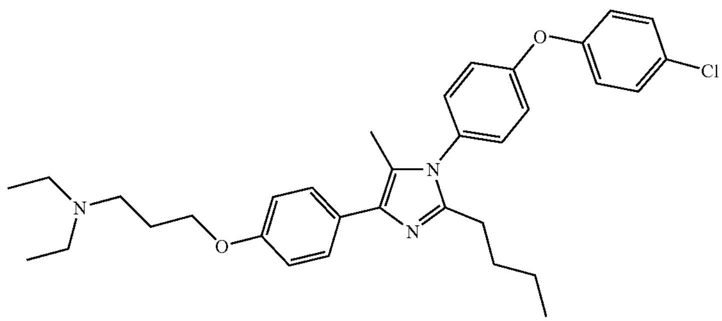 | [3-(4-{2-butyl-1-[4-(4-chloro-phenoxy)-phenyl]-5-methyl-1H-imidazol-4-yl)-phenoxy)-propyl]-diethyl-amine |
| 470 | 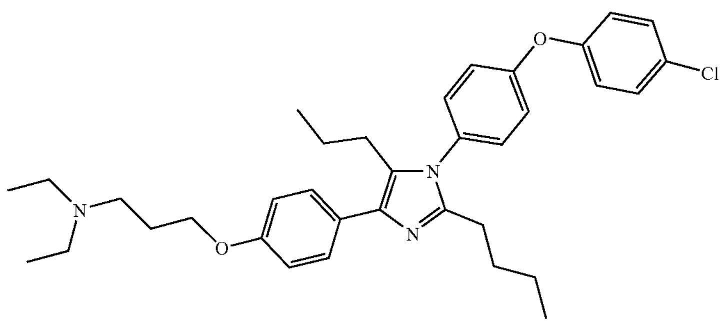 | [3-(4-{2-butyl-1-[4-(4-chloro-phenoxy)-phenyl]-5-propyl-1H-imidazol-4-yl}-phenoxy)-propyl]-diethyl-amine |
| 471 | 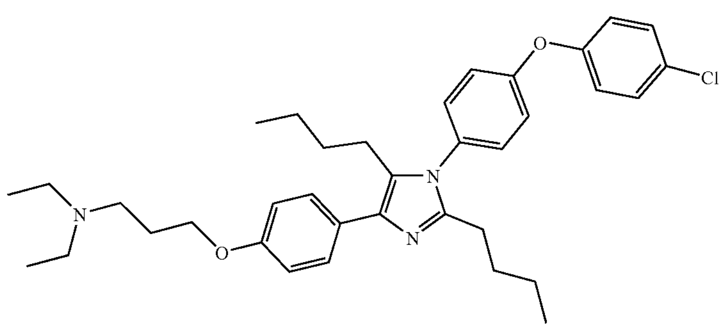 | [3-(4-{2,5-dibutyl-1-[4-(4-chloro-phenoxy)-phenyl]-1H-imidazol-4-yl}-phenoxy)-propyl]-diethyl-amine |
| 472 | 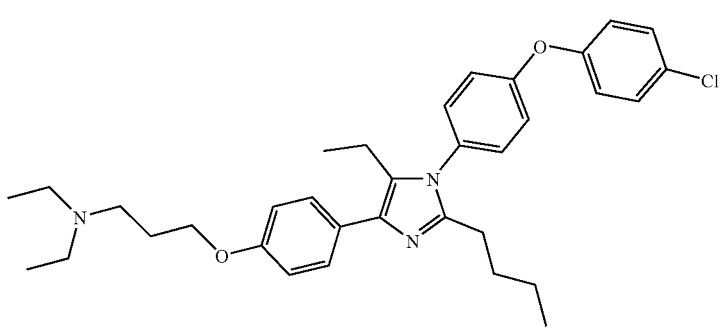 | [3-(4-{2-butyl-1-[4-(4-chloro-phenoxy)-phenyl]-5-ethyl-1H-imidazol-4-yl}-phenoxy)-propyl]-diethyl-amine |

TABLE 1-continued

| Ex. | Structure | Name |
| --- | --- | --- |
| 473 | 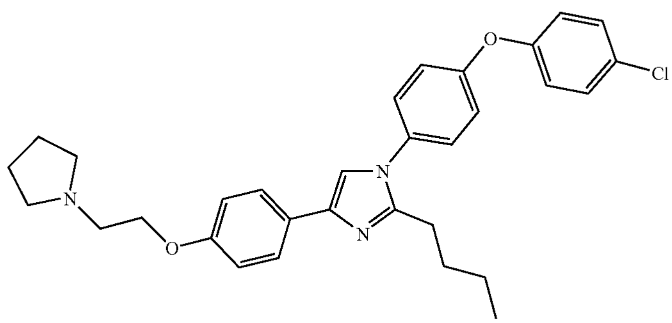 | 2-butyl-1-[4-(4-chloro-phenoxy)-phenyl]-4-[4-(2-pyrrolidin-1-yl-ethoxy)-phenyl]-1H-imidazole |
| 474 | 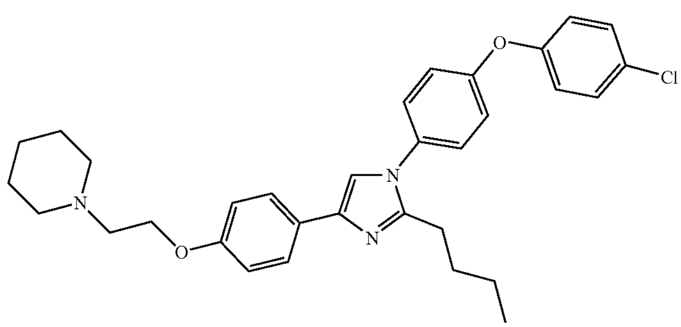 | 1-[2-(4-{2-butyl-1-[4-(4-chloro-phenoxy)-phenyl]-1H-imidazol-4-yl]-phenoxy)-ethyl]-piperidine |
| 475 | 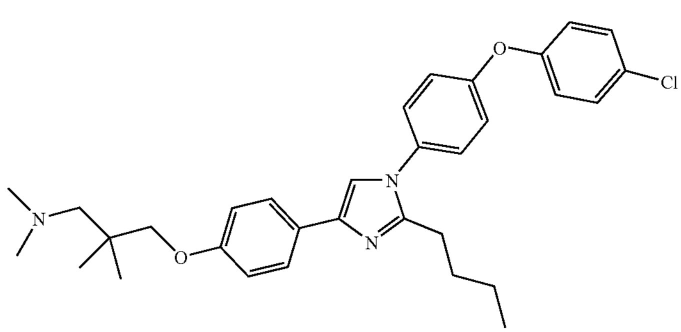 | [3-(4-{2-butyl-1-[4-(4-chloro-phenoxy)-phenyl]-1H-imidazol-4-yl}-phenoxy)-2,2-dimethyl-propyl]-dimethyl-amine |
| 476 | 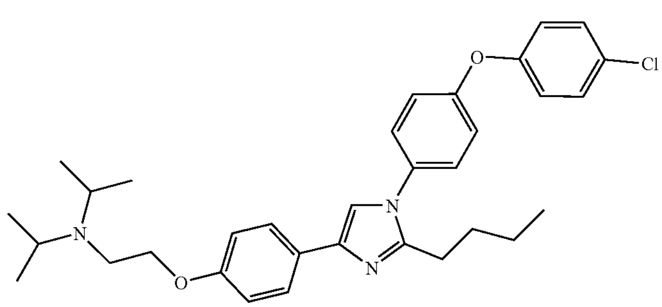 | [2-(4-{2-butyl-1-[4-(4-chloro-phenoxy)-phenyl]-1H-imidazol-4-yl}-phenoxy)-ethyl]-diisopropyl-amine |

TABLE 1-continued

| Ex. | Structure | Name |
|---|---|---|
| 477 | 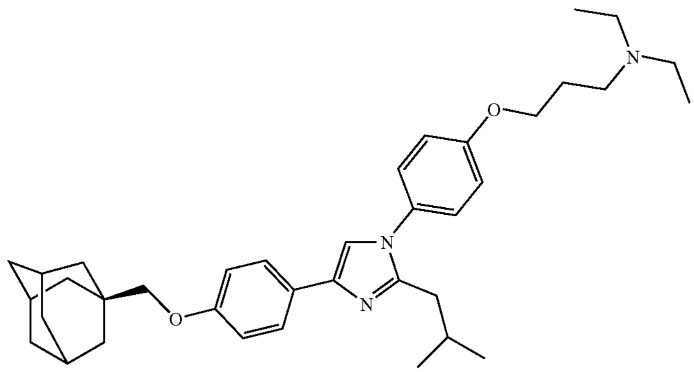 | [3-(4-{4-[4-(adamantan-1-ylmethoxy)-phenyl]-2-isobutyl-imidazol-1-yl}-phenoxy)-propyl]-diethyl-amine |
| 478 | 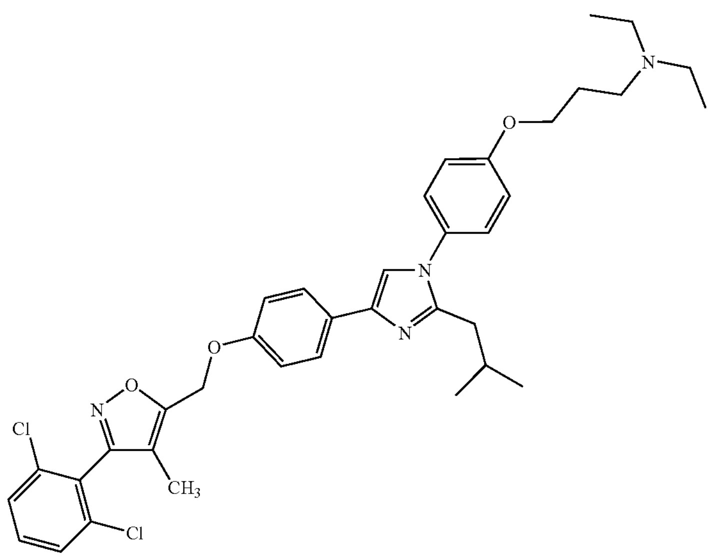 | {3-[4-(4-{4-[3-(2,6-dichloro-phenyl)-4-methyl-isoxazol-5-ylmethyloxy]-phenyl}-2-isobutyl-imidazol-1-yl)-phenoxy]-propyl}-diethyl-amine |
| 479 | 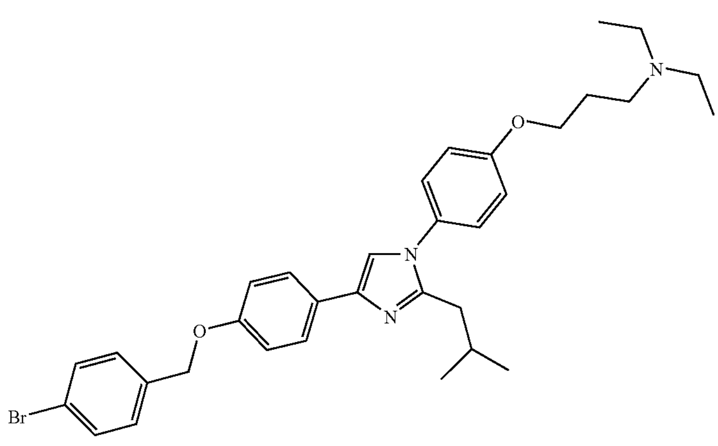 | [3-(4-{4-[4-(4-bromo-benzyloxy)-phenyl]-2-isobutyl-imidazol-1-yl}-phenoxy)-propyl]-diethyl-amine |

TABLE 1-continued

| Ex. | Structure | Name |
|---|---|---|
| 480 | 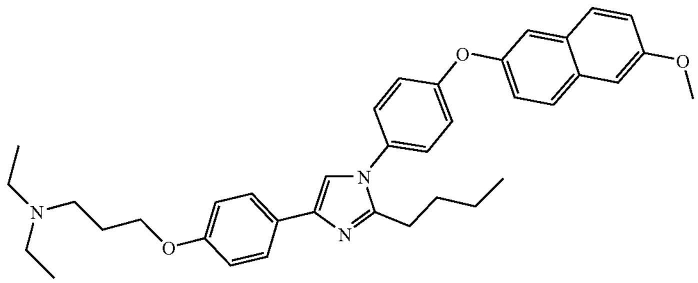 | [3-(4-{2-butyl-1-[4-(6-methoxy-naphthalen-2-yloxy)-phenyl]-1H-imidazol-4-yl}-phenoxy)-propyl]-diethyl-amine |
| 481 | 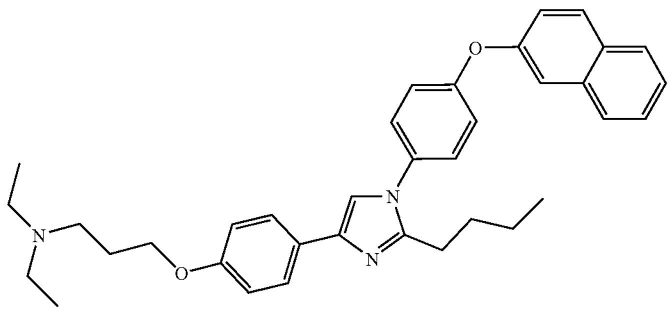 | [3-(4-{2-butyl-1-[4-(naphthalen-2-yloxy)-phenyl]-1H-imidazol-4-yl}-phenoxy)-propyl]-diethyl-amine |
| 482 | 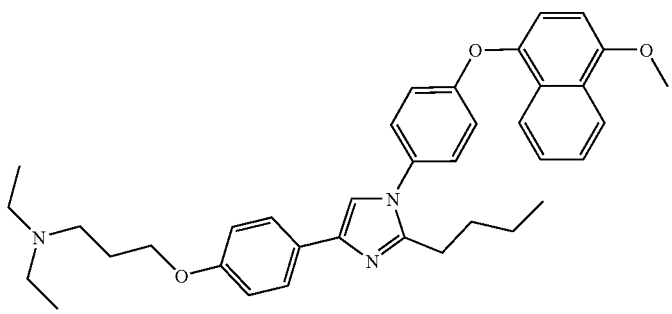 | [3-(4-(2-butyl-1-[4-(4-methoxy-naphthalen-1-yloxy)-phenyl]-1H-imidazol-4-yl}-phenoxy)-propyl]-diethyl-amine |
| 483 | 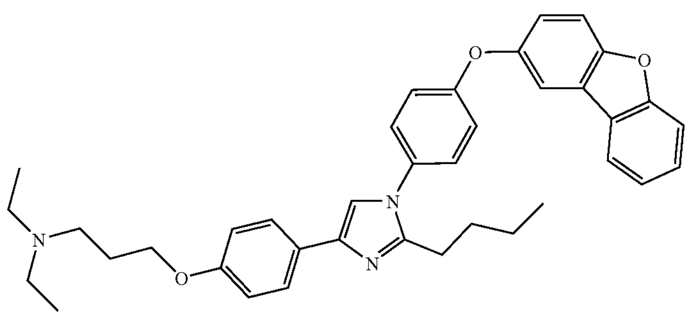 | [3-(4-{2-butyl-1-[4-(dibenzofuran-2-yloxy)-phenyl]-1H-imidazol-4-yl}-phenoxy)-propyl]-diethyl-amine |
| 484 | 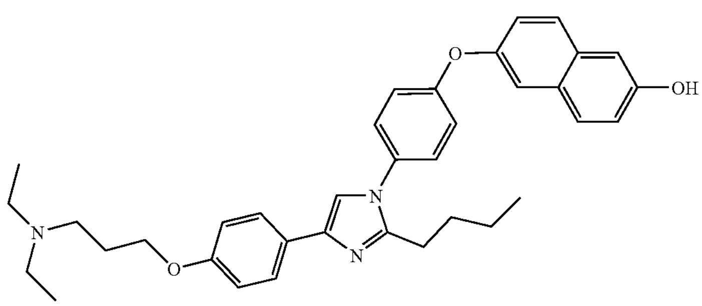 | 6-(4-{2-butyl-4-[4-(3-diethylamino-propoxy)-phenyl]-imidazol-1-yl}-phenoxy)-naphthalen-2-ol |

TABLE 1-continued

| Ex. | Structure | Name |
|---|---|---|
| 485 | 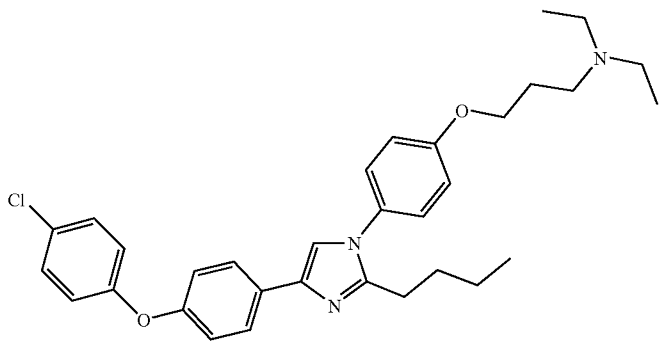 | [3-(4-{2-butyl-4-[4-(4-chloro-phenoxy)-phenyl]-imidazol-1-yl}-phenoxy)-propyl]-diethyl-amine |
| 486 | 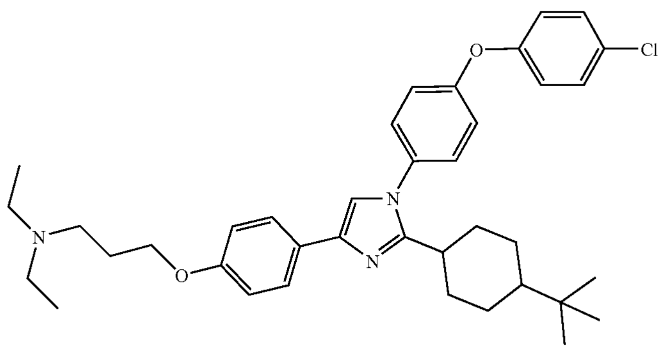 | [3-(4-{2-(4-tert-butyl-cyclohexyl)-1-[4-(4-chloro-phenoxy)-phenyl]-1H-imidazol-4-yl}-phenoxy)-propyl]-diethyl-amine |
| 487 | 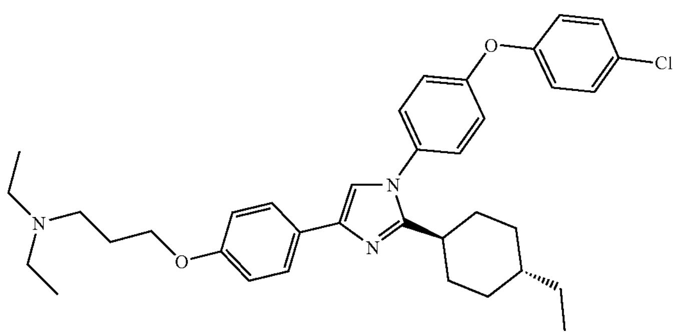 | [3-{4-[1-[4-(4-chloro-phenoxy)-phenyl]-2-(trans-4-ethyl-cyclohexyl)-1H-imidazol-4-yl]-phenoxy}-propyl]-diethyl-amine |
| 488 | 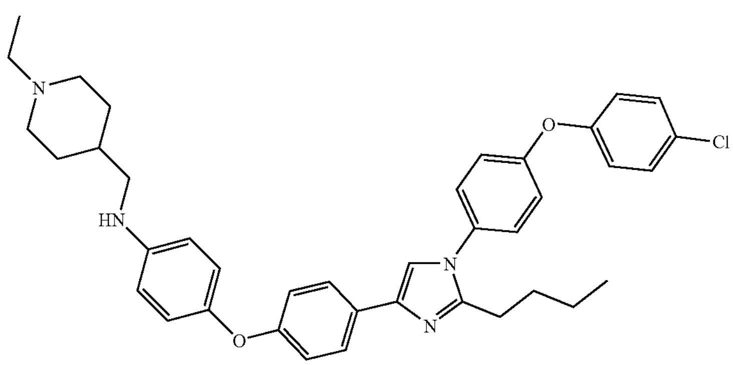 | [4-(4-{2-butyl-1-[4-(4-chloro-phenoxy)-phenyl]-1H-imidazol-4-yl}-phenoxy)-phenyl]-(1-ethyl-piperidin-4-ylmethyl)-amine |

TABLE 1-continued

| Ex. | Structure | Name |
|---|---|---|
| 489 | 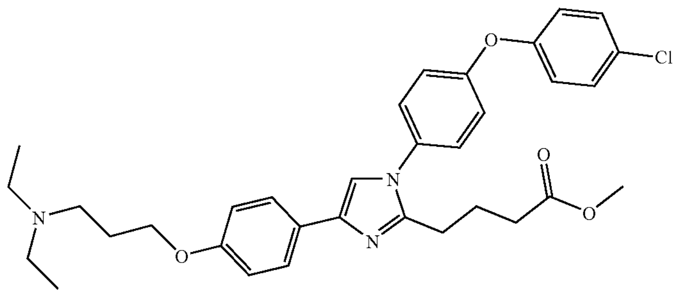 | [4-{1-[4-(4-chloro-phenoxy)-phenyl]-4-[4-(3-diethylaminopropoxy)-phenyl]-1H-imidazol-2-yl]-butyric acid methyl ester |
| 490 | 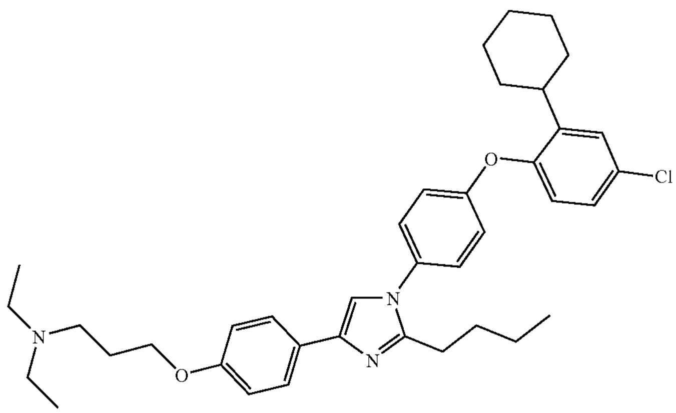 | [3-(4-{2-butyl-1-[4-(4-chloro-2-cyclohexyl-phenoxy)-phenyl]-1H-imidazol-4-yl}-phenoxy)-propyl]-diethyl-amine |
| 491 | 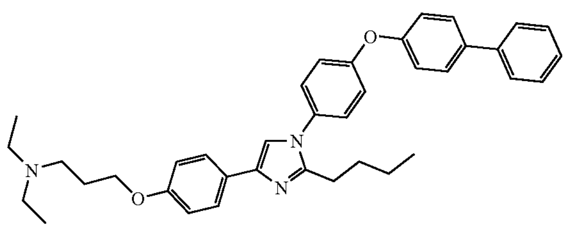 | [3-(4-{1-[4-(biphenyl-4-yloxy)-phenyl]-2-butyl-1H-imidazol-4-yl)-phenoxy)-propyl]-diethyl-amine |
| 492 | 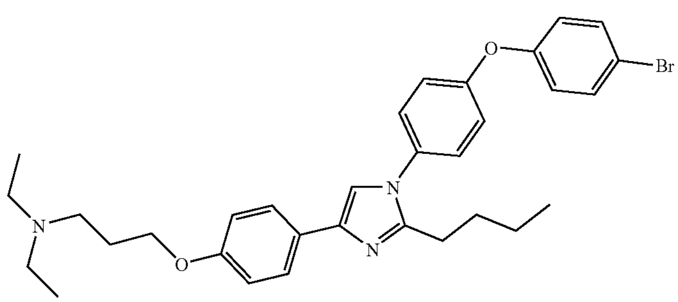 | [3-(4-{1-[4-(4-bromo-phenoxy)-phenyl]-2-butyl-1H-imidazol-4-yl]-phenoxy)-propyl]-diethyl-amine |
| 493 | 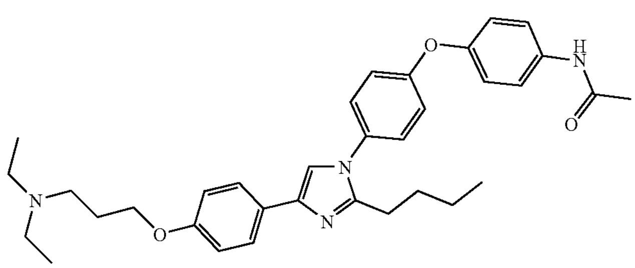 | N-[4-(4-{2-butyl-4-[4-(3-diethylamino-porpoxy)-phenyl]-imidazol-1-yl}-phenoxy)-phenyl]-acetamide |

TABLE 1-continued

| Ex. | Structure | Name |
|---|---|---|
| 494 | 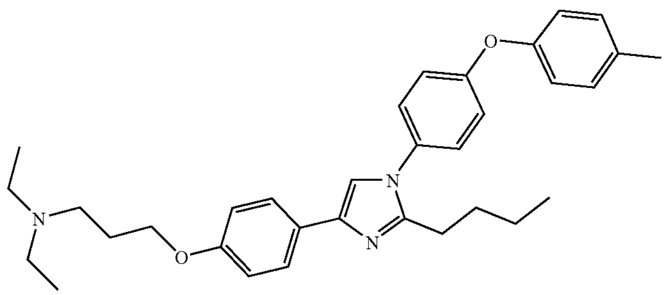 | (3-{4-[2-butyl-1-(4-p-tolyloxy-phenyl)-1H-imidazol-4-yl]-phenoxy}-propyl)-diethyl-amine |
| 495 | 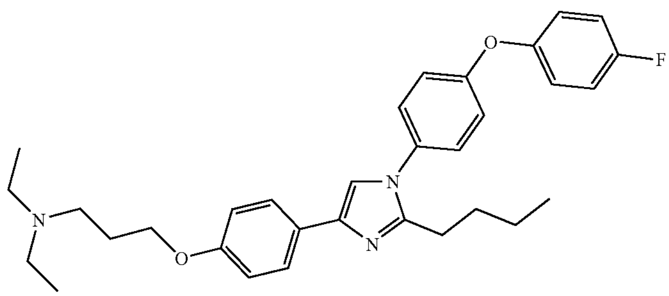 | [3-(4-{2-butyl-1-[4-(4-fluoro-phenyl)-phenyl]-1H-imidazol-4-yl}-phenoxy)-propyl]-diethyl-amine |
| 496 | 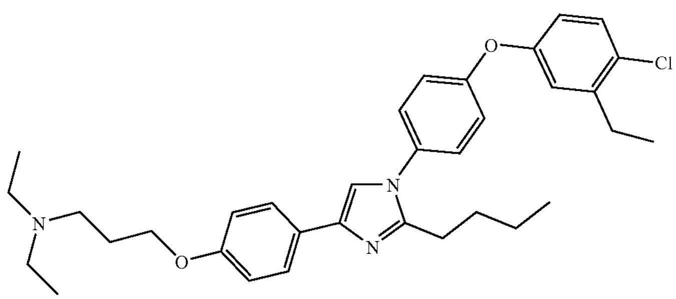 | [3-(4-{2-butyl-1-[4-(4-chloro-3-ethyl-phenoxy)-phenyl]-1H-imidazol-4-yl}-phenoxy)-propyl]-diethyl-amine |
| 497 | 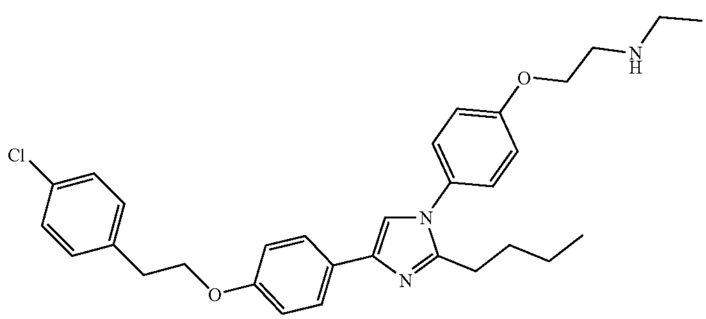 | {2-[4-(2-butyl-4-{4-[2-(4-chloro-phenyl)-ethoxy]-phenyl}-imidazol-1-yl)-phenoxy]-ethyl}-ethyl-amine |
| 498 | 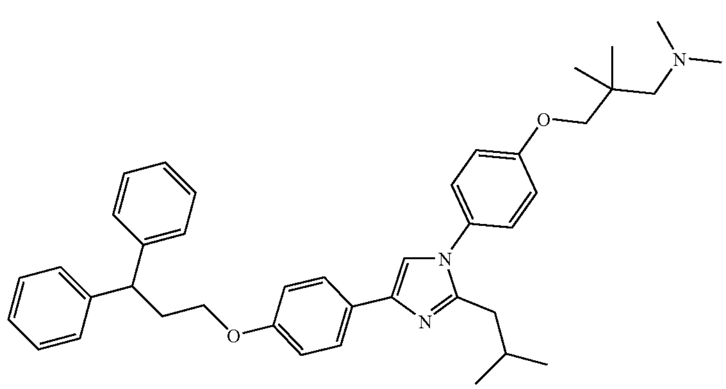 | [3-(4-{5-butyl-4-[4-(3,3-diphenyl-propoxy)-phenyl]-2-isobutyl-1H-imidazol-4-yl}-phenoxy)-2,2-dimethyl-propyl]-dimethyl-amine |

TABLE 1-continued

| Ex. | Structure | Name |
|---|---|---|
| 499 | 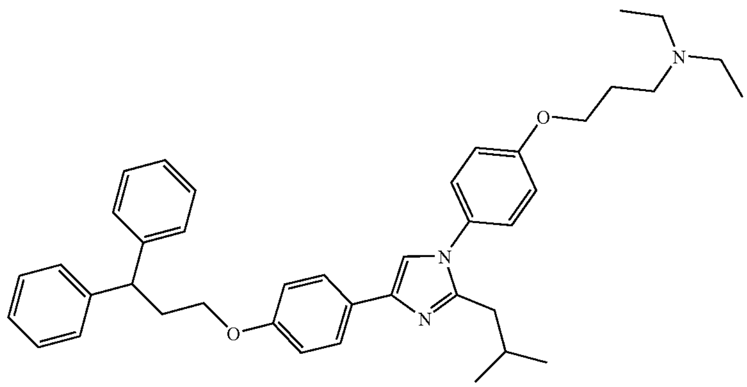 | [3-(4-{4-[4-(3,3-diphenyl-propoxy)-phenyl]-2-isobutyl-imidazol-1-yl}-phenoxy)-propyl]-diethyl-amine |
| 500 | 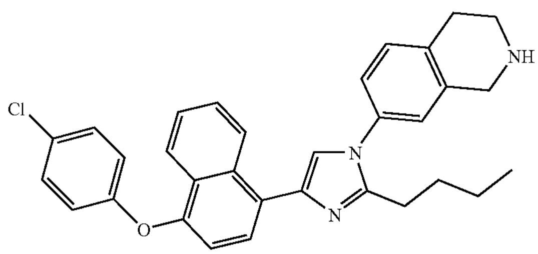 | 7-{2-butyl-4-[4-(4-chloro-phenoxy)-naphthalen-1-yl]-imidazol-1-yl}-1,2,3,4-tetrahydro-isoquinoline |
| 501 | 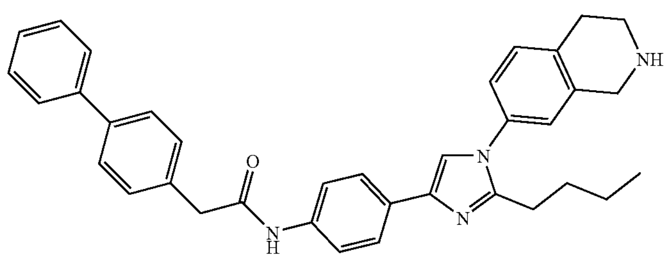 | 2-biphenyl-4-yl-N-{4-[2-butyl-1-(1,2,3,4-tetrahydro-isoquinolin-7-yl)-1H-imidazol-4-yl]-phenyl}-acetamide |
| 502 | 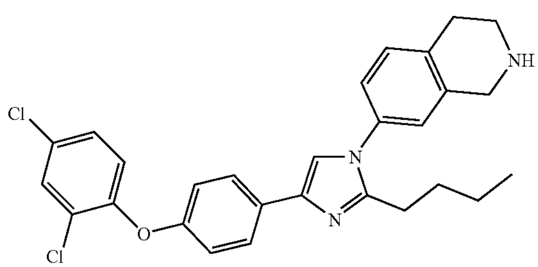 | 7-{2-butyl-4-[4-(2,4-dichloro-phenoxy)-phenyl]-imidazol-1-yl}-1,2,3,4-tetrahydro-isoquinoline |
| 503 | 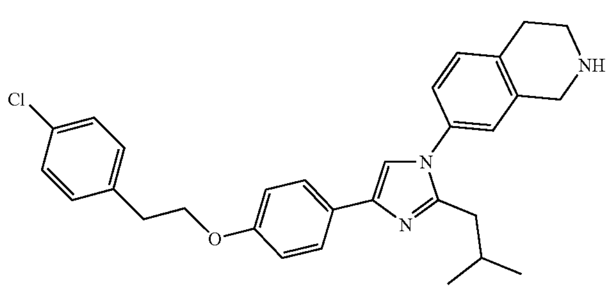 | 7-(2-butyl-4-{4-[2-(4-chloro-phenyl)-ethoxy]-phenyl}-2-isobutyl-imidazol-1-yl)-1,2,3,4-tetrahydro-isoquinoline |

TABLE 1-continued

| Ex. | Structure | Name |
|---|---|---|
| 504 | 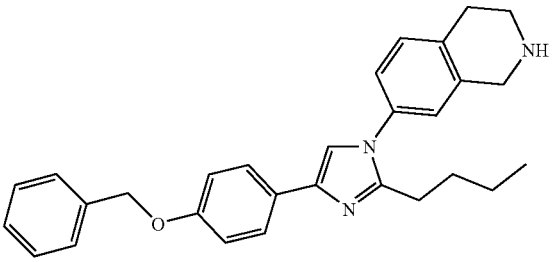 | 7-[4-(4-benzyloxy-phenyl)-2-butyl-imidazol-1-yl]-1,2,3,4-tetrahydro-isoquinoline hydrochloride hydrochloride |
| 505 | 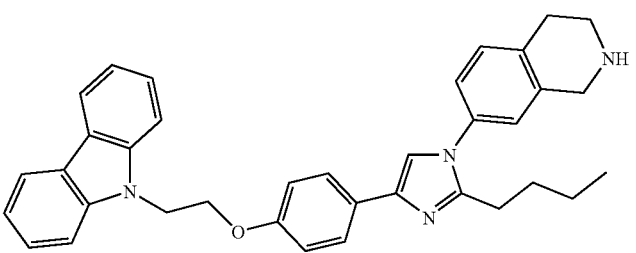 | 9-(2-{4-[2-butyl-1-(1,2,3,4-tetrahydro-isoquinolin-7-yl)-1H-imidazol-4-yl]-phenoxyl-ethyl-9H-carbazole |
| 506 | 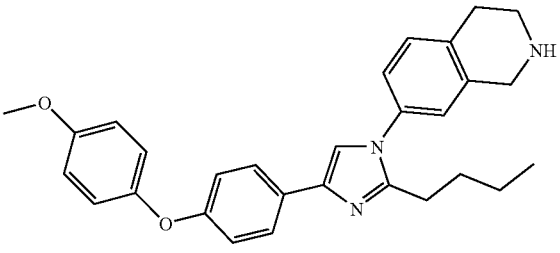 | 7-{2-butyl-4-[4-(4-methoxy-phenoxy)-phenyl]-imidazol-1-yl}-1,2,3,4-tetrahydro-isoquinoline |
| 507 | 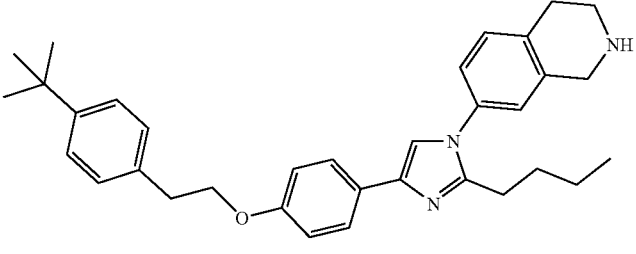 | 7-(2-butyl-4-{4-[2-(4-tert-butyl-phenyl)-ethoxy]-phenyl}-imidazol-1-yl)-1,2,3,4-tetrahydro-isoquinoline hydrochloride |
| 508 | 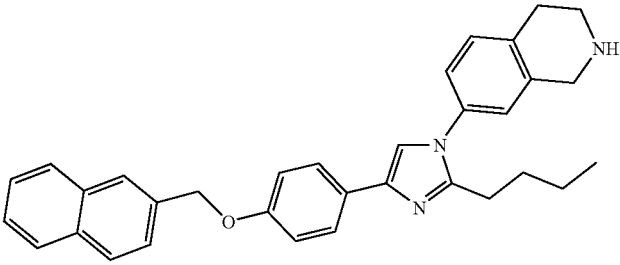 | 7-{2-butyl-4-[4-(naphthalen-2-ylmethoxy)-phenyl]-imidazol-1-yl}-1,2,3,4-tetrahydro-isoquinoline hydrochloride |
| 509 | 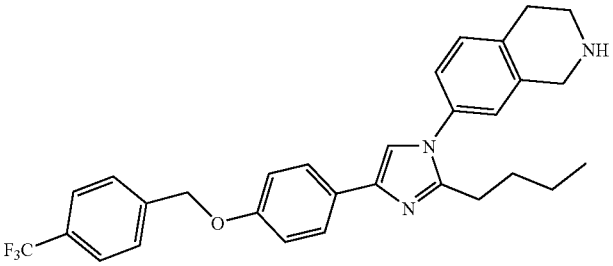 | 7-{2-butyl-4-[4-(4-trifluoromethyl-phenoxy)-phenyl]-imidazol-1-yl}-1,2,3,4-tetrahydro-isoquinoline hydrochloride |

TABLE 1-continued

| Ex. | Structure | Name |
|---|---|---|
| 510 | 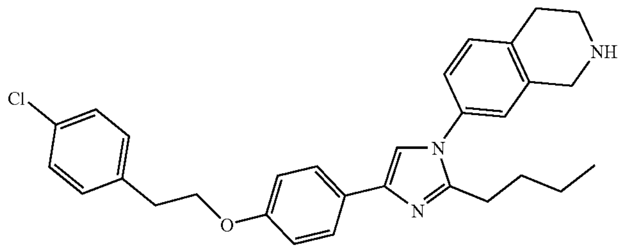 | 7-(2-butyl-4-{4-[2-(4-chloro-phenyl)-ethoxy]-phenyl}-imidazol-1-yl)-1,2,3,4-tetrahydro-isoquinoline |
| 511 | 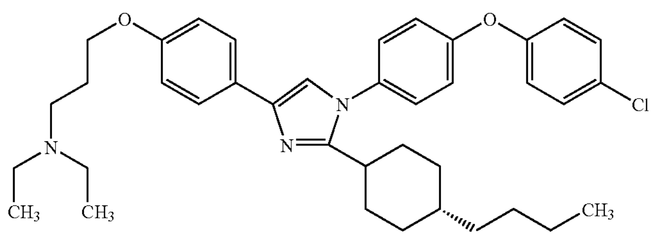 | [3-(4-{2-(4-Butyl-cyclohexyl)-1-[4-(4-chloro-phenoxy)-phenyl]-1H-imidazol-4-yl}-phenoxy)-propyl]-diethyl-amine |
| 512 | 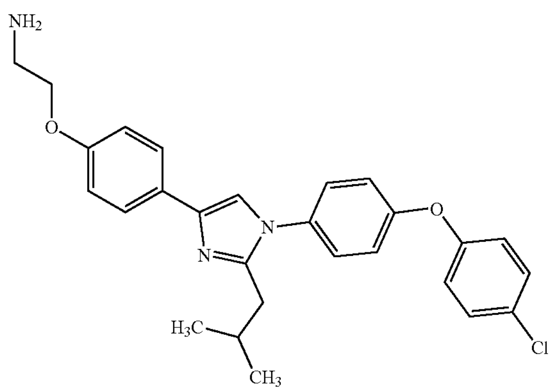 | 2-(4-{1-[4-(4-Chloro-phenoxy)-phenyl]-2-isobutyl-1H-imidazol-4-yl}-phenoxy)-ethylamine |
| 513 | 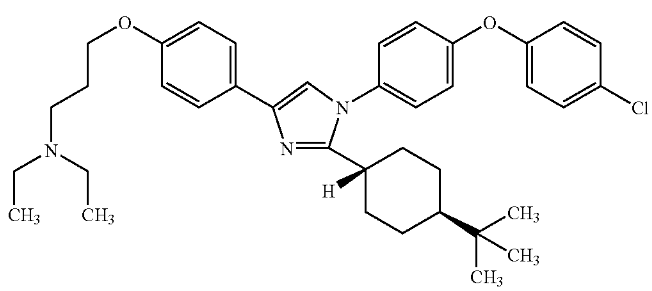 | [3-(4-{2-(trans-4-tert-Butyl-cyclohexyl)-1-[4-(4-chloro-phenoxy)-phenyl]-1H-imidazol-4-yl}-phenoxy)-propyl]-diethyl-amine |
| 514 | 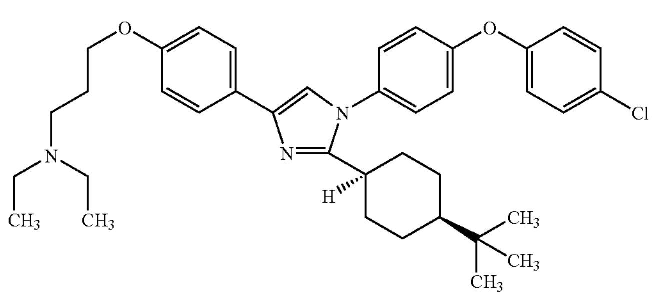 | [3-(4-{2-(cis-4-tert-Butyl-cyclohexyl)-1-[4-(4-chloro-phenoxy)-phenyl]-1H-imidazol-4-yl]-phenoxy)-propyl]-diethyl-amine |

TABLE 1-continued

| Ex. | Structure | Name |
|---|---|---|
| 515 | 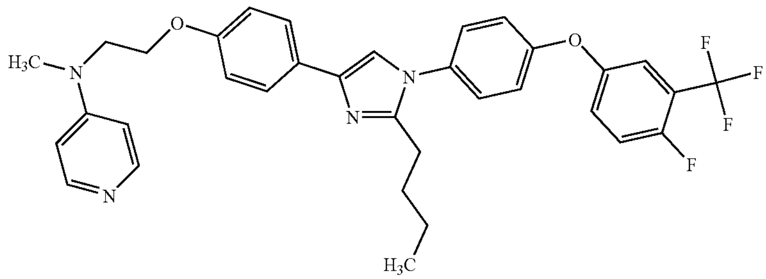 | [2-(4-{2-Butyl-1-[4-(4-fluoro-3-trifluoromethyl-phenoxy)-phenyl]-1H-imidazol-4-yl}-phenoxy)-ethyl]-methyl-pyridin-4-yl-amine |
| 516 | 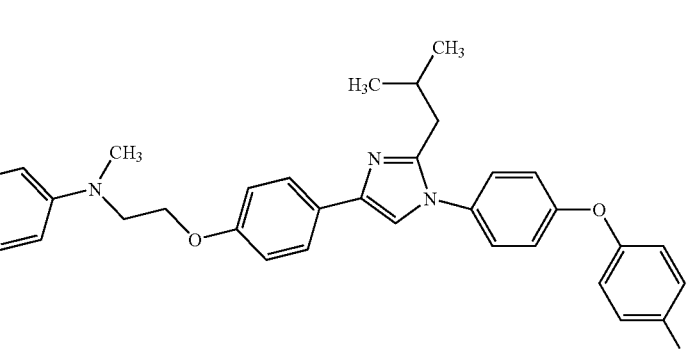 | [2-(4-{1-[4-(4-Fluoro-phenoxy)-phenyl]-2-isobutyl-1H-imidazol-4-yl}-phenoxy)-ethyl]-methyl-pyridin-4-yl-amine |
| 517 | 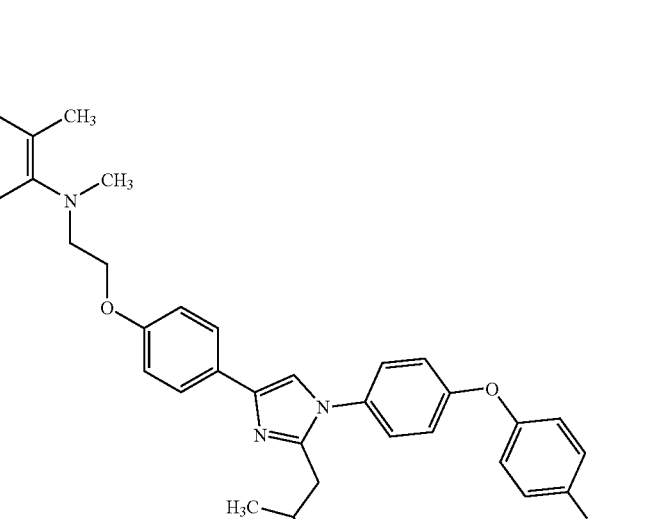 | [2-(4-{1-[4-(4-Fluoro-phenoxy)-phenyl]-2-isobutyl-1H-imidazol-4-yl}-phenoxy)-ethyl]-methyl-(3-methyl-pyridin-4-yl)-amine |
| 518 | 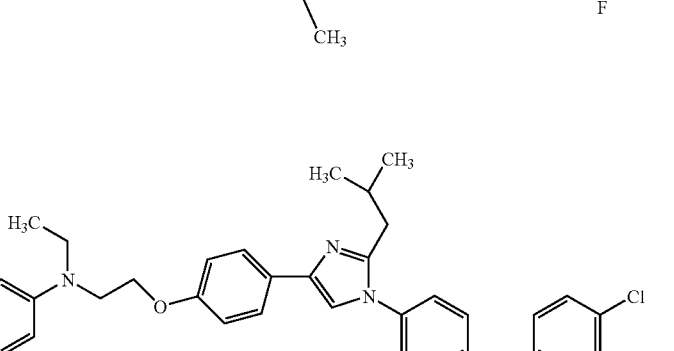 | [2-(4-{1-[4-(4-Chloro-phenoxy)-phenyl]-2-isobutyl-1H-imidazol-4-yl}-phenoxy)-ethyl]-ethyl-pyridin-4-yl-amine |

TABLE 1-continued

| Ex. | Structure | Name |
|---|---|---|
| 519 | 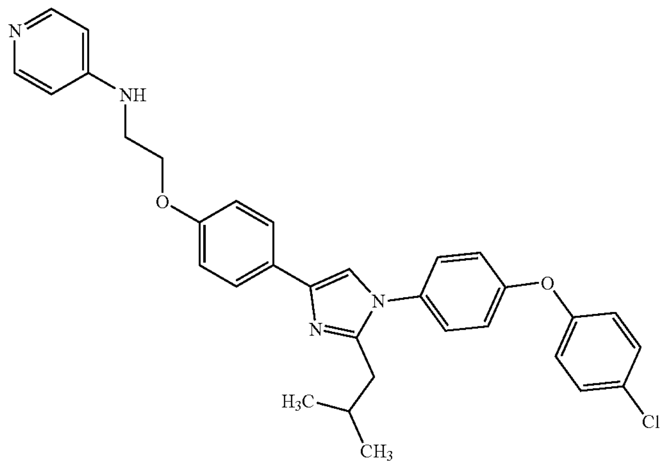 | [2-(4-{1-[4-(4-Chloro-phenoxy)-phenyl]-2-isobutyl-1H-imidazol-4-yl]-phenoxy)-ethyl]-pyridin-4-yl-amine |
| 520 | 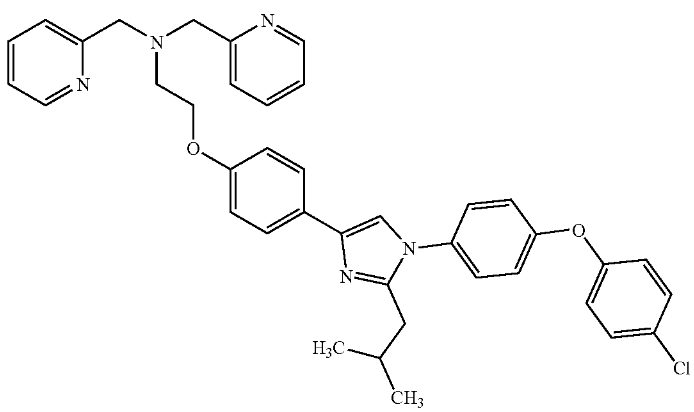 | [2-(4-{1-[4-(4-Chloro-phenoxy)-phenyl]-2-isobutyl-1H-imidazol-4-yl}-phenoxy)-ethyl]-bis-pyridin-2-ylmethyl-amine |
| 521 | 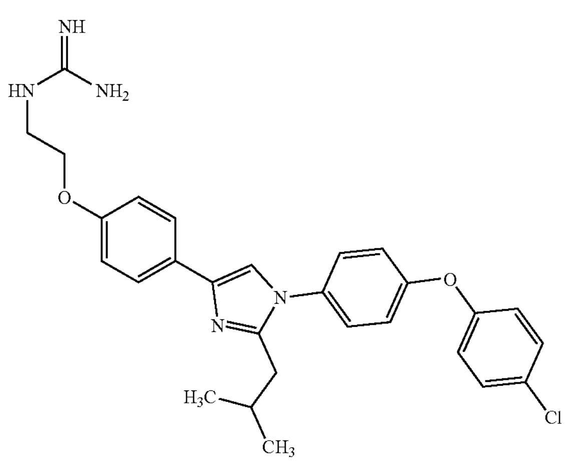 | N-(2-(4-{1-[4-(4-Chloro-phenoxy)-phenyl]-2-isobutyl-1H-imidazol-4-yl}-phenoxy)-ethyl]-guanidine |

TABLE 1-continued

| Ex. | Structure | Name |
|---|---|---|
| 522 | 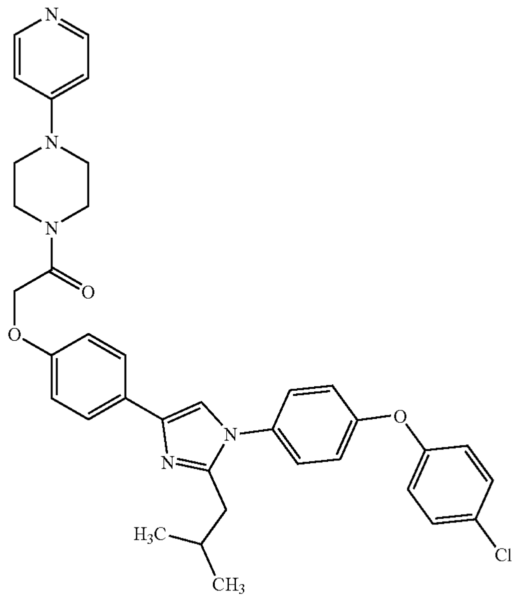 | 2-(4-{1-[4-(4-Chloro-phenoxy)-phenyl]-2-isobutyl-1H-imidazol-4-yl}-phenoxy)-1-(4-pyridin-4-yl-piperazin-1-yl)-ethanone |
| 523 | 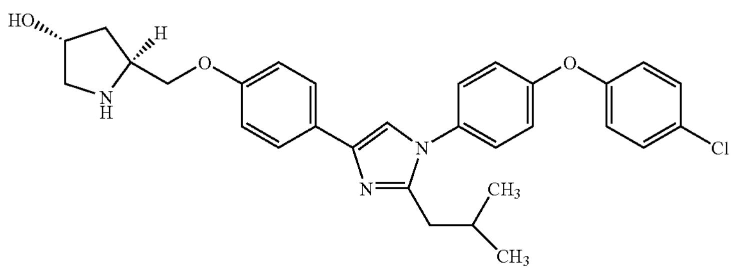 | 5-(4-{1-[4-(4-Chloro-phenoxy)-phenyl]-2-isobutyl-1H-imidazol-4-yl)-phenoxymethyl)-pyrrolidin-3-ol |
| 524 | 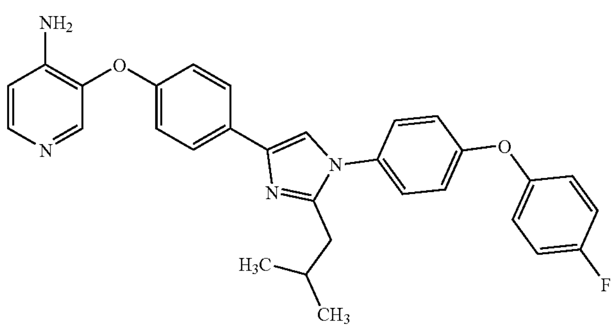 | 3-(4-{1-[4-(4-Fluoro-phenoxy)-phenyl]-2-isobutyl-1H-imidazol-4-yl}-phenoxy)-pyridin-4-ylamine |
| 525 | 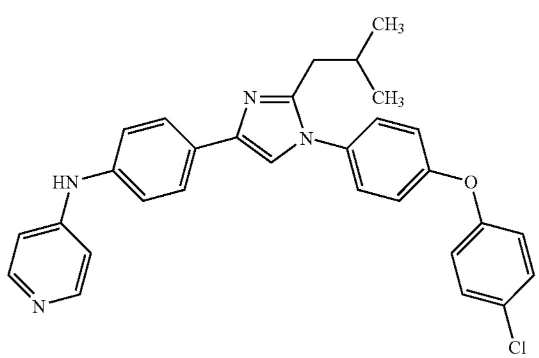 | (4-{1-[4-(4-Chloro-phenoxy)-phenyl]-2-isobutyl-1H-imidazol-4-yl]-phenyl)-pyridin-4-yl-amine |

TABLE 1-continued

| Ex. | Structure | Name |
|---|---|---|
| 526 | 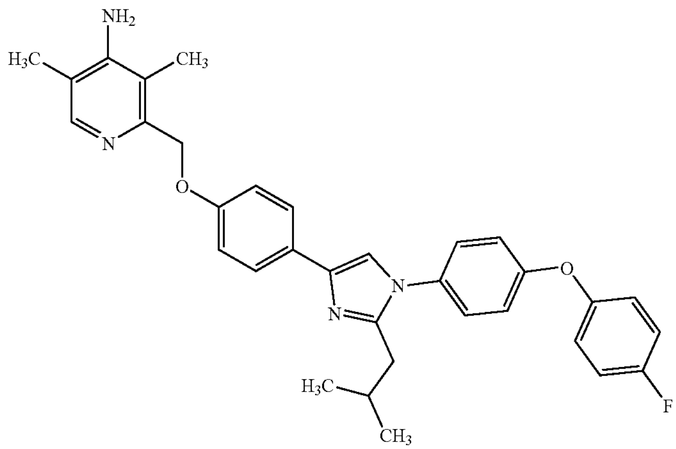 | 2-(4-{1-[4-(4-Fluoro-phenoxy)-phenyl]-2-isobutyl-1H-imidazol-4-yl}-phenoxymethyl)-3,5-dimethyl-pyridin-4-ylamine |
| 527 | 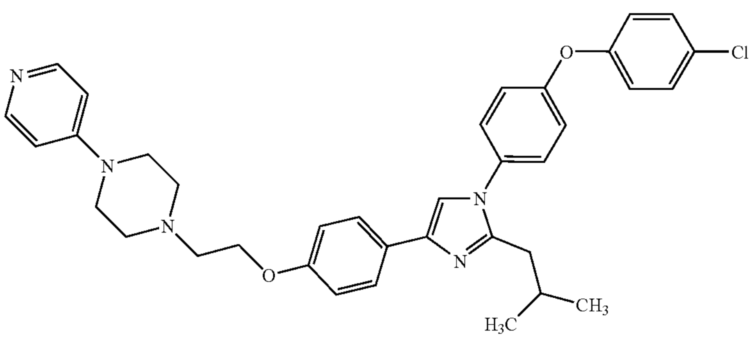 | 1-[2-(4-{1-[4-(4-Chloro-phenoxy)-phenyl]-2-isobutyl-1H-imidazol-4-yl}-phenoxy)-ethyl]-4-pyridin-4-yl-piperazine |
| 528 | 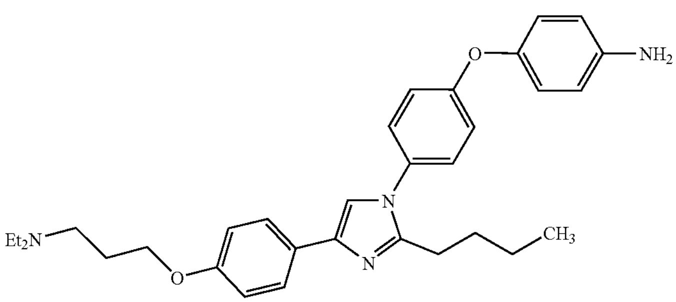 | 4-(4-{2-Butyl-4-[4-(3-diethylamino-propoxy)-phenyl]-imidazol-1-yl}-phenoxy)-phenylamine |
| 529 | 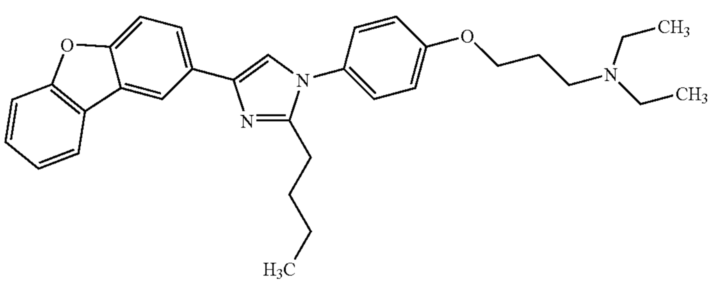 | {3-[4-(2-Butyl-4-dibenzofuran-2-yl-imidazol-1-yl)-phenoxy]-propyl}-diethyl-amine |

TABLE 1-continued

| Ex. | Structure | Name |
|---|---|---|
| 530 | 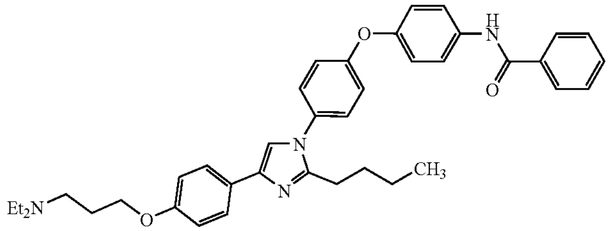 | N-[4-(4-{2-Butyl-4-[4-(3-diethylamino-propoxy)-phenyl]-imidazol-1-yl}-phenoxy)-phenyl]-benzamide |
| 531 | 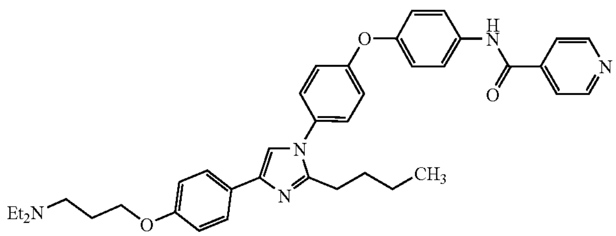 | N-[4-(4-{2-Butyl-4-[4-(3-diethylamino-propoxy)-phenyl]-imidazol-1-yl}-phenoxy)-phenyl]-isonicotinamide |
| 532 | 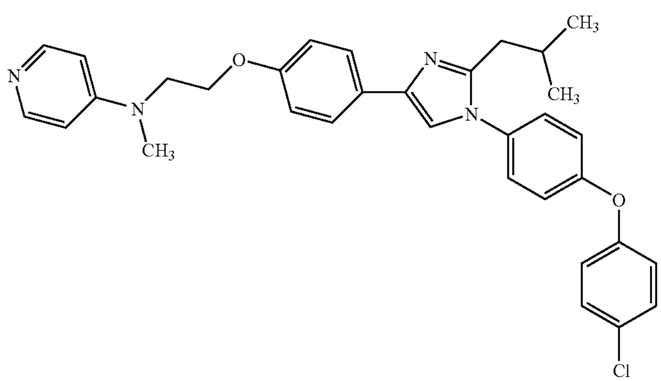 | [2-(4-{1-[4-(4-Chloro-phenoxy)-phenyl]-2-isobutyl-1H-imidazol-4-yl}-phenoxy)-ethyl]-methyl-pyridin-4-yl-amine |
| 533 | 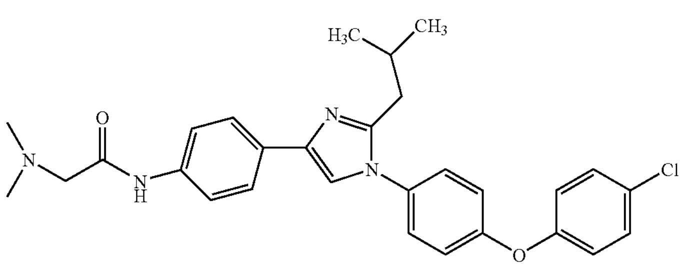 | N-(4-{1-[4-(4-Chloro-phenoxy)-phenyl]-2-isobutyl-1H-imidazol-4-yl}-phenyl)-2-dimethylamino-acetamide |

TABLE 1-continued

| Ex. | Structure | Name |
| --- | --- | --- |
| 534 | 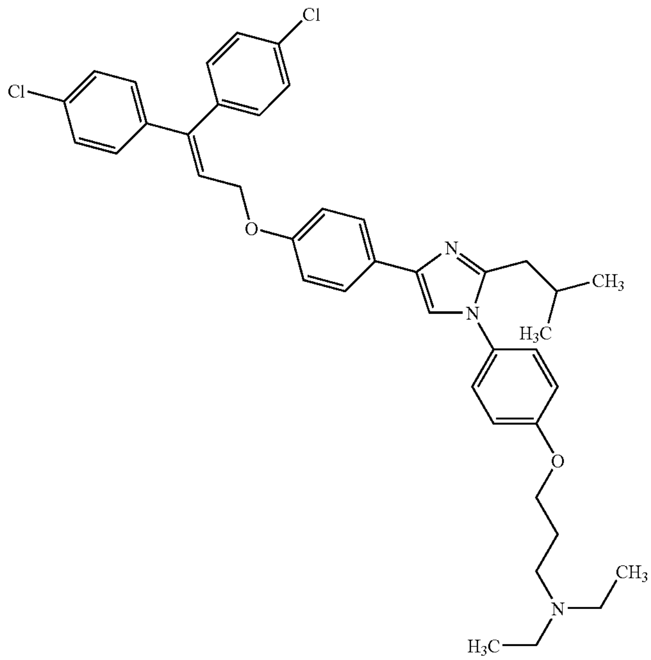 | {3-[4-(4-{4-[3,3-Bis-(4-chloro-phenyl)-allyloxy]-phenyl}-2-isobutyl-imidazol-1-yl)-phenoxy]-propyl}-diethyl-amine |
| 535 | 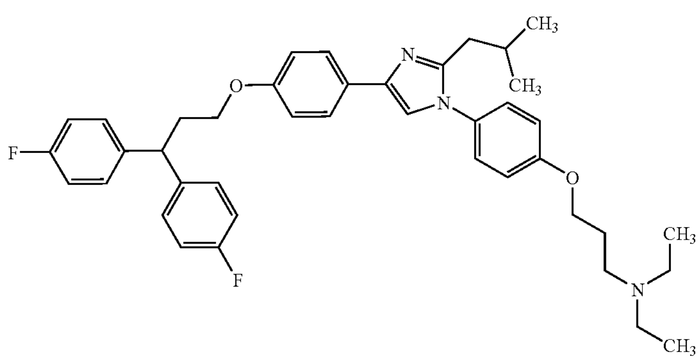 | {3-[4-(4-{4-[3,3-Bis-(4-fluoro-phenyl)-propoxy]-phenyl}-2-isobutyl-imidazol-1-yl)-phenoxy]-propyl}-diethyl-amine |
| 536 | 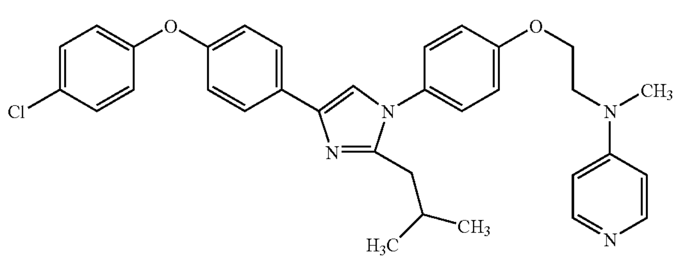 | [2-(4-{4-[4-(4-Chloro-phenoxy)-phenyl]-2-isobutyl-imidazol-1-yl]-phenoxy)-ethyl]-methyl-pyridin-4-yl-amine |

| Ex. | Structure | Name |
| --- | --- | --- |
| 537 | 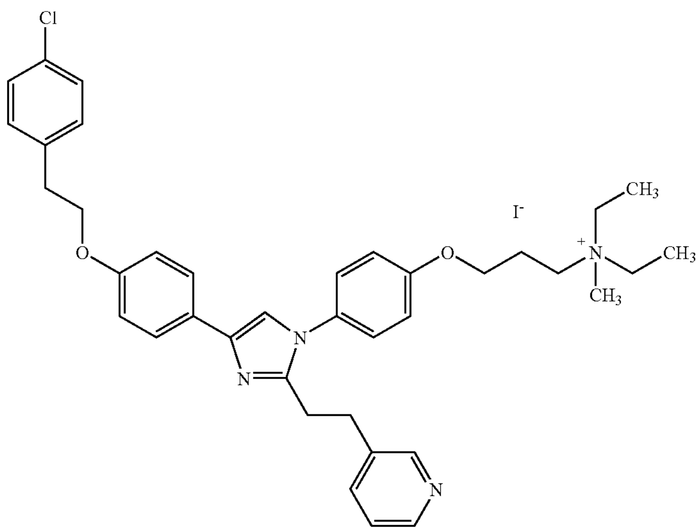 | [3-(4-{4-{4-[2-(4-Chloro-phenyl)-ethoxy]-phenyl]-2-[2-[(1-methyl-pyridin-3-yl)-ethyl]-imidazol-1-yl}-phenoxy)-propyl]-diethylmethyl ammonium iodide |
| 538 | 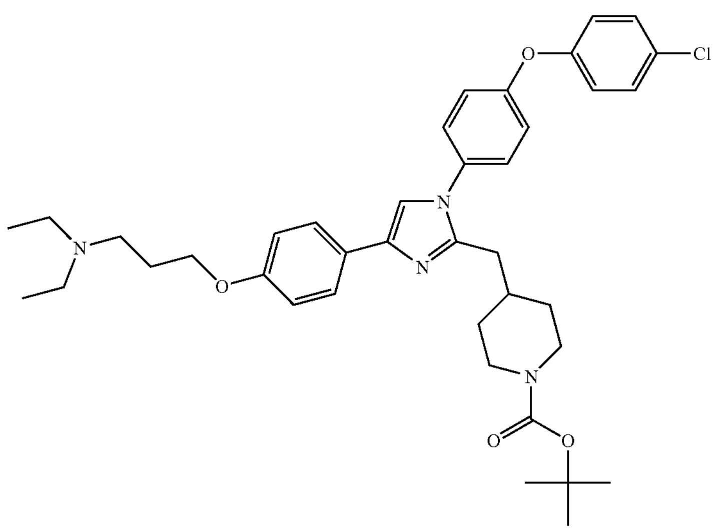 | [3-(4-{2-(N-BOC-piperidine-4-ylmethyl)-1-[4-(4-chloro-phenoxy)-phenyl]-1H-imidazol-4-yl}-phenoxy)-propyl]-diethyl-amine |
| 539 | 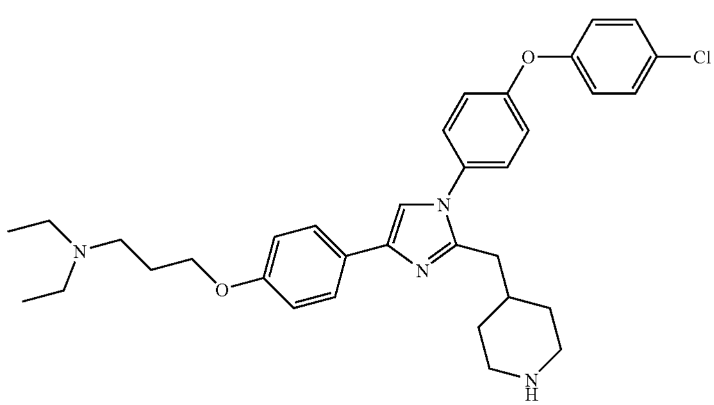 | [3-(4-{2-(Piperidine-4-ylmethyl)-1-[4-(4-chloro-phenoxy)-phenyl]-1H-imidazol-4-yl}-phenoxy)-propyl]-diethyl-amine |

TABLE 1-continued

| Ex. | Structure | Name |
|---|---|---|
| 540 | 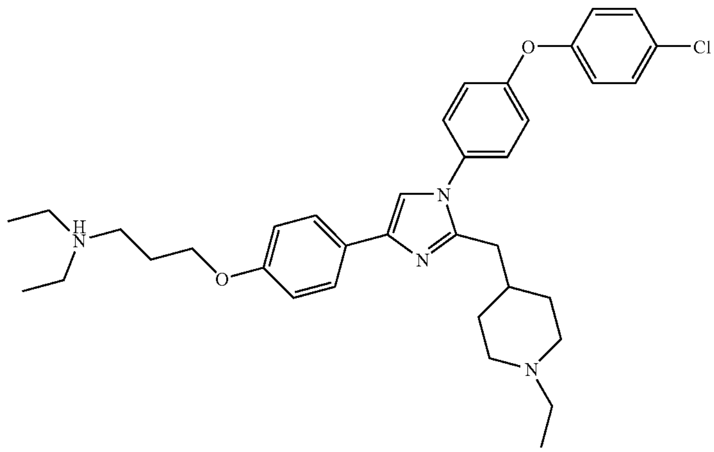 | [3-(4-{2-(N-ethyl-piperidine-4-ylmethyl)-1-[4-(4-chloro-phenoxy)-phenyl]-1H-imidazol-4-yl]-phenoxy)-propyl]-diethyl-amine |
| 541 | 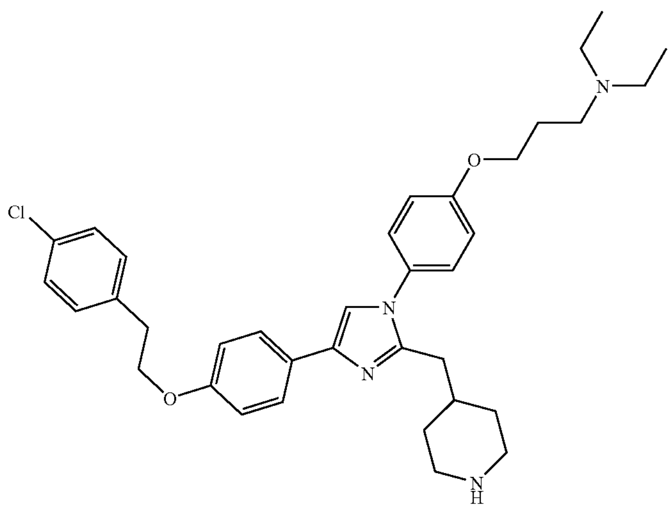 | [3-(4-{2-(piperidine-4-ylmethyl)-4-[4-(4-chloro-phenoxy)-phenyl]-imidazol-1-yl}-phenoxy)-propyl]-diethyl-amine |
| 542 | 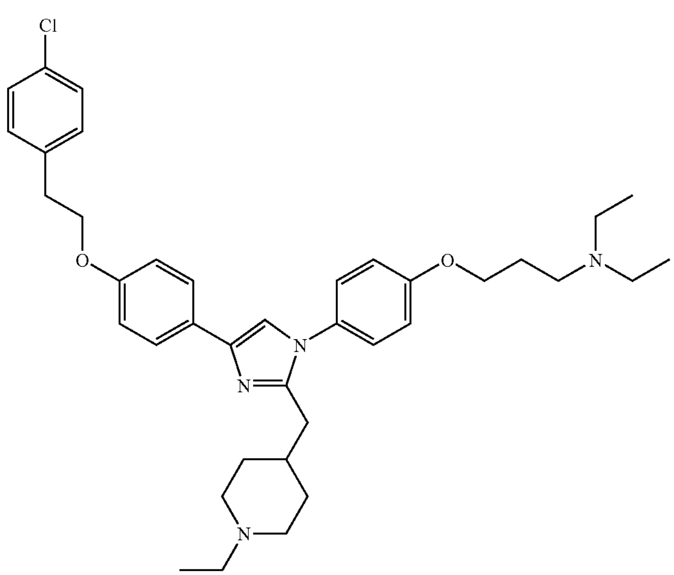 | [3-(4-{2-(N-ethylpiperidine-4-ylmethyl)-4-[4-(4-chloro-phenoxy)-phenyl]-imidazol-1-yl}-phenoxy)-propyl]-diethyl-amine |

TABLE 1-continued
| Ex. | Structure | Name |
|---|---|---|
| 543 | 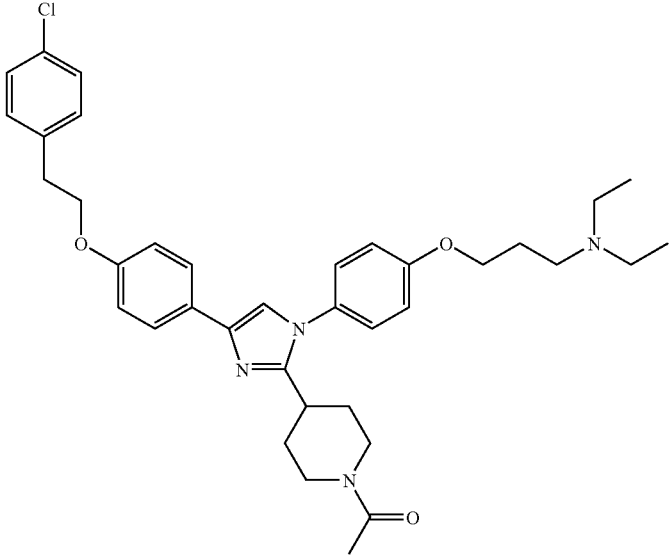 | [3-(4-{2-(N-acetylpiperidine-4-yl)-4-[4-(4-chloro-phenoxy)-phenyl]-imidazol-1-yl]-phenoxy)-propyl]-diethyl-amine |
| 544 | 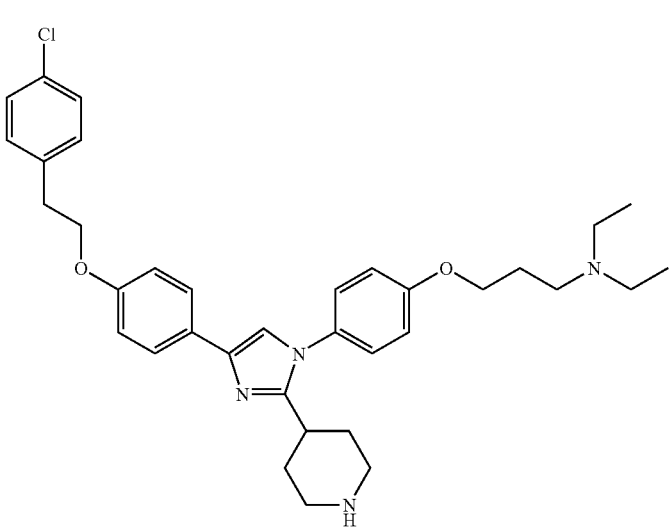 | [3-(4-{2-(piperidine-4-yl)-4-[4-(4-chloro-phenoxy)-phenyl]-imidazol-1-yl}-phenoxy)-propyl]-diethyl-amine |

TABLE 1-continued
| Ex. | Structure | Name |
|---|---|---|
| 545 | 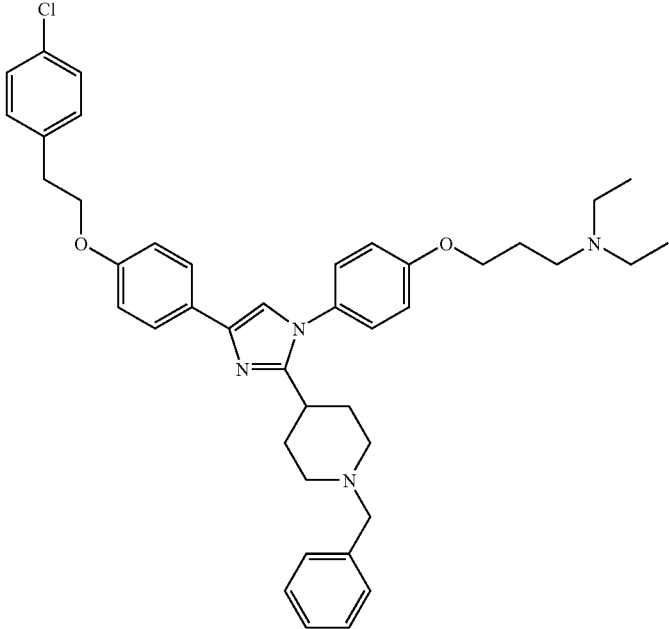 | [3-(4-{2-(N-Benzylpiperidine-4-yl)-4-[4-(4-chloro-phenoxy)-phenyl]-imidazol-1-yl}-phenoxy)-propyl]-diethyl-amine |
| 546 | 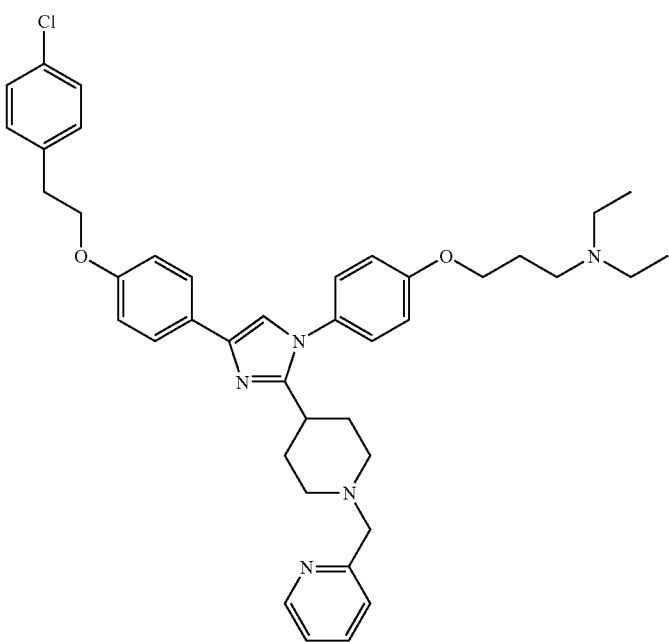 | [3-(4-{2-(N-(2-Pyridylmethyl)piperidine-4-yl)-4-[4-(4-chloro-phenoxy)-phenyl]-imidazol-1-yl}-phenoxy)-propyl]-diethyl-amine |

TABLE 1-continued
| Ex. | Structure | Name |
|---|---|---|
| 547 | 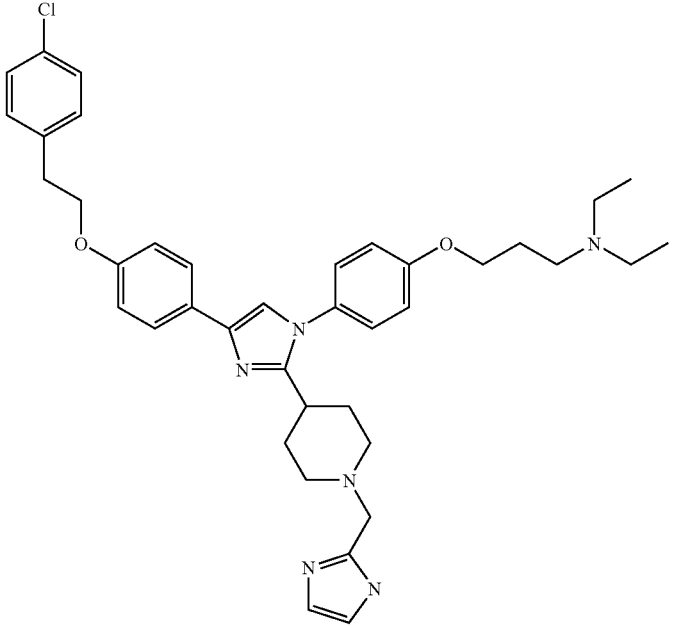 | [3-(4-{2-(N-(2-Imidazolylmethyl)piperidine-4-yl)-4-[4-(4-chloro-phenoxy)-phenyl]-imidazol-1-yl}-phenoxy)-propyl]-diethyl-amine |
| 548 | 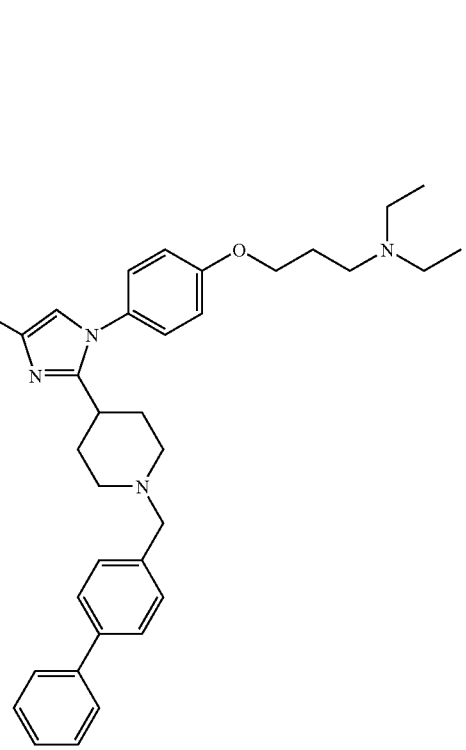 | [3-(4-{2-(N-(4-biphenyl)methylpiperidine-4-yl)-4-[4-(4-chloro-phenoxy)-phenyl]-imidazol-1-yl}-phenoxy)-propyl]-diethyl-amine |

TABLE 1-continued

| Ex. | Structure | Name |
|---|---|---|
| 549 | 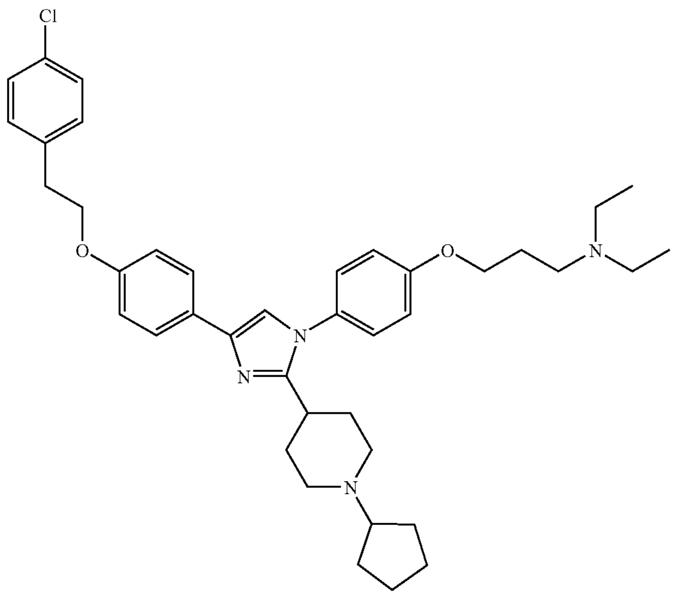 | [3-(4-{2-(N-Cyclohexylpiperidine-4-yl)-4-[4-(4-chloro-phenoxy)-phenyl]-imidazol-1-yl}-phenoxy)-propyl]-diethyl-amine |
| 550 | 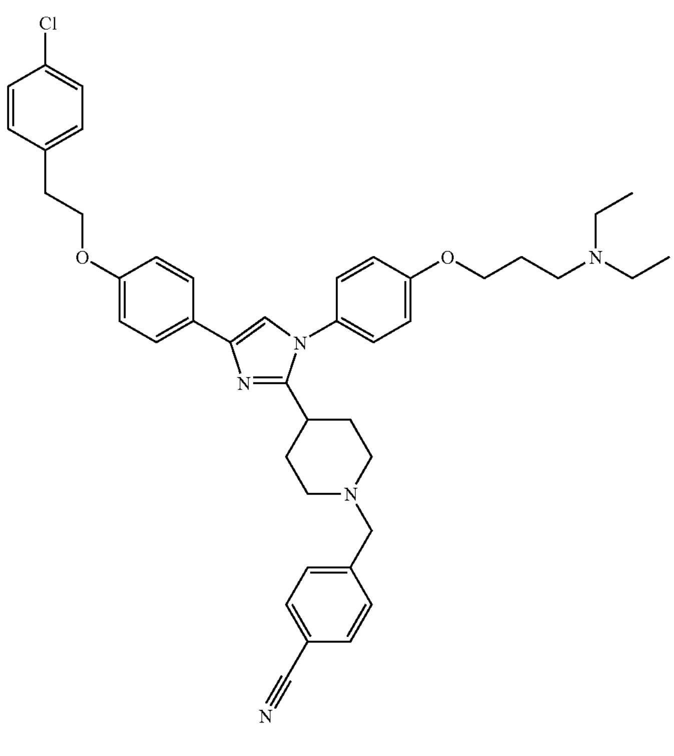 | [3-(4-{2-(N-(4-Cyanobenzyl)piperidine-4-yl)-4-[4-(4-chloro-phenoxy)-phenyl]-imidazol-1-yl}-phenoxy)-propyl]-diethyl-amine |

TABLE 1-continued

| Ex. | Structure | Name |
|---|---|---|
| 551 | 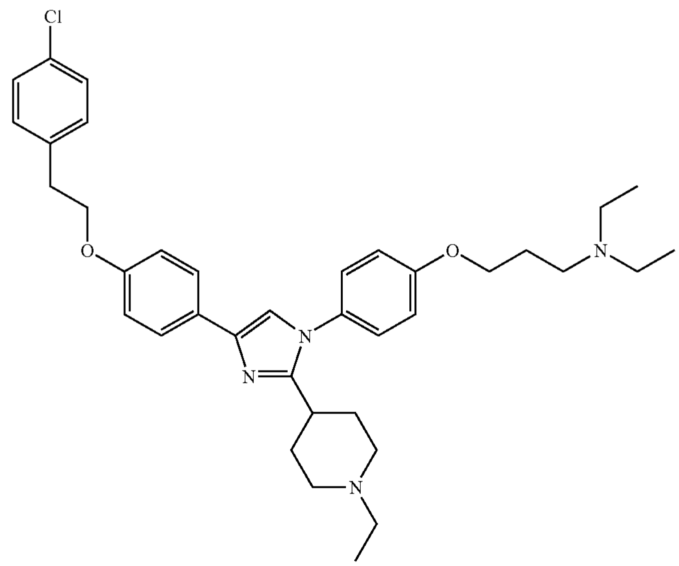 | [3-(4-{2-(N-Ethylpiperidine-4-yl)-4-[4-(4-chloro-phenoxy)-phenyl]-imidazol-1-yl]-phenoxy)-propyl]-diethyl-amine |

Definitions of Terms

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ atoms. Examples of "alkylene" as used herein include, but are not limited to, methylene, ethylene, and the like.

As used herein, the term "alkyline" refers to a straight or branched chain trivalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkyline" as used herein include, but are not limited to, methine, 1,1,2-ethyline, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or S(O)$_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to an alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "hpterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclyl containing at least one basic nitrogen atom" refers to a "heterocyclic" "heterocyclyl" group as defined above, wherein said heterocyclyl group contains at least one nitrogen atom flanked by hydrogen, alkyl, alkylene, or alkylyne groups, wherein said alkyl and/or alkylene groups are not substituted by oxo. Examples of "heterocyclyl containing at least one basic nitrogen atom" include, but are not limited to, piperazine-2-yl, pyrrolidine-2-yl, azepine-4-yl,

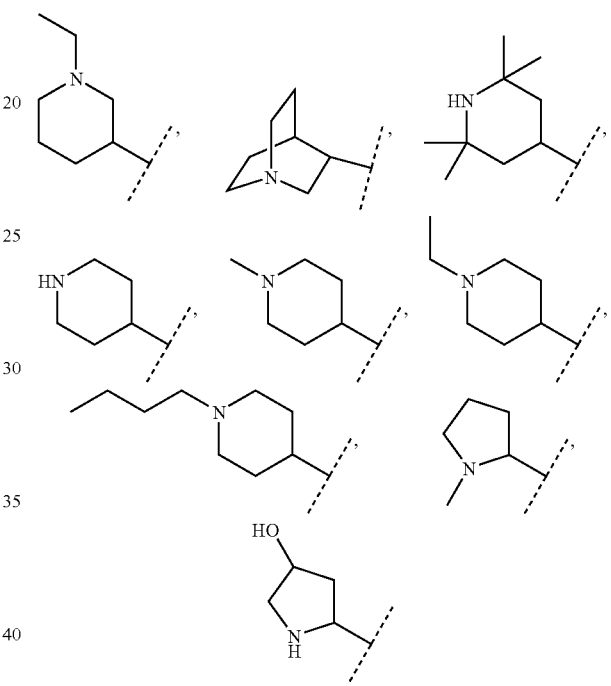

and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy optionally substituted by acyl, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to one or more cycloalkyl groups fused to an aryl group, the aryl and cycloalkyl groups having two atoms in common, and wherein the aryl group is the point of substitution. Examples of "fused cycloalkylaryl" used herein include 5-indanyl, 5,6,7,8-tetrahydro-2-naphthyl,

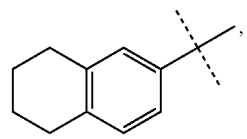

and the like.

As used herein, the term "fused cycloalkylarylene" refers to a fused cycloalkylaryl, wherein the aryl group is divalent. Examples include

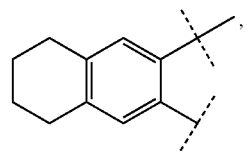

and the like.

As used herein, the term "fused arylcycloalkyl" refers to one or more aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl),

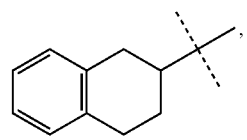

and the like.

As used herein, the term "fused arylcycloalkylene" refers to a fused arylcycloalkyl, wherein the cycloalkyl group is divalent. Examples include 9,1-fluorenylene,

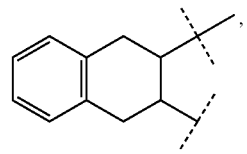

-continued

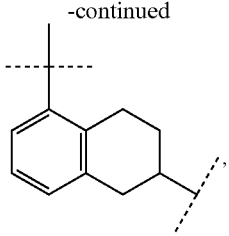

and the like.

As used herein, the term "fused heterocyclylaryl" refers to one or more heterocyclyl groups fused to an aryl group, the aryl and heterocyclyl groups having two atoms in common, and wherein the aryl group is the point of substitution. Examples of "fused heterocyclylaryl" used herein include 3,4-methylenedioxy-1-phenyl,

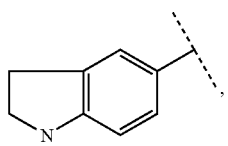

and the like

As used herein, the term "fused heterocyclylarylene" refers to a fused heterocyclylaryl, wherein the aryl group is divalent. Examples include

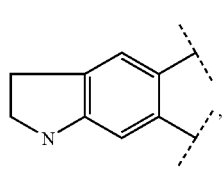

and the like.

As used herein, the term "fused arylheterocyclyl" refers to one or more aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl),

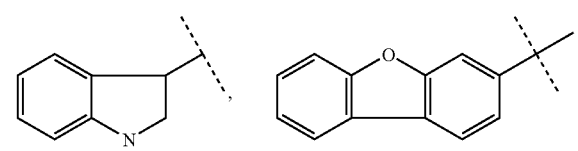

and the like.

As used herein, the term "fused arylheterocyclyl containing at least one basic nitrogen atom" refers to a "fused arylheterocyclyl" group as defined above, wherein said heterocyclyl group contains at least one nitrogen atom flanked by hydrogen, alkyl, alkylene, or alkylyne groups, wherein said alkyl and/or alkylene groups are not substituted by oxo. Examples of "fused arylheterocyclyl containing at least one basic nitrogen atom" include, but are not limited to,

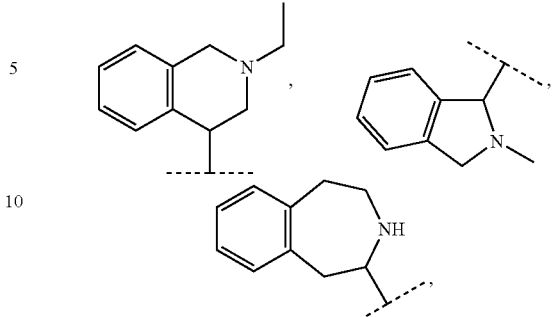

and the like.

As used herein, the term "fused arylheterocyclylene" refers to a fused arylheterocyclyl, wherein the heterocyclyl group is divalent. Examples include

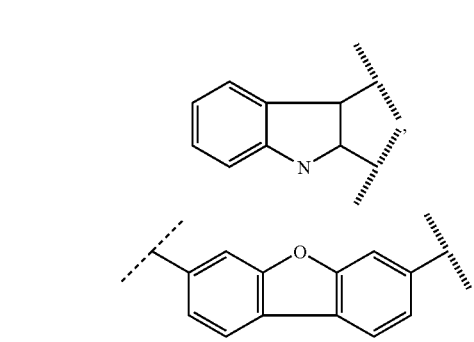

and the like.

As used herein, the term "fused cycloalkylheteroaryl" refers to one or more cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl,

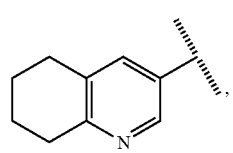

and the like.

As used herein, the term "fused cycloalkylheteroarylene" refers to a fused cycloalkylheteroaryl, wherein the heteroaryl group is divalent. Examples include

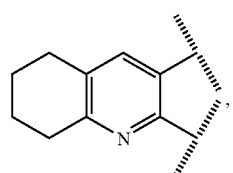

and the like.

As used herein, the term "fused heteroarylcycloalkyl" refers to one or more heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl,

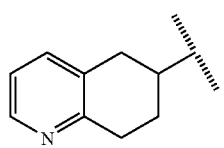

and the like.

As used herein, the term "fused heteroarylcycloalkylene" refers to a fused heteroarylcycloalkyl, wherein the cycloalkyl group is divalent. Examples include

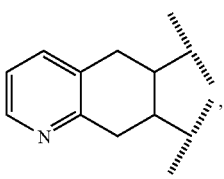

and the like.

As used herein, the term "fused heterocyclylheteroaryl" refers to one or more heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl,

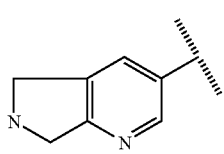

and the like.

As used herein, the term "fused heterocyclylheteroarylene" refers to a fused heterocyclylheteroaryl, wherein the heteroaryl group is divalent. Examples include

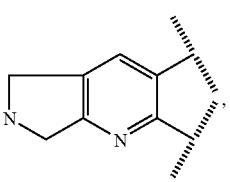

and the like.

As used herein, the term "fused heteroarylheterocyclyl" refers to one or more heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include -5-aza-2,3-dihydrobenzofuran-2-yl,

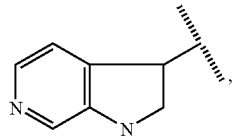

and the like.

As used herein, the term "fused heteroarylheterocyclyl containing at least one basic nitrogen atom" refers to a "fused heteroarylheterocyclyl" group as defined above, wherein said heterocyclyl group contains at least one nitrogen atom flanked by hydrogen, alkyl, alkylene, or alkylyne groups, wherein said alkyl and/or alkylene groups are not substituted by oxo. Examples of "fused heteroarylheterocyclyl containing at least one basic nitrogen atom" include, but are not limited to,

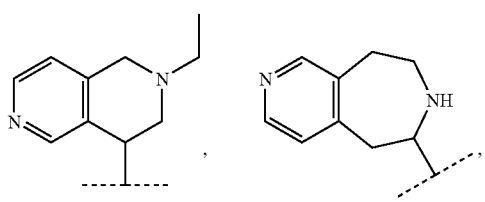

and the like.

As used herein, the term "fused heteroarylheterocyclylene" refers to a fused heteroarylheterocyclyl, wherein the heterocyclyl group is divalent. Examples include

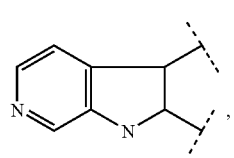

and the like.

As used herein, the term "acid isostere" refers to a substituent group which will ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO-$, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "alkoxycarbonyl" refers to the group $R_aOC(O)$—, where $R_a$ is alkyl, alkenyl, alkynyl, cycloalkyl, cycloalkenyl, or heterocyclyl.

As used herein, the term "aryloxycarbonyl" refers to the group $R_aOC(O)$—, where $R_a$ is aryl or heteroaryl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of Formula (I): for example, the lactam formed by a carboxylic group in $R_2$ and an amine in $R_4$, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" or "treating" as used herein, refers to the full spectrum of treatments for a given disorder from which the patient is suffering, including alleviation of one, most of all symptoms resulting from that disorder, to an outright cure for the particular disorder or prevention of the onset of the disorder.

The present invention also provides a method for the synthesis of compounds useful as intermediates in the preparation of compounds of Formula (I) along with methods for the preparation of compounds of Formula (I). Unless otherwise indicated, variables refer to those for Formula (I).

An aldehyde (1) (Scheme 1) may be condensed with a diamine compound (2) in a solvent such as ethanol at a temperature of from 25 to 100 degrees Celsuis, to obtain the product benzimidazole (3), where the intermediate adduct undergoes spontaneous oxidation. Alternately, the acid (1a) may be coupled with the diamine compound (2) employing a reagent such as HBTU to afford (2a). The reaction may also afford some of the compound where the carboxylic acid has coupled to the secondary aniline nitrogen. Either product (2a) may be cyclized to (3). One nonlimiting method is to heat (2a) in a solvent such as acetic acid at a temperature of from 25 to 100 degrees Celsuis, to obtain the cyclized product (3). $Ar_1$ is a group such as but not limited to an optionally substituted aryl or heteroaryl ring system.

$Ar_2$—OH provides (7), where the $Ar_2$—O— substituent is bonded to the same atom as the F in (6).

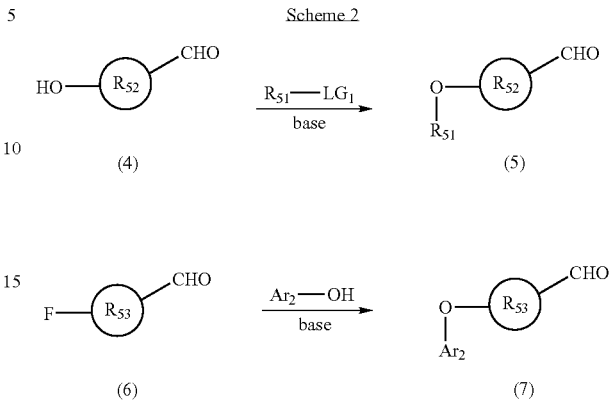

In Scheme 3, an aldehyde (8) posessing two free hydroxyl groups, two free phenolic groups, of a combination of phenolic and hydroxyl groups may be treated with two equivalents of an alkylating agent $R_{51}$-$LG_1$, in the presence of a suitable base such as potassium carbonate or DIEA, in a solvent such as DMF, to afford (9). Alternately, where $R_{53}$ is

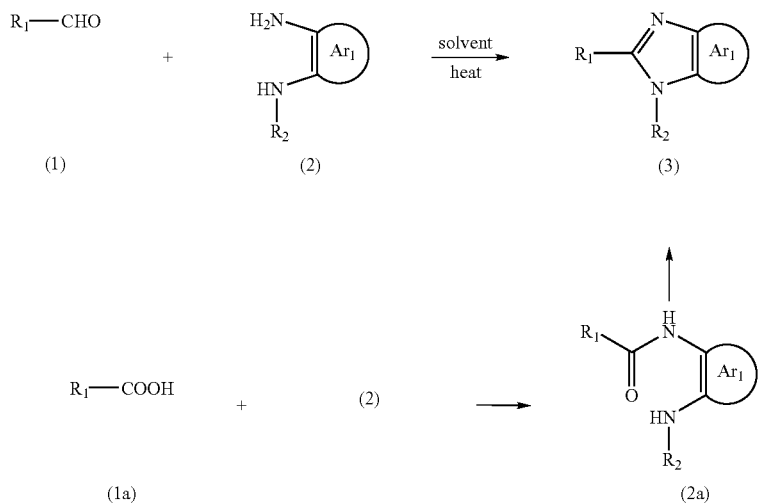

Where $R_{52}$ is aryl, heteroaryl, or contains an aryl or heteroaryl group possessing a phenolic substituent, or where $R_{52}$ possesses a free hydroxyl group, an aldehyde of formula (4) (Scheme 2) may be treated with an optionally substituted alkyl halide $R_{51}$-$LG_1$ and a base such as potassium carbonate, in a solvent such as DMF, at a temperature of from 0 to 120° C., to afford (5). $LG_1$ represents a nucleofugal group such as iodide, bromide, methanesulfonate, or toluenesulfonate (Scheme 2). Where $R_{53}$ in (6) represents an aryl or heteroaryl ring system, direct treatment of (6) in the presence of a base such as DIEA or TEA with an aryl or heteroaryl phenol an aryl ring posessing ortho and para hydroxyl groups relative to the aldehyde group, treatment of (8) with one equivalent of base and an alkylating agent $R_{51}$-$LG_1$ in the presence of a suitable base such as DIEA of potassium carbonate, followed by treatment with a second alkylating agent $R_{54}$-$LG_2$ in the presence of base, affords (10). The ortho, para difluoro aldehyde (11), where $R_{53}$ is a heteroaryl or aryl ring, may be treated with an alcohol $R_{55}$—OH in the presence of base such as DIEA, followed by treatment with a phenol $Ar_3$-OH in the presence of a base such as DIEA or potassium carbonate, to afford (12).

Scheme 3

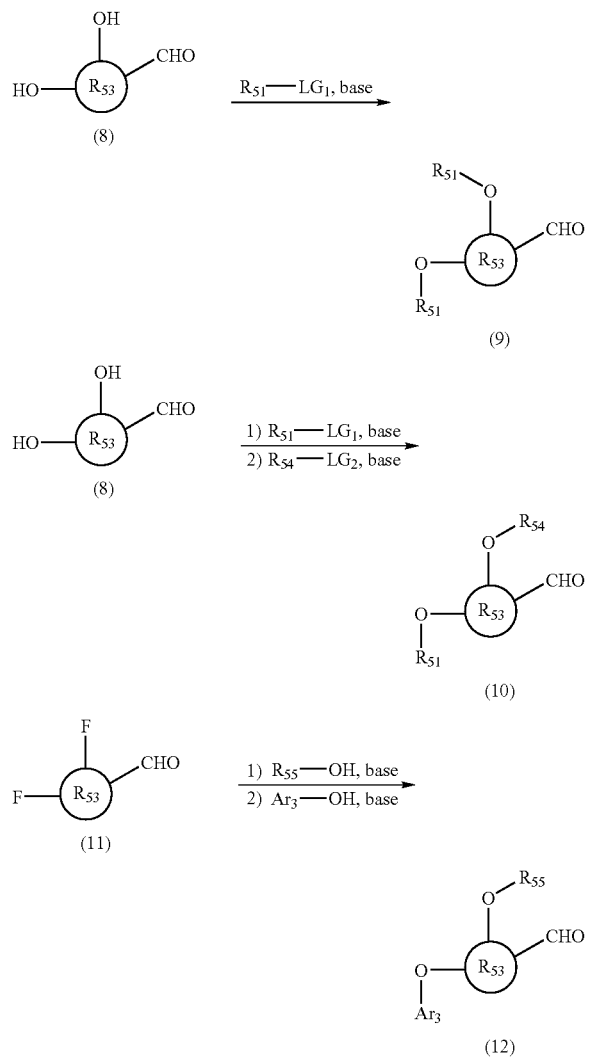

Scheme 4 describes the synthesis of substituted arylenediamines.

Scheme 4

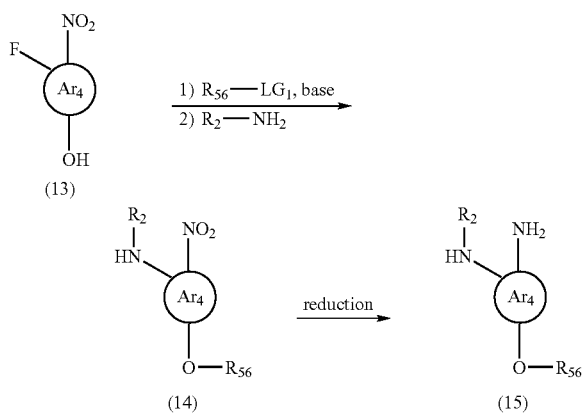

In Scheme 4, an ortho-fluoro nitrophenol such as (13) may be alkylated with an alkyl halide or other alkylating agent $R_{56}$-$LG_1$, in the presence of an alkali metal carbonate as base in a solvent such as DMF or acetonitrile. $LG_1$ may represent a nucleofugal group such as iodide, bromide, methanesulfonate, and the like. In this transformation, $R_{56}$ is a group such as but not limited to alkyl. The intermediate may be treated with an amine $R_2$—$NH_2$ in the presence or absence of a tertiary amine base, in a solvent such as THF, at a temperature of from 0° C. to 100° C., to afford (14). Reduction of the nitro group in (14) may be accomplished by treatment of (14) in acidic or neutral ethanol with stannous chloride at a temperature of from 25° C. to 100° C. to afford the aniline (15). Alternately, (14) may be reduced by treatment of (14) with a noble metal catalyst such as palladium on charcoal and a hydrogen source such as gaseous hydrogen or ammonium formate, in a solvent such as ethanol, at a temperature of from 25° C. to 80° C., to afford (15). The difluoronitroaromatic compound (16) may be employed in similar manner, where in (16), one fluoro is ortho to the nitro group. Treatment of (16) with the one equivalent of amine $R_2$—$NH_2$ gives preferential substitution of the ortho fluorine. The second fluorine in the intermediate may be substituted by an alcohol $R_{57}$—OH to afford (17). In this instance, $R_{57}$ may also be aryl. Reduction of the nitro group in (17) as before with stannous chloride provides (18). $Ar_4$ represents a group such as but not limited to aryl or heteroaryl.

Scheme 5 describes synthesis of aryl diamines. The 2,4,6-trifluoronitroaromatic compound (19) may be treated with one equivalent of an amine $R_2$—NH2 to afford the product of substitution at one ortho fluoro; excess $R_{58}$—OH may then be employed in the presence of a base such as potassium tert-butoxide or sodium hydride to afford (20). Reduction of the nitro group as for Scheme 4 affords the aniline (21). Similarly, a 3,5-difluorophenolic aromatic compound (22) may be nitrated under strong nitrating conditions, e.g. fuming nitric acid, to afford the ortho nitro phenol (23) along with the para nitrophenol (24). Each individually may be processed by sequential phenol alkylation, ortho fluoro displacement by $R_2$—$NH_2$, and para or ortho fluorodisplacement by $R_{58}$—OH, to afford (25) and (26) after reduction, following chemistries in the predeceding general procedures. $Ar_5$ represents a group such as but not limited to aryl or heteroaryl.

Scheme 5

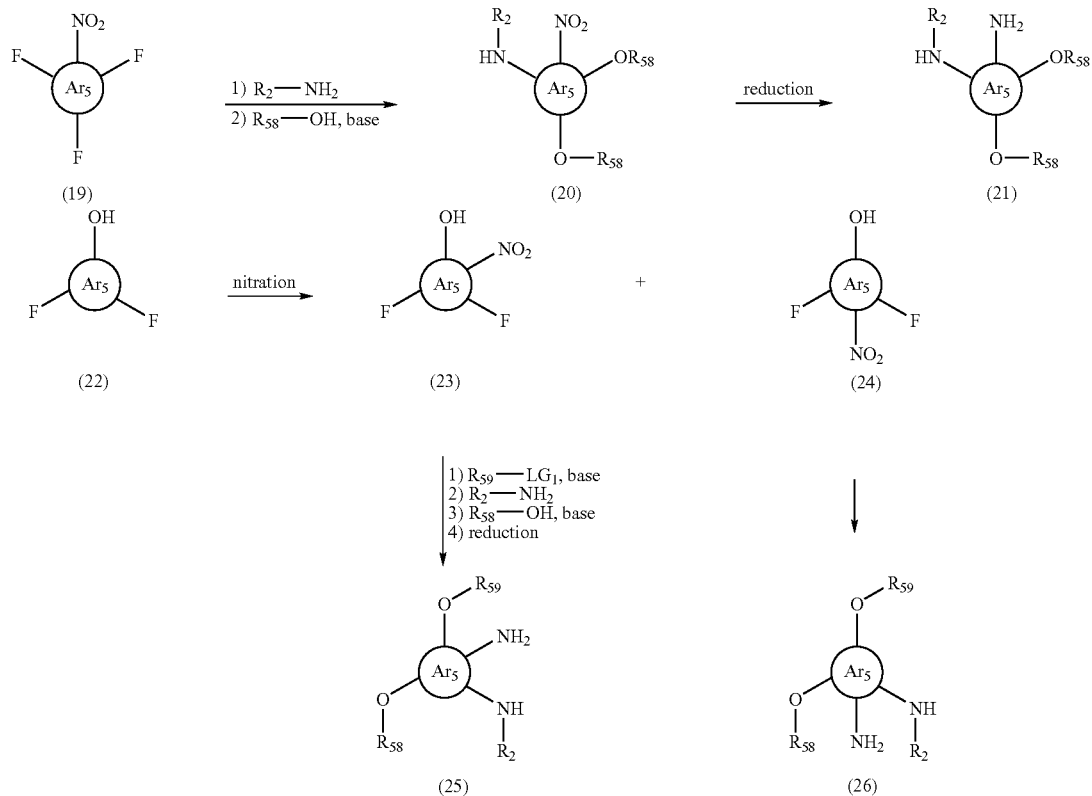

Scheme 6 describes the synthesis of mono and di alkoxy-substituted aminoaryl and aminoheteroaryl compounds. A fluoronitroaromatic (27), where F is preferably ortho or para to the nitro, may be treated with an alcohol or phenol $R_{60}$—OH and a base such as potassium tert-butoxide or sodium hydride, to afford the ipso adduct. Reduction of the nitro group to amino following preceding methods affords (28).

Similarly, displacement of the fluoro groups in (29) with $R_{60}$—OH followed by reduction as before give (30). The nitro compound (31) may be treated with a base and $R_{61}$-$LG_1$ to afford the alkylation product, then treated with $R_{60}$—OH and a base, then reduced as above to give (32). Alternately, (33) may be processed similarly to give (32). $Ar_6$ represents a group such as but not limited to aryl or heteroaryl.

Scheme 6

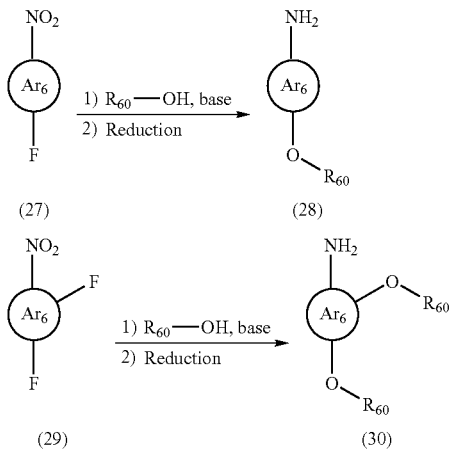

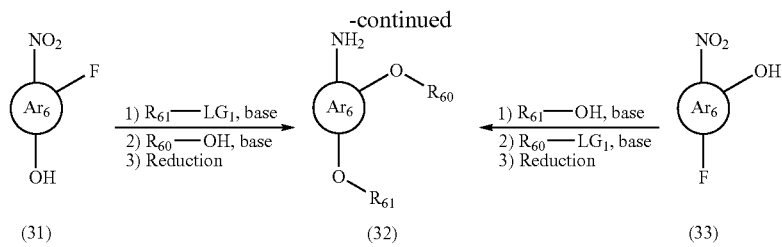

Scheme 7 describes a general synthesis of imidazoles. An aniline containing a basic side chain (—O—R$_{62}$) (40) may be coupled with a bromoketone containing a non-basic side chain (—O—R$_{63}$) (41) to give the aminoketone (42), which may then be treated with acetic acid, heat, an aldehyde R$_1$—CHO, and ammonium acetate to afford (43). Alternately, (42) may be treated with an acid chloride R$_1$—COCl to afford (44), which may subsequently be treated with ammonium acetate, acetic acid and heat to afford (43). Ar$_7$ and Ar$_8$ represent groups such as but not limited to aryl or heteroaryl.

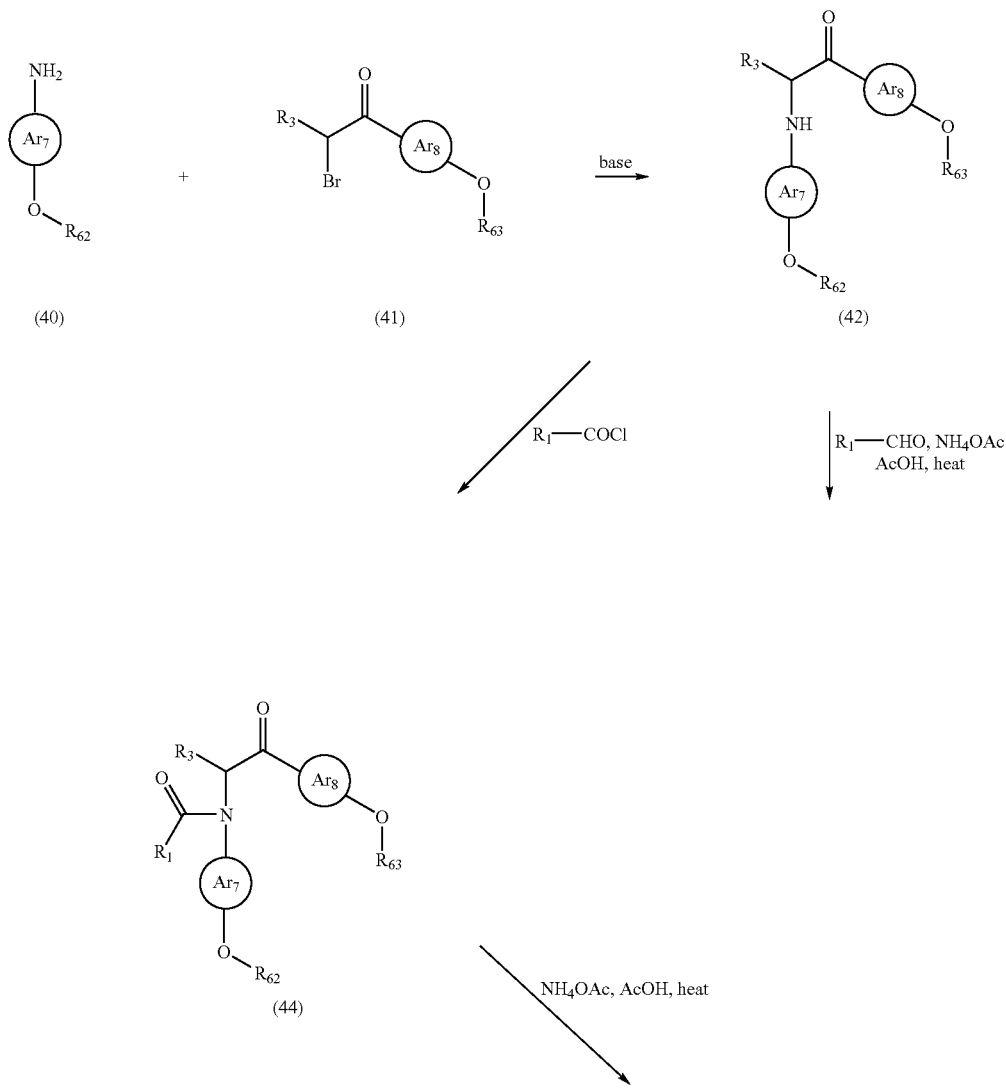

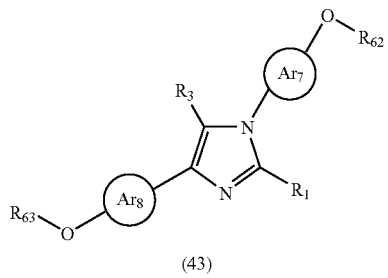

Scheme 8 describes another general synthesis of imidazoles. An aniline containing a non-basic side chain (45) may be coupled with a bromoketone containing a basic side chain (46) to give the aminoketone (47), which may then be treated with acetic acid, heat, an aldehyde R$_1$—CHO, and ammonium acetate to afford (48). Alternately, (42) may be treated with an acid chloride R$_1$—COCl to afford (49), which may subsequently be treated with ammonium acetate, acetic acid and heat to afford (43). Ar$_7$ and Ar$_8$ represent groups such as but not limited to aryl or heteroaryl.

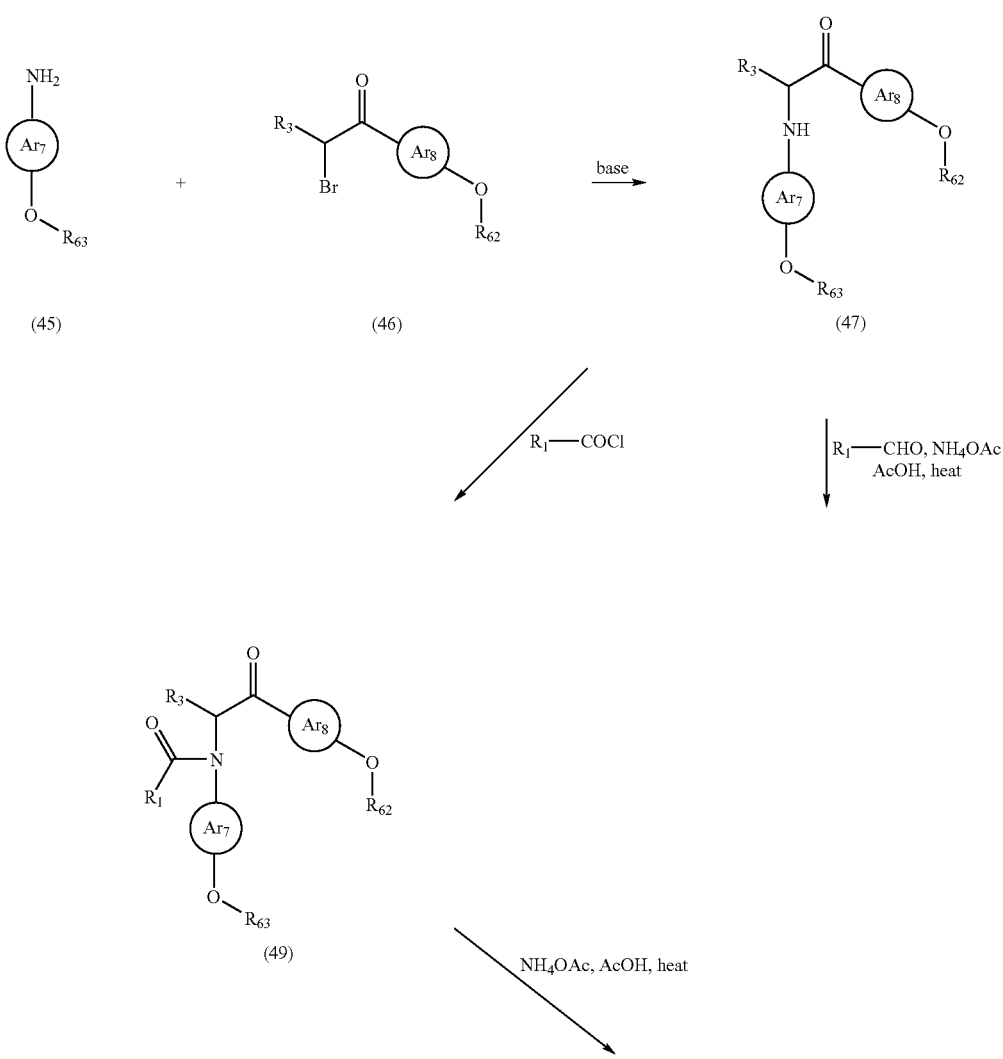

Scheme 8

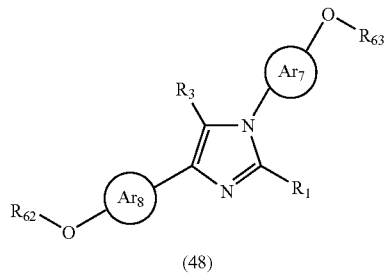

(48)

Scheme 9 describes another general synthesis of imidazoles. An aniline containing a basic side chain (40) may be coupled with a bromoketone (50) to give the aminoketone (51), which may then be treated with an acid chloride $R_1$—COCl to afford (52), which may subsequently be treated with ammonium acetate, acetic acid and heat to afford (53). The phenol is then alkylated with a alkylating agent $R_{63}$-$LG_5$ to generate the desired imidazole (54). $R_{63}$ is a group such as but not limited to substituted alkyl, and $LG_5$ is a leaving group such as iodide or methanesulfonate. $Ar_7$ and $Ar_8$ represent groups such as but not limited to aryl or heteroaryl.

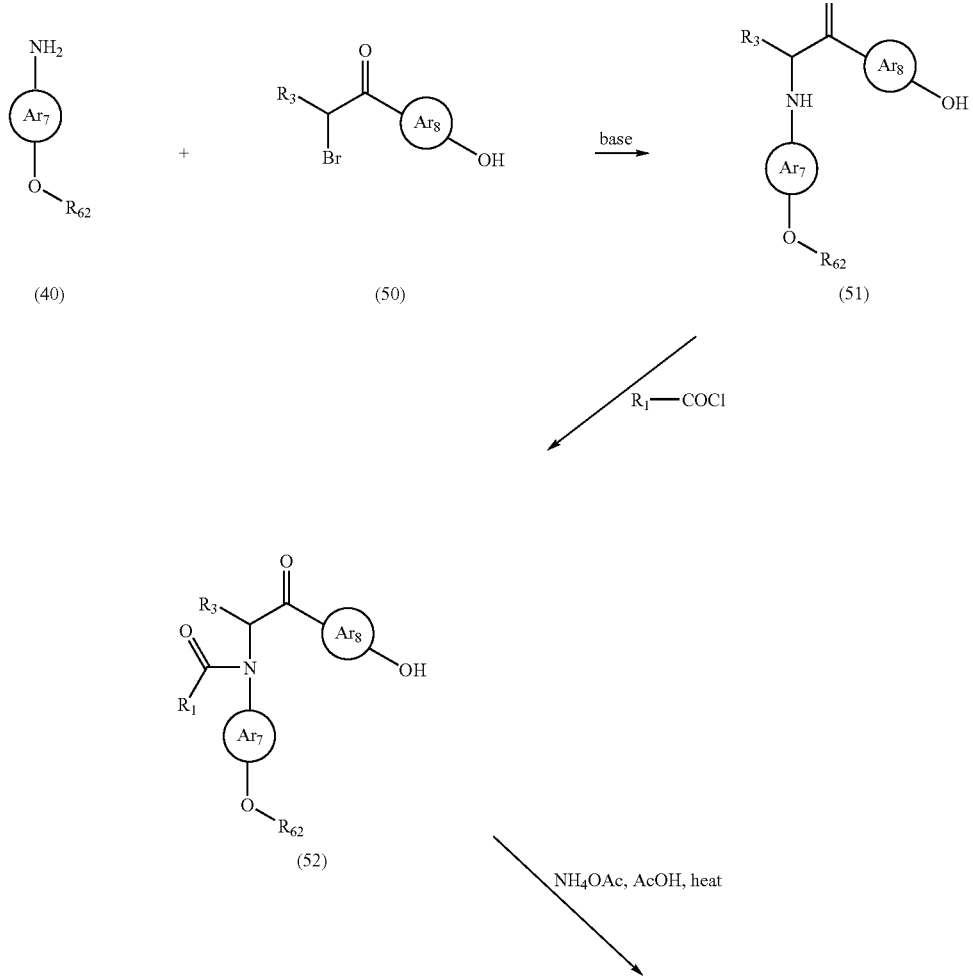

Scheme 9

-continued

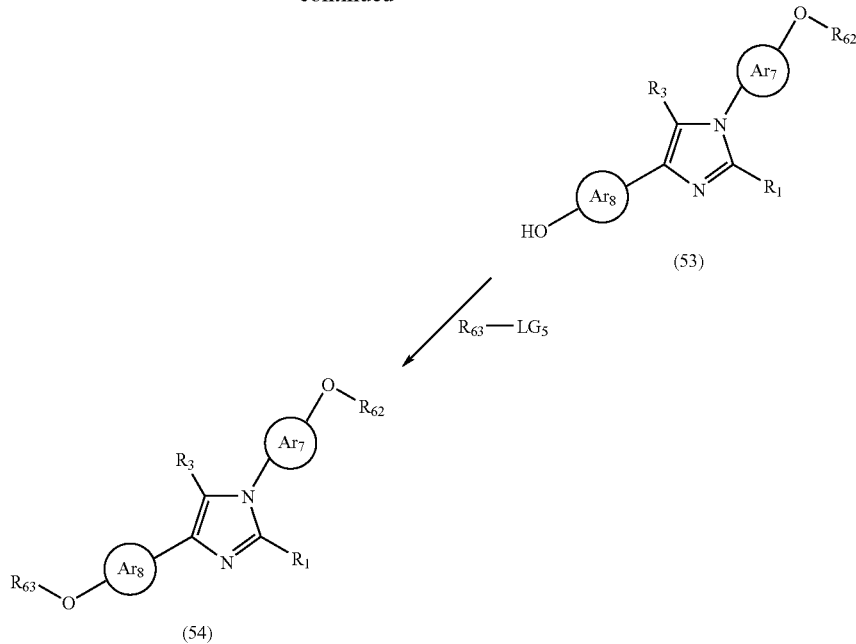

Scheme 10 describes another general synthesis of imidazoles. An aniline containing a hydrophobic side chain (40) may be coupled with a bromoketone (55) to give the aminoketone (56), which may then be treated with an acid chloride $R_1$—COCl to afford (57), which may subsequently be treated with ammonium acetate, acetic acid and heat to afford (58). The phenol is then deprotected; $PG_1$ may be a group sych as but not limited to benzyl, which may be removed with treatment with hydrogen over palladium on carbon. The free phenolic group is subsequently alkylated with an alkylating agent $R_{63}$-$LG_5$ to generate the desired imidazole (59). $R_{63}$ is a group such as but not limited to substituted alkyl, and $LG_5$ is a leaving group such as iodide or methanesulfonate.

Scheme 10

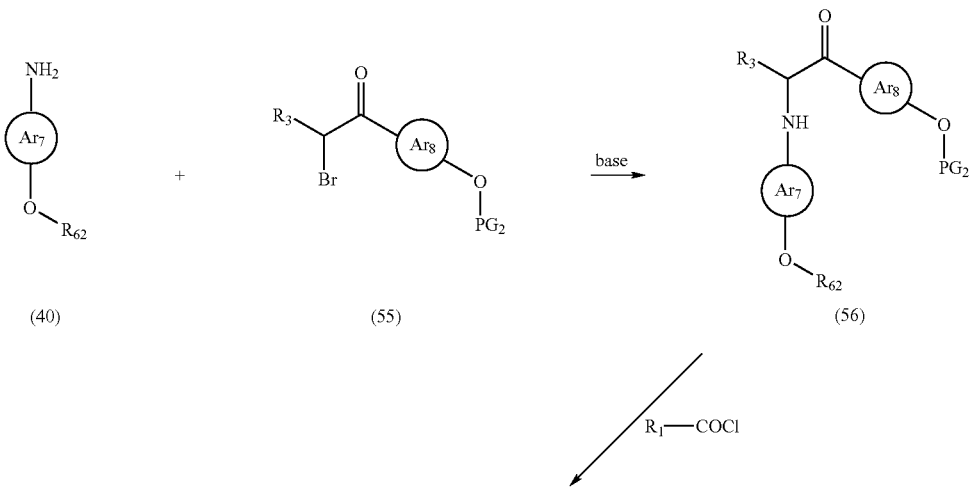

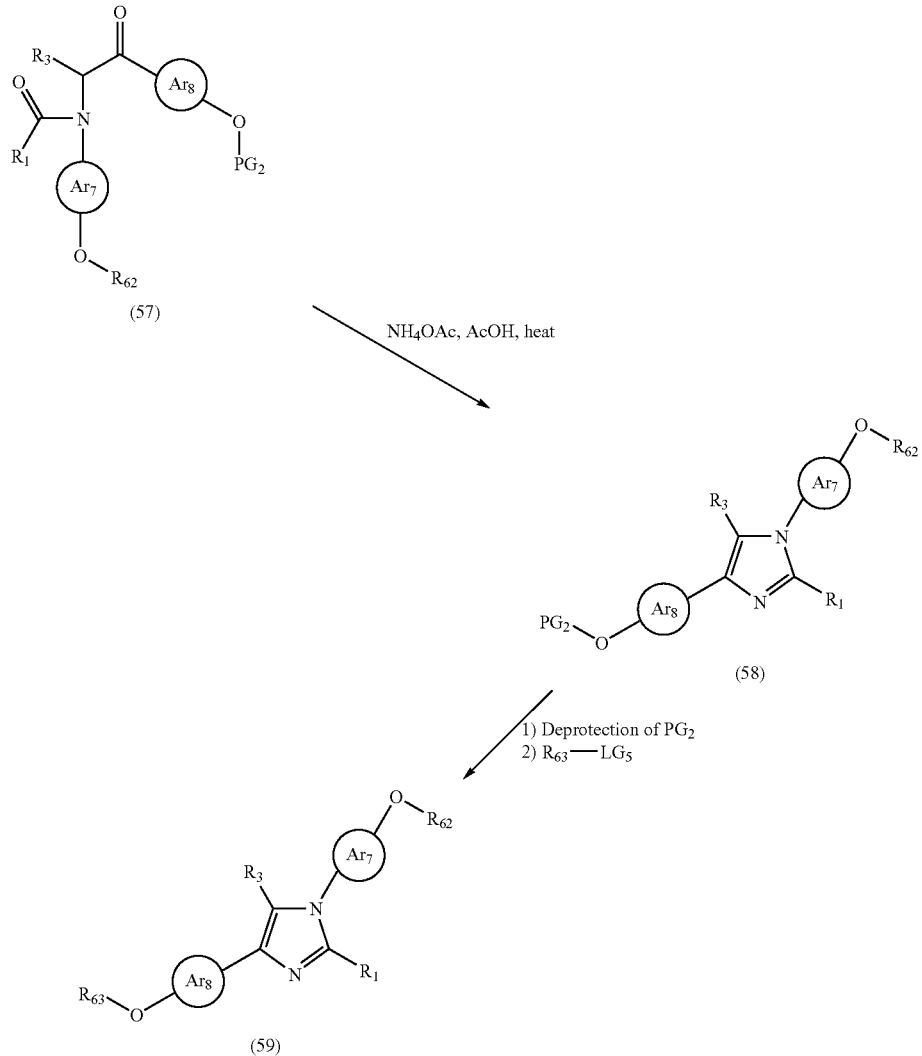

Scheme 11 describes the symnthesis of diones or bromoketones. A aryl ketone (60) may be treated with base and an alkylating agent $R_{64}$-$LG_6$ to generate the phenyl ether. $R_{64}$ is a group such as but not limited to substituted alkyl, and $LG_6$ is a leaving group such as iodide or methanesulfonate. The product may be brominated with a reagent such as but not limited to pyrrolidinium hydrotribromide, to (61) and the bromide may be oxidized by treatment with DMSO to afford (62). (63) may be treated with $Ar_{10}$—OH and base, followed by bromination, to afford (64). Oxidation as before gives the dione (65). $Ar_9$ is a group such as but not limited to aryl or heteroaryl.

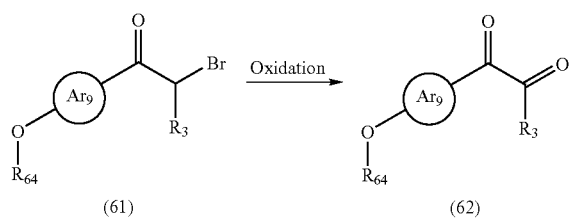

-continued

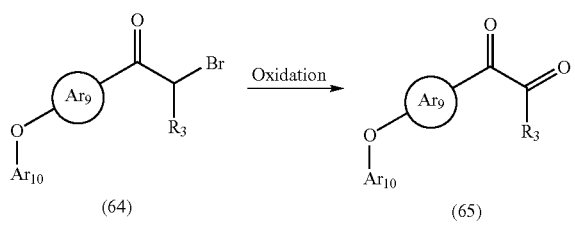

Scheme 12 describes the synthesis of imidazoles. (66) may be treated with (67) and an aldehyde $R_1$—CHO to afford (68). Alternately, (66) may be coupled with the bromoketone (70) to give the aminoketone (71), which may be treated with acetic acid, heat, an aldehyde $R_1$—CHO, and ammonium acetate to afford (68). $Ar_{11}$ and $Ar_{12}$ are groups such as but not limited to aryl or heteroaryl.

Scheme 13 describes the synthesis of imidazoles. A dione (72) may be treated with $R_1$—CHO and ammonium acetate-acetic acid to afford (74). Alternately, an amine $R_2$—$NH_2$ may be used in place of ammonium acetate to give (75).

Scheme 13

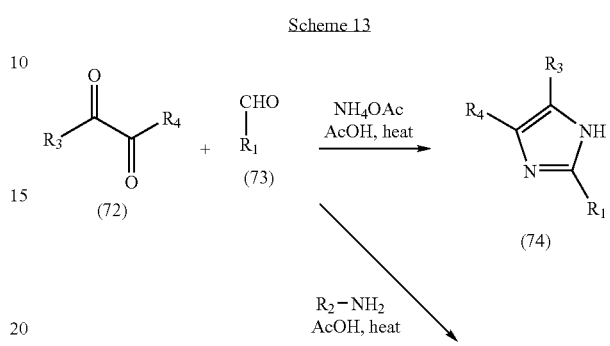

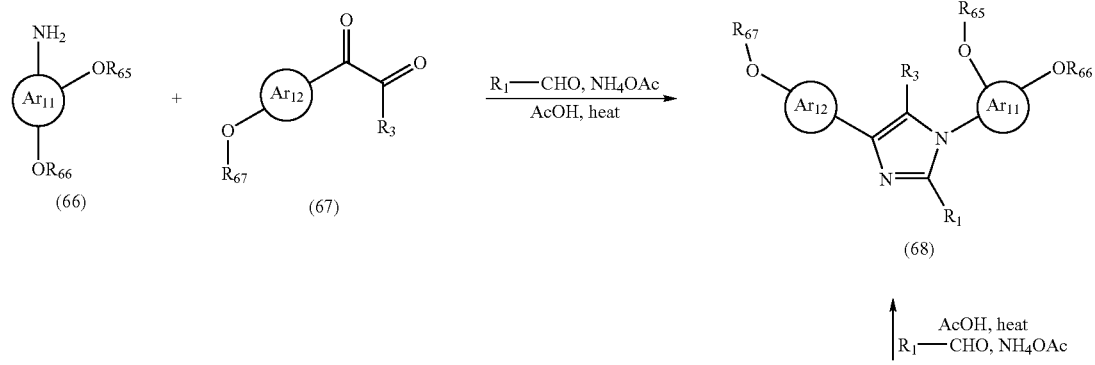

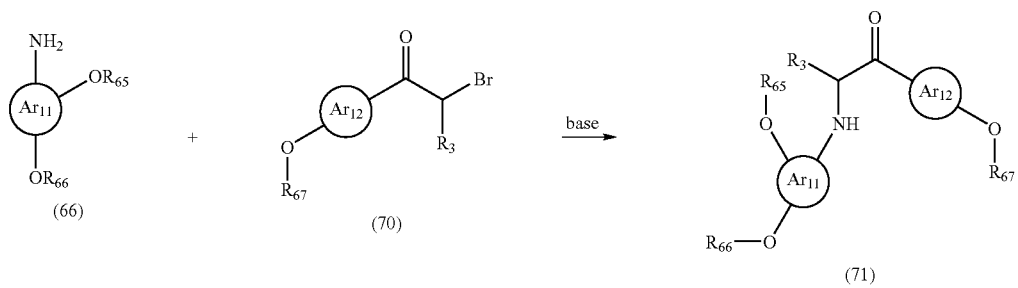

-continued

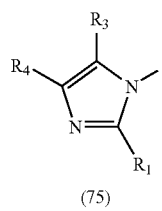

(75)

Scheme 14 describes another synthesis of imidazoles. (76) may be coupled with the bromoketone (77) to give the aminoketone (78), which may be treated with acetic acid, heat, an aldehyde $R_1$—CHO, and ammonium acetate to afford (80). Alternately, (78) may be treated with an acid chloride $R_1$—COCl to afford (79), which may subsequently be treated with ammonium acetate, acetic acid and heat to afford (80). The group $R_{68}$ may be an amino protecting group, such as BOC, which may be removed by treament of (80) with TFA. The amine may be directly alkylated or reductively alkylated by methods known in the art. For example, treatment of the NH compound with acetaldehyde and sodium cyanoborohydride in a solvent such as acetic acid affords (80) where $R_{68}$ is ethyl. $Ar_{12}$ is a group such as but not limited to aryl or heteroaryl.

Scheme 14

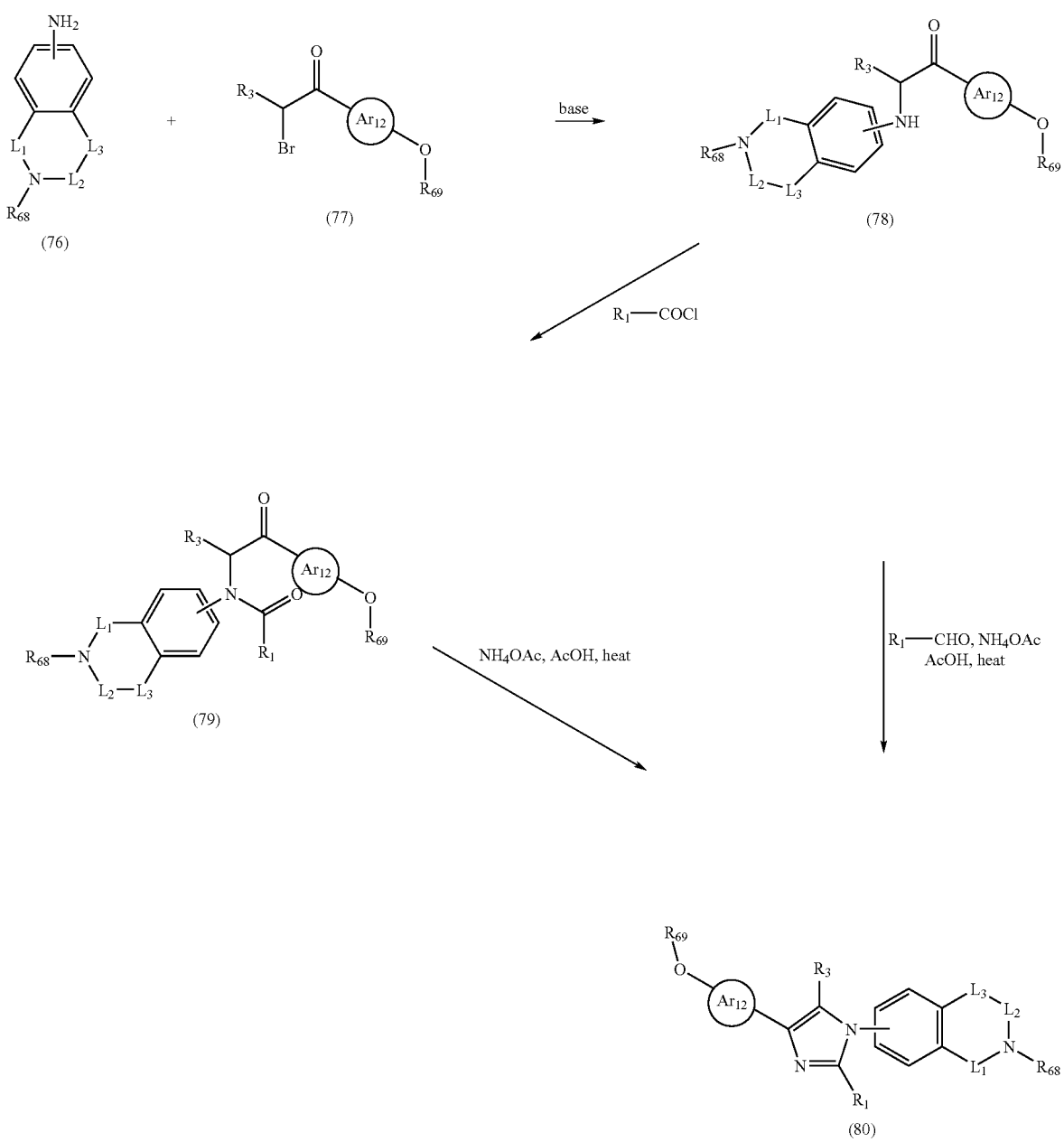

Scheme 15 describes the synthesis of imidazoles. A dione (81) may be treated with $R_1$—CHO and an amine (76) in acetic acid, in the presence of ammonium acetate, at a temperature of from 50 to 140° C., to afford (83). If the group $R_{68}$ is an amine protecting group, then said protecting group may be removed and the nitrogen alkylated as described in Scheme 14.

Scheme 15

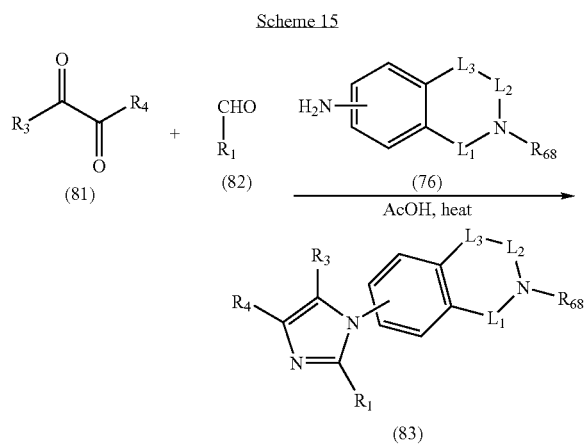

The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected amino" or "protected amino group" defines an amino group substituted with an amino-protecting group discussed above.

The term "hydroxylprotecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected hydroxyl" or "protected alcohol" defines a hydroxyl group substituted with a hydroxyl-protecting group as discussed above.

The term "carboxylprotecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxylprotecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The general procedures used in the methods of the present invention are described below.

Methods

LC-MS data is obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient is run from 25% B (97.5% acetonitrile, 2.5% water, 0.05% TFA) and 75% A (97.5% water, 2.5% acetonitrile, 0.05% TFA) to 100% B. The mass spectrometer used is a Micromass ZMD instrument. All data is obtained in the positive mode unless otherwise noted. $^1$H NMR and $^{13}$C NMR data is obtained on a Varian 400 MHz spectrometer.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
Et=ethyl
iPr=isopropyl
Bn=benzyl
Me=methyl
tBu=tert-butyl
Pr=propyl
Bu=butyl
iBu=isobutyl
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N, N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PS-carbodiimide=N-cyclohexylcarbodiimide-N'-propyloxymethyl polystyrene
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time General Synthesis of Monoalkoxybenzaldehydes:

General Procedure A

To a stirred solution of a 2-, 3-, or 4-hydroxybenzaldehyde (2 mmol) in DMF (6 mL) at rt solid $K_2CO_3$ (4 mmol) is added. An alkyl halide or mesylate (prepared from the corresponding alcohol and methanesulfonyl chloride) (2.2 mmol) is added to the reaction mixture and heated to 80° C. until the reaction is complete as indicated by TLC or HPLC. After cooling to rt, the reaction mixture is poured into EtOAc (20 ml) and washed with water (2×10 ml) and brine (15 ml). The organic layer is dried over magnesium sulfate and after removal of the drying agent, the solvent is removed under high vacuum to afford the desired product. The crude product may be used for further transformation without any purification or after purifying using silica gel column chromatography.

General Synthesis of Monoaryloxybenzaldehydes:

General Procedure B

To a stirred solution of a 2-, 3-, or 4-fluorobenzaldehyde (2 mmol) in DMF (6 mL) at rt requisite phenol (2.2) is added followed by solid $K_2CO_3$ (3 mmol). The reaction mixture is heated to 100° C. until the reaction is complete as indicated by TLC or HPLC. After cooling to rt, the reaction mixture is poured into EtOAc (20 ml) and washed with water (2×10 ml) and brine (15 ml). The organic layer is dried over magnesium sulfate and after removal of the drying agent, the solvent is removed under high vacuum to afford the desired product. The crude product may be used for further transformation without any purification or after purifying using silica gel column chromatography.

General Synthesis of Homosubstituted 2,4-Dialkoxybenzaldehydes:

General Procedure C

To a stirred solution of 2,4-dihydroxybenzaldehyde (2 mmol) in DMF (8 mL) at rt solid $Cs_2CO_3$ (6 mmol) is added. An alkyl halide or mesylate (prepared from the corresponding alcohol and methanesulfonyl chloride, see General Procedure P2) (4.4 mmol) is added to the reaction mixture and heated to 80° C. until the reaction is complete as indicated by TLC or HPLC. After cooling to rt, the reaction mixture is poured into EtOAc (20 ml) and washed with water (2×10 ml) and brine (15 ml). The organic layer is dried over magnesium sulfate and after removal of the drying agent, the solvent is removed under high vacuum to afford the desired product. The crude product may be used for further transformation without any purification or after purifying using silica gel column chromatography.

General Synthesis of Heterosubstituted 2,4-Dialkoxybenzaldehydes:

General Procedure D1

To a stirred solution of 2,4-dihydroxybenzaldehyde (2.2 mmol) in DMF (5 mL) at rt solid $KHCO_3$ (2.2 mmol) is added. An alkyl halide or mesylate (prepared from the corresponding alcohol and methanesulfonyl chloride, see General Procedure P2) (2.0 mmol) is added to the reaction mixture and heated at 130° C. for 4 h. After cooling to rt, the reaction mixture is treated with cold $H_2O$ (15 mL), and extracted with EtOAc (2×10 mL). The combined organic layers is washed with brine, and dried over sodium sulfate. The crude product is purified by flash chromatography to provide the 2-hydroxy-4-alkoxybenzaldehyde intermediate.

General Procedure D2

To a stirred solution of aforementioned 2-hydroxy-4-alkoxybenzaldehyde intermediate (2 mmol) in DMSO (5 mL) at rt solid $Cs_2CO_3$ (3 mmol) is added. An alkyl halide or mesylate (prepared from the corresponding alcohol and methanesulfonyl chloride, see General Procedure P2) (3 mmol) is added to the reaction mixture and heated to 90° C. until the reaction is complete as indicated by TLC or HPLC. After cooling to rt, the reaction mixture is treated with cold $H_2O$ (15 mL), and extracted with EtOAc (2×10 mL). The combined organic layers is washed with $H_2O$ (10 mL) and brine (10 mL) and dried over sodium sulfate. After removal of the drying agent, the solvent is removed under high vacuum to afford the desired product. The crude product may be used for further transformation without any purification or after purifying using silica gel column chromatography.

General Synthesis of 2-Alkoxy-4-Aryloxybenzaldehydes:

General Procedure E

A solution of 2,4-difluorobenzaldehyde (2 mmol) in DMF (2 mL) is added dropwise to a precooled (0° C.) solution of sodium alkoxide (2 mmol) in DMF (6 ml) [prepared by stirring a mixture of sodium hydride (2 mmol), and the corresponding alcohol (2 mmol) in DMF]. The resulting reaction mixture is warmed to rt and stirred for an additional 3 h. To the same reaction vessel, solid potassium carbonate (2 mmol) and requisite phenol (2 mmol)) is introduced and the reaction mixture is heated at 90° C. in an oil bath for 24. After cooling to rt, the reaction mixture is poured into EtOAc (20 ml) and washed with water (2×10 ml) and brine (15 ml). The organic layer is dried over magnesium sulfate and after removal of the drying agent, the solvent is removed under high vacuum to afford the desired product. The crude product may be used for further transformation without any purification or after purifying using silica gel column chromatography.

General Synthesis of Monoalkoxy Ortho-Phenylenediamines:

Method A

General Procedure F1

To a stirred solution of 3-fluoro-4-nitrophenol (4 mmol) in DMF (6 mL) at rt solid $K_2CO_3$ (8 mmol) is added. An alkyl halide or mesylate (prepared from the corresponding alcohol and methanesulfonyl chloride, see General Procedure P2) (4.4 mmol) is added to the reaction mixture and heated to 80° C. until the reaction is complete as indicated by TLC or HPLC. After cooling to rt, the reaction mixture is poured into EtOAc (40 ml) and washed with water (2×20 ml) and brine (30 ml). The organic layer is dried over magnesium sulfate and after removal of the drying agent, the solvent is removed under vacuum to afford the desired product. The crude product may be used for further transformation without any purification or after purifying using silica gel column chromatography.

General Procedure F2

To a stirred solution of 2-fluoro-4-alkoxynitrobenzene (2 mmol) obtained above, TEA (4 mmol) in DMF (5 mL) is added dropwise a solution of requisite alkylamine (2.2 mmol) in DMF (2 mL) at rt within 15 min, and then stirred at rt for 5 h. The reaction mixture is treated with cold $H_2O$ (10 mL), and extracted with EtOAc (2×15 mL), The combined organic layers is washed with $H_2O$ (10 mL) and brine (10 mL) and dried over sodium sulfate. After removal of the drying agent, the solvent is removed under high vacuum to afford the desired 2-alkylamino-4-alkoxynitrobenzene intermediate. The crude product may be used for further transformation without any purification or after purifying using silica gel column chromatography.

Method B

General Procedure G1

To a stirred solution of 2,4-difluoronitrobenzene (2 mmol), TEA (4 mmol) in DMF (5 mL) is added dropwise a solution of requisite alkylamine (2.2 mmol) in DMF (2 mL) at rt within 15 min, and then stirred at rt for 5 h. The reaction mixture is treated with cold $H_2O$ (10 mL), and extracted with EtOAc (2×15 mL), The combined organic layers is washed with $H_2O$ (10 mL) and brine (10 mL) and dried over sodium sulfate. After removal of the drying agent, the solvent is removed under high vacuum to afford the desired 2-alkylamino-4-fluoronitrobenzene. The crude product may be used for further transformation without any purification or after purifying using silica gel column chromatography.

General Procedure G2

To a stirred solution of 2-alkylamino-4-fluoronitrobenzene as obtained above (2.0 mmol) in anhydrous THF (4 mL), an alcohol (2.4 mmol) is added followed by powdered $KOBu^t$ (2.4 mmol) in one portion at rt and under the $N_2$ stream. The reaction mixture is then refluxed until the reaction is complete as indicated by TLC or HPLC. After cooling to rt, the reaction mixture is treated with cold $H_2O$ (15 mL), and extracted with EtOAc (2×10 mL). The combined organic layers is washed with brine, and dried over sodium sulfate. Evaporation of the solvent in vacuo afforded 2-alkylamino-4-alkoxynitrobenzene intermediate. The crude product may be used for further transformation without any purification or after purifying using silica gel column chromatography.

Reduction of Monoalkoxy Nitrobenzenes:

General Procedure H

The nitro intermediate (2 mmol) obtained above as in Method A or B is dissolved in MeOH (10 mL) and hydrogenated in the presence of 10% Pd/C (10 mg) until the reaction is complete as indicated by TLC or HPLC. The reaction mixture is then filtered through a celite pad to remove the catalyst. The solvent is removed under high vacuum to afford the desired diamine, which is used directly for further transformation without further purification.

General Procedure I

To a stirred solution of afforded 2-alkylamino-4-alkoxynitrobenzene intermediate [as obtained in (b)] (2 mmol) in EtOH (20 mL), $SnCl_2.2H_2O$ (8 mmol) is added and the mixture is refluxed until the reaction is complete as indicated by TLC or HPLC. After completion of the reduction, the solvent is removed in vacuo, and the residue is treated with saturated $NaHCO_3$ to pH~8. The resulting yellow suspension is extracted with DCM (2×20 mL), washed with brine, and dried. The solvent is removed under high vacuum to afford the desired diamine, which is used directly for further transformation without further purification.

General Synthesis of Homo Disubstituted Dialkoxy Ortho-Phenylenediamines:

General Procedure J1

To a stirred solution of 2,4,6-trifluoronitrobenzene (3.0 mmol) and triethylamine (6.0 mmol) in DMF (6 mL), a solution of alkyl amine (3.0 mmol) in DMF (2 mL) is added dropwise at rt within 15 min, and then stirred at rt for 5 h. The reaction mixture is treated with cold $H_2O$ (10 mL), and extracted with EtOAc (2×15 mL), The combined organic layers is washed with $H_2O$ (10 mL) and brine (10 mL) and dried over sodium sulfate. After removal of the drying agent, the solvent is removed under high vacuum to afford the desired 2-alkylamino-4,6-difluoronitrobenzene. The crude product may be used for further transformation without any purification or after purifying using silica gel column chromatography.

General Procedure J2

To a stirred solution of 2-alkylamino-4,6-difluoronitrobenzene as obtained above (2.0 mmol) in anhydrous THF (4 mL), an alcohol (4.4 mmol) is added followed by powdered $KOBu^t$ (4.4 mmol) in one portion at rt and under the $N_2$ stream. The reaction mixture is then refluxed until the reaction is complete as indicated by TLC or HPLC. After cooling to rt, the reaction mixture is treated with cold $H_2O$ (15 mL), and extracted with EtOAc (2×15 mL). The combined organic layers is washed with brine, and dried over sodium sulfate. Evaporation of the solvent in vacuo afforded 2-alkylamino-4,6-dialkoxynitrobenzene intermediate. The crude product may be used for further transformation without any purification or after purifying using silica gel column chromatography.

The nitro intermediate (2 mmol) obtained may be reduces to the amino compound employing general procedures H or I.

General Synthesis of Hetero Disubstituted Dialkoxy Ortho-Phenylenediamines:

General Procedure J3

To a stirred solution of 3,5-difluorophenol (3 g; 17 mmol) in dichloromethane (30 mL) at 0° C., conc. $HNO_3$ (2-5 mL) is added dropwise over 10 min. The reaction mixture is then stirred at 0° C. for 60 min at which the nitration is complete as indicated by TLC. After the reaction is complete cold $H_2O$ (30 mL) is added to the reaction flask and stirred. The contents are then poured into a separatory funnel and the layers removed. The aqueous layer is then extracted with EtOAc (2×30 mL) and the combined organic layers are dried over magnesium sulfate. After removal of the drying agent, the solvent is removed under vacuum to the crude product mixture is purified using silica gel column chromatography to provide the nitrodifluorophenol.

General Procedure J4

To a stirred solution of 3,5-difluoro-4-nitrophenol (4 mmol) in DMF (6 mL) at rt solid $K_2CO_3$ (8 mmol) is added. An alkyl halide or mesylate (prepared from the corresponding alcohol and methanesulfonyl chloride, see General Procedure P2) (4.4 mmol) is added to the reaction mixture and heated to 80° C. until the reaction is complete as indicated by TLC or HPLC. After cooling to rt, the reaction mixture is poured into EtOAc (40 ml) and washed with water (2×20 ml) and brine (30 ml). The organic layer is dried over magnesium sulfate and after removal of the drying agent, the solvent is removed under vacuum to afford the desired product. The crude product may be used for further transformation without any purification or after purifying using silica gel column chromatography.

General Procedure J5

To a stirred solution of 2,6-difluoro-4-alkoxynitrobenzene obtained above (3.0 mmol) and triethylamine (6.0 mmol) in DMF (6 mL), a solution of alkyl amine (3.0 mmol) in DMF (2 mL) is added dropwise at rt within 15 min, and then stirred at rt for 5 h. The reaction mixture is treated with cold $H_2O$ (10 mL), and extracted with EtOAc (2×15 mL), The combined organic layers is washed with $H_2O$ (10 mL) and brine (10 mL) and dried over sodium sulfate. After removal of the drying agent, the solvent is removed under high vacuum to afford the desired 2-alkylamino-4-alkoxy-6-fluoronitrobenzene. The crude product may be used for further transformation without any purification or after purifying using silica gel column chromatography.

General Procedure J6

To a stirred solution of 2-alkylamino-4-alkoxy-6-fluoronitrobenzene as obtained above (2.0 mmol) in anhydrous THF (5 mL) at 0° C., a 1M solution of an alkoxide (2.2 mmol) in THF (may be generated by adding the corresponding alcohol to a 1M solution of $KOBu^t$ in THF) is added dropwise and under the $N_2$ stream. The reaction mixture is maintained at 0° C. until the reaction is complete as indicated by TLC or HPLC. The reaction mixture is then treated with cold $H_2O$ (15 mL), and extracted with EtOAc (2×15 mL). The combined organic layers is washed with brine, and dried over sodium sulfate. Evaporation of the solvent in vacuo afforded the desired hetero dialkoxy substituted nitro intermediate. The crude product may be used for further transformation without any purification or after purifying using silica gel column chromatography.

General Procedure J7

The nitro intermediate (2 mmol) obtained above is dissolved in MeOH (10 mL) and hydrogenated in the presence of 10% Pd/C (10 mg) until the reaction is complete as indicated by TLC or HPLC. The reaction mixture is then filtered through a celite pad to remove the catalyst. The solvent is removed under high vacuum to afford the desired hetero disubstituted dialkoxy ortho-phenylenediamine.

General Procedure for Synthesis of Benzimidazoles:

General Procedure K

A solution of an ortho phenylenediamine (2 mmol) and an appropriate aryl aldehyde in ethanol is refluxed until the reaction is complete as indicated by TLC or HPLC. The solvent is removed in vacuo and the residue obtained is purified by silica gel column chromatography to afford the desired 2-arylbenzimidazole.

General Procedure for Synthesis of Monoalkoxyanilines:

Method A

General Procedure L1

To a stirred solution of 4-fluoronitrobenzene (2.0 mmol) in anhydrous THF (5 mL) at 0° C., a 1M solution of a potassium alkoxide (2.2 mmol) in THF (may be generated by adding the corresponding alcohol to a 1M solution of $KOBu^t$ in THF) is added dropwise and under the $N_2$ stream. The reaction mixture is stirred at 0° C. until completion, as indicated by TLC or HPLC. The reaction mixture is then treated with cold $H_2O$ (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product could be used directly for further transformation without any purification, or after purifying using silica gel column chromatography.

Method B

General Procedure M1

To a stirred solution of 4-nitrophenol (2 mmol) in DMF (6 mL) at rt, solid potassium carbonate (4 mmol) is added. An alkyl halide or mesylate (prepared from the corresponding alcohol and methanesulfonyl chloride, see General Procedure P2) (2.2 mmol) is then added to the reaction mixture and heated to 80° C. until completion, as indicated by TLC or HPLC. After cooling to rt, the reaction mixture is then treated with cold $H_2O$ (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product could be used directly for further transformation without any purification, or after purifying using silica gel column chromatography.

General Procedure for Synthesis of Homo Disubstituted Alkoxy-Anilines:

Method C

General Procedure N1

To a stirred solution of 2,4-difluoronitrobenzene (2.0 mmol) in anhydrous THF (4 mL) at 0° C., an alcohol (4.4 mmol) is added followed by powdered potassium t-butoxide (4.4 mmol) in one portion under a $N_2$ stream. The reaction mixture is then warmed to rt and heated under reflux until completion, as indicated by TLC or HPLC. After cooling to rt, the reaction mixture is treated with cold $H_2O$ (15 mL), and extracted with EtOAc (2×15 mL). The combined organic layers were washed with brine and dried over sodium sulfate. Evaporation of the solvent in vacuuo afforded the 2,4-dialkoxynitrobenzene. The crude product could then be used for further transformation without any purification, or after purifying using silica gel column chromatography.

General Procedure for Synthesis of Alkoxy-Anilines:

General Procedure O2

To a stirred solution of 4-alkoxy-2-fluoronitrobenzene obtained above (2.0 mmol) in anhydrous THF (5 mL) at 0° C., a 1M solution of an alkoxide (2.2 mmol) in THF (may be generated by adding the corresponding alcohol to a 1M solution of potassium t-butoxide in THF) is added dropwise and under a $N_2$ stream. The reaction mixture is maintained at 0° C. until completion, as indicated by TLC or HPLC. The reaction mixture is then treated with cold $H_2O$ (15 mL), and extracted with EtOAc (2×15 mL). The combined organic layers were washed with brine, and dried over sodium sulfate. Evaporation of the solvent in vacuuo afforded the desired heterosubstituted dilkoxynitrobenzene. The crude product may be used for further transformation without any purification or after purifying using silica gel column chromatography.

Method E

General Procedure P1

To a stirred solution of a 2-nitro-5-fluorophenol (2.0 mmol) in anhydrous THF (4 mL) at 0° C., an alcohol (2.2 mmol) is added followed by powdered potassium t-butoxide (4.2 mmol) in one portion under a $N_2$ stream. The reaction mixture is then warmed up to rt and heated under reflux until completion, as indicated by TLC or HPLC. After cooling to rt, the crude reaction mixture is treated with an alkyl halide or mesylate (2.2 mmol, prepared from the corresponding alcohol and methanesulfonyl chloride) and heated under reflux until completion, as indicated by TLC or HPLC. The reaction mixture is then cooled to rt, treated with cold $H_2O$ (15 mL), and extracted with EtOAc (2×15 mL). The combined organic layers were washed with brine, and dried over sodium sulfate. Evaporation of the solvent in vacuuo afforded the heterosubstituted dilkoxynitrobenzene. The crude product may be used for further transformation without any purification or after purifying using silica gel column chromatography.

General Procedure P2

A primary or secondary alcohol (20 mmol, 1 eq) is dissolved in DCM (25 mL), TEA (40 mmol, 2 eq) is added and the mixture is cooled to 0° C. To this mixture, methanesulfonyl chloride (30 mmol, 1.5 eq) is added slowly with stirring and the reaction mixture is stirred at 0° C. for an hour and at rt for another hour (until the reaction is complete by HPLC). The solvent is removed and to this saturated aqueous sodium bicarbonate is added. The product is extracted with EtOAc (3×) and washed with sodium bicarbonate and water. The solvent is removed in vacuuo to afford the product methanesulfonate.

General Procedure for Synthesis of Alkyl Phenones;

Method F

General Procedure Q1

To a stirred solution of 4'-hydroxyacetophenone (1.2 mmol) in DMF (10 mL) at rt, solid potassium carbonate (3.0 mmol) is added. An alkyl halide or mesylate (prepared from the corresponding alcohol and methanesulfonyl chloride, see General Procedure P2) (1.0 mmol) is added to the reaction mixture and heated to 80° C. until completion, as indicated by TLC or HPLC. After cooling to rt, the reaction mixture is quenched by removing solvent in vacuuo and treating the residue with saturated sodium bicarbonate. The aqueous layer is poured into EtOAc (20 ml) and washed with $H_2O$ (2×10 ml) and brine (15 ml). The organic layer is dried over magnesium sulfate, and the solvent is removed in vacuuo to afford the desired product. The crude alkylated product may be used for further transformation without any purification or after purifying using silica gel column chromatography.

Method G

General Procedure Q2

To a stirred solution of an alcohol (75 mmol) in DMSO (80 mL) at rt, solid cesium carbonate (150 mmol) is added. 4'-fluoro-alkylphenone (50 mmol) is added to the reaction mixture and heated to 90° C. until completion, as indicated by TLC or HPLC. After cooling to rt, the reaction mixture is treated with saturated sodium bicarbonate (150 ml). The aqueous layer is extracted with diethyl ether (4×100 ml). The organic layer is washed with $H_2O$ (2×10 ml) and brine (15 ml). The organic layer is dried over magnesium sulfate, and the solvent is removed in vacuuo to afford the desired alkoxy acetophenone. The crude alkylated acetophenone may be used for further transformation without any purification or after purifying using silica gel column chromatography.

General Procedure for N-Aryl Imidazoles:

Method H

General Procedure R1

To a stirred solution of alkoxyacetophenone (2 mmol) in anhydrous MeOH (5 mL) at 0° C., pyrrolidone hydrotribromide (1.2 eq.) is added. The reaction mixture is stirred under nitrogen at 0° C. for 1 h and is allowed to warm to ambient temperature until completion, as indicated by TLC or HPLC.

The solvent is then removed in vacuuo and the crude alpha-bromoacetophenone is used for further transformation.

General Procedure R2

To a stirred solution of an alkoxy aniline (1.2 eq., 2 mmol) in anhydrous DMF (5 mL) diisopropylethylamine (3 eq. 6 mmol) is added, followed by a slow addition of the alpha-bromoacetophenone described above (1.6 mmol). The reaction mixture is stirred under nitrogen at rt until completion, as indicated by TLC or HPLC. The reaction mixture is then diluted with cold $H_2O$ and the product is isolated in EtOAc. The combined organic layers were washed with brine and dried over sodium sulfate. Evaporation of solvent in vacuuo afforded the desired product. The crude alkylated aniline is purified by chromatography (Silica gel). Pure product obtained from 2-4% MeOH/DCM (yield ~50-60%).

General Procedure R3

To a stirred solution of alkylated aniline described above (2 mmol) in anhydrous DCM (5 mL) at 0° C., TEA (3 eq., 6 mmol) is added, followed by a slow addition of an acid chloride or anhydride (3 eq., 6 mmol). The reaction mixture is stirred under nitrogen at 0° C. for 1 h and allowed to warm to ambient temperature until completion, as indicated by TLC or HPLC. The solvent is removed in vacuuo, and the crude amide is used for further transformation.

General Procedure R4

To a stirred solution of the amide described above (2 mmol) in AcOH (2 mL), ammonium acetate (excess, ~20 eq.) is added. The reaction mixture is stirred at 90° C. overnight. The reaction mixture is then cooled down and neutralized with saturated sodium bicarbonate solution. Usual extractive work up with EtOAc gave the product imidazole, which is purified by column chromatography (Silica gel). Pure product is obtained from 4-6% MeOH/DCM (yield 40-50%).

General Procedure S1

To a stirred solution of an alkoxy aniline (2 mmol) in DCM (4 mL) at rt, TEA (2.5 mmol) is added followed by an acid chloride or anhydride (2.5 mmol). The reaction mixture is stirred under nitrogen at rt until completion, as indicated by TLC or HPLC. The reaction mixture is treated with saturated aqueous sodium bicarbonate solution (5 mL), then extracted with EtOAc (2×15 mL). The combined organic layers were washed with $H_2O$ (2×15 mL) and brine, and dried over sodium sulfate. Evaporation of the solvent in vacuuo afforded the anilide. The crude product is used for further transformation.

General Procedure S2

To a stirred solution of the anilide (2 mmol) obtained as above in anhydrous THF (4 mL) solid sodium hydride (60% dispersion in oil; 2.2 mmol) is added in portions. After the addition, a solution of a bromo-acetophenone (2.2 mmol) (prepared as described earlier) in anhydrous THF (2 mL) is added to the reaction mixture. The reaction is then allowed to proceed at rt or heated under reflux as needed. Upon completion of the reaction, EtOAc (20 mL) is added to the reaction mixture followed by $H_2O$ (10 mL). The organic layer is washed with $H_2O$ (2×15 mL) and brine, and dried over sodium sulfate. Evaporation of the solvent in vacuuo afforded the N-alkylated anilide. The crude product may be used for further transformation.

General Procedure S3

To a stirred solution of the N-alkylated anilide (1 mmol) obtained as above in AcOH (3 mL), solid $NH_4OAc$ (20 mmol) is added in one portion. The reaction mixture is then heated to 100° C. overnight. The reaction mixture is cooled to rt, and treated with saturated aqueous sodium bicarbonate solution while stirring to until the pH is 7-8. The contents were extracted with EtOAc (2×15 mL). The combined organic layers is washed with $H_2O$ (2×15 mL) and brine, and dried over sodium sulfate. Evaporation of the solvent in vacuuo afforded the desired N-aryl imidazole. The crude product is purified using silica gel column chromatography.

General Procedure T1

4N hydrogen chloride in dioxane solution (4 mmol) is added to a mixture of BOC-amino compound (1 mmol) in anhydrous DCM (5 mL), and the mixture is stirred at rt until complete. Evaporation of the solvents in vacuo afforded deprotected amine hydrochloride.

General Procedure T2

A benzyl alkyl ether, benzyl ester, or a benzyl phenyl ether is dissolved in MeOH and hydrogenated in the presence of 10% Pd/C catalyst until the reaction is complete. reaction mixture is then filtered through a celite pad to remove the catalyst. Evaporation of the solvent in vacuo afforded the alcohol, carboxylic acid, or phenol, respectively.

General Procedure T3

A phenol (0.2 mmol) in anhydrous DMF (5 mL) is alkylated by a bromide or a mesylate (0.3 mmol) at rt (for a bromide, 60% NaH as base) or at 90° C. (for a mesylate, $K_2CO_3$ as base). The reaction is quenched by adding sat. $NaHCO_3$. The resulting mixture is extracted with EtOAc washed with brine and dried. The crude product is purified by silica gel column chromatography if desired.

EXAMPLE 1

1-Butyl-2-(3-cyclohexylmethoxy-phenyl)-6-(2-piperazin-1-yl-ethoxy)-1H-benzimidazole Hydroxy benzimidazole was formed employing 1-BOC-4-[2-(4-amino-3-butylamino-phenoxy)-ethyl]-piperazine (synthesized via General Procedures G1 and G2 and H) (2.92 g; 10 mmol) and 3-hydroxybenzaldehyde (1.34 g, 11 mmol) in ethanol (20 mL) following the general procedure K. The crude product was purified by silica gel column chromatography using 2% MeOH in DCM (3.2 g).

MS m/z 396 $(M+H)^+$

A solution of above mentioned hydroxybenzimidazole compound (39.4 mg, 0.1 mmol) in THF (2 ml) was added cyclohexylmethyl bromide (19.5 mg, 0.11 mmol) and NaH (0.8 mg, 60%, 0.12 mmol) at 0° C. The resulting reaction mixture was warmed to rt and stirred for additional 12 h. The mixture was quenched with brine and extracted into EtOAc (2×10 mL). Combined organic EtOAc extracts were dried over sodium sulfate and concentrated to give compound which was purified by silica gel column chromatography using dichloromethane and 2% methanol in dichloromethane as eluent, to give N—BOC compound, which was subjected to General Procedure T1 affording 1-butyl-2-(3-cyclohexyl-methoxy-phenyl)-6-(2-piperazin-1-yl-ethoxy)-1H-benzimidazole as a hydrochloride salt, 36.8 mg.

MS m/z 491 $(M+H)^+$

EXAMPLE 2

(3-(3-butyl-2-(3-,5-di-tert-butyl-2-methoxy-phenyl)-3H-benzimidazol-5-yloxy-propyl)-diiethyl-amine This compound was prepared according to the general procedure K by refluxing a mixture of 3,5-di-t-butyl-5-methoxybenzaldehyde (100 mg) and $N^2$-Butyl-4-(3-diethylamino-propoxy)-benzene-1,2-diamine (synthesized via General Procedures G1 and G2 and H) (50 mg) in ethanol overnight. Ethanol was removed in vacuo and the residue was purified by silica gel chromatography using 5% MeOH in DCM to give (3-(3-butyl-2-(3-,5-di-tert-butyl-2-methoxy-phenyl)-3H-benzimidazol-5-yloxy-propyl)-diiethyl-amine (45.0 mg).

MS: m/z 522 (M+H)$^+$

EXAMPLE 3

(2-(3-butyl-2-(3-(4-tert-butyl-phenoxy)-phenyl)-3H-benzimidazol-5-yloxy-ethyl)-diisopropyl-amine A solution of 2-(n-butylamino)-4-(2-diisopropylaminoethoxy)aniline (synthesized via General Procedures G1 and G2 and H) (61.4 mg, 0.2 mmol) and (3-(4-tert-butyl-phenoxy)-benzaldehyde (synthesized via General Procedure B) (56 mg, 0.22 mmol) in ethanol (2 mL) was condensed following General Procedure K. The crude product was purified by silica gel column chromatography using 10% MeOH in DCM with a gradual increment of triethylamine (0.2 to 1.0%) as eluent to afford (2-(3-butyl-2-(3-(4-tert-butyl-phenoxy)-phenyl)-3H-benzimidazol-5-yloxy-ethyl)-diisopropyl-amine (54 mg).

MS m/z 542 (M+H)+

EXAMPLE 4

(3-{4-[1-butyl-6-(4-tert-butyl-phenoxy)-1H-benzimidazol-2-yl]-phenoxy}-propyl)-diethyl-amine To a stirred solution of 4-hydroxybenzaldehyde (20 mmol) in DMSO (80 mL) at rt, solid $Cs_2CO_3$ (50 mmol) was added. A mesylate (prepared from 3-diethylamino-1-propanol and methanesulfonyl chloride, General Procedure P2) (30 mmol) was added to the reaction mixture and heated to 90° C. until the reaction was complete as indicated by LC-MS (10 h). After cooling to rt, the reaction was quenched by cold $H_2O$ (100 mL), and the resulting mixture was extracted with EtOAc (3×100 mL). The combined EtOAc extracts were washed with brine (3×50 mL) and dried (anhydrous $Na_2SO_4$). The solvent was removed in vacuo, and the crude product was purified by silica gel column chromatography, eluting with 10% MeOH in DCM+0.5% $Et_3N$, giving the desired 4-(3-diethylaminopropoxy)benzaldehyde.

A solution of 2-t-butylamino-4-(4-n-butylphenoxy)aniline (synthesized via General Procedures G1 and G2 and H) (130 mg, 0.4 mmol) and 4-(3-diethylaminopropoxy)benzaldehyde obtained above (70 mg, 0.3 mmol) in MeOH (10 mL) was subjected to General Procedure K. The solvent was removed in vacuo and the residue was purified by silica gel column chromatography, eluting with 10% MeOH in DCM with a gradual increment of $Et_3N$ (0.5 to 1%), affording the desired benzimidazole (120 mg).

MS m/z 528 (M+H)$^+$ $^1$H NMR (400 MHz, CDCl$_3$): δ 0.84 (t, 3H), 1.05 (t, 6H), 1.24 (m, 2H), 1.31 (s, 9H), 1.75 (m, 2H), 1.98 (m, 2H), 2.58 (q, 4H), 2.66 (t, 2H), 4.09 (t, 2H), 4.13 (t, 2H), 6.93 (d, 2H,), 7.00 (dd, 1H), 7.02 (d, 2H), 7.07 (d, 1H), 7.33 (d, 2H,), 7.62 (d, 2H), 7.72 (d, 1H) ppm.

EXAMPLE 5

1-butyl-6-(4-tert-butyl-phenoxy)-2-[3-(2-pyrrolidin-1-yl-ethoxy)-phenyl]-1H-benzimidazole To a stirred solution of 3-hydroxybenzaldehyde (20 mmol) in DMSO (50 mL) at rt, solid $Cs_2CO_3$ (60 mmol) was added. 1-(2-chloroethyl)pyrrolidine hydrochloride (30 mmol) was added to the reaction mixture and heated to 90° C. for 9 h. After cooling to rt, the reaction was quenched by cold $H_2O$ (50 mL), and the resulting mixture was extracted with EtOAc (3×100 mL). The combined EtOAc extracts were washed with brine (3×50 mL) and dried (anhydrous $Na_2SO_4$). The solvent was removed in vacuo to afford crude 3-(2-pyrrolidin-1-yl-ethoxy)benzaldehyde.

A solution of 2-t-butylamino-4-(4-n-butylphenoxy)aniline (synthesized via General Procedures G1 and G2 and H) (130 mg, 0.4 mmol) and 3-(2-pyrrolidin-1-yl-ethoxy)benzaldehyde obtained above (70 mg, ~0.3 mmol) in MeOH (10 mL) was subjected to General Procedure K. The solvent was removed in vacuo and the residue was purified by silica gel column chromatography, eluting with 10% MeOH in DCM with a gradual increment of $Et_3N$ (0.5 to 1%), to afford the desired benzimidazole (100 mg).

MS m/z 512 (M+H)$^+$ $^1$H NMR (400 MHz, CDCl$_3$): δ0.83 (t, 3H), 1.22 (m, 2H), 1.29 (s, 9H), 1.74 (m, 2H), 1.87 (m, 4H), 2.78 (m, 4H), 3.03 (m, 2H), 4.16 (t, 2H), 4.25 (m, 2H), 6.94 (d, 2H), 7.01 (br d, 1H), 7.07 (m, 2H), 7.26 (m, 2H), 7.33 (d, 2H), 7.41 (t, 1H), 7.74 (d, 1H) ppm.

The following Examples were synthesized according to the Methods employed for Examples 1-5;

| Example | Name |
|---|---|
| 6 | 1-butyl-6-(4-tert-butyl-phenoxy)-2-[2-(2-pyrrolidin-1-yl-ethoxy)-phenyl]-1H-benzimidazole |
| 7 | 1-butyl-2-[3-(naphthalen-2-yloxy)-phenyl]-6-(2-piperazin-1-yl-ethoxy)-1H-benzoimidazole |
| 8 | 2-biphenyl-4-yl-1-butyl-6-(2-piperazin-1-yl-ethoxy)-1H-benzimidazole |
| 9 | 1-butyl-6-(4-tert-butyl-phenoxy)-2-[4-(2-pyrrolidin-1-yl-ethoxy)-phenyl]-1H-benzimidazole |
| 10 | 1-butyl-2-[3-(3,3-dimethyl-butoxy)-phenyl]-6-(2-piperazin-1-yl-ethoxy)-1H-benzoimidazole |
| 11 | 1-butyl-6-(4-fluoro-3-trifluoromethyl-phenoxy)-2-[4-(2-pyrrolidin-1-yl-ethoxy)-phenyl]-1H-benzimidazole |
| 12 | 1-butyl-2-(3-phenoxy-phenyl)-6-(2-piperazin-1-yl-ethoxy)-1H-benzoimidazole |
| 13 | 1-butyl-2-[3-(4-tert-butyl-phenoxy)-phenyl]-6-(2-piperidin-1-yl-ethoxy)-1H-benzimidazole |

-continued

| Example | Name |
|---|---|
| 14 | 1-butyl-2-[3-(3,4-dichloro-phenoxy)-phenyl]-6-(2-piperidin-1-yl-ethoxy)-1H-benzimidazole |
| 15 | 1-butyl-6-[2-(4-chloro-phenyl)-ethoxy]-2-[4-(2-pyrrolidin-1-yl-ethoxy)-phenyl]-1H-benzimidazole |
| 16 | 1-butyl-2-[3-(3,5-dichloro-phenoxy)-phenyl]-6-(2-piperidin-1-yl-ethoxy)-1H-benzimidazole |
| 17 | 1-butyl-2-(4-tert-butyl-phenyl)-6-(2-piperazin-1-yl-ethoxy)-1H-benzoimidazole |
| 18 | dibutyl-{4-[1-butyl-6-(3-diethylamino-propoxy)-1H-benzimidazol-2-yl]-phenyl}-amine |
| 19 | (2-{3-butyl-2-[3-(3,5-dichloro-phenoxy)-phenyl]-3H-benzoimidazol-5-yloxy}-ethyl)-diisopropyl-amine |
| 20 | {3-[3-butyl-2-(4-tert-butyl-phenyl)-3H-benzimidazol-5-yloxy]-propyl}-diethyl-amine |
| 21 | 1-butyl-2-(3,5-di-tert-butyl-2-methoxy-phenyl)-6-(2-piperazin-1-ylethoxy)-1H-benzoimidazole |
| 22 | {3-[3-butyl-2-(3-{4-[2-(4-methoxy-phenyl)-ethoxy]-phenyl}-propyl)-3H-benzimidazol-5-yloxy]-propyl}-diethyl-amine |
| 23 | 1-butyl-2-naphthalen-2-yl-6-(2-piperazin-1-yl-ethoxy)-1H-benzimidazole |
| 24 | (2-{3-butyl-2-[3-(4-tert-butyl-phenoxy)-phenyl]-3H-benzoimidazol-5-yloxy}-ethyl)-dimethyl-amine |
| 25 | 2-benzofuran-2-yl-1-butyl-6-(2-piperazin-1-yl-ethoxy)-1H-benzimidazole |
| 26 | 1-butyl-6-(2-piperazin-1-yl-ethoxy)-2-[3-(3-trifluoromethyl-phenoxy)-phenyl]-1H-benzimidazole |
| 27 | 2-benzhydryl-1-butyl-6-(2-piperazin-1-yl-ethoxy)-1H-benzimidazole |
| 28 | 1-Butyl-2-(4-chloro-phenyl)-6-(2-piperazin-1-yl-ethoxy)-1H-benzoimidazole |
| 29 | {3-[3-Butyl-2-(4-isopropoxy-phenyl)-3H-benzoimidazol-5-yloxy]-propyl}-diethyl-amine |
| 30 | 1-Butyl-6-(2-piperazin-1-yl-ethoxy)-2-[3-(4,4,4-trifluoro-butoxy)-phenyl]-1H-benzoimidazole |

EXAMPLE 31

(2-(3-butyl-2-(2,4,4-trimethylpentyl)-3H-benzimidazol-5-yloxy-propyl)-diethyl-amine

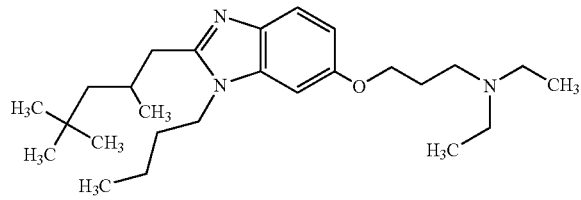

A solution of 2-(n-butylamino)-4-(3-diethylaminopropoxy) aniline (synthesized via General Procedures G1 and G2 and H) (58.6 mg, 0.2 mmol) and 3,5,5-trimethylhexanal (31.2 mg, 0.22 mmol) in ethanol (2 mL) was subjected to General Procedure K. The crude product was purified by silica gel column chromatography using 10% MeOH in DCM with a gradual increment of triethylamine (0.2 to 1.0%) as eluent to afford (2-(3-butyl-2-(2,4,4-trimethylpentyl)-3H-benzimidazol-5-yloxy-propyl)-diethyl-amine (41.0 mg).

MS m/z 416 (M+H)+

EXAMPLE 32

1-[(5-pyrrolidin-1-yl)pentyl-6-(3-diethylaminopropoxy)-2-piperidin-3-yl-1H-benzimidazole A solution of 1-(t-butyloxycarbonyl)piperidine-3-carboxaldehyde (235 mg; 1.1 mmol) and 2-[(5-pyrrolidin-1-yl)pentylamino]-4-(3-diethylaminopropoxy)-4-(2-diethylaminoethoxy)aniline (synthesized via General Procedures G1 and G2 and H) (362 mg; 1 mmol) in ethanol (5 mL) was subjected to General Procedure K. The crude product was purified by silica gel column chromatography using 10% MeOH in DCM with a gradual increment of triethylamine (0.2 to 1.0%) as eluent to afford 410 mg of tert-butyl 3-{[1-(5-pyrrolidin-1-yl)pentyl]-6-(3-diethylaminopropoxy)-1H-benzimidazol-2-yl}piperidine-1-carboxylate.

A solution of tert-butyl 3-{[1-(5-pyrrolidin-1-yl)pentyl]-6-(3-diethylaminopropoxy)-1H-benzimidazol-2-yl}piperidine-1-carboxylate (271 mg; 0.5 mmol) in DCM (2 mL) was subjected to General Procedure T1. The resulting mixture was stirred for 4-5 h and the solvent was removed in vacuo. The residue obtained was washed with ether twice and dried under vacuum to afford 1-[(5-pyrrolidin-1-yl)pentyl-6-(3-diethylaminopropoxy)-2-piperidin-3-yl-1H-benzimidazole trihydrochloride (210 mg).

MS m/z 442 (M+H)+

EXAMPLE 33

1-[(5-pyrrolidin-1-yl)pentyl -6-(3-diethylaminopropoxy)-2-piperidin-4-yl-1H-benzimidazole A solution of 1-(t-butyloxycarbonyl)piperdine-4-carboxaldehyde (235 mg; 1.1 mmol) and 2-[(5-pyrrolidin-1-yl)pentylamino]-4-(3-diethylaminopropoxy)-4-(2-diethylaminoethoxy)aniline (362 mg; 1 mmol) in ethanol (5 mL) was subjected to General Procedure K. The crude product was purified by silica gel column chromatography using 10% MeOH in DCM with a gradual increment of triethylamine (0.2 to 1.0%) as eluent to afford 430 mg of tert-butyl 4-{[1-(5-pyrrolidin-1-yl)pentyl]-6-(3-diethylaminopropoxy)-1H-benzimidazol-2-yl}piperidine-1-carboxylate.

A solution of tert-butyl 4-{[1-(5-pyrrolidin-1-yl)pentyl]-6-(3-diethylaminopropoxy)-1H-benzimidazol-2- yl}piperidine-1-carboxylate (271 mg; 0.5 mmol) in DCM (2 mL) was subjected to General Procedure T1. The resulting mixture was stirred for 4-5 h and the solvent was removed in vacuo. The residue obtained was washed with ether twice and dried under vacuum to afford 1-[(5-pyrrolidin-1-yl)pentyl-6-(3-diethylaminopropoxy)-2-piperidin-4-yl-1H-benzimidazole trihydrochloride (220 mg).

MS m/z 442 (M+H)$^+$

EXAMPLE 34

{1-butyl-[4,6-di(3-diethylaminopropoxy)]-2-piperidin-4-yl]-1H-benzimidazole

A solution of 1-(t-butyloxycarbonyl)piperdine-4-carboxaldehyde (235 mg; 1.1 mmol) and 2-butylamino-4,6-di(3-diethylaminopropoxy)aniline (synthesized via General Procedures J1 and J2 and I) (424 mg; 1 mmol) in ethanol (5 mL) was subjected to General Procedure K. The crude product was purified by silica gel column chromatography using 10% MeOH in DCM with a gradual increment of triethylamine (0.2 to 1.0%) as eluent to afford 425 mg of tert-butyl {4-[1-butyl-4,6-di(3-diethylaminopropoxy)-1H-benzimidazol-2-yl]}piperidine-1-carboxylate.

A solution of tert-butyl 4-[1-butyl-4,6-di(3-diethylaminopropoxy)-1H-benzimidazol-2-yl]piperidine-1-carboxylate (308 mg; 0.5 mmol) in DCM (2 mL) was subjected to General Procedure T1. The resulting mixture was stirred for 4-5 h and the solvent was removed in vacuo. The residue obtained was washed with ether twice and dried under vacuum to afford {1-butyl-[4,6-di(3-diethylaminopropoxy)]-2-piperidin-4-yl}-1H-benzimidazole trihydrochloride (260 mg).

MS m/z 516 (M+H)$^+$

EXAMPLE 35

(3-(3-butyl-2-(3-(4-tert-butyl-phenoxy)-phenyl)-7-(2-pyrrolidin-1-yl-ethoxy)-3H-benzimidazol-5-yloxy-propyl)-diiethyl-amine Example 35 was formed employing 3-(4-t-butyl-phenoxy) benzaldehyde (synthesized via General Procedure B) (50 mg; 0.20 mmol) and 2-butylamino-4-(3-diethylaminopropoxy)-6-(2-pyrrolidin-1-yl-ethoxy)aniline (synthesized via General Procedures J3-J7) (39 mg; 0.20 mmol) in ethanol (1 mL) according to General Procedure K. The crude product was purified by silica gel column chromatography using 10% MeOH in DCM with a gradual increment of triethylamine (0.2 to 1.0%) as eluent to afford 40 mg of Example 243.

MS m/z 641 (M+H)$^+$

EXAMPLE 36

1-butyl-2-(4-[2-(4-chlorophenyl)ethoxy]-phenyl}-6-(2-pyrrolidin-1-yl-ethoxy)-1H-benzimidazole

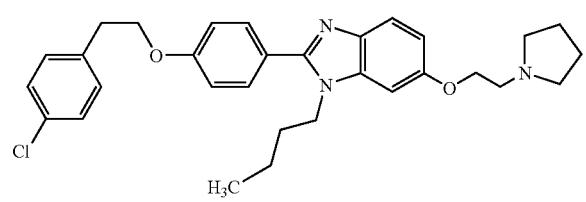

This compound was prepared according to the General Procedure K by refluxing a mixture of 4-[2-(4-chloro-phenyl)-ethoxy]-bezaldehyde (synthesized via General Procedure A) (100 mg) and N$^2$-Butyl-4-(2-pyrrolidin-1-ylethoxy)-benzene-1,2-diamine (synthesized via General Procedures G1 and G2 and H) (50 mg) in ethanol overnight. Ethanol was removed in vacuo and the residue was purified by silica gel chromatography using 5% MeOH in DCM to give pure 1-butyl-2-{4-[2-(4-chlorophenyl)ethoxy]-phenyl}-6-(2-pyrrolidin-1-yl-ethoxy)-1H-benzimidazole (37.0 mg, 40%).

MS: m/z 518 (M+H)$^+$

EXAMPLE 37

1-butyl-2-{3-[3-tert-butyl-phenoxy]-phenyl}-6-(2-piperazin-1-yl-ethoxy)-1H-benzimidazole A mixture of 1-BOC-4-[2-(4-amino-3-butylamino-phenoxy)-ethyl]-piperazine (synthesized via General Procedures G1 and G2 and H) (0.130 g, 0.512 mmol) and 3-(3-tert-butylphenoxy)benzaldehyde was subjected to General Procedure K. Reaction was concentrated and purified on silica gel-chromatography using DCM-2% MeOH/DCM. The BOC-group was removed employing General Procedure T1 to give 1-butyl-2-{3-[3-tert-butyl-phenoxy]-phenyl}-6-(2-piperazin-1-yl-ethoxy)-1H-benzimidazole (0.10 g).

MS (m/z): 527 (M+H)$^+$

EXAMPLE 38

1-butyl-2-{3-[biphenyl-4-yloxy]-phenyl}-6-(2-piperazin-1-yl-ethoxy)-1H-benzimidazole A mixture of 3-bromobenzaldehyde (1.05 g) and 1-BOC-4-[2-(4-amino-3-butylamino-phenoxy)-ethyl]-piperazine (1.85 g) was subjected to General Procedure K. The ethanol was removed in vacuo and the residue purified on silica gel using 1-2% MeOH/DCM.

To a solution of the aryl bromide (0.07 mmol) in pyridine (1 mL) was added copper powder (0.14 mmol) followed by K$_2$CO$_3$ (0.35 mmol) and the respective substituted phenol (0.14 mmol). The mixture was heated at 110° C. overnight, then diluted with water (2 mL) and extracted with EtOAc (3×2 mL). The combined organic extract was dried over Na$_2$SO$_4$, filtered and concentrated to an oil, which was purified by column chromatography on silica gel. The pure product was obtained from 1-6% methanol/DCM (yield 28-42%). The BOC-group was removed via General Procedure T1 to give 1-butyl-2-{3-[biphenyl-4-yloxy]-phenyl}-6-(2-piperazin-1-yl-ethoxy)-1H-benzimidazole.

MS (m/z): 547 (M+H)$^+$

EXAMPLE 39

1-butyl-2-{4-[2-(4-chlorophenyl)ethoxy]-phenyl}-6-(2-piperazin-1-yl-ethoxy)-1H-benzimidazole A mixture of 4-[2-(4-chloro-phenyl)-ethoxy]-benzaldehyde (0.08 g) and 1-BOC-4-[2-(4-amino-3-butylamino-phenoxy)-ethyl]-piperazine (0.10 g) was subjected to General Procedure K. Ethanol was removed in vacuo and the residue purified on silica gel with 1-2% MeOH/DCM. The BOC-group was removed employing General Procedure T1 to give 1-butyl-2-(4-[2-(4-chlorophenyl)ethoxy]-phenyl)-6-(2-piperazin-1-yl-ethoxy)-1H-benzimidazole (0.081 g).

MS(m/z): 533 (M+H)$^+$

The following Examples were synthesized according to the Methods employed for Examples 35-39;

| Example | Name |
|---|---|
| 40 | [3-(3-butyl-2-{3-[2-(4-chloro-phenyl)-ethoxy]-4-nitro-phenyl}-3H-benzimidazol-5-yloxy)-propyl]-diethyl-amine |
| 41 | [2-(3-butyl-2-{4-[2-(4-chloro-phenyl)-ethoxy]-phenyl}-3H-benzimidazol-5-yloxy)-ethyl]-diethyl-amine |
| 42 | 1-butyl-2-[3-(3,5-dichloro-phenoxy)-phenyl]-6-(piperidin-4-ylmethoxy)-1H-benzoimidazole |
| 43 | 1-butyl-2-{3-[2-(4-chloro-phenyl)-ethoxy]-phenyl}-6-(2-piperazin-1-yl-ethoxy)-1H-benzoimidazole |
| 44 | {3-[3-butyl-2-(2-{4-[2-(4-chlorophenyl)-ethoxy]-phenyl}-ethyl)-3H-benzimidazol-5-yloxy]-propyl}-diethyl-amine |
| 45 | 1-butyl-2-[3-(3,5-dichloro-phenoxy)-phenyl]-6-(2-piperazin-1-yl-ethoxy)-1H-benzimidazole |
| 46 | 1-butyl-6-[2-(4-butyl-piperazin-1-yl)-ethoxy]-2-[3-(3-trifluoromethyl-phenoxy)-phenyl]-1H-benzimidazole |
| 47 | {3-[3-butyl-2-(2-{4-[2-(4-chlorophenyl)-ethoxy]-phenyl}-ethyl)-3H-benzimidazol-5-yloxy]-propyl}-diethyl-amine |
| 48 | (3-{3-butyl-2-[3-(4-methoxy-phenoxy)-phenyl]-3H-benzimidazol-5-yloxy}-propyl)-diethyl-amine |
| 49 | {3-[2-{4-[2-(4-chloro-phenyl)-ethoxy]-phenyl}-6-(2-diethylamino-ethoxy)-benzimidazol-1-yl]-propyl}-diethyl-amine |
| 50 | [3-(1-butyl-2-{4-[2-(4-chloro-phenyl)-ethoxy]-phenyl}-1H-benzimidazol-4-yloxy)-propyl]-diethyl-amine |
| 51 | [3-(1-butyl-2-{4-[2-(4-chloro-phenyl)-ethoxy]-phenyl}-1H-benzimidazol-5-yl)-propyl]-diethyl-amine |
| 52 | 1-butyl-2-[3-(2-isopropyl-phenoxy)-phenyl]-6-(2-piperazin-1-yl-ethoxy)-1H-benzoimidazole |
| 53 | {3-[3-butyl-2-(2-{4-[3-(4-methoxy-phenyl)-propoxy]-phenyl}-ethyl)-3H-benzimidazol-5-yloxy]-propyl}-diethyl-amine |
| 54 | {3-[3-butyl-2-(2-{4-[4-(4-methoxy-phenyl)-butoxy]-phenyl}-ethyl)-3H-benzimidazol-5-yloxy]-propyl}-diethyl-amine |
| 55 | [3-(3-butyl-2-{4-[2-(4-chloro-phenyl)-ethoxy]-3-ethoxy-phenyl}-3H-benzimidazol-5-yloxy)-propyl]-diethyl-amine |
| 56 | (3-{3-butyl-2-[3-(3-trifluoromethyl-phenoxy)-phenyl]-3H-benzimidazol-5-yloxy}-propyl)-diethyl-amine |
| 57 | 1-butyl-2-[3-(4-chloro-phenoxy)-phenyl]-6-(2-piperazin-1-yl-ethoxy)-1H-benzoimidazole |
| 58 | 1-butyl-2-[3-(3,4-dichloro-phenoxy)-phenyl]-6-(2-piperazin-1-yl-ethbxy)-1H-benzoimidazole |
| 59 | 1-butyl-2-{4-[2-(4-chloro-phenyl)-ethoxy]-phenyl}-6-(piperidin-4-yloxy)-1H-benzoimidazole |
| 60 | 3-(3-butyl-2-{4-[2-(4-chloro-phenyl)-ethoxy]-phenyl}-3H-benzoimidazol-5-yloxy)-1-aza-bicyclo[2.2.2]octane |
| 61 | 1-butyl-2-{4-[2-(4-chloro-phenyl)-ethoxy]-phenyl}-6-(2,2,6,6,-tetramethyl-piperidin-4-yloxy)-1H-benzoimidazole |
| 62 | 2-[3-(4-butoxy-phenoxy)-phenyl]-1-butyl-6-(2-piperazin-1-yl-ethoxy)-1H-benzoimidazole |
| 63 | [3-(3-butyl-2-{4-[2-(4-chloro-phenyl)-ethoxy]-phenyl}-3H-benzimidazol-5-yloxy)-propyl]-diethyl-amine |
| 64 | {3-[2-{4-[2-(4-chloro-phenyl)-ethoxy]-phenyl}-3-(3-methyl-butyl)-3H-benzimidazol-5-yloxy]-propyl}-diethyl-amine |
| 65 | [3-(2-{4-[2-(4-chloro-phenyl)-ethoxy]-phenyl}-3-hexyl-3H-benzimidazol-5-yloxy)-propyl]-diethyl-amine |
| 66 | {3-[2-{4-[2-(4-chloro-phenyl)-ethoxy]-phenyl}-6-(2-diethylamino-ethoxy)-benzimidazol-1-yl]-propyl}-dimethyl-amine |
| 67 | 1-butyl-2-[4-(4-fluoro-3-trifluoromethyl-phenoxy)-phenyl]-6-(2-piperazin-1-ylethoxy)-1H-benzoimidazole |
| 68 | [3-(3-butyl-2-{4-[2-(4-chloro-phenyl)-ethoxy]-phenyl}-3H-benzimidazol-5-yloxy)-propyl]-diethyl-amine |
| 69 | {3-[2-(4-benzyloxy-3,5-dimethyl-phenyl)-3-butyl-3H-benzimidazol-5-yloxy]-propyl}-diethyl-amine |
| 70 | {3-[3-butyl-2-[3-(3,4-dichloro-phenoxy)-phenyl]-3H-benzimidazol-5-yloxy]-propyl}-diethyl-amine |
| 71 | 1-butyl-6-[2-(4-methyl-piperazin-1-yl)-ethoxy]-2-[3-(3-trifluoromethyl-phenoxy)-phenyl]-1H-benzimidazole |
| 72 | 1-butyl-6-[2-(4-isopropyl-piperazin-1-yl)-ethoxy]-2-[3-(3-trifluoromethyl-phenoxy)-phenyl]-1H-benzoimidazole |
| 73 | 1-butyl-2-{4-[2-(4-chloro-phenyl)-ethoxy]-phenyl}-6-(3-piperazin-1-yl-propoxy)-1H-benzoimidazole |
| 74 | (3-{3-butyl-2-[3-(3,4-dichloro-phenoxy)-phenyl]-3H-benzimidazol-5-yloxy}-propyl)-diethyl-amine |
| 75 | 1-butyl-2-[3-(3,4-dimethoxy-phenoxy)-phenyl]-6-(2-piperidin-4-yloxy)-1H-benzoimidazole |
| 76 | 1-butyl-2-[3-(4-chloro-benzyloxy)-phenyl]-6-(2-piperazin-1-yl-ethoxy)-1H-benzoimidazole |
| 77 | 1-butyl-2-[3-(3,5-dichloro-phenoxy)-phenyl]-6-(2-piperazin-1-yl-ethoxy)-1H-benzoimidazole |

-continued

| Example | Name |
|---|---|
| 78 | (3-{2-[2-(4-benzyloxy-phenyl)-ethyl]-3-butyl-3H-benzimidazol-5-yloxy}-propyl)-diethyl-amine |
| 79 | (3-{3-butyl-2-[2-(4-phenethyloxy-phenyl)-ethyl]-3H-benzimidazol-5-yloxy}-propyl)-diethyl-amine |
| 80 | {3-[3-butyl-2-(2-{4-[2-(4-fluoro-phenyl)-ethoxy]-phenyl}-ethyl)-3H-benzimidazol-5-yloxy]-propyl}-diethyl-amine |
| 81 | [3-(3-butyl-2-{2-[4-(4-chloro-benzyloxy)-phenyl]-ethyl}-3H-benzimidazol-5-yloxy)-propyl]-diethyl-amine |
| 82 | (3-{3-butyl-2-[4-(4-fluoro-benzyloxy)-phenyl]-3H-benzimidazol-5-yloxy}-propyl)-diethyl-amine |
| 83 | {3-[2-(3-benzyloxy-phenyl)-3-butyl-3H-benzimidazol-5-yloxy]-propyl}-diethyl-amine |
| 84 | [3-(3-butyl-2-{4-chloro-3-[2-(4-chloro-phenyl)-ethoxy]-phenyl}-3H-benzimidazol-5-yloxy)-propyl]-diethyl-amine |
| 85 | 1-butyl-2-[3-(4-tert-butyl-phenoxy)-phenyl]-6-(2-piperazin-1-yl-ethoxy)-1H-benzimidazole |
| 86 | 1-butyl-2-[4-(4-isopropyl-phenoxy)-phenyl]-6-(2-piperazin-1-yl-ethoxy)-1H-benzoimidazole |
| 87 | 1-butyl-2-{4-[2-(4-chloro-phenyl)-ethoxy]-phenyl}-6-[3-(4-methyl-piperazin-1-yl)-propoxy]-1H-benzoimidazole |
| 88 | 1-butyl-6-[2-(4-butyl-piperazin-1-yl)-ethoxy]-2-{4-[2-(4-chloro-phenyl)-ethoxy]-phenyl}-1H-benzoimidazole |
| 89 | 1-butyl-2-[3-(3,4-dimethoxy-phenoxy)-phenyl]-6-(2-piperazin-1-yl-ethoxy)-1H-benzoimidazole |
| 90 | 1-butyl-2-[4-(4-tert-butyl-benzyl)-phenyl]-6-(2-piperazin-1-yl-ethoxy)-1H-benzoimidazole |
| 91 | N-{4-[1-butyl-6-(3-diethylamino-propoxy)-1H-benzimidazol-2-yl]-2-[2-(4-chloro-phenyl)-ethoxy]-phenyl}-2,2-dimethyl-propioinamide |
| 92 | (3-{3-butyl-2-[4-(4-fluoro-3-trifluoromethyl-phenoxy)-phenyl]-3H-benzimidazol-5-yloxy}-propyl)-diethyl-amine |
| 93 | 1-butyl-2-[4-(naphthalen-2-yloxy)-phenyl]-6-(2-piperazin-1-yl-ethoxy)-1H-benzoimidazole |
| 94 | 1-butyl-2-[3-(4-fluoro-3-trifluoromethyl-phenoxy)-phenyl]-6-(2-piperazin-1-yl-ethoxy)-1H-benzoimidazole |
| 95 | [3-(3-butyl-2-{4-[2-(4-methoxy-phenyl)-ethoxy]-phenyl}-3H-benzimidazol-5-yloxy)-propyl]-diethyl-amine |
| 96 | 4-[1-butyl-6-(3-diethylamino-propoxy)-1H-benzimidazol-2-yl]-2-[2-(4-chloro-phenyl)-ethoxy]-phenylamine |
| 97 | 1-{4-[1-butyl-6-(3-diethylamino-propoxy)-1H-benzimidazol-2-yl]-2-[2-(4-chloro-phenyl)-ethoxy]-phenyl}-3-isopropyl-urea |
| 98 | {3-[2-{4-[2-(4-chloro-phenyl)-ethoxy]-phenyl}-6-(2-dimethylamino-ethoxy)-benzimidazol-1-yl]-propyl}-dimethyl-amine |
| 99 | 1-butyl-2-[3-(4-tert-butyl-phenoxy)-phenyl]-6-[2-(4-methyl-piperazin-1-yl)-ethoxy]-1H-benzimidazole |
| 100 | 1-butyl-6-(4-cyclopentyl-phenoxy)-2-[4-(4-methyl-piperazin-1-ylmethyl)-phenyl]-1H-benzoimidazole |
| 101 | {3-[2-(4-benzyloxy-phenyl)-3-cyclopentylmethyl-3H-benzimidazol-5-yloxy]-propyl}-diethyl-amine |
| 102 | 1-butyl-6-(4-butyl-phenoxy)-2-{3,5-dimethyl-4-[2-(1-methyl-pyrrolidin-2-yl)-ethoxy]-phenyl}-1H-benzoimidazole |
| 103 | 1-butyl-2-{4-[2-(4-chloro-phenyl)-ethoxy]-phenyl}-6-(3-pyrrolidin-1-yl-propoxy)-1H-benzoimidazole |
| 104 | {3-[2-(4-benzyloxy-phenyl)-3-isobutyl-3H-benzimidazol-5-yloxy]-propyl}-diethyl-amine |
| 105 | [3-(3-butyl-2-{3-[2-(4-chloro-phenyl)-ethoxy]-phenyl}-3H-benzimidazol-5-yloxy)-propyl]-diethyl-amine |
| 106 | 1-butyl-6-(1-butyl-piperidin-4-yloxy)-2-[3-(3,5-dichloro-phenoxy)-phenyl]-1H-benzoimidazole |
| 107 | 1-butyl-2-[3-(3,5-dichloro-phenoxy)-phenyl]-6-(1-ethyl-piperidin-4-yloxy)-1H-benzoimidazole |
| 108 | 1-butyl-6-(4-fluoro-3-trifluoromethyl-phenoxy)-2-[4-(4-methyl-piperazin-1-ylmethyl)-phenyl]-1H-benzoimidazole |
| 109 | diethyl-{3-[3-isobutyl-2-(2-{4-[2-(4-methoxy-phenyl)-ethoxy]-phenyl}-ethyl)-3H-benzimidazol-5-yloxy]-propyl}-amine |
| 110 | {3-[2-(2-{4-[2-(4-chlorophenyl)-ethoxy]-phenyl}-ethyl)-3-isobutyl-3H-benzimidazol-5-yloxy]-propyl}-diethyl-amine |
| 111 | 1-butyl-6-(2-piperazin-1-yl-ethoxy)-2-[3-(3-trifluoromethyl-phenoxy)-phenyl]-1H-benzoimidazole |
| 112 | 1-butyl-2-[3-(4-tert-butyl-phenoxy)-phenyl]-6-(2-pyrrolidin-1-yl-ethoxy)-1H-benzimidazole |
| 113 | 1-butyl-2-{4-[2-(4-chloro-phenyl)-ethoxy]-phenyl}-6-[2-(4-methyl-piperazin-1-yl)-ethoxy]-1H-benzimidazole |
| 114 | {3-[2-(4-benzyloxy-phenyl)-3-cyclopentyl-3H-benzimidazol-5-yloxy)-propyl]-diethyl-amine |
| 115 | 1-Butyl-2-{4-[2-(4-chloro-phenyl)-ethoxy]-phenyl}-5-(4-methyl-piperazin-1-ylmethyl)-1H-benzoimidazole |

-continued

| Example | Name |
|---------|------|
| 116 | [2-(3-butyl-2-{4-[2-(4-chloro-phenyl)-ethoxy]-phenyl}-3H-benzimidazol-5-yloxy)-ethyl]-dimethyl-amine |
| 117 | [2-(3-butyl-2-{4-[2-(4-chloro-phenyl)-ethoxy]-phenyl}-3H-benzimidazol-5-yloxy)-ethyl]-diisopropyl-amine |
| 118 | 1-butyl-2-[3-(3,5-dichloro-phenoxy)-phenyl]-6-[2-(4-methyl-piperazin-1-yl)-ethoxy]-1H-benzimidazole |
| 119 | (3-{1-butyl-2-[3-(4-tert-butyl-phenoxy)-phenyl]-1H-benzimidazol-4-yloxy}-propyl)-diethyl-amine |
| 120 | 2-(3-butoxy-phenyl)-1-butyl-6-(2-piperazin-1-yl-ethoxy)-1H-benzimidazole |
| 121 | 1-butyl-2-[3-(4-methanesulfonyl-benzyloxy)-phenyl]-6-(2-piperazin-1-yl-ethoxy)-1H-benzoimidazole |
| 122 | 4'{3-[1-butyl-6-(2-piperazin-1-yl-ethoxy)-1H-benzoimidazol-2-yl]-phenoxy}-biphenyl-4-carbonitrile |
| 123 | {3-[2-(4-benzyloxy-phenyl)-3-butyl-3H-benzimidazol-5-yloxy]-propyl}-diethyl-amine |
| 124 | 1-Butyl-2-[4-(3-chloro-phenoxy)-phenyl]-6-(2-pyrrolidin-1-yl-ethoxy)-1H-benzoimidazole |
| 125 | 1-butyl-2-{4-[2-(4-chloro-phenyl)-ethoxy]-phenyl}-6-[2-(4-isopropyl-piperazin-1-yl)-ethoxy]-1H-benzoimidazole |
| 126 | {3-[2-(3-benzyloxy-4-methoxy-phenyl)-3-butyl-3H-benzimidazol-5-yloxy]-propyl}-diethyl-amine |
| 127 | (3-{3-butyl-2-[3-(4-tert-butyl-phenoxy)-phenyl]-3H-benzimidazol-5-yloxy}-propyl)-diethyl-amine |
| 128 | {3-[3-butyl-2-(3-phenoxy-phenyl)-3H-benzimidazol-5-yloxy]-propyl}-diethyl-amine |
| 129 | 1-butyl-2-[3-(3,5-dichloro-phenoxy)-phenyl]-6-[2-(4-ethyl-piperazin-1-yl)-ethoxy]-1H-benzimidazole |
| 130 | 1-butyl-2-[4-(2,3-di-methoxy-phenoxy)-phenyl]-6-(2-piperazin-1-ylethoxy)-1H-benzoimidazole |
| 131 | [3-(3-butyl-2-{2-[4-(4-chloro-benzyloxy)-phenyl]-ethyl}-3H-benzimidazol-5-yloxy)-propyl]-diethyl-amine |
| 132 | (3-{3-butyl-2-[3-(4-chloro-phenoxy)-phenyl]-3H-benzimidazol-5-yloxy}-propyl)-diethyl-amine |
| 133 | {3-[2-(4-benzyloxy-phenyl)-3-isopropyl-3H-benzimidazol-5-yloxy]-propyl}-diethyl-amine |
| 134 | (2-{3-butyl-2-[3-(3-trifluoromethyl-phenoxy)-phenyl]-3H-benzoimidazol-5-yloxy}-ethyl)-diisopropyl-amine |
| 135 | 1-butyl-6-[2-(4-ethyl-piperazin-1-yl)-ethoxy]-2-[3-(3-trifluoromethyl-phenoxy)-phenyl]-1H-benzimidazole |
| 136 | {3-[3-butyl-2-[3-(3,5-dichloro-phenoxy)-phenyl]-3H-benzimidazol-5-yloxy]-propyl}-diethyl-amine |
| 137 | (3-{2-butyl-2-[3-(4-tert-butyl-phenoxy)-phenyl]-3H-benzimidazol-5-yloxy}-ethyl)-cyclohexyl-methyl-amine |
| 138 | 1-butyl-6-[2-(4-propyl-piperazin-1-yl)-ethoxy]-2-[3-(3-trifluoromethyl-phenoxy)-phenyl]-1H-benzimidazole |
| 139 | 1-butyl-6-(4-butyl-phenoxy)-2-[4-(4-methyl-piperazin-1-ylmethyl)-phenyl]-1H-benzoimidazole |
| 140 | 1-butyl-2-[3-(4-tert-butyl-phenoxy)-phenyl]-6-(2-morpholin-4-yl-ethoxy)-1H-benzimidazole |
| 141 | 4-[1-butyl-6-(3-diethylamino-propoxy)-1H-benzimidazol-2-yl]-2-phenethyloxy-phenylamine |
| 142 | {2-[2-(4-benzyloxy-phenyl)-3-phenethyl-3H-benzimidazol-5-yloxy]-ethyl}-diethyl-amine |
| 143 | {3-[3-butyl-2-(4-phenoxy-phenyl)-3H-benzimidazol-5-yloxy]-propyl}-diethyl-amine |
| 144 | 3-[4-(2-{3-butyl-2-[3-(3,4-dichloro-phenoxy)-phenyl]-3H-benzimidazol-5-yloxy}-ethyl)-piperazin-1-yl]-propan-1-ol |
| 145 | 1-butyl-6-(2-pyrrolidin-1-yl-ethoxy)-2-[3-(3-trifluoromethyl-phenoxy)-phenyl]-1H-benzimidazole |
| 146 | {2-[2-[4-[2-(4-chloro-phenyl)-ethoxy]-phenyl}-6-(2-diethylamino-ethoxy)-benzimidazol-1-yl]-ethyl}-dimethyl-amine |
| 147 | 1-butyl-6-(2-morpholin-4-yl-ethoxy)-2-[3-(3-trifluoromethyl-phenoxy)-phenyl]-1H-benzimidazole |
| 148 | 1-butyl-2-[3-(3,5-dichloro-phenoxy)-phenyl]-6-(1-methyl-piperidin-4-yloxy)-1H-benzoimidazole |
| 149 | N'-[3-butyl-2-(2-{4-[2-(4-chloro-phenyl)-ethoxy]-phenyl}-ethyl)-3H-benzimidazol-5-yl]-N,N-diethyl-propane-1,3-diamine |
| 150 | 1-butyl-2-[3-(2,4-dichloro-phenoxy)-phenyl]-6-(2-pyrrolidin-1-yl-ethoxy)-1H-benzimidazole |
| 151 | 1-butyl-2-{4-[2-(4-chloro-phenyl)-ethoxy]-phenyl}-6-(2-morpholin-4-yl-ethoxy)-1H-benzimidazole |
| 152 | 1-butyl-6-(2-piperazin-1-yl-ethoxy)-2-[4-(4-trifluoromethyl-phenoxy)-phenyl]-1H-benzoimidazole |
| 153 | 2-[4-(biphenyl-4-yloxy)-phenyl]-1-butyl-6-(2-piperazin-1-yl-ethoxy)-1H-benzoimidazole |

-continued

| Example | Name |
|---|---|
| 154 | 1-butyl-2-[3-(3,5-dichloro-phenoxy)-phenyl]-6-(2-morpholin-4-yl-ethoxy)-1H-benzimidazole |
| 155 | 1-butyl-2-[3-(3,4-dimethoxy-phenoxy)-phenyl]-6-(2-piperazin-1-yl-ethoxy)-1H-benzoimidazole |
| 156 | 1-butyl-2-[3-(4-tert-butyl-phenoxy)-phenyl]-5-(1H-imidazol-4-ylmethoxy)-1H-benzoimidazole |
| 157 | {3-[2-(2-benzyloxy-phenyl)-3-butyl-3H-benzimidazol-5-yloxy]-propyl}-diethyl-amine |
| 158 | {3-[1-Butyl-6-(3-diethylamino-propoxy)-2-piperidin-4-yl-1H-benzoimidazol-4-yloxy]-propyl}-diethyl-amine |
| 159 | (2-{2-[2-(4-Benzyloxy-phenyl)-ethyl]-3-phenethyl-3H-benzoimidazol-5-yloxy}-ethyl)-diethyl-amine |
| 160 | [3-(3-Butyl-2-{3-[4-(4-fluoro-benzyloxy)-phenyl]-propyl}-3H-benzoimidazol-5-yloxy)-propyl]-diethyl-amine |
| 161 | [3-(4-Benzyloxy-phenyl)-propyl]-[1-butyl-6-(3-diethylamino-propoxy)-1H-benzoimidazol-2-yl]-amine |
| 162 | {3-[3-Butyl-2-(3-{4-[2-(4-chloro-phenyl)-ethoxy]-phenyl}-propyl)-3H-benzoimidazol-5-yloxy]-propyl}-diethyl-amine |
| 163 | 1-Butyl-2-[3-(3,5-dichloro-phenoxy)-phenyl]-6-(2-imidazol-1-yl-ethoxy)-1H-benzoimidazole |
| 164 | 1-[4-(2-{3-Butyl-2-[3-(3-trifluoromethyl-phenoxy)-phenyl]-3H-benzoimidazol-5-yloxy}-ethyl)-piperazin-1-yl]-ethanone |
| 165 | N-[3-Butyl-2-(2-{4-[2-(4-chloro-phenyl)-ethoxy]-phenyl}-ethyl)-3H-benzoimidazol-5-yl]-N-(3-diethylamino-propyl)-N',N'-diethyl-propane-1,3-diamine |

EXAMPLE 166

(3-(1-Butyl-2-{4-[2-(4-chlorophenyl)-ethoxy]-phenyl}-6-(3-diethylaminopropoxy)-1H-benzimidazole-4-yloxy)-propyl)diethyl-amine This compound was prepared according to General Procedure K by refluxing a mixture of 4-[2-(4-chloro-phenyl)-ethoxy]-bezaldehyde (300 mg) and $N^1$-Butyl-3,5-bis-(3-diethylamino-propoxy)-benzene-1,2-diamine (synthesized via General Procedures J1 and J2 and I) (200 mg) in ethanol overnight. Ethanol was removed in vacuo and the residue was purified by silica gel chromatography using 5% MeOH in DCM to give pure (3-(1-Butyl-2-{4-[2-(4-chlorophenyl)-ethoxy]-phenyl}-6-(3-diethylaminopropoxy)-1H-benzimidazole-4-yloxy)-propyl)diethyl-amine (100 mg).

MS: m/z 663 (M+H)+

EXAMPLE 167

{3-[1-Butyl-2-[3-(4-tert-butyl-phenoxy)-phenyl]-6-(3-diethylaminopropoxy)-1H-benzimidazole-4-yloxy]-propyl}diethyl-amine {3-[1-Butyl-2-[3-(4-tert-butyl-phenoxy)-phenyl]-6-(3-diethylaminopropoxy)-1H-benzimidazole-4-yloxy]-propyl}diethyl-amine was formed employing 3(4-t-butyl-phenoxy)benzaldehyde (127 mg; 0.50 mmol) and 2-butylamino-4,6-di(3-diethylaminopropoxy)aniline (synthesized via General Procedures J1 and J2 and I) (1.6 mg; 0.25 mmol) in ethanol (1 mL) following General Procedure K. The crude product was purified by silica gel column chromatography using 10% MeOH in DCM with a gradual increment of triethylamine (0.2 to 1.0%) as eluent to afford 145 mg (76%) of {3-[1-Butyl-2-[3-(4-tert-butyl-phenoxy)-phenyl]-6-(3-diethylaminopropoxy)-1H-benzimidazole-4-yloxy]-propyl}diethyl-amine.

MS: m/z 657 (M+H)+

EXAMPLE 168

{3-[2-(2-[4-[2-(4-chloro-phenyl)-ethoxy])-phenyl]-ethyl)-6-(3-diethylaminopropoxy)-3H-benzimidazole-4-yloxy]-propyl}diethyl-amine

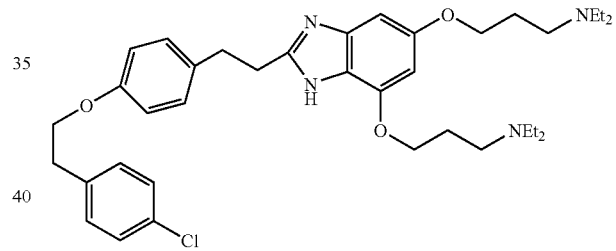

This compound was prepared according to the General Procedure K by refluxing a mixture of 3-{4-[2-(4-chloro-phenyl)-ethoxy]-propionaldehyde (100 mg) and 3,5-Bis-(3-diethylamino-propxy)-benzene-1,2-diamine (synthesized via General Procedures J1 and J2 and I) (50 mg) in ethanol overnight. Ethanol was removed in vacuo and the residue was purified by silica gel chromatography using 10% MeOH in DCM to give {3-[2-(2-[4-[2-(4-chloro-phenyl)-ethoxy])-phenyl]-ethyl)-6-(3-diethylaminopropoxy)-3H-benzimidazole-4-yloxy]-propyl}diethyl-amine (30 mg).

MS: m/z 635 (M+H)+

EXAMPLE 169

(3-(1-Butyl-6-(3-diethylaminopropoxy)-2-[4-(4-chloro-3-trifluoromethyl-phenoxy)-phenyl]-1H-benzimidazole-4-yloxy)-propyl)diethyl-amine 4-(4-Chloro-3-trifluoromethyl)phenoxybenzaldehyde (synthesized employing General Procedure B) (150 mg) and 2-butylamino-4,6-di(3-diethylaminopropoxy)aniline (synthesized via General Procedures J1 and J2 and I) 106 mg; 0.25 mmol) in ethanol (1 mL) were condensed employing General Procedure K. The crude product was purified by silica gel column chromatography using 10% MeOH in DCM with a gradual increment of triethylamine (0.2 to 1.0%) as eluent to afford 160 mg of (3-(1-Butyl-6-(3-diethylaminopropoxy)-2-[4-(4-chloro-3-trifluoromethyl-phenoxy)-phenyl]-1H-benzimidazole-4-yloxy)-propyl)diethyl-amine.
MS: m/z 703 (M+H)$^+$

EXAMPLE 170

(3-(1-Butyl-6-(3-diethylaminopropoxy)-2-[4-(4-fluoro-3-trifluoromethyl-phenoxy)-phenyl]-1H-benzimidazole-4-yloxy)-propyl)diethyl-amine

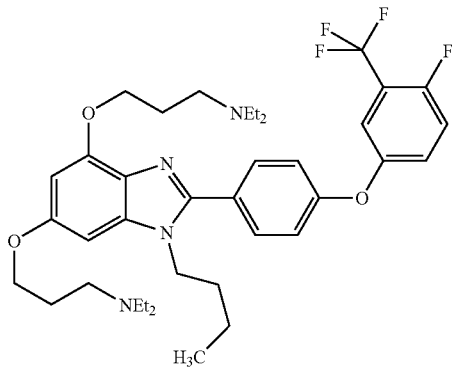

A solution of 2-butylamino-4,6-di(3-diethylaminopropoxy)aniline (synthesized via General Procedures J1 and J2 and I) (84.4 mg, 0.2 mmol) and 4-(4-fluoro-3-trifluoromethyl)phenoxybenzaldehyde (synthesized employing General Procedure B) (62.5 mg, 0.2 mmol) in ethanol (2 mL) was heated to reflux following the General Procedure K. The crude product was purified by silica gel column chromatography using 10% MeOH in DCM with a gradual increment of triethylamine (0.2 to 1.0%) as eluent to afford 3-(1-Butyl-6-(3-diethylaminopropoxy)-2-[4-(4-fluoro-3-trifluoromethyl-phenoxy)-phenyl]-1H-benzimidazole-4-yloxy)-propyl)diethyl-amine (62 mg).

MS m/z 687 (M+H)

The following Examples were synthesized according to the Methods employed for Examples 166-170;

| Example | Name |
| --- | --- |
| 171 | {3-[2-[3-(3,5-Dichloro-phenoxy)-phenyl]-6-(3-diethylamino-propoxy)-1H-benzoimidazol-4-yloxy]-propyl}-diethyl-amine |
| 172 | 1-Butyl-2-{4-[2-(4-chloro-phenyl)-ethoxy]-phenyl}-4,6-bis-(2-pyrrolidin-1-yl-ethoxy)-1H-benzoimidazole |
| 173 | {3-[2-[3-(3,4-Dichloro-phenoxy)-phenyl]-6-(3-diethylamino-propoxy)-1H-benzoimidazol-4-yloxy]-propyl}-diethyl-amine |
| 174 | (3-{6-(3-diethylamino-propoxy)-2-[3-(3-trifluoromethyl-phenoxy)-phenyl]-1H-benzimidazole-4-yloxy}-propyl)-1H-benzimidazole-4-yloxy}-propyl)-diethyl-amine |
| 175 | {3-[1-Butyl-2-[3-(3,4-dichloro-phenoxy)-phenyl]-6-(3-diethylamino-propoxy)-1H-benzoimidazol-4-yloxy]-propyl}-diethyl-amine |
| 176 | {3-[2-[3-(4-Chloro-phenoxy)-phenyl]-6-(3-diethylamino-propoxy)-1H-benzoimidazol-4-yloxy]-propyl}-diethyl-amine |
| 177 | {3-[1-Butyl-2-[3-(4-chloro-phenoxy)-phenyl]-6-(3-diethylamino-propoxy)-1H-benzoimidazol-4-yloxy]-propyl}-diethyl-amine |
| 178 | {3-[1-Butyl-6-(3-diethylamino-propoxy)-2-(3-p-tolyloxy-phenyl)-1H-benzoimidazol-4-yloxy]-propyl}-diethyl-amine |
| 179 | {3-[1-Butyl-2-[3-(3,5-dichloro-phenoxy)-phenyl]-6-(3-diethylamino-propoxy)-1H-benzoimidazol-4-yloxy]-propyl}-diethyl-amine |
| 180 | 1-Butyl-2-[3-(4-tert-butyl-phenoxy)-phenyl]-4,6-bis-(2-pyrrolidin-1-yl-ethoxy)-1H-benzoimidazole |
| 181 | {3-[3-Butyl-2-{4-[2-(4-chloro-phenyl)-ethoxy]-phenyl}-7-(2-pyrrolidin-1-yl-ethoxy)-3H-benzoimidazol-5-yloxy]-propyl}-diethyl-amine |
| 182 | (3-{1-butyl-6-(3-diethylamino-propoxy)-2-[4-(3-fluoro-phenoxy)-phenyl]-1H-benzimidazol-4-yloxy}-propyl)-diethyl-amine |
| 183 | {3-[2-{4-[2-(4-chloro-phenyl)-ethoxy]-phenyl}-6-(3-diethylamino-propoxy)-1-isopropyl-1H-benzimidazol-4-yloxy]-propyl}-diethyl-amine |
| 184 | {3-[1-Butyl-2-{4-[2-(4-chloro-phenyl)-ethoxy]-phenyl}-6-(2-pyrrolidin-1-yl-ethoxy)-1H-benzoimidazol-4-yloxy]-propyl}-diethyl-amine |
| 185 | 2-{4-[1-butyl-4,6-bis-(3-diethylamino-propoxy)-1H-benzimidazol-2-yl-phenoxy}-benzoic acid methyl ester |
| 186 | {3-[2-[4-(biphenyl-4-yloxy)-phenyl]-1-butyl-6-(3-diethylamino-propoxy)-1H-benzoimidazol-4-yloxy]-propyl}-diethyl-amine |
| 187 | {3-[2-[4-(3,5-Bis-trifluoromethyl-phenoxy)-phenyl]-6-(3-diethylamino-propoxy)-1H-benzoimidazol-4-yloxy]-propyl}-diethyl-amine |
| 188 | {3-[1-butyl-2-[4-(4-chloro-benzylsulfanyl)-phenyl]-6-(3-diethylamino-propoxy)-1H-benzimidazol-4-yloxy]-propyl}-diethyl-amine |
| 189 | {3-[2-{4-[2-(4-chloro-phenyl)-ethoxy]-phenyl}-6-(3-diethylamino-propoxy)-3H-benzimidazol-4-yloxy]-propyl}-diethyl-amine |
| 190 | (3-{1-butyl-6-(3-diethylamino-propoxy)-2-[3-(3-trifluoromethyl-phenoxy)-phenyl]-1H-benzimidazol-4-yloxy}-propyl)-diethyl-amine |

-continued

| Example | Name |
|---|---|
| 191 | [3-(1-butyl-6-(3-diethylamino-propoxy)-2-{4-[2-(4-fluoro-phenyl)-ethoxy]-phenyl}-1H-benzimidazol-4-yloxy}-propyl)-diethyl-amine |
| 192 | (3-{1-butyl-6-(3-diethylamino-propoxy)-2-[4-(3-trifluoromethyl-phenoxy)-phenyl]-1H-benzimidazol-4-yloxy}-propyl)-diethyl-amine |
| 193 | {3-[2-[3-(4-tert-Butyl-phenoxy)-phenyl]-6-(3-diethylamino-propoxy)-1H-benzoimidazol-4-yloxy]-propyl}-diethyl-amine |
| 194 | (3-{1-Butyl-6-(3-diethylamino-propoxy)-2-[4-(4-fluoro-3-trifluoromethyl-phenoxy)-2-trifluoromethyl-phenyl]-1H-benzoimidazol-4-yloxy}-propyl)-diethyl-amine |
| 195 | {3-[1-Butyl-2-[4-chloro-2-(4-chloro-3-trifluoromethyl-phenoxy)-phenyl]-6-(3-diethylamino-propoxy)-1H-benzoimidazol-4-yloxy]-propyl}-diethyl-amine |
| 196 | 2-[3-(4-Chloro-phenoxy)-phenyl]-4,6-bis-(2-pyrrolidin-1-yl-ethoxy)-1H-benzoimidazole |
| 197 | 1-Butyl-2-[3-(4-chloro-phenoxy)-phenyl]-4,6-bis-(2-pyrrolidin-1-yl-ethoxy)-1H-benzoimidazole |
| 198 | {3-[3-butyl-2-[4-(4-fluoro-3-trifluoromethyl-phenoxy)-phenyl]-7-(2-pyrrolidin-1-yl-ethoxy)-3H-benzimidazol-5-yloxy]-propyl}-diethyl-amine |
| 199 | {2-[1-butyl-2-[3-(4-tert-butyl-phenoxy)-phenyl]-6-(2-diisopropylamino-ethoxy)-1H-benzimidazol-4-yloxy]-ethyl}-diethyl-amine |
| 200 | {3-[2-[4-(3,5-Bis-trifluoromethyl-phenoxy)-phenyl]-1-butyl-6-(3-diethylamino-propoxy)-1H-benzoimidazol-4-yloxy]-propyl}-diethyl-amine |
| 201 | {3-[2-[4-(3,5-Bis-trifluoromethyl-phenoxy)-phenyl]-1-butyl-6-(3-diethylamino-propoxy)-1H-benzoimidazol-4-yloxy]-propyl}-diethyl-amine |
| 202 | (3-{1-butyl-6-(3-diethylamino-propoxy)-2-[4-(4-methoxy-phenoxy)-phenyl]-1H-benzoimidazol-4-yloxy}-propyl)-diethyl-amine |
| 203 | 1-Butyl-2-[4-(4-chloro-3-trifluoromethyl-phenoxy)-phenyl]-4,6-bis-(2-pyrrolidin-1-yl-ethoxy)-1H-benzoimidazole |
| 204 | 2-{4-[2-(4-Chloro-phenyl)-ethoxy]-phenyl}-4,6-bis-(2-pyrrolidin-1-yl-ethoxy)-1H-benzoimidazole |
| 205 | 1-Butyl-2-[4-(4-tert-butyl-phenoxy)-phenyl]-4,6-bis-(2-pyrrolidin-1-yl-ethoxy)-1H-benzoimidazole |
| 206 | 1-Butyl-2-[4-(4-fluoro-3-trifluoromethyl-phenoxy)-phenyl]-4,6-bis-(2-pyrrolidin-1-yl-ethoxy)-1H-benzoimidazole |
| 207 | {3-[1-Butyl-2-[4-(3-chloro-phenoxy)-phenyl]-6-(3-diethylamino-propoxy)-1H-benzoimidazol-4-yloxy]-propyl}-diethyl-amine |
| 208 | 2-[5,7-bis-(2-pyrrolidin-1-yl-ethoxy)-1H-benzimidazol-2-yl]-5-[2-(4-chloro-phenyl)-ethoxy]-phenol |
| 209 | 2-[3-(4-tert-butyl-phenoxy)-phenyl]-4,6-bis-(2-pyrrolodin-1-yl-ethoxy)-1H-benzimidazole |
| 210 | (3-{6-(3-Diethylamino-propoxy)-2-[2-(1,1-difluoro-ethyl)-4-(4-fluoro-3-trifluoromethyl-phenoxy)-phenyl]-1H-benzoimidazol-4-yloxy}-propyl)-diethyl-amine |
| 211 | {3-[1-Butyl-2-[4-(4-tert-butyl-phenoxy)-phenyl]-6-(3-diethylamino-propoxy)-1H-benzoimidazol-4-yloxy]-propyl}-diethyl-amine |
| 212 | 2-[4-(4-tert-Butyl-phenoxy)-phenyl]-4,6-bis-(2-pyrrolidin-1-yl-ethoxy)-1H-benzoimidazole |
| 213 | {3-[1-Butyl-2-[3-(4-tert-butyl-phenoxy)-phenyl]-6-(2-pyrrolidin-1-yl-ethoxy)-1H-benzoimidazol-4-yloxy]-propyl}-diethyl-amine |
| 214 | [3-(3-butyl-2-{4-[2-(4-chloro-phenyl)-ethoxy]-phenyl}-6-diethylaminomethyl-3H-benzimidazol-5-yloxy)-propyl]-diethyl-amine |
| 215 | (3-{6-(3-Diethylamino-propoxy)-2-[4-(4-fluoro-3-trifluoromethyl-phenoxy)-phenyl]-1H-benzoimidazol-4-yloxyl}-propyl)-diethyl-amine |
| 216 | (3-{1-butyl-6-(3-diethylamino-propoxy)-2-[4-(4-trifluoromethyl-pyrimidin-2-ylsulfanyl)-phenyl]-1H-benzoimidazol-4-yloxy}-propyl)-diethyl-amine |
| 217 | {3-[6-(3-Diethylamino-propoxy)-2-(3-p-tolyloxy-phenyl)-1H-benzoimidazol-4-yloxy]-propyl}-diethyl-amine |
| 218 | 4-{3-[1-Butyl-4,6-bis-(3-diethylamino-propoxy)-1H-benzoimidazol-2-yl]-phenoxy}-benzonitrile |
| 219 | [3-(3-Butyl-2-{4-[2-(4-chloro-phenyl)-ethoxy]-phenyl}-7-pyrrolidin-1-yl-3H-benzimidazol-5-yloxy)-propyl]-diethyl-amine |
| 220 | {3-[1-butyl-2-[4-(4-chloro-phenylmethanesulfinyl)-phenyl]-6-(3-diethylamino-propoxy)-1H-benzimidazol-4-yloxy]-propyl}-diethyl-amine |
| 221 | (3-{1-butyl-6-(3-diethylamino-propoxy)-2-[4-(naphthalen-2-yloxy)-phenyl]-1H-benzoimidazole-4-yloxy}-propyl)-diethyl-amine |
| 222 | (3-{6-(3-diethylamino-propoxy)-2-[4-(3-trifluoromethyl-phenoxy)-phenyl]-1H-benzimidazol-4-yloxy}-propyl)-diethyl-amine |
| 223 | (3-{1-butyl-6-(3-diethylamino-propoxy)-2-[3-(4-methoxy-phenoxy)-phenyl]-1H-benzimidazol-4-yloxy}-propyl)-diethyl-amine |
| 224 | 2-[3-(3,4-Dichloro-phenoxy)-phenyl]-4,6-bis-(2-pyrrolidin-1-yl-ethoxy)-1H-benzoimidazole |
| 225 | {3-[2-[4-(4-tert-Butyl-phenoxy)-phenyl]-6-(3-diethylamino-propoxy)-1H-benzoimidazol-4-yloxy]-propyl}-diethyl-amine |

-continued

| Example | Name |
|---|---|
| 226 | {3-[3-butyl-2-{4-[2-(4-chloro-phenyl)-ethoxy]-phenyl}-7-[2-(tetrahydro-furan-2-yl)-ethoxy]-3H-benzimidazol-5-yloxy}-propyl)-diethyl-amine |
| 227 | 1-Butyl-2-[4-(3-chloro-phenoxy)-phenyl]-4,6-bis-(2-pyrrolidin-1-yl-ethoxy)-1H-benzoimidazole |
| 228 | [3-(7-Butoxy-3-butyl-2-{4-[2-(4-chloro-phenyl)-ethoxy]-phenyl}-3H-benzoimidazol-5-yloxy)-propyl]-diethyl-amine |
| 229 | 4-{3-[4,6-Bis-(3-diethylamino-propoxy)-1H-benzoimidazol-2-yl]-phenoxy}-benzonitrile |
| 230 | 2-[3-(3,5-Dichloro-phenoxy)-phenyl]-4,6-bis-(2-pyrrolidin-1-yl-ethoxy)-1H-benzoimidazole |
| 231 | {3-[1-butyl-2-(2-{4-[2-(4-chloro-phenyl)-ethoxy]-phenyl}-ethyl)-6-(3-diethylamino-propoxy)-1H-benzimidazol-4-yloxy]-propyl}-diethyl-amine |
| 232 | {3-[1-butyl-6-(3-diethylamino-propoxy)-2-(3-phenoxy-phenyl)-1H-benzimidazol-4-yloxy]-propyl}-diethyl-amine |
| 233 | {3-[1-Butyl-2-[2-(4-chloro-3-trifluoromethyl-phenoxy)-phenyl]-6-(3-diethylamino-propoxy)-1H-benzoimidazol-4-yloxy]-propyl}-diethyl-amine |
| 234 | 2-[4-(4-Chloro-3-trifluoromethyl-phenoxy)-phenyl]-4,6-bis-(2-pyrrolidin-1-yl-ethoxy)-1H-benzoimidazole |
| 235 | {3-[1-Butyl-2-[4-(4-fluoro-3-trifluoromethyl-phenoxy)-phenyl]-6-(2-pyrrolidin-1-yl-ethoxy)-1H-benzoimidazol-4-yloxy]-propyl}-diethyl-amine |
| 236 | [3-(3-butyl-2-{4-[2-(4-chloro-phenyl)-ethoxy]-phenyl}-6-methyl-3H-benzimidazol-5-yloxy)-propyl]-diethyl-amine |
| 237 | {3-[1-butyl-6-(3-diethylamino-propoxy)-2-(4-phenoxy-phenyl)-1H-benzimidazol-4-yloxy]-propyl}-diethyl-amine |
| 238 | 5-[4,6-bis-(3-diethylamino-propoxy)-1H-benzoimidazlo-2-yl]-2-[2-(4-chloro-phenyl)-ethoxy]-phenol |
| 239 | [3-(6-Butoxy-1-butyl-2-{4-[2-(4-chloro-phenyl)-ethoxy]-phenyl}-1H-benzoimidazol-4-yloxy)-propyl]-diethyl-amine |
| 240 | {3-[2-[4-Chloro-2-(4-chloro-3-trifluoromethyl-phenoxy)-phenyl]-6-(3-diethylamino-propoxy)-1H-benzoimidazol-4-yloxy]-propyl}-diethyl-amine |
| 241 | 1-butyl-4-(4-chloro-benzyloxy)-2-{4-[2-(4-chloro-phenyl)-ethoxy]-phenyl}-6-(2-pyrrolidin-1-yl-ethoxy)-1H-benzimidazole |
| 242 | 4-{4-[1-butyl-4,6-bis-(3-diethylamino-propoxy)-1H-benzimidazol-2-yl]-phenoxy}-benzonitrile |
| 243 | [3-(1-Butyl-2-{4-[2-(4-chloro-phenyl)-ethoxy]-phenyl}-6-fluoro-1H-benzoimidazol-4-yloxy)-propyl]-diethyl-amine |
| 244 | (3-{6-(3-diethylamino-propoxy)-2-[3-(4-methoxy-phenoxy)-phenyl]-1H-benzimidazol-4-yloxy}-propyl)-diethyl-amine |
| 245 | (3-{6-(3-diethylamino-propoxy)-2-[4-(4-methoxy-phenoxy)-phenyl]-1H-benzimidazol-4-yloxy}-propyl)-diethyl-amine |
| 246 | {3-[1-butyl-2-[4-(4-chloro-3-fluoro-phenoxy)-phenyl]-6-(3-diethylamino-propoxy)-1H-benzimidazol-4-yl]-propyl}-diethyl-amine |
| 247 | (3-{1-butyl-6-(3-diethylamino-propoxy)-2-[4-(quinolin-8-yloxy)-phenyl]-1H-benzimidazol-4-yloxy}-propyl)-diethyl-amine |
| 248 | {3-[2-[2-(4-chloro-3-trifluoromethyl-phenoxy)-phenyl]-6-(3-diethylamino-propoxy)-1H-benzoimidazol-4-yloxy]-propyl}-diethyl-amine |
| 249 | 2-[{2-[1-Butyl-2-{4-[2-(4-chloro-phenyl)-ethoxy]-phenyl}-6-(2-morpholin-4-yl-ethoxy)-1H-benzoimidazol-4-yloxy]-ethyl}-(2-chloro-ethyl)-amino]-ethanol |
| 250 | (3-{6-(3-Diethylamino-propoxy)-2-[3-(4-fluoro-3-trifluoromethyl-phenoxy)-phenyl]-1H-benzoimidazol-4-yloxy}-propyl)-diethyl-amine |
| 251 | [3-(3-butyl-2-{4-[2-(4-chloro-phenyl)-ethoxy]-phenyl}-7-isopropoxy-3H-benzimidazol-5-yloxy)-propyl]-diethyl-amine |
| 252 | [3-(1-Butyl-2-{4-[2-(4-chloro-phenyl)-ethoxy]-phenyl}-6-cyclopentylmethoxy-1H-benzoimidazol-4-yloxy)-propyl]-diethyl-amine |
| 253 | 1-Butyl-2-{4-[2-(4-chloro-phenyl)-ethoxy]-phenyl}-4,6-bis-(2-morpholin-4-yl-ethoxy)-1H-benzoimidazole |
| 254 | {3-[2-[4-[2-(4-Chloro-phenyl)-ethoxy]-3-(3-diethylamino-propoxy)-phenyl]-6-(3-diethylamino-propoxy)-1H-benzoimidazol-4-yloxy]-propyl}-diethyl-amine |

EXAMPLE 255

{3-[2-[1-butyl-6-(4-tert-butyl-phenoxy)-1H-benzimidazol-2-yl]-5-(3-diethylamino-propoxy)-phenoxy]-propyl}-diethyl-amine To a stirred solution of 2,4-dihydroxybenzaldehyde (10 mmol) in DMSO (50 mL) at rt, solid $Cs_2CO_3$ (45 mmol) was added. A mesylate (prepared from 3-diethylamino-1-propanol and methanesulfonyl chloride, General Procedure P2) (25 mmol) was added to the reaction mixture and heated to 90° C. until the reaction was complete as indicated by LC-MS (~10 h). After cooling to rt, the reaction was quenched by cold $H_2O$ (100 mL), and the resulting mixture was extracted with EtOAc (3×100 mL). The combined EtOAc extracts were washed with brine (3×50 mL) and dried (anhydrous $Na_2SO_4$).

The solvent was removed in vacuo to afford the desired 2,4-bis(3-diethylaminopropoxy)benzaldehyde which was used for further transformation.

To a stirred solution of 2,4-difluoronitrobenzene (50 mmol), Et₃N (100 mmol) and DMF (80 mL) was added dropwise a solution of n-butylamine (51 mmol) in DMF (20 mL) at rt, and the mixture was stirred at rt for 5 h. The reaction was quenched by cold H₂O (100 mL), and the resulting mixture was extracted with EtOAc (4×100 mL). The combined EtOAc extracts were washed with brine (3×60 mL) and dried (anhydrous Na₂SO₄). The solvent was removed in vacuo to afford the desired 2-nbutylamino-4-fluoronitrobenzene which was used for further transformation.

A mixture of 2-n-butylamino-4-fluoronitrobenzene (10 mmol), 4-t-butylphenol (13 mmol), solid K₂CO₃ (30 mmol) and DMF (30 mL) was heated with stirring at 90° C. for 10 h. The reaction was quenched by cold H₂O (50 mL), and the resulting mixture was extracted with EtOAc (3×100 mL). The combined EtOAc extracts were washed with brine (2×50 mL) and dried (anhydrous Na₂SO₄). The solvent was removed in vacuo, and the crude products were purified by silica gel column chromatography (eluting with 10% EtOAc in hexane), giving 2-n-butylamino-4-(4-t-butylphenoxy)nitrobenzene.

The nitro intermediate (2 mmol) obtained above was dissolved in MeOH (10 mL) and hydrogenated in the presence of 10% Pd/C (50 mg) until completion as indicated by LC-MS (~4 h). The reaction mixture was then filtered through a celite pad to remove the catalyst. The MeOH solution containing 2-n-butylamino-4-(4-t-butylphenoxy)aniline was used directly for further transformation.

A solution of 2-n-butylamino-4-(4-t-butylphenoxy)aniline (130 mg, 0.4 mmol) and 2,4-bis(3-diethylaminopropoxy)benzaldehyde obtained above (110 mg, 0.3 mmol) in MeOH (10 mL) was refluxed until the reaction was complete. The solvent was removed in vacuo and the residue was purified by silica gel column chromatography, eluting with 10% MeOH in DCM with a gradual increment of Et₃N (0.5 to 1%), to afford the desired benzimidazole (100 mg).

MS m/z 657 (M+H)⁺

¹H NMR (400 MHz, CDCl₃) of HCl salt of the benzimidazole: δ 0.80 (t, 3H), 1.19 (m, 2H), 1.26 (t, 6H), 1.32 (s, 9H), 1.41 (t, 6H), 1.74 (m, 2H), 2.44 (m, 4H), 3.12-3.39 (m, 12H), 4.21 (t, 2H), 4.29 (m, 4H), 6.68 (br d, 1H), 6.79 (br s, 1H), 6.98 (d, 2H), 7.17 (d, 1H), 7.22 (dd, 1H), 7.35 (d, 1H), 7.40 (d, 2H), 8.06 (d, 1H), 11.4 (br, N.HCl), 11.9 (br, N.HCl) ppm.

EXAMPLE 256

(3-{2-[1-butyl-6-(3-diethylamino-propoxy)-1H-benzimidazol-2-yl]-5-[2-(4-chloro-phenyl)-ethoxy]-phenoxy}-propyl)-diethylamine A solution of 2-(3-diethylaminopropoxy)-4-[2-(4-chlorophenyl)ethoxy]benzaldehyde (synthesized via General Procedures D1 and D2) (429 mg; 1.1 mmol) and 2-(n-butylamino)-4-(3-diethylaminopropoxy)aniline (synthesized via General Procedures G1 and G2 and I) (293 mg; 1 mmol) in ethanol (5 mL) was heated to reflux following General Procedure K. The crude product was purified by silica gel column chromatography using 10% MeOH in DCM with a gradual increment of triethylamine (0.2 to 1.0%) as eluent to afford of (3-{2-[1-butyl-6-(3-diethylamino-propoxy)-1H-benzimidazol-2-yl]-5-[2-(4-chloro-phenyl)-ethoxy]-phenoxy}-propyl)-diethylamine (430 mg)

MS m/z 663 (M+H)⁺.

EXAMPLE 257

(3-{1-butyl-6-(4-tert-butyl-phenoxy)-2-[4-(3-diethylamino-propoxy)-phenyl]-1H-benzimidazol-4-yloxy}propyl)-diethyl-amine To a stirred solution of 4-hydroxybenzaldehyde (20 mmol) in DMSO (80 mL) at rt, solid Cs₂CO₃ (50 mmol) was added. The mesylate prepared from 3-diethylamino-1-propanol and methanesulfonyl chloride, General Procedure P2 (30 mmol) was added to the reaction mixture and heated to 90° C. until the reaction was complete. After cooling to rt, the reaction was quenched by cold H₂O (100 mL), and the resulting mixture was extracted with EtOAc (3×100 mL). The combined EtOAc extracts were washed with brine (3×50 mL) and dried (anhydrous Na₂SO₄). The solvent was removed in vacuo, and the crude product was purified by silica gel column chromatography (eluting with 10% MeOH in DCM+0.5% Et₃N) to afford 4-(3-diethylaminopropoxy)benzaldehyde.

To a stirred solution of 6-(3-diethylaminopropoxy)-2,4-difluoronitrobenzene (11 mmol) and triethylamine (22 mmol) in DMF (20 mL), a solution of n-butylamine (11 mmol) in DMF (8 mL) was added dropwise at rt, and the mixture was stirred at rt for 10 h. The reaction was quenched by cold H₂O (50 mL), and the resulting mixture was extracted with EtOAc (3×100 mL). The combined EtOAc extracts were washed with brine (3×50 mL) and dried (anhydrous Na₂SO₄). The solvent was removed in vacuo to afford the desired 2-n-butylamino-6-(3-diethylaminopropoxy)-4-fluoronitrobenzene which was used for further transformation.

A mixture of 2-n-butylamino-6-(3-diethylaminopropoxy)-4-fluoronitrobenzene obtained above (3 mmol), 4-t-butylphenol (4 mmol), solid K₂CO₃ (9 mmol) and DMF (15 mL) was heated with stirring at 90° C. for 15 h. The reaction was quenched by cold H₂O (30 mL), and the resulting mixture was extracted with EtOAc (3×100 mL). The combined EtOAc extracts were washed with brine (2×50 mL) and dried (anhydrous Na₂SO₄). The solvent was removed in vacuo, and the crude products were purified by silica gel column chromatography (eluting with 10% MeOH in DCM), giving 2-nbutylamino-4-(4-t-butylphenoxy)-6-(3-diethylaminopropoxy)nitrobenzene.

The nitro intermediate (1 mmol) obtained above was dissolved in MeOH (10 mL) and hydrogenated in the presence of 10% Pd/C (40 mg) until completion as indicated by LC-MS (~4 h). The reaction mixture was then filtered to remove the catalyst. The MeOH solution containing 2-n-butylamino-4-(4-t-butylphenoxy)-6-(3-diethylaminopropoxy)aniline was used directly for further transformation.

A solution of 2-n-butylamino-4-(4-t-butylphenoxy)-6-(3-diethylaminopropoxy)-aniline (90 mg, 0.2 mmol) and 4-(3-diethylaminopropoxy)benzaldehyde obtained above (65 mg, 0.25 mmol) in MeOH (10 mL) was refluxed until the reaction was complete as indicated by LC-MS (~10 h). The solvent was removed in vacuo and the residue was purified by silica gel column chromatography, eluting with 10% MeOH in DCM with a gradual increment of Et₃N (0.5 to 1%), to afford the desired benzimidazole (80 mg).

MS m/z 657 (M+H)⁺

¹H NMR (400 MHz, CDCl₃) of HCl salt of the benzimidazole: δ 0.80 (t, 3H), 1.21 (m, 2H), 1.31 (s, 9H), 1.40 (m, 12H), 1.74 (m, 2H), 2.39 (m, 2H), 2.52 (m, 2H), 3.17-3.27 (m, 12H), 3.80 (m, 2H), 4.18 (m, 4H), 6.60 (br s, 1H), 6.62 (br s, 1H), 6.95 (d, 2H), 7.14 (br, 2H), 7.39 (d, 1H), 7.80 (br, 2H), 11.17 (br, N.HCl), 11.83 (br, N.HCl) ppm.

EXAMPLE 258

2-{2,4-bis-[2-(1-methyl-pyrrolidin-2-yl)-ethoxy]-phenyl}-1-butyl-6-(4-tert-butyl-phenoxy)-1H-benzimidazole A solution of 2-n-butylamino-4-(4-t-butylphenoxy)aniline (synthesized via General Procedures J3-J7) (100 mg, 0.3 mmol) and 2,4-bis[2-(1-methyl-2-pyrrolidin-2-yl)-ethoxy] benzaldehyde (synthesized via General Procedure C) (55 mg, 0.15 mmol) in MeOH (10 mL) was subjected to General Procedure K. The solvent was removed in vacuo and the residue was purified by silica gel column chromatography, eluting with 10% MeOH in DCM with a gradual increment of Et$_3$N (0.5 to 1%), to afford the desired benzimidazole (50 mg).

MS m/z 653 (M+H)$^+$ $^1$H NMR (400 MHz, CDCl$_3$): δ 0.73 (t, 3H), 1.10-2.53 (m, 22H), 1.32 (s, 9H), 2.20 (s, 3H), 2.39 (s, 3H), 3.94-3.99 (m, 6H), 6.50 (m, 2H), 6.92 (d, 2H), 6.98 (m, 1H), 7.05 (d, 1H), 7.32 (d, 2H), 7.42 (d, 1H), 7.70 (d, 1H) ppm.

EXAMPLE 259

2-[2,4-bis-(2-pyrrolidin-1-yl)-ethoxy]-phenyl}-1-butyl-6-(4-butyl-phenoxy)-1H-benzimidazole A solution of 2-n-butylamiino-4-(4-n-butylphenoxy) aniline (synthesized via General Procedures G1 and G2 and I) (80 mg, 0.25 mmol) and 2,4-bis(2-pyrrolidin-1-yl-ethoxy) benzaldehyde (synthesized via General Procedure C) (50 mg, 0.15 mmol) was subjected to General procedure K. The solvent was removed in vacuo and the residue was purified by silica gel column chromatography, eluting with 10% MeOH in DCM with a gradual increment of Et$_3$N (0.5 to 1%), to afford the desired benzimidazole (80 mg).

MS m/z 625 (M+H)$^+$ $^1$H NMR (400 MHz, CDCl$_3$): δ0.73 (t, 3H), 0.92 (t, 3H), 1.10 (m, 2H), 1.35 (m, 2H), 1.55-1.60 (m, 4H), 1.64 (m, 4H), 1.83 (m, 4H), 2.39 (m, 4H), 2.58 (t, 2H), 2.65 (m, 4H), 2.73 (t, 2H), 2.93 (t, 2H), 3.96 (t, 2H), 4.07 (t, 2H), 4.16 (t, 2H), 6.60 (br s, 1H), 6.62 (dd, 1H), 6.92 (d, 2H), 6.96 (dd, 1H), 7.04 (d, 1H), 7.12 (d, 2H), 7.40 (d, 1H), 7.70 (d, 1H) ppm.

The following Examples were synthesized according to the Methods employed for Examples 255-259;

| Example | Name |
|---|---|
| 260 | 1-butyl-2-[4-[2-(4-chloro-phenyl)-ethoxy]-2-(2-pyrrolodin-1-yl-ethoxy)-phenyl]-6-(2-pyrrolodin-1-yl-ethoxy)-1H-benzoimidazole |
| 261 | {3-[2-{1-butyl-6-[2-(4-chloro-phenyl)-ethoxy]-1H-benzimidazol-2-yl]-5-(3-diethylamino-propoxy)-phenoxy]-propyl}-diethyl-amine |
| 262 | 2-{2,4-bis-[2-(1-methyl-pyrrolidin-2-yl)-ethoxy]-phenyl}-1-butyl-6-(4-butyl-phenoxy)-1H-benzoimidazole |
| 263 | {3-{2-[1-butyl-5-(4-tert-butyl-phenoxy)-1H-benzimidazol-1-yl]-5-(3-diethylamino-propoxy)-phenoxy]-propyl}-diethyl-amine |
| 264 | 1-Butyl-2-[3-(3,5-dichloro-phenoxy)-phenyl]-4,6-bis-(2-pyrrolidin-1-yl-ethoxy)-1H-benzoimidazole |
| 265 | 2-[2,4-bis-(2-pyrrolidin-1-yl-ethoxy)-phenyl]-1-butyl-6-(4-cyclopentyl-phenoxy)-1H-benzoimidazole |
| 266 | 2-{2,4-bis-[2-(1-methyl-pyrrolidin-2-yl)-ethoxy]-phenyl}-1-butyl-6-(4-cyclopentyl-phenoxy)-1H-benzoimidazole |
| 267 | {3-[2-[1-butyl-6-(4-iospropyl-phenoxy)-1H-benzimidazol-2-yl]-5-(3-diethylamino-propoxy)-phenoxy]-propyl}-diethyl-amine |
| 268 | (2-{1-butyl-6-(2-dimethylamino-ethylsulfanyl)-2-[4-(4-fluoro-3-trifluoromethyl-phenoxy)-2-(2-pyrrolidin-1-yl-ethoxy)-phenyl]-1H-benzoimidazol-4-ylsulfanyl}-ethyl)-dimethyl-amine |
| 269 | 2-[2,4-bis-(2-pyrrolidin-1-yl-ethoxy)-phenyl]-1-butyl-6-(4-tert-butyl-phenoxy)-1H-benzoimidazole |
| 270 | {3-[2-[1-butyl-6-(4-butyl-phenoxy)-1H-benzimidazol-2-yl]-5-(3-diethylamino-propoxy)-phenoxy]-propyl}-diethyl-amine |
| 271 | {3-[2-[1-butyl-6-(4-fluoro-3-trifluoromethyl-phenoxy)-1H-benzimidazol-2-yl]-5-(3-diethylamino-propoxy)-phenoxy]-propyl}-diethyl-amine |
| 272 | 2-[2,4-bis-(2-pyrrolidin-1-yl-ethoxy)-phenyl]-1-butyl-6-(4-isopropyl-phenoxy)-1H-benzoimidazole |
| 273 | 1-Butyl-2-[3-(3,4-dichloro-phenoxy)-phenyl]-4,6-bis-(2-pyrrolidin-1-yl-ethoxy)-1H-benzoimidazole |
| 274 | (3-{3-Butyl-2-[4-(4-fluoro-3-trifluoromethyl-phenoxy)-2-(2-pyrrolidin-1-yl-ethoxy)-phenyl]-3H-benzoimidazol-5-yloxy}-propyl)-diethyl-amine |
| 275 | {3-[2-[1-butyl-6-(4-cyclopentyl-phenoxy)-1H-benzimidazol-2-yl]-5-(3-diethylamino-propoxy)-phenoxy]-propyl}-diethyl-amine |
| 276 | {3-[2-[1-butyl-4-(4-tert-butyl-phenoxy)-1H-benzimidazol-2-yl]-5-(3-diethylamino-propoxy)-phenoxy]-propyl}-diethyl-amine |
| 277 | 2-{2,4-bis-[2-(1-methyl-pyrrolidin-2-yl)-ethoxy]-phenyl}-1-butyl-6-(4-isopropyl-phenoxy)-1H-benzoimidazole |
| 278 | (3-{5-[2-(4-chloro-phenyl)-ethoxy]-2-[6-(3-diethylamino-propoxy)-1-isopropyl-1H-benzimidazol-2-yl]-phenoxy}-propyl)-diethyl-amine |
| 279 | 1-Butyl-2-[4-(4-fluoro-3-trifluoromethyl-phenoxy)-2-(2-pyrrolidin-1-yl-ethoxy)-phenyl]-6-(2-pyrrolidin-1-yl-ethoxy)-1H-benzoimidazole |
| 280 | 1-butyl-2-{4-[2-(4-chloro-phenyl)-ethoxy]-phenyl}-4,6-bis-(1-methyl-piperidin-4-yloxy)-1H-benzoimidazole |

-continued

| Example | Name |
|---|---|
| 281 | {3-[2-[6-(4-tert-butyl-phenoxy)-1H-benzimidazol-2-yl]-5-(3-diethylamino-propoxy)-phenoxy]-propyl}-diethyl-amine |
| 282 | 1-butyl-2-[3-(3,4-dichloro-phenoxy)-phenyl]-4,6-bis-(1-methyl-pyrrolidin-2-ylmethoxy)-1H-benzoimidazole |
| 283 | (3-{3-butyl-2-[4-[2-(4-chloro-phenyl)-ethoxy]-2-(2-diethylamino-ethoxy)-phenyl]-3H-benzimidazol-5-yloxy}-propyl)-diethyl-amine |
| 284 | (3-{2-[1-Butyl-6-(2-imidazol-1-yl-ethoxy)-1H-benzoimidazol-2-yl]-5-[2-(4-chloro-phenyl)-ethoxy]-phenoxy}-propyl)-diethyl-amine |
| 285 | (3-{2-[1-Butyl-6-(2-pyrrolidin-1-yl-ethoxy)-1H-benzoimidazol-2-yl]-5-[2-(4-chloro-phenyl)-ethoxy]-phenoxy}-propyl)-diethyl-amine |
| 286 | {3-[2-(3,5-bis-benzyloxy-phenyl)-3-butyl-3H-benzimidazol-5-yloxy]-propyl}-diethyl-amine |
| 287 | 4,6-bis-(2-azepan-1-yl-ethoxy)-1-butyl-2-[3-(4-tert-butyl-phenoxy)-phenyl]-1H-benzoimidazole |
| 288 | 1-butyl-2-[3-(4-butyl-phenoxy)-phenyl]-4,6-bis-(2-pyrrolidin-1-yl-ethoxy)-1H-benzoimidazole |
| 289 | 1-butyl-2-[3-(4-tert-butyl-phenoxy)-phenyl]-4,6-bis-(1-methyl-pyrrolidin-2-ylmethoxy)-1H-benzoimidazole |
| 290 | (2-{1-butyl-6-(2-dimethylamino-ethylsulfanyl)-2-[3-(3-trifluoromethyl-phenoxy)-phenyl]-1H-benzoimidazole-4-ylsufanyl}-ethyl)-dimethyl-amine |
| 291 | (3-{1-butyl-6-(3-diethylamino-propoxy)-2-[4-(4-isopropyl-phenoxy)-phenyl]-1H-benzimidazol-4-yloxy}-propyl)-diethyl-amine |
| 292 | 4,6-bis-(2-azepan-1-yl-ethoxy)-1-butyl-2-[3-(3,5-dichlorophenoxy)-phenyl]-1H-benzoimidazole |
| 293 | 1-butyl-2-[3-(4-tert-butyl-phenoxy)-phenyl]-4,6-bis-[2-(cyclohexyl-methyl-amino)-ethoxy]-1H-benzoimidazole |
| 294 | {3-[1-butyl-2-[3-(3,5-dichloro-phenoxy)-phenyl]-6-(2-imidazol-1-yl-ethoxy)-1H-benzimidazol-4-yloxy]-propyl}-diethyl-amine |
| 295 | [3-(2-{3,4-bis-[2-(4-chloro-phenyl)-ethoxy]-phenyl}-3-butyl-3H-benzimidazol-5-yloxy)-propyl]-diethyl-amine |
| 296 | 1-butyl-4,6-bis-(1-methyl-piperidin-4-yloxy)-2-[3-(3-trifluoromethyl-phenoxy)-phenyl]-1H-benzoimidazole |
| 297 | 4,6-bis-(2-azepan-1-yl-ethoxy)-1-butyl-2-[3-(3-trifluoromethyl-phenoxy)-phenyl]-1H-benzoimidazole |
| 298 | 1-butyl-2-[3-(3,4-dichloro-phenoxy)-phenyl]-4,6-bis-(1-ethyl-pyrrolidin-2-ylmethoxy)-1H-benzoimidazole |
| 299 | [3-(2-{2-benzyloxy-4-[2-(4-chloro-phenyl)-ethoxy]-phenyl}-3-butyl-3H-benzimidazol-5-yloxy)-propyl]-diethyl-amine |
| 300 | {3-[2-[1-Butyl-6-(3-diethylamino-propoxy)-1H-benzoimidazol-2-yl]-5-(4-fluoro-3-trifluoromethyl-phenoxy)-phenoxy]-propyl}-diethyl-amine |
| 301 | {3-[2-[1-Butyl-6-(2-pyrrolidin-1-yl-ethoxy)-1H-benzoimidazol-2-yl]-5-(4-fluoro-3-trifluoromethyl-phenoxy)-phenoxy]-propyl}-diethyl-amine |
| 302 | 1-butyl-2-[3-(3,4-dimethoxy-phenoxy)-phenyl]-4,6-bis-(2-pyrrolidin-1-yl-ethoxy)-1H-benzoimidazole |
| 303 | (2-{1-butyl-2-{4-[2-(4-chloro-phenyl)-ethoxy]-phenyl}-6-(2-dimethylamino-ethylsulfanyl)-1H-benzoimidazol-4-ylsulfanyl}-ethyl)-dimethyl-amine |
| 304 | 1-butyl-2-[3-(4-tert-butyl-phenoxy)-phenyl]-4,6-bis-(1-ethyl-pyrrolidin-3-yloxy)-1H-benzoimidazole |
| 305 | {3-[2-[3-(3,4-bis-benzyloxy-phenyl)-3-butyl-3H-benzimidazol-5-yloxy]-propyl}-diethyl-amine |
| 306 | (3-{5-[2-(4-chloro-phenyl)-ethoxy]-2-[6-(3-diethylamino-propoxy)-1H-benzimidazol-2-yl]-phenoxy}-propyl)-diethyl-amine |
| 307 | 1-butyl-2-[4-(2-diethylamino-ethoxy)-phenyl]-4,6-bis-[2-(methyl-phenyl-amino)-ethoxy]-1H-benzoimidazole |
| 308 | {3-[3-butyl-2-{4-[2-(4-chlorophenyl)-ethoxy]-phenyl}-7-(pyridin-3-yloxy)-3H-benzimidazol-5-yloxy]-propyl}-diethyl-amine |
| 309 | {2-[1-butyl-2-[3-(3,4-dichloro-phenoxy)-phenyl]-6-(2-diisopropylamino-ethoxy)-1H-benzimidazol-4-yloxy]-ethyl}-diethyl-amine |
| 310 | {3-[3-butyl-2-{4-[2-(4-chloro-phenyl)-ethoxy]-phenyl}-7-(pyridin-3-ylmethoxy)-3H-benzimidazol-5-yloxy]-propyl}-diethyl-amine |
| 311 | 2-[1-butyl-6-(3-diethylamino-propoxy)-1H-benzoimidazlo-2-yl]-5-[2-(4-chloro-phenyl)-ethoxy]-phenol |
| 312 | {3-[3-butyl-2-[2-(4-chloro-phenylsulfanyl)-phenyl]-7-(3-diethylamino-propoxy)-3H-benzimidazol-4-yloxy}-propyl)-diethyl-amine |

-continued

| Example | Name |
|---|---|
| 313 | (3-{1-butyl-6-(3-diethylamino-propoxy)-2-[4-(4-fluoro-2-methoxy-phenoxy)-phenyl]-1H-benzimidazol-4-yloxy}-propyl)-diethyl-amine |
| 314 | [3-(3-butyl-2-{4-[2-(4-chloro-phenyl)-ethoxy]-2-isopropoxy-phenyl}-3H-benzimidazol-5-yloxy)-propyl]-diethyl-amine |
| 315 | {2-[1-butyl-6-(3-diethylamino-propoxy)-1H-benzoimidazlo-2-yl]-5-[2-(4-chloro-phenyl)-ethoxy]-phenoxy}-acetic acid methyl ester |
| 316 | (3-{2-[1-butyl-6-(4-tert-butyl-phenoxy)-1H-benzimidazol-2-yl]-5-[2-(4-chloro-phenyl)-ethoxy]-phenoxy}-propyl)-diethyl-amine |
| 317 | (3-{1-butyl-6-(3-diethylamino-propoxy)-2-[4-(2-isopropoxy-phenoxy)-phenyl]-1H-benzoimidazol-4-yloxy}-propyl)-diethyl-amine |
| 318 | (3-{1-butyl-6-(3-diethylamino-propoxy)-2-[4-(2,3-dimethoxy-phenoxy)-phenyl]-1H-benzimidazol-4-yloxy}-propyl)-diethyl-amine |
| 319 | (3-{3-Butyl-2-[4-[2-(4-chloro-phenyl)-ethoxy]-2-(2-pyrrolidin-1-yl-ethoxy)-phenyl]-3H-benzoimidazol-5-yloxy}-propyl)-diethyl-amine |
| 320 | (2-{1-butyl-6-fluoro-2-[3-(3-trifluoromethyl-phenoxy)-phenyl]-1H-benzoimidazole-4-ylsufanyl}-ethyl)-dimethyl-amine |
| 321 | Methanesulfonic acid 5-[2-(4-chloro-phenyl)-ethoxy]-2-[6-(3-diethylamino-propoxy)-1H-benzoimidazol-2-yl]-phenyl ester |
| 322 | 5-[2-(4-Chloro-phenyl)-ethoxy]-2-[6-(3-diethylamino-propoxy)-1H-benzoimidazol-2-yl]-phenol |
| 323 | {3-[1-butyl-6-(3-diethylamino-propoxy)-2-(4-pyrrolidin-1-yl-phenyl)-1H-benzoimidazol-4-yloxy]-propyl}-diethyl-amine |
| 324 | 1-butyl-2-[3-(4-tert-butyl-phenoxy)-phenyl]-4,6-bis-(1-methyl-piperidin-4-yloxy)-1H-benzimidazole |
| 325 | 1-butyl-2-[3-(3,5-dichloro-phenoxy)-phenyl]-4,6-bis-(2-imidazol-1-yl-ethoxy)-1H-benzoimidazole |
| 326 | [2-(1-butyl-2-{4-[2-(4-chloro-phenyl)-ethoxy]-phenyl}-6-fluoro-1H-benzoimidazol-4-ylsulfanyl)-ethyl]-dimethyl-amine |

EXAMPLE 327

{3-[1-Butyl-2-[4-[2-(4-chloro-phenyl)-ethoxy]-2-(2-(pyrrolidin-1-yl-ethoxy)-phenyl]-6-(3-diethylamino-propoxy)-1H-benzimidazol-4-yloxy]-propyl}-diethyl-amine 4-[2-(4-chloro-phenyl)-ethoxy]-[2-(2-pyrrolidin-1-yl-ethoxy]-benzaldehyde (synthesized via General Procedures D1 and D2) (0.0309, 0.080 mM) and N-butyl-3,5-bis(3-dimethylamino-propoxy)benzene-1,2-diamine (0.035 g, 0.080 mM) were subjected to General Procedure K. After removal of ethanol, the residue was purified on silica gel using 10% MeOH/DCM with 0.1-0.4% Et₃N, yield 0.025 g. LC/MS (m/z): 776 (M+H)⁺

EXAMPLE 328

1-Butyl-2-[4-(4-fluoro-3-trifluoromethyl-phenoxy)-2-(2-pyrrolidin-1-yl-ethoxy)-phenyl]-4,6-bis-(2-pyrrolidin-1-yl-ethoxy)-1H-benzimidazole A solution of 2-butylamino-4,6-bis(2-pyrrolidinyl-1-ethoxy)aniline (synthesized via General Procedures G1 and G2 and H) (78.4 mg, 0.2 mmol) and 2-pyrrolidin-1-yl-ethoxy-4-(4-fluoro-3-trifluoromethyl)phenoxybenzaldehyde (synthesized via General Procedure E) (91 mg, 0.22 mmol) was subjected to General Procedure K. The crude product was purified by silica gel column chromatography using 10% MeOH in DCM with a gradual increment of triethylamine (0.2 to 1.0%) as eluent to afford Example 328 (62 mg).

MS m/z 768 (M+H)⁺.

EXAMPLE 329

1-Butyl-2-[4-(4-Chloro-3-trifluoromethyl-phenoxy)-2-(2-pyrrolidin-1-yl-ethoxy)-phenyl]-4,6-bis-(2-pyrrolidin-1-yl-ethoxy)-1H-benzimidazole

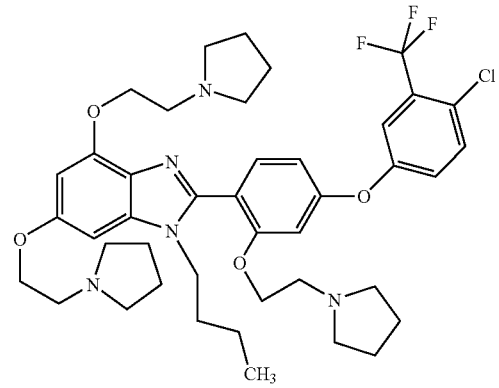

A solution of 2-butylamino-4,6-bis(2-pyrrolidinyl-1-ethoxy)aniline (synthesized via General Procedures G1 and G2 and H) (78.4 mg, 0.2 mmol) and 2-pyrrolidin-1-yl-ethoxy-4-(4-chloro-3-trifluoromethyl)phenoxybenzaldehyde (synthesized via General Procedure E) (91 mg, 0.22 mmol) in ethanol (2 mL) was subjected to General Procedure K. The crude product was purified by silica gel column chromatography using 10% MeOH in DCM with a gradual increment of triethylamine (0.2 to 1.0%) as eluent to afford Example 329 (62.5 mg)

MS m/z 784 (M+H)⁺

EXAMPLE 330

(3-{2-[1-butyl-6-(3-diethylamino-propoxy)-4-(2-pyrrolidin-1-yl-ethoxy)-1H-benzimidazol-2-yl]-5-[2-(4-chloro-phenyl)-ethoxy]-phenoxy}-propyl)-diethyl-amine A solution of 2-(3-diethylaminopropoxy)-4-[2-(4-chlorophenyl)ethoxy]benzaldehyde (synthesized via General Procedure E) (858; 2.2 mmol) and 2-(n-butylamino)-4-(N,N-diethylaminopropoxy)-6-(N-pyrrolidineethoxy)aniline (synthesized via General Procedures J3-J7) (816 mg; 2 mmol) in ethanol (5 mL) was subjected to General Procedure K. The crude product was purified by silica gel column chromatography using 10% MeOH in DCM with a gradual increment of triethylamine (0.2 to 1.0%) as eluent to afford 520 mg (34%) of Example 330.

MS m/z 776 (M+H)$^+$

EXAMPLE 331

(3-{2-[1-butyl-4,6-bis-(3-diethylamino-propoxy)-1H-benzimidazol-2-yl]-5-[2-(4-chloro-phenyl)-ethoxy]-phenoxy}-propyl)-diethyl-amine To a stirred solution of 2-(4-chlorophenyl)ethanol (20.0 mL, 148 mmol), TEA (31.0 mL, 222 mmol) in anhydrous DCM (100 mL) was added dropwise MsCl (12.0 mL, 156 mmol) at 0° C. within 8 min, and stirred at the same temperature for 2 h. The resulting yellow suspension was diluted with DCM (200 mL), washed with cold H$_2$O and brine, and dried. Removal of the solvent afforded the mesylate (33.0 g).

A mixture of the mesylate obtained as above (23.6 g, 100 mmol), 2,4-dihydroxybenzaldehyde (16.6 g, 120 mmol) and KHCO$_3$ (12.0 g, 120 mmol) in anhydrous DMF (150 mL) was heated at 130° C. for 4 h following the general procedure described for disubstitued benzaldehydes. The crude products were purified by flash chromatography (eluting with 10% EtOAc in hexanes), giving 4-(4-chlorophenyl)ethoxysalicylaldehyde (12.5 g) as a white solid.

Methanesulfonyl chloride, General Procedure P2 (2.90 mL, 37.5 mmol) was added dropwise at 0° C. to a stirred solution of 3-diethylaminopropanol (5.75 mL, 38.8 mmol), TEA (7.0 mL, 50.0 mmol) in anhydrous DCM (25 mL), and the mixture was stirred at the same temperature for 1 h, and at rt for an additional 1 h. After the removal of the solvent in vacuo, the solid residue was mixed with the aldehyde formed above (7.0 g, 25.0 mmol), Cs$_2$CO$_3$ (20.4 g, 62.5 mmol) and anhydrous DMSO (100 mL), and the whole mixture was heated at 90° C. for 6 h. following the general procedure described for disubstitued benzaldehydes to obtain oily 2-(3-diethylaminopropoxy)-4-[2-(4-chlorophenyl)ethoxy]benzaldehyde (11.0 g, ~100% yield), which solidified upon standing.

To a stirred solution of 2,4,6-trifluoronitrobenzene (5.31 g, 30 mmol), TEA (8.37 mL, 60 mmol) and DMF (50 mL) was added dropwise a solution of n-butylamine (2.96 mL, 30 mmol) in DMF (20 mL) at rt following General Procedure G1 to obtain crude 2-butylamino-4,6-difluoronitrobenzene (9.0 g). This product was mixed with 3-diethylaminopropanol (11.1 mL, 75 mmol) and anhydrous THF (150 mL), and then powdered KOBu$^t$ (8.5 g, 75 mmol) was added following General Procedure G2 to afford crude 2-butylamino-4,6-di(3-diethylaminopropoxy)nitrobenzene (15.5 g).

The nitro compound formed above (6.8 g, 15 mmol) dissolved in MeOH (90 mL) was hydrogenated following general procedure H and 2-butylamino-4,6-di(3-diethylaminopropoxy)aniline obtained was used directly for the next step.

Example 331 was formed employing phenylenediamine formed above (848 mg; 2 mmol) and 2-(3-diethylaminopropoxy)-4-[2-(4-chlorophenyl)ethoxy]benzaldehyde (858; 2.2 mmol) in ethanol (5 mL) following the general procedure K. The crude product was purified by silica gel column chromatography using 10% MeOH in DCM with a gradual increment of triethylamine (0.2 to 1.0%) to afford 400 mg of Example 331.

MS m/z 792 (M+H)$^+$

EXAMPLE 332

(3-{2-[1-Butyl-4,6-bis-(2-pyrrolidin-1-yl-ethoxy)-1H-benzoimidazol-2-yl]-5-[2-(4-chloro-phenyl)-ethoxy]-phenoxy}-propyl)-diethyl-amine 2-butylamino-4,6-difluoronitrobenzene (9.0 g) was mixed with 1-pyrrolidineethanol (8.81 mL, 75 mmol) and anhydrous THF (150 mL), and then powdered KOBu$^t$ (8.5 g, 75 mmol) was added following general procedures G1 and G2 described for homo disubstitued phenylenediamine to afford crude 2-butylamino-4,6-di(pyrrolidineethoxy)nitrobenzene (13.5 g).

The nitro compound formed above (6.3 g, 15 mmol) dissolved in MeOH (90 mL) was hydrogenated following general procedure H and 2-butylamino-4,6-di(pyrrolidineethoxy)aniline obtained was used directly for the next step.

Example 332 was formed employing phenylenediamine formed above (784 mg; 2 mmol) and 2-(3-diethylaminopropoxy)-4-[2-(4-chlorophenyl)ethoxy]benzaldehyde (858; 2.2 mmol) in ethanol (5 mL) following the general procedure K. The crude product was purified by silica gel column chromatography using 10% MeOH in DCM with a gradual increment of triethylamine (0.2 to 1.0%) as eluent to afford 380 mg of Example 332.

MS m/z 760 (M+H)$^+$

EXAMPLE 333

(3-{1-Butyl-6-(3-diethylamino-propoxy)-2-[4-(4-fluoro-3-trifluoromethyl-phenoxy)-2-(2-pyrrolidin-1-yl-ethoxy)-phenyl]-1H-benzoimidazol-4-yloxy}-propyl)-diethyl-amine A solution of 2,4-difluorobenzaldehyde (2.13 g, 15.0 mmol) in DMF (10 ml) was added dropwise to a precooled (0° C.) solution of sodium 2-pyrrolidinoethoxide in DMF (50 ml), which was made by stirring a mixture of sodium hydride (600 mg, 15.0 mmol, 60% in mineral oil) and N-(2-hydroxyethyl)pyrrolidine (1.72 g, 15.0 mmol). The resulting reaction mixture was warmed to rt and stirred for additional 3 h. To the same reaction flask was introduced potassium carbonate (2.10 g, 15.0 mmol) and 3-fluoro-4-trifluoromethylphenol (2.7 g, 15.0 mmol) and the reaction mixture was heated at 90° C. as described in the General Procedure E for 2-alkoxy-4-aryloxybenzaldehydes. The crude product was purified by silica gel column chromatography using dichloromethane and 5% methanol in dichloromethane as eluent, to give 2-(2-pyrrolidineethoxy)-4-(3-fluoro-4-trifluoromethyl)phenoxybenzaldehyde (2 g) as a brown oil.

MS m/z 399 (M+H)$^+$

Example 333 was formed employing the aldehyde formed above (873 mg; 2.2 mmol) and 2-butylamino-4,6-di(3-diethylaminopropoxy)aniline (848; 2.0 mmol) following the general procedure K. The crude product was purified by silica gel column chromatography using 10% MeOH in DCM with a gradual increment of triethylamine (0.2 to 1.0%) as eluent to afford 390 mg of Example 333.

MS m/z 800 (M+H)$^+$

EXAMPLE 334

(3-[1-Butyl-2-[4-(4-fluoro-3-trifluoromethyl-phenoxy)-2-(2-pyrrolidin-1-yl-ethoxy)-phenyl]-6-(2-pyrrolidin-1-yl-ethoxy)-1H-benzoimidazol-4-yloxy]-propyl}-diethyl-amine MsCl (1.4 mL, 18.0 mmol) was added dropwise at 0° C. to a stirred solution of pyrrolidineehanol (1.90 mL, 16.0 mmol), TEA (2.8 mL, 20.0 mmol) in anhydrous DCM (20 mL), and the mixture was stirred at rt for 1 h. After the removal of the solvent in vacuo, the solid residue was mixed with 3,5-difluoro-4-nitrophenol (1.75 g; 10 mmol) and K2CO3 (5.5 g; 40 mmol) following General Procedure F1. The product, 2,6-difluoro-4-(N-pyrrolidineethoxy)nitrobenzene (1.5 g) was used directly To a stirred solution of 2,6-difluoro-4-(N-pyrrolidineethoxy)nitrobenzene obtained above (1.4 g; 5.1 mmol) and triethylamine (1.4 mL; 10.0 mmol) in DMF (10 mL), a solution of n-butylamine (505 μL; 5.1 mmol) in DMF (3 mL) was added according to General Procedure G1. The crude product, 2-(n-butylamino)-4-(N-pyrrolidineethoxy)-6-fluoronitrobenzene. (1.5 g) was used for further transformation without any purification.

A solution of 3-diethylaminopropanol (652 μL; 4.4 mmol) in anhydrous THF 4.4 mL was added with powdered KOBu$^t$ (493 mg; 4.4 mmol) and stirred at rt for 5 min. This solution was added dropwise to a stirred solution of 2-(n-butylamino)-4-(N-pyrrolidineethoxy)-6-fluoronitrobenzene (1.32 g; 4.0 mmol) in anhydrous THF (10 mL) according to General Procedure G2. The crude product, 2-(n-butylamino)-4-(N-pyrrolidineethoxy)-6-(N,N-diethylaminopropoxy)nitrobenzene. (1.5 g) was used directly.

The nitro compound formed above (1.31 g, 4 mmol) dissolved in MeOH (20 mL) was hydrogenated following general procedure H. The proiduct obtained (1.15 g) was used directly for the next step.

Example 334 was formed employing phenylenediamine formed above (816 mg; 2 mmol) and 2-(2-pyrrolidineethoxy)-4-(3-fluoro-4-trifluoromethyl)phenoxybenzaldehyde (873 mg; 2.2 mmol) in ethanol (5 mL) following general procedure K. The crude product was purified by silica gel column chromatography using 10% MeOH in DCM with a gradual increment of triethylamine (0.2 to 1.0%) as eluent to afford 375 mg of Example 334.

MS m/z 784 (M+H)$^+$

EXAMPLE 335

{3-[2-[1-Butyl-6-(3-diethylamino-propoxy)-4-(2-pyrrolidin-1-yl-ethoxy)-1H-benzoimidazol-2-yl]-5-(4-fluoro-3-trifluoromethyl-phenoxy)-phenoxy]-propyl}-diethyl-amine A solution of 2,4-difluorobenzaldehyde (2.13 g, 15.0 mmol) in DMF (10 ml) was added dropwise to a precooled (0° C.) solution of sodium 3-diethylaminopropoxide in DMF (50 ml), which was made by stirring a mixture of sodium hydride (600 mg, 15.0 mmol, 60% in mineral oil) and 3-diethylaminopropanol (1.97 g, 15.0 mmol). The resulting reaction mixture was warmed to rt and stirred for additional 3 h. To the same reaction flask was introduced potassium carbonate (2.10 g, 15.0 mmol) and 3-fluoro-4-trifluoromethylphenol (2.7 g, 15.0 mmol) and the reaction mixture was heated at 90° C. as described general procedure E. The crude product was purified by silica gel column chromatography using dichloromethane and 5% methanol in dichloromethane as eluent, to give 2-(3-diethylaminopropoxy)-4-(3-fluoro-4-trifluoromethyl)phenoxybenzaldehyde (2.2 g).

Methanesulfonyl chloride (General Procedure P2) (1.55 mL, 20.0 mmol) was added dropwise at 0° C. to a stirred solution of 3-diethylaminopropanol (2.70 mL, 18.0 mmol), TEA (2.8 mL, 20.0 mmol) in anhydrous DCM (30 mL), and the mixture was stirred at rt for 1 h. After the removal of the solvent in vacuo, the solid residue was mixed with 3,5-difluoro-4-nitrophenol (2.65 g; 15 mmol) and K$_2$CO$_3$ (6.9 g; 50 mmol) according to General Procedure F1. The crude product, 2,6-difluoro-4-(3-diethylaminopropoxy)nitrobenzene (3.9 g) was used for further transformation.

To a stirred solution of 2,6-difluoro-4-(3-diethylaminopoxy)nitrobenzene obtained above (1.9 g; 6.6 mmol) and triethylamine (1.4 mL; 10.0 mmol) in DMF (12 mL), a solution of n-butylamine (656 μL; 6.6 mmol) in DMF (4 mL) was added dropwise at rt within 15 min, and the rest was followed as described in the general methods. The crude product, 2-(n-butylamino)-4-(3-diethylaminopropoxy)-6-fluoronitrobenzene (2.0 g) was used for further transformation without any purification.

A solution of 3-diethylaminopropanol (516 L; 4.4 mmol) in anhydrous THF 4.4 mL was added with powdered KOBu$^t$ (493 mg; 4.4 mmol) and stirred at room temperature for 5 min. This solution was added dropwise to a stirred solution of 2-(n-butylamino)-4-(3-diethylaminopropoxy)-6-fluoronitrobenzene (1.37 g; 4.0 mmol) in anhydrous THF (10 mL) at 0° C. under a N$_2$ stream. The reaction mixture was maintained at 0° C. for 1 h at which time the reaction was complete the rest was followed as described in the general methods. The crude product, 2-(n-butylamino)-4-(3-diethylaminopropoxy)-6-(N-pyrrolidineethoxy)nitrobenzene. (1.6 g) was used for further transformation without any purification.

The nitro compound formed above (1.31 g, 4 mmol) dissolved in MeOH (20 mL) was hydrogenated following the general procedure and 2-(n-butylamino)-4-(N-pyrrolidineethoxy)-6-(N,N-diethylaminopropoxy)aniline (1.15 g) obtained was used directly for the next step reaction without further purification.

Example 335 was formed employing phenylenedimaine formed above (816 mg; 2 mmol) and 2-(3-diethylaminopropoxy)-4-(3-fluoro-4-trifluoromethyl)phenoxybenzaldehyde (910 mg; 2.2 mmol) in ethanol (5 mL) following the general procedure. The crude product was purified by silica gel column chromatography using 10% MeOH in DCM with a gradual increment of triethylamine (0.2 to 1.0%) as eluent to afford 380 mg of Example 335.

MS m/z 800 (M+H)$^+$

EXAMPLE 336

{3-[2-[1-Butyl-4,6-bis-(2-pyrrolidin-1-yl-ethoxy)-1H-benzoimidazol-2-yl]-5-(4-fluoro-3-trifluoromethyl-phenoxy)-phenoxy]-propyl}-diethyl-amine A solution of 2,4-difluorobenzaldehyde (2.13 g, 15.0 mmol) in DMF (10 ml) was added dropwise to a precooled (0° C.) solution of sodium 3-dimethylaminopropoxide in DMF (50 ml), which was made by stirring a mixture of sodium hydride (600 mg, 15.0 mmol, 60% in mineral oil) and 3-dimethylaminopropanol (1.55 g, 15.0 mmol). The resulting reaction mixture was warmed to rt and stirred for additional 3 h. To the same reaction flask was introduced potassium carbonate (2.10 g, 15.0 mmol) and 3-fluoro-4-trifluoromethylphenol (2.7 g, 15.0 mmol) and the reaction mixture was heated at 90° C. as described in General Procedure E for 2-alkoxy-4-aryloxybenzaldehydes. The crude product was purified by silica gel column chromatography using dichloromethane and 5% methanol in dichloromethane as eluent, to give 2-(3-dimethylaminopropoxy)-4-(3-fluoro-4-trifluoromethyl)phenoxybenzaldehyde (2.0 g).

Example 336 was formed employing the aldehyde formed above (823 mg; 2.2 mmol) and 2-butylamino-4,6-di(pyrrolidineethoxy)aniline (784; 2.0 mmol) in ethanol (5 mL) following General Procedure K. The crude product was purified by silica gel column chromatography using 10% MeOH in DCM with a gradual increment of triethylamine (0.2 to 1.0%) as eluent to afford 380 mg of Example 336.

MS m/z 784 (M+H)+

EXAMPLE 337

{3-[3-butyl-2-[4-[2-(4-chloro-phenyl)-ethoxy]-2-(2-pyrrolidin-1-yl-ethoxy)-phenyl}-7-(2-pyrrolidin-1-yl-ethoxy)-3H-benzimidazol-5-yloxy]-propyl}-diethyl-amine A solution of 2,4-difluorobenzaldehyde (2.13 g, 15.0 mmol) in DMF (10 ml) was added dropwise to a precooled (0° C.) solution of sodium 3-dimethylaminopropoxide in DMF (50 ml), which was made by stirring a mixture of sodium hydride (600 mg, 15.0 mmol, 60% in mineral oil) and 3-dimethylaminopropanol (1.55 g, 15.0 mmol). The resulting reaction mixture was warmed to rt and stirred for additional 3 h. To the same reaction flask was introduced potassium carbonate (2.10 g, 15.0 mmol) and 3-fluoro-4-trifluoromethylphenol (2.7 g, 15.0 mmol) and the reaction mixture was heated at 90° C. as described in General Procedure E for 2-alkoxy-4-aryloxybenzaldehydes. The crude product was purified by silica gel column chromatography using dichloromethane and 5% methanol in dichloromethane as eluent, to give 2-(3-dimethylaminopropoxy)-4-(3-fluoro-4-trifluoromethyl)phenoxybenzaldehyde (2.0 g).

Example 337 was formed employing the aldehyde formed above (823 mg; 2.2 mmol) and 2-butylamino-4,6-di(pyrrolidineethoxy)aniline (784; 2.0 mmol) in ethanol (5 mL) following General Procedure K. The crude product was purified by silica gel column chromatography using 10% MeOH in DCM with a gradual increment of triethylamine (0.2 to 1.0%) as eluent to afford 380 mg of Example 337.

MS m/z 759 (M+H)+

EXAMPLE 338

(3-{2-[1-Butyl-4-(3-diethylamino-propoxy)-6-(2-pyrrolidin-1-yl-ethoxy)-1H-benzoimidazol-2-yl]-5-[2-(4-chloro-phenyl)-ethoxy]-phenoxy}-propyl)-diethyl-amine 2-(3-diethylaminopropoxy)-4-[2-(4-chlorophenyl)ethoxy]benzaldehyde (858; 2.2 mmol) and 2-(n-butylamino)-4-(N-pyrrolidineethoxy)-6-(N,N-diethylaminopropoxy) aniline (816 mg; 2 mmol) were condensed to form the benzimidazole following General Procedure K. The crude product was purified by silica gel column chromatography using 10% MeOH in DCM with a gradual increment of triethylamine (0.2 to 1.0%) as eluent to afford 390 mg of Example 338.

MS m/z 776 (M+H)+

The following Examples were synthesized according to the Methods employed for Examples 327-338;

| Example | Name |
|---|---|
| 339 | {3-[1-butyl-2-[4-(3,4-dichloro-phenoxy)-2-(2-pyrrolidin-1-yl-ethoxy)-phenyl]-6-(3-diethylamino-propoxy)-1H-benzimidazol-4-yloxy]-propyl}-diethyl-amine |
| 340 | {3-[2-[2,4-bis-(3-diethylamino-propoxy)-phenyl]-1-butyl-6-(4-tert-butyl-phenoxy)-1H-benzoimidazol-4-yloxy]-propyl}-diethyl-amine |
| 341 | {3-[1-butyl-2-[4-[2-(4-chloro-phenyl)-ethoxy]-2-(pyridin-2-ylmethoxy)-phenyl]-6-(3-diethylamino-propoxy)-1H-benzimidazol-4-yl]-phenyl}-diethyl-amine |
| 342 | {3-[2-[4-[2-(4-Chloro-phenyl)-ethoxy]-2-(2-pyrrolidin-1-yl-ethoxy)-phenyl]-6-(3-diethylamino-propoxy)-1H-benzimidazol-4-yloxy]-propyl}-diethyl-amine |
| 343 | 1-Butyl-2-[4-[2-(4-chloro-phenyl)-ethoxy]-2-(2-pyrrolidin-1-yl-ethoxy)-phenyl]-4,6-bis-(2-pyrrolidin-1-yl-ethoxy)-1H-benzoimidazole |
| 344 | {3-[1-Butyl-2-[4-(4-chloro-3-trifluoromethyl-phenoxy)-2-(2-pyrrolidin-1-yl-ethoxy)-phenyl]-6-(3-diethylamino-propoxy)-1H-benzoimidazol-4-yloxy]-propyl}-diethyl-amine |
| 345 | (3-{6-(3-Diethylamino-propoxy)-2-[4-(4-fluoro-3-trifluoromethyl-phenoxy)-2-(2-pyrrolidin-1-yl-ethoxy)-phenyl]-1H-benzoimidazol-4-yloxy}-propyl)-diethyl-amine |
| 346 | {3-[2-[1-Butyl-4-(3-diethylamino-propoxy)-6-(2-pyrrolidin-1-yl-ethoxy)-1H-benzoimidazol-2-yl]-5-(4-fluoro-3-trifluoromethyl-phenoxy)-phenoxy]-propyl}-diethyl-amine |
| 347 | {3-[3-Butyl-2-[4-(4-fluoro-3-trifluoromethyl-phenoxy)-2-(2-pyrrolidin-1-yl-ethoxy)-phenyl]-7-(2-pyrrolidin-1-yl-ethoxy)-3H-benzoimidazol-5-yloxy]-propyl}-diethyl-amine |
| 348 | {3-[1-butyl-2-[4-[2-(4-chloro-phenyl)-ethoxy]-2-(2-pyrrolidin-1-yl-ethoxy)-phenyl]-6-(2-pyrrolidin-1-yl-ethoxy)-1H-benzimidazol-4-yloxy]-propyl}-diethyl-amine |
| 349 | {3-[2-[1-butyl-4,6-bis-(2-pyrrolodin-1-yl-ethoxy)-1H-benzimidazol-2-yl]-5-(4-fluoro-3-trifluoromethyl-phenoxy)-phenyl]-propyl}-diethyl-amine |

-continued

| Example | Name |
|---|---|
| 350 | {3-[1-butyl-2-{4-[2-(4-chloro-phenyl)-ethoxy]-3-diethylaminomethyl-phenyl}-6-(3-diethylamino-propoxy)-1H-benzimidazol-4-yloxy]-propyl}-diethyl-amine |
| 351 | {3-[2-[4-[2-(4-chloro-phenyl)-ethoxy]-2-(pyridin-2-ylmethoxy)-phenyl]-6-(3-diethylamino-propoxy)-1H-benzimidazol-4-yl]-propyl}-diethyl-amine |
| 352 | 3-(7-Butoxy-3-butyl-2-{4-[2-(4-chloro-phenyl)-ethoxy]-2-cyclopentylmethoxy-phenyl}-3H-benzoimidazol-5-yloxy)-propan-1-ol |
| 353 | 3-(7-Butoxy-2-{4-[2-(4-chloro-phenyl)-ethoxy]-2-cyclopentylmethoxy-phenyl}-3H-benzoimidazol-5-yloxy)-propan-1-ol |
| 354 | (3-{1-Butyl-6-(3-diethylamino-propoxy)-2-[4-(4-fluoro-3-trifluoromethyl-phenoxy)-2-(pyridin-2-ylmethoxy)-phenyl]-1H-benzoimidazol-4-yloxy}-propyl)-diethyl-amine |
| 355 | {3-[2-[1-Butyl-4,6-bis-(3-diethylamino-propoxy)-1H-benzoimidazol-2-yl]-5-(4-fluoro-3-trifluoromethyl-phenoxy)-phenoxy]-propyl}-diethyl-amine |
| 356 | 2-(3,5-bis-benzyloxy-phenyl)-1-butyl-4,6-bis-(2-pyrrolodin-1-yl-ethoxy)-1H-benzimidazole |
| 357 | {3-[2-[1-butyl-4,6-bis-(3-diethylamino-propoxy)-1H-benzimidazol-2-yl]-5-(4-fluoro-3-trifluoromethyl-phenoxy)-phenyl]-propyl}-diethyl-amine |
| 358 | 1-butyl-2-[4-[2-(4-chloro-phenyl)-ethoxy]-2-(2-pyrrol-1-yl-ethoxy)-phenyl]-4,6-bis-(2-pyrrolodin-1-yl-ethoxy)-1H-benzoimidazole |
| 359 | {3-[2-{4-[2-(4-chloro-phenyl)-ethoxy]-2-(3-diethylamino-propoxy)-phenyl}-6-(3-diethylamino-propoxy)-1H-benzimidazol-4-yloxy]-propyl}-diethyl-amine |
| 360 | {3-[1-Butyl-2-[4-[2-(4-chloro-phenyl)-ethoxy]-2-(pyridin-3-ylmethoxy)-phenyl]-6-(3-diethylamino-propoxy)-1H-benzoimidazol-4-yloxy]-propyl}-diethyl-amine |
| 361 | (3-{3-Butyl-2-[4-[2-(4-chloro-phenyl)-ethoxy]-2-(3-diethylamino-propoxy)-phenyl]-7-isopropoxy-3H-benzoimidazol-5-yloxy}-propyl)-diethyl-amine |
| 362 | {3-[1-Butyl-2-[4-[2-(4-chloro-phenyl)-ethoxy]-2-(pyridin-4-ylmethoxy)-phenyl]-6-(3-diethylamino-propoxy)-1H-benzoimidazol-4-yloxy]-propyl}-diethyl-amine |
| 363 | {3-[2-[4-[2-(4-Chloro-phenyl)-ethoxy]-2-(pyridin-4-ylmethoxy)-phenyl]-6-(3-diethylamino-propoxy)-1H-benzoimidazol-4-yloxy]-propyl}-diethyl-amine |
| 364 | 1-Butyl-2-[4-(4-fluoro-3-trifluoromethyl-phenoxy)-2-(pyridin-2-ylmethoxy)-phenyl]-4,6-bis-(2-pyrrolidin-1-yl-ethoxy)-1H-benzoimidazole |
| 365 | 2-[4-[2-(4-chloro-phenyl)-ethoxy]-2-(2-pyrrolidin-1-yl-ethoxy)-phenyl]-5,7-bis-(2-pyrrolidin-1-yl-ethoxy)-1H-benzimidazole |
| 366 | {3-[1-Butyl-2-{4-[2-(4-chloro-phenyl)-ethoxy]-2-methoxy-phenyl}-6-(3-diethylamino-propoxy)-1H-benzoimidazol-4-yloxy]-propyl}-diethyl-amine |
| 367 | {3-[2-{4-[2-(4-Chloro-phenyl)-ethoxy]-2-methoxy-phenyl}-6-(3-diethylamino-propoxy)-1H-benzoimidazol-4-yloxy]-propyl}-diethyl-amine |
| 368 | (3-{1-Butyl-2-[4-[2-(4-chloro-phenyl)-ethoxy]-2-(3-diethylamino-propoxy)-phenyl]-6-isopropoxy-1H-benzoimidazol-4-yloxy}-propyl)-diethyl-amine |
| 369 | {3-[1-Butyl-2-[4-(4-chloro-3-methyl-phenoxy)-2-(pyridin-2-ylmethoxy)-phenyl]-6-(3-diethylamino-propoxy)-1H-benzoimidazol-4-yloxy]-propyl}-diethyl-amine |
| 370 | 1-Butyl-2-[4-(4-chloro-3-trifluoromethyl-phenoxy)-2-cyclopentylmethoxy-phenyl]-4,6-bis-(2-pyrrolidin-1-yl-ethoxy)-1H-benzoimidazole |
| 371 | (2-{1-butyl-6-(2-dimethylamino-ethoxy)-2-[4-(4-fluoro-3-trifluoromethyl-phenoxy)-2-(2-pyrrolidin-1-yl-ethoxy)-phenyl]-1H-benzoimidazole-4-yloxy}-ethyl)-dimethyl-amine |
| 372 | 2-[1-butyl-4,6-bis-(3-diethylamino-propoxy)-1H-benzimidazol-2-yl]-5-[2-(4-chloro-phenyl)-ethoxy]-phenol |
| 373 | 1-Butyl-2-[4-(4-chloro-3-methyl-phenoxy)-2-(pyridin-2-ylmethoxy)-phenyl]-4,6-bis-(2-pyrrolidin-1-yl-ethoxy)-1H-benzoimidazole |
| 374 | 2-[4-(4-Chloro-3-trifluoromethyl-phenoxy)-2-cyclopentylmethoxy-phenyl]-4,6-bis-(2-pyrrolidin-1-yl-ethoxy)-1H-benzoimidazole |
| 375 | 2-[4-(4-Fluoro-3-trifluoromethyl-phenoxy)-2-(2-pyrrolidin-1-yl-ethoxy)-phenyl]-4,6-bis-(2-pyrrolidin-1-yl-ethoxy)-1H-benzoimidazole |
| 376 | {3-[2-(3,5-bis-benzyloxy-phenyl)-1-butyl-6-(3-diethylamino-propoxy)-1H-benzimidazol-4-yloxy]-propyl}-diethyl-amine |
| 377 | (3-{1-butyl-6-(3-dimethylamino-propoxy)-2-[4-(3-fluoro-phenoxy)-2-(2-pyrrolidin-1-yl-ethoxy)-phenyl]-1H-benzoimidazole-4-yloxy}-propyl)-diethyl-amine |
| 378 | {3-[2-{1-butyl-4-(4-chloro-benzyloxy)-6-(2-pyrrolidin-1-yl-ethoxy)-1H-benzimidazol-2-yl]-5-[2-(4-chloro-phenyl)-ethoxy]-phenoxy)-propyl)-diethyl-amine |
| 379 | {3-[2-{4-[2-(4-chloro-phenyl)-ethoxy]-2-(3-diethylamino-propoxy)-phenyl}-6-(3-diethylamino-propoxy)-3H-benzimidazol-4-yloxy]-propyl}-diethyl-amine |

| Example | Name |
|---|---|
| 380 | {3-[2-[4-(3,4-dichloro-phenoxy)-2-(2-pyrrolidin-1-yl-ethoxy)-phenyl]-6-(3-diethylamino-propoxy)-1H-benzimidazol-4-yloxy]-propyl}-diethyl-amine |
| 381 | {3-[1-Butyl-2-[4-(4-chloro-3-trifluoromethyl-phenoxy)-2-cyclopentylmethoxy-phenyl]-6-(3-diethylamino-propoxy)-1H-benzoimidazol-4-yloxy]-propyl}-diethyl-amine |
| 382 | {3-[2-[4-(4-chloro-3-trifluoromethyl-phenoxy)-2-cyclopentylmethoxy-phenyl]-6-(3-diethylamino-propoxy)-1H-benzimidazol-4-yloxy]-propyl}-diethyl-amine |
| 383 | (3-{1-butyl-6-(4-tert-butyl-phenoxy)-2-[4-[2-(4-chloro-phenyl)-ethoxy]-2-(3-diethylamino-propoxy)-phenyl]-1H-benzimidazol-4-yloxy}-propyl)-diethyl-amine |
| 384 | 2-{2,4-bis-[2-(4-chloro-phenyl)-ethoxy]-phenyl}-1-butyl-4,6-bis-(2-pyrrolidin-1-yl-ethoxy)-1H-benzimidazole |
| 385 | (2-{1-butyl-6-(2-dimethylamino-ethoxy)-2-[4-(3-fluoro-phenoxy)-2-(2-pyrrolidin-1-yl-ethoxy)-phenyl]-1H-benzimidazole-4-yloxy}-ethyl)-dimethyl-amine |
| 386 | {3-[2-[4-(3,5-bis-trifluoromethyl-phenoxy)-2-(2-pyrrolidin-1-yl-ethoxy)-phenyl]-1-butyl-6-(3-diethylamino-propoxy)-1H-benzimidazol-4-yloxy]-propyl}-diethyl-amine |
| 387 | {3-[1-butyl-2-[4-[2-(4-chloro-phenyl)-ethoxy]-2-(2-pyrrolidin-1-yl-ethoxy)-phenyl]-6-(3-diethylamino-propoxy)-1H-benzimidazol-4-yloxy]-propyl}-diethyl-amine |
| 388 | (3-{2-(1-Butyl-4,6-diisopropoxy-1H-benzoimidazol-2-yl)-5-[2-(4-chloro-phenyl)-ethoxy]-phenoxy}-propyl)-diethyl-amine |
| 389 | {3-[1-butyl-2-{3-[2-(4-chloro-phenyl)-ethoxy]-4-diethylaminomethyl-phenyl}-6-(3-diethylamino-propoxy)-1H-benzimidazol-4-yloxy]-propyl}-diethyl-amine |
| 390 | (3-{1-Butyl-6-(3-diethylamino-propoxy)-2-[4-fluoro-2-(2-pyrrolidin-1-yl-ethoxy)-phenyl]-1H-benzoimidazol-4-yloxy}-propyl)-diethyl-amine |
| 391 | (2-{1-butyl-6-fluoro-2-[4-(4-fluoro-3-trifluoromethyl-phenoxy)-2-(2-pyrrolidin-1-yl-ethoxy)-phenyl]-1H-benzoimidazol-4-ylsulfanyl}-ethyl)-dimethyl-amine |
| 392 | {3-[1-Butyl-2-[4-[2-(4-chloro-phenyl)-ethoxy]-3-(3-diethylamino-propoxy)-phenyl]-6-(3-diethylamino-propoxy)-1H-benzoimidazol-4-yloxy]-propyl}-diethyl-amine |

EXAMPLE 393

(4-benzyloxy-benzyl)-[1-butyl-6-(3-diethylamino-propoxy)-1-H-benzimidazol-2-ylmethyl]-hexyl-amine

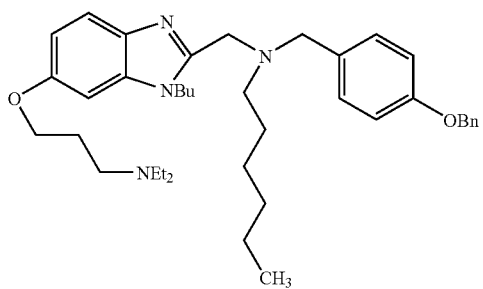

To 2-butylamino-4-(3-diethylaminopropoxy)aniline (3.44 g; 11.7 mmol) and BOC-glycine (2.46 g, 14.1 mmol) in DCM (20 mL) was added DCC (2.90 g, 14.1 mmol) and the reaction mixture was stirred for 4 h. The solid was removed by filtration and the filtrate was concentrated to afford the desired product. The crude product was used for further transformation without any purification.

To the product (11.7 mmol) obtained above in dioxane (7.5 mL) was added acetic acid (2.5 mL) and the reaction mixture was heated at 80° C. until the reaction was complete. Saturated sodium bicarbonate was added and the mixture was extracted with EtOAc. The combined organic layer was washed with water and brine, dried over sodium sulfate. Evaporation of the solvent in vacuo afforded desired 1-butyl-2-boc-aminomethyl-6-(3-diethylaminopropxy)-1-H-benzimidazole. The product obtained was treated with 4 N HCl in dioxane according to General Procedure H to give 1-butyl-2-aminomethyl-6-(3-diethylaminopropxy)-1-H-benzimidazole hydrochloride.

To 1-butyl-2-aminomethyl-6-(3-diethylaminopropxy)-1-H-benzimidazole (1.0 mmol) in DCM (8 mL) were added Et$_3$N (3.0 mmol) and 4-benzoxybenzaldehyde (1.0 mmol) and the mixture was stirred for 4 h, then NaBH(OAc)$_3$ (4.0 mmol) was added and stirred for another 4 h, then sodium bicarbonate was added and the mixture was extracted with EtOAc. The combined organic layer was washed with brine, and dried over sodium sulfate. The crude product was purified by silica gel column chromatography using DCM with a gradual increment of MeOH (1% to 10%) as eluent to afford 1-butyl-2-(4-benzyloxy-benzyl)-aminomethyl-6-(3-diethylaminopropoxy)-1-H-benzimidazole.

To 1-butyl-2-(4-benzyloxy-benzyl)-aminomethyl-6-(3-diethylaminopropxy)-1-H-benzimidazole (16 mg, 0.03 mmol) in DCM (2 mL) were added hexanal (8.3 mg, 0.083 mmol) and the mixture was stirred for 10 min, then NaBH(OAc)$_3$ (32 mg, 0.15 mmol) was added and stirred for 3 h, then sodium bicarbonate was added and the mixture was extracted with EtOAc (3×10 mL). The combined organic layer was washed with brine, and dried over sodium sulfate. The crude product was purified by silica gel column chromatography using DCM with a gradual increment of MeOH (1% to 5%) as eluent to afford 14 mg of Example 393.

MS m/z 613 [M+H]$^+$

EXAMPLE 394

(4-benzyloxy-benzyl)-[1-butyl-6-(3-diethylamino-propoxy)-1-H-benzimidazol-2-ylmethyl]-isobutyl-amine

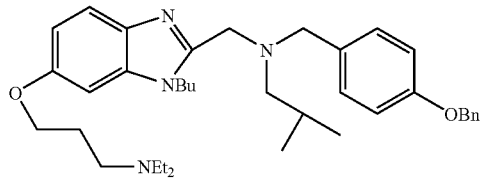

To 1-butyl-2-(4-benzyloxy-benzyl)-aminomethyl-6-(3-diethylaminopropxy)-1-H-benzimidazole (16 mg, 0.03 mmol) in DCM (2 mL) were added isbutrylaldehyde (8.6 mg, 0.10 mmol) and the mixture was stirred for 10 min, then NaBH(OAc)$_3$ (32 mg, 0.15 mmol) was added and stirred for 3 h, then sodium bicarbonate was added and the mixture was extracted with EtOAc. The combined organic layer was washed with brine, and dried over sodium sulfate. The crude product was purified by silica gel column chromatography using DCM with a gradual increment of MeOH (1% to 5%) as eluent to afford 12 mg of Example 394.

MS m/z 585 [M+H]$^+$

EXAMPLE 395

[3-(2-[(4-benzyloxy-benzyl)-cyclopentylmethyl-amino]-methyl}-3-butyl-3-H-benzimidazol-5-yloxy)-propyl]-diethylamine

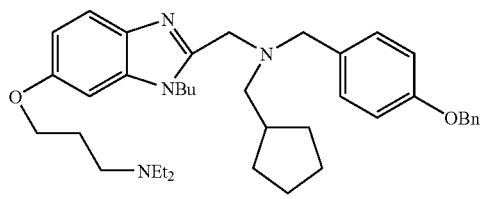

To 1-butyl-2-(4-benzyloxy-benzyl)-aminomethyl-6-(3-diethylaminopropxy)-1-H-benzimidazole (16 mg, 0.03 mmol) in DCM (2 mL) were added cyclopentyl carboxaldehyde (11 mg, 0.10 mmol) and the mixture was stirred for 10 min, then NaBH(OAc)3 (32 mg, 0.15 mmol) was added and stirred for 3 h, then sodium bicarbonate was added and the mixture was extracted with EtOAc (3×10 mL). The combined organic layer was washed with brine, and dried over sodium sulfate. The crude product was purified by silica gel column chromatography using DCM with a gradual increment of MeOH (1% to 5%) as eluent to afford 8.0 mg of Example 395.

MS m/z 611 [M+H]$^+$

EXAMPLE 396

N-(4-benzyloxy-benzyl)-N-[1-butyl-6-(3-diethylaminopropoxy)-1-H-benzimidazol-2-ylmethyl]-benzamide

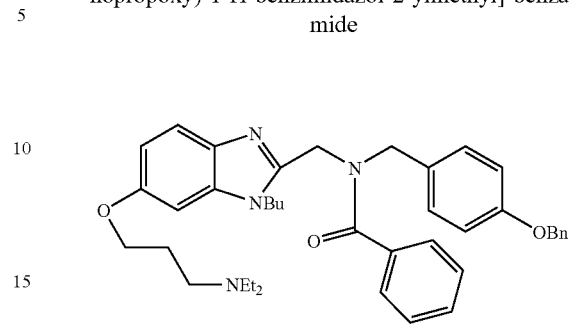

To 1-butyl-2-(4-benzyloxy-benzyl)-aminomethyl-6-(3-diethylaminopropxy)-1-H-benzimidazole (32 mg, 0.06 mmol) in DCM (3 mL) were added benzoyl chloride (34 mg, 0.24 mmol), TEA (24 mg, 0.24 mmol), DMAP (catalytic amount) and the mixture was stirred for 12 h, then sodium bicarbonate was added and the mixture was extracted with EtOAc (3×10 mL). The combined organic layer was washed with brine, and dried over sodium sulfate. The crude product was purified by silica gel column chromatography using DCM with a gradual increment of MeOH (0 to 1%) as eluent to afford 30 mg of Example 396.

MS m/z 633 [M+H]$^+$

EXAMPLE 397

(3-{3-butyl-2-[(dibenzylamino)-methyl]-3H-benzimidazol-5-yloxy)-propyl]-diethyl-amine

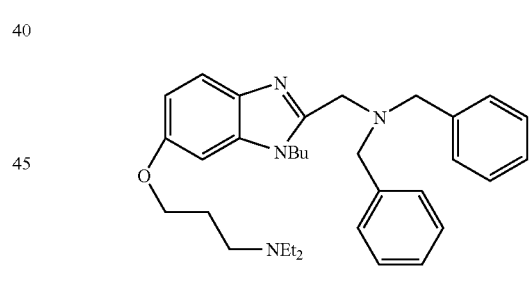

To 1-butyl-2-aminomethyl-6-(3-diethylaminopropxy)-1-H-benzimidazole (15 mg, 0.034 mmol) in DCM (2 mL) were added Et$_3$N (0.10 mmol) and benzaldehyde (180 mg, 0.17 mmol) and the mixture was stirred for 10 min, then NaBH(OAc)$_3$ (72 mg, 0.34 mmol) was added and stirred for 3 h, then sodium bicarbonate was added and the mixture was extracted with EtOAc. The combined organic layer was washed with brine, and dried over sodium sulfate. The crude product was purified by silica gel column chromatography using DCM with a gradual increment of MeOH (1% to 2%) as eluent to afford 10 mg of Example 397.

MS m/z 513 [M+H]$^+$

The following Examples were synthesized according to the Methods employed for Examples 393-397;

| Example | Name |
|---|---|
| 398 | (3-{2-[(4-benzyloxy-benzylamino)-methyl]-3-butyl-3H-benzimidazol-5-yloxy}-propyl)-diethyl-amine |
| 399 | N-(4-benzyloxy-benzyl)-N-[1-butyl-6-(3-diethylamino-propoxy)-1H-benzimidazol-2-ylmethyl]-methanesulfonamide |
| 400 | N-(4-benzyloxy-benzyl)-N-[1-butyl-6-(3-diethylamino-propoxy)-1H-benzimidazol-2-ylmethyl]-acetamide |
| 401 | {3-[3-butyl-2-({4-[2-(4-chloro-phenyl)-ethoxy]-benzylamino}-methyl)-3H-benzimidazol-5-yloxy)-propyl]-diethyl-amine |
| 402 | [3-(2-{[Bis-(4-benzyloxy-benzyl)-amino]-methyl}-3-butyl-3H-benzoimidazol-5-yloxy)-propyl]-diethyl-amine |
| 403 | [3-(2-{[Benzyl-(4-benzyloxy-benzyl)-amino]-methyl}-3-butyl-3H-benzoimidazol-5-yloxy)-propyl]-diethyl-amine |

EXAMPLE 404

{3-[4-(2-butyl-4-{4-[2-(4-chloro-phenyl)-ethoxy]-phenyl}-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold $H_2O$ and extracted with EtOAc. The combined organic layers were washed with brine and dried over sodium sulfate. Evaporation of the solvent in vacuuo afforded the desired 4-alkoxynitrobenzene.

The N,N-diethyl-N-[3-(4-nitrophenoxy)propyl]amine (2 mmol) obtained above was dissolved in MeOH (10 mL) and hydrogenated in the presence of 10% Pd/C (10 mg), according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion, according to General Procedure Q1. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of valeryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography on silica gel (yield: 270 mg).

MS m/z 561 $(M+H)^+$:

$^1$H NMR: δ 7.85 (s, 1H), 7.71 (d, 2H), 7.56 (d, 2H), 7.32 (m, 4H), 7.24 (d, 2H), 7.06 (d, 2H), 4.25 (t, 2H), 3.43 (t, 2H), 3.35 (m, 6H), 3.12 (t, 2H), 2.97 (t, 2H), 2.31 (m, 2H), 1.65 (m, 2H), 1.41 (t, 6H), 1.37 (m, 2H), 0.85 (t, 3H) ppm.

EXAMPLE 405

{3-[4-(4-{4-[2-(4-chloro-phenyl)-ethoxy]-phenyl}-2-isobutyl-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. until completion, as indicated by TLC or HPLC. The reaction mixture was then treated with cold $H_2O$ (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation without any purification, or after purifying using silica gel column chromatography.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (1.2 mmol) in DMF (10 mL) at rt, solid potassium carbonate (3.0 mmol) was added. 4-chlorophenethyl mesylate (1.0 mmol) was added to the reaction mixture and heated to 80° C. until completion according to General Procedure Q1, as indicated by TLC or HPLC. After cooling to rt, the reaction mixture was quenched by removing solvent in vacuuo and treating the residue with saturated sodium bicarbonate. The aqueous layer was poured into EtOAc (20 ml) and washed with $H_2O$ (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation without any purification or after purifying using silica gel column chromatography.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of the N,N-diethyl-N-[3-(4-nitrophenoxy)propyl]amine (1.2 eq, 2 mmol) in anhydrous DMF (5 mL) DIEA (3 eq 6 mmol) was added, followed by a slow addition of the 2-bromo-1-(4-[3-(diethylamino)propoxy]phenyl)ethanone described above (1.6 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM.

To a stirred solution of 1-{4-[2-(4-chloro-phenyl)-ethoxy]-phenyl}-2-[4-(3-diethylamino-propoxy)-phenylamino]-ethanone described above (2 mmol) in anhydrous DCM (5 mL) at 0° C., TEA (3 eq, 6 mmol) was added, followed by a slow addition of isovaleryl chloride (3 eq, 6 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (2 mmol) in acetic acid (2 mL), ammonium acetate (excess, ~20 eq) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (Yield: 390 mg).

MS m/z 560 (M+H)$^+$ $^1$H NMR: δ 7.86 (s, 1H), 7.65 (d, 2H), 7.59 (d, 2H), 7.31 (m, 4H), 7.23 (d, 2H), 7.13 (d, 2H), 4.51 (m, 2H), 3.42 (t, 2H), 3.31 (m, 6H), 3.05 (t, 2H), 2.87 (t, 2H), 2.31 (m, 2H), 1.95 (m, 1H), 1.49 (t, 6H), 0.86 (d, 6H) ppm.

EXAMPLE 406

[3-(4-{2-butyl-1-[4-(4-chloro-phenoxy)-phenyl]-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL), and 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product 1-{4-[3-(diethylamino)propoxy]phenyl}ethanone was extracted with EtOAc and washed with sodium bicarbonate and water. The solvent was removed in vacuuo and the product was purified by flash chromatography (going by increasing gradient up to 10% MeOH in DCM). T To a stirred solution of 1-{4-[3-(diethylamino)propoxy]phenyl}ethanone (5 mmol) in anhydrous MeOH (10 mL) at 0° C., pyrrolidone hydrotribromide (6 mmol, 1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-chlorophenoxy aniline (1 eq, 5 mmol) in anhydrous DMF (10 mL), DIEA (3 eq 15 mmol) was added, followed by addition of the 2-bromo-1-{4-[3-(diethylamino)propoxy]phenyl}ethanone described above (5 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM.

To a stirred solution of 2-[4-(4-chlorophenoxy)-phenylamino]-1-[4-(3-diethylamino-propoxy)-phenyl]-ethanone (2 mmol) in anhydrous DCM (8 mL) at 0° C., TEA (3 eq, 6 mmol) was added, followed by a slow addition of valeryl chloride (3 eq, 6 mmol). The reaction mixture was stirred under nitrogen at 0° C. for 1 h and allowed to warm to rt until completion as indicated by TLC or HPLC, according to General Procedure R3. The solvent was removed in vacuuo, and the crude amide was used for further transformation.

To a stirred solution of the amide described above (2 mmol) in acetic acid (8 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography on silica gel elutiopn with 4-6% MeOH/DCM) (yield 424 mg).

MS m/z 532 (M+H)$^+$:

$^1$H NMR (CDCl$_3$): δ 7.68 (d, 2H), 7.34 (d, 2H), 7.28 (d, 2H), 7.14 (s, 1H), 7.07 (d, 2H), 7.01 (d, 2H,), 6.89 (d, 2H) 4.04 (t, 2H), 2.64-2.78 (m, 8H), 1.99 (m, 2H), 1.64 (m, 2H), 1.30 (m, 2H), 1.09 (t, 6H), 0.83 (t, 3H) ppm.

EXAMPLE 407

1-[4-(4-{2-butyl-1-[4-(4-fluoro-3-trifluoromethyl-phenoxy)-phenyl]-1H-imidazol-4-yl}-phenoxy)-butyl]-piperazine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography on silica gel (elution with 5-20% EtOAc/Hexane).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol). The reaction mixture was stirred under nitrogen at 0° C. for 1 h and allowed to warm to ambient temperature until completion as indicated by TLC and HPLC, according to General Procedure R3. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography on silica gel (elution with 5-15% EtOAc/Hexane). MS: m/z 562 (M+H)$^+$)

The benzyl imidazole from above was dissolved in MeOH (20 mL), and Pd/C (100 mg) was added and the heterogeneous mixture was stirred overnight under hydrogen atmosphere using a balloon, according to General Procedure H. The catalyst was removed by filtration. The solvent was removed in vacuuo, and the crude phenol (MS: m/z 472 (M+H)$^+$) was used directly.

To a stirred solution of the phenol (0.16 mmol) obtained above in anhydrous DMF (5 mL) solid sodium hydride (60% dispersion in oil; 1.0 mmol) was added in portions. After the addition, a solution of 4-bromobutyl methanesulfonate (0.2 mmol) (prepared as described earlier) in anhydrous THF (2 mL) was added to the reaction mixture. The reaction was then allowed to proceed at rt. Upon completion of the reaction, piperazine (5.0 eq) was added. The mixture was stirred overnight. Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Product was purified by column chromatography on silica gel (elution with 5-10% MeOH/DCM) (yield 54.0 mg)

MS m/z 612 (M+H)$^+$:

EXAMPLE 408

4-(4-{2-butyl-1-[4-(4-fluoro-3-trifluoromethyl-phenoxy)-phenyl]-1H-imidazol-4-yl}-phenoxy)-1-methyl-piperidine To a stirred solution of 4-benzyloxyacetophenone (7.0 mmol) in anhydrous DCM (30.0 mL) and MeOH (5.0 mL) at rt, pyridinium bromide perbromide (1.1 eq.) was added, according to General Procedure R1. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography on silica gel (elution with 5-20% EtOAc/Hexane).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to rt until completion. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography on silica gel (elution with 5-15% EtOAc/Hexane).

MS: m/z 562 (M+H)$^+$)

The above product was dissolved in MeOH (20 mL), and Pd/C (100 mg) was added and the heterogeneous mixture was stirred overnight under hydrogen atmosphere using a balloon, according to General Procedure T2. The Pd/C was removed by filtration. The solvent was removed in vacuuo, and the crude 4-(1-{4-[4-fluoro-3-(trifluoromethyl)phenoxy]phenyl}-2-butyl-1H-imidazol-4-yl)phenol (MS: m/z 472 (M+H)$^+$) was used directly.

A stirred solution of the 4-(1-{4-[4-fluoro-3-(trifluoromethyl)phenoxy]phenyl}-2-butyl-1H-imidazol-4-yl)phenol (1.0 eq) in anhydrous DMF (5.0 mL) was treated with solid sodium hydride (60% dispersion in oil; 1.0 mmol), added in portions. The mesylate of 1-methylpiperidin-4-ol (1.5-2.0 eq) was then added to the reaction mixture, which was heated at 90° C. overnight, according to General Procedure T3. After cooling the mix to rt, Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained from chromatography in 5-10% MeOH/DCM (yield 14 mg).

MS m/z value (M+H)$^+$: 569

$^1$H NMR (CDCl$_3$): δ7.70 (d, 2H), 7.20-7.35 (m, 5H), 7.14 (s, 1H), 7.08 (d, 2H), 6.92 (d, 2H), 4.4 (bs, 1H), 1.0 3.05 (m, 17H) ppm.

EXAMPLE 409

1-[5-(4-{2-butyl-1-[4-(4-fluoro-3-trifluoromethyl-phenoxy)-phenyl]-1H-imidazol-4-yl}-phenoxy)-pentyl]-piperazine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained from 5-20% EtOAc/Hexane.

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 5-15% EtOAc/Hexane.

MS: m/z 562 (M+H)$^+$)

The above product was dissolved in MeOH (20 mL), and Pd/C (100 mg) was added and the heterogeneous mixture was stirred overnight under hydrogen atmosphere using a balloon, according to General Procedure H. The Pd/C was removed by filtration. The solvent was removed in vacuuo, and the crude phenol (MS: m/z 472 (M+H)$^+$) was used for further transformation.

To a stirred solution of the imidazole (0.16 mmol) obtained above in anhydrous DMF (5 mL) solid sodium hydride (60% dispersion in oil; 1.0 mmol) was added in portions. After the addition, a solution of 5-bromopentyl methanesulfonate (0.2 mmol) anhydrous THF (2 mL) was added to the reaction mixture. The reaction was then allowed to proceed at rt. Upon completion of the reaction, piperazine (100 mg) added. The mixture was stirred overnight. Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure product was obtained after chromatography on slilca gel (elution with 5-10% MeOH/DCM) (yield 36.0 mg).

MS m/z 626 (M+H)$^+$:

EXAMPLE 410

{3-[4-(4-{4-[2-(4-chloro-phenyl)-ethoxy]-phenyl}-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation without any purification, or after purifying using silica gel column chromatography.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired N,N-diethyl-N-[3-(4-nitrophenoxy)propyl]amine, which was used directly for further transformation without further purification.

To a stirred solution of 4'-hydroxyacetophenone (1.2 mmol) in DMF (10 mL) at rt, solid potassium carbonate (3.0 mmol) was added. 4-chlorophenethyl mesylate (1.0 mmol) was added to the reaction mixture and heated to 80° C. until completion according to General Procedure Q1, as indicated by TLC or HPLC. After cooling to rt, the reaction mixture was quenched by removing solvent in vacuuo and treating the residue with saturated sodium bicarbonate. The aqueous layer was poured into EtOAc (20 ml) and washed with H$_2$O (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidinone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of the N,N-diethyl-N-[3-(4-nitrophenoxy)propyl]amine (1.2 eq, 2 mmol) in anhydrous DMF (5 mL) DIEA (3 eq 6 mmol) was added, followed by a slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM.

The 1-{4-[2-(4-chloro-phenyl)-ethoxy]-phenyl}-2-[4-(3-diethylamino-propoxy)-phenylamino]-ethanone obtained as above (1 mmol) was dissolved in formic acid (2 mL) and treated with ammonium formate (20 mmol). The resulting mixture was heated to 90° C. overnight. The reaction mixture was then cooled to rt and neutralized with saturated sodium bicarbonate solution. Usual extractive work up with EtOAc gave the product imidazole, which was purified by column chromatography on silica gel (elution with 4-6% MeOH/DCM) (yield 161 mg).

MS m/z 504 (M+H)$^+$:

$^1$H NMR (CDCl$_3$): δ 7.77 (s, 1H), 7.73 (d, 2H), 7.38 (s, 1H), 7.10-7.35 (m, 6H), 6.97 (d, 2H), 6.92 (d, 2H), 4.17 (t, 2H), 4.06 (broad t, 2H), 3.07 (t, 2H), 2.81 (broad q, 4H) 1.95-2.15 (broad m, 4H), 1.17 (t, 6H) ppm.

EXAMPLE 411

{3-[3-(4-{4-[2-(4-chloro-phenyl)-ethoxy]-phenyl}-imidazol-1-yl)-phenoxy]-propyl}-diethyl-amine To a stirred solution of 3-nitrophenol (2 mmol) in DMF (6 mL) at rt, solid potassium carbonate (4 mmol) was added. A solution of the mesylate of N,N-diethylaminopropanol (2.2 mmol) in DMF (2 mL) was then added to the reaction mixture and heated to 80° C. until completion, according to General Procedure Q1, as indicated by TLC or HPLC. After cooling to rt, the reaction mixture was then treated with cold $H_2O$ (15 mL), and extracted with EtOAc (2×15 mL). The combined organic layers were washed with brine and dried over sodium sulfate. Evaporation of the solvent in vacuuo afforded the desired N,N-diethyl-N-[3-(3-nitrophenoxy)propyl]amine. The crude product was used directly for further transformation.

The N,N-diethyl-N-[3-(3-nitrophenoxy)propyl]amine (1 mmol) was dissolved in MeOH (5 mL) and hydrogenated in the presence of 10% Pd/C (50 mg) until completion as indicated by TLC or HPLC, according to General Procedure H. The reaction mixture was then filtered to remove the catalyst. The solvent was removed in vacuuo to afford the desired N-[3-(3-aminophenoxy)propyl]-N,N-diethylamine, which was used directly for further transformation without further purification.

To a stirred solution of N-[3-(3-aminophenoxy)propyl]-N,N-diethylamine (1 mmol) in anhydrous DMF (3 mL), DIEA (3 mmol) was added followed by a slow addition of 1-bromo-4'-(4-chlorophenethoxy)acetophenone (0.8 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography on silica gel (elutiion with 2-4% MeOH/DCM).

The 1-{4-[2-(4-chloro-phenyl)-ethoxy]-phenyl}-2-[4-(3-diethylamino-propoxy)-phenylamino]-ethanone obtained as above (0.5 mmol) was dissolved in formic acid (1 mL) and treated with ammonium formate (10 mmol). The resulting mixture was heated to 90° C. overnight. The reaction mixture was then cooled down and neutralized with saturated sodium bicarbonate solution. Usual extractive work up with EtOAc gave the product imidazole, which was purified by column chromatography on silica gel (elution with 4-6% MeOH/DCM).

MS m/z value (M+H)$^+$: 504

$^1$H NMR (CDCl$_3$): δ7.89 (s, 1H), 7.74 (d, 2H), 7.47 (s, 1H), 7.30-7.10 (m, 7H), 6.92 (d, 2H) 6.85 (t, 1H) 4.10-4.20 (m, 4H), 3.00-3.20 (m, 6H), 2.31 (broad, 2H), 1.36 (t, 6H) ppm.

EXAMPLE 412

[3-(4-{1-[4-(4-tert-butyl-phenoxy)-phenyl]-1H-imidazol-4-yl)-phenoxy)-propyl]-diethyl-amine To a stirred solution of 4-fluoronitrobenzene (2.0 mmol) in anhydrous THF (5 mL) at 0° C., a 1M solution of potassium 4-tert-butyl-phenoxide (2.2 mmol) in THF (may be generated by adding the corresponding alcohol to a 1M solution of KOBu$^t$ in THF) was added dropwise and under a nitrogen stream, according to General Procedure L1. The reaction mixture was stirred at 0° C. until completion, as indicated by TLC or HPLC. The solvent was then removed in vacuo and the reaction mixture was treated with cold $H_2O$ (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The nitro intermediate (2 mmol) obtained above was dissolved in MeOH (10 mL) and hydrogenated in the presence of 10% Pd/C (10 mg) until completion, as indicated by TLC or HPLC, according to General Procedure H. The reaction mixture was then filtered. The solvent was removed in vacuuo to afford the desired 4-alkoxyaniline, which was used directly for further transformation without further purification.

To a stirred solution of 4'-hydroxyacetophenone (2.2 mmol) in DMF (10 mL) at rt, solid $K_2CO_3$ (8.0 mmol) was added. The mesylate of N,N-diethyaminopropanol (prepared from the corresponding alcohol and methanesulfonyl chloride, 2.0 mmol) was added to the reaction mixture and heated to 80° C. until completion according to General Procedure Q1, as indicated by TLC or HPLC. After cooling to rt, the reaction mixture was diluted with $H_2O$ and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude 1-{4-[3-(diethylamino)propoxy]phenyl}ethanone was purified using silica gel column chromatography (elution with 2-3% MeOH/DCM).

To a stirred solution of the 1-{4-[3-(diethylamino)propoxy]phenyl}ethanone (1 mmol) described above 48% HBr (3 eq, 3 mmol) in DMSO (4 mL) was added. The reaction mixture was heated to 80° C. until completion, as indicated by TLC or HPLC. After cooling to rt, the reaction mixture was neutralized with 2N sodium hydroxide solution and the product was isolated in EtOAc. The combined organic layers were washed with H$_2$O (2×15 ml) and brine (15 ml). The organic layer was dried over magnesium sulfate, and the solvent was removed in vacuuo to afford the desired product. The crude ketoaldehyde was used for further transformation.

To a stirred solution of the ketoaldehyde (1 mmol) in AcOH (5 mL) 4-tert-butyl-phenoxy aniline (1.2 eq., 1.2 mmol), formaldehyde (excess, ~30 eq.) and ammonium acetate (excess, ~30 eq.) were added, according to General Procedure R4. The reaction mixture was heated to 80° C. until completion, as indicated by TLC or HPLC. After cooling to rt, the reaction mixture was neutralized with saturated sodium bicarbonate solution and the product was isolated in EtOAc. Usual extractive work up gave the desired product, which was purified by column chromatography on silica gel (elution with 3-4% MeOH/DCM) (Yield 150 mg).

MS: m/z 498 (M+H)$^+$ $^1$H NMR (CDCl$_3$): δ7.64 (s, 1H), 7.39 (d, 2H), 7.12 (s, 1H), 7.06 (d, 2H) 7.02 (d, 2H) 6.97 (m, 2H) 6.79 (d, 2H), 3.98 (t, 2H), 2.66 (m, 6H), 2.02 (m, 2H), 1.31 (s, 9H), 1.08 (t, 6H) ppm.

EXAMPLE 413

[3-(4-{2-butyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (2.0 mmol) in anhydrous THF (5 mL) at 0° C., a 1M solution of a potassium 4-fluoro-3-trifluoromethyl-phenoxide (2.2 mmol) in THF (may be generated by adding the corresponding alcohol to a 1M solution of potassium t-butoxide in THF) was added dropwise and under a nitrogen stream, according to General Procedure L1. The reaction mixture was stirred at 0° C. until completion, as indicated by TLC or HPLC. The solvent was then removed in vacuuo and the reaction mixture was treated with cold H$_2$O (15 mL), and extracted with EtOAc (2×15 mL). The combined organic layers were washed with brine and dried over sodium sulfate. Evaporation of the solvent in vacuuo afforded the desired 1-fluoro-4-(4-nitrophenoxy)-2-(trifluoromethyl)benzene. The crude product could be used directly for further transformation.

The 1-fluoro-4-(4-nitrophenoxy)-2-(trifluoromethyl)benzene (2 mmol) obtained above was dissolved in MeOH (10 mL) and hydrogenated in the presence of 10% Pd/C (10 mg) until completion, as indicated by TLC or HPLC, according to General Procedure H. The reaction mixture was then filtered. The solvent was removed in vacuuo to afford the desired 4-alkoxyaniline, which was used directly for further transformation without further purification.

To a stirred solution of 4'-hydroxyacetophenone (2.2 mmol) in DMF (10 mL) at rt, solid potassium carbonate (8.0 mmol) was added. The mesylate of N,N-diethyaminopropanol (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude 1-{4-[3-(diethylamino)propoxy]phenyl}ethanone was purified using silica gel column chromatography. Pure product was obtained after elution with 2-3% MeOH/DCM. (yield 50-60%)

To a stirred solution of the 1-{4-[3-(diethylamino)propoxy]phenyl}ethanone described above (1 mmol) in anhydrous MeOH (5 mL) at 0° C., pyrrolidone hydrotribromide (1.2 eq, 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate and the product was isolated in EtOAc. The combined organic layers were washed with water (2×15 ml) and brine (15 ml). The organic layer was dried over magnesium sulfate, and the solvent was removed in vacuuo to afford the desired product. The crude 2-bromo-1-{4-[3-(diethylamino)propoxy]phenyl}ethanone was used for further transformation.

To a stirred solution of the 4-fluoro-3-trifluoromethyl-phenoxy aniline (1.2 eq., 1.2 mmol) in anhydrous DMF (5 mL) DIEA (3 eq. 3 mmol) was added, followed by slow addition of the 2-bromo-1-{4-[3-(diethylamino)propoxy]phenyl}ethanone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3 mmol) was added, followed by slow addition of valeryl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was used for further transformation.

To a stirred solution of the amide described above (1 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained after elution with 4-6% MeOH/DCM (Yield 175 mg).

MS m/z 584 (M+H)$^+$

EXAMPLE 414 diethyl-[3-(4-{1-[4-(4-trifluoromethoxy-phenoxy)-phenyl]-1H-imidazol-4-yl}-phenoxy)-propyl]-amine To a stirred solution of 4-fluoronitrobenzene (2.0 mmol) in anhydrous THF (5 mL) at 0° C., a 1M solution of potassium 4-trifluoromethoxy-phenoxide (2.2 mmol) in THF (may be generated by adding the corresponding alcohol to a 1M solution of KOBu$^t$ in THF) was added dropwise under a nitrogen stream, according to General Procedure L1. The reaction mixture was stirred at 0° C. until completion, as indicated by TLC or HPLC. The solvent was then removed in vacuo and the reaction mixture was treated with cold H$_2$O (15 mL), and extracted with EtOAc (2×15 mL). The combined organic layers were washed with brine and dried over sodium sulfate. Evaporation of the solvent in vacuo afforded the desired 4-alkoxynitrobenzene. The crude product was used directly for further transformation.

The nitro intermediate (2 mmol) obtained above was dissolved in MeOH (10 mL) and hydrogenated in the presence of 10% Pd/C (10 mg) until completion, as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (10 mL) at rt, solid $K_2CO_3$ (8.0 mmol) was added. The mesylate of N,N-diethyaminopropanol (prepared from the corresponding alcohol and methanesulfonyl chloride, 2.0 mmol) was added to the reaction mixture and heated to 80° C. until completion according to General Procedure Q1, as indicated by TLC or HPLC. After cooling to rt, the reaction mixture was diluted with $H_2O$ and the product was isolated in EtOAc. The combined organic layers were washed with saturated sodium bicarbonate (2×15 ml), $H_2O$ (2×15 ml) and brine (15 ml). The organic layer was dried over magnesium sulfate, and the solvent was removed in vacuuo to afford the desired product. The crude 1-{4-[3-(diethylamino)propoxy]phenyl}ethanone was purified using silica gel column chromatography. Pure product was obtained with 2-3% MeOH/DCM.

To a stirred solution of the 1-{4-[3-(diethylamino)propoxy]phenyl}ethanone (1 mmol) described above 48% HBr (3 eq, 3 mmol) in DMSO (4 mL) was added. The reaction mixture was heated to 80° C. until completion, as indicated by TLC or HPLC. After cooling to rt, the reaction mixture was neutralized with saturated sodium bicarbonate solution and the product was isolated in EtOAc. The combined organic layers were washed with water (2×15 ml) and brine (15 ml). The organic layer was dried over magnesium sulfate, and the solvent was removed in vacuuo to afford the desired product. The crude ketoaldehyde was used for further transformation.

To a stirred solution of the ketoaldehyde (1 mmol) in AcOH (5 mL), 4-trifluoromethoxy-phenoxy-aniline (1.2 eq., 1.2 mmol), formaldehyde (excess, ~30 eq.) and ammonium acetate (excess, ~30 eq.) were added, according to General Procedure R4. The reaction mixture was heated to 80° C. until completion, as indicated by TLC or HPLC. After cooling to rt, the reaction mixture was neutralized with saturated sodium bicarbonate solution and the product was isolated in EtOAc. Usual extractive work up with EtOAc gave the desired product, which was purified by column chromatography on silica gel, elution with 3-4% MeOH/DCM) (Yield 130 mg).

MS: m/z 526 (M+H)$^+$ $^1$H NMR (CDCl$_3$): δ 7.91 (s, 1H), 7.41 (d, 2H), 7.28 (d, 2H), 7.05 (d, 2H), 6.98 (m, 4H) 6.81 (d, 2H) 3.99 (t, 2H), 2.96 (m, 6H), 2.18 (m, 2H), 1.22 (t, 6H) ppm.

EXAMPLE 415

[3-(4-{2-butyl-1-[4-(3,4-dichloro-phenoxy)-phenyl]-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The product from the previous step (20 mmol, 1 eq) was dissolved in anhydrous DMF (25 mL) to which 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the 1-{4-[3-(diethylamino)propoxy]phenyl}ethanone was purified by flash chromatography (going by increasing gradient up to 10% MeOH in DCM).

3,4-Dichlorophenol (10 mmol) was dissolved in 15 ml of anhydrous DMF and potassium carbonate (30 mmol) was added with stirring at rt. 4-Fluoronitrobenzene (10 mmol) was added to this mixture, which was then heated under reflux at 80° C. for 18 h. The reaction was quenched with 30 ml of water and 30 ml of sodium bicarbonate, extracted with EtOAc (3×50 ml) and washed with sodium bicarbonate and water. The EtOAc layer was dried over anhydrous sodium sulfate and filtered, after which the solvent was removed in vacuuo.

The nitro intermediate (10 mmol) obtained above was dissolved in EtOH (30 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-(3,4-dichlorophenoxy)aniline, which was used directly for further transformation without further purification To a stirred solution of 1-{4-[3-(diethylamino)propoxy]phenyl}ethanone (2 mmol) in anhydrous MeOH (6 mL) at 0° C., pyrrolidone hydrotribromide (2.4 mmol, 1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(3,4-dichlorophenoxy) aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM.

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (excess, ~20 eq) was added according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography on silica gel (elution with 4-6% MeOH/DCM) (yield 170 mg).

MS m/z 567 (M+H)$^+$:

$^1$H NMR (400 MHz, CDCl$_3$): δ 7.7 (d, 2H), 7.3 (m, 3H), 6.9-7.1 (m, 7H), 4.0 (t, 2H), 2.7 (m, 8H), 2.0 (m, 2H), 1.6 (m, 2H), 1.3 (m, 2H), 1.1 (t, 6H), 0.8 (t, 3H) ppm.

EXAMPLE 416

[3-(4-{2-cyclobutyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H$_2$O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL), methanesulfonyl chloride (60 mmol) was added dropwise and the reaction mixture was stirred for 2 h at 0° C., followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H$_2$O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL), DIEA (12 mmol) was added followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added followed by a slow addition of cyclobutanecarbonyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added according to General Procedure R4. The reaction mixture was stirred at 100° C. for 2-5 h (as monitored by LC-MS). The reaction mixture was then cooled to rt and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (yield 64 mg).

MS m/z 582 (M+H)$^+$:

$^1$H NMR (400 MHz, CDCl$_3$): δ1.05 (t, 6H), 1.90-2.20 (m, 6H), 2.56 (m, 2H), 2.58 (q, 4H), 2.66 (t, 2H), 3.44 (m, 1H), 4.02 (t, 2H), 6.91 (d, 2H), 7.05 (d, 2H), 7.14 (s, 1H), 7.22-7.26 (m, 3H), 7.31 (d, 2H), 7.72 (d, 2H) ppm.

EXAMPLE 417

[3-(4-{2-cyclopentyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H$_2$O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold $H_2O$ (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethylphenoxy)aniline (4.8 mmol) dissolved in anhydrous DMF (10 mL), DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added, followed by a slow addition of cyclopentanecarbonyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (overall yield: 60-70%) (yield 77 mg).

MS m/z 596 (M+H)$^+$:

$^1$H NMR (400 MHz, CDCl$_3$): δ 1.03-2.00 (m, 11H), 1.07 (t, 6H), 2.59 (q, 4H), 2.65 (t, 2H), 4.03 (t, 2H), 6.91 (d, 2H), 7.08 (d, 2H), 7.14 (s, 1H), 7.24-7.27 (m, 3H), 7.33 (d, 2H), 7.71 (d, 2H) ppm.

EXAMPLE 418

[3-(4-{2-cyclohexyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold $H_2O$ (60 mL). The resulting mixture was extracted with EtOAc (3×100 mL). The combined EtOAc extracts were washed with $H_2O$ (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification.

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold $H_2O$ (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA.

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL), DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA.

To a stirred solution of the alkylated aniline described above (0.2 mmol) in anhydrous DCM (5 mL) at 0° C., TEA (1.2 mmol, 6 eq) was added, followed by a slow addition of cyclohexanecarbonyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+0.2% TEA (yield 74 mg).

MS m/z 610 (M+H)$^+$:
$^1$H NMR (400 MHz, CDCl$_3$): δ1.02-2.00 (m, 13H), 1.06 (t, 6H), 2.60 (q, 4H), 2.67 (t, 2H), 4.02 (t, 2H), 6.90 (d, 2H), 7.07 (d, 2H), 7.09 (s, 1H), 7.22-7.26 (m, 3H), 7.30 (d, 2H,), 7.69 (d, 2H) ppm.

EXAMPLE 419 diethyl-[3-(4-{1-[4-(4-fluoro-3-trifluoromethyl-phenoxy)-phenyl]-2-isobutyl-1H-imidazol-4-yl}-phenoxy)-propyl]-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H$_2$O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H$_2$O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA.

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL), DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA.

To a stirred solution of the alkylated aniline described above (0.2 mmol) in anhydrous DCM (5 mL) at 0° C., TEA (1.2 mmol, 6 eq) was added, followed by a slow addition of isovaleryl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+0.2% TEA (yield 70 mg).

MS m/z 584 (M+H)$^+$:
$^1$H NMR (400 MHz, CDCl$_3$): δ0.86 (d, 6H) 1.07 (t, 6H), 1.97 (m, 2H), 2.04 (m, 1H), 2.55 (d, 2H), 2.61 (q, 4H), 2.69 (t, 2H), 4.03 (t, 2H), 6.90 (d, 2H), 7.07 (d, 2H), 7.14 (s, 1H), 7.22-7.25 (m, 3H), 7.30 (d, 2H), 7.70 (d, 2H) ppm.

EXAMPLE 420

[3-(4-{2-but-3-enyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H₂O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H₂O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL), DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added, followed by a slow addition of pent-4-enoyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (yield 58 mg).

MS m/z 582+H)⁺:

¹H NMR (400 MHz, CDCl₃): δ 1.12 (t, 6H), 2.03 (m, 2H), 2.45 (t, 2H), 2.63 (t, 2H,), 2.73 (q, 4H), 2.77 (t, 2H), 4.04 (t, 2H), 4.94 (dd, 1H), 5.00 (dd, 1H), 5.79 (m, 1H), 6.90 (d, 2H), 7.07 (d, 2H), 7.15 (s, 1H), 7.24-7.25 (m, 3H), 7.32 (d, 2H, 7.70 (d, 2H) ppm.

EXAMPLE 421

[3-(4-{2-tert-butyl-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H₂O (60 mL). The resulting mixture was extracted with EtOAc (3×100 mL). The combined EtOAc extracts were washed with H₂O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H₂O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA.

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethyldinino)propoxy]phenyl}ethanone was directly used for further transformation.

To a stirred solution of 4-(4'-fluoro-3'-trifluoromethylphenoxy)aniline (4.8 mmol) dissolved in anhydrous. DMF (10 mL), DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA.

To a stirred solution of the alkylated aniline described above (0.2 mmol) in anhydrous DCM (5 mL) at 0° C., TEA (1.2 mmol, 6 eq) was added, followed by a slow addition of pivaloyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+0.2% TEA (yield 76 mg).

MS m/z 584 (M+H)$^+$ $^1$H NMR (400 MHz, CDCl$_3$): δ1.09 (t, 6H), 1.24 (s, 9H), 1.99 (m, 2H), 2.64 (q, 4H), 2.72 (t, 2H), 4.02 (t, 2H), 6.89 (d, 2H), 7.02 (s, 1H), 7.03 (d, 2H), 7.23-7.25 (m, 3H), 7.35 (d, 2H), 7.69 (d, 2H) ppm.

EXAMPLE 422 diethyl-[3-(4-{2-(4-fluoro-phenyl)-1-[4-(4-fluoro-3-trifluoromethyl-phenoxy)-phenyl]-1H-imidazol-4-yl}-phenoxy)-propyl]-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H$_2$O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H$_2$O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-(4-[3-(diethylamino)propoxy]phenyl)ethanone was directly used for further transformation.

To a stirred solution of 4-(4'-fluoro-3'-trifluoromethylphenoxy)aniline (4.8 mmol) dissolved in anhydrous DMF (10 mL), DIEA (12 mmol) was added, followed by a slow addition of the 2-bromo-1-(4-[3-(diethylamino)propoxy]phenyl)ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added, followed by a slow addition of 4-fluorobenzoyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (overall yield: 60-70%) (yield 75 mg).

MS m/z 622 (M+H)$^+$:

¹H NMR (400 MHz, CDCl₃): δ1.11 (t, 6H), 2.01 (m, 2H), 2.67 (q, 4H), 2.75 (t, 2H), 4.05 (t, 2H), 6.93 (d, 2H), 6.98-7.26 (m, 7H), 7.01 (d, 2H), 7.33 (s, 1H), 7.43 (d, 2H), 7.44 (d, 1H), 7.78 (d, 2H) ppm.

EXAMPLE 423

[3-(4-{1-[4-(3,5-bis-trifluoromethyl-phenoxy)-phenyl]-2-butyl-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the 1-{4-[3-(diethylamino)propoxy]phenyl}ethanone was purified by flash chromatography (going by increasing gradient up to 10% MeOH in DCM). The overall yield was 60%.

3,5-bis-trifluoromethylphenol (10 mmol) was dissolved in 15 ml of anhydrous DMF and potassium carbonate (30 mmol) was added with stirring at rt. 4-Fluoronitrobenzene (10 mmol) was added to this mixture, which was then heated under reflux at 80° C. for 18 h. The reaction was quenched with 30 ml of water and 30 ml of sodium bicarbonate, extracted with EtOAc (3×50 ml) and washed with sodium bicarbonate and water. The EtOAc layer was dried over anhydrous sodium sulfate and filtered, after which the solvent was removed in vacuuo.

The nitro intermediate (10 mmol) obtained above was dissolved in EtOH (30 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-(3,5-bis-trifluoromethyl)phenoxyaniline, which was used directly for further transformation without further purification (yield 80%).

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(3,5-bis-trifluoromethyl)phenoxyaniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Removal of solvent in vacuuo afforded the desired product. The crude alkylated aniline was purified by chromatography (Silica gel). Pure product obtained from 2-4% MeOH/DCM (yield 50%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 139 mg).

MS m/z 635 (M+H)⁺:

¹H NMR (400 MHz, CDCl₃): δ 7.7 (d, 2H), 7.3 (m, 3H), 7.1 (m, 5H), 6.9 (d, 2H), 4.0 (t, 2H), 2.6-2.8 (m, 8H), 2.0 (m, 2H), 1.6 (m, 2H), 1.3 (m, 2H), 1.1 (t, 6H), 0.8 (t, 3H) ppm.

EXAMPLE 424

(3-{4-[1-(4-benzyloxy-phenyl)-2-butyl-1H-imidazol-4-yl]-phenoxy}-propyl)-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product was purified by flash chromatography (going by increasing gradient up to 10% MeOH in DCM). The overall yield was 60%.

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-benzyloxyaniline (1 eq, 2 mmol) in anhydrous DMF (6 mL), DIEA (3 eq 6 mmol) was added, followed by addition of the 2-bromo-1-{4-[3-(diethylamino) propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 56%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 205 mg).

MS m/z 513 (M+H)$^+$;

$^1$H NMR (CDCl$_3$): δ 7.68 (d, 2H), 7.40 (m, 5H), 7.23 (d, 2H), 7.11 (s, 1H), 7.05 (d, 2H), 6.89 (d, 2H), 5.12 (s, 2H), 4.02 (t, 2H), 2.62-2.73 (m, 8H), 1.98 (m, 2H), 1.63 (m, 2H), 1.28 (m, 2H), 1.07 (t, 6H), 0.82 (t, 3H) ppm.

EXAMPLE 425

{3-[4-(2-tert-butyl-4-{4-[2-(4-chloro-phenyl)-ethoxy]-phenyl}-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained from 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of pivaloyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 270 mg).

MS m/z 561 (M+H)$^+$:

¹H NMR (400 MHz, CDCl₃): δ7.69 (d, 2H), 7.23-7.25 (m, 6H), 6.98 (s, 1H), 6.84 (m 4H), 4.15 (t, 2H), 4.08 (t, 2H), 3.05 (t, 2H), 2.85 (m, 6H), 2.16 (s, 9H), 2.05 (m, 2H), 1.19 (t, 6H) ppm.

EXAMPLE 426

[3-(4-{2-butyl-1-[4-(3-fluoro-4-trifluoromethyl-phenoxy)-phenyl]-1H-imidazol-4-yl}-phenoxy)-propyl]-diethyl-amine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H₂O (2×50 ml), brine (30 ml) and dried with magnesium sulfate. The solvent was then removed in vacuuo to give a white solid. The alpha-bromoacetophenone was used for further transformation without further purification.

To a stirred solution of 4-(3-fluoro-4-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H₂O and the product was isolated in Et₂O. The combined organic layers were washed with brine and dried over sodium sulfate. Evaporation of solvent in vacuuo afforded the desired product. The crude alkylated aniline was purified by chromatography (Silica gel). Pure product was obtained from 5-20% EtOAc/Hexane (yield ~50-60%).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 5-15% EtOAc/Hexane (yield 80%). (MS: m/z 562 (M+H)⁺)

The above product was dissolved in MeOH (20 mL), and Pd/C (100 mg) was added and the heterogeneous mixture was stirred overnight under hydrogen atmosphere using a balloon, according to General Procedure H. The Pd/C was removed by filtration. The solvent was removed in vacuuo, and the crude phenol (MS: m/z 472 (M+H)⁺) was used for further transformation.

To a stirred solution of the phenol (1.0 eq) obtained above in anhydrous DMF (5.0 mL) solid sodium hydride (60% dispersion in oil; 1.0 mmol) was added in portions. After the addition, the requisite alkylhalide or the mesylate (prepared from the corresponding alcohol and methanesulfonyl chloride) (1.5-2.0 eq) was added to the reaction mixture. The reaction mixture was heated at 90° C. overnight. After cooling the mix to rt, Et₂O (30 mL) was added to the reaction mixture followed by H₂O (10 mL). The organic layer was washed with H₂O (2×15 mL) and brine, and dried over sodium sulfate. The solvent was removed in vacuuo. Pure product was obtained from 5-10% MeOH/DCM (yield 65.0 mg).

MS m/z 557 (M+H)⁺:

¹H NMR (CDCl₃): δ 7.70 (d, 2H), 7.20-7.35 (m, 5H), 7.14 (s, 1H), 7.08 (d, 2H), 6.92 (d, 2H), 4.02 (t, 2H), 2.66 (t, 2H), 2.47 (t, 2H), 2.26 (s, 6H), 1.96 (m, 2H), 1.64 (m, 2H), 1.29 (m, 2H) 0.9 (t, 3H) ppm.

EXAMPLE 427 diethyl-[3-(4-{4-[4-(4-fluoro-3-trifluoromethyl-phenoxy)-phenyl]-imidazo-1-yl}-phenoxy)-propyl]-amine To a stirred solution of N-[3-(4-aminophenoxy)propyl]-N,N-diethylamine (1.2 eq, 2 mmol) in anhydrous DMF (5 mL) DIEA (3 eq 6 mmol) was added, followed by a slow addition of 2-bromo-1-(4-bromophenyl)ethanone (1.6 mmol), according to General Procedure R2. The reaction mixture was stirred under nitrogen at rt until completion, as indicated by TLC or HPLC. The reaction mixture was then diluted with cold H₂O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM (yield ~50-60%).

To a stirred solution of 1-(4-bromophenyl)-2-({4-[3-(diethylamino)propoxy]phenyl}amino)ethanone (2 mmol) in acetic acid (2 mL), ammonium acetate (excess, ~20 eq) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 40-50%).

To a solution of N-(3-{4-[4-(4-bromophenyl)-1H-imidazol-1-yl]phenoxy}propyl)-N,N-diethylamine (0.07 mmol) in pyridine (1 mL), copper powder was added (0.14 mmol), followed by potassium carbonate (0.35 mmol) and 4-fluoro-3-methylphenol (0.14 mmol). The mixture was heated at 110° C. overnight, then diluted with H₂O (2 mL) and extracted with EtOAc (3×2 mL). The combined organic extract was dried over sodium sulfate, filtered and concentrated to an oil, which was purified by column chromatography (Silica gel). The pure product was obtained from 1-6% MeOH/DCM.

MS m/z 528 (M+H)⁺:

¹H NMR (400 MHz, CDCl₃): δ 7.86-7.78 (m, 3H), 7.54-7.44 (m, 2H), 7.38-7.34 (m, 2H), 7.28-7.24 (m, 1H), 7.20-7.16 (m, 2H), 7.06-6.80 (m, 3H), 4.10 (t, 2H), 2.80-2-60 (m, 6H), 2.10-2.00 (m, 2H), 1.30 (t, 3H), 1.10 (t, 3H) ppm.

EXAMPLE 428

(3-{4-[4-{4-[2-(4-chloro-phenyl)-ethoxy]-phenyl}-2-(4-fluoro-phenyl)-imidazol-1-yl]-phenoxy}-propyl)-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H₂O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl) ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained from 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy] phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 4-fluorobenzoyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 334 mg).

MS m/z 598 (M+H)⁺:

$^1$H NMR (400 MHz, CDCl$_3$): δ7.76 (d, 2H), 7.41 (m, 2H), 7.26 (m, 2H), 7.21 (d, 2H), 7.16 (d, 2H), 7.01 (m, 7H), 4.16 (t, 2H), 4.05 (t, 2H), 3.05 (t, 2H), 2.97 (m, 6H), 2.18 (m, 2H), 1.24 (t, 6H) ppm

EXAMPLE 429

{3-[4-(4-{4-[2-(4-chloro-phenyl)-ethoxy]-phenyl}-2-cyclopropyl-imidazol-1-yl)-phenoxy]-propyl}-di-ethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H₂O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl) ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained from 20-30% EtOAc/hexane.

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation .

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of cyclopropanecarbonyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 260 mg).

MS m/z 544 (M+H)$^+$:

$^1$H NMR (400 MHz, CDCl$_3$): δ7.65 (d, 2H), 7.31 (m, 4H), 7.21 (d, 2H), 7.18 (s, 1H), 6.98 (d, 2H), 6.88 (d 2H), 4.18 (t, 2H), 4.08 (t, 2H), 3.07 (t, 2H), 3.12 (m, 1H) 2.78 (m, 6H), 2.57 (m, 4H), 2.06 (m, 2H), 1.12 (t, 6H) ppm

EXAMPLE 430

{3-[4-(4-{4-[2-(4-chloro-phenyl)-ethoxy]-phenyl}-2-cyclopentyl-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation .

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation .

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained from 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-(4-[3-(diethylamino)propoxy]phenyl)ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of cyclopentanecarbonyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 366 mg)

MS m/z 572 (M+H)⁺:

EXAMPLE 431

[3-(4-{4-[4-(biphenyl-4-yloxy)-phenyl]-imidazol-1-yl}-phenoxy)-propyl]-diethyl-amine To a stirred solution of N-[3-(4-aminophenoxy)propyl]-N, N-diethylamine (1.2 eq, 2 mmol) in anhydrous DMF (5 mL) DIEA (3 eq 6 mmol) was added, followed by a slow addition of the 2-bromo-1-(4-bromophenyl)ethanone described above (1.6 mmol), according to General Procedure R2. The reaction mixture was stirred under nitrogen at rt until completion, as indicated by TLC or HPLC. The reaction mixture was then diluted with cold H₂O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM (yield ~50-60%).

To a stirred solution of 1-(4-bromophenyl)-2-({4-[3-(diethylamino)propoxy]phenyl}amino)ethanone (2 mmol) in acetic acid (2 mL), ammonium acetate (excess, ~20 eq) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 40-50%).

To a solution of the N-(3-{4-[4-(4-bromophenyl)-1H-imidazol-1-yl]phenoxy}propyl)-N,N-diethylamine (0.07 mmol) in pyridine (1 mL), copper powder was added (0.14 mmol), followed by potassium carbonate (0.35 mmol) and 1,1'-biphenyl-4-ol (0.14 mmol). The mixture was heated at 110° C. overnight, then diluted with H₂O (2 mL) and extracted with EtOAc (3×2 mL). The combined organic extract was dried over sodium sulfate, filtered and concentrated to an oil, which was purified by column chromatography (Silica gel). The pure product was obtained from 1-6% MeOH/DCM (yield 11 mg).

MS m/z 518 (M+H)⁺:
¹H NMR (400 MHz, CDCl₃): δ 7.83-7.79 (m, 3H), 7.59-7.57 (m, 4H), 7.45-7.43 (m, 4H), 7.42-7.34 (m, 4H), 7.11 (d, 2H), 7.05 (d, 3H), 4.10 (t, 2H), 2.80-2-60 (m, 6H), 2.00-2.10 (m, 2H), 1.30 (t, 3H), 1.10 (t, 3H) ppm.

EXAMPLE 432 diethyl-[3-(4-{4-[4-(3-trifluoromethyl-phenoxy)-phenyl]-imidazol-1-yl}-phenoxy)-propyl]-amine To a stirred solution of N-[3-(4-aminophenoxy)propyl]-N, N-diethylamine (1.2 eq, 2 mmol) in anhydrous DMF (5 mL) DIEA (3 eq 6 mmol) was added, followed by a slow addition of 2-bromo-1-(4-bromophenyl)ethanone (1.6 mmol), according to General Procedure R2. The reaction mixture was stirred under nitrogen at rt until completion, as indicated by TLC or HPLC. The reaction mixture was then diluted with cold H₂O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM (yield ~50-60%).

To a stirred solution of 1-(4-bromophenyl)-2-({4-[3-(diethylamino)propoxy]phenyl}amino)ethanone (2 mmol) in acetic acid (2 mL), ammonium acetate (excess, ~20 eq) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 40-50%).

To a solution of N-(3-{4-[4-(4-bromophenyl)-1H-imidazol-1-yl]phenoxy}propyl)-N,N-diethylamine (0.07 mmol) in pyridine (1 mL), copper powder was added (0.14 mmol), followed by potassium carbonate (0.35 mmol) and 3-(trifluoromethyl)phenol (0.14 mmol). The mixture was heated at 110° C. overnight, then diluted with H₂O (2 mL) and extracted with EtOAc (3×2 mL). The combined organic extract was dried over sodium sulfate, filtered and concentrated to an oil, which was purified by column chromatography (Silica gel). The pure product was obtained from 1-6% MeOH/DCM (yield 10 mg).

MS m/z 510 (M+H)⁺:

EXAMPLE 433

[3-(4-{4-[4-(3,4-dichloro-phenoxy)-phenyl]-imidazol-1-yl}-phenoxy)-propyl]-diethyl-amine To a stirred solution of N-[3-(4-aminophenoxy)propyl]-N, N-diethylamine (1.2 eq, 2 mmol) in anhydrous DMF (5 mL) DIEA (3 eq 6 mmol) was added, followed by a slow addition of 2-bromo-1-(4-bromophenyl)ethanone (1.6 mmol), according to General Procedure R2. The reaction mixture was stirred under nitrogen at rt until completion, as indicated by TLC or HPLC. The reaction mixture was then diluted with cold H₂O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product was obtained from 2-4% MeOH/DCM (yield ~50-60%).

To a stirred solution of 1-(4-bromophenyl)-2-({4-[3-(diethylamino)propoxy]phenyl}amino)ethanone (2 mmol) in acetic acid (2 mL), ammonium acetate (excess, ~20 eq) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 40-50%).

To a solution of N-(3-{4-[4-(4-bromophenyl)-1H-imidazol-1-yl]phenoxy}propyl)-N,N-diethylamine (0.07 mmol) in pyridine (1 mL), copper powder was added (0.14 mmol) followed by potassium carbonate (0.35 mmol), and 3,4-dichlorophenol (0.14 mmol). The mixture was heated at 110° C. overnight, then diluted with H₂O (2 mL) and extracted with EtOAc (3×2 mL). The combined organic extract was dried over sodium sulfate, filtered and concentrated to an oil, which was purified by column chromatography (Silica gel). The pure product was obtained from 1-6% MeOH/DCM (yield 15 mg)

MS m/z 510 (M+H)⁺: .

EXAMPLE 434

[3-(4-{2-butyl-1-[4-(4-methoxy-phenoxy)-phenyl]-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and to this saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxy-acetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the 1-{4-[3-(diethylamino)propoxy]phenyl}ethanone was purified by flash chromatography (going by increasing gradient up to 10% MeOH in DCM). The overall yield was 60%.

4-Methoxyphenol (10 mmol) was dissolved in 15 ml of anhydrous DMF and potassium carbonate (30 mmol) was added with stirring at rt. 4-Fluoronitrobenzene (10 mmol) was added to this mixture, which was then heated under reflux at 80° C. for 18 h. The reaction was quenched with 30 ml of water and 30 ml of sodium bicarbonate, extracted with EtOAc (3×50 ml) and washed with sodium bicarbonate and water. The EtOAc layer was dried over anhydrous sodium sulfate and filtered, after which the solvent was removed in vacuuo.

The nitro intermediate (10 mmol) obtained above was dissolved in EtOH (30 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-(4-methoxyphenoxy)aniline, which was used directly for further transformation without further purification (yield 80%).

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(4-methoxyphenoxy) aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 52%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 190 mg).

MS m/z 529 (M+H)$^+$:

$^1$H NMR (CDCl$_3$): δ7.7 (d, 2H), 7.2 (d, 2H), 7.16 (s, 1H), 6.8-7.1 (m, 8H), 4.0 (t, 2H), 3.8 (s, 3H), 2.8-3.0 (m, 8H), 2.6 (m, 2H), 2.2 (m, 2H), 1.6(m, 2H), 1.2 (t, 6H), 0.8 (t, 3H) ppm.

EXAMPLE 435

1-[2-(4-{2-butyl-1-[4-(3-fluoro-4-trifluoromethyl-phenoxy)-phenyl]-1H-imidazol-4-yl}-phenoxy)-ethyl]-piperazine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(3-fluoro-4-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained from 5-20% EtOAc/Hexane (yield ~50-60%).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 5-15% EtOAc/Hexane (yield 80%). (MS: m/z 562 (M+H)$^+$)

The above product was dissolved in MeOH (20 mL), and Pd/C (100 mg) was added and the heterogeneous mixture was stirred overnight under hydrogen atmosphere using a balloon, according to General Procedure H. The Pd/C was removed by filtration. The solvent was removed in vacuuo, and the crude phenol (MS: m/z 472 (M+H)$^+$) was used for further transformation.

To a stirred solution of the phenol (0.16 mmol) obtained above in anhydrous DMF (5 mL) solid sodium hydride (60% dispersion in oil; 1.0 mmol) was added in portions. After the addition, 4-(2-methanesulfonyloxy)-piperazine-1-carboxylic acid tertbutylester (2.0 mmol) was added to the reaction mixture. The reaction mixture was heated at 90° C. overnight. After cooling the mix to rt, Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure product was obtained from 5-10% MeOH/DCM (yield ~45%).

This product was dissolved in DCM (10 mL) and HCl (4.0 M in dioxane, 1.0 mL) was added and stirrings continued overnight until reaction completed as indicated by HPLC. EtOAc (40 ml) added, followed by sodium bicarbonate (sat, 15 mL). The organic layer was washed with brine (10 mL) and dried with magnesium sulfate. The solvent was removed in in vacuuo to give the title compound as white solid (yield 37 mg).

MS m/z 584 (M+H)$^+$:

$^1$H NMR (CDCl$_3$): δ7.70 (d, 2H), 7.20-7.35 (m, 5H), 7.14 (s, 1H), 7.08 (d, 2H), 6.92 (d, 2H), 4.05 (t, 2H), 3.0 (m, 4H), 2.8 (t, 2H), 3.4 (m, 6H), 1.6 (m, 2H), 1.3 (m, 3H), 0.9 (t, 3H) ppm.

EXAMPLE 436

{3-[4-(4-{4-[2-(4-chloro-phenyl)-ethoxy]-phenyl}-imidazol-1-yl)-phenoxy]-propyl}-dimethyl-amine To a stirred solution of 4-aminophenol (4.8 mmol) in MeOH (20 mL), 1-bromo-4'-(4-chlorophenethoxy)acetophenone (4 mmol) was added at rt. The resulting mixture was then heated to reflux for 45 min. The reaction mixture was then cooled to rt and the solvent was removed in vacuuo. The resulting solid was dissolved in EtOAc (30 mL), washed with H$_2$O (2×20 mL) and brine (20 mL) and dried over sodium sulfate. Evaporation of solvent in vacuuo afforded the desired 1-(4-hydroxyphenyl)amino-4'-(4-chlorophenethoxy)acetophenone, which was used for further transformation .

The aminoacetophenone obtained as above (3 mmol) was dissolved in formic acid (3 mL) and added with ammonium formate (60 mmol). The resulting mixture was heated to 90° C. overnight. The reaction mixture was then cooled down and neutralized with saturated sodium bicarbonate solution. Usual extractive work up with EtOAc gave the product, 4-{4-[2-(4-chlorophenyl)ethoxy]phenyl}-1-[(4-hydroxy)phenyl]-1H-imidazole, which was purified by column chromatography (Silica gel). Pure product was obtained from 4-6% MeOH/DCM (yield ~50%).

To a solution of the product obtained above (0.5 mmol) in anhydrous THF (2 mL), NaH (60% dispersion in oil; 1 mmol) was added at 0° C. The resuting mixture was added with a solution of the mesylate of N,N-dimethylpropanol (0.6 mmol) in THF (1 mL). The reaction mixture was then heated to 70° C. overnight. Usual extractive work up with EtOAc gave the product imidazole, which was purified by column chromatography (Silica gel). Pure product was obtained from 4-6% MeOH/DCM.

MS m/z 476 (M+H)$^+$:

$^1$H NMR (CDCl$_3$): δ7.76 (s, 1H), 7.73 (d, 2H), 7.38 (s, 1H), 7.31 (d, 2H), 7.25 (ABq, 4H), 6.99 (d, 2H), 6.92 (d, 2H,), 4.18 (t, 2H), 4.05 (t, 2H), 3.07 (t, 2H), 2.49 (t, 2H), 2.28 (s, 6H), 1.99 (q, 2H) ppm.

EXAMPLE 437

4-{4-[2-(4-chloro-phenyl)-ethoxy]-phenyl}-1-{4-[2-(1-methyl-pyrrolidin-2-yl)-ethoxy]-phenyl}-1H-imidazole To a stirred solution of 4-aminophenol (4.8 mmol) in MeOH (20 mL), 1-bromo-4'-(4-chlorophenethoxy)acetophenone (4 mmol) was added at rt. The resulting mixture was then heated to reflux for 45 min. The reaction mixture was then cooled to rt and the solvent was removed in vacuuo. The resulting solid was dissolved in EtOAc (30 mL), washed with H$_2$O (2×20 mL) and brine (20 mL) and dried over sodium sulfate. Evaporation of solvent in vacuuo afforded the desired 1-(4-hydroxyphenyl)amino-4'-(4-chlorophenethoxy)acetophenone, which was used for further transformation .

The aminoacetophenone obtained as above (3 mmol) was dissolved in formic acid (3 mL) and added with ammonium formate (60 mmol). The resulting mixture was heated to 90° C. overnight. The reaction mixture was then cooled down and neutralized with saturated sodium bicarbonate solution. Usual extractive work up with EtOAc gave the product, 4-{4-[2-(4-chlorophenyl)ethoxy]phenyl}-1-[(4-hydroxy)phenyl]-1H-imidazole, which was purified by column chromatography (Silica gel). Pure product was obtained from 4-6% MeOH/DCM (yield ~50%).

To a solution of the product-obtained above (0.5 mmol) in anhydrous THF (2 mL), NaH (60% dispersion in oil; 1 mmol) was added at 0° C. The resuting mixture was added with a solution of the mesylate of 2-(N-methylpyrrolidin-2-yl)ethanol (0.6 mmol) in THF (1 mL). The reaction mixture was then heated to 70° C. overnight. Usual extractive work up with EtOAc gave the product imidazole, which was purified by column chromatography (Silica gel). Pure product was by obtained by elution with 4-6% MeOH/DCM (yield 125 mg)

MS m/z 503 (M+H)$^+$:

$^1$H NMR (CDCl$_3$): δ7.75 (s, 1H), 7.72 (d, 2H), 7.38 (s, 1H), 7.31 (d, 2H), 7.26 (ABq, 4H), 6.95 (d, 2H), 6.92 (d, 2H), 4.17 (t, 2H), 3.04 (t, 2H), 2.90-2.50 (m, 4H), 2.43 (s, 3H), 2.30-1.50 (m, 7H) ppm.

EXAMPLE 438

1-{2-[4-(4-{4-[2-(4-chloro-phenyl)-ethoxy]-phenyl}-imidazol-1-yl)-phenoxy]-ethyl}-piperazine To a stirred solution of 4-aminophenol (4.8 mmol) in MeOH (20 mL), 1-bromo-4'-(4-chlorophenethoxy)acetophenone (4 mmol) was added at rt. The resulting mixture was then heated to reflux for 45 min. The reaction mixture was then cooled to rt and the solvent was removed in vacuuo. The resulting solid was dissolved in EtOAc (30 mL), washed with H$_2$O (2×20 mL) and brine (20 mL) and dried over sodium sulfate. Evaporation of solvent in vacuuo afforded the desired 1-(4-hydroxyphenyl)amino-4'-(4-chlorophenethoxy)acetophenone, which was used for further transformation.

The aminoacetophenone obtained as above (3 mmol) was dissolved in formic acid (3 mL) and added with ammonium formate (60 mmol). The resulting mixture was heated to 90° C. overnight. The reaction mixture was then cooled down and neutralized with saturated sodium bicarbonate solution. Usual extractive work up with EtOAc gave the product, 4-{4-[2-(4-chlorophenyl)ethoxy]phenyl}-1-[(4-hydroxy)phenyl]-1H-imidazole, which was purified by column chromatography (Silica gel). Pure product was obtained by elution with 4-6% MeOH/DCM (yield ~50%).

To a solution of the product obtained above (0.5 mmol) in anhydrous THF (2 mL), NaH (60% dispersion in oil; 1 mmol) was added at 0° C. The resuting mixture was added with a solution of the mesylate of 1-(t-butyloxycarbonyl)-2-(2-hydroxy)ethylpiperazine (0.6 mmol) in THF (1 mL). The reaction mixture was then heated to 70° C. overnight. Usual extractive work up with EtOAc gave the product imidazole, which was purified by column chromatography (Silica gel). Pure product was obtained by elution with 4-6% MeOH/DCM (yield ~50%).

The product obtained above was treated with 4M HCl in dioxane (1 mL) and the resulting mixture was stirred at rt for 4 h. Evaporation of the solvent, repeated washing of the hydrochloride salt thus obtained with diethyl ether and subsequent drying in vacuuo afforded the desired product.

MS m/z 503 (M+H)$^+$:

$^1$H NMR (CD$_3$OD): δ9.47 (s, 1H), 8.28(s, 1H), 7.76 (d, 2H), 7.72 (d, 2H), 7.33 (d, 2H), 7.29 (s, 4H), 7.06 (d, 2H), 4.58 (broad t, 2H), 4.22 (t, 2H), 3.83 (broad t, 4H), 3.74 (broad t, 6H), 3.06 (t, 2H) ppm.

EXAMPLE 439

[3-(4-{2-(3-cyclohexyl-propyl)-1-[4-(4-fluoro-3-trifluoromethyl-phenoxy)-phenyl]-1H-imidazol-4-yl}-phenoxy)-propyl]-diethyl-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold H$_2$O (60 mL). The resulting mixture was extracted with EtOAc (3×100 mL). The combined EtOAc extracts were washed with H$_2$O (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold H$_2$O (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy]phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL): DIEA (12 mmol) was added, followed by a slow addition of the 2-bromo-1-{4-[3-(diethylamino)propoxy]phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added, followed by a slow addition of 4-cyclohexylbutanoyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (overall yield: 60-70%) (yield 78 mg).

MS m/z 652 (M+H)$^+$:

$^1$H NMR (400 MHz, CDCl$_3$): δ 0.75-1.65 (m, 15H), 1.07 (t, 6H), 1.97 (m, 2H), 2.62 (q, 4H), 2.63-2.70 (m, 4H), 4.02 (t, 2H), 6.90 (d, 2H), 7.07 (d, 2H), 7.14 (s, 1H), 7.22 (br s, 1H), 7.23 (br d, 1H), 7.25 (d, 1H), 7.31 (d, 2H), 7.69 (d, 2H) ppm.

EXAMPLE 440 diethyl-(3-{4-[1-[4-(4-fluoro-3-trifluoromethyl-phenoxy)-phenyl]-2-(3-phenoxy-propyl)-1H-imidazol-4-yl]-phenoxy}-propyl)-amine To a stirred solution of 4-fluoronitrobenzene (20 mmol), 4-fluoro-3-trifluoromethylphenol (22 mmol) in DMF (50 mL) at rt, solid potassium carbonate (60 mmol) was added, and the reaction mixture was heated to 90° C. for 5 h (monitored by TLC), according to General Procedure L1. After cooling to rt, the reaction mixture was poured into cold $H_2O$ (60 mL). The resulting mixture was extracted with EtOAc (3×100 mL). The combined EtOAc extracts were washed with $H_2O$ (2×40 mL) and brine (50 mL), and dried over anhydrous sodium sulfate. The solvent was removed in vacuuo to afford the desired 1-fluoro-4-(4-nitrophenoxy)-2-(trifluoromethyl)benzene. The crude product was used directly for further transformation without further purification.

The nitro intermediate (2 mmol) obtained above was dissolved in MeOH (10 mL) and hydrogenated in the presence of 10% Pd/C (50 mg) until completion as indicated by TLC or LC-MS, according to General Procedure H. The reaction mixture was then filtered to remove the catalyst. The solvent was removed in vacuuo to afford 4-(4'-fluoro-3'-trifluoromethyl-phenoxy)aniline, which was used directly for further transformation without purification (overall yield: 95%).

To a stirred solution of ice-cold 3-diethylaminopropanol (63 mmol) and TEA (80 mmol) dissolved in anhydrous DCM (50 mL) was added dropwise methanesulfonyl chloride (60 mmol), and the reaction mixture was stirred for 2 h at 0° C. and followed by additional 1 h at rt. After the removal of the solvents in vacuuo, the crude mesylate was dissolved in DMF (100 mL). 4-Hydroxyacetophenone (40 mmol) and cesium carbonate (100 mmol) were added, and the mixture was heated with stirring at 90° C. for 18 h (monitored by LC-MS). After cooling to rt, the reaction was quenched with cold $H_2O$ (100 mL), and the resulting mixture was extracted with EtOAc (4×100 mL). The combined EtOAc extracts were washed with brine (3×60 ml), and dried over anhydrous sodium sulfate. The solvent was removed in vacuuo, and the crude 1-{4-[3-(diethylamino)propoxy]phenyl}ethanone was purified by silica gel column chromatography eluting with 10% MeOH in EtOAc+0.2% TEA (yield: 75%).

To a stirred solution of 1-{4-[3-(diethylamino)propoxy] phenyl}ethanone (4 mmol) in MeOH (10 mL) at rt, pyrrolidone hydrotribromide (4.8 mmol) was added, according to General Procedure R1. The reaction mixture was stirred at rt for 1 h (monitored by LC-MS). The solvent was then removed in vacuuo and the crude 2-bromo-1-{4-[3-(diethylamino)propoxy]phenyl}ethanone was directly used for further transformation.

To a stirred solution of 4-(4'-fluoro-3'-trifluoromethyl-phenoxy)aniline (4.8 mmol) dissolved in anhydrous DMF (10 mL), DIEA (12 mmol) was added, followed by a slow addition of the 2-bromo-1-{4-[3-(diethylamino)propoxy] phenyl}ethanone obtained above (~4 mmol), according to General Procedure R2. The reaction mixture was stirred at rt and under nitrogen until completion (~5 h), as indicated by LC-MS. The reaction was quenched with saturated sodium bicarbonate (50 mL), and the resulting mixture was extracted with EtOAc (3×100 mL). The combined EtOAc extracts were washed with brine (3×40 mL), and dried over anhydrous sodium sulfate. The solvent was removed in vacuuo, and the crude product was purified by silica gel column chromatography eluting with 10% MeOH in EtOAc+0.2% TEA (yield: 64%).

To a stirred solution of the alkylated aniline described above (0.2 mmol) in anhydrous DCM (5 mL) at 0° C., TEA (1.2 mmol, 6 eq) was added, followed by a slow addition of 4-phenoxybutanoyl chloride (0.6 mmol, 3 eq), according to General Procedure R3. The reaction mixture was stirred under nitrogen at 0° C. for 1 h and allowed to warm to rt until completion, as indicated by LC-MS. The solvent was removed in vacuuo, and the crude amide was used directly for further transformation.

To a stirred solution of the amide described above (~0.2 mmol) in acetic acid (2 mL), ammonium acetate (excess, ~30 eq) was added, according to General Procedure R4. The reaction mixture was stirred at 100° C. for 2-5 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+0.2% TEA (yield 73 mg).

MS m/z 662 $(M+H)^+$:

$^1$H NMR (400 MHz, CDCl$_3$): δ1.06 (t, 6H), 1.97 (m, 2H), 2.24 (m, 2H), 2.60 (q, 4H), 2.67 (t, 2H), 2.88 (t, 2H), 3.99 (t, 2H), 4.03 (t, 2H), 6.80 (d, 2H), 6.90-7.25 (m, 8H), 7.01 (d, 2H), 7.15 (s, 1H), 7.28 (d, 1H), 7.70 (d, 2H) ppm.

EXAMPLE 441

{3-[4-(4-{4-[2-(4-chloro-phenyl)-ethoxy]-phenyl}-2-methyl-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold $H_2O$ (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of acetyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 250 mg).

MS m/z 519 (M+H)$^+$:

$^1$H NMR (400 MHz, CDCl$_3$): δ7.67 (d, 2H), 7.22 (d, 2H), 7.21 (m, 5H), 6.96 (d, 2H), 6.84 (d, 2H), 4.17 (t, 2H), 4.07 (t, 2H), 3.06 (t, 2H), 2.78 (t, 2H), 2.74 (m, 4H), 2.36 (s, 3H), 2.06 (m, 2H), 1.13 (t, 6H) ppm

EXAMPLE 442

3-(4-{2-butyl-1-[4-(4-fluoro-3-trifluoromethyl-phenoxy)-phenyl]-1H-imidazol-4-yl}-phenoxy)-1-ethyl-piperidine To a stirred solution of 4-benzyloxyacetophenone (7.0 mmol) in anhydrous DCM (30.0 mL) and MeOH (5.0 mL) at rt, pyridinium bromide perbromide (1.1 eq.) was added, according to General Procedure R1. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The 1-[4-(benzyloxy)phenyl]-2-bromo-ethanone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the 1-[4-(benzyloxy)phenyl]-2-bromoethanone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired alkylated aniline, which was purified by chromatography (Silica gel). Pure product was obtained by elution with 5-20% EtOAc/Hexane (yield ~50-60%).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained by elution with 5-15% EtOAc/Hexane (yield 80%).

The above product was dissolved in MeOH (20 mL), and Pd/C (100 mg) was added and the heterogeneous mixture was stirred overnight under hydrogen atmosphere using a balloon, according to General Procedure T2. The Pd/C was removed by filtration. The solvent was removed in vacuuo, and the crude 4-(1-{4-[4-fluoro-3-(trifluoromethyl)phenoxy]phenyl}-2-butyl-1H-imidazol-4-yl)phenol was used for further transformation.

A stirred solution of the 4-(1-{4-[4-fluoro-3-(trifluoromethyl)phenoxy]phenyl}-2-butyl-1H-imidazol-4-yl)phenol (1.0 eq) in anhydrous DMF (5.0 mL) was treated with solid sodium hydride (60% dispersion in oil; 1.0 mmol) in portions. The mesylate of 1-(methylamino)piperidin-3-ol was then added to the reaction mixture, which was heated at 90° C. overnight, according to General Procedure T3. After cooling the mix to rt, Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained by elution with chromatography in 5-10% MeOH/DCM (yield 52.0 mg)

MS m/z 583 (M+H)$^+$:

¹H NMR (CDCl₃): δ 7.7 (m, 2H), 7.3 (m, 3H), 7.24 (m, 2H), 7.13 (s, 1H), 7.07 (d, 2H, J=8.8 Hz), 6.94 (m, 2H), 0.9-4.4 (m, 23H) ppm.

EXAMPLE 443 diethyl-[3-(4-{1-[4-(4-fluoro-3-trifluoromethyl-phenoxy)-phenyl]-2-methyl-1H-imidazol-4-yl}-phenoxy)-propyl]-amine To a stirred solution of 4-fluoronitrobenzene (2.0 mmol) in anhydrous THF (5 mL) at 0° C., a 1M solution of a potassium 4-fluoro-3-trifluoromethyl-phenoxide (2.2 mmol) in THF (may be generated by adding the corresponding alcohol to a 1M solution of potassium t-butoxide in THF) was added dropwise and under a nitrogen stream, according to General Procedure L1. The reaction mixture was stirred at 0° C. until completion, as indicated by TLC or HPLC. The solvent was then removed in vacuo and the reaction mixture was treated with cold H₂O (15 mL), and extracted with EtOAc (2×15 mL). The combined organic layers were washed with brine and dried over sodium sulfate. Evaporation of the solvent in vacuuo afforded the desired 1-fluoro-4-(4-nitrophenoxy)-2-(trifluoromethyl)benzene. The crude product could be used directly for further transformation.

The nitro intermediate (2 mmol) obtained above was dissolved in MeOH (10 mL) and hydrogenated in the presence of 10% Pd/C (10 mg) until completion, as indicated by TLC or HPLC, according to General Procedure H. The reaction mixture was then filtered to remove the catalyst. The solvent was removed in vacuuo to afford the desired-4-[4-fluoro-3-(trifluoromethyl)phenoxy]aniline, which was used directly for further transformation without further purification.

To a stirred solution of 4'-hydroxyacetophenone (2.2 mmol) in DMF (10 mL) at rt, solid potassium carbonate (8.0 mmol) was added. The mesylate of N,N-diethyaminopropanol (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired 1-{4-[3-(diethylamino)propoxy] phenyl}ethanone. The crude alkylated product was purified using silica gel column chromatography. Pure product was obtained with 2-3% MeOH/DCM. (yield 50-60%)

To a stirred solution of the 1-{4-[3-(diethylamino)propoxy]phenyl}ethanone described above (1 mmol) in anhydrous MeOH (5 mL) at 0° C., pyrrolidone hydrotribromide (1.2 eq., 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo, the residue was treated with saturated sodium bicarbonate and the product was isolated in EtOAc. The combined organic layers were washed with water (2×15 ml) and brine (15 ml). The organic layer was dried over magnesium sulfate, and the solvent was removed in vacuuo to afford the desired product. The crude 2-bromo-1-{4-[3-(diethylamino)propoxy]phenyl}ethanone was used for further transformation.

To a stirred solution of the 4-fluoro-3-trifluoromethyl-phenoxy aniline (1.2 eq., 1.2 mmol) in anhydrous DMF (5 mL) DIEA (3 eq. 3 mmol) was added, followed by slow addition of the 2-bromo-1-{4-[3-(diethylamino)propoxy] phenyl}ethanone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3.0 mmol) was added, followed by slow addition of acetyl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was purified using silica gel chromatography. Pure product was obtained by elution with 3-4% MeOH/DCM (Yield 40-45%).

To a stirred solution of the amide described above (0.5 mmol) in acetic acid (1 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 108 mg).

MS m/z 542 (M+H)⁺:

¹H NMR (400 MHz, CDCl₃): δ7.69 (d, 2H), 7.33 (m, 5H), 7.18 (s, 1H), 7.09 (d, 2H), 6.91 (d, 2H) 4.03 (t, 2H), 2.63 (m, 6H), 2.41 (s, 3H), 2.01 (m, 2H), 1.08 (t, 6H) ppm

EXAMPLE 444

(3-{4-[4-(4-benzyloxy-phenyl)-2-butyl-imidazol-1-yl]-phenoxy}-propyl)-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H₂O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-(N,N-diethylaminopropoxy)aniline, which was used directly for further transformation without further purification.

To a stirred solution of the 4'-benzyloxyacetophenone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 mL) and the product was isolated in EtOAc (2×20 mL). The combined organic layers were washed with saturated sodium thiosulfate (2×10 mL), water (2×10 mL) and brine (15 mL). The organic layer was dried over magnesium sulfate, and the solvent was removed in vacuuo to afford the desired product. The crude alpha-bromoacetophenone was purified by chromatography (Silica gel). Pure product was obtained by elution with 20-30% EtOAc/hexane (yield ~70-75%).

To a stirred solution of the 4-(N,N-diethylaminopropoxy) aniline (1.2 eq., 2 mmol) in anhydrous DMF (5 mL) the alpha-bromoacetophenone (1.6 mmol) described above was added slowly, according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.6 mmol) in anhydrous DCM (5 mL) at 0° C., TEA (3 eq., 4.8 mmol) was added, followed by slow addition of valeryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column, chromatography (Silica gel). Pure product was obtained by elution with 4-6% MeOH/DCM (yield 179 mg).

MS m/z 512 (M+H)$^+$:

$^1$H NMR (CDCl$_3$): δ7.69 (d, 2H), 7.15-7.50 (m, 8H), 7.09 (s, 1H), 6.96 (m, 3H), 5.05 (s, 2H), 4.12 (t, 2H), 3.21 (broad m, 2H), 3.15 (q, 4H), 2.64 (t, 2H) 2.38 (broad m, 2H), 1.60 (q, 2H) 1.41 (t, 6H) 1.20-1.35 (m, 2H), 0.81 (t, 6H) ppm.

EXAMPLE 445

[3-(4-{2-butyl-1-[4-(2,5-difluoro-benzyloxy)-phenyl]-1H-imidazol-4-yl}-phenoxy)-propyl]-diethylamine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product 1-{4-[3-(diethylamino)propoxy]phenyl}ethanone was purified by flash chromatography (going by increasing gradient up to 10% MeOH in DCM). The overall yield was 60%.

To a stirred solution of 4-fluoronitrobenzene (2.0 mmol) in anhydrous THF (6 mL) at 0° C., a 1M solution of a potassium alkoxide (2.2 mmol) in THF (may be generated by adding the 2,5-difluorobenzyl alcohol to a 1M solution of KOBu$^t$ in THF) was added dropwise and under a nitrogen stream, according to General Procedure L1. The reaction mixture was stirred at 0° C. until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product could be used directly for further transformation without any purification, or after purifying using silica gel column chromatography.

The nitro intermediate (2 mmol) obtained above was dissolved in MeOH (6 mL) and hydrogenated in the presence of 10% Pd/C (10 mg) until completion, as indicated by TLC or HPLC, according to General Procedure H. The reaction mixture was then filtered to remove the catalyst. The solvent was removed in vacuuo to afford 4-(2,5-difluoro-benzyloxy) aniline, which was used directly for further transformation without further purification (yield 80%).

To a stirred solution of 1-{4-[3-(diethylamino)propoxy] phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(2,5-difluoro-benzyloxy)aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product by elution with 2-4% MeOH/DCM (yield 50%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 mmol, 20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield 208 mg).

MS m/z 549 (M+H)$^+$:

$^1$H NMR (CDCl$_3$): δ7.68 (d, 2H), 7.24 (m, 5H), 7.13 (s, 1H), 7.06 (d, 2H), 6.89 (d, 2H), 5.17 (s, 2H), 4.02 (t, 2H), 2.62-2.78 (m, 8H), 1.98 (m, 2H), 1.60 (m, 2H), 1.27 (m, 2H), 1.11 (t, 6H), 0.82 (t, 3H) ppm.

EXAMPLE 446

3-(S)-(4-{2-butyl-1-[4-(4-fluoro-3-trifluoromethyl-phenoxy)-phenyl]-1H-imidazol-4-yl}-phenoxymethyl)-1-ethyl-piperidine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 5-20% EtOAc/Hexane (yield ~50-60%).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained by elution with 5-15% EtOAc/Hexane (yield 80%). (MS: m/z 562 (M+H)$^+$)

The above product was dissolved in MeOH (20 mL), and Pd/C (100 mg) was added and the heterogeneous mixture was stirred overnight under hydrogen atmosphere using a balloon, according to General Procedure T2. The Pd/C was removed by filtration. The solvent was removed in vacuuo, and the crude 4-(1-{4-[4-fluoro-3-(trifluoromethyl)phenoxy]phenyl}-2-butyl-1H-imidazol-4-yl)phenol (MS: m/z 472 (M+H)$^+$) was used for further transformation.

A stirred solution of the 4-(1-{4-[4-fluoro-3-(trifluoromethyl)phenoxy]phenyl}-2-butyl-1H-imidazol-4-yl)phenol (1.0 eq) in anhydrous DMF (5.0 mL) was treated with solid sodium hydride (60% dispersion in oil; 1.0 mmol) in portions. The mesylate of [(3S)-1-ethylpiperidin-3-yl]methanol (1.5-2.0 eq) was added to the reaction mixture, which was heated at 90° C. overnight, according to General Procedure T3. After cooling the mix to rt, Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained by elution with chromatography in 5-10% MeOH/DCM (yield 50.0 mg).

MS m/z 597 (M+H)$^+$:

$^1$H NMR (CDCl$_3$): δ 7.70 (d, 2H), 7.20-7.35 (m, 5H), 7.14 (s, 1H), 7.08 (d, 2H), 6.92 (d, 2H), 4.05 (m, 1H), 3.92 (m, 2H), 2.60 (m, 4H), 1.0-2.5 (m, 18H) ppm.

EXAMPLE 447

(3-{4-[4-{2-(4-chloro-phenyl)-ethoxy]-phenyl}-2-(2,4,4-trimethyl-pentyl)-imidazol-1-yl]-phenoxy}-propyl)-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 3,5,5-trimethyl hexanoyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then dilutad with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 296 mg).

MS m/z value (M+H)+: 617

$^1$H NMR (400 MHz, CDCl$_3$): δ7.69 (d, 2H), 7.22 (d, 2H), 7.21 (m, 5H), 6.96 (d, 2H), 6.88 (d, 2H), 4.18 (t, 2H), 4.07 (t, 2H), 3.09 (t, 2H), 2.88 (d, 2H), 2.79 (m, 6H), 2.05 (m, 3H), 1.11 (t, 6H), 0.97 (d, 2H), 0.87 (d, 3H), 0.78 (s, 9H) ppm

EXAMPLE 448

3-(R)-(4-{2-butyl-1-[4-(4-fluoro-3-trifluoromethyl-phenoxy)-phenyl]-1H-imidazol-4-yl}-phenoxymethyl)-1-ethyl-piperidine To a stirred solution of 4-benzyloxyacetophenone (7.0 mmol) in anhydrous DCM (30.0 mL) and MeOH (5.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromoacetophenone was used for further transformation without further purification.

To a stirred solution of 4-(4-fluoro-3-trifluoromethyl-phenoxy)-aniline (1.64 mmol) in anhydrous DMF (30 mL) DIEA (3 eq) was added, followed by slow addition of the alpha-bromoacetophenone described above (2 eq), according to General Procedure R2. The reaction mixture was stirred under nitrogen at rt until completion, as indicated by TLC and HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 5-20% EtOAc/Hexane (yield ~50-60%).

To a stirred solution of alkylated aniline described above (1.0 mmol) in anhydrous THF (20 mL) at 0° C., TEA (3 eq, 3 mmol) was added, followed by slow addition of valeryl chloride (3 eq, 3.0 mmol), according to General Procedure R3. The reaction mixture was stirred under nitrogen at 0° C. for 1 h and allowed to warm to ambient temperature until completion, as indicated by TLC and HPLC. The solvent was removed in vacuuo, and the crude amide was used for further transformation.

To a stirred solution of the amide described above (1.0 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained by elution with 5-15% EtOAc/Hexane (yield 80%). (MS: m/z 562 (M+H)+)

The above product was dissolved in MeOH (20 mL), and Pd/C (100 mg) was added and the heterogeneous mixture was stirred overnight under hydrogen atmosphere using a balloon, according to General Procedure T2. The Pd/C was removed by filtration. The solvent was removed in vacuuo, and the crude 4-(1-{4-[4-fluoro-3-(trifluoromethyl)phenoxy]phenyl}-2-butyl-1H-imidazol-4-yl)phenol (MS: m/z 472 (M+H)+) was used for further transformation.

A stirred solution of the 4-(1-{4-[4-fluoro-3-(trifluoromethyl)phenoxy]phenyl}-2-butyl-1H-imidazol-4-yl)phenol (1.0 eq) in anhydrous DMF (5.0 mL) was treated with solid sodium hydride (60% dispersion in oil; 1.0 mmol) in portions. The mesylate of [(3R)-1-ethylpiperidin-3-yl]methanol (1.5-2.0 eq) was added to the reaction mixture, which was heated at 90° C. overnight, according to General Procedure T3. After cooling the mix to rt, Et$_2$O (30 mL) was added to the reaction mixture followed by H$_2$O (10 mL). The organic layer was washed with H$_2$O (2×15 mL) and brine, and dried over sodium sulfate.

The solvent was removed in vacuuo. Pure imidazole was obtained by elution with chromatography in 5-10% MeOH/DCM (yield 50.0 mg).

MS m/z 597 (M+H)+:

$^1$H NMR (CDCl$_3$): δ 7.70 (d, 2H), 7.20-7.35 (m, 5H), 7.14 (s, 1H), 7.08 (d, 2H,), 6.92 (d, 2H), 4.05 (m, 1H), 3.92 (m, 2H), 2.60 (m, 4H), 1.0-2.5 (m, 18H). ppm.

EXAMPLE 449

[3-(4-{2-butyl-1-[4-(3-tert-butyl-phenoxy)-phenyl]-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxy-acetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product 1-{4-[3-(diethylamino)propoxy]phenyl}ethanone was purified by flash chromatography (going by increasing gradient up to 10% MeOH in DCM). The overall yield was 60%.

4-Methoxyphenol (10 mmol) was dissolved in 15 ml of anhydrous DMF and potassium carbonate (30 mmol) was added with stirring at rt. 4-Fluoronitrobenzene (10 mmol) was added to this mixture, which was then heated under reflux at 80° C. for 18 h. The reaction was quenched with 30 ml of water and 30 ml of sodium bicarbonate, extracted with EtOAc (3×50 ml) and washed with sodium bicarbonate and water. The EtOAc layer was dried over anhydrous sodium sulfate and filtered, after which the solvent was removed in vacuuo.

The nitro intermediate (10 mmol) obtained above was dissolved in EtOH (30 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-(3-tert-butyl-phenoxy)aniline, which was used directly for further transformation without further purification (yield 80%).

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(3-tert-butyl-phenoxy)aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product by elution with 2-4% MeOH/DCM (yield 51%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield 177 mg).

MS m/z 555 (M+H)$^+$:

$^1$H NMR (400 MHz, CDCl$_3$): δ 7.7 (d, 2H), 7.3 (m, 4H), 7.1-7.2 (m, 5H), 6.9 (d, 2H), 4.0 (t, 2H), 2.8-3.0 (m, 8H), 2.0 (m, 2H), 1.6 (m, 2H), 1.4(m, 2H), 1.2 (15H), 0.8 (t, 3H) ppm

EXAMPLE 450

{3-[4-(4-{4-[2-(4-chloro-phenyl)-ethoxy]-phenyl}-2-methoxymethyl-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of methoxy acetyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 265 mg).

MS m/z 549 (M+H)$^+$:

$^1$H NMR (400 MHz, CDCl$_3$): δ7.72 (d, 2H), 7.37 (d, 2H), 7.48 (m, 5H), 6.98 (d, 2H), 6.85 (d, 2H), 4.41 (s, 2H), 4.18 (t, 2H), 4.07 (t, 2H), 3.45 (s, 3H), 3.06 (t, 2H), 2.86 (m, 6H), 2.08 (m, 2H), 1.17 (t, 6H) ppm

EXAMPLE 451

(3-{4-[4-{4-[2-(4-chloro-phenyl)-ethoxy]-phenyl}-2-(1-ethyl-propyl)-imidazol-1-yl]-phenoxy}-propyl)-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation .

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation .

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation .

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 2-ethyl butyryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 230 mg).

MS m/z 575 (M+H)$^+$:

$^1$H NMR (400 MHz, CDCl$_3$): δ7.71 (d, 2H), 7.27 (m, 6H), 7.06 (s, 1H), 6.95 (d, 2H), 6.87 (d, 2H), 4.09 (t, 2H), 4.02 (t,

2H), 3.07 (t, 2H), 2.72 (m, 6H), 2.49 (m, 1H), 2.06 (m, 2H), 1.82 (m, 2H), 1.68 (m, 2H), 1.08 (t, 6H), 0.96 (t, 3H), 0.88 (t, 3H) ppm

EXAMPLE 452

(3-{4-[4-{4-[2-(4-chloro-phenyl)-ethoxy]-phenyl}-2-(3-phenoxy-propyl)-imidazol-1-yl]-phenoxy}-propyl)-diethyl-amine The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation .

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 4-phenoxy butyryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 250 mg).

MS m/z 638 (M+H)$^+$:

$^1$H NMR (400 MHz, CDCl$_3$): δ7.69 (d, 2H), 7.23-7.25 (m, 8H), 7.12 (s, 1H), 6.92 (m 5H), 6.81 (d, 2H), 4.18 (t, 2H), 4.09 (t, 2H), 3.95 (t, 2H), 3.07 (t, 2H), 2.85 (m, 8H), 2.22 (m, 2H), 2.05 (m, 2H), 1.20 (t, 6H) ppm

EXAMPLE 453

(3-{4-[4-{2-(4-chloro-phenyl)-ethoxy]-phenyl}-2-(1-propyl-butyl)-imidazol-1-yl]-phenoxy}-propyl)-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation .

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation .

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 2-N-propyl-N-valeryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 288 mg).

MS m/z 602 (M+H)$^+$:

$^1$H NMR (400 MHz, CDCl$_3$): δ7.69 (d, 2H), 7.23-7.25 (m, 6H), 7.04 (s, 1H), 6.97 (d, 2H), 6.87 (d, 2H), 4.18 (t, 2H), 4.09 (t, 2H), 3.06 (t, 2H), 2.87 (m, 6H), 2.63 (m, 1H), 2.13 (m, 2H), 1.81 (m, 2H), 1.54 (m, 2H), 1.17 (t, 10H), 0.89 (t, 6H) ppm

EXAMPLE 454

{3-[4-(2-(4-chloro-phenoxymethyl)-4-{4-[2-(4-chloro-phenyl)-ethoxy]-phenyl}-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of 4-chlorophenoxy acetyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 250 mg).

MS m/z 644 (M+H)$^+$:

$^1$H NMR (400 MHz, CDCl$_3$): δ7.72 (d, 2H), 7.36 (d, 2H), 7.23-7.25 (m, 4H), 7.23 (m, 4H), 6.91 (m, 5H), 4.95 (s, 2H), 4.17 (t, 2H), 4.05 (t, 2H), 3.07 (m, 8H), 2.21 (m, 2H), 1.27 (t, 6H) ppm

EXAMPLE 455

{3-[4-(2-benzyloxymethyl-4-{4-[2-(4-chloro-phenyl)-ethoxy]-phenyl}-imidazol-1-yl)-phenoxy]-propyl}-diethyl-amine To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of benzyloxyacetyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield: 350 mg).

MS m/z 624 (M+H)$^+$:

$^1$H NMR (400 MHz, CDCl$_3$): δ7.71 (d, 2H), 7.68 (d, 2H), 7.31 (m, 7H), 7.25 (d, 2H), 7.21 (s, 1H), 6.94 (d, 2H), 6.89 (d, 2H), 4.58 (s, 2H), 4.49 (s, 2H), 4.15 (t, 2H), 4.08 (t, 2H), 3.11 (t, 2H), 2.89 (m, 6H), 2.18 (m, 2H), 1.35 (t, 6H) ppm

EXAMPLE 456

{3-[4-(4-{4-[2-(4-chloro-phenyl)-ethoxy]-phenyl}-2-isobutyl-5-methyl-imidazol-1-yl)-phenoxy]-propyl}-diethyl-amine To a stirred solution of 1-{4-[2-(4-chloro-phenyl)-ethoxy]phenyl}-propan-1-one (1.0 mmol) in dioxane (10.0 mL) at rt, pyridinium bromide perbromide (1.1 eq) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate, The solvent was then removed in vacuuo to give a white solid. The alpha-bromoketone was used for further transformation without further purification.

A solution of the above alpha-bromoketone (1.0 eq), N,N-diethyl-N-[3-(4-nitrophenoxy)propyl]amine (1.0 eq), and DIEA (1.5 eq) in anhydrous DMF (10 mL) was stirred under nitrogen at rt until completion, as indicated by HPLC. The reaction mixture was then diluted with cold H$_2$O and the product was isolated in Et$_2$O. The combined organic layers were washed with brine and dried over sodium sulfate. The solvent was removed in vacuuo afforded the desired product. The crude alkylated aniline was purified by chromatography (Silica gel). Pure product was obtained by elution with 2-7% MeOH/DCM (yield ~55%).

To a stirred solution of alkylated aniline described above (0.55 mmol) in anhydrous THF (5 mL) at 0° C., TEA (3.0 mmol) was added, followed by slow addition of isovaleryl chloride (5.0 mmol), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.55 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the product imidazole (yield 190 mg)
MS m/z 574 (M+H)$^+$:

EXAMPLE 457

{3-[4-(4-{4-[2-(4-chloro-phenyl)-ethoxy]-phenyl}-2-isobutyl-5-propyl-imidazol-1-yl)-phenoxy]-propyl}-diethyl-amine

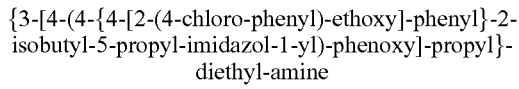

To a stirred solution of 1-{4-[2-(4-chloro-phenyl)-ethoxy]phenyl}-pentan-1-one (1.0 mmol) in dioxane (10.0 mL) at rt, pyridinium bromide perbromide (1.1 eq.) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromophenone was used for further transformation.

A solution of the above alpha-bromophenone (1.0 eq), N,N-diethyl-N-[3-(4-nitrophenoxy)propyl]amine (1.0 eq), and DIEA (1.5 eq) in anhydrous DMF (10 mL) was stirred under nitrogen at rt until completion, as indicated by HPLC. The reaction mixture was then diluted with cold H$_2$O and the product was isolated in Et$_2$O. The combined organic layers were washed with brine and dried over sodium sulfate. The solvent was removed in vacuuo afforded the desired product. The crude alkylated aniline was purified by chromatography (Silica gel). Pure product was obtained by elution with 2-5% MeOH/DCM (yield ~50%).

To a stirred solution of alkylated aniline described above (0.48 mmol) in anhydrous THF (5 mL) at 0° C., DMAP (0.25 eq) was added, followed by slow addition of isovaleryl chloride (5.0 mmol), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.48 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the product imidazole (yield 180 mg).
MS m/z 602 (M+H)$^+$:

$^1$H NMR (CDCl$_3$): δ7.58 (d, 2H), 7.28 (d, 2H), 7.21 (d, 2H), 7.11 (d, 2H), 6.98 (d, 2H), 6.91 (d, 2H), 4.17 (t, 2H), 4.08 (t, 2H), 3.07 (t, 2H), 2.6 (t, 2H), 2.57 (q, 6H), 2.47 (t, 4H), 2.36 (d, 2H), 2.0 (m, 3H), 1.3 (m, 2H), 1.05 (t, 6H), 0.82 (d, 6H), 0.72 (t, 3, H) ppm.

EXAMPLE 458

{3-[4-(5-butyl-4-{4-[2-(4-chloro-phenyl)-ethoxy]-phenyl}-2-isobutyl-imidazol-1-yl)-phenoxy]-propyl}-diethyl-amine

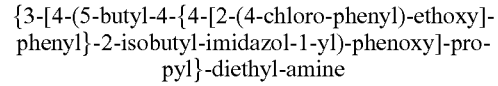

To a stirred solution of 1-{4-[2-(4-chloro-phenyl)-ethoxy]phenyl}-hexan-1-one (0.785 mmol) in dioxane (10.0 mL) at rt, pyridinium bromide perbromide (1.1 eq) was added. The reaction mixture was stirred under nitrogen at rt until completion, as indicated by TLC. The mixture was diluted with EtOAc (100 ml) and washed with H$_2$O (2×50 ml), brine (30 ml) and dried with magnesium sulfate. The solvent was then removed in vacuuo to give a white solid. The alpha-bromophenone was used for further transformation.

A solution of the above alpha-bromophenone (1.0 eq), N,N-diethyl-N-[3-(4-nitrophenoxy)propyl]amine (1.0 eq), and DIEA (1.5 eq), in anhydrous DMF (10 mL) was stirred under nitrogen at rt for 24 hour. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 2-7% MeOH/DCM (yield ~47%).

To a stirred solution of alkylated aniline described above (0.31 mmol) in anhydrous THF (5 mL) at 0° C., DMAP (0.25 eq) was added, followed by slow addition of isovaleryl chloride (5.0 mmol), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.31 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the product imidazole (yield 108 mg).
MS m/z 616 (M+H)$^+$:

$^1$H NMR (CDCl$_3$): δ7.6 (d, 2H), 7.28 (d, 2H), 7.21 (d, 2H), 7.11 (d, 2H), 7.00 (d, 2H), 6.90 (d, 2H), 4.18 (t, 2H), 4.08 (t, 2H), 3.06 (t, 2H), 2.45-2.65 (m, 8H), 2.36 (d, 2H), 2.0 (m, 4H), 0.7-1.3 (m, 18H) ppm.

EXAMPLE 459

{4-{4-{2-(4-chloro-phenyl)-ethoxy]-phenyl}-1-[4-(3-diethylamino-propoxy)-phenyl]-1H-imidazol-2-yl}-MeOH

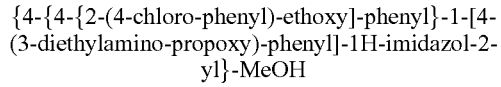

To a stirred solution of 4-fluoronitrobenzene (2.0 mmol) in anhydrous THF (5 mL) at 0° C., a 1M solution of a potassium diethylaminopropoxide (2.2 mmol) in THF was added dropwise and under a nitrogen stream, according to General Procedure L1. The reaction mixture was stirred at 0° C. for 1 h and allowed to warm to rt until completion, as indicated by TLC or HPLC. The reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product was used directly for further transformation.

The N,N-diethyl-N-[3-(4-nitrophenoxy)propyl]amine (2 mmol) obtained above was dissolved in MeOH (10 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired 4-alkoxyaniline, which was used directly for further transformation without further purification.

To a stirred solution of 4'-hydroxyacetophenone (2.2 mmol) in DMF (5 mL) at rt, solid potassium carbonate (9.0 mmol) was added. 4-chlorophenethyl mesylate (2.0 mmol) was added to the reaction mixture and heated to 80° C. until completion according to General Procedure Q1, as indicated by TLC or HPLC. After cooling to rt, the reaction mixture was quenched using cold water (20 ml) and the product was isolated in EtOAc (2×20 ml). The combined organic layers were washed with saturated sodium bicarbonate (2×10 ml), water (2×10 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated acetophenone was used for further transformation.

To a stirred solution of the 1-{4-[2-(4-chlorophenyl)ethoxy]phenyl}ethanone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and the product was isolated in EtOAc (2×20 ml). The combined organic layers were washed with saturated sodium bicarbonate (2×10 ml), and brine (15 ml). The organic layer was dried over magnesium sulfate, and the solvent was removed in vacuuo to afford the desired product. The crude 2-bromo-1-{4-[3-(diethylamino)propoxy]phenyl}ethanone was purified by chromatography (Silica gel). Pure product was obtained by elution with 20-30% EtOAc/hexane (yield ~70-75%).

To a stirred solution of the N,N-diethyl-N-[3-(4-nitrophenoxy)propyl]amine (1.2 eq., 2 mmol) in anhydrous DMF (5 mL) DIEA (3 eq. 6 mmol) was added, followed by slow addition of the 2-bromo-1-{4-[3-(diethylamino)propoxy]phenyl}ethanone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of 1-{4-[2-(4-chloro-phenyl)-ethoxy]-phenyl}-2-[4-(3-diethylamino-propoxy)-phenylamino]-ethanone described above (1.6 mmol) in anhydrous DCM (5 mL) at 0° C., TEA (3 eq., 4.8 mmol) was added, followed by slow addition of benzyloxyacetyl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with cold water and the product was isolated in DCM. The solvent was removed in vacuuo, and the crude amide was used for further transformation.

To a stirred solution of the amide described above (1.6 mmol) in acetic acid (4 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained by elution with 4-6% MeOH/DCM (yield 30-40%).

To a stirred solution of the pure imidazole (0.48 mmol) described above 6N HCl was added and the reaction mixture was refluxed overnight. The reaction mixture was then cooled to rt and neutralized with 3N sodium hydroxide solution. Usual extractive work up with EtOAc gave the product imidazole, which was purified by column chromatography (Silica gel). Pure product was obtained by elution with 4-6% MeOH/DCM (yield: 130 mg).

MS m/z 534 (M+H)$^+$:

$^1$H NMR (400 MHz, CDCl$_3$): δ7.66 (d, 2H), 7.41 (d, 2H), 7.28 (d, 2H), 7.22 (m, 3H), 6.99 (d, 2H), 6.89 (d, 2H), 4.62 (s, 2H), 4.17 (t, 2H), 4.08 (t, 2H), 3.07 (t, 2H), 2.88 (m, 6H), 2.18 (m, 2H), 1.24 (t, 6H) ppm

EXAMPLE 460 diethyl-[3-(4-{2-isobutyl-4-[4-(4-phenoxy-benzyloxy)-phenyl]-imidazol-1)-yl}-phenoxy)-propyl]-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under H$_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of the 4-{1-[4-(3-diethylamino-propoxy)-phenyl]-2-isobutyl-1H-imidazol-4-yl}-phenol (1.0 eq) obtained above in anhydrous DMF (5.0 mL) was treated with solid sodium hydride (60% dispersion in oil; 1.0 mmol) in portions. The mesylate of (4-phenoxyphenyl)methanol (1.1 eq) was added to the reaction mixture, which was stirred at rt overnight, according to General Procedure T3. Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained by elution with chromatography in 5-10% MeOH/DCM (yield 70.0 mg).

MS m/z 604 (M+H)$^+$:

$^1$H NMR (CDCl$_3$): δ 7.70 (d, 2H) 6.9-7.4 (m, 16H), 5.0 (s, 2H), 4.1 (t, 2H), 3.0 (m, 6H), 2.52 (d), 2.26 (m, 2H), 2.01 (m, 1H), 1.31 (t, 6H), 0.84 (d, 6H) ppm.

EXAMPLE 461

[3-(4-{4-[4-(4-benzyloxy-benzyloxy)-phenyl]-2-isobutyl-imidazol-1-yl}-phenoxy)-propyl]-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under H$_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. The mesylate of [4-(benzyloxy)phenyl]methanol (1.1 eq) was added to the reaction mixture, and stirred at rt overnight, according to General Procedure T3. Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained from chromatography with 5-10% MeOH/DCM (yield 70.0 mg)

MS m/z 618 (M+H)$^+$:

$^1$H NMR (CDCl$_3$): δ7.70 (d, 2H), 7.3-7.45 (m, 7H), 7.21 (d, 2H), 7.1 (s, 1H), 6.9 (m, 6H), 5.07 (s, 2H), 5.00 (s, 2H), 4.1 (t, 2H), 3.0 (m, 6H), 2.52 (d, 2H), 2.26 (m, 2H), 2.01 (m, 1H), 1.31 (t, 6H), 0.84 (d, 6H) ppm.

EXAMPLE 462

[3-(4-{4-[4-(2-benzenesulfonylmethyl-benzyloxy)-phenyl]-2-isobutyl-imidazol-1-yl}-phenoxy)-propyl]-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of 1-[4-(benzyloxy)phenyl]-2-bromoethanone (2.5 mmol). The reaction mixture was stirred under nitrogen at rt until completion, as indicated by HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained by elution with 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under H$_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. The mesylate of {2-[(phenylsulfonyl)methyl]phenyl}methanol (1.1 eq) was added to the reaction mixture, and stirred at rt overnight, according to General Procedure T3. Et$_2$O (30 mL) was added to the reaction mixture followed by H$_2$O (10 mL).

The organic layer was washed with H₂O (2×15 mL) and brine, and dried over sodium sulfate. The solvent was removed in vacuuo. Pure imidazole was obtained from chromatography with 5-10% MeOH/DCM (yield 77 mg).

MS m/z 666 (M+H)⁺:

¹H NMR (CDCl₃): δ 7.6-7.73 (m, 6), 7.3-7.5 (m, 4H), 7.20 (d, 2H), 7.1 (m, 2H), 6.97 (d, 2H), 6.9 (d, 2H), 4.93 (s, 2H), 4.5 (s, 2H), 4.07 (t, 2H), 2.6 (t, 2H), 2.63 (q, 4H), 2.53 (d, 2H), 2.01 (m, 3H), 1.08 (t, 6H), 0.85 (d, 6H) ppm.

EXAMPLE 463 diethyl-[3-(4-{2-isobutyl-4-[4-(3,4,5-trimethoxy-benzyloxy)-phenyl]-imidazol-1-yl}-phenoxy)-propyl]-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold H₂O and the product was isolated in Et₂O. The combined organic layers were washed with brine and dried over sodium sulfate. Evaporation of solvent in vacuuo afforded the desired product. The crude alkylated aniline was purified by chromatography (Silica gel). Pure product was obtained from 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under H₂ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification. A stirred solution of 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. The mesylate of (3,4,5-trimethoxyphenyl)methanol (1.1 eq) was added to the reaction mixture, and stirred at rt overnight, according to General Procedure T3. Et₂O (30 mL) was added to the reaction mixture followed by H₂O (10 mL). The organic layer was washed with H₂O (2×15 mL) and brine, and dried over sodium sulfate. The solvent was removed in vacuuo. Pure imidazole was obtained from chromatography with 5-10% MeOH/DCM (yield 66 mg).

MS m/z 602 (M+H)⁺:

¹H NMR (CDCl₃): δ7.71 (d, 2H), 7.21 (d, 2H), 6.97 (m, 4H), 6.66 (s, 1H), 5 (s, 2H), 4.1 (t, 2H), 3.86 (s, 6H), 3.82 (s, 3H), 3.0 (m, 6H), 2.51 (d, 2H), 2.25 (m, 2H), 2.01 (m, 1H), 1.3 (t, 6H), 0.84 (d, 6H) ppm.

EXAMPLE 464

[3-(4-{1-[4-(4-chloro-phenoxy)-phenyl]-2-isobutyl-1H-imidazol-4-yl}-phenoxy)-propyl]-diethyl-amine To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with H₂O (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (5.2 mmol) in anhydrous MeOH (10 mL) at 0° C., pyrrolidone hydrotribromide (1.2 eq., 6.2 mmol) was added slowly in small portions, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-amino-4'-chlorodiphenyl ether (1.2 eq., 6.2 mmol) in anhydrous DMF (10 mL) DIEA (3 eq. 16 mmol) was added, followed by slow addition of the 2-bromo-1-{4-[3-(diethylamino)propoxy]phenyl}ethanone described above (5.2 mmol), according to General Procedure R2. The reaction mixture was stirred under nitrogen at rt until completion, as indicated by TLC or HPLC. The reaction mixture was then diluted with cold H₂O and the product was extracted in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~22%).

To a stirred solution of alkylated 4-amino-4'-chlorodiphenyl ether described above (0.4 mmol) in anhydrous DCM (5 mL) at 0° C., TEA (3 eq., 1.2 mmol) was added, followed by slow addition of isovaleryl chloride (3 eq., 1.2 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the 2-[4-(4-chlorophenoxy)-phenylamino]-1-[4-(3-diethylamino-propoxy)-phenyl]-ethanone (0.4 mmol) obtained as above in acetic acid (3 mL), solid ammonium acetate (8 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with H₂O (2×15 mL) and brine, and dried over sodium sulfate. Evaporation of the solvent in vacuuo afforded the desired N-aryl imidazole. The crude product was purified using silica gel column chromatography (2-5% MeOH/DCM) (yield 117 mg).

MS m/z 532 (M+H)+:
$^1$H NMR (CDCl$_3$): δ7.63 (d, 2H), 7.28 (d, 2H), 7.21 (d, 2H), 7.06 (s, 1H), 7.01 (d, 2H), 6.98 (d, 2H), 6.83 (d, 2H), 3.99 (t, 2H), 2.79 (t, 2H), 2.72 (q, 4H), 2.49 (d, 2H), 2.30-1.90 (m, 3H), 1.10 (t, 6H), 0.80 (d, 6H) ppm.

EXAMPLE 465

[3-(4-{1-[4-(4-chloro-phenoxy)-phenyl]-2-(2-cyclopentyl-ethyl)-1H-imidazol-4-yl}-phenoxy)-propyl]-diethyl-amine To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with H$_2$O (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (5.2 mmol) in anhydrous MeOH (10 mL) at 0° C., pyrrolidone hydrotribromide (1.2 eq., 6.2) was added slowly in small portions, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-amino-4'-chlorodiphenyl ether (1.2 eq., 6.2 mmol) in anhydrous DMF (10 mL) DIEA (3 eq. 16 mmol) was added, followed by slow addition of the 2-bromo-1-{4-[3-(diethylamino)propoxy]phenyl}ethanone described above (5.2 mmol), according to General Procedure R2. The reaction mixture was stirred under nitrogen at rt until completion, as indicated by TLC or HPLC. The reaction mixture was then diluted with cold H$_2$O and the product was extracted in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~22%).

To a stirred solution of alkylated 4-amino-4'-chlorodiphenyl ether described above (0.4 mmol) in anhydrous DCM (5 mL) at 0° C., TEA (3 eq., 1.2 mmol) was added, followed by slow addition of 3-cyclopentylpropionyl chloride (3 eq., 1.2 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the 2-[4-(4-chlorophenoxy)-phenylamino]-1-[4-(3-diethylamino-propoxy)-phenyl]-ethanone (0.4 mmol) obtained as above in acetic acid (3 mL), solid ammonium acetate (8 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with H$_2$O (2×15 mL) and brine, and dried over sodium sulfate. Evaporation of the solvent in vacuuo afforded the desired N-aryl imidazole. The crude product was purified using silica gel column chromatography (2-5% MeOH/DCM) (yield 180 mg).

MS m/z 572 (M+H)+:
$^1$H NMR (CDCl$_3$): δ7.69 (d, 2H), 7.35 (d, 2H), 7.29 (d, 2H), 7.14 (s, 1H), 7.08 (d, 2H), 7.02 (d, 2H), 6.89 (d, 2H), 4.05 (t, 2H), 2.95 (t, 2H) 2.85 (q, 4H), 2.71-2.65 (m, 2H), 2.19-2.12 (m, 3H), 1.72-1.61 (m, 4H), 1.59-1.42 (m, 4H), 1.21 (t, 6H), 1.01 (m, 2H) ppm.

EXAMPLE 466

[3-(4-{1-[4-(4-chloro-phenoxy)-phenyl]-2-phenethyl-1H-imidazol-4-yl}-phenoxy)-propyl]-diethyl-amine To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with H$_2$O (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (5.2 mmol) in anhydrous MeOH (10 mL) at 0° C., pyrrolidone hydrotribromide (1.2 eq., 6.2) was added slowly in small portions, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-amino-4'-chlorodiphenyl ether (1.2 eq., 6.2 mmol) in anhydrous DMF (10 mL) DIEA (3 eq. 16 mmol) was added, followed by slow addition of the 2-bromo-1-{4-[3-(diethylamino)propoxy]phenyl}ethanone described above (5.2 mmol), according to General Procedure R2. The reaction mixture was stirred under nitrogen at rt until completion, as indicated by TLC or HPLC. The reaction mixture was then diluted with cold H$_2$O and the product was extracted in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~22%).

To a stirred solution of the alkylated 4-chloroalkoxy aniline described above (0.4 mmol) in anhydrous DCM (5 mL) at 0° C., TEA (3 eq., 1.2 mmol) was added, followed by slow addition of hydrocinnamoyl chloride (3 eq., 1.2 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the 2-[4-(4-chlorophenoxy)-phenylamino]-1-[4-(3-diethylamino-propoxy)-phenyl]-ethanone (~0.4 mmol) obtained as above in acetic acid (3 mL), solid ammonium acetate (8 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with $H_2O$ (2×15 mL) and brine, and dried over sodium sulfate. Evaporation of the solvent in vacuuo afforded the desired N-aryl imidazole. The crude product was purified using silica gel column chromatography (2-4% MeOH/DCM) (yield 50 mg).

MS m/z 580 $(M+H)^+$:
$^1H$ NMR ($CDCl_3$): δ8.41 (m, 2H), 7.92 (m, 2H), 7.62 (d, 2H, 7.33 (d, 2H), 7.25-7.21 (m, 2H), 7.13-7.08 (m, 1H), 7.04 (s, 1H), 6.98 (m, 2H), 6.92 (m, 2H), 6.75 (m, 2H), 4.05 (t, 2H), 3.31 (m, 2H), 3.26-3.05 (m, 6H), 2.35 (m, 2H), 1.40 (t, 6H), 1.21 (m, 2H) ppm.

EXAMPLE 467

[3-(4-{2-(4-tert-butyl-phenoxymethyl)-1-[4-(4-chloro-phenoxy)-phenyl]-1H-imidazol-4-yl}-phenoxy)-propyl]-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and to this saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxy-acetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product 1-{4-[3-(diethylamino)propoxy]phenyl}ethanone was purified by flash chromatography (going by increasing gradient up to 10% MeOH in DCM). The overall yield was 60%.

To a stirred solution of 1-{4-[3-(diethylamino)propoxy] phenyl}ethanone (5 mmol) in anhydrous MeOH (10 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-chlorophenoxy aniline (1 eq, 5 mmol) in anhydrous DMF (10 mL), DIEA (3 eq 15 mmol) was added, followed by addition of the 2-bromo-1-{4-[3-(diethylamino) propoxy]phenyl}ethanone described above (5 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 52%).

To a solution of 2-[4-(4-chlorophenoxy)-phenylamino]-1-[4-(3-diethylamino-propoxy)-phenyl]-ethanone described above (2 mmol) in anhydrous DCM (5 mL), PS-carbodimide (2 eq, 4 mmol) and 4-t-butylphenoxy-acetic acid (3 mmol) were added. The reaction mixture was shaken overnight and next day filtered to give the desired amide. The crude amide was used for further transformation.

To a stirred solution of the amide described above (2 mmol) in acetic acid (8 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 255 mg)

MS m/z 638 $(M+H)^+$:
$^1H$ NMR ($CDCl_3$): δ7.72 (d, 2H), 7.44 (d, 2H), 7.28-7.35 (m, 5H), 6.8-7.1 (m, 8H), 5.01 (s, 2H), 4.06 (t, 2H), 3.13-3.24 (m, 6H), 2.28 (m, 2H), 1.23-1.38 (m, 15H) ppm.

EXAMPLE 468

[3-(4-{2-butyl-1-[4-(2,4-dichloro-phenoxy)-phenyl]-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 2,4-dichlorophenol (10 mmol) to the reaction mixture and heating to 80° C. until the reaction was complete as indicated by TLC or HPLC. After cooling to rt, the reaction mixture was poured into $H_2O$ (100 ml), extracted with EtOAc (2×50 mL), washed with $H_2O$ (2×50 ml) and brine (50 ml), and dried over sodium sulfate. The solvent was removed in vacuuo to afford the desired 4-(2,4-dichloro-phenoxy)-1-nitrobenzene. The crude product was used for further transformation.

The nitro intermediate (10 mmol) obtained above was dissolved in MeOH (20 mL), and treated with $SnCl_2.2H_2O$ (50 mmol), according to General Procedure I. The reaction mixture was heated under reflux until completion, as indicated by TLC or HPLC. The solvent was removed in vacuuo and the residue was treated with 4.0 N aqueous NaOH to pH ~8. The residue was extracted with EtOAc (2×50 mL), washed with 1.0 N aqueous NaOH (50 mL), brine (50 mL) and dried over sodium sulfate. The solvent was removed in vacuuo to afford the desired 4-(2,4-dichloro-phenoxy)aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-(4-[3-(diethylamino)propoxy]phenyl)ethanone. The crude alkylated product was used for further transformation after purifying using silica gel column chromatography (1-4% MeOH/DCM).

To a stirred solution of 1-{4-[3-(diethylamino)propoxy]phenyl}ethanone (4.4 mmol) in anhydrous MeOH (10 mL) at 0° C., pyrrolidone hydrotribromide (1.2 eq., 5.3 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(2,4-dichloro-phenoxy)aniline described above (1.2 eq., 5.2 mmol) in anhydrous DMF (20 mL) DIEA (3 eq. 15 mmol) was added, followed by slow addition of the 2-bromo-1-{4-[3-(diethylamino)propoxy]phenyl}ethanone described above (4.4 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~5%).

To a stirred solution of alkylated 4-(2,4-dichloro-phenoxy)aniline described above (0.2 mmol) in anhydrous DCM (5 mL) at 0° C., TEA (3 eq., 0.6 mmol) was added, followed by slow addition of valeryl chloride (3 eq., 0.6 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (0.2 mmol) obtained as above in acetic acid (3 mL), solid ammonium acetate (6 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with $H_2O$ (2×15 mL) and brine, and dried over sodium sulfate. Evaporation of the solvent in vacuuo afforded the desired N-aryl imidazole. The crude product was purified using silica gel column chromatography (2-5% MeOH/DCM).

MS m/z 566 (M+H)$^+$:
$^1$H NMR (CDCl$_3$): δ7.96 (s, 1H), 7.87 (m, 2H), 7.64 (d, 2H), 7.42 (m, 2H), 7.30 (d, 2H), 7.15 (s, 1H), 6.94-6.84 (m, 2H), 4.12 (m, 2H), 3.71-3.42 (m, 6H), 3.14 (m, 2H), 2.29 (t, 2H), 1.59-1.50 (m, 2H), 1.41-1.32 (m, 2H), 1.31 (t, 6H), 0.85 (m, 3H) ppm.

EXAMPLE 469

[3-(4-{2-butyl-1-[4-(4-chloro-phenoxy)-phenyl]-5-methyl-1H-imidazol-4-yl}-phenoxy)-propyl]-diethyl-amine To a stirred solution of the 1-[4-(3-diethylamino-propoxy)-phenyl]-propane-1-one (1.08 mmol) in anhydrous MeOH (15 mL), pyrrolidone hydrotribromide (1.6 eq.) was added, according to General Procedure R1. The reaction mixture was heated under reflux overnight. The solvent was then removed in vacuuo and the crude alpha-bromophenone was used for further transformation.

To a stirred solution of the above alpha-bromoketone (1.0 eq), 4-(4-chloro-phenoxy)-aniline (1.0 eq) in anhydrous DMF (10 mL) DIEA (1.0 eq) was added. The reaction mixture was stirred under nitrogen at 90° C. until completion, as indicated by HPLC. The reaction mixture was cooled to rt then diluted with Et$_2$O (100 mL) and washed with sodium bicarbonate (10%, 30 ml), $H_2O$ (2×30 mL), brine (30 mL) and dried with magnesium sulfate. Evaporation of solvent in vacuuo gave a crude oil. The crude alkylated aniline was purified by chromatography (Silica gel). Pure product was obtained from 2-7% MeOH/DCM (yield ~20%).

To a stirred solution of alkylated aniline described above (0.2 mmol) in anhydrous THF (10 mL) at 0° C., DMAP (0.3 eq.) was added, followed by slow addition of valeryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.2 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 66 mg).

MS m/z 546 (M+H)$^+$:
$^1$H NMR (CDCl$_3$): δ7.59 (d, 2H), 7.35 (d, 2H), 7.19 (d, 2H), 7.08 (d, 2H), 7.03 (d, 2H), 6.93 (d, 2H), 4.02 (t, 2H), 2.51-2.64 (m, 8H), 2.13 (s, 3H), 1.94 (m, 2H), 1.58 (m, 2H), 1.27 (m, 2H), 1.04 (t, 6H), 0.82 (t, 3H) ppm.

EXAMPLE 470

[3-(4-{2-butyl-1-[4-(4-chloro-phenoxy)-phenyl]-5-propyl-1H-imidazol-4-yl}-phenoxy)-propyl]-diethyl-amine To a stirred solution of the 1-[4-(3-diethylamino-propoxy)-phenyl]-pentane-1-one (1.08 mmol) in anhydrous MeOH (15 mL), pyrrolidone hydrotribromide (1.6 eq.) was added, according to General Procedure R1. The reaction mixture was heated under reflux overnight. The solvent was then removed in vacuuo and the crude alpha-bromophenone was used for further transformation.

To a stirred solution of the above alpha-bromoketone (1.0 eq), 4-(4-chloro-phenoxy)-aniline (1.0 eq) in anhydrous DMF (10 mL) DIEA (1.0 eq) was added. The reaction mixture was stirred under nitrogen at 90° C. until completion, as indicated by HPLC. The reaction mixture was cooled to rt then diluted with Et$_2$O (100 mL) and washed with sodium bicarbonate (10%, 30 ml), $H_2O$ (2×30 mL), brine (30 mL) and dried with magnesium sulfate. Evaporation of solvent in vacuuo gave a crude oil. The crude alkylated aniline was purified by chromatography (Silica gel). Pure product was obtained from 2-7% MeOH/DCM (yield ~20%).

To a stirred solution of alkylated aniline described above (0.2 mmol) in anhydrous THF (10 mL) at 0° C., DMAP (0.3 eq.) was added, followed by slow addition of valeryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.2 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 73 mg).

MS m/z 574 (M+H)$^+$:

$^1$H NMR (CDCl$_3$): δ 7.50 (d, 2H), 7.34 (d, 2H), 7.20 (d, 2H), 7.07 (d, 2H), 7.02 (d, 2H), 6.87 (d, 2H), 4.07 (t, 2H), 3.1-3.2 (m, 6H), 2.40-2.6 (m, 4H), 2.2 (m, 2H), 1.2-1.4 (m, 12H), 0.79 (t, 3H), 0.72 (t, 3H) ppm.

EXAMPLE 471

[3-(4-{2,5-dibutyl-1-[4-(4-chloro-phenoxy)-phenyl]-1H-imidazol-4-yl}-phenoxy)-propyl]-diethyl-amine To a stirred solution of the 1-[4-(3-diethylamino-propoxy)-phenyl]-hexanane-1-one (1.08 mmol) in anhydrous MeOH (15 mL), pyrrolidone hydrotribromide (1.6 eq.) was added, according to General Procedure R1. The reaction mixture was heated under reflux overnight. The solvent was then removed in vacuuo and the crude alpha-bromophenone was used for further transformation.

To a stirred solution of the above alpha-bromoketone (1.0 eq), 4-(4-chloro-phenoxy)-aniline (1.0 eq) in anhydrous DMF (10 mL) DIEA (1.0 eq) was added. The reaction mixture was stirred under nitrogen at 90° C. until completion, as indicated by HPLC. The reaction mixture was cooled to rt then diluted with Et$_2$O (100 mL) and washed with sodium bicarbonate (10%, 30 ml), H$_2$O (2×30 mL), brine (30 mL) and dried with magnesium sulfate. Evaporation of solvent in vacuuo gave a crude oil. The crude alkylated aniline was purified by chromatography (Silica gel). Pure product was obtained from 2-7% MeOH/DCM (yield ~20%).

To a stirred solution of alkylated aniline described above (0.2 mmol) in anhydrous THF (10 mL) at 0° C., DMAP (0.3 eq.) was added, followed by slow addition of valeryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.2 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was obtained from 4-6% MeOH/DCM (yield 67.0 mg).

MS m/z 588 (M+H)$^+$:

$^1$H NMR (CDCl$_3$): δ 7.54 (d, 2H), 7.36 (d, 2H), 7.24 (d, 2H), 7.09 (d, 2H), 7.03 (d, 2H), 6.90 (d, 2H), 4.07 (t, 2H), 3.2-3.3 (m, 6H), 2.45-2.6 (m, 4H), 2.2 (m, 2H), 1.1-1.6 (m, 14H), 0.8 (t, 3H), 0.70 (t, 3H) ppm.

EXAMPLE 472

[3-(4-{2-butyl-1-[4-(4-chloro-phenoxy)-phenyl]-5-ethyl-1H-imidazol-4-yl}-phenoxy)-propyl]-diethyl-amine To a stirred solution of the 1-[4-(3-diethylamino-propoxy)-phenyl]-butane-1-one (1.08 mmol) in anhydrous MeOH (15 mL), pyrrolidone hydrotribromide (1.6 eq.) was added, according to General Procedure R1. The reaction mixture was heated under reflux overnight. The solvent was then removed in vacuuo and the crude alpha-bromophenone was used for further transformation.

To a stirred solution of the above alpha-bromoketone (1.0 eq), 4-(4-chloro-phenoxy)-aniline (1.0 eq) in anhydrous DMF (10 mL) DIEA (1.0 eq) was added. The reaction mixture was stirred under nitrogen at 90° C. until completion, as indicated by HPLC. The reaction mixture was cooled to rt then diluted with Et$_2$O (100 mL) and washed with sodium bicarbonate (10%, 30 ml), H$_2$O (2×30 mL), brine (30 mL) and dried with magnesium sulfate. Evaporation of solvent in vacuuo gave a crude oil. The crude alkylated aniline was purified by chromatography (Silica gel). Pure product was obtained from 2-7% MeOH/DCM (yield ~20%).

To a stirred solution of alkylated aniline described above (0.2 mmol) in anhydrous THF (10 mL) at 0° C., DMAP (0.3 eq.) was added, followed by slow addition of valeryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.2 mmol) in acetic acid (2 mL), ammonium acetate (excess, ~20 eq.) was added, according to General Procedure R4. The reaction mixture was stirred at 90° C. overnight. The reaction mixture was then cooled down and neutralized with saturated sodium bicarbonate solution. Usual extractive work up with EtOAc gave the product imidazole, which was purified by column chromatography (Silica gel). Pure product was by elution with 4-6% MeOH/DCM (yield 70 mg).

MS m/z 560 (M+H)$^+$:

$^1$H NMR (CDCl$_3$): δ7.58 (d, 2H), 7.36 (d, 2H), 7.22 (d, 2H), 7.09 (d, 2H), 7.04 (d, 2H), 6.93 (d, 2H), 4.03 (t, 2H), 2.56 (m, 10H), 1.94 (m, 2H), 1.59 (m, 2H), 1.27 (m, 2H), 1.03 (t, 6H,), 0.97 (t, 3H), 0.82 (t, 3H) ppm.

EXAMPLE 473

2-butyl-1-[4-(4-chloro-phenoxy)-phenyl]-4-[4-(2-pyrrolidin-1-yl-ethoxy)-phenyl]-1H-imidazole To a stirred solution of NaH (3 eq., 6.0 mmol) in DMF (10 mL) at rt, 4'-hydroxyacetophenone (2.2 mmol) was added. The mesylate of 1-(2-hydroxyethyl)-pyrrolidine (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with cold water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude alkylated product was purified using silica gel column chromatography. Pure product was obtained with 2-3% MeOH/DCM. (yield 50-60%)

To a stirred solution of the alkoxyacetophenone described above (1 mmol) in anhydrous MeOH (5 mL) at 0° C., pyrrolidone hydrotribromide (1.2 eq., 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and washed with water (2×15 ml) and brine (15 ml). The organic layer was dried over magnesium sulfate, and the solvent was removed in vacuuo to afford the desired product. The crude alpha-bromoacetophenone was used for further transformation.

To a stirred solution of 4-chloro-phenoxy aniline (1.2 eq., 1.2 mmol) in anhydrous DMF (10 mL) DIEA (3 eq. 3.0 mmol) was added, followed by slow addition of the alpha-bromoacetophenone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3.0 mmol) was added, followed by slow addition of valeryl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was purified using silica gel chromatography. Pure product was obtained from 3-4% MeOH/DCM (Yield 40-45%).

To a stirred solution of the amide described above (0.5 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 105 mg).

MS m/z 516 (M)$^+$:
$^1$H NMR (400 MHz, CDCl$_3$): δ7.69 (d, 2H), 7.34 (d, 2H), 7.29 (d, 2H), 7.09 (s, 1H), 7.05 (m, 4H), 6.95 (d, 2H), 4.19 (t, 2H), 3.05 (t, 2H), 2.84 (m, 4H), 2.77 (t, 2H), 1.89 (m, 4H), 1.65 (m, 2H), 1.34 (m, 2H), 0.85 (t, 3H) ppm

EXAMPLE 474

1-[2-(4-{2-butyl-1-[4-(4-chloro-phenoxy)-phenyl]-1H-imidazol-4-yl}-phenoxy)-ethyl]-piperidine To a stirred solution of NaH (3 eq., 6.0 mmol) in DMF (10 mL) at rt, 4'-hydroxyacetophenone (2.2 mmol) was added. The mesylate of 1-(2-hydroxyethyl)-piperidine (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with cold water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude alkylated product was purified using silica gel column chromatography. Pure product was obtained with 2-3% MeOH/DCM. (yield 50-60%)

To a stirred solution of the alkoxyacetophenone described above (1 mmol) in anhydrous MeOH (5 mL) at 0° C., pyrrolidone hydrotribromide (1.2 eq., 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and washed with water (2×15 ml) and brine (15 ml). The organic layer was dried over magnesium sulfate, and the solvent was removed in vacuuo to afford the desired product. The crude alpha-bromoacetophenone was used for further transformation.

To a stirred solution of 4-chloro-phenoxy aniline (1.2 eq., 1.2 mmol) in anhydrous DMF (10 mL) DIEA (3 eq. 3.0 mmol) was added, followed by slow addition of the alpha-bromoacetophenone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3.0 mmol) was added, followed by slow addition of valeryl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was purified using silica gel chromatography. Pure product was obtained from 3-4% MeOH/DCM (Yield 40-45%).

To a stirred solution of the amide described above (0.5 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 92 mg).

MS m/z 530 (M+H)$^+$:
$^1$H NMR (400 MHz, CDCl$_3$): δ7.49 (d, 2H), 7.34 (d, 2H), 7.15 (d, 2H), 6.97 (s, 1H), 6.93 (m, 4H), 6.84 (d, 2H), 4.18 (t, 2H), 3.33 (m, 4H), 2.81 (t, 2H), 2.68 (t, 2H), 1.67 (m, 2H), 1.55 (m, 2H), 1.37 (m, 2H), 1.02 (m, 4H) 0.65 (t, 3H) ppm

EXAMPLE 475

[3-(4-{2-butyl-1-[4-(4-chloro-phenoxy)-phenyl]-1H-imidazol-4-yl}-phenoxy)-2,2-dimethyl-propyl]-dimethyl-amine To a stirred solution of 4'-hydroxyacetophenone (2.2 mmol) in DMF (10 mL) at rt, solid potassium carbonate (8.0 mmol) was added. The mesylate of 3-dimethylamino-2,2-dimethyl-1-propanol (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude alkylated product was purified using silica gel column chromatography. Pure product was obtained with 2-3% MeOH/DCM. (yield 50-60%)

To a stirred solution of the alkoxyacetophenone described above (1 mmol) in anhydrous MeOH (5 mL) at 0° C., pyrrolidone hydrotribromide (1.2 eq., 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate and the product was isolated in EtOAc. The combined organic layers were washed with water (2×15 ml) and brine (15 ml). The organic layer was dried over magnesium sulfate, and the solvent was removed in vacuuo to afford the desired product. The crude alpha-bromoacetophenone was used for further transformation.

To a stirred solution of 4-chloro-phenoxy aniline (1.2 eq., 1.2 mmol) in anhydrous DMF (5 mL) DIEA (3 eq. 3.0 mmol) was added, followed by slow addition of the alpha-bromoacetophenone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3.0 mmol) was added, followed by slow addition of valeryl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was purified using silica gel chromatography. Pure product was obtained from 3-4% MeOH/DCM (Yield 40-50%).

To a stirred solution of the amide described above (0.5 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield: 105 mg).

MS m/z 532 (M+H)$^+$:

$^1$H NMR (400 MHz, CDCl$_3$): δ7.69 (d, 2H), 7.34 (d, 2H), 7.29 (d, 2H), 7.09 (s, 1H), 7.06 (d, 2H), 7.02 (d, 2H), 6.93 (d, 2H), 3.75 (s, 2H), 2.68 (t, 2H), 2.42 (s, 2H), 2.35 (s, 6H), 1.65 (m, 2H), 1.29 (m, 2H), 1.05 (s, 6H), 0.85 (t, 3H) ppm

EXAMPLE 476

[2-(4-{2-butyl-1-[4-(4-chloro-phenoxy)-phenyl]-1H-imidazol-4-yl}-phenoxy)-ethyl]-diisopropyl-amine To a stirred solution of 4'-hydroxyacetophenone (2.2 mmol) in DMF (10 mL) at rt, solid potassium carbonate (8.0 mmol) was added. The mesylate of 2-(diisopropylamino) ethanol (prepared from the corresponding alcohol and methanesulfonyl chloride) (2.0 mmol) was added to the reaction mixture and heated to 80° C. until completion according to General Procedure Q1, as indicated by TLC or HPLC. After cooling to rt, the reaction mixture was diluted with water and the product was isolated in EtOAc. The combined organic layers were washed with saturated sodium bicarbonate (2×15 ml), water (2×15 ml) and brine (15 ml). The organic layer was dried over magnesium sulfate, and the solvent was removed in vacuuo to afford the desired product. The crude alkylated product was purified using silica gel column chromatography. Pure product was obtained with 2-3% MeOH/DCM. (yield 50-60%)

To a stirred solution of the alkoxyacetophenone described above (1 mmol) in anhydrous MeOH (5 mL) at 0° C., pyrrolidone hydrotribromide (1.2 eq., 1.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate and the product was isolated in EtOAc. The combined organic layers were washed with water (2×15 ml) and brine (15 ml). The organic layer was dried over magnesium sulfate, and the solvent was removed in vacuuo to afford the desired product. The crude alpha-bromoacetophenone was used for further transformation.

To a stirred solution of 4-chloro-phenoxy aniline (1.2 eq., 1.2 mmol) in anhydrous DMF (5 mL) DIEA (3 eq. 3.0 mmol) was added, followed by slow addition of the alpha-bromoacetophenone described above (1.0 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.0 mmol) in anhydrous DCM (5 mL) at 0° C., TEA (3 eq., 3.0 mmol) was added, followed by slow addition of valeryl chloride (2 eq., 2.0 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was purified using silica gel chromatography. Pure product was obtained from 3-4% MeOH/DCM (Yield 40-50%).

To a stirred solution of the amide described above (0.5 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM.

MS m/z 546 (M+H)$^+$:

EXAMPLE 477

[3-(4-{4-[4-(adamantan-1-ylmethoxy)-phenyl]-2-isobutyl-imidazol-1-yl}-phenoxy)-propyl]-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold $H_2O$ and the product was isolated in $Et_2O$. The combined organic layers were washed with brine and dried over sodium sulfate. Evaporation of solvent in vacuuo afforded the desired product. The crude alkylated aniline was purified by chromatography (Silica gel). Pure product was obtained from 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under $H_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of the 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. After the addition, the mesylate of 1-adamantylmethanol (1.1 eq) was added to the reaction mixture, and stirred at rt overnight, according to General Procedure T3. $Et_2O$ (30 mL) was added to the reaction mixture followed by $H_2O$ (10 mL). The organic layer was washed with $H_2O$ (2×15 mL) and brine, and dried over sodium sulfate. The solvent was removed in vacuuo. Pure imidazole was obtained from chromatography with 5-10% MeOH/DCM (yield 60 mg).

MS m/z 570 (M+H)$^+$:

$^1$H NMR (CDCl$_3$): δ 7.68 (d, 2H), 7.20 (d, 2H), 7.09 (s, 1H), 6.97 (d, 2H), 6.90 (d, 2H), 4.06 (t, 2H), 3.5 (s, 2H), 2.6 (t, 2H), 2.58 (q, 4H), 2.52 (d), 1.6-2.1 (m, 18H), 1.05 (t, 6H), 0.85 (d, 6H) ppm.

EXAMPLE 478

{3-[4-(4-{4-[3-(2,6-dichloro-phenyl)-4-methyl-isoxazol-5-ylmethyloxy]-phenyl}-2-isobutyl-imidazol-1-yl)-phenoxy]-propyl}-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold $H_2O$ and the product was isolated in $Et_2O$. The combined organic layers were washed with brine and dried over sodium sulfate. Evaporation of solvent in vacuuo afforded the desired product. The crude alkylated aniline was purified by chromatography (Silica gel). Pure product was obtained from 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under $H_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

To a stirred solution of the 4-{1-[4-(3-diethylamino-propoxy)-phenyl]-2-isobutyl-1H-imidazol-4-yl}-phenol (1.0 eq) obtained above in anhydrous DMF (5.0 mL) solid sodium hydride (60% dispersion in oil; 1.0 mmol) was added in portions. After the addition, the requisite alkylhalide or the mesylate (prepared from the corresponding alcohol and methanesulfonyl chloride) (1.1 eq) was added to the reaction mixture. The reaction mixture was stirred at rt overnight. $Et_2O$ (30 mL) was added to the reaction mixture followed by $H_2O$ (10 mL). The organic layer was washed with $H_2O$ (2×15 mL) and brine, and dried over sodium sulfate. The solvent was removed in vacuuo. Pure product was obtained from 5-10% MeOH/DCM (yield 57 mg).

MS m/z 661 (M+H)$^+$:

$^1$H NMR (CDCl$_3$): δ 7.65 (d, 2H), 7.2-7.44 (m, 5H), 7.08 (s, 1H), 6.96 (d, 2H), 0.677 (d, 2H), 4.74 (s, 2H), 4.13 (t, 2H), 2.9-3.15 (m, 6H), 2.6 (s, 3H), 2.51 (d, 2H), 2.3 (m, 3H), 1.35 (t, 6H), 0.83 (t, 6H) ppm

EXAMPLE 479

[3-(4-{4-[4-(4-bromo-benzyloxy)-phenyl]-2-isobutyl-imidazol-1-yl}-phenoxy)-propyl]-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold $H_2O$ and the product was isolated in $Et_2O$. The combined organic layers were washed with brine and dried over sodium sulfate. Evaporation of solvent in vacuuo afforded the desired product. The crude alkylated aniline was purified by chromatography (Silica gel). Pure product was obtained from 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under $H_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of the 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. The mesylate of (4-bromophenyl)methanol (1.1 eq) was added to the reaction mixture, and stirred at rt overnight, according to General Procedure T3. $Et_2O$ (30 mL) was added to the reaction mixture followed by $H_2O$ (10 mL). The organic layer was washed with $H_2O$ (2×15 mL) and brine, and dried over sodium sulfate. The solvent was removed in vacuuo. Pure imidazole was obtained from chromatography with 5-10% MeOH/DCM (yield 95 mg).

MS m/z 591 (M+H)$^+$:

$^1$H NMR (CDCl$_3$): δ7.7 (d, 2H), 7.5 (d, 2H), 7.32 (d, 2H), 7.21 (d, 2H), 7.11 (s, 1H), 6.96 (m, 4H), 5.03 (s, 2H), 4.07 (t, 2H), 2.5-2.8 (m, 8H), 2.0 (m, 3H), 1.07 (t, 6H), 0.84 (d, 6H) ppm.

EXAMPLE 480

[3-(4-{2-butyl-1-[4-(6-methoxy-naphthalen-2-yloxy)-phenyl]-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 6-methoxy-2-naphthol (10 mmol) to the reaction mixture and heating to 80° C. until the reaction was complete as indicated by TLC or HPLC. After cooling to rt, the reaction mixture was poured into $H_2O$ (100 mL), extracted with EtOAc (2×50 mL), washed with $H_2O$ (2×50 mL) and brine (50 mL), and dried over sodium sulfate. The solvent was removed in vacuuo to afford the desired 4-(6-methoxy-naphthalen-2-yloxy)-1-nitrobenzene. The crude product was used for further transformation.

The nitro intermediate (10 mmol) obtained above was dissolved in EtOAc (50 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-(6-methoxy-naphthalen-2-yloxy)aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (4.6 mmol) in anhydrous MeOH (10 mL) at 0° C., pyrrolidone hydrotribromide (1.2 eq., 5.5 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of an 4-(6-methoxy-naphthalen-2-yloxy)aniline (5 mmol) in anhydrous DMF (20 mL) DIEA (15 mmol) was added, followed by slow addition of the 2-bromo-1-{4-[3-(diethylamino)propoxy]phenyl}ethanone described above (4.6 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation without additional purification.

To a stirred solution of alkylated 4-(6-methoxy-naphthalen-2-yloxy)aniline described above (4.6 mmol) in anhydrous DCM (10 mL) at 0° C., TEA (3 eq., 15 mmol) was added, followed by slow addition of valeryl chloride (3 eq., 15 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~4.6 mmol) obtained as above in acetic acid (10 mL), solid ammonium acetate (92 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×40 mL). The combined organic layers was washed with $H_2O$ (2×40 mL) and brine, and dried over sodium sulfate. Evaporation of the solvent in vacuuo afforded the desired N-aryl imidazole. The crude product was purified using silica gel column chromatography (2-5% MeOH/DCM) (yield 500 mg).

MS m/z 578 (M+H)$^+$:

$^1$H NMR (CDCl$_3$): δ8.51 (d, 1H), 8.42 (m, 1H), 8.31 (d, 1H), 7.75 (m, 2H), 7.62 (m, 2H) 7.37 (s, 1H), 7.23 (m, 2H), 7.12 (m, 2H), 7.08 (s, 1H), 6.97-6.79 (m, 2H), 3.98 (t, 2H), 3.41 (s, 3H), 3.23-3.05 (m, 6H), 2.75 (m, 2H), 2.45 (m, 2H), 1.75-1.48 (m, 4H), 1.37 (t, 6H), 0.80 (m, 3H) ppm.

EXAMPLE 481

[3-(4-{2-butyl-1-[4-(naphthalen-2-yloxy)-phenyl]-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 2-naphthol (10 mmol) to the reaction mixture and heating to 80° C. until the reaction was complete as indicated by TLC or HPLC. After cooling to rt, the reaction mixture was poured into $H_2O$ (100 mL), extracated with EtOAc (2×50 mL), washed with $H_2O$ (2×50 mL) and brine (50 mL), and dried over sodium sulfate. The solvent was removed in vacuuo to afford the desired 4-(naphthalen-2-yloxy)-1-nitrobenzene. The crude product was used for further transformation.

The nitro intermediate (10 mmol) obtained above was dissolved in EtOH (50 mL) and hydrogenated in the presence of 10% Pd/C (300 mg) until completion according to General Procedure H, as indicated by TLC or HPLC. The reaction mixture was then filtered to remove the catalyst. The solvent was removed in vacuuo to afford the desired 4-(naphthalen-2-yloxy)aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C.until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (4.6 mmol) in anhydrous MeOH (10 mL) at 0° C., pyrrolidone hydrotribromide (1.2 eq., 5.5 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(naphthalen-2-yloxy)aniline (1.2 eq., 5 mmol) in anhydrous DMF (5 mL) DIEA (3 eq. 15 mmol) was added, followed by slow addition of the 2-bromo-1-{4-[3-(diethylamino)propoxy]phenyl}ethanone described above (4.6 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation without additional purification.

To a stirred solution of alkylated 4-(naphthalen-2-yloxy) aniline described above (4.6 mmol) in anhydrous DCM (5 mL) at 0° C., TEA (3 eq., 15 mmol) was added, followed by slow addition of valeryl chloride (3 eq., 15 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~4.6 mmol) obtained as above in acetic acid (10 mL), solid ammonium acetate (92 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×50 mL). The combined organic layers was washed with $H_2O$ (50 mL) and brine, and dried over sodium sulfate. Evaporation of the solvent in vacuuo afforded the desired N-aryl imidazole. The crude product was purified using silica gel column chromatography (2-5% MeOH/DCM) (yield 170 mg).

MS m/z 548 (M+H)$^+$:

$^1$H NMR (CDCl$_3$): δ7.91 (t, 1H), 7.84 (t, 1H), 7.77 (m, 1H), 7.71 (m, 2H) 7.56-7.42 (m, 4H), 7.32 (m, 2H), 7.18 (s, 1H), 7.16-7.03 (m, 2H), 7.00-6.86 (m, 2H), 4.02 (t, 2H), 3.00-2.76 (m, 6H), 2.70 (m, 2H), 2.12 (m, 2H), 1.44-1.28 (m, 4H), 1.23 (t, 6H), 0.93 (m, 3H) ppm.

EXAMPLE 482

2-butyl-4-[4-(4-ethyl-hexyloxy)-phenyl]-1-[4-(4-methoxy-naphthalen-1yl-oxy)-phenyl]-1H-imidazole To a stirred solution of 1-fluoro-4-nitrobenzene (10 mmol) in DMF (20 mL) at rt, solid potassium carbonate (30 mmol) was added followed by addition of 4-methoxy-1-naphthol (10 mmol) to the reaction mixture and heating to 80° C. until the reaction was complete as indicated by TLC or HPLC. After cooling to rt, the reaction mixture was poured into $H_2O$ (100 mL), extracted with EtOAc (2×50 mL), washed with $H_2O$ (2×50 mL) and brine (50 mL), and dried over sodium sulfate. The solvent was removed in vacuuo to afford the desired 4-(4-methoxynaphthalen-1-yloxy)-1-nitrobenzene. The crude product was used for further transformation .

The nitro intermediate (10 mmol) obtained above was dissolved in EtOAc (50 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-(4-methoxy-naphthalen-1-yloxy)aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.3 mmol) in anhydrous MeOH (5 mL) at 0° C., pyrrolidone hydrotribromide (1.2 eq., 2.7 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(4-methoxy-naphthalen-1-yloxy)aniline (1.2 eq., 2.5 mmol) in anhydrous DMF (5 mL) DIEA (3 eq. 7.5 mmol) was added, followed by slow addition of the 2-bromo-1-{4-[3-(diethylamino)propoxy]phenyl}ethanone described above (2.3 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated 4-(4-methoxynaphthalen-1-yloxy)aniline described above (2.3 mmol) in anhydrous DCM (5 mL) at 0° C., TEA (3 eq., 7.5 mmol) was added, followed by slow addition of valeryl chloride (3 eq., 7.5 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (2.3 mmol) obtained as above in acetic acid (5 mL), solid ammonium acetate (46 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×30 mL). The combined organic layers was washed with $H_2O$ (2×30 mL) and brine, and dried over sodium sulfate. Evaporation of the solvent in vacuuo afforded the desired N-aryl imidazole. The crude product was purified using silica gel column chromatography (2-5% MeOH/DCM) (yield 213 mg).

MS m/z 578 (M+H)$^+$:

$^1$H NMR (CDCl$_3$): δ8.35 (dd, 1H), 7.60 (dd, 1H), 7.72 (m, 2H), 7.55 (m, 2H), 7.24 (s, 1H), 7.23 (m, 2H), 7.15 (t, 1H), 7.04 (m, 2H), 6.90 (m, 2H), 6.80 (d, 1H), 4.04 (s, 3H), 3.95 (t, 2H), 3.00-2.87 (m, 6H), 2.67 (t, 2H), 2.10 (m, 2H), 1.65 (m, 2H), 1.38 (m, 2H), 1.21 (t, 6H), 0.95 (m, 3H) ppm.

EXAMPLE 483

[3-(4-{2-butyl-1-[4-(dibenzofuran-2-yloxy)-phenyl]-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 2-hydroxydibenzofuran (10 mmol) to the reaction mixture and heating to 80° C. until the reaction was complete as indicated by TLC or HPLC. After cooling to rt, the reaction mixture was poured into $H_2O$ (100 mL), extracted with EtOAc (2×50 mL), washed with $H_2O$ (2×50 mL) and brine (50 mL), and dried over sodium sulfate. The solvent was removed in vacuuo to afford the desired 4-(dibenzofuran-2-yloxy)-1-nitrobenzene. The crude product was used for further transformation.

The nitro intermediate (10 mmol) obtained above was dissolved in EtOAc (50 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-(dibenzofuran-2-yloxy)aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.3 mmol) in anhydrous MeOH (5 mL) at 0° C., pyrrolidone hydrotribromide (1.2 eq, 2.7 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(dibenzofuran-2-yloxy)aniline (1.2 eq., 2.5 mmol) in anhydrous DMF (5 mL) DIEA (3 eq. 7.5 mmol) was added, followed by slow addition of the 2-bromo-1-{4-[3-(diethylamino)propoxy]phenyl}ethanone described above (2.3 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated 4-(dibenzofuran-2-yloxy) aniline described above (~2.3 mmol) in anhydrous DCM (5 mL) at 0° C., TEA (3 eq., 7.5 mmol) was added, followed by slow addition of valeryl chloride (3 eq., 7.5 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (2.3 mmol) obtained as above in acetic acid (5 mL), solid ammonium acetate (46 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×30 mL). The combined organic layers was washed with $H_2O$ (2×30 mL) and brine, and dried over sodium sulfate. Evaporation of the solvent in vacuuo afforded the desired N-aryl imidazole. The crude product was purified using silica gel column chromatography (2-5% MeOH/DCM) (yield 164 mg).

MS m/z 588 (M+H)$^+$:

$^1$H NMR (CDCl$_3$): δ7.92 (d, 1H), 7.71 (m, 2H), 7.62 (d, 2H), 7.51 (t, 1H), 7.37 (t, 1H), 7.32-7.26 (m, 3H), 7.23 (m, 2H), 7.16 (s, 1H), 7.13-7.09 (m, 1H), 6.91 (d, 2H), 4.08 (t, 2H), 2.97-2.75 (m, 6H), 2.69 (t, 2H), 2.19 (m, 2H), 1.69 (m, 2H), 1.39-1.25 (m, 2H), 1.29 (t, 6H), 0.89 (t, 3H) ppm.

EXAMPLE 484

6-(4-{2-butyl-4-[4-(3-diethylamino-propoxy)-phenyl]-imidazol-1-yl}-phenoxy)-naphthalen-2-ol To a stirred solution of 1-fluoro-4-nitrobenzene (10 mmol) in DMF (20 mL) at rt, solid potassium carbonate (30 mmol) was added followed by addition of 6-methoxy-2-naphthol (10 mmol) to the reaction mixture and heating to 80° C. until the reaction was complete as indicated by TLC or HPLC. After cooling to rt, the reaction mixture was poured into $H_2O$ (100 mL), extracted with EtOAc (2×50 mL), washed with $H_2O$ (2×50 mL) and brine (50 mL), and dried over sodium sulfate. The solvent was removed in vacuuo to afford the desired 4-(6-methoxy-2-naphthalen-2-yloxy)-1-nitrobenzene. The crude product was used for further transformation .

The nitro intermediate (10 mmol) obtained above was dissolved in EtOAc (50 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-(6-methoxy-naphthalen-2-yloxy)aniline, which was used directly for further transformation without additional purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (4.6 mmol) in anhydrous MeOH (10 mL) at 0° C., pyrrolidone hydrotribromide (1.2 eq., 5.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of an 4-(6-methoxy-naphthalen-2-yloxy)aniline (5 mmol) in anhydrous DMF (20 mL) DIEA (15 mmol) was added, followed by slow addition of the 2-bromo-1-{4-[3-(diethylamino)propoxy]phenyl}ethanone described above (4.6 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation without additional purification.

To a stirred solution of alkylated 4-(6-methoxy-2-naphthalenoxy)aniline described above (4.6 mmol) in anhydrous DCM (10 mL) at 0° C., TEA (3 eq., 15 mmol) was added, followed by slow addition of valeryl chloride (3 eq., 15 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~4.6 mmol) obtained as above in acetic acid (10 mL), solid ammonium acetate (92 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×40 mL). The combined organic layers was washed with $H_2O$ (2×40 mL) and brine, and dried over sodium sulfate. Evaporation of the solvent in vacuuo afforded the desired N-aryl imidazole. The crude product was purified using silica gel column chromatography (2-5% MeOH/DCM) (Yield: 19%).

The N-aryl imidazole (0.12 mmol) previously described was dissolved in 5 mL of 48% aqueous HBr and heated to 90° C. for 36 h until the reaction was complete by HPLC. The reaction mixture was cooled to rt and treated with ice-cold saturated aqueous sodium bicarbonate solution until pH 8. The mixture was extracted with EtOAc (2×15 mL). The combined organic layers was washed with $H_2O$ (2×15 mL) and brine, and dried over sodium sulfate. Evaporation of the solvent in vacuuo afforded the demethylated N-aryl imidazole. The crude product was purified using silica gel column chromatography (2-5% MeOH/DCM) (yield 20 mg).

MS m/z 564 (M+H)$^+$:

$^1$H NMR (CDCl$_3$): δ7.62 (d, 2H), 7.60 (s, 1H), 7.58-7.54 (m, 2H), 7.32 (d, 1H), 7.18 (s, 1H), 7.16 (d, 1H), 7.15-7.10 (m, 2H), 7.08 (s, 1H), 7.02 (d, 2H), 6.78 (d, 2H), 3.95 (t, 2H), 3.00-2.81 (m, 6H), 2.60 (t, 2H), 2.12 (m, 2H), 1.56 (m, 2H), 1.30 (t, 2H), 1.21 (t, 6H), 0.75 (t, 3H) ppm.

EXAMPLE 485

[3-(4-{2-butyl-4-[4-(4-chloro-phenoxy)-phenyl]-imidazol-1-yl}-phenoxy)-propyl]-diethyl-amine A mixture of 4-fluoroacetophone (50 mmol), 4-chlorophenol (75 mmol, 1.5 eq), cesium carbonate (150 mmol, 3 eq) and anhydrous DMSO (80 mL) was heated with stirring at 90° C. for 20 h (monitored by TLC). After cooling to rt, the reaction mixture was treated with cold H₂O (150 mL), and the resulting mixture was extracted with ether (4×100 mL). The combined organic layers were washed with 2N NaOH (4×100 mL), H₂O (2×100 mL) and brine (100 mL), and dried over anhydrous sodium sulfate. The crude 1-[4-(4-chlorophenoxy)phenyl]ethanone was purified by flash chromatography (eluting with 5-10% EtOAc in hexane) to give 4-(4'-chlorophenoxy)acetophone as an almost colorless solid (yield: 80%).

To a stirred solution of 4-fluoronitrobenzene (50 mmol) and 3-diethylaminoproanol (70 mmol) dissolved in anhydrous THF (50 mL) at 0° C. and under a nitrogen stream was added KOBu$^t$ (70 mmol) in portions, and the reaction mixture was allowed to warm to rt, and stirred overnight, according to General Procedure L1. The reaction mixture was then treated with cold H₂O (80 mL), and extracted with EtOAc (3×100 mL). The combined organic layers were washed with brine (2×60 mL) and dried over anhydrous sodium sulfate. Evaporation of the solvent in vacuuo afforded the desired N,N-diethyl-N-[3-(4-nitrophenoxy)propyl]amine, which was used for further transformation without further purification (yield: ~98%).

The crude N,N-diethyl-N-[3-(4-nitrophenoxy)propyl] amine (~33 mmol) was dissolved in MeOH (50 mL), and hydrogenated in the presence of 10% Pd/C (0.8 g) until the reaction was complete as indicated by LC-MS (~4 h), according to General Procedure H. The reaction mixture was then filtered to remove the catalyst. The solvent was removed under high vacuum to afford N,N-diethyl-N-[3-(4-nitrophenoxy)propyl]amine which was used directly for further transformation without further purification (yield: ~96%).

1-[4-(4-chlorophenoxy)phenyl]ethanone (24 mmol) was dissolved in 1,4-dioxane (100 mL) and pyridine hydrotribromide (25.2 mmol, 1.05 eq) was added, according to General Procedure R1. After being stirred at rt for 7 h (monitored by TLC), the reaction was quenched with cold H₂O (100 mL). The resulting mixture was extracted with ether (4×100 mL). The combined ether extracts were washed with brine (3×50 mL), and dried over anhydrous sodium sulfate. The solvent was then removed in vacuuo and the crude 2-bromo-1-[4-(4-chlorophenoxy)phenyl]ethanone was directly used for further transformation.

To a stirred solution of ice-cold N,N-diethyl-N-[3-(4-nitrophenoxy)propyl]amine (22 mmol, 1.1 eq) dissolved in DCM (40 mL) was added dropwise a solution of the 2-bromo-1-[4-(4-chlorophenoxy)phenyl]ethanone (20 mmol) dissolved in DMF (30 mL), according to General Procedure R2. The mixture was stirred at 0° C. for 3 h, and then allowed to warm to rt, continuing the stirring for additional 2 h (monitored by LC-MS). The reaction mixture was treated with saturated sodium bicarbonate (100 mL), and the resulting mixture was extracted with EtOAc (4×100 mL). The combined EtOAc extracts were washed with brine (3×50 mL), and dried over anhydrous sodium sulfate. The solvent was removed in vacuuo, and the crude product was purified by silica gel column chromatography eluting with 10% MeOH in EtOAc+0.2% TEA (overall yield from 1-[4-(4-chlorophenoxy)phenyl]ethanone: 60%).

To a stirred solution of the alkylated aniline described above (10 mmol) dissolved in anhydrous DCM (100 mL) at 0° C., TEA (40 mmol, 4 eq) was added, followed by a slow addition of valeryl chloride (20 mmol, 2 eq), according to General Procedure R3. The reaction mixture was stirred under nitrogen at 0° C. for 2 h and allowed to warm to rt until completion, as indicated by LC-MS. The solvent was removed in vacuuo, and the crude amide was used directly for further transformation.

The crude amide described above (~6 mmol) was suspended in acetic acid (10 mL), and ammonium acetate (excess, ~30 eq) was added, according to General Procedure R4. The reaction mixture was stirred at 90° C. for 6 h (as monitored by LC-MS). The reaction mixture was then cooled down and neutralized with saturated sodium bicarbonate and solid sodium carbonate. The resulting mixture was extracted with EtOAc (4×100 mL). The combined EtOAc extracts were washed with H₂O (2×60 mL) and brine (2×60 mL), and dried over anhydrous sodium sulfate. The solvent was removed in vacuuo, and the crude product was purified by silica gel column chromatography eluting with 10% MeOH in EtOAc+0.2% TEA affording Example 485.

MS m/z 532 (M+H)$^+$:

$^1$H NMR (400 MHz, CDCl₃): δ0.83 (t, 3H), 1.04 (t, 6H), 1.28 (m, 2H), 1.63 (m, 2H), 1.96 (m, 2H), 2.56 (q, 4H), 2.61-2.65 (m, 4H), 4.06 (t, 2H), 6.93 (d, 2H), 6.98 (d, 2H), 7.00 (d, 2H), 7.16 (s, 1H), 7.22 (d, 2H), 7.26 (d, 2H), 7.76 (d, 2H) ppm.

EXAMPLE 486

[3-(4-{2-(4-tert-butyl-cyclohexyl)-1-[4-(4-chlorophenoxy)-phenyl]-1H-imidazol-4-yl}-phenoxy)-propyl]-diethyl-amine To a stirred solution of 1-{4-[3-(diethylamino)propoxy] phenyl}ethanone (80 mmol) in MeOH (200 mL) at rt, pyrrolidone hydrotribromide (96 mmol, 1.2 eq) was added in portions at rt, according to General Procedure R1. The reaction mixture was stirred at rt for 2 h (monitored by LC-MS). The solvent was then removed in vacuuo and the crude 2-bromo-1-{4-[3-(diethylamino)propoxy]phenyl}ethanone was directly used for further transformation.

The solution of the crude 2-bromo-1-{4-[3-(diethylamino) propoxy]phenyl}ethanone dissolved in anhydrous DMF (180 mL) was chilled to 0° C., and 4-(4'-chlorophenoxy)aniline (88 mmol, 1.1 eq) was added, followed by slowly adding DIEA (240 mmol, 3 eq), according to General Procedure R2. After being stirred at 0° C. for 1 h and at rt for additional 4 h, the reaction mixture was treated with saturated sodium bicarbonate (250 mL). The resulting mixture was extracted with EtOAc (4×200 mL). The combined EtOAc extracts were washed with brine (3×100 mL), and dried over anhydrous sodium sulfate. The solvent was removed in vacuuo, and the crude product was purified by silica gel column chromatography eluting with 10% MeOH in EtOAc+0.2% TEA.

Oxayl chloride (420 mmol, 3 eq) was added slowly to an ice-cold solution of 4-t-butylcyclohexanecarboxylic acid (140 mmol) dissolved in anhydrous DCM (80 mL), and the reaction mixture was stirred at 0° C. for 3 h and at rt for additional 3 h. The solvent was removed in vacuuo, and the resulting acid chloride was pumped under high vacuum for about 30 min, and used for next step reaction without further purification.

To a stirred solution of the 2-[4-(4-chlorophenoxy)-phenylamino]-1-[4-(3-diethylamino-propoxy)-phenyl]-ethanone described above (35 mmol) dissolved in anhydrous DCM (200 mL) at 0° C., TEA (140 mmol, 4 eq) was added, followed by a slow addition of the freshly prepared acid chloride (70 mmol, 2 eq). The reaction mixture was stirred under nitrogen at 0° C. for 2 h and allowed to warm to rt until completion, as indicated by LC-MS. The solvent was removed in vacuuo, and the crude amide was used directly for further transformation.

The crude amide described above (~35 mmol) was suspended in acetic acid (50 mL), and ammonium acetate (excess, ~30 eq) was added, according to General Procedure R4. The reaction mixture was stirred at 100° C. for 6 h (as monitored by LC-MS). The reaction mixture was then cooled down and neutralized with saturated sodium bicarbonate and solid sodium carbonate. The resulting mixture was extracted with EtOAc (4×200 mL). The combined EtOAc extracts were washed with $H_2O$ (2×100 mL) and brine (2×100 mL), and dried over anhydrous sodium sulfate. The solvent was removed in vacuuo, and the crude product was purified by silica gel column chromatography eluting with 10% MeOH in EtOAc+0.2% TEA affording the title compound as cis/trans (1:2 ratio) mixture (yield 14.5 g).

LC: 1.06 min; MS: m/z 614 (M+H)⁺

EXAMPLE 487

[3-{4-[1-[4-(4-chloro-phenoxy)-phenyl]-2-(4-ethyl-cyclohexyl)-1H-imidazol-4-yl]-phenoxy}-propyl)-diethyl-amine To a stirred solution of 1-{4-[3-(diethylamino)propoxy]phenyl}ethanone (80 mmol) in MeOH (200 mL) at rt, pyrrolidone hydrotribromide (96 mmol, 1.2 eq) was added in portions at rt, according to General Procedure R1. The reaction mixture was stirred at rt for 2 h (monitored by LC-MS). The solvent was then removed in vacuuo and the crude 2-bromo-1-{4-[3-(diethylamino)propoxy]phenyl}ethanone was directly used for further transformation.

The solution of the crude 2-bromo-1-{4-[3-(diethylamino)propoxy]phenyl}ethanone dissolved in anhydrous DMF (180 mL) was chilled to 0° C., and 4-(4'-chlorophenoxy)aniline (88 mmol, 1.1 eq) was added, followed by slowly adding DIEA (240 mmol, 3 eq), according to General Procedure R2. After being stirred at 0° C. for 1 h and at rt for additional 4 h, the reaction mixture was treated with saturated sodium bicarbonate (250 mL). The resulting mixture was extracted with EtOAc (4×200 mL). The combined EtOAc extracts were washed with brine (3×100 mL), and dried over anhydrous sodium sulfate. The solvent was removed in vacuuo, and the crude product was purified by silica gel column chromatography eluting with 10% MeOH in EtOAc+0.2% TEA (yield: 45%).

Oxayl chloride (3 mmol, 3 eq) was added slowly to an ice-cold solution of trans-4-ethylcyclohexanecarboxylic acid (1 mmol) dissolved in anhydrous DCM (5 mL), and the reaction mixture was stirred at 0° C. for 2 h and at rt for additional 1 h. The solvent was removed in vacuuo, and the resulting acid chloride was pumped under high vacuum for about 30 min, and used without further purification.

To a stirred solution of the 2-[4-(4-chlorophenoxy)-phenylamino]-1-[4-(3-diethylamino-propoxy)-phenyl]-ethanone (0.3 mmol) described above dissolved in anhydrous DCM (10 mL) at 0° C., TEA (1.2 mmol, 4 eq) was added, followed by slow addition of the freshly prepared acid chloride (~1 mmol, ~3 eq). The reaction mixture was stirred under nitrogen at 0° C. for 2 h and allowed to warm to rt until completion, as indicated by LC-MS. The solvent was removed in vacuuo, and the crude amide was used directly for further transformation.

To a stirred solution of the amide described above (~0.3 mmol) in acetic acid (2 mL), ammonium acetate (excess, ~30 eq.) was added, according to General Procedure R4. The reaction mixture was stirred at 100° C. for 3 h (as monitored by LC-MS). The reaction mixture was then cooled to rt and neutralized with saturated sodium bicarbonate. The resulting mixture was extracted with EtOAc (3×50 mL). The combined EtOAc extracts were washed with brine (3×20 ml), and dried over anhydrous sodium sulfate. The solvent was removed in vacuuo, and the pure product was obtained by silica gel column chromatography eluting with 10% MeOH/EtOAc+0.2% $Et_3N$ (yield 123 mg).

MS m/z 586 (M+H)⁺:

¹H NMR (400 MHz, CDCl₃): δ0.85 (t, 3H), 1.06 (t, 6H), 1.16-1.82 (m, 12H), 1.96 (m, 2H), 2.61 (q, 4H), 2.68 (t, 2H), 4.01 (t, 2H), 6.89 (d, 2H), 7.03 (d, 2H), 7.06 (d, 2H), 7.08 (s, 1H), 7.27 (d, 2H), 7.35 (d, 2H), 7.68 (d, 2H) ppm.

EXAMPLE 488

[4-(4-{2-butyl-1-[4-(4-chloro-phenoxy)-phenyl]-1H-imidazol-4-yl}-phenoxy)-phenyl]-(1-ethyl-piperidin-4ylmethyl)-amine To a stirred solution of the 4'-(4-nitro-phenoxy)acetophenone (2 mmol) in anhydrous MeOH (5 mL) at 0° C., pyrrolidone hydrotribromide (1.2 eq., 2.2 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the residue was treated with saturated sodium bicarbonate. The aqueous layer was poured into EtOAc (20 ml) and washed with water (2×15 ml) and brine (15 ml). The organic layer was dried over magnesium sulfate, and the solvent was removed in vacuuo to afford the desired product. The crude alpha-bromoacetophenone was used for further transformation.

To a stirred solution of the 4-chloro-phenoxy aniline (1.2 eq., 2.2 mmol) in anhydrous DMF (10 mL) DIEA (3 eq. 6 mmol) was added, followed by slow addition of the alpha-bromoacetophenone described above (1.6 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated aniline described above (1.6 mmol) in anhydrous DCM (5 mL) at 0° C., TEA (3 eq., 4.8 mmol) was added, followed by slow addition of valeryl chloride (2 eq., 3.2 mmol), according to General Procedure R3. The reaction mixture was stirred under nitrogen at 0° C. for 1 h and allowed to warm to rt until completion, as indicated by TLC or HPLC. The reaction mixture was then diluted with water and the product was isolated in DCM. The solvent was removed in vacuuo, and the crude amide was used for further transformation.

To a stirred solution of the amide described above (1 mmol) in acetic acid (2 mL), ammonium acetate (excess, ~20 eq.) was added, according to General Procedure R4. The reaction mixture was stirred at 90° C. overnight. The reaction mixture was then cooled to rt and neutralized with saturated sodium bicarbonate solution. Usual extractive work up with EtOAc gave the cyclized imidazole, which was purified by column chromatography (Silica gel). Pure product was obtained from 30-40% ethylacetate/hexane (yield 50-55%).

The cyclized imidazole intermediate obtained above (0.5 mmol) obtained above was dissolved in MeOH (5 mL) and hydrogenated in the presence of 10% Pd/C (10 mg) until completion as indicated by TLC or HPLC, according to General Procedure H. The reaction mixture was then filtered to remove the catalyst. The solvent was removed in vacuuo to afford the desired reduced imidazole, which was used directly for further transformation without further purification.

To a stirred solution of N-Boc-4-piperidineacetic acid (1.2 eq., 0.6 mmol) in anhydrous DCM (2 mL) was added DCC-PS (1.5 eq., 0.75 mmol). The solution was allowed to shake at rt for 20-30 min. This was followed by addition of the reduced cyclized imidazole described above (0.5 mmol). The reaction mixture was shaken overnight at rt until completion, as indicated by TLC or HPLC. The reaction mixture was then filtered and the product was isolated in DCM. The solvent was removed in vacuuo, and the crude amide was used for further transformation.

To a stirred solution of the amide described above (0.5 mmol) in anhydrous THF (2 mL) at 0° C., borane/THF (3 eq, 1.5 mmol) was added. The reaction mixture was stirred under nitrogen at 0° C. for 1 h and allowed to warm to rt until completion, as indicated by TLC or HPLC. The reaction mixture was then cooled to rt and the solvent was removed in vacuuo to give the product imidazole, which was purified by column chromatography (Silica gel). Pure product was obtained from 3-4% MeOH/DCM (yield 150 mg).

MS m/z 635 (M+H)$^+$:

$^1$H NMR (400 MHz, CDCl$_3$): δ 8.01 (s, 1H), 7.84 (d, 2H), 7.65 (d, 2H), 7.59 (d, 2H), 7.44 (d, 2H), 7.22 (m, 6H), 7.12 (d, 2H), 3.65 (d, 2H), 3.45 (d, 2H), 3.03 (t, 2H), 3.18 (m, 2H), 2.98 (m, 4H), 2.15 (m, 2H), 1.71 (m, 3H), 1.39 (m, 5H), 0.85 (t, 3H) ppm

EXAMPLE 489

[4-{1-[4-(4-chloro-phenyl)-phenyl]-4-[4-(3-diethylaminopropoxy)-phenyl]-1H-imidazol-2-yl}-butyric acid methyl ester As described in Example 406, 2-[4-(4-chlorophenoxy)-phenylamino]-1-[4-(3-diethylamino-propoxy)-phenyl]-ethanone (0.5 mmol) was dissolved in anhydrous DCM (10 mL) and cooled to 0° C. TEA (2 mmol, 4 eq) was added to the reaction mixture, followed by slow addition of methyl 4-(chloroformyl)butyrate (1.5 mmol, 3 eq), according to General Procedure R3. The reaction mixture was stirred under nitrogen at 0° C. for 2 h and allowed to warm to rt until completion, as indicated by LC-MS. The solvent was removed in vacuuo, and the crude amide was used directly for further transformation.

To a stirred solution of the amide described above in acetic acid (2 mL), ammonium acetate (excess, ~30 eq) was added, according to General Procedure R4. The reaction mixture was stirred at 100° C. for 3 h (as monitored by LC-MS). The reaction mixture was then cooled down and neutralized with saturated sodium bicarbonate. The resulting mixture was extracted with EtOAc (3×50 mL). The combined EtOAc extracts were washed with brine (3×20 mL), and dried over anhydrous sodium sulfate. The solvent was removed in vacuuo, and the pure product was obtained by silica gel column chromatography eluting with 10% MeOH in EtOAc+ 0.2% TEA (yield: ~70%) (yield 202 mg).

MS m/z 576 (M+H)$^+$:

$^1$H NMR (400 MHz, CDCl$_3$): δ1.04 (t, 6H), 1.94 (m, 2H), 2.02 (m, 2H), 2.39 (t, 2H), 2.56 (q, 4H), 2.63 (t, 2H), 2.72 (t, 2H), 3.59 (s, 3H), 4.02 (t, 2H), 6.91 (d, 2H), 7.03 (d, 2H), 7.07 (d, 2H), 7.14 (s, 1H), 7.29 (d, 2H), 7.35 (d, 2H), 7.68 (d, 2H) ppm.

EXAMPLE 490

[3-(4-{2-butyl-1-[4-(4-chloro-2-cyclohexyl-phenoxy)-phenyl]-1H-imidazol-4-yl}-phenoxy)-propyl]-diethyl-amine To a stirred solution of 1-fluoro-4-nitrobenzene (10 mmol) in DMF (10 mL) at rt, solid potassium carbonate (30 mmol) was added followed by addition of 4-chloro-2-cyclohexylphenol (10 mmol) to the reaction mixture and heating to 80° C. until the reaction was complete as indicated by TLC or HPLC. After cooling to rt, the reaction mixture was poured into EtOAc (80 ml), washed with H$_2$O (2×40 ml) and brine (60 mL), and dried over sodium sulfate. The solvent was removed in vacuuo to afford the desired 4-(4-chloro-2-cyclohexylphenoxy)-1-nitrobenzene. The crude product was used for further transformation .

The nitro intermediate (10 mmol) obtained above was dissolved in MeOH (20 mL), and treated with SnCl$_2$.2H$_2$O (50 mmol), according to General Procedure I. The reaction mixture was heated under reflux until completion, as indicated by TLC or HPLC. The solvent was removed in vacuuo and the residue was treated with 4.0 N aqueous NaOH to pH ~8. The residue was extracted with EtOAc (2×50 mL), washed with 1.0 N aqueous NaOH, brine and dried over sodium sulfate. The solvent was removed in vacuuo to afford the desired 4-(4-chloro-2-cyclohexylphenoxy) aniline, which was used directly for further transformation without further purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with H$_2$O (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.4 mmol) in anhydrous MeOH (5 mL) at 0° C., pyrrolidone hydrotribromide (1.2 eq, 2.9 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(4-chloro-2-cyclohexylphenoxy) aniline (1.2 eq., 2.5 mmol) in anhydrous DMF (5 mL) DIEA (3 eq. 6 mmol) was added, followed by slow addition of the 2-bromo-1-{4-[3-(diethylamino)propoxy]phenyl}ethanone described above (2.4 mmol), according to General Procedure R2. The reaction mixture was stirred under nitrogen at rt until completion, as indicated by TLC or HPLC. The reaction mixture was then diluted with cold H$_2$O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~50-60%).

To a stirred solution of alkylated 4-(4-chloro-2-cyclohexylphenoxy) aniline described above (2.4 mmol) in anhydrous DCM (5 mL) at 0° C., TEA (3 eq., 7.5 mmol) was added, followed by slow addition of valeryl chloride (3 eq., 7.5 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~2.4 mmol) obtained as above in acetic acid (5 mL), solid ammonium acetate (46 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×30 mL). The combined organic layers was washed with $H_2O$ (2×30 mL) and brine, and dried over sodium sulfate. Evaporation of the solvent in vacuuo afforded the desired N-aryl imidazole. The crude product was purified using silica gel column chromatography (2-5% MeOH/DCM) (yield 118 mg).

MS m/z 614 $(M+H)^+$:
$^1$H NMR $(CDCl_3)$ δ7.86 (d, 1H), 7.63 (d, 2H), 7.25 (d, 2H), 7.18 (s, 1H), 7.08 (s, 1H), 6.94 (d, 2H), 6.81 (d, 2H), 6.80 (d, 1H, 6.8 Hz), 4.12 (m, 2H), 3.20 (m, 2H), 2.98-2.79 (m, 6H), 2.60 (t, 2H), 2.21-2.19 (m, 2H), 2.15-2.05 (m, 1H), 1.78-1.72 (m, 2H), 1.59-1.50 (m, 2H), 1.36-1.24 (m, 4H), 1.21 (t, 6H), 0.84 (m, 4H), 0.79 (m, 3H) ppm.

EXAMPLE 491

[3-(4-{1-[4-(biphenyl-4-yloxy)-phenyl]-2-butyl-1H-imidazol-4-yl}-phenoxy)-propyl]-diethyl-amine To a stirred solution of 1-fluoro-4-nitrobenzene (10 mmol) in DMF (20 mL) at room temperature, solid $K_2CO_3$ (30 mmol) was added followed by addition of 4-hydroxybiphenyl (10 mmol) to the reaction mixture and heating to 80° C. until the reaction was complete as indicated by TLC or HPLC. After cooling to room temperature to room temperature, the reaction mixture was poured into EtOAc (100 mL), washed with water (2×50 mL) and brine (50 mL), and dried over sodium sulfate. The solvent was removed in vacuo to afford the desired 4-(biphenyl-4-oxy)-1-nitrobenzene. The crude product was used for further transformation.

The nitro intermediate (10 mmol) obtained above was dissolved in EtOAc (40 mL) and hydrogenated in the presence of 10% Pd/C (360 mg) until completion, as indicated by TLC or HPLC. The reaction mixture was then filtered to remove the catalyst. The solvent was removed in vacuo to afford the desired 4-(biphenyl-4-oxy)aniline, which was used directly for further transformation without further purification.

To a stirred solution of 4'-hydroxyacetophenone (91 mmol) in DMF (80 mL) at room temperature, solid $K_2CO_3$ (153 mmol) was added. The mesylate of 3-diethylamino-1-propanol and methanesulfonyl chloride (76 mmol) was added to the reaction mixture and heated to 80° C. until completion, as indicated by TLC or HPLC. After cooling to room temperature, the reaction mixture was quenched by treating the mixture with saturated sodium bicarbonate. The aqueous layer was poured into EtOAc (100 mL) and washed with water (2×50 mL) and brine (50 mL). The organic layer was dried over sodium sulfate, and the solvent was removed in vacuuo to afford the desired product. The crude alkylated product was used for further transformation after purifying using silica gel column chromatography (1-4% methanol/DCM).

To a stirred solution of 1-{4-[3-(diethylamino)propoxy]phenyl}ethanone (2.4 mmol) in anhydrous MeOH (5 mL) at 0° C., pyrrolidone hydrotribromide (1.2 eq., 2.9 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(biphenyl-4-oxy)aniline (1.2 eq., 2.5 mmol) in anhydrous DMF (5 mL) DIEA (3 eq. 6 mmol) was added, followed by slow addition of the 2-bromo-1-{4-[3-(diethylamino)propoxy]phenyl}ethanone described above (2.4 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~13%

To a stirred solution of alkylated 4-(biphenyl-4-oxy) aniline described above (0.3 mmol) in anhydrous DCM (3 mL) at 0° C., TEA (3 eq., 0.9 mmol) was added, followed by slow addition of valeryl chloride (3 eq., 0.9 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~0.3 mmol) obtained as above in acetic acid (3 mL), solid ammonium acetate (6 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with $H_2O$ (2×15 mL) and brine, and dried over sodium sulfate. Evaporation of the solvent in vacuuo afforded the desired N-aryl imidazole. The crude product was purified using silica gel column chromatography (2-5% MeOH/DCM).

MS m/z 574 $(M+H)^+$
$^1$H NMR $(CDCl_3)$ δ7.86 (d, 1H), 7.63 (d, 2H), 7.25 (d, 2H), 7.18 (s, 1H), 7.08 (s, 1H), 6.94 (d, 2H), 6.81 (d, 2H), 6.80 (d, 1H), 4.12 (m, 2H), 3.20 (m, 2H), 2.98-2.79 (m, 6H), 2.60 (t, 2H), 2.21-2.19 (m, 2H), 2.15-2.05 (m, 1H), 1.78-1.72 (m, 2H), 1.59-1.50 (m, 2H), 1.36-1.24 (m, 4H), 1.21 (t, 6H), 0.84 (m, 4H), 0.79 (m, 3H) ppm

EXAMPLE 492

[3-(4-{1-[4-(4-bromo-phenoxy)-phenyl]-2-butyl-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 4-bromophenol (10 mmol) to the reaction mixture and heating to 80° C. until the reaction was complete as indicated by TLC or HPLC. After cooling to rt, the reaction mixture was poured into EtOAc (100 mL), washed with H₂O (2×50 mL) and brine (50 mL), and dried over sodium sulfate. The solvent was removed in vacuuo to afford the desired 4-bromophenoxy-1-nitrobenzene. The crude product was used for further transformation .

The nitro intermediate (10 mmol) obtained above was dissolved in EtOAc (50 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-bromophenoxyaniline, which was used directly for further transformation without additional purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with H₂O (2×50 mL) and brine (50 mL). The organic layer was dried over sodium sulfate, and the solvent was removed in vacuuo to afford the desired 1-(4-[3-(diethylamino)propoxy]phenyl)ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.4 mmol) in anhydrous MeOH (5 mL) at 0° C., pyrrolidone hydrotribromide (1.2 eq., 2.9 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-bromophenoxyaniline (1.2 eq., 2.5 mmol) in anhydrous DMF (5 mL) DIEA (3 eq. 7.5 mmol) was added, followed by slow addition of the 2-bromo-1-{4-[3-(diethylamino)propoxy]phenyl}ethanone described above (2.4 mmol), according to General Procedure R2. The reaction mixture was stirred under nitrogen at rt until completion, as indicated by TLC or HPLC. The reaction mixture was then diluted with cold H₂O and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM.

To a stirred solution of alkylated 4-bromophenoxyaniline described above (0.45 mmol) in anhydrous DCM (5 mL) at 0° C., TEA (3 eq., 1.35 mmol) was added, followed by slow addition of valeryl chloride (3 eq., 1.35 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~0.45 mmol) obtained as above in acetic acid (3 mL), solid ammonium acetate (9 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with H₂O (2×15 mL) and brine, and dried over sodium sulfate. Evaporation of the solvent in vacuuo afforded the desired N-aryl imidazole. The crude product was purified using silica gel column chromatography (2-5% MeOH/DCM) (yield 66 mg).

MS m/z 577 (M+H)⁺:

$^1$H NMR (CDCl₃): δ7.63 (d, 2H), 7.43 (d, 2H), 7.23 (d, 2H), 7.08 (s, 1H), 7.02 (d, 2H), 6.90 (d, 2H), 6.83 (d, 2H) 4.05 (t, 2H), 2.92-2.72 (m, 6H), 2.60 (t, 2H), 2.05-2.15 (m, 2H), 1.60 (m, 2H), 1.33 (m, 2H), 1.20 (t, 6H), 0.80 (t, 3H) ppm

EXAMPLE 493

N-[4-(4-{2-butyl-4-[4-(3-diethylamino-porpoxy)-phenyl]-imidazol-1-yl}-phenoxy)-phenyl]-acetamide 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for 1 h and at rt for 1 h (until the reaction was complete by HPLC). The solvent was removed and to this saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxyacetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product 1-{4-[3-(diethylamino)propoxy]phenyl}ethanone was purified by flash chromatography (going by increasing gradient up to 10% MeOH in DCM). The overall yield was 60%.

4-Acetamidophenol (10 mmol) was dissolved in 15 ml of anhydrous DMF and potassium carbonate (30 mmol) was added with stirring at rt. 4-Fluoronitrobenzene (10 mmol) was added to this mixture, which was then heated under reflux at 80° C. for 18 h. The reaction was quenched with 30 ml of water and 30 ml of sodium bicarbonate, extracted with EtOAc (3×50 ml) and washed with sodium bicarbonate and water. EtOAc layer was dried over anhydrous sodium sulfate and filtered, after which the solvent was removed in vacuuo.

The nitro intermediate (10 mmol) obtained above was dissolved in EtOH (30 mL) and hydrogenated in the presence of 10% Pd/C (10 mg) until completion according to General Procedure H, as indicated by TLC or HPLC. The reaction mixture was then filtered to remove the catalyst. The solvent was removed in vacuuo to afford the desired 4-(3,4-dichlorophenoxy)aniline, which was used directly for further transformation without further purification (yield 80%).

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(4-acetamidophenoxy) aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 54%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 210 mg).

MS m/z 555 (M+H)$^+$:
$^1$H NMR: (CDCl$_3$): δ7.68 (d, 2H), 7.51 (d, 2H), 7.25 (d, 2H), 7.13 (s, 1H), 6.88-7.00 (m, 6H), 4.02 (t, 2H), 2.62-2.70 (m, 8H), 2.20 (s, 3H), 2.16 (m, 2H), 1.97 (m, 2H), 1.16 (m, 2H), 1.05 (t, 6H), 0.83 (t, 3H) ppm

EXAMPLE 494

(3-{4-[2-butyl-1-(4-p-tolyloxy-phenyl)-1H-imidazol-4-yl]-phenoxy}-propyl)-diethyl-amine 3-Diethylaminopropanol (20 mmol, 1 eq) was dissolved in DCM (25 mL), TEA (40 mmol, 2 eq) was added and the mixture was cooled to 0° C. To this mixture, methanesulfonyl chloride (30 mmol, 1.5 eq) was added slowly with stirring and the reaction mixture was stirred at 0° C. for an hour and at rt for another hour (until the reaction was complete by HPLC). The solvent was removed and to this saturated aqueous sodium bicarbonate was added. The product was extracted with EtOAc (3×) and washed with sodium bicarbonate and water. The solvent was removed in vacuuo.

The mesylate from the previous step (20 mmol, 1 eq) was dissolved in anhydrous DMF (25 mL) to which 4-hydroxy-acetophenone (20 mmol, 1 eq) and potassium carbonate (60 mmol, 3 eq) were added. The mixture was heated under reflux at 85° C. for 18 h (until the reaction was complete by HPLC), after which it was cooled to rt. Saturated aqueous sodium bicarbonate was added to the mixture, which was then transferred to a separatory funnel. The product was extracted with EtOAc and washed with sodium bicarbonate and water. The solvent was removed in vacuuo and the product 1-{4-[3-(diethylamino)propoxy]phenyl}ethanone was purified by flash chromatography (going by increasing gradient up to 10% MeOH in DCM). The overall yield was 60%.

To a stirred solution of 1-{4-[3-(diethylamino)propoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-tolyloxy aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 56%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product was obtained from 4-6% MeOH/DCM (yield 204 mg).

MS m/z 512 (M+H)$^+$:
$^1$H NMR (CDCl$_3$): δ 7.68 (d, 2H), 7.23 (d, 2H), 7.19 (d, 2H), 7.13 (s, 1H), 7.04 (d, 2H), 6.97 (d, 2H), 6.87 (d, 2H) 4.04 (t, 2H), 2.88-2.96 (m, 8H), 2.36 (s, 3H), 2.12 (m, 2H), 1.59 (m, 2H), 1.23(m, 2H), 1.18 (t, 6H), 0.83 (t, 3H) ppm

EXAMPLE 495

[3-(4-{2-butyl-1-[4-(4-fluoro-phenoxy)-phenyl]-1H-imidazol-4-yl}-phenoxy)-propyl]-diethyl-amine To a stirred solution of 1-fluoro-4-nitrobenzene (10 mmol) in DMF (20 mL) at rt, solid potassium carbonate (30 mmol) was added followed by addition of 4-fluorophenol (10 mmol) to the reaction mixture and heating to 80° C. until the reaction was complete as indicated by TLC or HPLC. After cooling to rt, the reaction mixture was poured into EtOAc (100 mL), washed with H$_2$O (2×50 mL) and brine (50 mL), and dried over sodium sulfate. The solvent was removed in vacuuo to afford the desired 4-fluorophenoxy-1-nitrobenzene. The crude product may be used for further transformation.

The nitro intermediate (10 mmol) obtained above was dissolved in EtOAc (30 mL) and hydrogenated in the presence of 10% Pd/C (360 mg) until completion according to General Procedure H, as indicated by TLC or HPLC. The reaction mixture was then filtered to remove the catalyst. The solvent was removed in vacuuo to afford the desired 4-fluorophenoxyaniline, which was used directly for further transformation without additional purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.3 mmol) in anhydrous MeOH (5 mL) at 0° C., pyrrolidone hydrotribromide (1.2 eq., 2.8 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-fluorophenoxyaniline (1.2 eq., 2.5 mmol) in anhydrous DMF (5 mL) DIEA (3 eq. 7.5 mmol) was added, followed by slow addition of the 2-bromo-1-{4-[3-(diethylamino)propoxy]phenyl}ethanone described above (2.3 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield ~30%).

To a stirred solution of alkylated 4-fluorophenoxyaniline described above (0.8 mmol) in anhydrous DCM (5 mL) at 0° C., TEA (3 eq., 2.4 mmol) was added, followed by slow addition of valeryl chloride (3 eq., 2.4 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~0.8 mmol) obtained as above in acetic acid (3 mL), solid ammonium acetate (16 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×15 mL). The combined organic layers was washed with $H_2O$ (2×15 mL) and brine, and dried over sodium sulfate. Evaporation of the solvent in vacuuo afforded the desired N-aryl imidazole. The crude product was purified using silica gel column chromatography (2-5% MeOH/DCM) (yield 214 mg).

MS m/z 516 (M+H)$^+$:

$^1$H NMR (CDCl$_3$): δ7.88 (d, 2H), 7.46 (d, 2H), 7.23 (d, 2H), 7.31 (s, 1H), 7.22 (d, 2H), 7.09 (d, 2H), 7.06 (d, 2H) 4.22 (t, 2H), 3.16 (m, 2H), 3.21 (q, 4H), 2.84 (t, 2H), 2.39-2.19 (m, 2H), 1.83 (m, 2H), 1.50 (m, 2H), 1.35 (t, 6H), 1.03 (t, 3H) ppm

EXAMPLE 496

[3-(4-{2-butyl-1-[4-(4-chloro-3-ethyl-phenoxy)-phenyl]-1H-imidazol-4-yl}-phenoxy)-propyl]-diethylamine To a stirred solution of 1-fluoro-4-nitrobenzene (10 mmol) in DMF (20 mL) at rt, solid potassium carbonate (30 mmol) was added followed by addition of 4-chloro-3-ethylphenol (10 mmol) to the reaction mixture and heating to 80° C. until the reaction was complete as indicated by TLC or HPLC. After cooling to rt, the reaction mixture was poured into EtOAc (100 mL), washed with $H_2O$ (2×50 mL) and brine (50 mL), and dried over sodium sulfate. The solvent was removed in vacuuo to afford the desired 4-(4-chloro-3-ethylphenoxy)-1-nitrobenzene. The crude product was used for further transformation.

The nitro intermediate (10 mmol) obtained above was dissolved in MeOH (20 mL), and treated with $SnCl_2.2H_2O$ (50 mmol), according to General Procedure I. The reaction mixture was heated under reflux until completion, as indicated by TLC or HPLC. The solvent was removed in vacuuo and the residue was treated with 4.0 N aqueous NaOH to pH ~8. The residue was extracted with EtOAc (2×50 mL), washed with 1.0 N aqueous NaOH (50 mL), brine and dried over sodium sulfate. The solvent was removed in vacuuo to afford the desired 4-chloro-3-ethylphenoxyaniline, which was used directly for further transformation without additional purification.

To a stirred solution of 4'-hydroxyacetophenone (91 mmol) in DMF (80 mL) at rt, solid potassium carbonate (153 mmol) was added. The mesylate prepared from 3-diethylamino-1-propanol and methanesulfonyl chloride (76 mmol) was added to the reaction mixture and heated to 80° C. until completion according to General Procedure Q1, as indicated by TLC or HPLC. After cooling to rt, the reaction mixture was quenched by treating the mixture with saturated sodium bicarbonate. The aqueous layer was poured into EtOAc (100 mL) and washed with $H_2O$ (2×50 mL) and brine (50 mL). The organic layer was dried over sodium sulfate, and the solvent was removed in vacuuo to afford the desired 1-{4-[3-(diethylamino)propoxy]phenyl}ethanone. The crude alkylated product was used for further transformation after purifying using silica gel column chromatography (1-4% MeOH/DCM).

To a stirred solution of 1-{4-[3-(diethylamino)propoxy]phenyl}ethanone (2.4 mmol) in anhydrous MeOH (5 mL) at 0° C., pyrrolidone hydrotribromide (1.2 eq., 2.9 mmol) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a stirred solution of 4-(4-chloro-3-ethylphenoxy)-1-nitrobenzene (1.2 eq., 2.5 mmol) in anhydrous DMF (5 mL) DIEA (3 eq. 7.5 mmol) was added, followed by slow addition of the 2-bromo-1-{4-[3-(diethylamino)propoxy]phenyl}ethanone described above (2.4 mmol), according to General Procedure R2. The reaction mixture was stirred under nitrogen at rt until completion, as indicated by TLC or HPLC. The reaction mixture was then diluted with cold $H_2O$ and the product was isolated in EtOAc. The combined organic layers were washed with brine and dried over sodium sulfate. Evaporation of solvent in vacuuo afforded the desired product. The crude alkylated aniline was used for further transformation.

To a stirred solution of alkylated 4-(4-chloro-3-ethylphenoxy)-1-nitrobenzene described above (~2.4 mmol) in anhydrous DCM (5 mL) at 0° C., TEA (3 eq., 7.5 mmol) was added, followed by slow addition of valeryl chloride (3 eq., 7.5 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the N-alkylated anilide (~2.4 mmol) obtained as above in acetic acid (3 mL), solid ammonium acetate (46 mmol) was added in one portion, according to General Procedure R4. The reaction mixture was then heated to 100° C. overnight. The reaction mixture was cooled to rt, and treated with saturated aqueous sodium bicarbonate solution while stirring to until the pH was 7-8. The contents were extracted with EtOAc (2×30 mL). The combined organic layers was washed with H$_2$O (2×30 mL) and brine, and dried over sodium sulfate. Evaporation of the solvent in vacuuo afforded the desired N-aryl imidazole. The crude product was purified using silica gel column chromatography (2-5% MeOH/DCM) (yield 60 mg).

MS m/z 560 (M+H)$^+$:

$^1$H NMR (CDCl$_3$): δ8.30 (d, 1H), 7.64 (d, 2H), 7.28 (d, 2H), 7.21 (s, 1H), 7.18 (s, 1H), 7.03 (d, 2H), 6.90 (m, 1H), 6.83 (d, 2H) 4.22 (t, 2H), 2.85-2.75 (m, 2H), 2.89 (q, 4H), 2.61 (m, 2H), 2.24 (t, 2H), 2.14 (d, 3H), 2.09-1.98 (m, 2H), 1.58 (m, 2H), 1.28 (m, 2H), 1.25 (t, 6H), 0.93 (t, 3H) ppm.

EXAMPLE 497

{2-[4-(2-butyl-4-{4-[2-(4-chloro-phenyl)-ethoxy]-phenyl}-imidazol-1-yl)-phenoxy]-ethyl}-ethyl-amine To a stirred solution of 4'-hydroxyacetophenone (4 mmol) in DMF (10 mL) at rt, solid potassium carbonate (12.0 mmol) was added. 4-chlorophenthoxy mesylate (prepwered from the 4-chlorophenethanol and methanesulfonyl chloride) (4.4 mmol) was added to the reaction mixture and heated to 80° C. until completion according to General Procedure Q1, as indicated by TLC or HPLC. After cooling to rt, the reaction mixture was quenched with saturated sodium bicarbonate. The aqueous layer was poured into EtOAc (30 ml) and washed with water (2×15 ml) and brine (15 ml). The organic layer was dried over magnesium sulfate, and the solvent was removed in vacuuo to afford the desired 1-{4-[2-(4-chlorophenyl)ethoxy]phenyl}ethanone. The crude alkylated product was purified by silica gel chromatography and the pure product obtained from 10% EtOAc/hexanes (yield 70%).

To a stirred solution of 4-fluoronitrobenzene (4.0 mmol) in anhydrous THF (12 mL) at 0° C., a 1M solution of a potassium alkoxide (4.4 mmol) in THF (may be generated by adding the N-Boc, N-ethyl ethanolamine to a 1M solution of KOBu$^t$ in THF) was added dropwise and under a nitrogen stream, according to General Procedure L1. The reaction mixture was stirred at 0° C. until completion, as indicated by TLC or HPLC. The solvent was removed and the reaction mixture was then treated with cold H$_2$O (15 mL), and extracted with EtOAc (2×15 mL). The combined organic layers were washed with brine and dried over sodium sulfate. Evaporation of the solvent in vacuuo afforded the desired 4-alkoxynitrobenzene. The crude product could be used directly for further transformation.

The nitro intermediate (2 mmol) obtained above was dissolved in EtOH (8 mL) and hydrogenated in the presence of 10% Pd/C (10 mg) until completion, according to General Procedure H, as indicated by TLC or HPLC. The reaction mixture was then filtered to remove the catalyst. The solvent was removed in vacuuo to afford 4-(N-Boc-N-ethylaminoethoxy)aniline, which was used directly for further transformation without further purification (yield 80%).

To a stirred solution of 1-{4-[2-(4-chlorophenyl)ethoxy]phenyl}ethanone (2 mmol) in anhydrous MeOH (6 mL) at 0° C., pyrrolidone hydrotribromide (1.2 eq) was added, according to General Procedure R1. The reaction mixture was stirred under nitrogen at 0° C. for 1 h and was allowed to warm to rt until completion, as indicated by TLC or HPLC. The solvent was then removed in vacuuo and the crude 2-bromo-1-{4-[3-(diethylamino)propoxy]phenyl}ethanone was used for further transformation.

To a solution of 4-(N-Boc-N-ethylethoxy)aniline (1 eq, 2 mmol) in anhydrous DMF (6 mL), DIEA (3 eq 6 mmol) was added, followed by addition of the 2-bromo-1-{4-[3-(diethylamino)propoxy]phenyl}ethanone described above (2 mmol), according to General Procedure R2. The reaction mixture was stirred under nitrogen at rt until completion, as indicated by TLC or HPLC. The reaction mixture was then diluted with cold water and the product was isolated in EtOAc. The combined organic layers were washed with brine and dried over sodium sulfate. Evaporation of solvent in vacuuo afforded the desired product. The crude alkylated aniline was purified by chromatography (Silica gel). Pure product obtained from 2-4% MeOH/DCM (yield 52%).

To a stirred solution of alkylated aniline described above (1 mmol) in anhydrous DCM (4 mL) at 0° C., TEA (3 eq, 3 mmol) was added, followed by a slow addition of valeryl chloride (3 eq, 3 mmol), according to General Procedure R3. The reaction mixture was stirred under nitrogen at 0° C. for 1 h and allowed to warm to rt until completion, as indicated by TLC or HPLC. The solvent was removed in vacuuo, and the crude amide was used for further transformation.

To a stirred solution of the amide described above (1 mmol) in acetic acid (4 mL), ammonium acetate (20 eq) was added, according to General Procedure R4. The reaction mixture was stirred at 90° C. overnight. The reaction mixture was then cooled to rt and neutralized with saturated sodium bicarbonate solution. Usual extractive work up with EtOAc gave the product imidazole, which was purified by column chromatography (Silica gel). Pure product obtained from 4-6% MeOH/DCM was treated with HCl in dioxane for 2 h to give the hydrochloride salt of {2-[4-(2-butyl-4-{4-[2-(4-chloro-phenyl)-ethoxy]-phenyl}-imidazol-1-yl)-phenoxy]-ethyl}-ethyl-amine (yield 177 mg).

MS m/z 518 (M+H)$^+$:

$^1$H NMR (400 MHz, CDCl$_3$): δ 7.7 (d, 2H), 7.2 (m, 4H), 7.1 (m, 3H), 6.8-7.0 (m, 4H), 4.0-4.3 (m, 6H), 3.0-3.2 (m, 6H), 2.9 (m, 2H), 2.6 (m, 2H), 1.2 (t, 3H), 0.8 (t, 3H) ppm

EXAMPLE 498

[3-(4-{5-butyl-4-[4-(3,3-diphenyl-propoxy)-phenyl]-2-isobutyl-1H-imidazol-4-yl}-phenoxy)-2,2-dimethyl-propyl]-dimethyl-amine To a stirred solution of ice-cold 4-hydroxy-n-hexanophenone (18 mmol), 3,3-diphenyl-1-propanol (22.6 mmol, 1.25 eq), triphenylphosphine (22.6 mmol, 1.25 eq) dissolved in anhydrous THF (100 mL) was added dropwise diisopropyl azodicarboxylate (DIAD) (22.6 mmol, 1.25 eq). The reaction mixture was stirred at 0° C. for 1 h, and then allowed to warm to rt, continuing the stirring for additional 6 h (monitored by TLC). The solvent was removed in vacuuo, and the crude product was purified by silica gel column chromatography eluting with 10% EtOAc in hexane (yield: 100%).

The acetophone described as above (18 mmol) was dissolved in 1,4-dioxane (100 mL), and treated with pyridine hydrotribromide (18.9 mmol, 1.05 eq), according to General Procedure R1. After stirring at rt for 6 h (monitored by TLC), the reaction was quenched with cold H$_2$O (100 mL). The resulting mixture was extracted with EtOAc (4×100 mL). The combined EtOAc extracts were washed with brine (3×50 mL), and dried over anhydrous sodium sulfate. The solvent was then removed in vacuuo and the crude alpha-bromoacetophenone was directly used for further transformation.

To a stirred solution of the crude alpha-bromoacetophenone described as above (~12 mmol) and 4-benzyloxyaniline (12 mmol) dissolved in DMF (40 mL), DIEA (36 mmol, 3 eq) was added at rt, and the mixture was stirred at the same temperature for 12 h, according to General Procedure R2 (monitored by TLC and LC-MS). The reaction mixture was treated with saturated sodium bicarbonate (100 mL), and the resulting mixture was extracted with EtOAc (4×100 mL). The combined EtOAc extracts were washed with brine (3×50 mL), and dried over anhydrous sodium sulfate. The solvent was removed in vacuuo, and the crude product was purified by silica gel column chromatography eluting with 10-15% EtOAc in hexane (overall yield from the acetophone: ~50%).

To a stirred solution of ice-cold the alkylated aniline (1.7 mmol) obtained above and DMAP (3.4 mmol, 2 eq) dissolved in anhydrous DCM (200 mL), isovaleryl chloride (6.8 mmol, 4 eq) was added, according to General Procedure R3. The reaction mixture was stirred under nitrogen at 0° C. for 3 h and allowed to warm to rt until completion, as indicated by LC-MS. The solvent was removed in vacuuo, and the crude amide was used directly for further transformation.

The crude amide described above (~3.7 mmol) was suspended in acetic acid (10 mL), and ammonium acetate (excess, ~30 eq) was added, according to General Procedure R4. The reaction mixture was stirred at 120° C. for 20 h (as monitored by TLC and LC-MS). The reaction mixture was then cooled to rt and neutralized with saturated sodium bicarbonate and solid sodium carbonate. The resulting mixture was extracted with EtOAc (4×100 mL). The combined EtOAc extracts were washed with H$_2$O (2×60 mL) and brine (2×60 mL), and dried over anhydrous sodium sulfate. The solvent was removed in vacuuo, and the crude product was purified by silica gel column chromatography eluting with 10-20% EtOAc in hexane (overall yield from the alkylated aniline: 62%).

The product (2.9 mmol) obtained above was dissolved in MeOH (50 mL) and hydrogenated in the presence of 10% Pd/C (0.5 g) until completion as indicated by LC-MS (~2 h), according to General Procedure H. The reaction mixture was then filtered to remove the catalyst. The solvent was removed in vacuuo to afford the desired 1-(4'-hydroxyphenyl)imidazole, which was used directly for further transformation without purification (yield: 100%).

To a stirred solution of ice-cold 3-dimethylamino-2,2-dimethyl-1-propanol (1 mmol) and TEA (1.5 mmol) dissolved in anhydrous DCM (8 mmol) was added dropwise methanesulfonyl chloride (1.05 mmol), and the reaction mixture was stirred for 2 h at 0° C. and followed by additional 1 h at rt. After the removal of the solvents in vacuuo, the crude mesylate was dissolved in DMF (10 mL). 1-(4'-hydroxyphenyl) imidazole (0.5 mmol) obtained above and cesium carbonate (3 mmol) were added, and the mixture was heated with stirring at 90° C. for 3 h (monitored by LC-MS). After cooling to rt, the reaction was quenched with saturated sodium bicarbonate (20 mL), and the resulting mixture was extracted with EtOAc (3×50 mL). The combined EtOAc extracts were washed with brine (3×30 mL), and dried over anhydrous sodium sulfate. The solvent was removed in vacuuo, and the pure product was obtained by silica gel column chromatography eluting with 5-10% MeOH in EtOAc (yield 252 mg).

MS m/z 672 (M+H)$^+$:

$^1$H NMR (400 MHz, CDCl$_3$): δ0.70 (t, 3H), 0.83 (d, 6H), 1.03 (s, 6H), 1.13 (m, 2H), 1.28 (m, 2H), 1.96 (m, 1H), 2.29 (s, 6H), 2.31 (s, 2H), 2.36 (d, 2H), 2.47-2.56 (m, 4H), 3.77 (s, 2H), 3.91 (t, 2H), 4.26 (t, 1H), 6.86 (d, 2H), 7.00 (d, 2H), 7.11 (d, 2H), 7.19-7.28 (m, 10H), 7.56 (d, 2H) ppm

EXAMPLE 499

[3-(4-{4-[4-(3,3-diphenyl-propoxy)-phenyl]-2-isobutyl-imidazol-1-yl}-phenoxy)-propyl]-diethyl-amine To a stirred solution of N,N-diethyl-N-[3-(4-nitrophenoxy)propyl]amine (1.0 eq., 2.5 mmol) in anhydrous DMF (20 mL) DIEA (3 eq) was added, followed by slow addition of the 1-[4-(benzyloxy)phenyl]-2-bromoethanone (2.5 mmol). The reaction mixture was stirred under nitrogen at rt until completion, as indicated by HPLC. The reaction mixture was then diluted with cold H$_2$O and the product was isolated in Et$_2$O. The combined organic layers were washed with brine and dried over sodium sulfate. Evaporation of solvent in vacuuo afforded the desired product. The crude alkylated aniline was purified by chromatography (Silica gel). Pure product was obtained from 2-7% MeOH/DCM (yield ~30%).

To a stirred solution of the alkylated aniline described above (0.88 mmol) in anhydrous DCM (10 mL) at 0° C., TEA (3.0 mmol) was added, followed by slow addition of isovaleryl chloride (5.0 eq), according to General Procedure R3. The reaction mixture was stirred under nitrogen at 0° C. for 1 h and allowed to warm to ambient temperature until completion, as indicated by HPLC. The solvent was removed in vacuuo, and the crude amide was used for further transformation.

To a stirred solution of the amide described above (0.88 mmol) in acetic acid (2 mL), ammonium acetate (excess, ~20 eq.) was added, according to General Procedure R4. The reaction mixture was stirred at 100° C. overnight. The reaction mixture was then cooled down and neutralized with saturated sodium bicarbonate solution. Usual extractive work up with EtOAc gave the cyclized product, (crude ~80%) which was taken to the next transformation without purification.

The above product was dissolved in MeOH (20 mL), Pd/C (100 mg) was added and the heterogeneous mixture was stirred overnight under H$_2$ atmosphere using a balloon, according to General Procedure T2. The Pd/C was removed by filtration. The solvent was removed in vacuuo, and the crude 4-{1-[4-(3-diethylamino-propoxy)-phenyl]-2-isobutyl-1H-imidazol-4-yl}-phenol was used for further transformation without purification.

A stirred solution of the 4-{1-[4-(3-diethylamino-propoxy)-phenyl]-2-isobutyl-1H-imidazol-4-yl}-phenol (1.0 eq) in anhydrous DMF (5.0 mL) was treated with solid sodium hydride (60% dispersion in oil; 1.0 mmol) in portions. The mesylate of 3,3-diphenylpropan-1-ol (1.1 eq) was added to the reaction mixture, and stirred at rt overnight, according to General Procedure T3. Et$_2$O (30 mL) was added to the reaction mixture followed by H$_2$O (10 mL). The organic layer was washed with H$_2$O (2×15 mL) and brine, and dried over sodium sulfate. The solvent was removed in vacuuo. Pure imidazole was obtained from chromatography with 5-10% MeOH/DCM (yield 73 mg).

MS m/z 616 (M+H)$^+$:

$^1$H NMR (CDCl$_3$): δ7.67 (d, 2H), 7.15-7.3, (m, 12H), 7.09 (s, 1H), 6.96 (d, 2H), 6.84 (d, 2H), 4.25 (t, 1H), 4.07 (t, 2H), 3.9 (t, 2H), 3.74 (t, 1H), 2.46-2.75 (m, 10H), 2.0 (m, 3H), 1.0 (t, 6H), 0.84 (d, 6H) ppm.

EXAMPLE 500

7-{2-butyl-4-[4-(4-chloro-phenoxy)-naphthalen-1-yl]-imidazol-1-yl}-1,2,3,4-tetrahydro-isoquinoline hydrochloride 7-Nitro-1,2,3,4-tetrahydroisoquinoline hydrochloride (8.2 g, 42% yield) was prepared by slightly modifying the published procedure (*J. Med. Chem.*, 1997, 40, 3997-4005).

Di-tert-butyl dicarbonate (7.5 g, 33.8 mmol) was added to a solution of 7-nitro-1,2,3,4-tetrahydroisoquinoline hydrochloride (3.8 g, 16.9 mmol), $Et_3N$ (9.42 mL, 67.6 mmol) and DMAP (0.1 g) dissolved in anhydrous THF (60 mL). After being stirred overnight at rt, the reaction mixture was treated with saturated $NaHCO_3$ (50 mL), and the resulting mixture was extracted with EtOAc (3×100 mL). The combined organic layers were washed with brine and dried ($Na_2SO_4$). The crude products were purified by flash chromatography (eluting with 10-20% EtOAc in hexanes) to give 2-BOC-7-nitro-1,2,3,4-tetrahydroisoquinoline (4.1 g).

The nitro compound obtained above (4.1 g, 14.7 mmol) was dissolved in MeOH (80 mL) and hydrogenated in the presence of 10% Pd/C (0.3 g), according to General Procedure H. Workup afforded 7-amino-2-Boc-1,2,3,4-tetrahydroisoquinoline (2-Boc-TIQ aniline (3.6 g, 98% yield) as a light-brown solid.

4'-(4-chlorophenoxy)-1'-acetonaphthone was prepared from 4'-fluoro-1'-acetonaphthone and 4-chlorophenol following general procedure Q2. 4'-(4-chlorophenoxy)-1'-acetonaphthone was brominated following general procedure R1. The bromo ketone was condensed with 7-amino-2-Boc-1,2,3,4-tetrahydroisoquinoline following general procedure R2. The aminoketone intermediate was treated with n-penatnoyl chloride accoding to general procedure R3. The product amide was then subjected to imidazole formation employing general procedure R4. The BOC group of the product was removed employing general procedure T1 to afford 7-{2-Butyl-4-[4-(4-chloro-phenoxy)-naphthalen-1-yl]-imidazol-1-yl}-1,2,3,4-tetrahydro-isoquinoline hydrochloride.

LC-MS (m/z): 508 (M+H)$^+$.

EXAMPLE 501

2-biphenyl-4-yl-N-{4-[2-butyl-1-(1,2,3,4-tetrahydro-isoquinolin-7-yl)-1H-imidazol-4-yl]-phenyl}-acetamide hydrochloride 4-Nitrophenacyl bromide (5 mmol) was added to a stirred mixture of 2-BOC-7-nitro-1,2,3,4-tetrahydroisoquinoline (5 mmol) in DCM (20 mL) at rt, and the mixture was stirred at rt overnight. The reaction mixture was treated with sat. $NaHCO_3$ (30 mL), the resulting mixture was extracted with EtOAc (200 mL), washed with brine and dried. The crude product was purified by silica gel column chromatography (eluting with 8% EtOAc in hexane to give the amino ketone intermediate (0.33 g).

Following the general procedures R2, R3, and R4 as for Example 500, the amino ketone intermediate (330 mg, 0.8 mmol) was converted into a 4-nitrophenyl-substituted imidazole. The imidazole was reduced by Pd-carbon catalytic hydrogenation following general procedure H to the corresponding 4-aminophenyl imidazole.

PS-carbodiimide (1.27 mmol/g, 310 mg, 0.4 mmol) was added to a mixture of the 4-aminophenyl imidazole obtained above (45 mg, 0.1 mmol) and biphenylacetic acid (43 mg, 0.2 mmol) in anhydrous DCM (6 mL), and the mixture was slowly shaken at rt overnight. The pure product (25 mg, 40% yield) was obtained after silica gel column chromatography (20% EtOAc in hexane). 2-Biphenyl-4-yl-N-{4-[2-butyl-1-(1,2,3,4-tetrahydro-isoquinolin-7-yl)-1H-imidazol-4-yl]-phenyl}-acetamide hydrochloride (20 mg) was obtained by treating the product with 4N hydrogen chloride in dioxane solution, following the General Procedure T1.

LC-MS (m/z): 541 (M+1)$^+$.

EXAMPLE 502

7-{2-butyl-4-[4-(2,4-dichloro-phenoxy)-phenyl]-imidazol-1-yl}-1,2,3,4-tetrahydro-isoquinoline hydrochloride 1-[4-(2,4-Dichlorophenoxy)phenyl]ethan-1-one (282 mg, 1 mmol) was brominated by General Procedure R1. The bromo ketone was condensed with 7-amino-2-Boc-1,2,3,4-tetrahydroisoquinoline following general procedure R2. The aminoketone intermediate was treated with n-penatnoyl chloride accoding to General Procedure R3. The product amide was then subjected to imidazole formation employing general procedure R4. The BOG group of the product was removed employing general procedure T1 to afford 7-{2-butyl-4-[4-(2,4-dichloro-phenoxy)-phenyl]-imidazol-1-yl}-1,2,3,4-tetrahydro-isoquinoline hydrochloride (150 mg).

LC-MS (m/z): 493 (M+1)$^+$.

EXAMPLE 503

7-(2-butyl-4-{4-[2-(4-chloro-phenyl)-1,2,3,4-tetrahydro-isoquinoline hydrochloride 1-[4-(4-chlorophenylethoxy)]ethan-1-one (1 mmol) was brominated by General Procedure R1. The bromo ketone was condensed with 7-amino-2-Boc-1,2,3,4-tetrahydroisoquinoline following general procedure R2. The aminoketone intermediate was treated with n-pentanoyl chloride accoding to General Procedure R3. The product amide was then subjected to imidazole formation employing general procedure R4. The BOG group of the product was removed employing general procedure T1 to afford 7-(2-Butyl-4-{4-[2-(4-chloro-phenyl)-ethoxy]-phenyl}-2-isobutyl-imidazol-1-yl)-1,2,3,4-tetrahydro-isoquinoline hydrochloride (145 mg).

LC-MS (m/z): 486 (M+H)$^+$.

EXAMPLE 504

7-[4-(4-benzyloxy-phenyl)-2-butyl-imidazol-1-yl]-1,2,3,4-tetrahydro-isoquinoline hydrochloride 4-benzyloxyacetophone was brominated by General Procedure R1. The bromo ketone was condensed with 7-amino-2-Boc-1,2,3,4-tetrahydroisoquinoline following general procedure R2. The aminoketone intermediate was treated with n-pentanoyl chloride accoding to General Procedure R3. The product amide was then subjected to imidazole formation employing general procedure R4 to afford 7-[4-(4-Benzyloxy-phenyl)-2-butyl-imidazol-1-yl]-2-Boc-1,2,3,4-tetrahydro-isoquinoline. The BOC group of the product was removed employing general procedure T1 to afford 7-[4-(4-Benzyloxy-phenyl)-2-butyl-imidazol-1-yl]-1,2,3,4-tetrahydro-isoquinoline hydrochloride (170 mg).

LC-MS (m/z): 438 (M+1)$^+$.

EXAMPLE 505

9-(2-{4-[2-butyl-1-(1,2,3,4-tetrahydro-isoquinolin-7-yl)-1H-imidazol-4-yl]-phenoxy}-ethyl-9H-carbazole hydrochloride 7-[4-(4-Benzyloxy-phenyl)-2-butyl-imidazol-1-yl]-2-Boc-1,2,3,4-tetrahydro-isoquinoline was debenzylated according to General Procedure T2 to afford 7-[4-(4-hydroxyphenyl)-2-butyl-imidazol-1-yl]-2-Boc-1,2,3,4-tetrahydro-isoquinoline. The phenol was condensed with the mesylate of 9H-carbazole-9-ethanol following general procedure T3 to afford the ethylcarbazole ether intermediate. This ethylcarbazole intermediate was deprotected employing general procedure T1 to afford 9-(2-{4-[2-butyl-1-(1,2,3,4-tetrahydro-isoquinolin-7-yl)-1H-imidazol-4-yl]-phenoxy}-ethyl-9H-carbazole hydrochloride (55 mg).

LC-MS (m/z): 541 (M+1)+.

EXAMPLE 506

7-{2-butyl-4-[4-(4-methoxy-phenoxy)-phenyl]-imidazol-1-yl}-1,2,3,4-tetrahydro-isoquinoline hydrochloride 1-[4-(4-methoxyphenoxy)phenyl]ethan-1-one (1 mmol) was brominated by General Procedure R1. The bromo ketone was condensed with 7-amino-2-Boc-1,2,3,4-tetrahydroisoquinoline following general procedure R2. The aminoketone intermediate was treated with n-pentanoyl chloride accoding to General Procedure R3. The product amide was then subjected to imidazole formation employing general procedure R4. The BOC group of the product was removed employing general procedure T1 to afford 7-{2-butyl-4-[4-(4-methoxy-phenoxy)-phenyl]-imidazol-1-yl}-1,2,3,4-tetrahydro-isoquinoline hydrochloride (yield 135 mg)

LC-MS (m/z): 454 (M+1)+.

EXAMPLE 507

7-(2-butyl-4-{4-[2-(4-tert-butyl-phenyl)-ethoxy]-phenyl}-imidazol-1-yl)-1,2,3,4-tetrahydro-isoquinoline hydrochloride 7-[4-(4-hydroxyphenyl)-2-butyl-imidazol-1-yl]-2-Boc-1,2,3,4-tetrahydro-isoquinoline was condensed with the mesylate of 2-(4-t-butylphenyl)ethanol according to General Procedure T3 to afford the phenyl ether intermediate, which was deprotected according to general procedure T1 to afford 7-(2-butyl-4-{4-[2-(4-tert-butyl-phenyl)-ethoxy]-phenyl}-imidazol-1-yl)-1,2,3,4-tetrahydro-isoquinoline hydrochloride (35 mg).

LC-MS (m/z): 508 (M+1)+.

EXAMPLE 508

7-{2-butyl-4-[4-(naphthalen-2-ylmethoxy)-phenyl]-imidazol-1-yl}-1,2,3,4-tetrahydro-isoquinoline hydrochloride 7-[4-(4-hydroxyphenyl)-2-butyl-imidazol-1-yl]-2-Boc-1,2,3,4-tetrahydro-isoquinoline was condensed with 2-(bromomethyl)naphthalene according to general procedure T3 to afford the phenyl ether intermediate, which was deprotected according to general procedure T1 to afford 7-{2-butyl-4-[4-(naphthalen-2-ylmethoxy)-phenyl]-imidazol-1-yl}-1,2,3,4-tetrahydro-isoquinoline hydrochloride (32 mg).

LC-MS (m/z): 488 (M+1)+.

EXAMPLE 509

7-{2-butyl-4-[4-(4-trifluoromethyl-phenoxy)-phenyl]-imidazol-1-yl}-1,2,3,4-tetrahydro-isoquinoline hydrochloride 7-[4-(4-hydroxyphenyl)-2-butyl-imidazol-1-yl]-2-Boc-1,2,3,4-tetrahydro-isoquinoline was condensed with 4-trifluoromethylbenzyl bromide according to general procedure T3 to afford the phenyl ether intermediate, which was deprotected according to general procedure T1 to afford 77-{2-butyl-4-[4-(4-trifluoromethyl-phenoxy)-phenyl]-imidazol-1-yl}-1,2,3,4-tetrahydro-isoquinoline hydrochloride (45 mg).

LC-MS (m/z): 506 (M+1)+.

EXAMPLE 510

7-(2-butyl-4-{4-[2-(4-chloro-phenyl)-ethoxy]-phenyl}-imidazol-1-yl)-1,2,3,4-tetrahydro-isoquinoline hydrochloride 1-[4-(4-chlorophenylethoxy)]ethan-1-one (1 mmol) was brominated by General Procedure R1. The bromo ketone was condensed with 7-amino-2-Boc-1,2,3,4-tetrahydroisoquinoline following general procedure R2. The aminoketone intermediate was treated with n-pentanoyl chloride accoding to General Procedure R3. The product amide was then subjected to imidazole formation employing general procedure R4. The BOC group of the product was removed employing general procedure T1 to afford 7-(2-Butyl-4-{4-[2-(4-chloro-phenyl)-ethoxy]-phenyl}-imidazol-1-yl)-1,2,3,4-tetrahydro-isoquinoline hydrochloride (170 mg).

LC-MS (m/z): 486 (M+1)+.

EXAMPLE 511

[3-(4-{2-(4-Butyl-cyclohexyl)-1-[4-(4-chloro-phenoxy)-phenyl]-1H-imidazol-4-yl}-phenoxy)-propyl]-diethyl-amine Example 511 was synthesized by the method established for Example 406, using 4-butylcyclohexanecarbonyl chloride in place of valeryl chloride (yield 300 mg).

MS: m/z 614 (M+H)+

EXAMPLE 512

2-(4-{1-[4-(4-Chloro-phenoxy)-phenyl]-2-isobutyl-1H-imidazol-4-yl}-phenoxy)-ethylamine Example 512 was synthesized by the method established for Example 464, utilizing N—BOC-ethanolamine in plase of 3-dimethylamino-1-propanol to produce 2-(4-{1-[4-(4-chloro-phenoxy)-phenyl]-2-isobutyl-1H-imidazol-4-yl}-phenoxy)-ethylamino tert-butyl carbamate as an intermediate. This intermediate was deprotected employing general procedure T1 to afford Example 512 as the hydrochloride salt. (Yield: 115 mg).

MS: m/z 462 (M+H)+

EXAMPLE 513

[3-(4-{2-(trans-4-tert-Butyl-cyclohexyl)-1-[4-(4-chloro-phenoxy)-phenyl]-1H-imidazol-4-yl}-phenoxy)-propyl]-diethyl-amine Example 513 was prepared by chromatographic purification on silica gel of the compound of Example 486. 500 mg of Example 486 was separated by silica gel column chromatography, eluting with 5-10% MeOH in DCM, to give the cis-isomer (120 mg) followed by trans-isomer Example 513 (200 mg).

$^1$H NMR (400 MHz, CDCl$_3$): δ 0.82 (s, 9H), 1.08 (t, 6H), 1.50-2.50 (m, 12H), 2.66 (q, 4H), 2.73 (t, 2H), 4.02 (t, 2H), 6.89 (d, 2H), 7.04 (d, 2H), 7.07 (d, 2H), 7.08 (s, 1H), 7.27 (d, 2H), 7.36 (d, 2H), 7.69 (d, 2H) ppm MS: m/z 614 (M+H)$^+$

EXAMPLE 514

[3-(4-{2-(cis-4-tert-Butyl-cyclohexyl)-1-[4-(4-chloro-phenoxy)-phenyl]-1H-imidazol-4-yl}-phenoxy)-propyl]-diethyl-amine Example 514 was prepared by chromatographic purification on silica gel of the compound of Example 486. 500 mg of Example 486 was separated by silica gel column chromatography, eluting with 5-10% MeOH in DCM, to give the cis-isomer Example 514 (120 mg) followed by trans-isomer (200 mg).

MS: m/z 614 (M+H)$^+$

EXAMPLE 515

[2-(4-{2-Butyl-1-[4-(4-fluoro-3-trifluoromethyl-phenoxy)-phenyl]-1H-imidazol-4-yl}-phenoxy)-ethyl]-methyl-pyridin-4-yl-amine A mixture of 4-chloropyridine hydrochloride salt (15.0 g) and 2-methylaminoethanol (30 mL) was refluxed for 48 hour. After cooling to rt the crude mixture was added slowly to saturated solution of sodium bicarbonate (150 mL). The product was extracted with EtOAc (3×100 mL), the combined EtOAc was washed with brine (50 mL), dried (Na$_2$SO$_4$) and removed in vacuo to give the desired product 2-[methyl(pyridin-4-yl)amino]ethanol as yellow solid (7.0 g).

2-[methyl(pyridin-4-yl)amino]ethyl methanesulfonate was prepared according to general procedure P2.

4-{2-butyl-1-[4-(4-fluoro-3-trifluoromethyl-phenoxy)-phenyl]-1H-imidazole-4-yl}-phenol was prepared via a modification of the procedure employed to synthesize {1-[4-(4-chloro-phenoxy)-phenyl]-2-isobutyl-1H-imidazol-4-yl}phenol.

Sodium hydride (50.0 mg, 60% dispersion in oil) was added to a mixture of 100 mg of 4-{2-butyl-1-[4-(4-fluoro-3-trifluoromethyl-phenoxy)-phenyl]-1H-imidazol-4-yl}-phenol and 200 mg 2-[methyl(pyridin-4-yl)amino]ethyl methanesulfonate in DMF (5 mL). After 24 h of stirring at rt, the mixture was added to ether (50 mL) and the ether was washed with water and dried (Na$_2$SO$_4$). The solvent was removed in vacuo. Silica gel chromatography afforded 150 mg of Example 515.

MS: m/z 605 (M+H)$^+$

EXAMPLE 516

[2-(4-{1-[4-(4-Fluoro-phenoxy)-phenyl]-2-isobutyl-1H-imidazol-4-yl}-phenoxy)-ethyl]-methyl-pyridin-4-yl-amine 4-{1-[4-(4-fluoro-phenoxy)-phenyl]-2-isobutyl-1H-imidazole-4-yl}phenol was prepared in analogous fashion to 4-{1-[4-(4-chloro-phenoxy)-phenyl]-2-isobutyl-1H-imidazole-4-yl}phenol. Alkylation of the phenol proceeded as for Example 515 to afford Example 516 (47 mg).

MS: m/z 537 (M+H)$^+$ $^1$H NMR (CDCl$_3$): δ 8.23 (d, 2H), 7.70 (d, 2H), 7.53 (d, 2H,), 7.24 (s, 1H), 7.12 (d, 2H), 7.07 (m, 2H), 7.04 (d, 2H), 6.87 (d, 2H), 6.58 (d, 2H) 4.17 (t, 2H), 3.81 (t, 2H), 3.11 (s, 3H), 2.54 (d, 2H), 2.06 (m, 1H), 0.87 (d, 6H) ppm

EXAMPLE 517

[2-(4-{1-[4-(4-Fluoro-phenoxy)-phenyl]-2-isobutyl-1H-imidazol-4-yl}-phenoxy)-ethyl]-methyl-(3-methyl-pyridin-4-yl)-amine Example 517 was prepared in analogous fashion to Example 516, with the use of 3-methyl-4-chloropyridine in place of 4-chloropyridine. (Yield: 110 mg)

MS: m/z 551 (M+H)$^+$

EXAMPLE 518

[2-(4-{1-[4-(4-Chloro-phenoxy)-phenyl]-2-isobutyl-1H-imidazol-4-yl}-phenoxy)-ethyl]-ethyl-pyridin-4-yl-amine 2-[Ethyl(pyridin-4-yl)amino]ethanol was synthesized via an analogous methd as that employed for 2-[methyl(pyridin-4-yl)amino]ethanol.

2-[Ethyl(pyridin-4-yl)amino]ethanol was converted to the methanesulfonate via a modification of General Procedure P2.

{1-[4-(4-Chloro-phenoxy)-phenyl]-2-isobutyl-1H-imidazol-4-yl}phenol was synthesized by an analogous series of procedures as for Example 77.

Another procedure was below;

4-Acetoxyacetophenone (10.7 g, 60 mmol) in dioxane (200 mL) was treated with pyridinium hydrotribromide (21 g, 66 mmol, 1.1 eq) added in portions at rt, according to General Procedure R1. The reaction mixture was stirred at rt for 6 h. The reaction was quenched by adding cold H$_2$O (100 mL), and extracted with ether (4×100 mL). The ethereal solution was washed with H$_2$O (100 mL) and dried (anhydrous Na$_2$SO$_4$). The solvent was then removed in vacuo and the α-bromoacetophenone obtained above was added to a stirred solution of 4-(4'-chlorophenoxy)aniline (13.2 g, 60 mmol, 1.1 eq) and anhydrous DMF (100 mL) at rt, and the mixture was stirred at the same temperature for 5 h (monitored by LC-MS). The reaction mixture was treated with sat. NaHCO$_3$ (100 mL), and the resulting mixture was extracted with EtOAc (4×100 mL). The combined EtOAc extracts were washed with H$_2$O (2×100 mL) and brine (2×100 mL), and dried (Na$_2$SO$_4$). The solvent was removed in vacuo, and the alkylated aniline was used for next step To a stirred solution of the c alkylated aniline dissolved in anhydrous DCM (250 mL) at 0° C., triethylamine (15.2 mL, 180 mmol) was added, followed by slow addition of isovaleryl chloride (14.7 mL, 120 mmol), according to General Procedure R3. The reaction mixture was stirred under N₂ at 0° C. for 0.5 h and then at rt for another 2 h (or monitored by LC-MS). The solvent was removed in vacuo, and the crude amide was used directly for further transformation.

To a stirred suspension of the amide described above in AcOH (30 mL), ammonium acetate (80 g) was added, according to General Procedure R4. The reaction mixture was stirred at 10° C. for 2 h (as monitored by LC-MS). The reaction mixture was then cooled down and neutralized with sat. NaHCO₃ (100 mL) and solid Na₂CO₃. The resulting mixture was extracted with EtOAc (4×150 mL) and the organic phase was concentrated. The light-yellow solid product was collected after fiiltration. The filtrate was concentrated in vacuo to about 150 mL volume and after standing at rt the solid product was collected and dried, overall yield 11 g of {1-[4-(4-chloro-phenoxy)-phenyl]-2-isobutyl-1H-imidazol-4-yl}phenol.

Sodium hydride (50.0 mg, 60% dispersion in oil) was added to mixture of 100 mg of 4-{1-[4-(4-chloro-phenoxy)-phenyl]-2-isobutyl-1H-imidazole-4-yl}phenol and 180 mg of 2-[ethyl(pyridin-4-yl)amino]ethyl methanesulfonate in DMF (5 mL). After 24 h of stirring at rt, the mixture was added to ether (50 mL) and washed with water and dried (Na₂SO₄). The solvent was removed in vacuo. Chromatography on silica gel afforded Example 518 (36 mg).

MS: m/z 567 (M+H)⁺

EXAMPLE 519

[2-(4-{1-[4-(4-Chloro-phenoxy)-phenyl]-2-isobutyl-1H-imidazol-4-yl}-phenoxy)-ethyl]-pyridin-4-yl-amine 2-(4-{1-[4-(4-Chloro-phenoxy)-phenyl]-2-isobutyl-1H-imidazol-4-yl}-phenoxy)-ethylamine, the product of Example 512, was treated with 4-chloropyridine in DMF and was heated at 100° C. Aqueous workup and chromatography on silica gel afforded Example 519. (Yield: 80 mg)

MS: m/z 539 (M+H)⁺

EXAMPLE 520

[2-(4-{1-[4-(4-Chloro-phenoxy)-phenyl]-2-isobutyl-1H-imidazol-4-yl}-phenoxy)-ethyl]-bis-pyridin-2-ylmethyl-amine The methanesulfonate of N-Boc-glycinol was synthesized by modifying the general procedure P2.

{1-[4-(4-Chloro-phenoxy)-phenyl]-2-isobutyl-1H-imidazol-4-yl}phenol (2 mmol) was added to a solution of Cs₂CO₃ (10 eq., 20 mmol) in anhydrous DMF (5 ml). This was followed by addition of the mesylate obtained above and the reaction mixture was heated to 90° C. for 2-3 h. The reaction mixture was then cooled to rt, diluted with cold water and the product was extracted with DCM. The organic layer was dried over anhydrous sodium sulfate and concentrated in vacuo to give desired product, which was BOC-deprotected according to general procedure T1. The HCl salt was dissolved in water, neutralized with 4N NaOH solution and the crude product was extracted with EtOAc. The organic layer was dried over anhydrous sodium sulfate and concentrated in vacuo to give desired product amine.

The crude product obtained above was taken in anhydrous DCM (5 ml). 2-pyridylcarboxaldehyde (2.5 eq.) and Na(OAc)₃BH (2.5 eq.) was added to this solution and the reaction mixture was stirred at rt for 2-3 h. The product was concentrated in vacuo and extracted with EtOAc and the organic layer was washed with saturated sodium bicarbonate solution. The organic layer was dried over anhydrous sodium sulfate and concentrated in vacuo to give desired product, Example 520 (yield 96 mg).

MS: m/z 644 (M+H)⁺

EXAMPLE 521

N-[2-(4-{1-[4-(4-Chloro-phenoxy)-phenyl]-2-isobutyl-1H-imidazol-4-yl}-phenoxy)-ethyl]-guanidine 2-(4-{1-[4-(4-Chloro-phenoxy)-phenyl]-2-isobutyl-1H-imidazol-4-yl}-phenoxy)-ethylamine, the product of Example 512, was treated in acetonitile with DIEA and N,N'-bis-BOC-1-guanylpyrazole. The resulting mixture was then refluxed. The reaction mixture was then cooled to rt and diluted with EtOAc. The mixture was washed with water and brine and dried over anhydrous sodium sulfate. Solvent was removed in vacuo and the residue obtained was purified by silica gel column chromatography to afford the BOC-protected guanadino intermediate. The BOC-protected guanadino intermediate was treated with 4M HCl/dioxane to remove the BOC group as described in general procedure T1, affording Example 521.

MS: m/z 504 (M+H)⁺

EXAMPLE 522

2-(4-{1-[4-(4-Chloro-phenoxy)-phenyl]-2-isobutyl-1H-imidazol-4-yl}-phenoxy)-1-(4-pyridin-4-yl-piperazin-1-yl)-ethanone To a stirred solution of 4-pyridyl-piperazine (2 mmol) in DCM (4 mL) at 0° C., triethylamine (6.0 mmol) was added followed by addition of 2-chloroacetyl chloride (4 mmol). The reaction mixture was stirred under nitrogen at rt until completion, as indicated by TLC or HPLC. The reaction mixture was treated with saturated aqueous sodium bicarbonate solution (5 mL), then extracted with EtOAc (2×15 mL). The combined organic layers were washed with H₂O (2×15 mL) and brine, and dried over sodium sulfate. Evaporation of the solvent in vacuo afforded the amide. The crude product was used for further transformation.

To the above amide (2 mmol) in DMF (5 ml) was added Cesium carbonate (10 mmol, 5 eq), followed by the addition of {1-[4-(4-chloro-phenoxy)-phenyl]-2-isobutyl-1H-imidazol-4-yl}phenol (1.5 mmol) and the reaction was heated to 90° C. until completion, as indicated by TLC or HPLC. After cooling to rt, the reaction mixture was treated with saturated sodium bicarbonate (150 ml). The aqueous layer was extracted with EtOAc (4×100 ml). The organic layer was washed with water (2×10 ml) and brine (15 ml). The organic layer was dried over magnesium sulfate, and the solvent was removed in vacuo to afford the desired imidazole which was purified by was purified by chromatography over silica gel to afford Example 522.

MS: m/z 622 (M+H)⁺

EXAMPLE 523

5-(4-{1-[4-(4-Chloro-phenoxy)-phenyl]-2-isobutyl-1H-imidazol-4-yl}-phenoxymethyl)-pyrrolidin-3-ol Sodium borohydride (227 mg, 6 mmol) was added at 0° C. to a stirred solution of (2S,4R)—N—BOC-4-(t-butyldimethylsilyloxy)prolinaldehyde (522 mg, 1.58 mmol) in MeOH (10 mL), and the mixture was stirred at rt for 3 h. The reaction was quenched by adding sat. NaHCO$_3$ (20 mL), and the resulting mixture was extracted with EtOAc (3×50 mL). The EtOAc extracts were washed with brine (2×50 mL), and dried (Na$_2$SO$_4$). The solvent was removed in vacuo to give (2S, 4R)—N—BOC-4-(t-butyldimethylsilylhydroxy)prolinol (550 mg).

The acohol obtained above was converted to the methanesulfonate according to general procedure P2.

4-{1-[4-Chlorophenoxy)phenyl]-2-isobutyl-1H-imidazol-4-yl}phenol described above (840 mg, 2 mmol) was added to a stirred mixture of the mesylate obtained in the previous step, Cs$_2$CO$_3$ (1.95 g, 6 mmol) in anhydrous DMF (20 mL), and the mixture was heated with stirring at 90° C. for 15 h. The reaction was quenched by adding sat. NaHCO$_3$ and the resulting mixture was extracted with EtOAc. The EtOAc extracts were washed with brine and dried (Na$_2$SO$_4$). The solvent was removed in vacuo to give crude alkylated product.

2N hydrogen chloride in ethereal solution (2 mL) was added to a stirred mixture of the alkylated imidazole obtained above (150 mg) in DCM (8 mL) at rt. After being stirred at rt for 4 h, the reaction mixture was treated with sat. NaHCO$_3$. The resulting mixture was extracted with EtOAc. The EtOAc extracts were washed with brine and dried (Na$_2$SO$_4$). The solvent was removed in vacuo, and the residue was purified by silica gel column chromatography to give 5-(4-{1-[4-(4-chlorophenoxy)phenyl]-2-isobutyl-1H-imidazol-4-yl}phenoxymethyl)pyrrolidin-3-ol (50 mg).

LC-MS: m/z 518 (M+H)$^+$ $^1$H NMR (400 MHz, CDCl$_3$): δ 0.84 (d, 6H), 1.25-3.20 (m, 6H), 2.53 (d, 2H), 4.05 (m, 3H), 4.50 (m, 1H), 6.91 (d, 2H), 7.01 (d, 2H), 7.05 (d, 2H), 7.10 (s, 1H), 7.24 (d, 2H), 7.34 (d, 2H), 7.66 (d, 2H) ppm.

EXAMPLE 524

3-(4-{1-[4-(4-Fluoro-phenoxy)-phenyl]-2-isobutyl-1H-imidazol-4-yl}-phenoxy)-pyridin-4-ylamine To an ice-cold solution of 3-bromopyridine-N-oxide (4 mmol) in concentrated H$_2$SO$_4$ (4 ml), concentrated HNO$_3$ (0.5 ml) was added gradually. The reaction mixture was heated at 90° C. for 48 h. The reaction mixture was then cooled to rt, diluted with cold water and the product was extracted with EtOAc. The organic layer was dried over anhydrous sodium sulfate and concentrated in vacuo to give desired product, 3-bromo-4-nitropyridine N-oxide.

{1-[4-(4-Chloro-phenoxy)-phenyl]-2-isobutyl-1H-imidazol-4-yl}phenol (1.1 eq. 4.4 mmol) was added slowly to a solution of NaH (8 mmol) in anhydrous DMF (6 ml) at 0° C. This was followed by addition of 3-bromo-4-nitropyridine-N-oxide (4 mmol) and the reaction mixture was heated to 90° C. for 2-3 h or until the completion of reaction. The reaction mixture was then cooled to rt, diluted with cold water and the product was extracted with DCM. The organic layer was dried over anhydrous sodium sulfate and concentrated in vacuo to give desired product, which was taken up in acetic acid (4 ml). Powdered iron (2 eq., 8 mmol) was added and the reaction was heated to 90° C. for 2-3 h. The reaction mixture was then cooled to rt, diluted with cold water and the product was extracted with EtOAc. The organic layer was dried over anhydrous sodium sulfate and concentrated in vacuo to give desired product, Example 524. (Yield: 60 mg)

MS: m/z 495 (M+1)$^+$

EXAMPLE 525

(4-{1-[4-(4-Chloro-phenoxy)-phenyl]-2-isobutyl-1H-imidazol-4-yl}-phenyl)-pyridin-4-yl-amine

[4-(4-Chloro-phenoxy)-phenyl]-2-isobutyl-1H-imidazol-4-yl}-aniline was synthesized by procedures analogous to those for the similar 4-(4-aminophenyl) 1H-imidazole intermediate in the preparation of Example 501.

A mixture of 200 mg of 4-{1-[4-(4-chloro-phenoxy)-phenyl]-2-isobutyl-1H-imidazole-4-yl}aniline (200 mg, 0.47 mmole), 4-chloropyridine hydrochloride (0.5 g, 3.2 mmole) and potassium carbonate (0.5 g, 3.6 mmole) were heated at 100° C. in DMF (10 mL) for 24 h. After cooling to rt the mixture was diluted with ether, washed with water) and dried (Na$_2$SO$_4$). Silica gel chromatography of the crude material afforded Example 525 (50 mg).

MS: m/z 495 (M+H)$^+$

EXAMPLE 526

2-(4-{1-[4-(4-Fluoro-phenoxy)-phenyl]-2-isobutyl-1H-imidazol-4-yl}-phenoxymethyl)-3,5-dimethyl-pyridin-4-ylamine (3,5-dimethyl-4-nitro-2-pyridyl)methyl mesylate was synthesized by the general procedure P2.

{1-[4-(4-Chloro-phenoxy)-phenyl]-2-isobutyl-1H-imidazol-4-yl}phenol (2 mmol) was added to a solution of Cs$_2$CO$_3$ (10 eq., 20 mmol) in anhydrous DMF (5 ml). This was followed by addition of the mesylate obtained above and the reaction mixture was heated to 90° C. for 2-3 h. The reaction mixture was then cooled to rt, diluted with cold water and the product was extracted with DCM. The organic layer was dried over anhydrous sodium sulfate and concentrated in vacuo to give desired phenyl ether.

The crude product obtained above was taken in acetic acid (5 ml). Powdered iron (2 eq., 8 mmol) was added to the reaction mixture and the reaction was heated to 90° C. for 2-3 h or until the completion of reaction. The reaction mixture was then cooled to rt, diluted with cold water and the product was extracted with EtOAc. The organic layer was dried over anhydrous sodium sulfate and concentrated in vacuo to give desired product., Example 526. (Yield: 80 mg)

MS: m/z 537 (M+H)$^+$

EXAMPLE 527

1-[2-(4-{1-[4-(4-Chloro-phenoxy)-phenyl]-2-isobutyl-1H-imidazol-4-yl}-phenoxy)-ethyl]-4-pyridin-4-yl-piperazine The product of Example 522 was taken in 4 ml of THF to which was added 5 eq. of BH3-THF solution and the reaction was heated to reflux until the reaction was complete. The crude product was purified by silica gel chromatography to afford Example 527.

MS: m/z 608 (M+H)$^+$

EXAMPLE 528

4-(4-{2-Butyl-4-[4-(3-diethylamino-propoxy)-phenyl]-imidazol-1-yl}-phenoxy)-phenylamine Example 528 was prepared by modifying the procedures utilized in the synthesis of Example 493, with utilization of 4-tert-butoxycarbonylaminophenol in place of 4-acetamidophenol. The BOC group was removed from the intermediate utilizing general procedure T1 to afford the product, Example 528, as the HCl salt.

MS: m/z 513 (M+H)$^+$

EXAMPLE 529

{3-[4-(2-Butyl-4-dibenzofuran-2-yl-imidazol-1-yl)-phenoxy]-propyl}-diethyl-amine A solution of dibenzofuran (0.5 mmol) in anhydrous DCM was cooled to 0° C. AlCl$_3$ (1.5 eq., 0.75 mmol) was added followed by a slow addition of acetyl chloride (1.5 eq., 0.75 mmol). The reaction mixture was stirred at 0° C. for 2-3 h or until the completion of reaction. The product was extracted with DCM and washed with saturated sodium bicarbonate solution. The organic layer was dried over anhydrous sodium sulfate and concentrated in vacuo to give dibenzofuran-2-ylethan-2-one.

Example 529 was prepared by modifying the procedures utilized for the synthesis of Example 463, utilizing dibenzofuran-2-ylethan-2-one as the aryl ketone starting material. (Yield: 75 mg)

MS: m/z 496 (M+H)$^+$

EXAMPLE 530

N-[4-(4-{2-Butyl-4-[4-(3-diethylamino-propoxy)-phenyl]-imidazol-1-yl}-phenoxy)-phenyl]-benzamide Example 530 was prepared by modifying the procedures utilized in the synthesis of Example 493, with utilization of 4-(tert-butoxycarbonylamino)phenol in place of 4-acetamidophenol. The BOC group was removed from the intermediate utilizing general procedure T1 to afford the product, Example 528, as the HCl salt. The product was treated with benzoyl chloride and TEA in DCM to afford, after aqueous workup and purification by silica gel chromatography, Example 530.

MS: m/z 617 (M+H)$^+$

EXAMPLE 531

N-[4-(4-{2-Butyl-4-[4-(3-diethylamino-propoxy)-phenyl]-imidazol-1-yl}-phenoxy)-phenyl]-isonicotinamide Example 530 was prepared by modifying the procedures utilized in the synthesis of Example 493, with utilization of 4-(tert-butoxycarbonylamino)phenol in place of 4-acetamidophenol. The BOC group was removed from the intermediate utilizing general procedure T1 to afford the product, Example 528, as the HCl salt. The product was treated with 4-pyridylcarbonyl chloride and TEA in DCM to afford, after aqueous workup and purification by silica gel chromatography, Example 531.

MS: m/z 618 (M+H)$^+$

EXAMPLE 532

[2-(4-{1-[4-(4-Chloro-phenoxy)-phenyl]-2-isobutyl-1H-imidazol-4-yl}-phenoxy)-ethyl]-methyl-pyridin-4-yl-amine A mixture of 4-chloropyridine hydrochloride salt (15.0 g) and 2-methylaminoethanol (30 mL) was refluxed for 48 hour. After cooling to rt the crude mixture was added slowly to saturated solution of sodium bicarbonate (150 mL). The product was extracted with EtOAc (3×100 mL), the combined EtOAc was washed with brine (50 mL), dried (Na$_2$SO$_4$) and removed in vacuo to give the desired product 2-[methyl(pyridin-4-yl)amino]ethanol as yellow solid (7.0 g).

2-[methyl(pyridin-4-yl)amino]ethyl methanesulfonate was synthesized as described for Example 515.

Sodium hydride (50.0 mg, 60% dispersion in oil) was added to mixture of 150 mg of 4-{1-[4-(4-chloro-phenoxy)-phenyl]-2-isobutyl-1H-imidazole-4-yl}phenol and 2-[methyl(pyridin-4-yl)amino]ethyl methanesulfonate (75 mg) in DMF (5 mL). After 24 h of stirring at rt, the mixture was added to ether (50 mL) and the organic phase was washed with water and dried (Na$_2$SO$_4$). The solvent was removed in vacuo and the product purified by silica gel chromatography to afford 80 mg of Example 532.

MS: m/z 553 (M+H)$^+$

EXAMPLE 533

N-(4-{1-[4-(4-Chloro-phenoxy)-phenyl]-2-isobutyl-1H-imidazol-4-yl}-phenyl)-2-dimethylamino-acetamide 1-[4-(4-Chloro-phenoxy)-phenyl]-2-isobutyl-4-(4-nitrophenyl)-1H-imidazole was synthesized following the general procedures utilized in example 501. The nitro group was reduced accorgding to general procedure H to afford 1-[4-(4-chloro-phenoxy)-phenyl]-2-isobutyl-4-(4-aminophenyl)-1H-imidazole, which was coupled with N,N-dimethylglycine using PS-carbodiimide according to the procedure utilized in Example 502 to afford Example 533.

MS: m/z 503 (M+H)$^+$

EXAMPLE 534

{3-[4-(4-{4-[3,3-Bis-(4 chloro-phenyl)-allyloxy]-phenyl}-2-isobutyl-imidazol-1-yl)-phenoxy]-propyl}-diethyl-amine Example 534 was synthesized by modification of the procedures utilized for the synthesis of example 459. 3,3(4-chlorophenyl)-2-propene-1-ol was converted to the methanesulfonate and utilized in condensation with 4'-hydroxyacetophenone. Isovaleryl chloride was utilized in place of benzyloxyacetyl chloride (yield 35 mg).

MS: m/z 682 (M+H)$^+$

EXAMPLE 535

{3-[4-(4-{4-[3,3-Bis-(4-fluoro-phenyl)-propoxy]-phenyl)-2-isobutyl-imidazol-1-yl)-phenoxy]-propyl}-diethyl-amine The intermediate phenol 4-(4-hydroxyphenyl)-2-isobutyl-imidazol-1-yl)-phenoxy]-propyl}-diethyl-amine utilized in the synthesis of Example 477 was condensed with the methanesulfonate of 3,3(4-fluorophenyl)-1-propanol (synthesized according to general procedure P2). The condensation was conducted in accord with similar operation in the preparation of Example 477 to provide Example 535.

MS: m/z 652 (M+H)$^+$

EXAMPLE 536

[2-(4-{4-[4-(4-Chloro-phenoxy)-phenyl]-2-isobutyl-imidazol-1-yl}-phenoxy)-ethyl]-methyl-pyridin-4-yl-amine 4-Fluoronitrobenzene was condensed with 2-[methyl(pyridin-4-yl)amino]ethanol according to general procedure C and the nitro group was then reduced according to general procedure H to afford the aniline intermediate. This aniline was utilized in modification of the procedure for preparation of Example 485 to afford Example 536.

MS: m/z 553 (M+H)$^+$

EXAMPLE 537

[3-(4-{4-{4-[2-(4-Chloro-phenyl)-ethoxy]-phenyl}-2-[2-(1-methyl-pyridin-3-yl)-ethyl]-imidazol-1-yl}-phenoxy)-propyl]-diethylmethyl aminonium iodide {4-{4-[2-(4-Chloro-phenyl)-ethoxy]-phenyl}-2-[2-(pyridin-3-yl)-ethyl]-imidazol-1-yl}-phenoxy)-propyl]-diethyl-amine was synthesized modifying the procedures utilized in the preparation of Example 485, where 3-(3-pyridyl)-propionyl chloride was utilized in place of valeryl chloride. The product {4-{4-[2-(4-Chloro-phenyl)-ethoxy]-phenyl}-2-[2-(pyridin-3-yl)-ethyl]-imidazol-1-yl}-phenoxy)-propyl]-diethyl-amine was treated with excess methyl iodide, concentrated in vacuo, and the solid collected to afford the product, Example 537 (Yield: 37 mg)

MS: m/z 625 (M+H)$^+$

EXAMPLE 538

[3-(4-{2-(N—BOC-piperidine-4-ylmethyl)-1-[4-(4-chloro-phenoxy)-phenyl]-1H-imidazol-4-yl}-phenoxy)-propyl]-diethyl-amine The procedure utilized for the preparation of Example 486 was modified, employing N—BOC-piperidine-4-acetic acid in place of 4-tert-butylcyclohexanecarboxylic acid, to afford 270 mg of Example 538.

MS: m/z 673 (M+H)$^+$

EXAMPLE 539

[3-(4-{2-(Piperidine-4-ylmethyl)-1-[4-(4-chloro-phenoxy)-phenyl]-1H-imidazol-4-yl}-phenoxy)-propyl]-diethyl-amine The compound of Example 538 was deprotected according to General Procedure T1 to afford 116 mg of Example 539 as the HCl salt.

MS: m/z 573 (M+H)$^+$

EXAMPLE 540

[3-(4-{2-(N-ethyl-piperidine-4-ylmethyl)-1-[4-(4-chloro-phenoxy)-phenyl]-1H-imidazol-4-yl}-phenoxy)-propyl]-diethyl-amine

[3-(4-{2-(Piperidine-4-ylmethyl)-1-[4-(4-chloro-phenoxy)-phenyl]-1H-imidazol-4-yl}-phenoxy)-propyl]-diethyl-amine (Example 539) (0.1 mmol) was treated in anhydrous DCM (2 ml) with acetaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 49 mg of Example 540.

MS: m/z 601 (M+H)$^+$

EXAMPLE 541

[3-(4-{2-(piperidine-4-ylmethyl)-4-[4-(4-chloro-phenoxy)-phenyl]-imidazol-1-yl}-phenoxy)-propyl]-diethyl-amine The procedure of Example 485 was adapted, using 4-BOC-piperidine-1-acetic acid in place of valeryl chloride. The resulting imidazole was deprotected using General Procedure T1 to afford Example 541 (48 mg) as the HCl salt.

MS: m/z 602 (M+H)$^+$

EXAMPLE 542

[3-(4-{2-(N-ethylpiperidine-4-ylmethyl)-4-[4-(4-chloro-phenoxy)-phenyl}-imidazol-1-yl]-phenoxy)-propyl]-diethyl-amine The product of Example 541 was treated in anhydrous DCM (2 ml) with acetaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 50 mg of Example 542.

$^1$H NMR: δ 7.68 (d, 2H), 7.23 (m, 6H), 7.16 (s, 1H), 6.95 (m, 2H), 6.88 (d, 2H), 4.17 (t, 2H), 4.06 (t, 2H), 3.06 (t, 2H), 2.91 (d, 2H), 2.81 (broad, 1H), 2.57 (m, 6H), 2.43 (m, 6H), 1.95-2.05 (m, 6H), 1.09 (t, 9H) ppm MS: m/z 629 (M+H)$^+$

EXAMPLE 543

[3-(4-{2-(N-acetylpiperidine-4-yl)-4-[4-(4-chloro-phenoxy)-phenyl]-imidazol-1-yl}-phenoxy)-propyl]-diethyl-amine The procedure of Example 485 was adapted, using 4-acetyl-piperidine-1-carbonyl chloride in place of valeryl chloride, to afford Example 543 (40 mg).

MS: m/z 629 (M+H)$^+$

EXAMPLE 544

[3-(4-{2-(piperidine-4-yl)-4-[4-(4-chloro-phenoxy)-phenyl]-imidazol 1-yl}-phenoxy)-propyl]-diethyl-amine Example 543 (1 mmol, 125 mg) was taken in 6 N HCl (5 ml) and the reaction was refluxed. The reaction mixture was then cooled to rt, diluted with water and neutralized with 3N NaOH solution. Product was extracted with EtOAc and the organic layer was dried over anhydrous sodium sulfate, concenterated in vacuo to give crude product, which was purified by column chromatography on silica gel to afford 290 mg of Example 544.
MS: m/z 587 (M+H)$^+$

EXAMPLE 545

[3-(4-{2-(N-Benzylpiperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with benzaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concenterated in vacuo to give desired product, which was purified by column chromatography on silica gel to afford 50 mg of Example 545.
$^1$H NMR: δ 7.68 (d, 2H), 7.28 (d, 2H), 7.21-7.26 (m, 9H), 7.17 (s, 1H), 6.97 (d, 2H), 6.87 (d, 2H), 4.16 (t, 2H), 4.07 (t, 2H), 3.48 (s, 2H), 3.05 (t, 2H), 2.91 (broad, 1H), 2.74 (t, 2H), 2.66 (m, 8H), 2.05 (m, 6H), 1.11 (t, 6H) ppm
MS: m/z 677 (M+H)$^+$

EXAMPLE 546

[3-(4-{2-(N-(2-Pyridylmethyl)piperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with pyridine-2-carboxaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 40 mg of Example 546.
MS: m/z 678 (M+H)$^+$

EXAMPLE 547

[3-(4-{2-(N-(2-imidazolylmethyl)piperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with imidazole-2-carboxaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 40 mg of Example 547.
$^1$H NMR: δ 7.66 (d, 2H), 7.2-7.3 (m, 7H), 7.06 (s, 1H), 6.98 (m, 3H), 6.88 (d, 2H), 4.18 (t, 2H), 4.05 (t, 2H), 3.65 (s, 2H), 3.08 (t, 2H), 2.81 (broad, 1H), 2.75 (m, 2H), 2.55-2.65 (m, 8H), 1.95-2.08 (m, 6H), 1.09 (t, 6H) ppm
MS: m/z 667 (M+H)$^+$

EXAMPLE 548

[3-(4-{2-(N-(4-biphenyl)methylpiperidine-4-yl}-4-[4-(4-chloro-phenoxy)-phenyl]-imidazol-1-yl}-phenoxy)-propyl]-diethyl-amine The product of Example 544 was treated in anhydrous DCM (2 ml) with 4-biphenylcarboxaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 45 mg of Example 548.
$^1$H NMR: δ 7.68 (d, 2H), 7.59 (d, 2H), 7.54 (d, 2H), 7.38-7.44 (m, 5H), 7.19-7.29 (m, 6H), 7.09 (s, 1H), 6.79 (d, 2H), 6.88 (d, 2H), 4.18 (t, 2H), 4.08 (t, 2H), 3.55 (s, 2H), 3.08 (t, 2H), 2.98 (broad, 1H), 2.65 (t, 2H), 2.58-2.65 (m, 8H), 1.98-2.09 (m, 6H), 1.12 (t, 6H) ppm.
MS: m/z 753 (M+H)$^+$

EXAMPLE 549

[3-(4-{2-(N-Cyclohexylpiperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with cyclopentanone (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 52 mg of Example 549.
$^1$H NMR: δ 7.68 (d, 2H), 7.38 (m, 3H), 7.21 (m, 3H), 7.08 (s, 1H), 6.98 (m, 2H), 6.88 (d, 2H), 4.18 (t, 2H), 4.08 (t, 2H), 3.08 (t, 2H), 2.67 (t, 2H), 2.51-2.55 (m, 8H), 1.99-2.08 (m, 6H), 1.91 (broad, 4H), 1.68 (broad 2H), 1.51 (broad 4H), 1.12 (t, 6H) ppm.
MS: m/z 655 (M+H)$^+$

EXAMPLE 550

[3-(4-{2-(N-(4-Cyanobenzyl)piperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with 4-cyanobenzaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 70 mg of Example 550.

¹H NMR: δ 7.69 (d, 2H), 7.59 (d, 2H), 7.44 (d, 2H), 7.2-7.3 (m, 6H), 7.09 (s, 1H), 6.99 (d, 2H), 6.88 (d, 2H), 4.18 (t, 2H), 4.09 (t, 2H), 3.55 (s, 2H), 3.08 (t, 2H), 2.85 (broad, 1H), 2.5-2.8 (m, 10H), 1.9-2.1 (m, 6H), 1.09 (t, 6H) ppm.

MS: m/z 702 (M+H)⁺

EXAMPLE 551

[3-(4-{2-(N-Ethylpiperidine-4-yl)-4-[4-(4-chloro-phenoxy)-phenyl]-imidazol-1-yl}-phenoxy)-propyl]-diethyl-amine The product of Example 544 was treated in anhydrous DCM (2 ml) with acetaldehyde (1.2 eq.) followed by addition of Na(OAc)$_3$BH (1.5 eq.). The reaction mixture was stirred at rt. Crude product was extracted into EtOAc and washed with saturated sodium bicarbonate solution. The organic layer was dried over anhydrous sodium sulfate and concentrated in vacuo to give desired product, which was purified by column chromatography on silica gel to afford 50 mg of Example 551.

¹H NMR: δ 7.68 (d, 2H), 7.23 (d, 2H), 7.22 (m, 4H), 7.16 (s, 1H), 6.95 (d, 2H), 6.88 (d, 2H), 4.17 (t, 2H), 4.05 (t, 2H), 3.05-3.07 (m, 7H), 2.51-2.61 (m, 6H), 2.39 (q, 2H), 1.89-2.09 (m, 6H), 1.12 (t, 9H) ppm.

MS: m/z 678 (M+H)⁺

Biological Assay

The following assay method is utilized to identify compounds of Formula (I) which are effective in binding with RAGE, and hence useful as modulators, preferably antagonists of RAGE.

General Assay Procedure

S100b, β-amyloid and CML (500 ng/100 µL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 5 mM CaCl$_2$/MgCl$_2$) containing 1% bovine serum albumin (BSA) (300 µL/well) for 1 h at RT. The wells are aspirated.

Test compounds are dissolved in nanopure water (concentration: 10-100 µM). DMSO may be used as co-solvent. 25 µL of test compound solution in 4% DMSO is added, along with 75 µL sRAGE (6.75 nM FAC) to each well and samples are incubated for 1 h at 37° C. The wells are washed 4 times with 155 mM NaCl pH 7.2 buffer saline and are soaked 10 seconds between each wash.

Non-radioactive detection is performed by adding:

10 µL Biotinylated goat F(ab')2 Anti-mouse IgG. (8.0× 10⁻⁴ mg/mL, FAC)

5 µL Alk-phos-Sterptavidin (3×10⁻³ mg/mL FAC)

0.42 µL per 5 mL Monoclonal antibody for sRAGE (FAC 6.0×10⁻³ mg/mL)

to 5 mL 50 mM imidazole buffer saline (pH 7.2) containing 0.2% bovine serum albumin and 5 mM CaCl$_2$. The mixture is incubated for 30 minutes at RT. 100 µL complex is added to each well and incubation is allowed to proceed at rt for 1 h. Wells are washed 4 times with wash buffer and soaked 10 s between each wash. 100 µL 1 mg/mL (pNPP) in 1 M diethanolamine (pH adjusted to 9.8 with HCl) is added. Color is allowed to develop in the dark for 30 min to 1 h at rt. The reaction is quenched with 10 µL of stop solution (0.5 N NaOH in 50% ethanol) and the absorbance is measured spectrophotometrically with a microplate reader at 405 nm.

The Examples in Table 1 were tested according to the assay method described above, employing S100b as the RAGE ligand, and were found to possess $IC_{50}$ in the assay of less than 10 µM. $IC_{50}$ (µM) of ELISA assay represents the concentration of compound at which 50% signal has been inhibited.

The invention further provides pharmaceutical compositions comprising the RAGE modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about .1% up to about 99% of the formulation. More usually they will form up to about 80% of the formulation. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels. Also provided by the present invention are prodrugs of the invention.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Pharmaceutically acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methyliodide, Methylchloride, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as—COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methiodide, methbromide, methchloride, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug therof, and one or more pharmaceutically acceptable carriers, excipients, or diluents.

The compounds of the present invention selectively act as modulators of RAGE binding to a single endogenous ligand, i.e., selective modulators of β-amyloid—RAGE interaction, and therefore are especially advantageous in treatment of Alzheimer's disease and related dementias.

Further, the compounds of the present invention act as modulators of RAGE interaction with two or more endogenous ligands in preference to others. Such compounds are advantageous in treatment of related or unrelated pathologies mediated by RAGE, i.e., Alzheimer's disease and cancer.

Further, the compounds of the present invention act as modulators of RAGE binding to each and every one of its ligands, thereby preventing the generation of oxidative stress and activation of NF-κB regulated genes, such as the cytokines IL-1, and TNF-α. Thus, antagonizing the binding of physiological ligands to RAGE prevent targeted pathophysiological consequences and useful for management or treatment of diseases, i.e., AGE-RAGE interaction leading to diabetic complications, S100/EN-RAGE/calgranulin-RAGE interaction leading to inflammatory diseases, β-amyloid-RAGE interaction leading to Alzheimer's Disease, and amphoterin-RAGE interaction leading to cancer.

I. RAGE and the Complications of Diabetes

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., *J. Clin. Invest.*, 91:2463-2469 (1993); Reddy, S., et al., *Biochem.*, 34:10872-10878 (1995); Dyer, D., et al., *J. Biol. Chem.*, 266:11654-11660 (1991); Degenhardt, T., et al, *Cell Mol. Biol.*, 44:1139-1145 (1998)). Accumulation of AGEs in the vasculature can occur focally, as in the joint amyloid composed of AGE-$β_2$-microglobulin found in patients with dialysis-related amyloidosis (Miyata, T., et al., *J. Clin. Invest.*, 92:1243-1252 (1993); Miyata, T., et al., *J. Clin. Invest.*, 98:1088-1094 (1996)), or generally, as exemplified by the vasculature and tissues of patients with diabetes (Schmidt, A-M., et al., *Nature Med.*, 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., *J. Biol. Chem.*, 272:16498-16506 (1997);

Li, J., et al., *J. Biol. Chem.*, 273:30870-30878 (1998); Tanaka, N., et al, *J. Biol Chem,* 275:25781-25790(2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in the Amyloidoses

Also as noted above, the compounds of the present invention are useful in treating amyloidoses and Alzheimer's disease. RAGE appears to be a cell surface receptor which binds β-sheet fibrillar material regardless of the composition of the subunits (amyloid-β peptide, Aβ, amylin, serum amyloid A, prion-derived peptide) (Yan, S.-D., et al, *Nature,* 382:685-691 (1996); Yan, S-D., et al., *Nat. Med.,* 6:643-651 (2000)). Deposition of amyloid has been shown to result in enhanced expression of RAGE. For example, in the brains of patients with Alzheimer's disease (AD), RAGE expression increases in neurons and glia (Yan, S.-D., et al., *Nature* 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., *Neurosci. Program,* p141-#275.19 (2000)). Inhibition of RAGE-amyloid interaction has been shown to decrease expression of cellular RAGE and cell stress markers (as well as NF-kB activation), and diminish amyloid deposition (Yan, S-D., et al, *Nat. Med.,* 6:643-651 (2000)) suggesting a role for RAGE-amyloid interaction in both perturbation of cellular properties in an environment enriched for amyloid (even at early stages) as well as in amyloid accumulation.

III. RAGE and Propagation of the Immune/Inflammatory Response

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., *TIBS,* 21:134-140 (1996); Zimmer, D., et al., *Brain Res. Bull.,* 37:417-429 (1995); Rammes, A., et al., *J. Biol. Chem.,* 272:9496-9502 (1997); Lugering, N., et al., *Eur. J. Clin. Invest.,* 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade as implicated in the inflammatory diseases such as but not limited to rheumatoid arthritis and multiple sclerosis.

RAGE is also implicated in inflammatory diseases of the skin such as but not limited to atopic dermatitis, eczema, and psoriasis. Psoriasis in particular is characterized by inflamed itchy lesions. Psoriasis may be accompanied by arthropathic symptoms that are similar to those in seen in rheumatoid arthritis.

There is considerable evidence that psoriasis is a polygenic autoimmune disorder. Psoriatic lesions are rich in cytokines, in particular IL-1 and IL-8, both potent proinflammatory mediators. IL-8 in particular is a chemotactic factor for neutrophils; neutrophils are also known to synthesize and secrete S100 proteins, one of the ligands for RAGE which is implicated in propogation of the immune and inflammatory response. Psoriasin (S100A7) a new member of the S100 gene family, is a secreted protein isolated from psoriatic skin. Semprini et. al. (Hum. Genet. 2002 October, 111(4-5), 310-3) have shown a linkage of psoriasis genetic susceptibility to distinct overexpression of S100 proteins in skin. Therefore, a modulator of RAGE would be expected to regulate the immune response in psoriasis.

IV. RAGE and Amphoterin

As noted above, the compounds of the present invention are useful in treating tumor and tumor metastasis. For example, amphoterin is a high mobility group I nonhistone chromosomal DNA binding protein (Rauvala, H., et al., *J. Biol. Chem.*, 262:16625-16635 (1987); Parkikinen, J., et al., *J. Biol. Chem.* 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., *Nature* 405:354-360 (2000)), and spontaneously arising papillomas in mice expressing the v-Ha-ras transgene (Leder, A., et al., *Proc. Natl. Acad. Sci.*, 87:9178-9182 (1990)).

Amphoterin is a high mobility group I nonhistone chromosomal DNA binding protein (Rauvala, H. and R. Pihlaskari. 1987. Isolation and some characteristics of an adhesive factor of brain that enhances neurite outgrowth in central neurons. *J. Biol. Chem.* 262:16625-16635. (Parkikinen, J., E. Raulo, J. Merenmies, R. Nolo, E. Kajander, M. Baumann, and H. Rauvala. 1993. Amphoterin, the 30 kDa protein in a family of HIMG1-type polypeptides. *J. Biol. Chem.* 268:19 726-19738).

V. RAGE and Erectile Dysfunction

Relaxation of the smooth muscle cells in the cavernosal arterioles and sinuses results in increased blood flow into the penis, raising corpus cavernosum pressure to culminate in penile erection. Nitric oxide is considered the principle stimulator of cavernosal smooth muscle relaxation (See Wingard C J, Clinton W, Branam H, Stopper V S, Lewis R W, Mills T M, Chitaley K. Antagonism of Rho-kinase stimulates rat penile erection via a nitric oxide-independent pathway. Nature Medicine 2001 January; 7(1):119-122). RAGE activation produces oxidants (See Yan, S-D., Schmidt A-M., Anderson, G., Zhang, J., Brett, J., Zou, Y-S., Pinsky, D., and Stern, D. Enhanced cellular oxidant stress by the interaction of advanced glycation endproducts with their receptors/binding proteins. J. Biol. Chem. 269:9889-9887, 1994.) via an NADH oxidase-like enzyme, therefore suppressing the circulation of nitric oxide. Potentially by inhibiting the activation of RAGE signaling pathways by decreasing the intracellular production of AGEs, generation of oxidants will be attenuated. RAGE blockers may promote and facilitate penile erection by blocking the access of ligands to RAGE.

The calcium-sensitizing Rho-kinase pathway may play a synergistic role in cavernosal vasoconstriction to maintain penile flaccidity. The antagonism of Rho-kinase results in increased corpus cavernosum pressure, initiating the erectile response independently of nitric oxide (Wingard et al.). One of the signaling mechanisms activated by RAGE involves the Rho-kinase family such as cdc42 and rac (See Huttunen H J, Fages C, Rauvala H. Receptor for advanced glycation end products (RAGE)-mediated neurite outgrowth and activation of NF-kappaB require the cytoplasmic domain of the receptor but different downstream signaling pathways. J Biol Chem 1999 Jul. 9; 274(28):19919-24). Thus, inhibiting activation of Rho-kinases via suppression of RAGE signaling pathways will enhance and stimulate penile erection independently of nitric oxide.

VI. RAGE and Respiratory Diseases

Airway inflammation is important in the pathogenesis of asthma. Such inflammation may give rise to significant exacerbations and increases in asthma severity, as well as to be a major factor in a decline in asthmatic status. In severe exacerbations of asthma there is an intense, mechanistically heterogeneous inflammatory response involving neutrophil and eosinophil accumulation and activation. Neutrophils are a significant source of S100 proteins, key ligands for RAGE implicated in the propogation of the immune response and inflammation. Therefore, modulators of RAGE would be expected to possess therapeutic value in the treatment of asthma.

Further, the propagation step in the immune response in the lung driven by S100-RAGE interaction would be expected to lead to the activation and/or recruitment of inflammatory cells, such as neutrophils, which in chronic obstructive pulmonary diseases such as emphysema, are significant sources of damaging proteases. Therefore, a RAGE modulator would be expected possess potential in the treatment of chronic obstructive pulmonary diseases.

Thus, in a further aspect, the present invention provides a method for the inhibition of the interaction of RAGE with physiological ligands. In a preferred embodiment of this aspect, the present invention provides a method for treating a disease state selected from the group consisting of acute and chronic inflammation including but not limited to skin inflammation such as psoriasis nad atopic dermatitis and lung inflammation including asthma and chronic osbtructive pulmonary disease, vascular permeability, nephropathy, atherosclerosis, retinopathy, Alzheimer's disease, erectile dysfunction, and tumor invasion and/or metastasis, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of RAGE mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (I).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

In a further aspect of the present invention, the RAGE modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most or all symptoms resulting from that disorder, to an outright cure for the particular disorder or prevention of the onset of the disorder.

The following is a non-exhaustive listing of adjuvants and additional therapeutic agents which may be utilized in combination with the RAGE modulators of the present invention:
Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Anti-tumor antibodies
Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids
Pharmacologic classifications of treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin
Pharmacologic classifications of treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further preferred embodiment, the present invention provides a method of treating RAGE mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated systemically, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Also a dosage form intended for topical administration to the skin may be prepared at . 1% to 99% compound to topical excipient ratio and a dosage form intended for inhaled administration of 0.01 to 200 mg of compound in a suitable carrier to deliver an inhaled dosage of compound. Dosage unit forms of systemically delivered compound will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

While the invention has been described and illustrated with reference to certain preferred embodiments therof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:
1. A method for inhibiting the Receptor for Advanced Glycated Endproducts (RAGE) in a subject having Alzheimer's Disease comprising administering to the subject a therapeutically effective amount of a RAGE modulator compound of Formula (Ib)

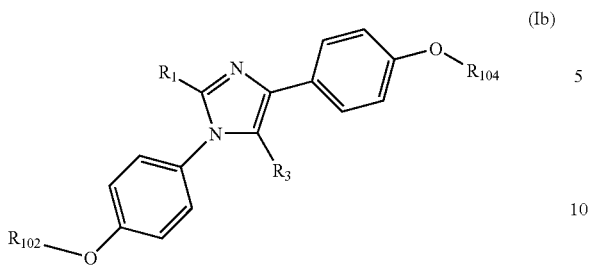

(Ib)

wherein
R$_1$ is -hydrogen, -alkyl, or -alkenyl;
R$_3$ is -hydrogen or -alkyl; and
R$_{102}$ and R$_{104}$ are independently selected from the group consisting of:
a) —H,
b) -alkyl,
c) -aryl,
d) -heteroaryl,
e) -alkylene-heteroaryl-aryl,
f) -alkylene-aryl,
g) -alkylene-W$_2$-R$_{18}$,
h) —Y$_4$—NR$_{23}$R$_{24}$,
i) —Y$_4$—NH—C(=NR$_{25}$)NR$_{23}$R$_{24}$,
j) —Y$_4$—C(=NR$_{25}$)NR$_{23}$R$_{24}$, and
k) —Y$_4$—Y$_5$-A$_2$,
wherein
W$_2$ is —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—S(O)$_2$—, —O—CO—,

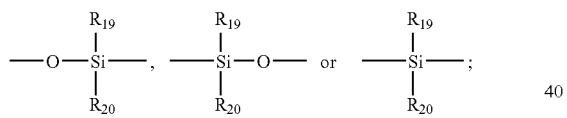

wherein R$_{19}$ and R$_{20}$ are independently selected from the group consisting of: -hydrogen, -aryl, -alkyl, -alkylene-aryl, alkoxy, and -alkylene-O-aryl;
R$_{18}$ is -aryl, -alkyl, -alkylene-aryl, -alkylene-heteroaryl, or alkylene-O-aryl;
Y$_5$ is a direct bond, —CH$_2$—, —O—, —N(H), —S—, SO$_2$—, —C(O)—, —CON(H)—, —NHC(O)—, —NHCON(H)—, —NHSO$_2$—, —SO$_2$N(H)—, —C(O)—O—, —NHSO$_2$NH—, —O—CO—,

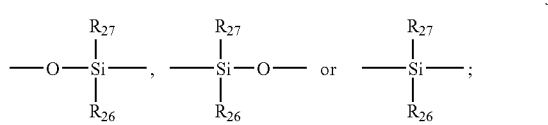

wherein R$_{27}$ and R$_{26}$ are independently selected from the group consisting of -aryl, -alkyl, -alkylene-aryl, alkoxy, and alkyl-O-aryl;
Y$_4$ is
a) -alkylene,
b) -alkenylene,
c) -alkynylene,
d) -arylene,
e) -heteroarylene,
f) -cycloalkylene,
g) -heterocyclylene,
h) -alkylene-arylene,
i) -alkylene-heteroarylene,
j) -alkylene-cycloalkylene,
k) -alkylene-heterocyclylene,
l) -arylene-alkylene,
m) -heteroarylene-alkylene,
n) -cycloalkylene-alkylene,
o) -heterocyclylene-alkylene,
p) —O—,
q) —S—,
r) —S(O)$_2$—, or
s) —S(O)—,
wherein said alkylene groups may optionally contain one or more O, S, S(O), or SO$_2$ atoms;
A$_2$ is
a) heterocyclyl, fused arylheterocyclyl, or fused heteroarylheterocyclyl, containing at least one basic nitrogen atom, or
b) -imidazolyl,
R$_{23}$, R$_{24}$, and R$_{25}$ are independently selected from the group consisting of: -hydrogen, -aryl, -heteroaryl, -alkylene-heteroaryl, alkyl, -alkylene-aryl, -alkylene-O-aryl, and -alkylene-O-heteroaryl; and R$_{23}$ and R$_{24}$ may be taken together to form a five membered ring having the formula —(CH$_2$)$_s$—X$_3$—(CH$_2$)$_t$- bonded to the nitrogen atom to which R$_{23}$ and R$_{24}$ are attached
wherein
s and t are, independently, 1, 2, 3, or 4; X$_3$ is a direct bond, —CH$_2$—, —O—, —S—, —S(O)$_2$—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

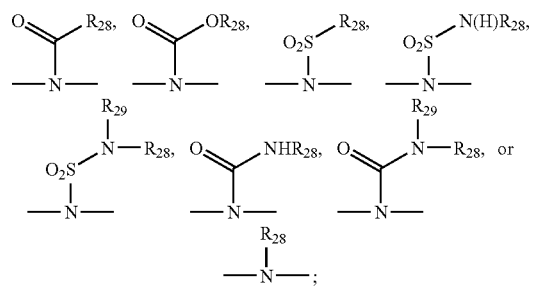

wherein R$_{28}$ and R$_{29}$ are independently selected from the group consisting of: -hydrogen, -aryl, -heteroaryl, -alkyl, -alkylene-aryl, and -alkylene-heteroaryl;
wherein
the alkyl and/or aryl groups of R$_{102}$ and R$_{104}$ may be optionally substituted 1-4 times with a substituent group selected from the group consisting of:
a) halogen,
b) perhaloalkyl,
c) alkyl,
d) cyano, e) alkyloxy,
f) aryl, and
g) aryloxy wherein the ring or rings containing a heteroatom in the heteroaryl, heteroarylene, heterocyclyl, heterocyclene, fused arylheterocyclyl, or fused heteroarylheterocyclyl groups in $R_{102}$ or $R_{104}$ or in a substituent of $R_{102}$ or $R_{104}$ is a five membered nitrogen containing ring, or a pharmaceutically acceptable salt thereof, wherein a therapeutically effective amount comprises sufficient compound to at least partially inhibit the binding of a ligand to RAGE.

2. The method according to claim 1 wherein the RAGE modulator compound is mixed with a pharmaceutical carrier.

3. The method according to claim 1 wherein the RAGE modulator compound is administered parenterally, orally, topically, rectally or by inhalation as a spray.

4. The method according to claim 1 wherein the RAGE modulator compound comprises a dosage ranging from 0.01 to 500 mg/kg/day.

5. The method according to claim 1 wherein the RAGE modulator compound comprises a dosage ranging from 0.01 to 200 mg/kg/day.

6. The method according to claim 1 wherein the RAGE modulator compound comprises a dosage ranging from 0.1 to 100 mg/kg/day.

7. The method according to claim 1 wherein the RAGE modulator compound comprises a unit dosage ranging from 5 to 500 mg.

8. A method for inhibiting the Receptor for Advanced Glycated Endproducts (RAGE) in a subject having Alzheimer's Disease comprising administering to the subject a therapeutically effective amount of the RAGE modulator compound [3-(4-{2-butyl-1-[4-(4-chloro-phenoxy)-phenyl]-1H-imidazol-4-yl}-phenoxy)-propyl]-diethyl-amine or a pharmaceutically acceptable salt thereof, wherein a therapeutically effective amount comprises sufficient compound to at least partially inhibit the binding of a ligand to RAGE.

9. The method according to claim 8 wherein the RAGE modulator compound is mixed with a pharmaceutical carrier.

10. The method according to claim 8 wherein the RAGE modulator compound is administered parenterally, orally, topically, rectally or by inhalation as a spray.

11. The method according to claim 8 wherein the RAGE modulator compound comprises a dosage ranging from 0.01 to 500 mg/kg/day.

12. The method according to claim 8 wherein the RAGE modulator compound comprises a dosage ranging from 0.01 to 200 mg/kg/day.

13. The method according to claim 8 wherein the RAGE modulator compound comprises a dosage ranging from 0.1 to 100 mg/kg/day.

14. The method according to claim 8 wherein the RAGE modulator compound comprises a unit dosage ranging from 5 to 500 mg.

* * * * *

UNITED STATES PATENT AND TRADEMARK OFFICE
CERTIFICATE OF CORRECTION

| | |
|---|---|
| PATENT NO. | : 7,714,013 B2 |
| APPLICATION NO. | : 11/511163 |
| DATED | : May 11, 2010 |
| INVENTOR(S) | : Adnan M. M. Mjalli et al. |

It is certified that error appears in the above-identified patent and that said Letters Patent is hereby corrected as shown below:

Page 1, Column 1, Inventors, line 5, please delete "Kwasi A. Avor,", please insert -- Kwasi S. Avor, --.

Page 2, Column 1, under U.S. Patent Documents, line 20, please delete "Hemaus et al.,", and insert -- Hurnaus et al. --.

Page 2, Column 2, under Other Publications, line 23, please delete "β-piene,", and insert -- β-pinene, --.

Page 2, Column 2, under Other Publications, line 33, please delete "Mailard", and insert -- Maillard --.

Page 3, Column 1, under Other Publications, line 12, please delete "Apollpoprotein", and insert -- Apolipoprotein --.

Page 3, Column 1, under Other Publications, line 35, please delete "Myeloic", and insert -- Myeloid --.

Page 3, Column 1, under Other Publications, line 56, please delete "4", and insert -- [4 --.

Page 3, Column 1, under Other Publications, line 57, please delete "phenoxyl)", and insert -- phenoxy] --.

Page 3, Column 2, under Other Publications, line 1, please delete "lmidazole", and insert -- Imidazole --.

Page 3, Column 2, under Other Publications, line 53, please delete "β-Estradoil", and insert -- β-Estradiol --.

Page 3, Column 2, under Other Publications, line 69, please delete "Vasculophathy:", and insert -- Vasculopathy: --.

Signed and Sealed this
Twelfth Day of April, 2011

David J. Kappos
*Director of the United States Patent and Trademark Office*

CERTIFICATE OF CORRECTION (continued)

U.S. Pat. No. 7,714,013 B2

Page 4, Column 1, under Other Publications, line 9, please delete "at", and insert -- et --.

Page 4, Column 1, under Other Publications, line 13, please delete "at", and insert -- et --.

Column 1, line 42, pease delete "mesengial", please insert -- mesangial --.

Column 10, line 31 (Approx.), please delete "-alkyene-O-aryl;", please insert -- -alkylene-O-aryl; --.

Column 12, line 65, please delete "(arylalkylene, (heteroary)", please insert -- (aryl)alkylene, (heteroaryl) --.

Column 14, line 7, please delete "2-cyclopropy-ethyl,", please insert -- 2-cyclopropyl-ethyl, --.

Column 14, line 14, please delete "substitutent", please insert -- substituent --.

Column 15, lines 11-12, please delete "—$(CH_2)S$—$X_3$—$(CH_2)_t$—", please insert -- —$(CH_2)_S$—$X_3$—$(CH_2)_t$— --.

Column 15, line 58, please delete "4-(4-isonicotinamido-", and insert -- 4-(4-isonicotinamide- --.

Column 17, line 40, please delete "4-(2", and insert -- 4-{2 --.

Column 17, line 41, please delete "ethoxy)-phenyl," and insert -- ethoxy}-phenyl, --.

Column 18, line 21, please delete "comprises-hydrogen,", and insert -- comprises -hydrogen, --.

Column 20, line 50, please delete "2-cyclopropy-ethyl,", and insert -- 2-cyclopropyl-ethyl, --.

Column 21, line 33, please delete "—$Y_{4-NR23R_{24}}$", and insert -- —$Y_4$—$NR_{23}R_{24}$ --.

Column 22, line 60 (approx.), please delete "$Y_6$—$(=NR_{35})$", and insert -- $Y_6$—$C(=NR_{35})$ --.

Column 23, lines 44-45 (approx.), please delete "-alkylene-O -aryl;", and insert -- -alkylene-O-aryl; --.

Column 24, line 29, please delete "-alkyene-O-aryl;", and insert -- -alkylene-O-aryl; --.

Column 24, line 59, please delete "—C—CO—,", and insert -- —O—CO—, --.

Column 26, lines 2-3, please delete "dimethyoxy", and insert -- dimethoxy --.

Column 26, line 18, please delete "3", and insert -- {3 --.

Column 26, line 18, please delete "phenyl]", and insert -- phenyl} --.

CERTIFICATE OF CORRECTION (continued)
U.S. Pat. No. 7,714,013 B2

Column 26, lines 35-36 (approx.), please delete "hygrogen;", and insert -- hydrogen; --.

Column 26, line 42, please delete "2-(4-[2-", and insert -- 2-{4[2- --.

Column 26, line 46, please delete "hygrogen;", and insert -- hydrogen; --.

Columns 35-36, (Ex. Name 22), line 1, please delete "(3-(4-", and insert -- (3-{4- --.

Columns 39-40, (Ex. Name 29), line 2, please delete "5-ytoxy]", and insert -- 5-yloxy] --.

Columns 39-40, (Ex. Name 33), line 3, please delete "benzoimldazol", and insert -- benzoimidazol --.

Columns 41-42, (Ex. Name 36), line 1, please delete "-2-(4-", and insert -- -2-{4- --.

Columns 45-46, (Ex. Name 44), line 2, please delete "-ethoxyl-", and insert -- -ethoxy]- --.

Columns 49-50, (Ex. Name 51), line 2, please delete "-phenyl]-", and insert -- -phenyl}- --.

Columns 49-50, (Ex. Name 53), line 1, please delete "-(4-[3-", and insert -- -{4-[3- --.

Columns 55-56, (Ex. Name 65), line 1, please delete "{4-(2-", and insert -- -{4-[2- --.

Columns 57-58, (Ex. Name 68), line 1, please delete "-2-(4-", and insert -- -2-{4- --.

Columns 57-58, (Ex. Name 70), line 1, please delete "-2-(3-", and insert -- -2-[3- --.

Columns 59-60, (Ex. Name 73), line 2, please delete "-phenyl)-", and insert -- -phenyl}- --.

Columns 61-62, (Ex. Name 81), line 2, please delete "-ethyl]-", and insert -- -ethyl}- --.

Columns 63-64, (Ex. Name 83), line 1, please delete "(3-[2-", and insert -- {3-[2- --.

Columns 65-66, (Ex. Name 87), line 1, please delete "-2-(4-", and insert -- -2-{4- --.

Columns 67-68, (Ex. Name 91), line 4, please delete "propioinamide", and insert -- propionamide --.

Columns 73-74, (Ex. Name 103), line 1, please delete "-2-(4-", and insert -- -2-{4- --.

Columns 77-78, (Ex. Name 114), line 3, please delete "yloxy)-propyl]", and insert -- yloxy]-propyl} --.

Columns 79-80, (Ex. Name 117), line 2, please delete "-phenyl)-", and insert -- -phenyl}- --.

CERTIFICATE OF CORRECTION (continued)

Columns 79-80, (Ex. Name 119), line 1, please delete "-2-(3-", and insert -- -2-[3- --.

Columns 81-82, (Ex. Name 122), line 3, please delete "phenoxyl-", and insert -- phenoxy}- --.

Columns 83-84, (Ex. Name 125), line 2, please delete "-phenyl)-", and insert -- -phenyl}- --.

Columns 83-84, (Ex. Name 126), line 1, "(3", and insert -- {3 --.

Columns 83-84, (Ex. Name 126), line 3, please delete "yloxy)-propyl]", and insert -- yloxy]-propyl} --.

Columns 85-86, (Ex. Name 131), line 2, please delete "-ethyl]-", and insert -- -ethyl}- --.

Columns 93-94, (Ex. Structure 149), line 1, please delete " 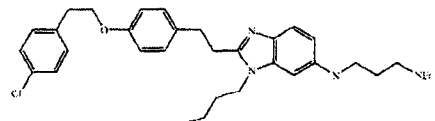 " and insert -- 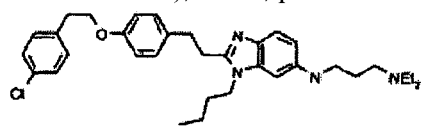 --.

Columns 95-96, (Ex. Name 151), line 2, please delete "phenyl]-", and insert -- -phenyl}- --.

Columns 101-102, (Ex. Name 162), line 1, please delete "(3-(4-", and insert -- (3-{4- --.

Columns 101-102, (Ex. Name 162), line 2, please delete "-phenyl]-", and insert -- -phenyl}- --.

Columns 103-104, (Ex. Name 169), line 1, please delete "{1-", and insert -- {3- --.

Columns 105-106, (Ex. Name 173), line 1, please delete "{3-(2-", and insert -- {3-[2- --.

Columns 105-106, (Ex. Name 174), line 1, please delete "-2-(3-", and insert -- -2-[3- --.

Columns 109-110, (Ex. Name 181), line 1, please delete "-2-(4-", and insert -- -2-{4- --.

Columns 109-110, (Ex. Name 181), line 4, please delete "propyl]-", and insert -- propyl}- --.

Columns 109-110, (Ex. Structure 183), line 1, please delete " 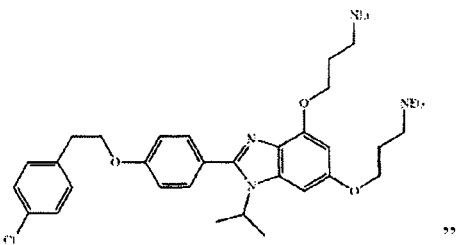 "

and insert -- 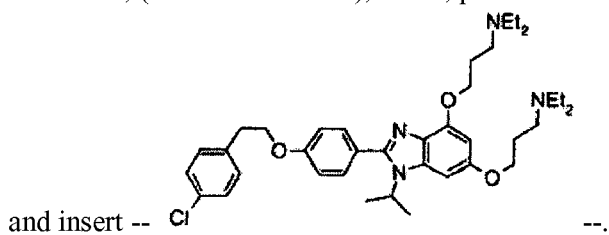 --.

Columns 109-110, (Ex. Name 183), line 4, please delete "-yloxyl-propyl]-", and insert -- yloxy]-propyl}- --.

Columns 111-112, (Ex. Name 185), line 3, please delete "-yl-", and insert -- -yl]- --.

Columns 111-112, (Ex. Name 186), line 1, please delete "(3-[2-", and insert -- {3-[2- --.

Columns 113-114, (Ex. Name 188), line 1, please delete "(3-[1-", and insert -- {3-[1- --.

Columns 113-114, (Ex. Name 191), line 1, please delete "[3-(1", and insert -- (3-{1 --.

Columns 115-116, (Ex. Name 193), line 3, please delete "-propyl]-", and insert -- -propyl}- --.

Columns 115-116, (Ex. Name 195), line 4, please delete "-yloxyl", and insert -- -yloxy] --.

Columns 121-122, (Ex. Name 207), line 3, please delete "-yloxyl", and insert -- -yloxy] --.

Columns 121-122, (Ex. Structure 208), line 1, please delete " 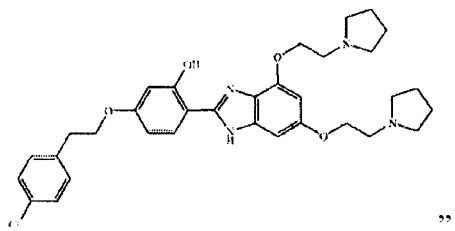 "

and insert -- 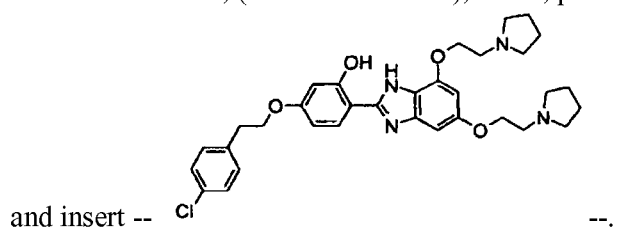 --.

CERTIFICATE OF CORRECTION (continued)
U.S. Pat. No. 7,714,013 B2

Columns 123-124, (Ex. Name 209), line 2, please delete "pyrrolodin-1", and insert -- pyrrolidin-1 --.

Columns 123-124, (Ex. Structure 212), line 1, please delete " 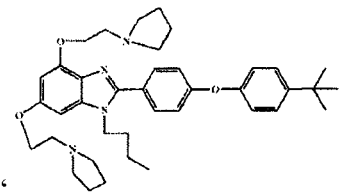 "

and insert -- 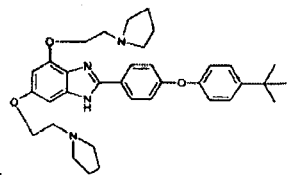 --.

Columns 123-124, (Ex. Structure 213), line 1, please delete " 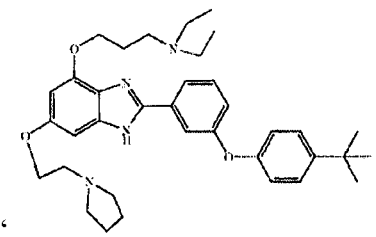 "

and insert -- 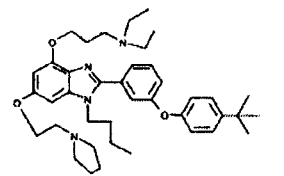 --.

Columns 125-126, (Ex. Name 214), line 1, please delete "-2-(4-", and insert -- -2-{4- --.

Columns 127-128, (Ex. Name 219), line 2, please delete "-phenyll-", and insert -- -phenyl} --.

Columns 129-130, (Ex. Name 223), line 3, please delete "-yloxyl-", and insert -- -yloxy} --.

Columns 129-130, (Ex. Name 225), line 2, please delete "phenyl)-", and insert -- phenyl]- --.

Columns 129-130, (Ex. Name 226), line 4, please delete "yloxy}-propyl)-", and insert -- yloxy]-propyl} --.

Columns 131-132, (Ex. Name 231), line 1, please delete " 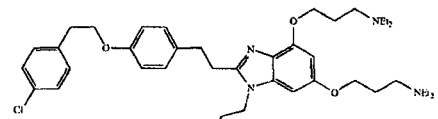 "

and insert -- 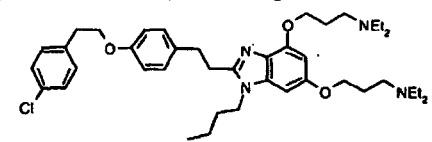 --.

CERTIFICATE OF CORRECTION (continued)
U.S. Pat. No. 7,714,013 B2

Columns 131-132, (Ex. Name 231), line 4, please delete "propyl]-", and insert -- propyl}- --.

Columns 133-134, (Ex. Name 232), line 3, please delete "-propyl]-", and insert -- -propyl}- --.

Columns 133-134, (Ex. Name 235), line 1, please delete "{3-(1-", and insert -- {3-[1- --.

Columns 133-134, (Ex. Name 235), line 4, please delete "-propyl)-", and insert -- -propyl}- --.

Columns 135-136, (Ex. Name 238), line 2, please delete "benzoimidazlo", and insert
 -- benzoimidazol --.

Columns 135-136, (Ex. Name 239), line 1, please delete "-2-(4-", and insert -- -2-{4- --.

Columns 139-140, (Ex. Name 248), line 1, please delete "{3-(2-", and insert -- {3-[2- --.

Columns 139-140, (Ex. Name 249), line 5, please delete "-aminol-", and insert -- -amino]- -- .

Columns 141-142, (Ex. Name 250), line 3, please delete "-yloxy)-", and insert -- -yloxy}- --.

Columns 141-142, (Ex. Name 252), line 2, please delete "phenyl]", and insert -- phenyl}- --.

Columns 143-144, (Ex. Name 258), line 1, please delete "-(2-", and insert -- -[2- --.

Columns 145-156, (Ex. Name 260), line 2, please delete "(2-pyrrolodin-1", and insert
 -- (2-pyrrolidin-1 --.

Columns 145-146, (Ex. Name 260), line 3, please delete "(2-pyrrolodin-1", and insert
 -- (2-pyrrolidin-1 --.

Columns 145-146, (Ex. Structure 261), line 1, please delete " 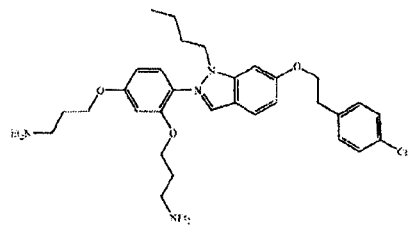 "
and insert -- 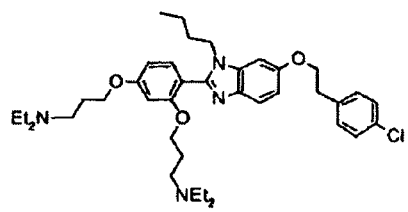 --.

Columns 145-146, (Ex. Name 261), line 1, please delete "[2-{1-butyl", and insert -- [2-[1-butyl --.

Columns 147-148, (Ex. Name 267), line 1, please delete "iospropyl-", and insert -- isopropyl- --.

Columns 147-148, (Ex. Name 267), line 2, please delete "p4henoxy)", and insert -- phenoxy) --.

Columns 149-150, (Ex. Name 270), line 4, please delete "propyl]", and insert -- propyl} --.

Columns 151-152, (Ex. Name 275), line 4, please delete "propyl]", and insert -- propyl} --.

Columns 151-152, (Ex. Structure 276), line 1, please delete " 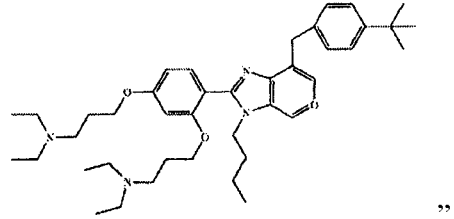 "

and insert -- 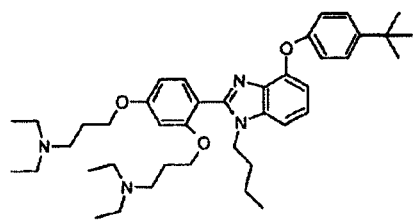 --.

Columns 153-154, (Ex. Name 281), line 4, please delete "propyl]", and insert -- propyl} --.

Columns 155-156, (Ex. Name 283), line 1, please delete "(3-(3-butyl", and insert -- (3-{3-butyl --.

Columns 155-156, (Ex. Structure 284), line 1, please delete " 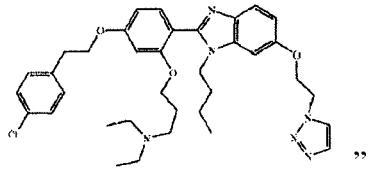 "

and insert -- 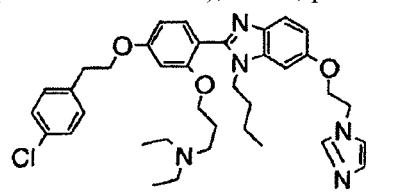 --.

Columns 165-166, (Ex. Name 303), line 1, please delete "2-(4-[2", and insert -- 2-{4-[2 --.

Columns 169-170, (Ex. Name 311), line 2, please delete "benzoimidazlo", and insert -- benzoimidazol --.

Columns 171-172, (Ex. Name 315), line 2, please delete "benzoimidazlo", and insert -- benzoimidazol --.

Columns 183-184, (Ex. Name 336), line 2, please delete "ethoxy).-1H", and insert -- ethoxy)-1H --.

Columns 185-186, (Ex. Name 339), line 5, please delete "propyl]", and insert -- propyl} --.

Columns 191-192, (Ex. Name 348), line 4, please delete "propyl]-", and insert -- propyl}- --.

Columns 191-192, (Ex. Name 349), line 1, please delete "pyrrolodin", and insert -- pyrrolidin --.

Columns 193-194, (Ex. Name 350), line 4, please delete "benzimidazoI", and insert -- benzimidazol --.

Columns 193-194, (Ex. Name 351), line 4, please delete "benzimidazoI", and insert -- benzimidazol --.

Columns 193-194, (Ex. Name 352), line 1, please delete "2-(4-[2", and insert -- 2-{4-[2 --.

Columns 197-198, (Ex. Name 356), line 2, please delete "pyrrolodin", and insert -- pyrrolidin --.

Columns 197-198, (Ex. Name 358), line 3, please delete "pyrrolodin", and insert -- pyrrolidin --.

Columns 199-200, (Ex. Name 359), line 1, please delete "[2-(4-[2", and insert -- [2-{4-[2 --.

Columns 199-200, (Ex. Structure 360), line 1, please delete " 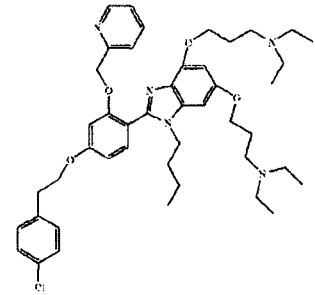 "

and insert -- 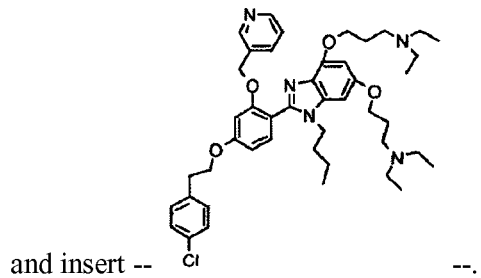 --.

Columns 199-200, (Ex. Name 361), line 4, please delete "yloxyl-propyl)", and insert -- yloxy}-propyl) --.

Columns 201-202, (Ex. Name 362), line 4, please delete "propyl]-", and insert -- propyl}- --.

CERTIFICATE OF CORRECTION (continued)

Columns 201-202, (Ex. Name 364), line 1, please delete "Butyl-Butyl-2", and insert -- Butyl-2 --.

Columns 203-204, (Ex. Name 366), line 4, please delete "propyl]-", and insert -- propyl}- --.

Columns 205-206, (Ex. Name 368), line 5, please delete "diethyl amine", and insert -- diethyl-amine --.

Columns 205-206, (Ex. Structure 369), line 1, please delete " 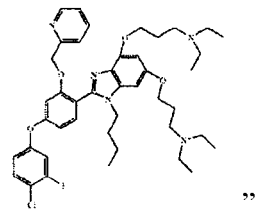 " and insert -- 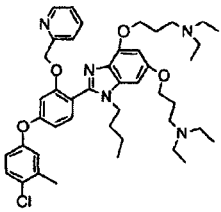 --.

Columns 211-212, (Ex. Structure 379), line 1, please delete " 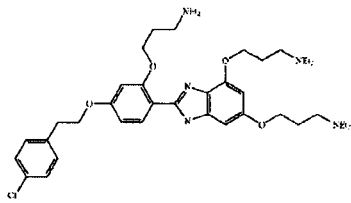 " and insert -- 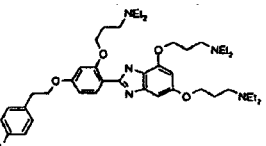 --.

Columns 213-214, (Ex. Name 383), line 4, please delete "yloxyl-propyl)", and insert -- yloxy}-propyl) --.

Columns 213-214, (Ex. Name 384), line 4, please delete "benzimidzole", and insert -- benzimidazole --.

Columns 215-216, (Ex. Name 387), line 4, please delete "yloxyl-propyl}", and insert -- yloxy]-propyl} --.

Columns 215-216, (Ex. Name 389), line 4, please delete "propyl)-", and insert -- propyl}- --.

Columns 217-218, (Ex. Name 395), line 2, please delete "methyl]-3", and insert -- methyl}-3 --.

Columns 221-222, (Ex. Name 404), line 3, please delete "propyl]-diethyl", and insert
-- propyl}-diethyl --.

Columns 221-222, (Ex. Name 405), line 3, please delete "propyl]-diethyl", and insert
-- propyl}-diethyl --.

Columns 221-222, (Ex. Name 407), line 3, please delete "yl]-phenoxy)", and insert -- yl}-phenoxy) --.

Columns 223-224, (Ex. Name 408), line 3, please delete "yl]phenoxy)", and insert -- yl}-phenoxy) --.

Columns 223-224, (Ex. Structure 410), line 1, please delete " 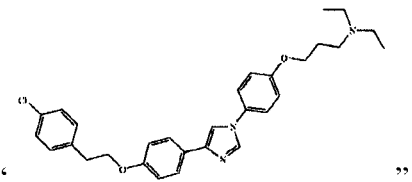 " and insert -- 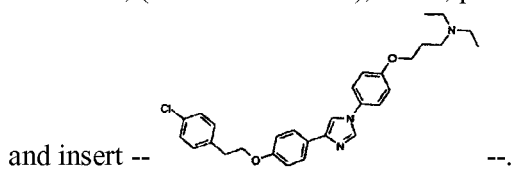 --.

Columns 223-224, (Ex. Structure 411), line 1, please delete " 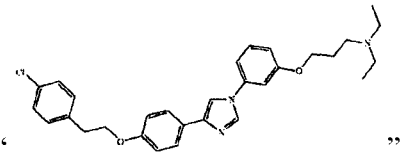 " and insert -- 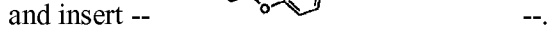 --.

Columns 225-226, (Ex. Structure 415), line 1, please delete " 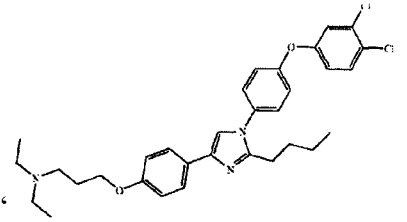 " and insert --  --.

CERTIFICATE OF CORRECTION (continued)
U.S. Pat. No. 7,714,013 B2

Columns 227-228, (Ex. Name 418), line 3, please delete "yl)-phenoxy)", and insert -- yl}-phenoxy) --.

Columns 231-232, (Ex. Name 425), line 3, please delete "phenoxyl-propyl}", and insert
-- phenoxy]-propyl} --.

Columns 231-232, (Ex. Structure 427), line 1, please delete " 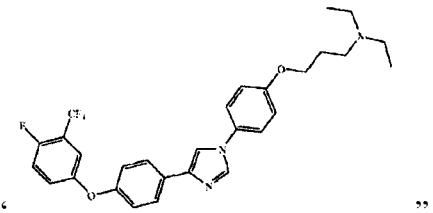 "

and insert -- 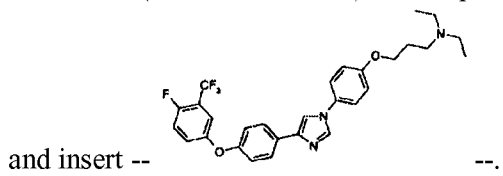 --.

Columns 233-234, (Ex. Name 429), line 1, please delete "(3-[4", and insert -- {3-[4 --.

Columns 233-234, (Ex. Name 429), line 2, please delete "phenyl)-2", and insert -- phenyl}-2 --.

Columns 233-234, (Ex. Name 431), line 2, please delete "yl]-phenoxy)", and insert -- yl}-phenoxy) --.

Columns 237-238, (Ex. Name 437), line 3, please delete "phenyl]-1H", and insert -- phenyl}-1H --.

Columns 239-240, (Ex. Structure 441), line 1, please delete " 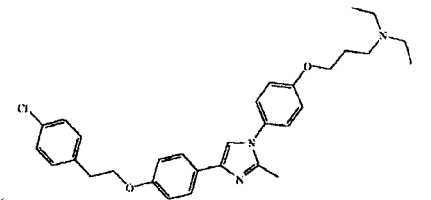 "

and insert -- 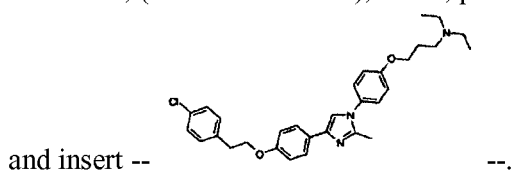 --.

Columns 239-240, (Ex. Name 441), line 3, please delete "propyl)-diethyl", and insert
-- propyl}-diethyl --.

Columns 241-242, (Ex. Structure 446), line 1, please delete " 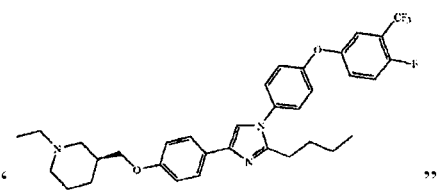 "

Columns 243-244, (Ex. Structure 448), line 1, please delete " 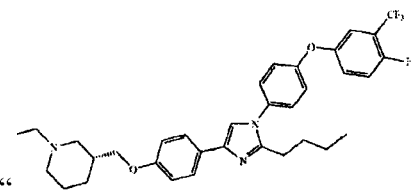 "

and insert -- 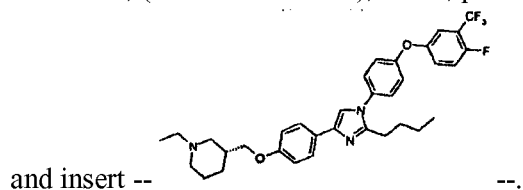 --.

Columns 243-244, (Ex. Name 450), line 3, please delete "phenoxyl-propyl]-", and insert
-- phenoxy]-propyl}- --.

Columns 243-244, (Ex. Name 451), line 2, please delete "2-( 1-ethyl", and insert -- 2-(1-ethyl --.

Columns 245-246, (Ex. Name 452), line 1, please delete "{4-t2-(4", and insert -- {4-[2-(4 --.

Columns 245-246, (Ex. Name 454), line 4, please delete "propyl]-diethyl", and insert
-- propyl}-diethyl --.

Columns 247-248, (Ex. Name 456), line 2, please delete "phenyl)-2", and insert -- phenyl}-2 --.

Columns 247-248, (Ex. Name 456), line 3, please delete "propyl]-", and insert -- propyl}- --.

Columns 247-248, (Ex. Name 457), line 2, please delete "phenyl)-2", and insert -- phenyl}-2 --.

Columns 247-248, (Ex. Name 458), line 1, please delete "4-(4", and insert -- 4-{4 --.

Columns 247-248, (Ex. Name 459), line 1, please delete "{4-{4", and insert -- {4-[4 --.

Columns 249-250, (Ex. Name 462), line 2, please delete "benzenesulfonylmethylbenzyloxy)",
and insert -- benzenesulfonylmethyl-benzyloxy) --.

Columns 251-252, (Ex. Structure 467), line 1 please delete " 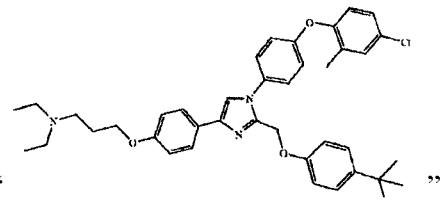 "

and insert -- 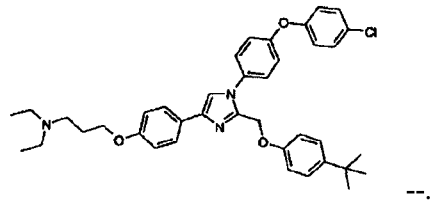 --.

Columns 253-254, (Ex. Name 469), line 3, please delete "yl)-phenoxy)", and insert -- yl}-phenoxy) --.

Columns 255-256, (Ex. Name 474), line 2, please delete "yl]-", and insert -- yl}- --.

Columns 255-256, (Ex. Structure 476), line 1, please delete " 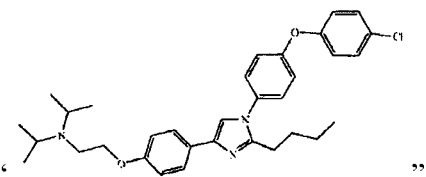 "

and insert --  --.

Columns 259-260, (Ex. Name 482), line 1, please delete "(4-(2", and insert -- (4-{2 --.

Columns 261-262, (Ex. Name 487), line 3, please delete "ylI-phenoxy}", and insert
-- yl]-phenoxy} --.

Columns 263-264, (Ex. Name 489), line 3, please delete "yl]-butyric", and insert -- yl}-butyric --.

Columns 263-264, (Ex. Name 491), line 2, please delete "yl)-", and insert -- yl}- --.

Columns 263-264, (Ex. Name 492), line 2, please delete "yl]-", and insert -- yl}- --.

Columns 263-264, (Ex. Name 493), line 2, please delete "porpoxy)", and insert -- propoxy) --.

Columns 265-266, (Ex. Name 497), line 3, please delete "ethyl)", and insert -- ethyl} --.

Columns 265-266, (Ex. Structure 498), line 1, please delete " 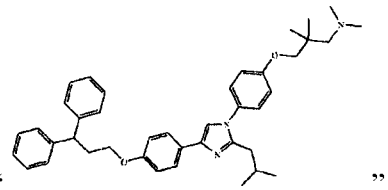 "

and insert -- 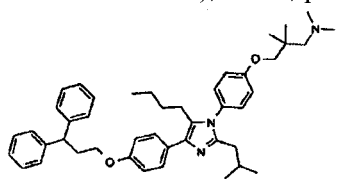 --.

Columns 269-270, (Ex. Name 504), lines 3-4, please delete "hydrochloride hydrochloride", and insert -- hydrochloride --.

Columns 269-270, (Ex. Name 505), line 3, please delete "yl]-phenoxyl", and insert -- yl]-phenoxy} --.

Columns 271-272, (Ex. Name 514), line 3, please delete "yl]-phenoxy)", and insert -- yl}-phenoxy) --.

Columns 275-276, (Ex. Name 519), line 2, please delete "yl]-", and insert -- yl}- --.

Columns 275-276, (Ex. Name 521), line 1, please delete "N-(2", and insert -- N-[2 --.

Columns 277-278, (Ex. Name 523), line 2, please delete "4-yl)", and insert -- 4-yl} --.

Columns 277-278, (Ex. Name 525), line 2, please delete "4-yl]", and insert -- 4-yl} --.

Columns 283-284, (Ex. Name 536), line 2, please delete "l-yl]", and insert -- l-yl} --.

Columns 285-286, (Ex. Name 537), line 2, please delete "phenyl]-2", and insert -- phenyl}-2 --.

Columns 287-288, (Ex. Name 540), line 3, please delete "yl]-phenoxy)", and insert -- yl}-phenoxy) --.

Columns 289-290, (Ex. Name 543), line 3, please delete "ylJ-phenoxy)", and insert -- yl}-phenoxy) --.

Columns 297-298, (Ex. Name 551), line 3, please delete "yl]-phenoxy)", and insert -- yl}-phenoxy) --.

Column 300, line 1, please delete ""hpterocyclic"", and insert -- "heterocyclic" --.

Column 303, line 29, After "like" please insert -- . --.

Column 303, line 55 (approx), After " 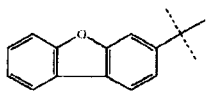 " please insert -- , --.

Column 309, line 19, please delete "Celsuis,", and insert -- Celsius, --.

Column 309, line 28, please delete "Celsuis,", and insert -- Celsius, --.

Column 310, line 25, please delete "posessing", and insert -- possessing --.

Column 310, line 56 (approx.), please delete "posessing", and insert -- possessing --.

Column 312, line 66, please delete "predceding", and insert -- preceding --.

Column 321, line 36 (approx.), please delete "sych", and insert -- such --.

Column 323, line 45, please delete "symnthesis", and insert -- synthesis --.

Column 325, line 19 (approx.), please delete "aminoketome", and insert -- aminoketone --.

Column 328, line 7, please delete "treament", and insert -- treatment --.

Column 330, line 10, please delete "hydroxylprotecting", and insert -- hydroxyl protecting --.

Column 330, line 19, please delete "triiospropylsilyl", and insert -- triisopropylsilyl --.

Column 330, line 33, please delete "carboxylprotecting", and insert -- carboxyl protecting --.

Column 330, line 42 (approx.), please delete "triiospropylsilyl", and insert -- triisopropylsilyl --.

Column 330, line 43 (approx.), please delete "carboxylprotecting", and insert -- carboxyl protecting --.

Column 331, line 19 (approx.), please delete "dimethypropylene", and insert -- dimethylpropylene --.

Column 335, line 43 (approx.), please delete "(2-5", and insert -- (2.5 --.

Column 337, line 54, please delete "dilkoxynitrobenzene", and insert -- dialkoxynitrobenzene --.

Column 338, line 7, please delete "dilkoxynitrobenzene", and insert -- dialkoxynitrobenzene --.

Column 340, line 18, please delete "reaction", and insert -- Reaction --.

Column 340, line 64, please delete "diiethyl", and insert -- diethyl --.

Column 341, line 7, please delete "diiethyl", and insert -- diethyl --.

Column 341, line 26, please delete "(M+H)+", and insert -- $(M+H)^+$ --.

Column 344, line 57 (approx.), please delete "piperdine", and insert -- piperidine --.

Column 345, line 12 (approx.), please delete "yl)-1H", and insert -- yl}-1H --.

Column 345, line 14 (approx.), please delete "piperdine", and insert -- piperidine --.

Column 345, line 38 (approx.), please delete "diiethyl", and insert -- diethyl --.

Column 346, line 1, please delete "bezaldehyde", and insert -- benzaldehyde --.

Column 346, line 63 (approx.), please delete "2-(4", and insert -- 2-{4 --.

Column 346, line 63 (approx.), please delete "phenyl)-6", and insert -- phenyl}-6 --.

Column 347, (Ex. Name 58), line 2, please delete "ethbxy)", and insert -- ethoxy) --.

Column 349, (Ex. Name 91), line 2, please delete "propioinamide", and insert -- propionamide --.

Column 349, (Ex. Name 102), line 2, please delete "phenyl]", and insert -- phenyl} --.

Column 349, (Ex. Name 114), lines 1-2, please delete "yloxy)-propyl]", and insert -- yloxy]-propyl} --.

Column 351, (Ex. Name 126), line 2, please delete "yloxy)-propyl]", and insert -- yloxy]-propyl} --.

Column 353, line 37 (approx.), please delete "bezaldehyde", and insert -- benzaldehyde --.

Column 353, line 56 (approx.), please delete "3(4-t", and insert -- 3-(4-t --.

Column 354, line 46 (approx.), please delete "propxy)", and insert -- propoxy) --.

Column 356, (Ex. Name 185), line 1, please delete "2-yl-", and insert -- 2-yl]- --.

Column 357, (Ex. Name 191), line 1, please delete "[3-(1", and insert -- (3-{1 --.

Column 357, (Ex. Name 209), line 1, please delete "pyrrolodin", and insert -- pyrrolidin --.

Column 357, (Ex. Name 215), line 2, please delete "yloxyl}", and insert -- yloxy} --.

Column 359, (Ex. Name 226), line 2, please delete "yloxy}-propyl)-", and insert
-- yloxy]-propyl}- --.

Column 359, (Ex. Name 238), line 1, please delete "benzoimidazlo", and insert -- benzoimidazol --.

Column 361, line 12, please delete "2-nbutylamino", and insert -- 2-n-butylamino --.

Column 361, line 66, After "mg)", please insert -- . --.

Column 362, lines 41-42 (approx.), please delete "2-nbutylamino", and insert -- 2-n-butylamino --.

Column 364, line 8, please delete "butylamiino", and insert -- butylamino --.

Column 364, (Ex. Name 260), line 1, please delete "(2-pyrrolodin-1", and insert -- (2-pyrrolidin-1 --.

Column 364, (Ex. Name 260), line 2, please delete "(2-pyrrolodin-1", and insert -- (2-pyrrolidin-1 --.

Column 364, (Ex. Name 261), line 1, please delete "[2-{1-butyl", and insert -- [2-[1-butyl --.

Column 364, (Ex. Name 263), line 1, please delete "{3-{2-[1", and insert -- {3-[2-[1 --.

Column 364, (Ex. Name 267), line 1, please delete "(4-iospropyl", and insert -- (4-isopropyl --.

Column 365, (Ex. Name 311), line 1, please delete "benzoimidazlo", and insert -- benzoimidazol --.

Column 367, (Ex. Name 315), line 1, please delete "benzoimidazlo", and insert -- benzoimidazol --.

Column 367, line 41, please delete "(0.0309,", and insert -- (0.030 g, --.

Column 369, line 38 (approx.), please delete "disubstitued", and insert -- disubstituted --.

Column 369, line 52 (approx.), please delete "disubstitued", and insert -- disubstituted --.

Column 370, line 25 (approx.), please delete "disubstitued", and insert -- disubstituted --.

Column 371, line 12 (approx.), please delete "(3-[1", and insert -- {3-[1 --.

Column 371, line 18, please delete "pyrrolidineehanol", and insert -- pyrrolidineethanol --.

Column 371, line 25, After "directly", please insert -- . --.

Column 371, line 45, please delete "proiduct", and insert -- product --.

Column 372, line 49, please delete "phenylenedimaine", and insert -- phenylenediamine --.

Column 373, line 26, please delete "phenyl}-7", and insert -- phenyl]-7 --.

Column 374, (Ex. Name 349), line 1, please delete "pyrrolodin", and insert -- pyrrolidin --.

Column 375, (Ex. Name 356), line 1, please delete "pyrrolodin", and insert -- pyrrolidin --.

Column 375, (Ex. Name 358), line 2, please delete "pyrrolodin", and insert -- pyrrolidin --.

Column 377, line 39 (approx.), please delete "1-H", and insert -- 1H --.

Column 378, line 38, please delete "diethylaminopropxy)-1-H", and insert -- diethylaminopropoxy)-1H --.

Column 378, line 41, please delete "diethylaminoproxy)-1-H", and insert -- diethylaminopropoxy)-1H --.

Column 378, lines 43-44, please delete "diethylaminopropxy)-1-H", and insert -- diethylaminopropoxy)-1H --.

Column 378, line 55 (approx.), please delete "1-H", and insert -- 1H --.

Column 378, line 56-57 (approx.), please delete "diethylaminoproxy)-1-H", and insert -- diethylaminopropoxy)-1H --.

Column 379, line 4, please delete "1-H", and insert -- 1H --.

Column 379, lines 18-19, please delete "diethylaminopropxy)-1-H", and insert -- diethylaminopropoxy)-1H --.

Column 379, line 35 (approx.), please delete "(2-[(4", and insert -- (2-{[(4 --.

Column 379, line 36 (approx.), please delete "3-H", and insert -- 3H --.

Column 379, lines 55-56 (approx.), please delete "diethylaminopropxy)-1-H", and insert -- diethylaminopropoxy)-1H --.

Column 380, line 4, please delete "1-H", and insert-- 1H --.

Column 380, lines 19-20, please delete "diethylaminopropxy)-1-H", and insert -- diethylaminopropoxy)-1H --.

CERTIFICATE OF CORRECTION (continued)
U.S. Pat. No. 7,714,013 B2

Column 380, lines 53-54, please delete "diethylaminopropxy)-1-H", and insert
-- diethylaminopropoxy)-1H --.

Column 383, line 33 (approx.), please delete "1-(4", and insert -- 1-{4 --.

Column 383, line 34 (approx.), please delete "phenyl)ethanone", and insert -- phenyl}ethanone --.

Column 384, line 31, After "DCM).", please delete "T".

Column 385, line 3, please delete "elutiopn", and insert -- elution --.

Column 385, line 56, please delete "MS:", and insert -- (MS: --.

Column 386, line 59, please delete "MS:", and insert -- (MS: --.

Column 387, line 67, please delete "MS:", and insert -- (MS: --.

Column 388, line 19, please delete "slilca", and insert -- silica --.

Column 390, line 7, please delete "(elutiion", and insert -- (elution --.

Column 390, line 52, please delete "diethyaminopropanol", and insert -- diethylaminopropanol --.

Column 391, lines 57-58, please delete "diethyaminopropanol", and insert -- diethylaminopropanol --.

Column 393, line 15, please delete "diethyaminopropanol", and insert -- diethylaminopropanol --.

Column 394, line 34, After "purification", please insert -- . --.

Column 394, line 66, please delete "-20 eq)", and insert -- ~20 eq) --.

Column 403, line 1, please delete "(diethyldinino)", and insert -- (diethylamino) --.

Column 403, line 5, please delete "anhydrous.", and insert -- anhydrous --.

Column 404, line 28 (approx), please delete "1-(4", and insert -- 1-{4 --.

Column 404, line 29 (approx.), please delete "phenyl)ethanone", and insert -- phenyl}ethanone --.

Column 404, line 34 (approx.), please delete "1-(4", and insert -- 1{4 --.

Column 404, line 34 (approx.), please delete "phenyl)", and insert -- phenyl} --.

Column 410, line 15, please delete "imidazo", and insert -- imidazol --.

Column 414, line 43, please delete "1-(4", and insert -- 1-{4 --.

Column 414, line 44, please delete "phenyl)ethanone", and insert -- phenyl}ethanone --.

Column 416, line 66, After "mg)", please insert -- . --.

Column 419, line 67, please delete "resuting", and insert -- resulting --.

Column 420, line 9, please delete "(ABq,", and insert -- $(AB_q,$ --.

Column 420, line 39 (approx.), please delete "product-obtained", and insert -- product obtained --.

Column 420, line 41 (approx.), please delete "resuting", and insert -- resulting --.

Column 420, line 51 (approx.), please delete "(ABq,", and insert -- $(AB_q,$ --.

Column 421, line 15, please delete "resuting", and insert -- resulting --.

Column 422, line 24 (approx.), please delete "mL):" and insert -- mL), --.

Column 427, line 2, please delete "J=8.8", and insert -- J 8.8 --.

Column 427, line 31, please delete "desired-4-[4", and insert -- desired 4-[4 --.

Column 427, lines 36-37, please delete "diethyaminopropanol", and insert -- diethylaminopropanol --.

Column 429, line 39, please delete "column,", and insert -- column --.

Column 433, line 28, please delete "dilutad", and insert -- diluted --.

Column 446, line 22, please delete "(1.5 eq),", and insert -- (1.5 eq) --.

Column 446, line 54, please delete "{4-{4", and insert -- {4-[4 --.

Column 456, line 47, please delete "$SnCl_2.2H_2O$", and insert -- $SnCl_2 \cdot 2H_2O$ --.

Column 457, line 2, please delete "(4", and insert -- {4 --.

Column 457, line 3, please delete "phenyl)", and insert -- phenyl} --.

Column 469, lines 35-36, please delete "extracated", and insert -- extracted --.

Column 469, line 53, please delete "C.until", and insert -- C. until --.

Column 474, line 66, please delete "4-fluoroacetophone", and insert -- 4-fluoroacetophenone --.

Column 475, lines 9-10, please delete "4-(4'-chlorophenoxy)acetophone", and insert -- 4-(4'-chlorophenoxy)acetophenone --.

Column 475, line 36, please delete "(100 mL)", and insert -- (100 mL), --.

Column 476, line 53, please delete "Oxayl", and insert -- Oxalyl --.

Column 477, line 49, please delete "Oxayl", and insert -- Oxalyl --.

Column 482, line 26, please delete "(yield ~13%", and insert -- (yield ~13%). --.

Column 483, line 24, please delete "1-(4-", and insert -- 1-{4- --.

Column 483, line 25, please delete "phenyl)", and insert -- phenyl} --.

Column 488, line 10 (approx.), please delete "$SnCl_2.2H_2O$", and insert -- $SnCl_2 \cdot 2H_2O$ --.

Column 489, line 28, please delete "(prepwered", and insert -- (prepared --.

Column 490, line 60, please delete "acetophone", and insert -- acetophenone --.

Column 491, line 15, please delete "acetopone:", and insert -- acetophenone: --.

Column 493, line 34, please delete "n-penatnoyl", and insert -- n-pentanoyl --.

Column 493, line 35, please delete "accoding", and insert -- according --.

Column 494, line 22 (approx), please delete "n-penatnoyl", and insert -- n-pentanoyl --.

Column 494, line 23 (approx), please delete "accoding", and insert -- according --.

Column 494, line 25, please delete "BOG", and insert -- BOC --.

Column 494, line 33 (approx.), please delete "phenyl)-1",and insert -- phenyl)-ethoxy]-phenyl}-2-isobutyl-imidazol-1-yl)-1 --.

Column 494, line 40, please delete "accoding", and insert -- according --.

Column 494, line 43, please delete "BOG", and insert -- BOC --.

Column 494, line 55, please delete "4-benzyloxyacetophone", and insert
-- 4-benzyloxyacetophenone --.

Column 494, line 59, please delete "accoding", and insert -- according --.

Column 495, line 17 (approx.), please delete "ethyl", and insert -- ethyl) --.

Column 495, line 31, please delete "accoding", and insert -- according --.

Column 496, line 33 (approx.), please delete "accoding", and insert -- according --.

Column 496, line 60, please delete "plase", and insert -- place --.

Column 498, line 36, please delete "methd", and insert -- method --.

Column 498, line 63, After "step", please insert -- . --.

Column 499, line 8, please delete "10° C.", and insert -- 100° C. --.

Column 499, line 13, please delete "fiiltration.", and insert -- filtration. --.

Column 500, line 15, please delete "acetonitile", and insert -- acetonitrile --.

Column 500, line 22, please delete "guanadino", and insert -- guanidino --.

Column 500, lines 22-23, please delete "guanadino", and insert -- guanidino --.

Column 501, line 8, please delete "acohol", and insert -- alcohol --.

Column 501, line 50, please delete "nitropyridine N-oxide.", and insert -- nitropyridine-N-oxide. --.

Column 503, line 26, please delete "concenterated", and insert -- concentrated --.

Column 504, line 38, please delete "accorgding", and insert -- according --.

Column 504, line 47 (approx.), please delete "Bis-(4 chloro", and insert -- Bis-(4-chloro --.

Column 504, line 63, please delete "phenyl)-", and insert -- phenyl}- --.

Column 505, line 29, please delete "aminonium", and insert -- ammonium --.

Column 506, line 16 (approx.), please delete "concenterated", and insert -- concentrated --.

Column 506, line 39 (approx.), please delete "phenyl}-imidazol-1-yl]", and insert
-- phenyl]-imidazol-1-yl} --.

Column 506, line 47 (approx.), please delete "concenterated", and insert -- concentrated --.

Column 507, line 4, please delete "imidazol 1-yl}", and insert -- imidazol-1-yl} --.

Column 507, lines 11-12, please delete "concenterated", and insert -- concentrated --.

Column 507, line 29, please delete "concenterated", and insert -- concentrated --.

Column 508, line 12, please delete "-yl}-", and insert -- -yl)- --.

Column 509, line 53, please delete "Sterptavidin", and insert -- Streptavidin --.

Column 511, line 8, please delete "alchol", and insert -- alcohol --.

Column 511, line 36, please delete "injectible", and insert -- injectable --.

Column 511, line 66, please delete ". 1%", and insert -- .1% --.

Column 512, lines 17-18, please delete "polepsilon", and insert -- polyepsilon --.

Column 512, line 49, please delete "Hydrocloride,", and insert -- Hydrochloride, --.

Column 512, line 64, please delete "oxlate,", and insert -- oxalate, --.

Column 512, line 65, please delete "tartarate,", and insert -- tartrate, --.

Column 513, line 14, please delete "therof,", and insert -- thereof, --.

Column 515, line 11, please delete "propogation", and insert -- propagation --.

Column 516, line 29, please delete "propogation", and insert -- propagation --.

Column 516, line 47, please delete "nad", and insert -- and --.

Column 516, line 48, please delete "osbtructive", and insert -- obstructive --.

Column 517, line 49, please delete "Mefformin", and insert -- Metformin --.

Column 518, line 27 (approx.), please delete ". 1%", and insert -- .1% --.

Column 518, line 43, please delete "therof,", and insert -- thereof, --.

Column 519, line 65, In Claim 1, please delete "$Y_4$is", and insert -- $Y_4$ is --.

Column 520, line 21, In Claim 1, please delete "$A_2$is", and insert -- $A_2$ is --.